United States Patent
Nakai et al.

(10) Patent No.: US 10,639,308 B2
(45) Date of Patent: May 5, 2020

(54) SGC STIMULATORS

(71) Applicant: Cyclerion Therapeutics, Inc., Cambridge, MA (US)

(72) Inventors: Takashi Nakai, Newton, MA (US); Joel Moore, Lexington, MA (US); Nicholas Robert Perl, Somerville, MA (US); Rajesh R. Iyengar, West Newton, MA (US); Ara Mermerian, Waltham, MA (US); G-Yoon Jamie Im, Cambridge, MA (US); Thomas Wai-Ho Lee, Lexington, MA (US); Colleen Hudson, Denver, CO (US); Glen Robert Rennie, Somerville, MA (US); Lei Jia, San Diego, CA (US); Paul Allan Renhowe, Sudbury, MA (US); Timothy Claude Barden, Waltham, MA (US); Xiang Y. Yu, Acton, MA (US); James Edward Sheppeck, Newtown, PA (US); Karthik Iyer, Cambridge, MA (US); Joon Jung, Newton, MA (US); George Todd Milne, Brookline, MA (US); Kimberly Kafadar Long, Boston, MA (US); Mark G. Currie, Sterling, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/178,771

(22) Filed: Nov. 2, 2018

(65) Prior Publication Data
US 2019/0167679 A1 Jun. 6, 2019

Related U.S. Application Data

(60) Continuation of application No. 15/245,697, filed on Aug. 24, 2016, now Pat. No. 10,183,021, which is a
(Continued)

(51) Int. Cl.
*A61K 31/506* (2006.01)
*A61K 31/517* (2006.01)
(Continued)

(52) U.S. Cl.
CPC .......... *A61K 31/506* (2013.01); *A61K 31/517* (2013.01); *A61K 31/519* (2013.01);
(Continued)

(58) Field of Classification Search
None
See application file for complete search history.

(56) References Cited

U.S. PATENT DOCUMENTS 5,470,862 A 11/1995 Lin et al.
8,748,442 B2 6/2014 Kim et al.
(Continued)

FOREIGN PATENT DOCUMENTS

WO 1993/11433 A1 6/1993
WO 2000/27394 A1 5/2000
(Continued)

OTHER PUBLICATIONS

Calhoun et al., Resistant hypertension: diagnosis, evaluation, and treatment: a scientific statement from the American Heart Association Professional Education Committee of the Council for High Blood Pressure Research. Circulation. Jun. 24, 2008;117(25):e510-26.
Persell, Prevalence of Resistant Hypertension in the United States, 2003-2008. Hypertension. Jun. 2011;57(6):1076-80.
Rees et al., Sickle-cell disease. Lancet. Dec. 11, 2010;376(9757):2018-31.
Selwood et al., Synthesis and biological evaluation of novel pyrazoles and indazoles as activators of the nitric oxide receptor, soluble guanylatecyclase. J Med Chem. 2001;44:78-93.
(Continued)

*Primary Examiner* — Anna Pagonakis
(74) *Attorney, Agent, or Firm* — McCarter & English, LLP; Steven G. Davis; Xin Zhang

(57) ABSTRACT

Compounds of Formulae I' and I are described, which are useful as stimulators of sGC, particularly NO-independent, heme-dependent stimulators. These compounds are also useful for treating, preventing or managing various disorders that are herein disclosed.

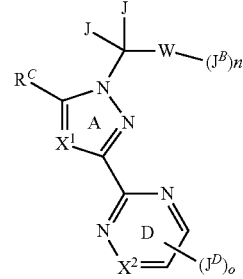

Formula I'

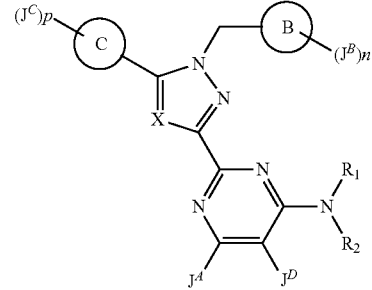

Formula I

31 Claims, No Drawings

Related U.S. Application Data division of application No. 14/775,954, filed as application No. PCT/US2014/028370 on Mar. 14, 2014, now Pat. No. 9,481,689.

(60) Provisional application No. 61/914,915, filed on Dec. 11, 2013, provisional application No. 61/790,637, filed on Mar. 15, 2013.

(51) Int. Cl.

| | | |
|---|---|---|
| *A61K 31/519* | (2006.01) | |
| *A61K 31/5377* | (2006.01) | |
| *A61K 31/541* | (2006.01) | |
| *A61K 31/55* | (2006.01) | |
| *C07D 413/14* | (2006.01) | |
| *C07D 417/14* | (2006.01) | |
| *C07D 471/04* | (2006.01) | |
| *C07D 487/04* | (2006.01) | |
| *C07D 495/04* | (2006.01) | |
| *C07D 403/04* | (2006.01) | |
| *C07D 487/10* | (2006.01) | |
| *C07D 491/107* | (2006.01) | |
| *C07D 498/04* | (2006.01) | |
| *C07D 401/14* | (2006.01) | |
| *C07D 471/08* | (2006.01) | |
| *C07D 471/10* | (2006.01) | |
| *A61K 45/06* | (2006.01) | |
| *C07D 451/02* | (2006.01) | |

(52) U.S. Cl.
CPC ........ *A61K 31/5377* (2013.01); *A61K 31/541* (2013.01); *A61K 31/55* (2013.01); *A61K 45/06* (2013.01); *C07D 401/14* (2013.01); *C07D 403/04* (2013.01); *C07D 413/14* (2013.01); *C07D 417/14* (2013.01); *C07D 451/02* (2013.01); *C07D 471/04* (2013.01); *C07D 471/08* (2013.01); *C07D 471/10* (2013.01); *C07D 487/04* (2013.01); *C07D 487/10* (2013.01); *C07D 491/107* (2013.01); *C07D 495/04* (2013.01); *C07D 498/04* (2013.01); *Y02A 50/423* (2018.01)

(56) References Cited

U.S. PATENT DOCUMENTS

| | | | |
|---|---|---|---|
| 9,061,030 | B2 | 6/2015 | Kim et al. |
| 9,139,564 | B2 | 9/2015 | Kim et al. |
| 9,309,235 | B2 | 4/2016 | Im et al. |
| 9,481,689 | B2 | 11/2016 | Nakai et al. |
| 9,586,937 | B2 | 3/2017 | Nakai et al. |
| 10,183,021 | B2 | 1/2019 | Nakai et al. |
| 2010/0144864 | A1 | 6/2010 | Currie et al. |
| 2012/0184516 | A1 | 7/2012 | Kim et al. |
| 2013/0178475 | A1 | 7/2013 | Moore et al. |
| 2013/0210824 | A1 | 8/2013 | Follmann et al. |
| 2014/0088071 | A1 | 3/2014 | Nakai et al. |
| 2014/0315934 | A1 | 10/2014 | Hitchcock et al. |
| 2015/0232461 | A1 | 8/2015 | Nakai et al. |
| 2015/0250795 | A1 | 9/2015 | Kim et al. |
| 2015/0342954 | A1 | 12/2015 | Kim et al. |
| 2016/0175307 | A1 | 6/2016 | Im et al. |
| 2017/0136019 | A1 | 5/2017 | Nakai et al. |
| 2017/0137439 | A1 | 5/2017 | Nakai et al. |

FOREIGN PATENT DOCUMENTS

| | | |
|---|---|---|
| WO | 2004/101555 A1 | 11/2004 |
| WO | 2012/003405 A1 | 1/2012 |
| WO | 2012/064559 A1 | 5/2012 |
| WO | 2013/101830 A1 | 7/2013 |
| WO | 2014/047111 A1 | 3/2014 |
| WO | 2014/144100 A2 | 9/2014 |
| WO | 2015/089182 A1 | 6/2015 |
| WO | 2015/106268 A1 | 7/2015 |

OTHER PUBLICATIONS

Sergievskii et al., Reactivity of 3,5-bis-(4-amino-1,2,5-oxadiazol-3-yl)-1,2,4-triazole. Russian Journal of Organic Chemistry. 2005;41(2):261-267.

Steinberg, Pathophysiologically based drug treatment of sickle cell disease. Trends Pharmacol Sci. Apr. 2006;27(4):204-10.

Takalo et al., Development of Luminescent Terbium(III) Chelates for Protein Labelling: Effect of triplet-state energy level. Helvetica Chimica Acta. Mar. 24, 1997;80(2):372-387.

Tarrago et al., Orientation de la reaction d'alkylation des pyrazoles dans des conditions neuters et an catalyse par transfer de phase. J Heterocycl Chem.1980;17(1):137-142.

Zabel et al., Iron and Cobalt Complexes of Tridentate N-Donor Ligands in Ethylene Polymerization: Efficient Shielding of the Active sites by Simple Phenyl Groups. Eur J Inorg Chem. 2008;23:3648-3654.

International Preliminary Report on Patentability for Application No. PCT/US2011/058902, dated May 14, 2013.

International Search Report for Application No. PCT/US2014/028370 dated Sep. 12, 2014.

Nossaman et al., Stimulators and activators of soluble guanylate cyclase: review and potential therapeutic indications. Crit Care Res Pract. 2012;2012:290805. 12 pages.

Stasch et al., Soluble guanylate cyclase as an emerging therapeutic target in cardiopulmonary disease. Circulation. May 24, 2011;123(20):2263-73.

U.S. Appl. No. 14/775,954, filed Sep. 14, 2015, U.S. Pat. No. 9,481,689, Issued.

U.S. Appl. No. 15/215,628, filed Jul. 21, 2016, U.S. Pat. No. 9,586,937, Issued.

U.S. Appl. No. 15/245,697, filed Aug. 24, 2016, U.S. Pat. No. 10,183,021, Issued.

U.S. Appl. No. 15/406,959, filed Jan. 16, 2017, 2017-0136019, Published.

U.S. Appl. No. 15/406,994, filed Jan. 16, 2017, 2017-0137439, Abandoned.

U.S. Appl. No. 15/915,899, filed Mar. 8, 2018, Abandoned.

SGC STIMULATORS

CROSS REFERENCE TO RELATED APPLICATIONS

This application is a continuation of U.S. patent application Ser. No. 15/245,697, filed Aug. 24, 2016; which is a divisional of U.S. patent application Ser. No. 14/775,954, filed Sep. 14, 2015 and now U.S. Pat. No. 9,481,689; which is a national stage entry of International Patent Application No. PCT/US2014/028370, filed Mar. 14, 2014; which claims the benefit of priority from U.S. Provisional Application Nos. 61/914,915, filed Dec. 11, 2013 and 61/790,637, filed Mar. 15, 2013. Each of the aforementioned applications is incorporated herein by reference in its entirety.

FIELD OF THE INVENTION

The present disclosure relates to stimulators of soluble guanylate cyclase (sGC), pharmaceutical formulations comprising them and their uses thereof, alone or in combination with one or more additional agents, for treating and/or preventing various diseases, wherein an increase in the concentration of nitric oxide (NO) or an increase in the concentration of cyclic Guanosine Monophosphate (cGMP) might be desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts GTP into the secondary messenger cyclic GMP (cGMP). The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure.

Experimental and clinical evidence indicates that reduced bioavailability and/or responsiveness to endogenously produced NO contributes to the development of cardiovascular, endothelial, renal and hepatic disease, as well as erectile dysfunction and other sexual disorders (e.g. female sexual disorder or vaginal atrophy). In particular, the NO signaling pathway is altered in cardiovascular diseases, including, for instance, systemic and pulmonary hypertension, heart failure, angina, stroke, thrombosis and other thromboembolic diseases, peripheral arterial disease, fibrosis of the liver, lung or kidney and atherosclerosis.

sGC stimulators are also useful in the treatment of lipid related disorders such as e.g., dyslipidemia, hypercholesterolemia, hypertriglyceridemia, sitosterolemia, fatty liver disease, and hepatitis.

Pulmonary hypertension (PH) is a disease characterized by sustained elevation of blood pressure in the pulmonary vasculature (pulmonary artery, pulmonary vein and pulmonary capillaries), which results in right heart hypertrophy, eventually leading to right heart failure and death. In PH, the bioactivity of NO and other vasodilators such as prostacyclin is reduced, whereas the production of endogenous vasoconstrictors such as endothelin is increased, resulting in excessive pulmonary vasoconstriction. sGC stimulators have been used to treat PH because they promote smooth muscle relaxation, which leads to vasodilation.

Treatment with NO-independent sGC stimulators also promoted smooth muscle relaxation in the corpus cavernosum of healthy rabbits, rats and humans, causing penile erection, indicating that sGC stimulators are useful for treating erectile dysfunction.

NO-independent, heme-dependent, sGC stimulators, such as those disclosed herein, have several important differentiating characteristics, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed. These compounds have been shown to produce anti-aggregatory, anti-proliferative and vasodilatory effects.

Since compounds that stimulate sGC in an NO-independent manner offer considerable advantages over other current alternative therapies, there is a need to develop novel stimulators of sGC. They are potentially useful in the prevention, management and treatment of disorders such as pulmonary hypertension, arterial hypertension, heart failure, atherosclerosis, inflammation, thrombosis, renal fibrosis and failure, liver cirrhosis, lung fibrosis, erectile dysfunction, female sexual arousal disorder and vaginal atrophy and other cardiovascular disorders; they are also potentially useful for the prevention, management and treatment of lipid related disorders.

SUMMARY OF THE INVENTION

The present invention is directed to compounds according to Formula I', or pharmaceutically acceptable salts thereof,

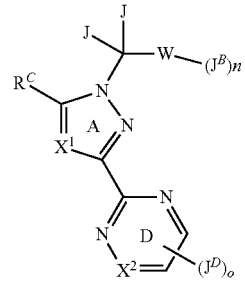

Formula I' wherein $X^1$ is selected from N, CH, C($C_{1-4}$ alkyl), C($C_{1-4}$haloalkyl), CCl and CF;

$X^2$ is independently selected from N or C;

W is either i) absent, with $J^B$ connected directly to the carbon atom bearing two J groups, each J is independently selected from hydrogen or methyl, n is 1 and $J^B$ is a $C_{1-7}$ alkyl chain optionally substituted by up to 9 instances of fluorine; wherein, optionally, one —$CH_2$— unit of said $C_{1-7}$ alkyl chain can be replaced by —O— or —S—.

ii) a ring B that is a phenyl or a 5 or 6-membered heteroaryl ring, containing 1 or 2 ring heteroatoms selected from N, O or S; wherein with ring B being the phenyl or 5 or 6-membered heteroaryl ring; each J is hydrogen; n is an integer selected from 0 to 3; and each $J^B$ is independently selected from halogen, —CN, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$; each $R^B$ is independently selected from hydrogen, a $C_{1-6}$ aliphatic or a $C_{3-8}$ cycloaliphatic; wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;

each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);

each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);

o is an integer selected from 1 to 3;

each $J^D$ is independently selected from $J^A$, halogen, —CN, —$NO_2$, —$OR^D$, —$SR^D$, —$C(O)R^D$, —$C(O)OR^D$, —$OC(O)R^D$, —$C(O)N(R^D)_2$, —$N(R^D)_2$, —$N(R^d)C(O)R^D$, —$N(R^d)C(O)OR^D$, —$N(R^d)C(O)N(R^D)_2$, —$OC(O)N(R^D)_2$, —$SO_2R^D$, —$SO_2N(R^D)_2$, —$N(R^d)SO_2R^D$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^D$ moiety, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of $R^{5d}$, wherein at least one $J^D$ is not hydrogen;

$J^A$ is selected from hydrogen, halogen, methyl, hydroxyl, methoxy, trifluoromethyl, trifluoromethoxy or —$NR^aR^b$; wherein $R^a$ and $R^b$ are each independently selected from hydrogen, $C_{1-6}$ alkyl or a 3-6 cycloalkyl ring; or wherein $R^a$ and $R^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;

each $R^D$ is independently selected from hydrogen, a $C_{1-6}$ aliphatic, —($C_{1-6}$ aliphatic)-$R^f$, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 10-membered heterocyclic ring, each said phenyl and each said 5 to 6-membered heteroaryl ring is optionally and independently substituted with up to 5 instances of $R^{5a}$; wherein when any $R^D$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —$N(R^d)$—, —CO— or —O—; provided that when $X^1$ is one of CH, C($C_{1-4}$ alkyl), C($C_{1-4}$ haloalkyl), CCl or CF; $X^2$ is C; and at least one $J^D$ is —$N(R^D)_2$ and is attached to one of the pyrimidine ring D carbons ortho to the two nitrogen atoms of said ring D, one instance of $R^D$ is not a pyridine or a pyrimidine;

each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$; wherein when any $R^d$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —$N(R^d)$—, —CO— or —O—;

each $R^f$ is independently selected from a $C_{1-3}$ alkyl, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N or S; and wherein each said $C_{3-8}$ cycloaliphatic ring, each said 4 to 10-membered heterocyclic ring, each said phenyl and each said 5 to 6-membered heteroaryl ring is optionally and independently substituted by up to 5 instances of $R^{5c}$;

when $J^D$ is —$C(O)N(R^D)_2$, —$N(R^D)_2$, —$N(R^d)C(O)N(R^D)_2$, —$OC(O)N(R^D)_2$ or —$SO_2N(R^D)_2$, the two $R^D$ groups together with the nitrogen atom attached to the two $R^D$ groups may form a 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O or S, in addition to the nitrogen atom to which the two $R^D$ groups are attached; and wherein each said 4 to 8-membered heterocyclic ring and each said 5-membered heteroaryl ring is optionally and independently substituted by up to 5 instances of $R^5$;

when $J^D$ is —$N(R^d)C(O)R^D$, the $R^D$ group together with the carbon atom attached to the $R^D$ group, with the nitrogen atom attached to the $R^d$ group, and with the $R^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, in addition to the nitrogen atom to which the $R^d$ group is attached; and wherein each said 4 to 8-membered heterocyclic ring and each said 5-membered heteroaryl ring is optionally and independently substituted by up to 5 instances of $R^5$;

when $J^D$ is —$N(R^d)C(O)OR^D$, the $R^D$ group together with the oxygen atom attached to the $R^D$ group, with the carbon atom of the —C(O)— portion of the —$N(R^d)C(O)OR^D$ group, with the nitrogen atom attached to the $R^d$ group, and with said $R^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —$N(R^d)C(O)N(R^D)_2$, one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —$N(R^d)SO_2R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

each $R^5$ is independently selected from halogen, —CN, $C_{1-6}$ alkyl, —($C_{1-6}$ alkyl)-$R^6$, —$OR^6$, —$SR^6$, —$COR^6$, —OC(O)$R^6$, —C(O)$OR^6$, —C(O)N($R^6$)$_2$, —C(O)N($R^6$)$SO_2R^6$, —N($R^6$)C(O)$R^6$, —N($R^6$)C(O)$OR^6$, —N($R^6$)C(O)N($R^6$)$_2$, —N($R^6$)$_2$, —$SO_2R^6$, —$SO_2OH$, —$SO_2NHOH$, —$SO_2N(R^6)_2$, —$SO_2N(R^6)COOR^6$, —$SO_2N(R^6)C(O)R^6$, —N($R^6$)$SO_2R^6$, —(C=O)$NHOR^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of the —($C_{1-6}$ alkyl)-$R^6$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —$CONH_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —$CONH_2$, —COO($C_{1-4}$ alkyl), —O($C_{1-4}$ alkyl), —O($C_{1-4}$ haloalkyl) or oxo;

two instances of $R^5$, attached to the same or different atoms of $J^D$, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —$CONH_2$, —OH or halogen; wherein R is hydrogen or a $C_{1-2}$ alkyl;

each $R^{5a}$ and each $R^{5b}$ is independently selected from halogen, —CN, $C_{1-6}$ alkyl, —($C_{1-6}$ alkyl)$R^{6a}$, —$OR^{6a}$, —$SR^{6a}$, —$COR^{6a}$, —OC(O)$R^{6a}$, —C(O)$OR^{6a}$, —C(O)N($R^{6a}$)$_2$, —C(O)N($R^{6a}$)$SO_2R^{6a}$, —N($R^{6a}$)C(O)$R^{6a}$, —N($R^{6a}$)C(O)$OR^{6a}$, —N($R^{6a}$)C(O)N($R^{6a}$)$_2$, —N($R^{6a}$)$_2$, —$SO_2R^{6a}$, —$SO_2OH$, —$SO_2NHOH$, —$SO_2N(R^{6a})_2$, —$SO_2N(R^{6a})COOR^{6a}$, —$SO_2N(R^{6a})C(O)R^{6a}$, —N($R^{6a}$)$SO_2R^{6a}$, —(C=O)$NHOR^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —$NH_2$, —NH($C_{1-4}$ alkyl), —N($C_{1-4}$ alkyl)$_2$, —CN, —COOH, —$CONH_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —$CONH_2$, —COO($C_{1-4}$ alkyl), —O($C_{1-4}$ alkyl), —O($C_{1-4}$ haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)$NH_2$, —NR(CO)O($C_{1-4}$ alkyl), —OH or halogen; wherein R is hydrogen or a $C_{1-2}$ alkyl;

each $R^{5c}$ is independently selected from halogen, —CN, $C_{1-6}$ alkyl, —($C_{1-6}$ alkyl)-$R^{6b}$, —$OR^{6b}$, —$SR^{6b}$, —OC(O)$R^{6b}$, —C(O)$OR^{6b}$, —C(O)N($R^{6b}$)$_2$, —C(O)N($R^{6b}$)$SO_2R^{6b}$, —N($R^{6b}$)C(O)$R^{6b}$, —N($R^{6b}$)C(O)$OR^{6b}$, —N($R^{6b}$)C(O)N($R^{6b}$)$_2$, —N($R^{6b}$)$_2$, —$SO_2R^{6b}$, —$SO_2OH$, —$SO_2NHOH$, —$SO_2N(R^{6b})_2$, —$SO_2N(R^{6b})COOR^{6b}$, —$SO_2N(R^{6b})C(O)R^{6b}$, —N($R^{6b}$)$SO_2R^{6b}$, —(C=O)$NHOR^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —$CONH_2$, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of R$^{5c}$ attached to the same or different atoms of R$^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each R$^{5d}$ is independently selected from halogen, —CN, $C_{1-6}$ alkyl, —($C_{1-6}$ alkyl)-R$^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)COR$^6$, —SO$_2$N(R$^6$)$_2$, —N(R$^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-R$^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of R$^{5d}$ attached to the same or different atoms of J$^D$, together with said atom or atoms of J$^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each R$^6$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each R$^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each R$^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S; wherein two instances of R$^6$ linked to the same nitrogen atom of R$^5$ or R$^{5d}$, together with said nitrogen atom of R$^5$ or R$^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of R$^{6a}$ linked to a nitrogen atom of R$^{5a}$ or R$^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of R$^{6b}$ linked to a nitrogen atom of R$^{5c}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two J$^D$ groups attached to two vicinal ring D atoms, taken together with said two vicinal ring D atoms, may form a 5 to 7-membered heterocycle or a 5-membered heteroaryl ring that is fused to ring D; wherein said 5 to 7-membered heterocycle or said 5-membered ring heteroaryl contains from 1 to 3 heteroatoms independently selected from N, O or S; and wherein said 5 to 7-membered heterocycle or said 5-membered heteroaryl ring is optionally and independently substituted by up to 3 instances of oxo or —(Y)—R$^9$;

wherein Y is either absent or is a linkage in the form of a $C_{1-6}$ alkyl chain, optionally substituted by up to 6 instances of fluoro; and wherein when Y is said $C_{1-6}$ alkyl chain, up to 3 methylene units of this alkyl chain, can be replaced by a group selected from —O—, —C(O)— or —N((Y)—R$^{90}$)—, wherein
  i) when Y is absent, each R$^{90}$ is independently selected from hydrogen, —COR$^{10}$, —C(O)OR$^{10}$, —C(O)N(R$^{10}$)$_2$, —C(O)N(R$^{10}$)SO$_2$R$^{10}$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —(C=O)NHOR$^{10}$, C$_{3-6}$ cycloalkyl ring, a 4-8-membered heterocyclic ring, a phenyl ring or a 5-6 membered heteroaroaryl ring; wherein each said 4 to 8-membered heterocyclic ring or 5 to 6-membered heteroaryl ring contains up to 4 ring heteroatoms independently selected from N, O or S; and wherein each of said C$_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$; and
  ii) when Y is present, each R$^{90}$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, C$_{3-6}$ cycloalkyl ring, a 4-8-membered heterocyclic ring, a phenyl ring or a 5-6 membered heteroaroaryl ring; wherein each said 4 to 8-membered heterocyclic ring or 5 to 6-membered heteroaryl ring contains up to 4 ring heteroatoms independently selected from N, O or S; and wherein each of said C$_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$;

each R$^9$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, C$_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said C$_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$;

each R$^{10}$ is independently selected from hydrogen, a C$_{1-6}$ alkyl, —(C$_{1-6}$ alkyl)-R$^{13}$, phenyl, benzyl, a C$_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said C$_{1-6}$ alkyl, C$_{1-6}$ alkyl portion of said —(C$_{1-6}$ alkyl)-R$^{13}$ moiety, each said phenyl, each said benzyl, each said C$_{3-8}$ cycloalkyl group, each said 4 to 7-membered heterocyclic ring and each 5 or 6-membered heteroaryl ring is optionally and independently substituted with up to 3 instances of R$^{11a}$;

each R$^{13}$ is independently selected from a phenyl, a benzyl, a C$_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said C$_{3-8}$ cycloalkyl group, each said 4 to 7-membered heterocyclic ring and each 5 or 6-membered heteroaryl ring is optionally and independently substituted with up to 3 instances of R$^{11b}$;

each R$^{11}$ is independently selected from halogen, oxo, C$_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said C$_{1-6}$ alkyl is optionally and independently substituted by up to 6 instances of fluoro and/or 3 instances of R$^{12}$;

each R$^{11a}$ is independently selected from halogen, oxo, C$_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said C$_{1-6}$ alkyl is optionally and independently substituted by up to 6 instances of fluoro and/or 3 instances of R$^{12}$; and each R$^{11b}$ is independently selected from halogen, C$_{1-6}$ alkyl, oxo, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said C$_{1-6}$ alkyl is optionally and independently substituted by up to 6 instances of fluoro and/or 3 instances of R$^{12}$;

each R$^{12}$ is selected from hydrogen, a C$_{1-6}$ alkyl, phenyl, benzyl, a C$_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said C$_{1-6}$ alkyl, each said phenyl, each said benzyl, each said C$_{3-8}$ cycloalkyl group, each said 4 to 7-membered heterocyclic ring and each 5 or 6-membered heteroaryl ring is optionally and independently substituted with up to 3 instances of halogen, C$_{1-4}$ alkyl, C$_{1-4}$ (fluoroalkyl), —OH, —NH$_2$, —NH(C$_{1-4}$ alkyl), —N(C$_{1-4}$alkyl)$_2$, —CN, —COOH, —CONH$_2$, —COO(C$_{1-4}$ alkyl), —O(C$_{1-4}$ alkyl), —O(C$_{1-4}$ fluoroalkyl) or oxo.

R$^C$ is either
  i) a ring C; or
  ii) is selected from halogen, —CN, C$_{1-6}$ alkyl, —(C$_{1-6}$ alkyl)-R$^N$, —COR$^7$, —C(O)OR$^7$, —C(O)N(R$^7$)$_2$, —N(R$^7$)C(O)R$^7$, —N(R$^7$)C(O)OR$^7$, —N(R$^7$)C(O)N(R$^7$)$_2$, —N(R$^7$)$_2$, —SO$_2$R$^7$, —SO$_2$N(R$^7$)$_2$, —C(O)N(R$^7$)SO$_2$R$^7$, —SO$_2$N(R$^7$)COOR$^7$, —SO$_2$N(R$^7$)C(O)R$^7$ or —N(R$^7$)SO$_2$R$^7$; wherein each said C$_{1-6}$ alkyl, each C$_{1-6}$ alkyl portion of said —(C$_{1-6}$ alkyl)-R$^N$, is optionally and independently substituted with up to 6 instances of fluoro and up to 2 instances of —CN, —OR$^8$, oxo, —N(R$^8$)$_2$, —N(R$^8$)C(O)R$^8$, —N(R$^8$)C(O)OR$^8$, —N(R$^8$)C(O)N(R$^8$)$_2$, —SO$_2$R$^8$, —SO$_2$N(R$^8$)$_2$, —NHOR$^8$, —SO$_2$N(R$^8$)COOR$^8$, —SO$_2$N(R$^8$)C(O)R$^8$, —N(R$^8$)SO$_2$R$^8$;

wherein each R$^7$ is independently selected from hydrogen, C$_{1-6}$ alkyl, C$_{1-6}$ fluoroalkyl, a C$_{3-8}$ cycloalkyl ring, phenyl, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

each R$^8$ is independently selected from hydrogen, C$_{1-6}$ alkyl, C$_{1-6}$ fluoroalkyl, a C$_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$haloalkyl) or oxo each R$^N$ is independently selected from a phenyl ring, a monocyclic 5 or 6-membered heteroaryl ring, a monocyclic C$_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic C$_{3-6}$ cycloaliphatic ring, or said monocyclic 4 to 6-membered heterocycle is optionally and independently substituted with up to 6 instances of fluoro and/or up to 3 instances of J$^M$;

each J$^M$ is independently selected from —CN, a C$_{1-6}$ aliphatic, —OR$^M$, —SR$^M$, —N(R$^M$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of R$^{7c}$;

each R$^M$ is independently selected from hydrogen, a C$_{1-6}$ aliphatic, a C$_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to p instances of J$^{C_1}$; wherein p is 0 or an integer selected from 1 to 3.

each J$^{C_1}$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of R$^{7d}$; or alternatively, two J$^{C_1}$ groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O or S;

each R$^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocyclic ring contains between 1 and 3 heteroatoms independently selected from O, N or S; alternatively, two instances of R$^H$ linked to the same nitrogen atom of —N(R$^H$)$_2$, together with said nitrogen atom of —N(R$^H$)$_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S;

each R$^{7c}$ is independently selected from hydrogen, halogen, —CN, —NO$_2$, C$_{1-4}$ alkyl, C$_{1-4}$ haloalkyl, C$_{3-8}$ cycloalkyl ring, —OR$^{8b}$, —SR$^{8b}$, —N(R$^{8b}$)$_2$, —C(O)O(C$_{1-4}$ alkyl), —C(O)OH, —NR(CO)CO(C$_{1-4}$ alkyl) or an oxo group; wherein each said cycloalkyl group is optionally and independently substituted with up to 3 instances of halogen;

each R$^{7d}$ is independently selected from hydrogen, halogen, —CN, —NO$_2$, C$_{1-4}$ alkyl, C$_{1-4}$ haloalkyl, C$_{3-8}$ cycloalkyl ring, —OR$^{8c}$, —SR$^{8c}$, —N(R$^{8c}$)$_2$, or an oxo group; wherein each said cycloalkyl group is optionally and independently substituted with up to 3 instances of halogen;

each R$^{8b}$ is independently selected from hydrogen, C$_{1-6}$ alkyl, C$_{1-6}$ fluoroalkyl, a C$_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

each R$^{8c}$ is independently selected from hydrogen, C$_{1-6}$ alkyl, C$_{1-6}$ fluoroalkyl, a C$_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

provided that the compound is not a compound depicted below:

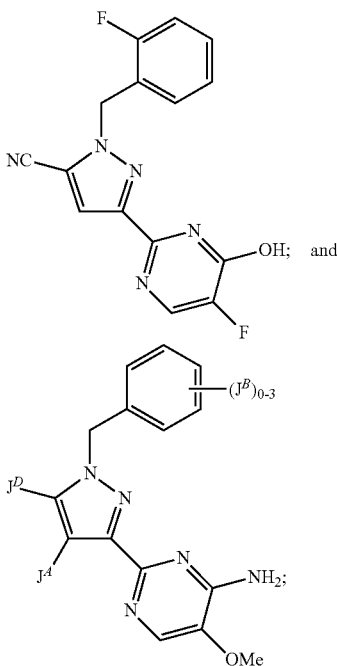

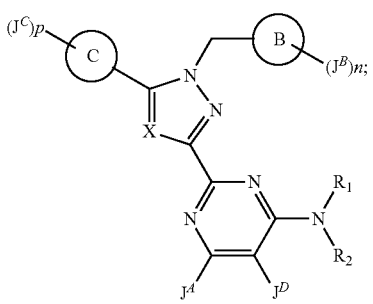

wherein $J^D$ is either an ethylene or —N(Me)$_2$; $J^A$ is either hydrogen or methyl; and $J^B$ is either fluoro or C$_{1-2}$ alkoxy.

The present invention is also directed to compounds according to Formula I, or pharmaceutically acceptable salts thereof, Formula I wherein:

X is selected from N, CH, C(C$_{1-4}$ alkyl), C(C$_{1-4}$ haloalkyl), CCl and CF;

ring B is a phenyl or a 6-membered heteroaryl ring containing 1 or 2 ring nitrogen atoms, or ring B is a thiophene;

n is 0 or an integer selected from 1 to 3;

each $J^B$ is independently selected from halogen, —CN, a C$_{1-6}$ aliphatic, —OR$^B$ or a C$_{3-8}$ cycloaliphatic ring; wherein each of said C$_{1-6}$ aliphatic and each of said C$_{3-8}$ cycloaliphatic group is optionally substituted with up to 3 instances of halogen;

each R$^B$ is independently selected from hydrogen, a C$_{1-6}$ aliphatic or a C$_{3-8}$ cycloaliphatic ring; wherein each of said R$^B$ that is a C$_{1-6}$ aliphatic and each of said R$^B$ that is a C$_{3-8}$ cycloaliphatic ring is optionally substituted with up to 3 instances of halogen;

$J^A$ is selected from hydrogen, halogen, methyl, methoxy, trifluoromethyl, trifluoromethoxy or —NR$^a$R$^b$, wherein R$^a$ and R$^b$ are each independently selected from hydrogen, C$_{1-6}$ alkyl or a 3-6 cycloalkyl ring;

$J^D$ is absent or selected from halogen, —CN, —CF$_3$, methoxy, trifluoromethoxy, nitro, amino or methyl;

R$^1$ and R$^2$, together with the nitrogen atom to which they are attached, form a 4 to 8-membered heterocyclic ring or 5 or 6-membered heteroaryl ring; wherein said 4 to 8-membered heterocyclic ring or 5 or 6-membered heteroaryl ring optionally contains in addition to the nitrogen atom up to 3 ring heteroatoms independently selected from N, O or S, and is optionally substituted by up to 5 instances of R$^5$; or alternatively, R$^1$ and R$^2$ are each independently selected from hydrogen, C$_{1-6}$ alkyl, a C$_{3-8}$ cycloalkyl ring, a 4 to 8-membered heterocyclic ring, a 5 or 6-membered heteroaryl or a C$_{1-6}$ alkyl-R$^Y$; wherein each of said 4 to 8-membered heterocyclic ring and each of said 5 or 6-membered heteroaryl ring contains up to 3 ring heteroatoms independently selected from N, O and S; and wherein each of said C$_{1-6}$ alkyl, C$_{3-8}$ cycloalkyl ring, 4 to 8-membered heterocyclic ring group, 5 or 6-membered heteroaryl and the C$_{1-6}$ alkyl portion of said C$_{1-6}$ alkyl-R$^Y$ is optionally and independently substituted with up to 5 instances of R$^{5a}$; provided that R$^1$ and R$^2$ are never simultaneously hydrogen; and provided than when X is one of CH, C(C$_{1-4}$ alkyl), C(C$_{1-4}$ haloalkyl), CCl or CF, one of R$^1$ and R$^2$ is not a pyridine or a pyrimidine; or alternatively, $J^D$ and one of R$^1$ or R$^2$ can form a 5-6 membered heterocyclic ring containing up to two heteroatoms selected from O, N and S and optionally substituted with up to 3 instances of oxo or —(Y)—R$^9$;

wherein Y is either absent or is a linkage in the form of a C$_{1-6}$ alkyl chain, optionally substituted with up to 6 instances of fluoro;

each R$^9$ is independently selected from hydrogen, fluoro, —CN, —OR$^{10}$, —SR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, a C$_{3-6}$ cycloalkyl ring, a 4-8-membered heterocyclic ring or a 5-6 membered heteroaryl ring; wherein each said 4 to 8-membered heterocyclic ring or 5 to 6-membered heteroaromatic ring contains up to 4 ring heteroatoms independently selected from N, O or S; and wherein each of said C$_{3-6}$ cycloalkyl rings, each of said 4 to 8-membered heterocyclic rings and each of said 5 to 6-membered heteroaromatic rings is optionally substituted with up to 3 instances of R$^{11}$;

each R$^{11}$ is independently selected from halogen, C$_{1-6}$ alkyl, —CN, —OR$^{12}$, —SR$^{12}$, —COR$^{12}$, —OC(O)R$^{12}$, —C(O)OR$^{12}$, —C(O)N(R$^{12}$)$_2$, —C(O)N(R$^{12}$)SO$_2$R$^{12}$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$, —SO$_2$N(R$^{12}$)COOR$^{12}$, —SO$_2$N(R$^{12}$)C(O)R$^{12}$, —N(R$^{12}$)SO$_2$R$^{12}$ and —N=OR$^{12}$; wherein each of said C$_{1-6}$ alkyl is optionally and independently substituted by up to 3 instances of fluoro, —OH, —O(C$_{1-4}$ alkyl), phenyl and —O(C$_{1-4}$ fluoroalkyl)

wherein each R$^{10}$ is independently selected from hydrogen, a C$_{1-6}$ alkyl, phenyl, benzyl, a C$_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said C$_{1-6}$ alkyl, each said phenyl, each said benzyl, each said C$_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo; and wherein each $R^{12}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo;

$R^Y$ is selected from a $C_{3-8}$ cycloalkyl ring, a 4 to 8-membered heterocyclic ring, phenyl, or a 5 to 6-membered heteroaromatic ring; wherein each of said 4 to 8-membered heterocyclic ring or 5 to 6-membered heteroaromatic ring contains up to 4 ring heteroatoms independently selected from N, O or S; and wherein each of said $C_{3-8}$ cycloalkyl ring, each of said 4 to 8-membered heterocyclic ring, each of said phenyl, and each of said 5 to 6-membered heteroaromatic ring is optionally substituted with up to 5 instances of $R^{5c}$;

each $R^{5c}$ is independently selected from halogen, —CN, $C_{1-6}$ alkyl, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo; or two instances of $R^{5c}$ attached to the same or different ring atoms of $R^Y$, together with said ring atom or atoms, may form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said $C_{3-8}$ cycloalkyl ring, 4 to 6-membered heterocyclic ring, phenyl or a 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR"(CO)CO($C_{1-4}$ alkyl), —OH or halogen; wherein R" is hydrogen or a $C_{1-2}$ alkyl;

each $R^{5a}$ is independently selected from halogen, —CN, $C_{1-6}$ alkyl, —OR$^{6a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$N(R$^{6a}$)$_2$, —SO$_2$N(R$^{6a}$)COOR$^{6a}$, —SO$_2$N(R$^{6a}$)C(O)$_R{}^{6a}$, —N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S; or when one of $R^1$ or $R^2$ is the $C_{3-8}$ cycloalkyl ring, 4 to 8-membered heterocyclic ring or 5 or 6-membered heteroaryl substituted with up to 5 instances of $R^{5a}$, two of the instances of $R^{5a}$ attached to the same or different ring atoms of said $R^1$ or $R^2$, together with said atom or atoms, may optionally form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)CO($C_{1-4}$ alkyl), —NR'(CO)CO($C_{1-4}$ alkyl) or halogen; wherein R' is hydrogen or a $C_{1-2}$ alkyl;

each $R^5$ is independently selected from halogen, —CN, $C_{1-6}$ alkyl, —$OR^6$, —$SR^6$, —$COR^6$, —OC(O)$R^6$, —C(O)$OR^6$, —C(O)N($R^6$)$_2$, —C(O)N($R^6$)SO$_2R^6$, —N($R^6$)C(O)$R^6$, —N($R^6$)C(O)$OR^6$, —N($R^6$)C(O)N($R^6$)$_2$, —N($R^6$)$_2$, —SO$_2R^6$, —SO$_2$N($R^6$)$_2$, —SO$_2$N($R^6$)COO$R^6$, —SO$_2$N($R^6$)C(O)$R^6$, —N($R^6$)SO$_2R^6$, —(C=O)NHO$R^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^6$ is independently selected from hydrogen, a $C_{1-6}$ alkyl, phenyl, benzyl, a $C_{3-8}$ cycloalkyl ring or a 4 to 7-membered heterocyclic ring, a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; or when $R^1$ and $R^2$ attached to the nitrogen atom form the 4 to 8-membered heterocyclic ring or 5 or 6-membered heteroaryl ring substituted with up to 5 instances of $R^5$, two of the instances of $R^5$ attached to the same or different atoms of said ring, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen; wherein R is hydrogen or a $C_{1-2}$ alkyl;

p is an integer selected from 0, 1 or 2;

ring C is a monocyclic 5-membered heteroaryl ring containing up to 4 ring heteroatoms selected from N, O or S; wherein said monocyclic 5-membered heteroaryl ring is not a 1,3,5-triazinyl ring;

each $J^C$ is independently selected from halogen or a $C_{1-4}$ aliphatic optionally and independently substituted by up to 3 instances of $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen.

The invention is also directed to a pharmaceutical composition comprising a compound according to Formula I or Formula I', or a pharmaceutically acceptable salt thereof, and at least one pharmaceutically acceptable excipient or carrier. The invention is also directed to a pharmaceutical formulation or dosage form comprising the pharmaceutical composition.

The invention also provides a method of treating or preventing a disease, health condition or disorder in a subject in need thereof, comprising administering, alone or in combination therapy, a therapeutically effective amount of a compound of Formula I or Formula I' or a pharmaceutically acceptable salt thereof to the subject; wherein the disease, health condition or disorder is a peripheral, pulmonary, hepatic, kidney, cardiac or cerebral vascular/endothelial disorder or condition, a urogenital-gynecological or sexual disorder or condition, a thromboembolic disease, a fibrotic disorder, a pulmonary or respiratory disorder, renal or hepatic disorder, ocular disorder, hearing disorder, CNS disorder, circulation disorder, topical or skin disorder, metabolic disorder, atherosclerosis, wound healing or a lipid related disorder that benefits from sGC stimulation or from an increase in the concentration of NO or cGMP.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

DEFINITIONS AND GENERAL TERMINOLOGY

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

As described herein, compounds of Formula I may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal to or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, relevant knowledge of the art.

A compound, such as the compounds of Formula I or other compounds herein disclosed, may be present in its free form (e.g. an amorphous form, or a crystalline form or a polymorph). Under certain conditions, compounds may also form co-forms. As used herein, the term co-form is synonymous with the term multi-component crystalline form. When one of the components in the co-form has clearly transferred a proton to the other component, the resulting co-form is referred to as a "salt". The formation of a salt is determined by how large the difference is in the pKas between the partners that form the mixture. For purposes of this disclosure, compounds include pharmaceutically acceptable salts, even if the term "pharmaceutically acceptable salts" is not explicitly noted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention. As an example, a substituent drawn as below:

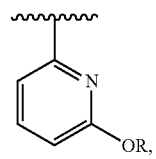

wherein R may be hydrogen, would include both compounds shown below:

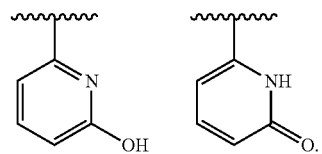 [SMILES: *c1cccc(O)n1 ; *c1cccc(=O)[nH]1]

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. To be perfectly clear, the term "aliphatic chain" may be used interchangeably with the term "aliphatic" or "aliphatic group".

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, $sp^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term can be used in the phrase "aromatic carbocycle", and in this case it refers to an "aryl group" as defined below.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_3$-$C_{12}$ hydrocarbon or a bicyclic $C_7$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Cycloalkyl", as used herein, refers to a ring system in which is completely saturated and which has a single point of attachment to the rest of the molecule. Unless otherwise specified, a cycloalkyl group may be monocyclic, bicyclic, tricyclic, fused, spiro or bridged. In one embodiment, the term "cycloalkyl" refers to a monocyclic $C_3$-$C_{12}$ saturated hydrocarbon or a bicyclic $C_7$-$C_{12}$ saturated hydrocarbon. In some embodiments, any individual ring in a bicyclic or tricyclic ring system has 3-7 members. Suitable cycloalkyl groups include, but are not limited to cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like.

"Heterocycle" (or "heterocyclyl" or "heterocyclic), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is on the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "aralkyl" refers to a radical having an aryl ring substituted with an alkylene group, wherein the open end of the alkylene group allows the aralkyl radical to bond to another part of the compound of Formula I. The alkylene group is a bivalent, straight-chain or branched, saturated hydrocarbon group. As used herein, the term "$C_{7-12}$ aralkyl" means an aralkyl radical wherein the total number of carbon atoms in the aryl ring and the alkylene group combined is 7 to 12. Examples of "aralkyl" include, but not limited to, a phenyl ring substituted by a $C_{1-6}$ alkylene group, e.g., benzyl and phenylethyl, and a naphthyl group substituted by a $C_{1-2}$ alkylene group.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6, 5 heteroaromatic system, as used herein, for example, is a six membered heteroaromatic ring fused to a second five membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to an atom or a chain of atoms connecting two different parts of a molecule. The two atoms that are connected through the bridge (usually but not always, two tertiary carbon atoms) are referred to as "bridgeheads". In addition to the bridge, the two bridgeheads are connected by at least two individual atoms or chains of atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. "Spiro" bicyclic ring systems share only one ring atom (usually a quaternary carbon atom) between the two rings.

The term "ring atom" refers to an atom such as C, N, O or S that is part of the ring of an aromatic ring, a cycloaliphatic ring, a heterocyclic or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR$^+$ (as in N-substituted pyrrolidinyl).

In some embodiments, two independent occurrences of a variable may be taken together with the atom(s) to which each variable is bound to form a 5-8-membered, heterocyclyl, aryl, or heteroaryl ring or a 3-8-membered cycloaliphatic ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, cycloaliphatic or aryl ring, wherein the group is attached to the rest of the molecule by a single point of attachment; and b) two independent occurrences of a substituent that are bound to different atoms and are taken together with both of those atoms to form a heterocyclyl, heteroaryl, cycloaliphatic or aryl ring, wherein the ring that is formed has two points of attachment with the rest of the molecule. For example, where a phenyl group is substituted with two occurrences of —OR$^o$ as in Formula D1:

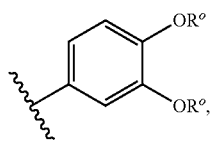

D₁ these two occurrences of —OR° are taken together with the carbon atoms to which they are bound to form a fused 6-membered oxygen containing ring as in Formula D2:

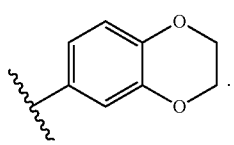

D₂

It will be appreciated that a variety of other rings can be formed when two independent occurrences of a substituent are taken together with the atom(s) to which each substituent is bound and that the examples detailed above are not intended to be limiting.

In some embodiments, an alkyl or aliphatic chain can be optionally interrupted with another atom or group. This means that a methylene unit of the alkyl or aliphatic chain can optionally be replaced with said other atom or group. Unless otherwise specified, the optional replacements form a chemically stable compound. Optional interruptions can occur both within the chain and/or at either end of the chain; i.e. both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to an H on the terminal end. For example, if —CH₂CH₂CH₃ were optionally interrupted with —O—, the resulting compound could be —OCH₂CH₃, —CH₂OCH₃, or —CH₂CH₂OH. In another example, if the divalent linker —CH₂CH₂CH₂— were optionally interrupted with —O—, the resulting compound could be —OCH₂CH₂—, —CH₂OCH₂—, or —CH₂CH₂O—. The optional replacements can also completely replace all of the carbon atoms in a chain. For example, a C₃ aliphatic can be optionally replaced by —N(R')—, —C(O)—, and —N(R')— to form —N(R')C(O)N(R')— (a urea).

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R^XO(O)C-alkyl is an example of a carboxy group used terminally. A group is internal when the group is present in the middle of a substituent at the end of the substituent bound to the rest of the chemical structure. Alkylcarboxy (e.g., alkyl-C(O)O— or alkyl-O(CO)—) and alkylcarboxyaryl (e.g., alkyl-C(O)O-aryl- or alkyl-O(CO)-aryl-) are examples of carboxy groups used internally.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

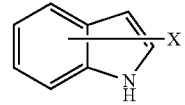

D₃

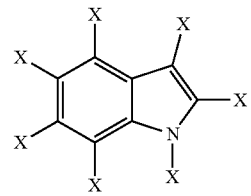

D₄

This also applies to multiple ring systems fused to optional ring systems (which would be represented by dotted lines). For example, in Formula D5, X is an optional substituent both for ring A and ring B.

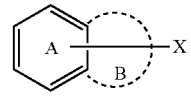

D₅

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

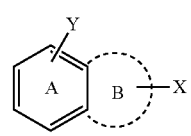

D₆

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

The terms $C_{n-m}$ "alkoxyalkyl", $C_{n-m}$ "alkoxyalkenyl", $C_{n-m}$ "alkoxyaliphatic", and $C_{n-m}$ "alkoxyalkoxy" mean alkyl, alkenyl, aliphatic or alkoxy, as the case may be, substituted with one or more alkoxy groups, wherein the combined total number of carbons of the alkyl and alkoxy groups, alkenyl and alkoxy groups, aliphatic and alkoxy groups or alkoxy and alkoxy groups, combined, as the case may be, is between the values of n and m. For example, a $C_{4-6}$ alkoxyalkyl has a total of 4-6 carbons divided between the alkyl and alkoxy portion; e.g. it can be —CH$_2$OCH$_2$CH$_2$CH$_3$, —CH$_2$CH$_2$OCH$_2$CH$_3$ or —CH$_2$CH$_2$CH$_2$OCH$_3$.

When the moieties described in the preceding paragraph are optionally substituted, they can be substituted in either or both of the portions on either side of the oxygen or sulfur. For example, an optionally substituted C$_4$ alkoxyalkyl could be, for instance, —CH$_2$CH$_2$OCH$_2$(Me)CH$_3$ or —CH$_2$(OH)O CH$_2$CH$_2$CH$_3$; a C$_5$ alkoxyalkenyl could be, for instance, —CH=CHO CH$_2$CH$_2$CH$_3$ or —CH=CHCH$_2$OCH$_2$CH$_3$.

The terms aryloxy, arylthio, benzyloxy or benzylthio, refer to an aryl or benzyl group attached to the molecule, or to another chain or ring, through an oxygen ("aryloxy", benzyloxy e.g., —O-Ph, —OCH$_2$Ph) or sulfur ("arylthio" e.g., —S-Ph, —S—CH$_2$Ph) atom. Further, the terms "aryloxyalkyl", "benzyloxyalkyl" "aryloxyalkenyl" and "aryloxyaliphatic" mean alkyl, alkenyl or aliphatic, as the case may be, substituted with one or more aryloxy or benzyloxy groups, as the case may be. In this case, the number of atoms for each aryl, aryloxy, alkyl, alkenyl or aliphatic will be indicated separately. Thus, a 5-6-membered aryloxy(C$_{1-4}$alkyl) is a 5-6 membered aryl ring, attached via an oxygen atom to a C$_{1-4}$ alkyl chain which, in turn, is attached to the rest of the molecule via the terminal carbon of the C$_{1-4}$ alkyl chain.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a C$_{1-3}$ haloalkyl could be —CFHCH$_2$CHF$_2$ and a C$_{1-2}$ haloalkoxy could be —OC(Br)HCHF$_2$. This term includes perfluorinated alkyl groups, such as —CF$_3$ and —CF$_2$CF$_3$.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a C$_{1-3}$ cyanoalkyl could be —C(CN)$_2$CH$_2$CH$_3$ and a C$_{1-2}$ cyanoalkenyl could be =CHC(CN)H$_2$.

As used herein, an "amino" group refers to —NH$_2$.

The terms "aminoalkyl", "aminoalkenyl", "aminoaliphatic", and "aminoalkoxy" mean alkyl, alkenyl, aliphatic or alkoxy, as the case may be, substituted with one or more amino groups. For example a C$_{1-3}$ aminoalkyl could be —CH(NH$_2$)CH$_2$CH$_2$NH$_2$ and a C$_{1-2}$ aminoalkoxy could be —OCH$_2$CH$_2$NH$_2$.

The term "hydroxyl" or "hydroxy" refers to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a C$_{1-3}$ hydroxyalkyl could be —CH$_2$(CH$_2$OH)CH$_3$ and a C$_4$ hydroxyalkoxy could be —OCH$_2$C(CH$_3$)(OH)CH$_3$.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$.

As used herein, in the context of resin chemistry (e.g. using solid resins or soluble resins or beads), the term "linker" refers to a bifunctional chemical moiety attaching a compound to a solid support or soluble support.

In all other situations, a "linker", as used herein, refers to a divalent group in which the two free valences are on different atoms (e.g. carbon or heteroatom) or are on the same atom but can be substituted by two different substituents. For example, a methylene group can be C$_1$ alkyl linker (—CH$_2$—) which can be substituted by two different groups, one for each of the free valences (e.g. as in Ph-CH$_2$-Ph, wherein methylene acts as a linker between two phenyl rings). Ethylene can be C$_2$ alkyl linker (—CH$_2$CH$_2$—) wherein the two free valences are on different atoms. The amide group, for example, can act as a linker when placed in an internal position of a chain (e.g. —CONH—). A linker can be the result of interrupting an aliphatic chain by certain functional groups or of replacing methylene units on said chain by said functional groups. E.g. a linker can be a C$_{1-6}$ aliphatic chain in which up to two methylene units are substituted by —C(O)— or —NH— (as in —CH$_2$—NH—CH$_2$—C(O)—CH$_2$— or —CH$_2$—NH—C(O)—CH$_2$—). An alternative way to define the same —CH$_2$—NH—CH$_2$—C(O)—CH$_2$— and —CH$_2$—NH—C(O)—CH$_2$— groups is as a C$_3$ alkyl chain optionally interrupted by up to two —C(O)— or —NH— moieties. Cyclic groups can also form linkers: e.g. a 1,6-cyclohexanediyl can be a linker between two R groups, as in

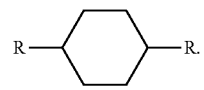

A linker can additionally be optionally substituted in any portion or position.

Divalent groups of the type R—CH= or R$_2$C=, wherein both free valences are in the same atom and are attached to the same substituent, are also possible. In this case, they will be referred to by their IUPAC accepted names. For instance an alkylidene (such as, for example, a methylidene (=CH$_2$) or an ethylidene (=CH—CH$_3$)) would not be encompassed by the definition of a linker in this disclosure.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W. et al., "Protective Groups in Organic Synthesis", Third Edition, John Wiley & Sons, New York: 1999, the entire contents of which is hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-ethyl-3-(3-dimethylaminopropyl)carbodiimide), DCC (dicyclohexylcarbodiimide), BOP (benzotriazol-1-yloxy-tris (dimethylamino)-phosphonium hexafluorophosphate), pyBOP ((benzotriazol-1-yloxy)tripyrrolidinophosphonium hexafluorophosphate), etc.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Compound Embodiments

In a first aspect the invention relates to a compound according to Formula I', or a pharmaceutically acceptable salt thereof,

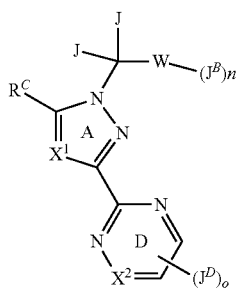

Formula I' wherein each of $X^1$ is selected from N, CH, $C(C_{1-4}$ alkyl), $C(C_{1-4}$ haloalkyl), CCl and CF;
$X^2$ is selected from N or C;
W is either:
i) absent, with $J^B$ connected directly to the carbon atom bearing two J groups, each J is independently selected from hydrogen or methyl, n is 1 and $J^B$ is a $C_{1-7}$ alkyl chain optionally substituted by up to 9 instances of fluorine; wherein, optionally, one —$CH_2$— unit of said $C_{1-7}$ alkyl chain can be replaced by —O— or —S—.
ii) a ring B that is a phenyl or a 5 or 6-membered heteroaryl ring, containing 1 or 2 ring heteroatoms selected from N, O or S; wherein with ring B being the phenyl or 5 or 6-membered heteroaryl ring; each J is hydrogen; n is an integer selected from 0 to 3; and each $J^B$ is independently selected from halogen, —CN, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$; each $R^B$ is independently selected from hydrogen, a $C_{1-6}$ aliphatic or a $C_{3-8}$ cycloaliphatic; wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;

each $R^3$ is independently selected from halogen, —CN, $C_{1-4}$ alkyl, $C_{1-4}$ haloalkyl, —$O(C_{1-4}$ alkyl) or —$O(C_{1-4}$ haloalkyl);
each $R^{3a}$ is independently selected from halogen, —CN, $C_{1-4}$ alkyl, $C_{1-4}$ haloalkyl, —$O(C_{1-4}$ alkyl) or —$O(C_{1-4}$ haloalkyl);
o is an integer selected from 1 to 3;
each $J^D$ is independently selected from $J^A$, halogen, —CN, —$NO_2$, —$OR^D$, —$SR^D$, —$C(O)R^D$, —$C(O)OR^D$, —$OC(O)R^D$, —$C(O)N(R^D)_2$, —$N(R^D)_2$, —$N(R^d)C(O)R^D$, —$N(R^d)C(O)OR^D$, —$N(R^d)C(O)N(R^D)_2$, —$OC(O)N(R^D)_2$, —$SO_2R^D$, —$SO_2N(R^D)_2$, —$N(R^d)SO_2R^D$, a $C_{1-6}$ aliphatic, —$(C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{1-6}$ aliphatic portion of the —$(C_{1-6}$ aliphatic)-$R^D$ moiety, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of $R^{5d}$;
$J^A$ is selected from hydrogen, halogen, methyl, hydroxyl, methoxy, trifluoromethyl, trifluoromethoxy or —$NR^aR^b$; wherein $R^a$ and $R^b$ are each independently selected from hydrogen, $C_{1-6}$ alkyl or a 3-6 cycloalkyl ring; or wherein $R^a$ and $R^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;
each $R^D$ is independently selected from hydrogen, a $C_{1-6}$ aliphatic, —$(C_{1-6}$ aliphatic)-$R^f$, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —$(C_{1-6}$ aliphatic)-$R^f$ moiety, each said $C_{3-8}$ cycloaliphatic ring, each said 4 to 10-membered heterocyclic ring, each said phenyl and each said 5 to 6-membered heteroaryl ring is optionally and independently substituted with up to 5 instances of $R^{5a}$; wherein when any $R^D$ is one of a $C_{1-6}$ aliphatic or a —$(C_{1-6}$ aliphatic)-$R^f$ group, one or two —$CH_2$— units that form said $C_{1-6}$ aliphatic chains may, optionally, be replaced by a group independently selected from —$N(R^d)$—, —CO— or —O—;
each $R^d$ is independently selected from hydrogen, a $C_{1-6}$ aliphatic, —$(C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —$(C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$; wherein when any $R^d$ is one of a $C_{1-6}$ aliphatic or a —$(C_{1-6}$ aliphatic)-$R^f$ group, one or two —$CH_2$— units that form said $C_{1-6}$ aliphatic chains may, optionally, be replaced by a group independently selected from —N(R$^d$)—, —CO— or —O—;
each R$^f$ is independently selected from a C$_{1-3}$ alkyl, a C$_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N or S; and wherein each said C$_{3-8}$ cycloaliphatic ring, each said 4 to 10-membered heterocyclic ring, each said phenyl and each said 5 to 6-membered heteroaryl ring is optionally and independently substituted by up to 5 instances of R$^{5c}$;

when J$^D$ is —C(O)N(R$^D$)$_2$, —N(R$^D$)$_2$, —N(R$^d$)C(O)N(R$^D$)$_2$, —OC(O)N(R$^D$)$_2$ or —SO$_2$N(R$^D$)$_2$, the two R$^D$ groups together with the nitrogen atom attached to the two R$^D$ groups may form a 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O or S, in addition to the nitrogen atom to which the two R$^D$ groups are attached; and wherein each said 4 to 8-membered heterocyclic ring and each said 5-membered heteroaryl ring is optionally and independently substituted by up to 5 instances of R$^5$;

when J$^D$ is —N(R$^d$)C(O)R$^D$, the R$^D$ group together with the carbon atom attached to the R$^D$ group, with the nitrogen atom attached to the R$^d$ group, and with the R$^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, in addition to the nitrogen atom to which the R$^d$ group is attached; and wherein each said 4 to 8-membered heterocyclic ring and each said 5-membered heteroaryl ring is optionally and independently substituted by up to 5 instances of R$^5$;

when J$^D$ is —N(R$^d$)C(O)OR$^D$, the R$^D$ group together with the oxygen atom attached to the R$^D$ group, with the carbon atom of the —C(O)— portion of the —N(R$^d$)C(O)OR$^D$ group, with the nitrogen atom attached to the R$^d$ group, and with said R$^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of R$^5$;

when J$^D$ is —N(R$^d$)C(O)N(R$^D$)$_2$, one of the R$^D$ groups attached to the nitrogen atom, together with said nitrogen atom, and with the N atom attached to the R$^d$ group and said R$^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of R$^5$;

when J$^D$ is —N(R$^d$)SO$_2$R$^D$, the R$^D$ group together with the sulfur atom attached to the R$^D$ group, with the nitrogen atom attached to the R$^d$ group, and with said R$^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of R$^5$;

each R$^5$ is independently selected from halogen, —CN, C$_{1-6}$ alkyl, —(C$_{1-6}$ alkyl)-R$^6$, —OR$^6$, —SR$^6$, —COR$^6$, —OC(O)R$^6$, —C(O)OR$^6$, —C(O)N(R$^6$)$_2$, —C(O)N(R$^6$)SO$_2$R$^6$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)$_2$, —SO$_2$N(R$^6$)COOR$^6$, —SO$_2$N(R$^6$)C(O)R$^6$, —N(R$^6$)SO$_2$R$^6$, —(C=O)NHOR$^6$, a C$_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, C$_{1-6}$ alkyl portion of the —(C$_{1-6}$ alkyl)-R$^6$ moiety, C$_{3-8}$ cycloalkyl ring, 4 to 7-membered heterocyclic ring, 5 or 6-membered heteroaryl ring, benzyl or phenyl group is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, C$_{1-4}$ alkyl, —OH, —NH$_2$, —NH(C$_{1-4}$ alkyl), —N(C$_{1-4}$ alkyl)$_2$, —CN, —COOH, —CONH$_2$, —COO (C$_{1-4}$ alkyl), —O(C$_{1-4}$ alkyl), —O(C$_{1-4}$ haloalkyl) or oxo;

two instances of R$^5$, attached to the same or different atoms of J$^D$, together with said atom or atoms to which they are attached, may optionally form a C$_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O or S; and wherein said C$_{3-8}$ cycloalkyl ring, 4 to 6-membered heterocyclic ring, phenyl or 5 or 6-membered heteroaryl ring is optionally and independently substituted by up to 3 instances of C$_{1-4}$ alkyl, C$_{1-4}$ haloalkyl, C$_{1-4}$ alkoxy, C$_{1-4}$ haloalkoxy, oxo, —C(O)O(C$_{1-4}$ alkyl), —C(O)OH, —NR (CO)O(C$_{1-4}$ alkyl), —CONH$_2$, —OH or halogen; wherein R is hydrogen or a C$_{1-2}$ alkyl;

each R$^{5a}$ and each R$^{5b}$ is independently selected from halogen, —CN, C$_{1-6}$ alkyl, —(C$_{1-6}$ alkyl)R$^{6a}$, —OR$^{6a}$, —SR$^{6a}$, —COR$^{6a}$, —OC(O)R$^{6a}$, —C(O)OR$^{6a}$, —C(O)N (R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$OH, —SO$_2$NHOH, —SO$_2$N(R$^{6a}$)$_2$, —SO$_2$N(R$^{6a}$)COOR$^{6a}$, —SO$_2$N(R$^{6a}$)C(O)R$^{6a}$, —N(R$^{6a}$)SO$_2$R$^{6a}$, —(C=O)NHOR$^{6a}$, a C$_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said C$_{1-6}$ alkyl, C$_{1-6}$ alkyl portion of the —(C$_{1-6}$ alkyl)R$^{6a}$ moiety, C$_{3-8}$ cycloalkyl ring, 4 to 7-membered heterocyclic ring, 5 or 6-membered heteroaryl ring, benzyl or phenyl group is optionally and independently substituted with up to 3 instances of halogen, C$_{1-4}$ alkyl, C$_{1-4}$ haloalkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$alkyl)$_2$, —CN, —COOH, —CONH$_2$, —COO($C_{1-4}$ alkyl), —O($C_{1-4}$ alkyl), —O($C_{1-4}$haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O($C_{1-4}$ alkyl), —OH or halogen; wherein R is hydrogen or a $C_{1-2}$ alkyl;

each $R^{5c}$ is independently selected from halogen, —CN, $C_{1-6}$ alkyl, —($C_{1-6}$ alkyl)-$R^{6b}$, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$OH, —SO$_2$NHOH, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5c}$ attached to the same or different atoms of $R^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each $R^{5d}$ is independently selected from halogen, —CN, $C_{1-6}$ alkyl, —($C_{1-6}$ alkyl)-$R^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)COR$^6$, —SO$_2$N(R$^6$)$_2$, —N(R$^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-$R^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5d}$ attached to the same or different atoms of $J^D$, together with said atom or atoms of $J^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each $R^6$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)$_{NH}$($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S; wherein two instances of $R^6$ linked to the same nitrogen atom of $R^5$ or $R^{5d}$, together with said nitrogen atom of $R^5$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6a}$ linked to a nitrogen atom of $R^{5a}$ or $R^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6b}$ linked to a nitrogen atom of $R^{5c}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two $J^D$ groups attached to two vicinal ring D atoms, taken together with said two vicinal ring D atoms, may form a 5 to 7-membered heterocycle or a 5-membered heteroaryl ring that is fused to ring D; wherein said 5 to 7-membered heterocycle or said 5-membered ring heteroaryl contains from 1 to 3 heteroatoms independently selected from N, O or S; and wherein said 5 to 7-membered heterocycle or said 5-membered heteroaryl ring is optionally and independently substituted by up to 3 instances of oxo or —(Y)—$R^9$; wherein Y is either absent or is a linkage in the form of a $C_{1-6}$ alkyl chain, optionally substituted by up to 6 instances of fluoro; and wherein when Y is said $C_{1-6}$ alkyl chain, up to 3 methylene units of this alkyl chain, can be replaced by a group selected from —O—, —C(O)— or —N((Y)—$R^{90}$)—, wherein i) when Y is absent, each $R^{90}$ is independently selected from hydrogen, —COR$^{10}$, —C(O)OR$^{10}$, —C(O)N(R$^{10}$)$_2$, —C(O)N(R$^{10}$)SO$_2$R$^{10}$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —(C=O)NHOR$^{10}$, $C_{3-6}$ cycloalkyl ring, a 4-8-membered heterocyclic ring, a phenyl ring or a 5-6 membered heteroaroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$; and ii) when Y is present, each $R^{90}$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^9$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^{10}$ is independently selected from hydrogen, a $C_{1-6}$ alkyl, —($C_{1-6}$ alkyl)-$R^{13}$, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of $R^{11a}$;

each $R^{13}$ is independently selected from a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of $R^{11b}$;

each $R^{11}$ is independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of $R^{12}$;

each $R^{11a}$ is independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C (O)N($R^{12}$)$_2$, —N($R^{12}$)$_2$, —SO$_2$$R^{12}$, —SO$_2$N($R^{12}$)$_2$ or —N($R^{12}$)SO$_2$$R^{12}$; wherein each of said $C_{1-6}$ alkyl is optionally and independently substituted by up to 6 instances of fluoro and/or 3 instances of $R^{12}$; and each $R^{11b}$ is independently selected from halogen, $C_{1-6}$ alkyl, oxo, —CN, —O$R^{12}$, —CO$R^{12}$, —C(O)O$R^{12}$, —C(O)N($R^{12}$)$_2$, —N($R^{12}$)C(O)$R^{12}$, —N($R^{12}$)C(O)O$R^{12}$, —N($R^{12}$)C(O)N($R^{12}$)$_2$, —N($R^{12}$)$_2$, —SO$_2$$R^{12}$, —SO$_2$N($R^{12}$)$_2$ or —N($R^{12}$)SO$_2$$R^{12}$; wherein each of said $C_{1-6}$ alkyl is optionally and independently substituted by up to 6 instances of fluoro and/or 3 instances of $R^{12}$;

each $R^{12}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ fluoroalkyl) or oxo.

$R^C$ is either i) a ring C; or ii) is selected from halogen, —CN, $C_{1-6}$ alkyl, —($C_{1-6}$ alkyl)-$R^N$, —CO$R^7$, —C(O)O$R^7$, —C(O)N($R^7$)$_2$, —N($R^7$)C(O)$R^7$, —N($R^7$)C(O)O$R^7$, —N($R^7$)C(O)N($R^7$)$_2$, —N($R^7$)$_2$, —SO$_2$$R^7$, —SO$_2$N($R^7$)$_2$, —C(O)N($R^7$)SO$_2$$R^7$, —SO$_2$N($R^7$)COO$R^7$, —SO$_2$N($R^7$)C(O)$R^7$, or —N($R^7$)SO$_2$$R^7$ or —(C═O)NHO$R^7$; wherein each said $C_{1-6}$ alkyl, each $C_{1-6}$ alkyl portion of said —($C_{1-6}$ alkyl)-$R^N$, is optionally and independently substituted with up to 6 instances of fluoro and up to 2 instances of —CN, —O$R^8$, oxo, —N($R^8$)$_2$, —N($R^8$)C(O)$R^8$, —N($R^8$)C(O)O$R^8$, —N($R^8$)C(O)N($R^8$)$_2$, —SO$_2$$R^8$, —SO$_2$N($R^8$)$_2$, —NHO$R^8$, —SO$_2$N($R^8$)COO$R^8$, —SO$_2$N($R^8$)C(O)$R^8$, —N($R^8$)SO$_2$$R^8$;

wherein each $R^7$ is independently selected from hydrogen, $C_{1-6}$ alkyl, $C_{1-6}$ fluoroalkyl, a $C_{3-8}$ cycloalkyl ring, phenyl, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^8$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^N$ is independently selected from a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$;

each $J^M$ is independently selected from —CN, a $C_{1-6}$ aliphatic, —O$R^M$, —S$R^M$, —N($R^M$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7c}$;

each $R^M$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to p instances of $J^{Ct}$; wherein p is 0 or an integer selected from 1 to 3;

each $J^{Ct}$ is independently selected from halogen, —CN, —NO$_2$, a $C_{1-6}$ aliphatic, —O$R^H$, —S$R^H$, —N($R^H$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7d}$; or alternatively, two $J^{Ct}$ groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; alternatively, two instances of $R^H$ linked to the same nitrogen atom of —N($R^H$)$_2$, together with said nitrogen atom of —N($R^H$)$_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S;

each $R^{7c}$ is independently selected from hydrogen, halogen, —CN, —NO$_2$, C$_{1-4}$ alkyl, C$_{1-4}$ haloalkyl, C$_{3-8}$ cycloalkyl ring, —OR$^{8b}$, —SR$^{8b}$, —N(R$^{8b}$)$_2$, —C(O)O(C$_{1-4}$ alkyl), —C(O)OH, —NR(CO)CO(C$_{1-4}$ alkyl) or an oxo group; wherein each said cycloalkyl group is optionally and independently substituted with up to 3 instances of halogen;

each $R^{7d}$ is independently selected from hydrogen, halogen, —CN, —NO$_2$, C$_{1-4}$ alkyl, C$_{1-4}$ haloalkyl, C$_{3-8}$ cycloalkyl ring, —OR$^{8c}$, —SR$^{8c}$, —N(R$^{8c}$)$_2$, or an oxo group; wherein each said cycloalkyl group is optionally and independently substituted with up to 3 instances of halogen;

each $R^{8b}$ is independently selected from hydrogen, C$_{1-6}$ alkyl, C$_{1-6}$ fluoroalkyl, a C$_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

each $R^{8c}$ is independently selected from hydrogen, C$_{1-6}$ alkyl, C$_{1-6}$ fluoroalkyl, a C$_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

provided that the compound is not a compound depicted below:

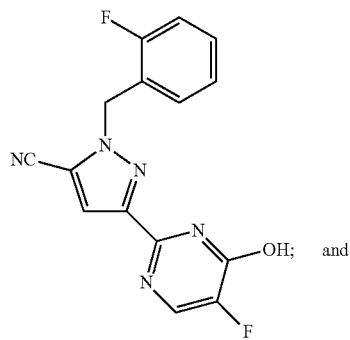

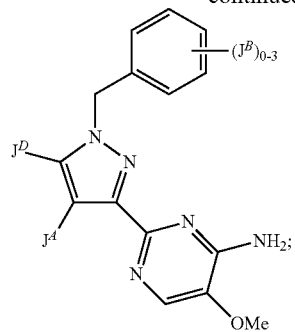

wherein $J^D$ is either an ethylene or —N(Me)$_2$; $J^A$ is either hydrogen or methyl and $J^B$ is either fluoro or C$_{1-2}$ alkoxy.

In some embodiments of the compounds of Formula I', W is absent. In some of these embodiments, wherein W is absent, the compound is represented by Formula II'a:

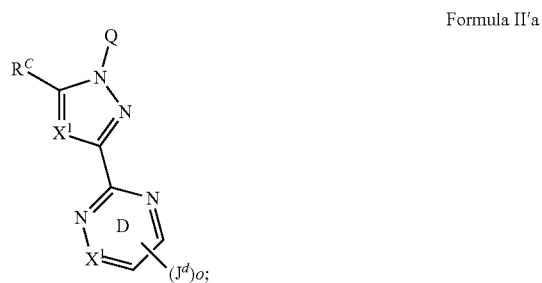

Formula II'a wherein Q represents a C$_{1-7}$ alkyl group, optionally substituted with up to 9 instances of fluorine. In other embodiments Q is substituted with up to 5 instances of fluorine.

In still other embodiments of Formula I' wherein W is absent, the compound is represented by Formula III'a:

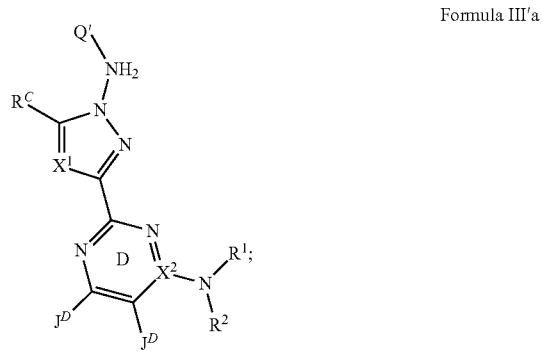

Formula III'a wherein,

Q' is a C$_{1-5}$ alkyl chain, optionally substituted by up to 6 instances of fluorine. In some of these embodiments, X$^2$ is N, and the moiety —N(R$^1$)(R$^2$) is absent. In other embodiments, X$^2$ is C, and the moiety —N(R$^1$)(R$^2$) is present. In some of these embodiments:

R$^1$ and R$^2$, together with the nitrogen atom to which they are attached, form a 4 to 8-membered heterocyclic ring or 5-membered heteroaryl ring; wherein said 4 to 8-membered heterocyclic ring or 5-membered heteroaryl ring optionally contains, in addition to the nitrogen atom to which R$^1$ and R$^2$ are attached, up to 3 ring heteroatoms independently selected from N, O or S, and is optionally substituted by up to 5 instances of $R^{5e}$;

each $R^{5e}$ is independently selected from halogen, —CN, $C_{1-6}$ alkyl, —($C_{1-4}$ alkyl)-$R^6$, a $C_{3-8}$ cycloalkyl ring, $C_{1-4}$ cyanoalkyl, —$OR^6$, —$SR^6$, —$OCOR^6$, —$COR^6$, —C(O)$OR^6$, —C(O)N($R^6$)$_2$, —N($R^6$)C(O)$R^6$, —N($R^6$)$_2$, —$SO_2R^6$, —$SO_2OH$, —$SO_2NHOH$, —$SO_2N(R^6)COR^6$, —$SO_2N(R^6)_2$, —N($R^6$)$SO_2R^6$, benzyl, phenyl or an oxo group; wherein each said phenyl ring and each said benzyl group, is optionally and independently substituted with up to 3 instances of halogen, —OH, —$NH_2$, —NH($C_{1-4}$ alkyl), —N($C_{1-4}$ alkyl)$_2$, —CN, $C_{1-4}$ alkyl, $C_{1-4}$ haloalkyl, —O($C_{1-4}$ alkyl) or —O($C_{1-4}$ haloalkyl); and wherein each said $C_{1-6}$ alkyl, each $C_{1-4}$ alkyl portion of said —($C_{1-4}$ alkyl)-$R^6$ moiety, and each said $C_{3-8}$ cycloalkyl ring is optionally and independently substituted with up to 3 instances of halogen; wherein each $R^6$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

two of the instances of $R^{5e}$ attached to the same or different atoms of said ring formed by $R^1$, $R^2$ and the nitrogen to which $R^1$ and $R^2$ are attached, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)$NH_2$, —NR(CO)O($C_{1-4}$ alkyl), —OH or halogen; wherein R is hydrogen or a $C_{1-2}$ alkyl.

In some of these embodiments, alternatively, $R^1$ and $R^2$ are each independently selected from hydrogen, $C_{1-6}$ alkyl, a $C_{3-8}$ cycloalkyl ring, a 4 to 8-membered heterocyclic ring, a 5 or 6-membered heteroaryl, phenyl or a $C_{1-6}$ alkyl-$R^Y$; wherein each of said 4 to 8-membered heterocyclic ring and each of said 5 or 6-membered heteroaryl ring contains up to 3 ring heteroatoms independently selected from N, O and S; and wherein each of said $C_{1-6}$ alkyl, $C_{1-6}$ alkyl portion of each said $C_{1-6}$ alkyl-$R^Y$ moiety, $C_{3-8}$ cycloalkyl, 4 to 8-membered heterocyclic ring group, 5 or 6-membered heteroaryl, phenyl and $C_{1-6}$ alkyl-$R^Y$ is optionally and independently substituted with up to 5 instances of $R^{5f}$;

$R^Y$ is selected from a $C_{3-8}$ cycloalkyl ring, a 4 to 8-membered heterocyclic ring, phenyl, or a 5 to 6-membered heteroaryl ring; wherein each of said 4 to 8-membered heterocyclic ring or 5 to 6-membered heteroaromatic ring contains between 1 and 4 ring heteroatoms independently selected from N, O or S; and wherein each of said $C_{3-8}$ cycloalkyl ring, each of said 4 to 8-membered heterocyclic ring, each of said phenyl, and each of said 5 to 6-membered heteroaryl ring is optionally substituted with up to 5 instances of $R^{5g}$;

each $R^{5f}$ is independently selected from halogen, —CN, $C_{1-6}$ alkyl, —($C_{1-4}$ alkyl)-$R^{6a}$, a $C_{7-12}$ aralkyl, $C_{3-8}$ cycloalkyl ring, $C_{1-4}$ cyanoalkyl, —$OR^{6a}$, —$SR^{6a}$, —$OCOR^{6a}$, —$COR^{6a}$, —C(O)$OR^{6a}$, —C(O)N($R^{6a}$)$_2$, —N($R^{6a}$)C(O)$R^{6a}$, —N($R^{6a}$)$_2$, —$SO_2R^{6a}$, —$SO_2N(R^{6a})_2$, —N($R^{6a}$)$SO_2R^{6a}$, —$SO_2OH$, —$SO_2NHOH$, —$SO_2N(R^{6a})COR^{6a}$, phenyl or an oxo group; wherein each said phenyl group is optionally and independently substituted with up to 3 instances of halogen, —OH, —$NH_2$, —NH($C_{1-4}$ alkyl), —N($C_{1-4}$ alkyl)$_2$, —$NO_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl, $C_{1-6}$ alkyl, $C_{1-4}$ alkyl portion of each said —($C_{1-4}$ alkyl)-$R^{6a}$ and each said $C_{3-8}$ cycloalkyl group is optionally and independently substituted with up to three instances of halogen;

each $R^{6a}$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

each $R^{5g}$ is independently selected from halogen, —CN, $C_{1-6}$ alkyl, —($C_{1-4}$ alkyl)-$R^{6b}$, a benzyl, $C_{3-8}$ cycloalkyl ring, $C_{1-4}$ cyanoalkyl, —$OR^{6b}$, —$SR^{6b}$, —$OCOR^{6b}$, —$COR^{6b}$, —C(O)$OR^{6b}$, —C(O)N($R^{6b}$)$_2$, —N($R^{6b}$)C(O)$R^{6b}$, —N($R^{6b}$)$_2$, —$SO_2R^{6b}$, —$SO_2N(R^{6b})_2$, —N($R^{6b}$)$SO_2R^{6b}$, —$SO_2OH$, —$SO_2NHOH$, —$SO_2N(R^{6b})COR^{6b}$, phenyl or an oxo group; wherein each said phenyl and each said benzyl group is optionally and independently substituted with up to 3 instances of halogen, —OH, —$NH_2$, —NH($C_{1-4}$ alkyl), —N($C_{1-4}$ alkyl)$_2$, —$NO_2$, —CN, $C_{1-4}$ alkyl, $C_{1-4}$ haloalkyl, —O($C_{1-4}$ alkyl) or —O($C_{1-4}$ haloalkyl); and wherein each said $C_{1-6}$ alkyl, $C_{1-4}$ alkyl portion of each said ($C_{1-4}$ alkyl)-$R^{6b}$ moiety and each said $C_{3-8}$ cycloalkyl group is optionally and independently substituted with up to 3 instances of halogen;

each $R^{6b}$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen.

In some embodiments, alternatively, two instances of $R^{5g}$ attached to the same or different ring atoms of $R^Y$, together with said ring atom or atoms, form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)$NH_2$, —NR"(CO)O($C_{1-4}$ alkyl), —OH or halogen; and R" is hydrogen or a $C_{1-2}$ alkyl.

In those embodiments when one of $R^1$ or $R^2$ is the $C_{3-8}$ cycloalkyl ring, 4 to 8-membered heterocyclic ring or 5 or 6-membered heteroaryl substituted with up to 5 instances of $R^{5f}$, two of the instances of $R^{5f}$ attached to the same or different ring atoms of said $R^1$ or $R^2$, together with said atom or atoms, form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)O(C$_{1-4}$ alkyl), —NR'(CO)O(C$_{1-4}$ alkyl) or halogen; wherein R' is hydrogen or a C$_{1-2}$ alkyl.

In some embodiments, the two $J^D$ groups attached to two vicinal ring D atoms, taken together with said two vicinal ring D atoms, may optionally form a 5 to 6-membered heterocycle or a 5-membered heteroaryl ring that is fused to ring D; wherein said 5 to 6-membered heterocycle or said 5-membered ring heteroaryl contains from 1 to 3 heteroatoms independently selected from N, O or S; and wherein said 5 to 6-membered heterocycle or said 5-membered heteroaryl ring is optionally and independently substituted by up to 3 instances of oxo or —(Y)—R$^9$, and R$^Y$ is defined as above.

In some embodiments of the first aspect, at least one of the two instances of X$^1$ and X$^2$ is N. In other embodiments, only one instance of X$^1$ and X$^2$ is N and the other one is C. In still other embodiments, X$^2$ is C on ring D and is optionally substituted with J$^D$.

In some embodiments of the compounds of Formula I', the compound is represented by Formula IV'a:

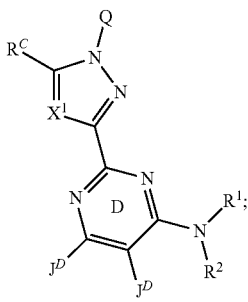

Formula IV'a $J^A$ is selected from hydrogen, halogen, methyl, hydroxyl, methoxy, trifluoromethyl, trifluoromethoxy or —NR$^a$R$^b$; in some of these embodiments, R$^a$ and R$^b$ are each independently selected from hydrogen, C$_{1-6}$ alkyl or a 3-6 cycloalkyl ring; alternatively, R$^a$ and R$^b$, together with the nitrogen atom to which they are both attached, may form a 4-8 membered heterocyclic ring or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine; J$^D$ is selected from hydrogen or fluorine; and R$^1$ and R$^2$ are as defined supra.

In other embodiments of the compounds of Formula I', the compound is represented by Formula II'b:

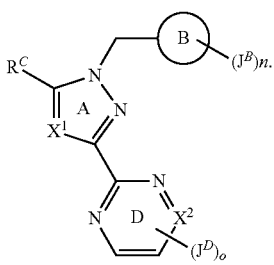

Formula II'b

In some of these embodiments, ring B is a phenyl. In other embodiments, ring B is a 5 or 6-membered heteroaryl ring, containing 1 or 2 ring heteroatoms selected from N, O or S.

In some embodiments of the compounds of Formula II'b, X$^2$ on ring D is carbon, optionally substituted by J$^D$. In other embodiments, X$^2$ on ring D is nitrogen.

In some embodiments of the compounds of Formula II'b, each J$^D$ is independently selected from J$^A$, halogen, a C$_{1-6}$ aliphatic, —N(R$^D$)$_2$, —N(R$^d$)COR$^D$, —N(R$^d$)COOR$^D$, —OR$^D$, —N(R$^d$)SO$_2$R$^D$, or an optionally substituted C$_{3-8}$ cycloaliphatic ring. In other embodiments, o is 2 and each J$^D$ is independently selected from a halogen atom or —N(R$^D$)$_2$, —N(R$^d$)COR$^D$, —OH, —N(R$^d$)COOR$^D$ or —N(R$^d$)SO$_2$R$^D$. In still other embodiments, o is 2 and one instance of J$^D$ is fluoro or chloro and the other instance of J$^D$ is —OH. In further embodiments of Formula II'b, o is 2 and one instance of J$^D$ is —NH$_2$ and the other one is independently selected from —N(R$^D$)$_2$, wherein at least one instance of R$^D$ is not hydrogen, or is —NHCOR$^D$, —N(R$^d$)COOR$^D$ or —N(R$^d$)SO$_2$R$^D$. In yet other embodiments, o is 2 and one instance of J$^D$ is independently selected from —N(R$^D$)$_2$ or —NHCOR$^D$ and the other instance of J$^D$ is selected from fluoro or chloro. In still other embodiments, o is 1 and J$^D$ is amino.

In some embodiments of the compounds of Formula I' or Formula II'b, the compound is represented by one of Formula III'b or III'c:

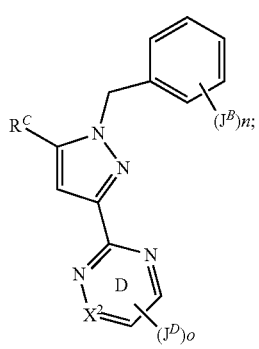

Formula III'b

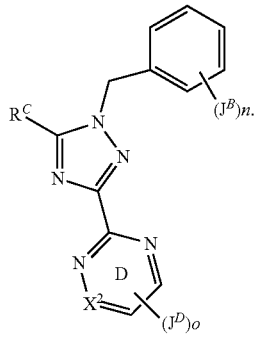

Formula III'c

In other embodiments of the compounds of Formula I' or Formula II'b, the compound is represented by Formula IV'b or Formula IV'c:

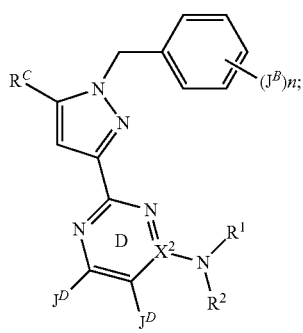

Formula IV'b

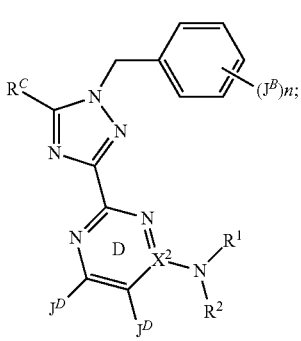

Formula IV'c

In some embodiments of the compounds of Formula IV'b or Formula IV'c, $X^2$ is nitrogen and the moiety —$NR_1R_2$ is absent. In other embodiments, $X^2$ is carbon and the moiety —$NR_1R_2$ is present.

In some embodiments of any one of the above depicted Formulae wherein W is ring B, the compound is represented by Formula V'b:

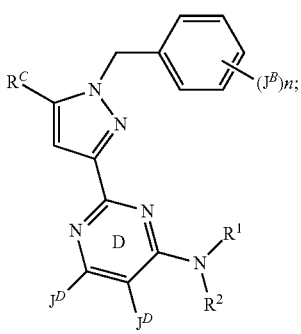

Formula V'b wherein, $J^A$ is selected from hydrogen, halogen, methyl, hydroxyl, methoxy, trifluoromethyl, trifluoromethoxy or —$NR^aR^b$; in some of these embodiments, $R^a$ and $R^b$ are each independently selected from hydrogen, $C_{1-6}$ alkyl or a 3-6 cycloalkyl ring; alternatively, in other embodiments, $R^a$ and $R^b$, together with the nitrogen atom to which they are both attached, may form a 4-8 membered heterocyclic ring or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine; and $J^D$ is either absent or is fluorine.

In some embodiments of the compounds of Formula I' or Formula II'b, ring B is phenyl. In other embodiments of the compounds of Formula I' or Formula II'b, ring B is a 6-membered heteroaryl ring. In some of these embodiments, n is an integer selected from 1, 2, or 3 and each $J^B$ is independently selected from halogen, a $C_{1-6}$ aliphatic or —$OR^B$. In other embodiments, each $J^B$ is independently selected from halogen. In other embodiments, each $J^B$ is independently selected from fluoro or chloro. In still other embodiments, $J^B$ is fluoro. In further embodiments, $J^B$ is methyl or ethyl. In yet other embodiments, n is 1. In some of these embodiments in which n is 1, $J^B$ is selected from halogen. In other embodiments, $J^B$ is fluoro or chloro. In still other embodiments, $J^B$ is fluoro.

In other embodiments of Formula I' or Formula II'b, at least one $J^B$ is ortho to the attachment of the methylene linker between ring B and ring A. In some of these embodiments in which at least one $J^B$ is ortho to the attachment of the methylene linker between ring B and ring A, the at least one $J^B$ that is ortho is independently selected from halogen. In other embodiments, the at least one $J^B$ is independently selected from fluoro or chloro. In still other embodiments, the at least one $J^B$ is fluoro. In yet other embodiments, n is 1 and the at least one $J^B$ ortho to the attachment of the methylene linker between ring B and ring A is fluoro.

In other embodiments of the compounds of Formula I' or Formula II'b, ring B is a 6-membered heteroaryl ring. In some of these embodiments, ring B is a pyridyl ring. In other embodiments, ring B is a pyrimidinyl ring.

In some embodiments of the compounds of Formula I', or Formula II'a, or Formula II'b, or Formula III'b or Formula III'c, o is an integer selected from 1, 2, and 3. In some of these embodiments in which o is selected from 1, 2, and 3, each $J^D$ is independently selected from halogen, a $C_{1-6}$ aliphatic, —$N(R^D)^2$, —$N(R^d)C(O)R^D$, —$N(R^d)C(O)OR^D$, —$N(R^d)C(O)N(R^D)_2$, —$SO_2R^D$, —$SO_2N(R^D)_2$, —$N(R^d)SO_2R^D$, —$OR^D$ or an optionally substituted $C_{3-8}$ cycloaliphatic ring.

In other embodiments of the compounds of Formula I' or Formula II'a, or Formula II'b, or Formula III'b or Formula III'c, o is 1 or 2 and each $J^D$ is independently selected from a halogen atom or —$N(R^D)_2$, —$N(R^d)COR^D$, —OH, —$N(R^d)COOR^D$, or —$N(R^d)SO_2R^D$. In some of these embodiments wherein o is 1 or 2, each $R^d$ is independently selected from hydrogen or $C_{1-4}$ alkyl. In other embodiments when o is 1 or 2, at least one instance of $J^D$ is independently selected from fluoro, chloro, oxo, hydroxyl or amino.

In some embodiments of the compounds of Formula I' or Formula II'a, the compounds is represented by one of Formulae Va or VI'a:

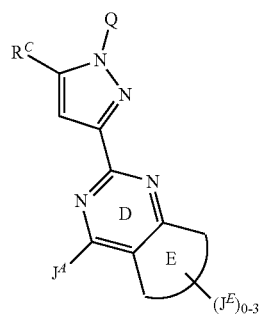

Formula V'a

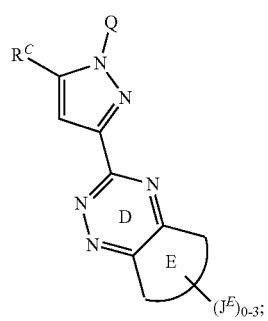

Formula VI'a wherein ring E is a 5 or 6-membered heterocyclic ring, containing up to 3 heteroatoms selected from N, O and S; and wherein each $J^E$ is independently selected from oxo or —(Y)—$R^9$.

In some of the embodiments of the compounds of Formula I' or Formula II'b, the compound is represented by one of Formulae VI'b or Formula VII'b:

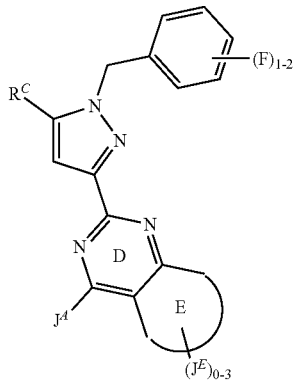

Formula VI'b

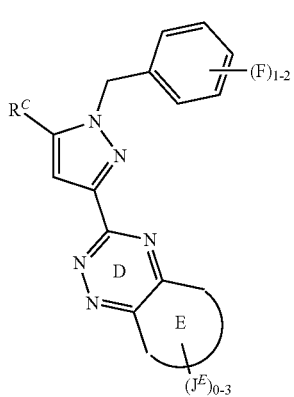

Formula VII'b wherein ring E is a 5 or 6-membered heterocyclic ring, containing up to 3 heteroatoms selected from N, O and S; and wherein each $J^E$ is independently selected from oxo or —(Y)—$R^9$.

In some of the embodiments of the compounds of Formula V'a, Formula VI'a, Formula VI'b or Formula VII'b, $J^A$ is selected from halogen, —NH$_2$, —OH, or hydrogen.

In some of the embodiments of the compounds of Formula V'a, Formula VI'a, Formula VI'b or Formula VII'b, ring E is a heterocyclic ring containing one nitrogen ring atom and at least one instance of $J^E$ is oxo. In some of these embodiments, one $J^E$ is oxo and two other instances of $J^E$ are independently selected from —(Y)—$R^9$.

In other embodiments of the compounds of Formula V'a, Formula VI'a, Formula VI'b or Formula VII'b, each —(Y)—$R^9$ is independently selected from a $C_{1-6}$ alkyl; a 5 or 6-membered heteroaryl ring containing between 1 and 3 heteroatoms independently selected from N, O or S and optionally substituted by one or more instances of $C_{1-6}$ alkyl or halogen; and —C(O)NH—$R^{10}$. In some of these embodiments, $R^{10}$ is a $C_{3-6}$ cycloalkyl ring.

In some embodiments of the compounds of Formula I' or Formula II'a, the compound is represented by FormulaVII'a:

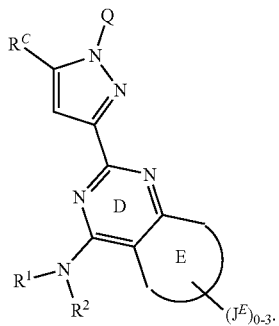

Formula VII'a

In these embodiments, ring E is a 5 or 6-membered heterocyclic ring, containing up to 3 heteroatoms selected from N, O and S; and each $J^E$ is independently selected from oxo or —(Y)—$R^9$.

In some of the compounds of Formula I' or Formula II'b, the compound is represented by FormulaVIII'b:

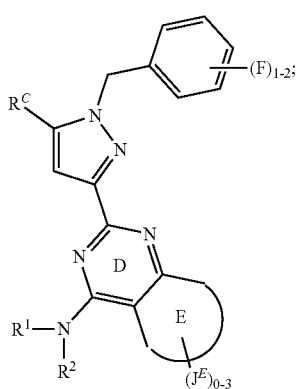

Formula VIII'b wherein ring E is a 5 or 6-membered heterocyclic ring, containing up to 3 heteroatoms selected from N, O and S; and each $J^E$ is independently selected from oxo or —(Y)—$R^9$.

In some of the embodiments of the compounds of FormulaVII'a and Formula VIII'b, one instance of $J^E$ is oxo and two other instances of $J^E$ are independently selected from $C_{1-6}$ alkyl; a 5 or 6-membered heteroaryl ring, containing between 1 and 3 heteroatoms independently selected from N, O or S and optionally substituted by one or more instances of $C_{1-6}$ alkyl or halogen; and —(CO)NH—$R^{10}$. In some of these embodiments, $R^{10}$ is a $C_{3-6}$ cycloalkyl ring.

In some of the embodiments of the compounds of Formula I' or Formula VII'a, the compound is represented by Formula VIII'a or Formula VIII'd:

Formula VIII'a

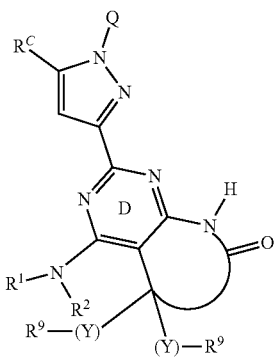

Formula VIII'd

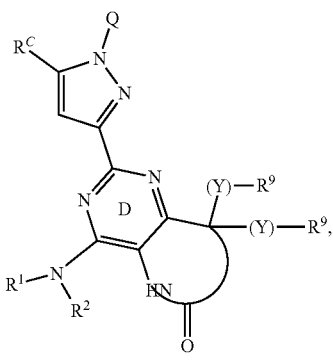

To be perfectly clear, both —(Y)—$R^9$ substituents may be attached to any of the available ring carbons, but are attached to the same carbon.

In some embodiments of the compounds of Formula I' or Formula VIII'b, the compound is represented by Formula XIX'b or Formula XIX'd:

Formula XIX'b

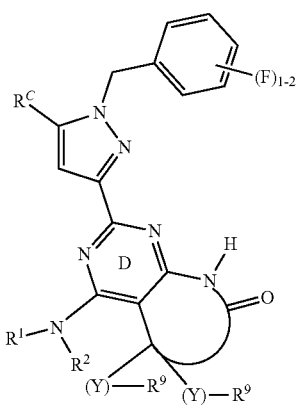

Formula XIX'd

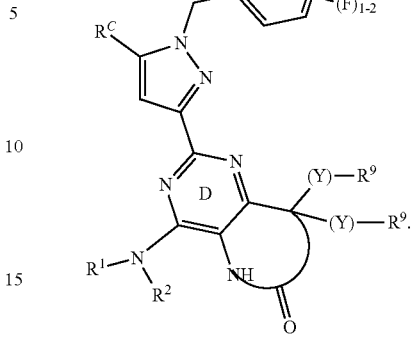

As above, both —(Y)—$R^9$ substituents may be attached to any of the available ring carbons, but are attached to the same carbon.

In some of the compounds of Formula I', the compound is represented by one of Formulae XIX'a or X'a, Formula XIX'a

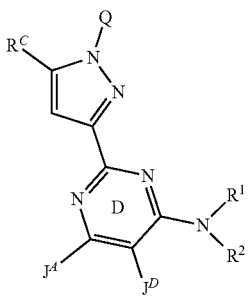

Formula X'a

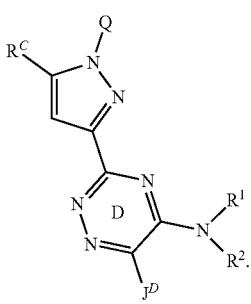

In these embodiments, each $J^A$ is independently selected from —$NH_2$ or hydrogen. In some embodiments, each $J^D$ is either absent or is halogen when $R^1$ and $R^2$ are not both hydrogen. In other embodiments, $R^1$ and $R^2$ are both simultaneously hydrogen, and each $J^D$ is independently selected from —C(O)$R^D$, —C(O)O$R^D$, —OC(O)$R^D$, —C(O)N($R^D$)$_2$, —N($R^D$)$_2$, —N($R^d$)C(O)$R^D$, —N($R^d$)C(O)O$R^D$, —N($R^d$)C(O)N($R^D$)$_2$, —OC(O)N($R^D$)$_2$, —SO$_2R^D$, —SO$_2$N($R^D$)$_2$ or —N($R^d$)SO$_2R^D$.

In some of the compounds of Formula I', the compound is represented by one of Formulae X'b or XI'b:

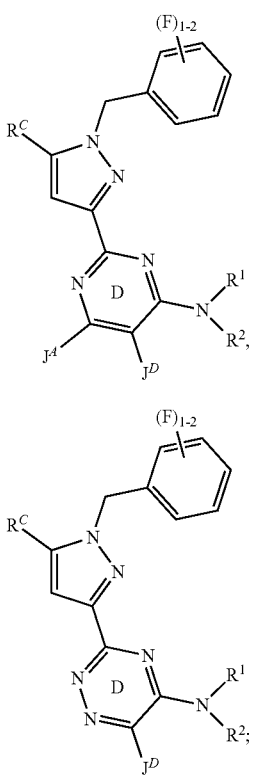

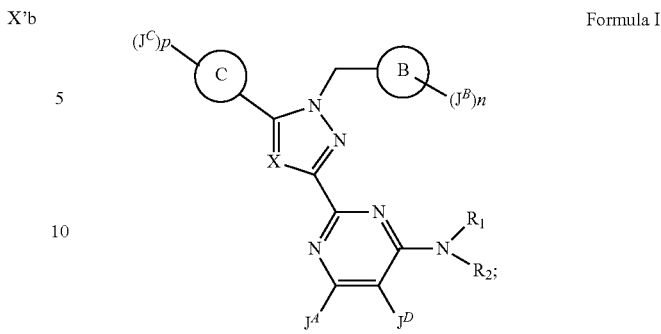

In these embodiments, each $J^A$ is independently selected from —NH$_2$ or hydrogen. In some embodiments, each $J^D$ is either absent or is halogen when $R^1$ and $R^2$ are not both hydrogen. In other embodiments, $R^1$ and $R^2$ are both simultaneously hydrogen, and each $J^D$ is independently selected from —C(O)R$^D$, —C(O)OR$^D$, —OC(O)R$^D$, —C(O)N(R$^D$)$_2$, —N(R$^D$)$_2$, —N(R$^d$)C(O)R$^D$, —N(R$^d$)C(O)OR$^D$, —N(R$^d$)C(O)N(R$^D$)$_2$, —OC(O)N(R$^D$)$_2$, —SO$_2$R$^D$, —SO$_2$N(R$^D$)$_2$ or —N(R$^d$)SO$_2$R$^D$.

In some of the embodiments of the compounds of Formula I', Formula XIX'a Formula X'a, Formula X'b, or Formula XI'b, $J^D$ is selected from —NH$_2$, —OH, and hydrogen.

In some embodiments, $R^C$ is not a ring. In some of these embodiments, $R^C$ is halogen, —CN, $C_{1-6}$ alkyl, —(C$_{1-6}$ alkyl)-R$^N$, —COOR$^7$, —COR$^7$, —C(O)OR$^7$, —C(O)N(R$^7$)$_2$, —N(R$^7$)C(O)R$^7$, —N(R$^7$)C(O)OR$^7$, —N(R$^7$)C(O)N(R$^7$)$_2$, —N(R$^7$)$_2$, —SO$_2$R$^7$, —SO$_2$N(R$^7$)$_2$, or —N(R$^7$)SO$_2$R$^7$. In some embodiments when $R^C$ is a $C_{1-6}$ alkyl or —(C$_{1-6}$ alkyl)-R$^N$, the $C_{1-6}$ alkyl or the (C$_{1-6}$ alkyl) portion of the —(C$_{1-6}$ alkyl)-R$^N$ moiety may be optionally and independently substituted with up to 6 instances of fluoro and/or up to 2 instances of R$^{7c}$. In other embodiments, $R^C$ is —CN, $C_{1-6}$ alkyl, —COR$^7$, —C(O)OR$^7$, —C(O)N(R$^7$)$_2$, —N(R$^7$)$_2$, —SO$_2$R$^7$, or —SO$_2$N(R$^7$)$_2$. In some embodiments when $R^C$ is a $C_{1-6}$ alkyl or —(C$_{1-6}$ alkyl)-R$^N$, the $C_{1-6}$ alkyl or the (C$_{1-6}$ alkyl) portion of the —(C$_{1-6}$ alkyl)-R$^N$ moiety may be optionally and independently substituted with up to 6 instances of fluoro and/or up to 2 instances of R$^{7c}$. In still other embodiments, $R^C$ is —COR$^7$, —C(O)OR$^7$, —C(O)N(R$^7$)$_2$, —N(R$^7$)$_2$, —SO$_2$R$^7$ or —SO$_2$N(R$^7$)$_2$.

In some embodiments, $R^C$ is a ring.

The present invention is further directed to compounds of Formula I, or pharmaceutically acceptable salts thereof, wherein:
X is selected from N, CH, C(C$_{1-4}$ alkyl), C(C$_{1-4}$ haloalkyl), CCl and CF;
ring B is a phenyl or a 6-membered heteroaryl ring containing 1 or 2 ring nitrogen atoms, or ring B is a thiophene;
n is 0 or an integer selected from 1 to 3;
each $J^B$ is independently selected from halogen, —CN, a $C_{1-6}$ aliphatic, —OR$^B$ or a $C_{3-8}$ cycloaliphatic ring; wherein each of said $C_{1-6}$ aliphatic and each of said $C_{3-8}$ cycloaliphatic group is optionally substituted with up to 3 instances of halogen;
each R$^B$ is independently selected from hydrogen, a $C_{1-6}$ aliphatic or a $C_{3-8}$ cycloaliphatic ring; wherein each of said R$^B$ that is a $C_{1-6}$ aliphatic and each of said R$^B$ that is a $C_{3-8}$ cycloaliphatic ring is optionally substituted with up to 3 instances of halogen;
$J^A$ is selected from hydrogen, halogen, methyl, methoxy, trifluoromethyl, trifluoromethoxy or —NR$^a$R$^b$, wherein R$^a$ and R$^b$ are each independently selected from hydrogen, $C_{1-6}$ alkyl or a 3-6 cycloalkyl ring;
$J^D$ is absent or selected from halogen, —CN, —CF$_3$, methoxy, trifluoromethoxy, nitro, amino or methyl;
$R^1$ and $R^2$, together with the nitrogen atom to which they are attached, form a 4 to 8-membered heterocyclic ring or 5 or 6-membered heteroaryl ring; wherein said 4 to 8-membered heterocyclic ring or 5 or 6-membered heteroaryl ring optionally contains in addition to the nitrogen atom up to 3 ring heteroatoms independently selected from N, O or S, and is optionally substituted by up to 5 instances of R$^5$; or
alternatively, $R^1$ and $R^2$ are each independently selected from hydrogen, $C_{1-6}$ alkyl, a $C_{3-8}$ cycloalkyl ring, a 4 to 8-membered heterocyclic ring, a 5 or 6-membered heteroaryl or a $C_{1-6}$ alkyl-R$^Y$; wherein each of said 4 to 8-membered heterocyclic ring and each of said 5 or 6-membered heteroaryl ring contains up to 3 ring heteroatoms independently selected from N, O and S; and wherein each of said $C_{1-6}$ alkyl, $C_{3-8}$ cycloalkyl ring, 4 to 8-membered heterocyclic ring group, 5 or 6-membered heteroaryl and the $C_{1-6}$ alkyl portion of said $C_{1-6}$ alkyl-R$^Y$ is optionally and independently substituted with up to 5 instances of R$^{5a}$; provided that $R^1$ and $R^2$ are never simultaneously hydrogen; or
alternatively, $J^D$ and one of $R^1$ or $R^2$ can form a 5-6 membered heterocyclic ring containing up to two heteroatoms selected from O, N and S and optionally substituted with up to 3 instances of oxo or —(Y)—R$^9$;
wherein Y is either absent or is a linkage in the form of a $C_{1-6}$ alkyl chain, optionally substituted by up to 6 instances of fluoro;
each R$^9$ is independently selected from hydrogen, fluoro, —CN, —OR$^{10}$, —SR$^{10}$, —COR$^{10}$, —OC(O)R$^{10}$, —C(O)

OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, a C$_{3-6}$ cycloalkyl ring, a 4-8-membered heterocyclic ring or a 5-6 membered heteroaroaryl ring; wherein each said 4 to 8-membered heterocyclic ring or 5 to 6-membered heteroaromatic ring contains up to 4 ring heteroatoms independently selected from N, O or S; and wherein each of said C$_{3-6}$ cycloalkyl rings, each of said 4 to 8-membered heterocyclic rings and each of said 5 to 6-membered heteroaromatic rings is optionally substituted with up to 3 instances of R$^{11}$;

each R$^{11}$ is independently selected from halogen, C$_{1-6}$ alkyl, —CN, —OR$^{12}$, —SR$^{12}$, —COR$^{12}$, —OC(O)R$^{12}$, —C(O)OR$^{12}$, —C(O)N(R$^{12}$)$_2$, —C(O)N(R$^{12}$)SO$_2$R$^{12}$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$, —SO$_2$N(R$^{12}$)COOR$^{12}$, —SO$_2$N(R$^{12}$)C(O)R$^{12}$, —N(R$^{12}$)SO$_2$R$^{12}$ and —N=OR$^{12}$; wherein each of said C$_{1-6}$ alkyl is optionally and independently substituted by up to 3 instances of fluoro, —OH, —O(C$_{1-4}$ alkyl), phenyl and —O(C$_{1-4}$ fluoroalkyl);

wherein each R$^{10}$ is independently selected from hydrogen, a C$_{1-6}$ alkyl, phenyl, benzyl, a C$_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said C$_{1-6}$ alkyl, each said phenyl, each said benzyl, each said C$_{3-8}$ cycloalkyl group, each said 4 to 7-membered heterocyclic ring and each 5 or 6-membered heteroaryl ring is optionally and independently substituted with up to 3 instances of halogen, C$_{1-4}$ alkyl, C$_{1-4}$ (fluoroalkyl), —OH, —NH$_2$, —NH(C$_{1-4}$ alkyl), alkyl)$_2$, —CN, —COOH, —COO(C$_{1-4}$ alkyl), —O(C$_{1-4}$ alkyl), —O(C$_{1-4}$ fluoroalkyl) or oxo; and wherein each R$^{12}$ is independently selected from hydrogen, a C$_{1-6}$ alkyl, phenyl, benzyl, a C$_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said C$_{1-6}$ alkyl, each said phenyl, each said benzyl, each said C$_{3-8}$ cycloalkyl group, each said 4 to 7-membered heterocyclic ring and each 5 or 6-membered heteroaryl ring is optionally and independently substituted with up to 3 instances of halogen, C$_{1-4}$ alkyl, C$_{1-4}$ (fluoroalkyl), —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$fluoroalkyl) or oxo;

R$^Y$ is selected from a C$_{3-8}$ cycloalkyl ring, a 4 to 8-membered heterocyclic ring, phenyl, or a 5 to 6-membered heteroaromatic ring; wherein each of said 4 to 8-membered heterocyclic ring or 5 to 6-membered heteroaromatic ring contains up to 4 ring heteroatoms independently selected from N, O or S; and wherein each of said C$_{3-8}$ cycloalkyl ring, each of said 4 to 8-membered heterocyclic ring, each of said phenyl, and each of said 5 to 6-membered heteroaromatic ring is optionally substituted with up to 5 instances of R$^{5c}$;

each R$^{5c}$ is independently selected from halogen, —CN, C$_{1-6}$ alkyl, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a C$_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said C$_{1-6}$ alkyl, each of said C$_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$haloalkyl) or oxo;

each R$^{6b}$ is independently selected from hydrogen, a C$_{1-6}$ alkyl, phenyl, benzyl, a C$_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said C$_{1-6}$ alkyl, each said phenyl, each said benzyl, each said C$_{3-8}$ cycloalkyl group, each said 4 to 7-membered heterocyclic ring and each 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo; or two instances of R$^{5c}$ attached to the same or different ring atoms of R$^Y$, together with said ring atom or atoms, may form a C$_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said C$_{3-8}$ cycloalkyl ring, 4 to 6-membered heterocyclic ring, phenyl or a 5 or 6-membered heteroaryl ring is optionally and independently substituted by up to 3 instances of C$_{1-4}$ alkyl, C$_{1-4}$ haloalkyl, C$_{1-4}$ alkoxy, C$_{1-4}$ haloalkoxy, oxo, —C(O)O(C$_{1-4}$ alkyl), —C(O)OH, —NR"(CO)CO(C$_{1-4}$ alkyl), —OH or halogen; wherein R" is hydrogen or a C$_{1-2}$ alkyl;

each R$^{5a}$ is independently selected from halogen, —CN, C$_{1-6}$ alkyl, —OR$^{6a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$N(R$^{6a}$)$_2$, —SO$_2$N(R$^{6a}$)COOR$^{6a}$, —SO$_2$N(R$^{6a}$)C(O)R$^{6a}$, —N(R$^{6a}$)SO$_2$R$^{6a}$, —(C=O)NHOR$^{6a}$, a C$_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S; or when one of $R^1$ or $R^2$ is the $C_{3-8}$ cycloalkyl ring, 4 to 8-membered heterocyclic ring or 5 or 6-membered heteroaryl substituted with up to 5 instances of $R^{5a}$, two of the instances of $R^{5a}$ attached to the same or different ring atoms of said $R^1$ or $R^2$, together with said atom or atoms, may optionally form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)CO($C_{1-4}$ alkyl), —NR' (CO)CO($C_{1-4}$ alkyl) or halogen; wherein R' is hydrogen or a $C_{1-2}$ alkyl;

each $R^5$ is independently selected from halogen, —CN, $C_{1-6}$ alkyl, —OR$^6$, —SR$^6$, —COR$^6$, —OC(O)R$^6$, —C(O)OR$^6$, —C(O)N(R$^6$)$_2$, —C(O)N(R$^6$)SO$_2$R$^6$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$N(R$^6$)$_2$, —SO$_2$N(R$^6$)COOR$^6$, —SO$_2$N(R$^6$)C(O)R$^6$, —N(R$^6$)SO$_2$R$^6$, —(C=O)NHOR$^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^6$ is independently selected from hydrogen, a $C_{1-6}$ alkyl, phenyl, benzyl, a $C_{3-8}$ cycloalkyl ring or a 4 to 7-membered heterocyclic ring, a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH ($C_{1-4}$ alkyl), —N($C_{1-4}$ alkyl)$_2$, —CN, —COOH, —COO ($C_{1-4}$ alkyl), —O($C_{1-4}$ alkyl), —O($C_{1-4}$ haloalkyl) or oxo; or when $R^1$ and $R^2$ attached to the nitrogen atom form the 4 to 8-membered heterocyclic ring or 5 or 6-membered heteroaryl ring substituted with up to 5 instances of $R^5$, two of the instances of $R^5$ attached to the same or different atoms of said ring, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen; wherein R is hydrogen or a $C_{1-2}$ alkyl;

p is an integer selected from 0, 1 or 2;

ring C is a monocyclic 5-membered heteroaryl ring containing up to 4 ring heteroatoms selected from N, O or S; wherein said monocyclic 5-membered heteroaryl ring is not a 1,3,5-triazinyl ring;

each $J^C$ is independently selected from halogen or a $C_{1-4}$ aliphatic optionally and independently substituted by up to 3 instances of $C_{1-4}$ alkoxy, $C_{1-4}$haloalkoxy, oxo, —C(O)O($C_{1-4}$ alkyl), —C(O)OH, —NR(CO)CO($C_{1-4}$ alkyl), —OH or halogen; or alternatively, ring C is absent, p is 1, and $J^C$ is selected from halogen, —CN, $C_{1-6}$ alkyl, —OR$^7$, —SR$^7$, —COR$^7$, —OC(O)R$^7$, —C(O)OR$^7$, —C(O)N(R$^7$)$_2$, —N(R$^7$)C(O) R$^7$, —N(R$^7$)C(O)OR$^7$, —N(R$^7$)C(O)N(R$^7$)$_2$, —N(R$^7$)$_2$, —SO$_2$R$^7$, —SO$_2$N(R$^7$)$_2$, —C(O)N(R$^7$)SO$_2$R$^7$, —SO$_2$N (R$^7$)COOR$^7$, —SO$_2$N(R$^7$)C(O)R$^7$, —N(R$^7$)SO$_2$R$^7$, —(C=O)NHOR$^7$ or an oxo group; wherein $C_{1-6}$ alkyl is optionally and independently substituted with up to 6 instances of fluoro and up to 2 instances of —CN, —OR$^8$, oxo, —N(R$^8$)$_2$, —N(R$^8$)C(O)R$^8$, —N(R$^8$)C(O)OR$^8$, —N(R$^8$)C(O)N(R$^8$)$_2$, —SO$_2$R$^8$, —SO$_2$N(R$^8$)$_2$, —NHOR$^8$, —SO$_2$N(R$^8$)COOR$^8$, —SO$_2$N(R$^8$)C(O)R$^8$, —N(R$^8$)SO$_2$R$^8$;

wherein each R$^7$ is independently selected from hydrogen, C$_{1-6}$ alkyl, C$_{1-6}$fluoroalkyl, a C$_{3-8}$ cycloalkyl ring, phenyl, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo; and wherein, each R$^8$ is independently selected from hydrogen, C$_{1-6}$ alkyl, C$_{1-6}$ fluoroalkyl, a C$_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, each of said phenyl, each of said C$_{3-8}$ cycloalkyl group, each of said 4 to 7-membered heterocyclic ring and each of said 5 or 6-membered heteroaryl ring is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo.

In some embodiments of the compounds of Formula I, or pharmaceutically acceptable salts thereof, n is an integer selected from 1 or 2 and each J$^B$ is independently selected from halogen, a C$_{1-4}$ alkyl or —OR$^B$. In other embodiments, each J$^B$ is independently selected from halogen atoms. In still other embodiments, each J$^B$ is independently selected from fluoro or chloro. In yet other embodiments, each J$^B$ is fluoro.

In some embodiments of the compounds of Formula I, or pharmaceutically acceptable salts thereof, each J$^B$ is a C$_{1-4}$ alkyl. In some of these embodiments, J$^B$ is ethyl or methyl. In some embodiments, J$^B$ is methyl.

In some embodiments of the compounds of Formula I, or pharmaceutically acceptable salts thereof, n is 1.

In some embodiments of the compounds of Formula I, or pharmaceutically acceptable salts thereof, n is 1 and each J$^B$ is independently selected from halogen, a C$_{1-4}$ alkyl or —OR$^B$. In some of these embodiments, J$^B$ is halogen. In some embodiments, J$^B$ is chloro or fluoro. In other embodiments, J$^B$ is fluoro. Alternatively, in other embodiments, J$^B$ is C$_{1-4}$ alkyl. In still other embodiments, J$^B$ is methyl or ethyl.

In some embodiments of the compounds of Formula I, or pharmaceutically acceptable salts thereof, at least one J$^B$ is ortho to the attachment of the methylene linker between ring B and the ring bearing X$^1$. In some of these embodiments, the at least one J$^B$ is independently selected from halogen atoms. In still other embodiments, each at least one J$^B$ is independently selected from fluoro or chloro. In yet other embodiments, each at least one J$^B$ is fluoro. In other embodiments, n is 1 and the J$^B$ ortho to the attachment of the methylene linker between ring B and the ring bearing X$^1$ is fluoro.

In some embodiments of the compounds of Formula I, or pharmaceutically acceptable salts thereof, n is an integer selected from 1 or 2 and each J$^B$ is independently selected from halogen, a C$_{1-4}$ alkyl or —OR$^B$, wherein at least one J$^B$ is ortho to the attachment of the methylene linker between ring B and the ring bearing X$^1$. In some of these embodiments, the halogen can be chloro or, preferably, fluoro. In other embodiments, at least one J$^B$ is halogen. Alternatively, at least one J$^B$ is a C$_{1-4}$ alkyl, e.g., methyl or ethyl. In some of these embodiments, n is 1. In some embodiments, the J$^B$ ortho to the attachment of the methylene linker between ring B and the ring bearing X$^1$ is fluoro.

In some embodiments of the compounds of Formula I, or pharmaceutically acceptable salts thereof, n is 2 and each J$^B$ is a halogen atom. In some embodiments, each J$^B$ is independently selected from chloro or fluoro. In other embodiments, one J$^B$ is fluoro and the other J$^B$ is chloro. In still other embodiments, each J$^B$ is fluoro.

In some embodiments of the compounds of Formula I, or pharmaceutically acceptable salts thereof, ring B is phenyl. In some of these embodiments, n is 1 or 2. In some of these embodiments, a J$^B$ is ortho to the attachment of the methylene linker between ring B and the ring bearing X$^1$, and the J$^B$ is halogen, e.g. chloro or, preferably, fluoro.

In some embodiments of the compounds of Formula I, or pharmaceutically acceptable salts thereof, ring B is a 6-membered heteroaryl ring or a thiophene ring. In other embodiments, ring B is a pyridyl ring. In still other embodiments, ring B is a pyrimidinyl ring. In yet other embodiments, ring B is a thiophene ring.

In some embodiments of the compounds of Formula I, or pharmaceutically acceptable salts thereof, J$^D$ is chloro, fluoro, or is absent. In some embodiments, J$^D$ is fluoro.

In some embodiments of the compounds of Formula I, or pharmaceutically acceptable salts thereof, J$^A$ is hydrogen.

In some embodiments of the compounds of Formula I, or pharmaceutically acceptable salts thereof, ring C is a monocyclic 5-membered heteroaryl ring containing 1 or 2 ring heteroatoms selected from N, O or S. In some of these embodiments, ring C is an oxazole or isoxazole ring. In some of these compounds, or pharmaceutically acceptable salts thereof, ring C is unsubstituted, and in yet other embodiments ring C is an unsubstituted oxazole or isoxazole ring.

In some embodiments of the compounds of Formula I, or pharmaceutically acceptable salts thereof, X$^1$ is N. In some of these embodiments, ring C is an oxazole or isoxazole ring. In other embodiments, ring C is unsubstituted, and in still embodiments, ring C is an unsubstituted oxazole or isoxazole ring. In some of these embodiments, ring B is phenyl. In some embodiments, J$^B$ is halogen, e.g., chloro or, preferably, fluoro. In other embodiments, there is a J$^B$ ortho to the methylene bridge between the ring bearing X$^1$ and ring B. In some of these compounds, or pharmaceutically acceptable salts thereof, n is 1. In some of these compounds, or pharmaceutically acceptable salts thereof, wherein n is 1, J$^B$ is ortho to the methylene bridge between the ring bearing X$^1$ and ring B. In some of these embodiments, J$^D$ is halogen, e.g., chloro or, preferably, fluoro.

In some embodiments of the compounds of Formula I, or pharmaceutically acceptable salts thereof, X$^1$ is N and p is 0. In some of these embodiments, ring C is an oxazole or isoxazole ring. In some of these embodiments, ring B is phenyl. In some of these embodiments, J$^B$ is halogen, e.g., chloro or, preferably, fluoro. In other embodiments, there is a J$^B$ ortho to the methylene bridge between the ring bearing X$^1$ and ring B. In some of these embodiments, n is 1. In some of these embodiments, n is 1, $J^B$ is ortho to the methylene bridge between the ring bearing $X^1$ and ring B, and $J^D$ is halogen, e.g., chloro or, preferably, fluoro.

In some embodiments of the compounds of Formula I, or pharmaceutically acceptable salts thereof, $X^1$ is N and ring C is an isoxazolyl ring. In some of these embodiments, ring B is phenyl. In some of these embodiments, wherein ring B is phenyl, $J^B$ is halogen, e.g., chloro or, preferably, fluoro. In other embodiments, wherein ring B is phenyl, n is 1. In still other embodiments, wherein ring B is phenyl and n is 1, $J^B$ is halogen, preferably, fluoro. In yet other embodiments, wherein ring B is phenyl, there is a $J^B$ ortho to the methylene bridge between the ring bearing $X^1$ and ring B. In yet other embodiments, wherein ring B is phenyl, the $J^B$ is ortho to the methylene bridge between the ring bearing $X^1$ and ring B, and $J^B$ is preferably halogen, e.g., chloro or fluoro. In some of these compounds, or pharmaceutically acceptable salts thereof, $J^D$ is halogen. In some of these compounds, or pharmaceutically acceptable salts thereof, $J^D$ is fluoro.

In some embodiments of the compounds of Formula I, or pharmaceutically acceptable salts thereof, $X^1$ is C with a substituent (resulting in, for instance, CH, C($C_{1-4}$ alkyl), C($C_{1-4}$ haloalkyl), CCl or CF). In some of these embodiments, ring C is an oxazole or isoxazole ring. In some of these embodiments, ring C is unsubstituted, and in still other embodiments, ring C is an unsubstituted oxazole or isoxazole ring. In some of these embodiments, ring B is phenyl. In some of these compounds, or pharmaceutically acceptable salts thereof, $J^B$ is halogen, e.g., chloro or, preferably, fluoro. In some of these embodiments, there is a $J^B$ ortho to the methylene bridge between the ring bearing $X^1$ and ring B. In some of these compounds, or pharmaceutically acceptable salts thereof, n is 1. In some of these compounds, or pharmaceutically acceptable salts thereof, wherein n is 1, $J^B$ is ortho to the methylene bridge between the ring bearing $X^1$ and ring B. In some of these compounds, or pharmaceutically acceptable salts thereof, $J^D$ is halogen, e.g., chloro or, preferably, fluoro.

In some embodiments of the compounds of Formula I, or pharmaceutically acceptable salts thereof, $X^1$ is C with a substituent (resulting in, for instance, CH, C($C_{1-4}$ alkyl), C($C_{1-4}$ haloalkyl), CCl or CF) and p is 0. In some of these embodiments, ring C is an oxazole or isoxazole ring. In some of these embodiments, ring B is phenyl. In some of these embodiments, $J^B$ is halogen, e.g., chloro or, preferably, fluoro. In other embodiments, there is a $J^B$ ortho to the methylene bridge between the ring bearing $X^1$ and ring B. In some of these compounds, or pharmaceutically acceptable salts thereof, n is 1. In some of these compounds, or pharmaceutically acceptable salts thereof, wherein n is 1, $J^B$ is ortho to the methylene bridge between the ring bearing $X^1$ and ring B. In some of these compounds, or pharmaceutically acceptable salts thereof, $J^D$ is halogen, e.g., chloro or, preferably, fluoro.

In some embodiments of the compounds of Formula I, or pharmaceutically acceptable salts thereof, $X^1$ is C with a substituent (resulting in, for instance, CH, C($C_{1-4}$ alkyl), C($C_{1-4}$ haloalkyl), CCl or CF) and ring C is an isoxazolyl group. In some of these embodiments, ring B is phenyl. In some of these embodiments wherein ring B is phenyl, $J^B$ is halogen, e.g., chloro or, preferably, fluoro. In other embodiments wherein ring B is phenyl, n is 1. In still other embodiments wherein ring B is phenyl and n is 1, $J^B$ is halogen, preferably, fluoro. In yet other embodiments wherein ring B is phenyl, there is a $J^B$ ortho to the methylene bridge between the ring bearing $X^1$ and ring B. In yet other embodiments wherein ring B is phenyl, the $J^B$ is ortho to the methylene bridge between the ring bearing $X^1$ and ring B, and $J^B$ is preferably halogen, e.g., chloro or fluoro. In some of these embodiments, $J^D$ is halogen. In some of these compounds, or pharmaceutically acceptable salts thereof, $J^D$ is fluoro.

The present invention is also directed to some embodiments of the compounds of Formula I having a structure as depicted in Formulae IIa or IIb, or pharmaceutically acceptable salts thereof:

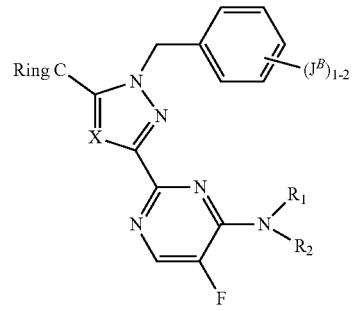

Formula IIa

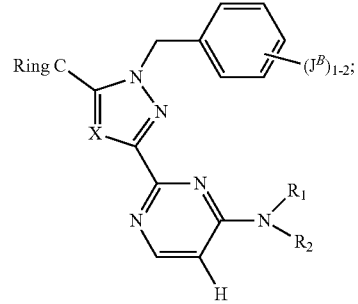

Formula IIb wherein each $J^B$ is halogen; and ring C is an unsubstituted oxazole or isoxazole ring.

The present invention is also directed to some embodiments of the compounds of Formula II having a structure as depicted in Formulae IIIa to IIId, or pharmaceutically acceptable salts thereof:

Formula IIIa-IIId,

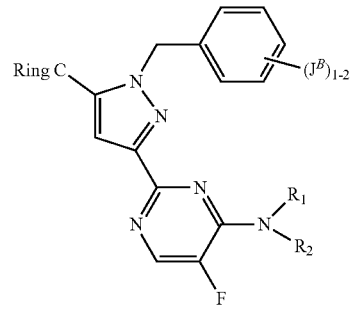

IIIa

-continued

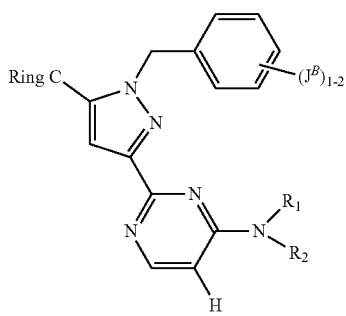

IIIb

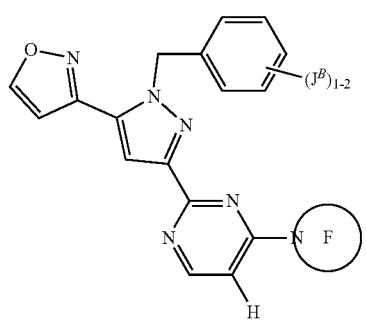

IIIc

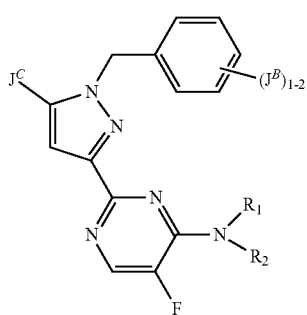

IIId wherein each $J^B$ is halogen; and ring C is an unsubstituted oxazole or isoxazole ring.

The present invention is also directed to some embodiments of the compounds of Formulae IIIa and IIIb having a structure as depicted in Formula IVa and Formula IVb, or pharmaceutically acceptable salts thereof:

Formula IVa

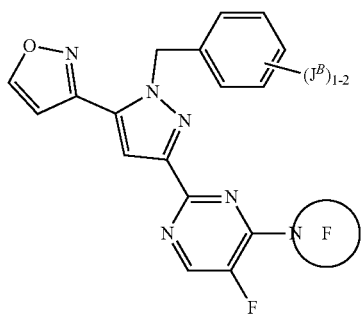

Formula IVb wherein each $J^B$ is halogen;

and ring F is a monocyclic or bicyclic 4 to 10-membered heterocyclic ring or a monocyclic or bicyclic 5 to 10-membered heteroaryl ring; wherein said 4 to 10-membered heterocyclic ring or 5 to 10-membered heteroaryl ring optionally contains up to 3 ring heteroatoms independently selected from N, O or S, and is optionally and independently substituted by up to 3 instances of $R^5$.

In some of the embodiments of the compounds of Formula IVa or Formula IVb, or pharmaceutically acceptable salts thereof, ring F is substituted by:

(i) 3 instances of $R^5$; wherein at least two of said instances are the same, or (ii) 0, 1 or 2 instances of $R^5$; wherein, when ring F is substituted by 2 instances of $R^5$, then each of the instances of $R^5$ is independently selected;

wherein each $R^5$ is selected from fluoro, methyl, ethyl, methoxy, trifluoromethyl, trifluoromethoxy, hydroxyl, $C_{1-6}$ (hydroxy)alkyl, oxo, —CN, —O($C_{1-6}$ alkyl)-COOR$^Z$, —NH($C_{1-6}$ alkyl)-COOR$^Z$, —($C_{1-6}$ alkyl)-COOR$^Z$, —COOR$^Z$, —COR$^Z$, —CON(R$^Z$)$_2$, —NHCOOR$^Z$, —NHCON(R$^Z$)$_2$, —CONHSO$_2$R$^Z$, —NHCOR$^Z$, —NH($C_{1-6}$ alkyl)-CON(R$^Z$)$_2$, —N(R$^Z$)$_2$, —SO$_2$R$^Z$, —SO$_2$N(R$^Z$)$_2$, —SO$_2$NHCOR$^Z$, —SO$_2$NHCOOR$^Z$, phenyl, benzyl, or a 5 or 6 membered heterocyclic or heteroaryl ring; wherein each of said phenyl, benzyl or 5-6 membered heteroaryl or heterocyclic ring is optionally substituted by 1 or 2 instances of $R^{Za}$;

wherein each $R^Z$ is independently selected from hydrogen, a $C_{3-6}$ cycloalkyl, a $C_{1-6}$ alkyl, a $C_{1-6}$ fluoroalkyl; and wherein each $R^{Za}$ is independently selected from hydrogen, halogen, a $C_{3-6}$ cycloalkyl, a $C_{1-6}$ alkyl, a $C_{1-6}$ fluoroalkyl, oxo and —COOH.

In some of the embodiments of the compounds of Formula IVa or Formula IVb, or pharmaceutically acceptable salts thereof, at least one instance of $R^5$ is a —COOH moiety or at least one instance of $R^5$ is substituted by a —COOH moiety.

The present invention is also directed to some embodiments of the compounds of Formula IVa or Formula IVb having a structure as depicted in Formula Va or Formula Vb, or pharmaceutically acceptable salts thereof:

Formula Va

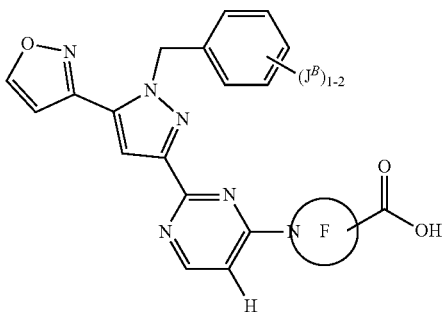

Formula Vb

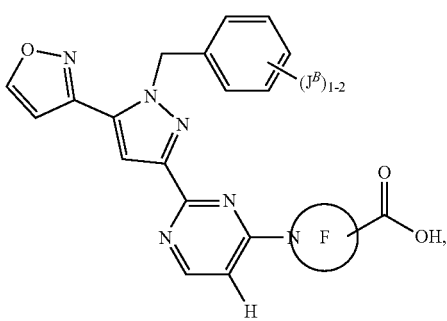

wherein F is a ring that includes the nitrogen attached to the pyrimidine, and wherein ring F is optionally and independently further substituted by 1 or 2 instances of $R^5$.

The present invention is also directed to some embodiments of the compounds of Formula I having a structure as depicted in Formula VIa or Formula VIb, or pharmaceutically acceptable salts thereof:

Formula VIa

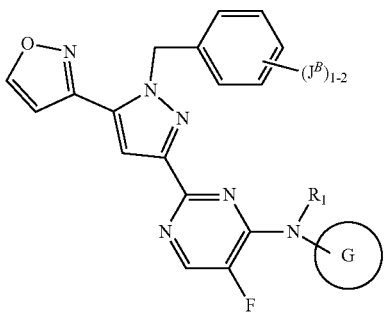

Formula VIb

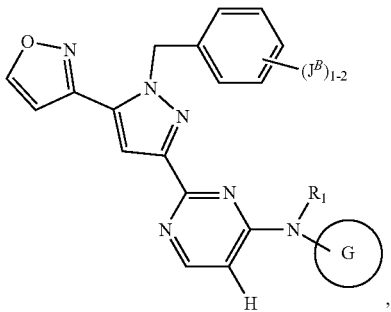

wherein each $J^B$ is halogen;

$R^1$ is hydrogen or $C_{1-6}$ alkyl;

and ring G is a monocyclic or bicyclic 4 to 10-membered heterocyclic ring or a monocyclic or bicyclic 5 to 10-membered heteroaryl ring; wherein said 4 to 10-membered heterocyclic ring or 5 to 10-membered heteroaryl ring optionally contains up to 3 ring heteroatoms independently selected from N, O or S, and is optionally and independently substituted by up to 3 instances of $R^{5a}$.

In some of these compounds, or pharmaceutically acceptable salts thereof, each $R^{5a}$ is selected from fluoro, methyl, ethyl, methoxy, trifluoromethyl, trifluoromethoxy, hydroxyl, $C_{1-6}$ (hydroxy)alkyl, oxo, —CN, —O($C_{1-6}$ alkyl)-COOR$^{Zb}$, —NH($C_{1-6}$ alkyl)-COOR$^{Zb}$, —($C_{1-6}$ alkyl)-COOR$^{Zb}$, —COOR$^{Zb}$, —COR$^{Zb}$, —CON(R$^{Zb}$)$_2$, —NHCOOR$^{Zb}$, —NHCON(R$^{Zb}$)$_2$, —CONHSO$_2$R$^{Zb}$, —NHCOR$^{Zb}$, —NH($C_{1-6}$ alkyl)-CON(R$^{Zb}$)$_2$, —N(R$^{Zb}$)$_2$, SO$_2$R$^{Zb}$, —SO$_2$N(R$^M$)$_2$, —SO$_2$NHCOR$^{Zb}$, —SO$_2$NHCOOR$^{Zb}$, phenyl, benzyl, or a 5 or 6 membered heterocyclic or heteroaryl ring; wherein each of said phenyl, benzyl or 5-6 membered heteroaryl or heterocyclic ring is optionally substituted by 1 or 2 instances of R$^{Zc}$; wherein each R$^{Zb}$ is independently selected from hydrogen, a $C_{1-4}$ alkyl, a $C_{1-4}$ fluoroalkyl; and wherein each R$^{Zc}$ is independently selected from hydrogen, halogen, a $C_{1-4}$ alkyl, a $C_{1-4}$ fluoroalkyl, oxo and —COOH.

In some of these compounds, or pharmaceutically acceptable salts thereof, at least one instance of $R^{5a}$ is a —COOH moiety or at least one instance of $R^{5a}$ comprises a —COOH moiety.

The present invention is also directed to some embodiments of the compounds of Formula VIa or Formula VIb having a structure as depicted in Formula VIIa or Formula VIIb, or pharmaceutically acceptable salts thereof:

Formula VIIa

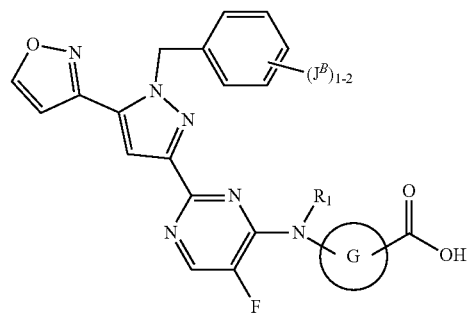

Formula VIIb

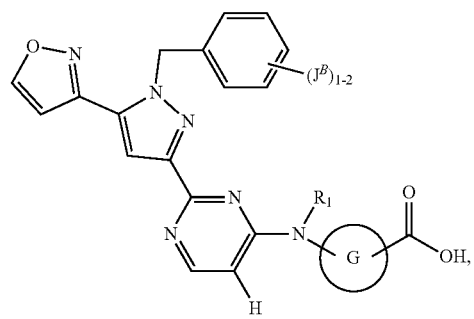

wherein ring G is optionally and independently further substituted by 1 or 2 instances of $R^{5a}$.

The present invention is also directed to some embodiments of the compounds of Formula IIIa or Formula IIIc having a structure as depicted in Formula VIIIa or Formula VIIIb, or pharmaceutically acceptable salts thereof:

Formula VIIIa

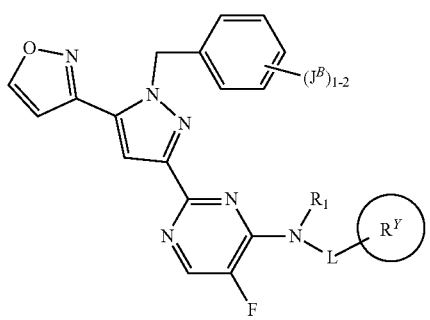

Formula VIIIb

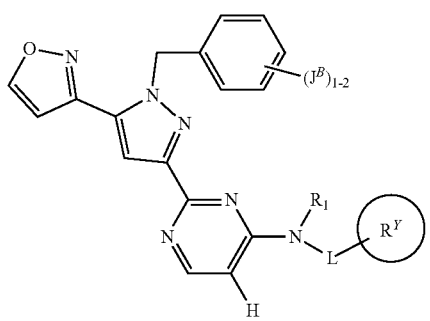

wherein $J^B$ is halogen; $R^1$ is hydrogen or $C_{1-6}$ alkyl; L is a $C_{1-6}$ alkyl group optionally and independently substituted by up to three instances of $R^{5a}$; and ring $R^Y$ is a monocyclic or bicyclic 4 to 10-membered heterocyclic ring or a monocyclic or bicyclic 5 to 10-membered heteroaryl ring; wherein said 4 to 10-membered heterocyclic ring or 5 to 10-membered heteroaryl ring optionally contains up to 3 additional heteroatoms independently selected from N, O or S, and is optionally and independently substituted by up to 3 instances of $R^{5b}$.

The present invention is also directed to some embodiments of the compounds of Formula VIIIa or Formula VIIIb having a structure as depicted in one of Formulae IXa or IXb or Formulae Xa or Xb, or pharmaceutically acceptable salts thereof:

Formula IXa

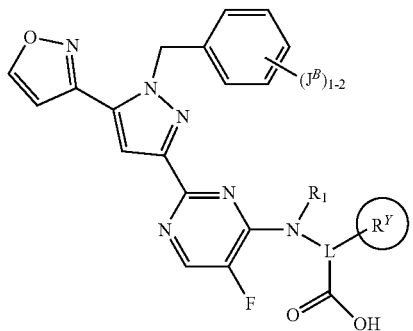

Formula IXb

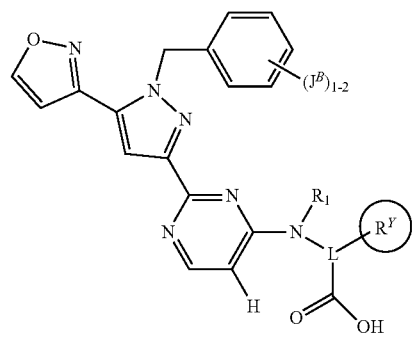

Formula Xa

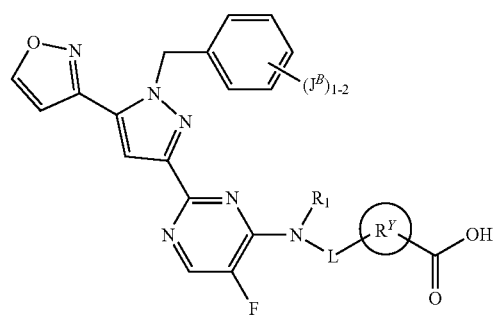

Formula Xb

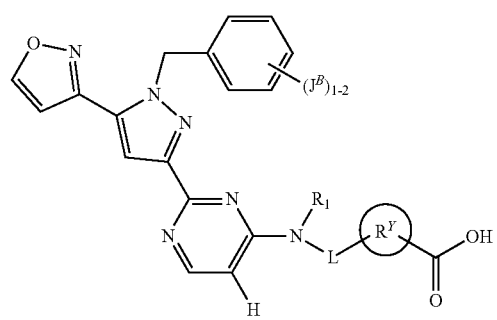

wherein in Formula IXa or Formula IXb, the linker L is further optionally and independently substituted by up to two instances of $R^{5a}$; and in Formula Xa or Formula Xb, ring $R^Y$ is further optionally and independently substituted by up to two instances of $R^{5b}$.

The present invention is also directed to some embodiments of the compounds of Formula IIIa or Formula IIIb having a structure as depicted in Formula XIa or Formula XIb, or pharmaceutically acceptable salts thereof:

Formula XIa
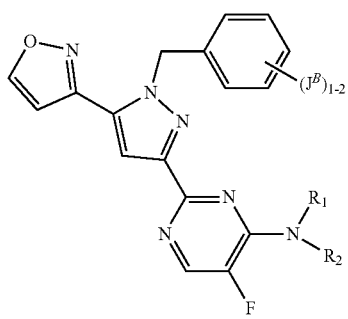
Formula XIb
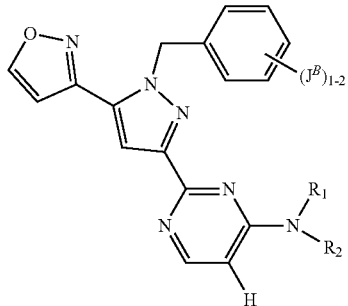
wherein $J^B$ is halogen; $R^1$ is hydrogen or $C_{1-6}$ alkyl; and $R^2$ is a $C_{1-6}$ alkyl group optionally and independently substituted by up to three instances of $R^{5a}$.
In some embodiments, the compounds of Formula I are selected from those listed in Table 1A, Table 1B, Table 1C and Table 1D.
TABLE 1A
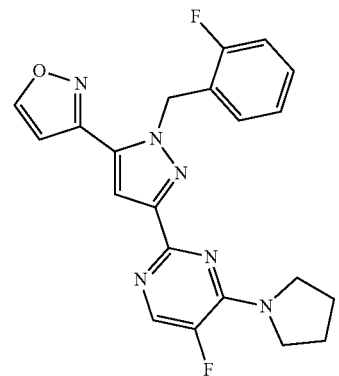 [SMILES: Fc1ccccc1Cn1nc(-c2ncc(F)c(N3CCCC3)n2)cc1-c1ccon1]  I-1
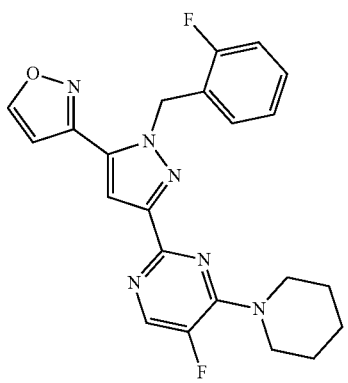 [SMILES: Fc1ccccc1Cn1nc(-c2ncc(F)c(N3CCCCC3)n2)cc1-c1ccon1]  I-2
TABLE 1A-continued
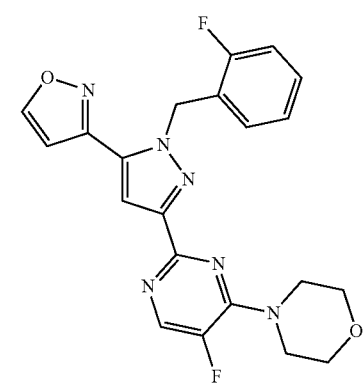 [SMILES: Fc1ccccc1Cn1nc(-c2ncc(F)c(N3CCOCC3)n2)cc1-c1ccon1]  I-3
I-4
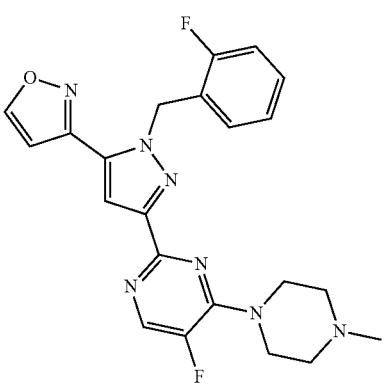 [SMILES: CN1CCN(c2nc(-c3cc(-c4ccon4)n(Cc4ccccc4F)n3)ncc2F)CC1]  I-5
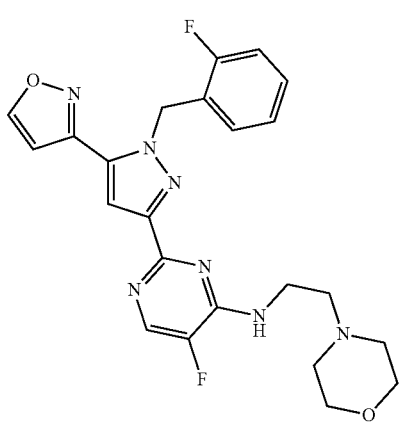 [SMILES: Fc1ccccc1Cn1nc(-c2ncc(F)c(NCCN3CCOCC3)n2)cc1-c1ccon1]  I-6

TABLE 1A-continued
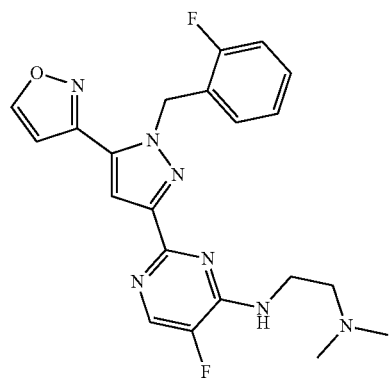 [SMILES: CN(C)CCNc1nc(-c2cc(-c3ccon3)n(Cc3ccccc3F)n2)ncc1F]
I-7
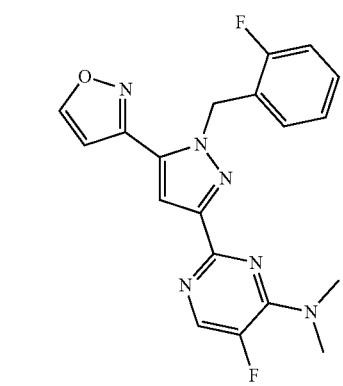 [SMILES: CN(C)c1nc(-c2cc(-c3ccon3)n(Cc3ccccc3F)n2)ncc1F]
I-8
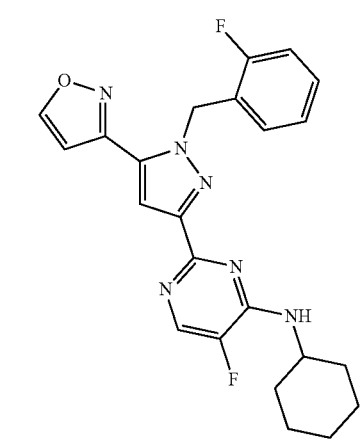 [SMILES: Fc1ccccc1Cn1nc(-c2ncc(F)c(NC3CCCCC3)n2)cc1-c1ccon1]
I-9
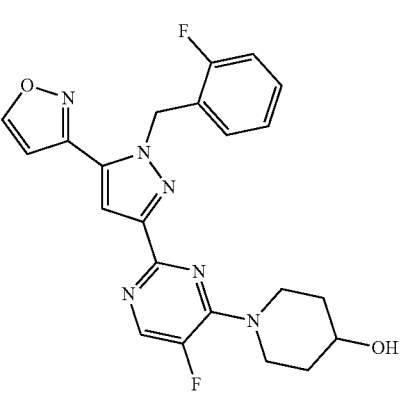
I-10
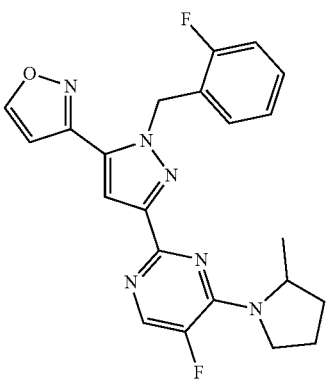 [SMILES: CC1CCCN1c1nc(-c2cc(-c3ccon3)n(Cc3ccccc3F)n2)ncc1F]
I-11
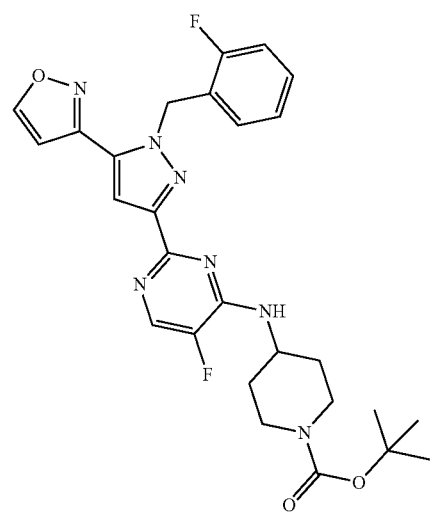 [SMILES: CC(C)(C)OC(=O)N1CCC(Nc2nc(-c3cc(-c4ccon4)n(Cc4ccccc4F)n3)ncc2F)CC1]
I-12
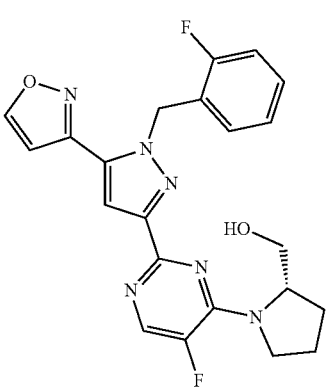 [SMILES: OC[C@@H]1CCCN1c1nc(-c2cc(-c3ccon3)n(Cc3ccccc3F)n2)ncc1F]
I-13
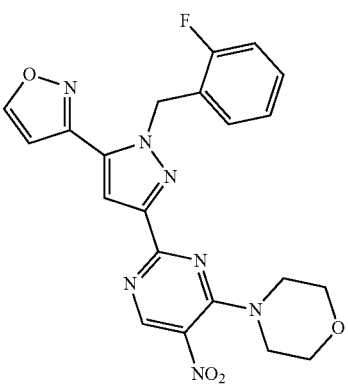 [SMILES: O=[N+]([O-])c1cnc(-c2cc(-c3ccon3)n(Cc3ccccc3F)n2)nc1N1CCOCC1]
I-14

TABLE 1A-continued
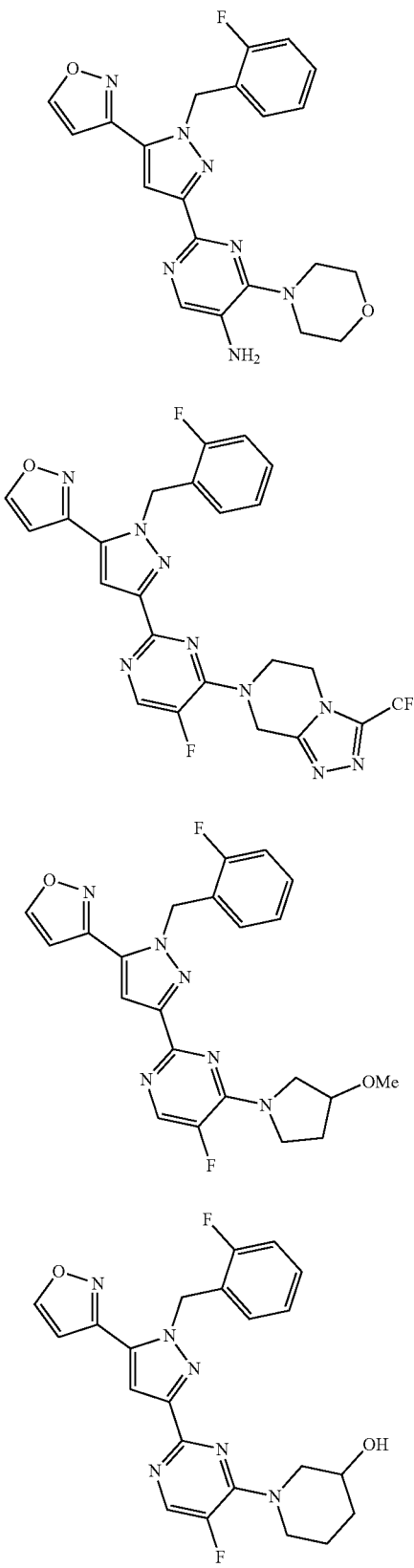
I-15
I-16
I-17
I-18
TABLE 1A-continued
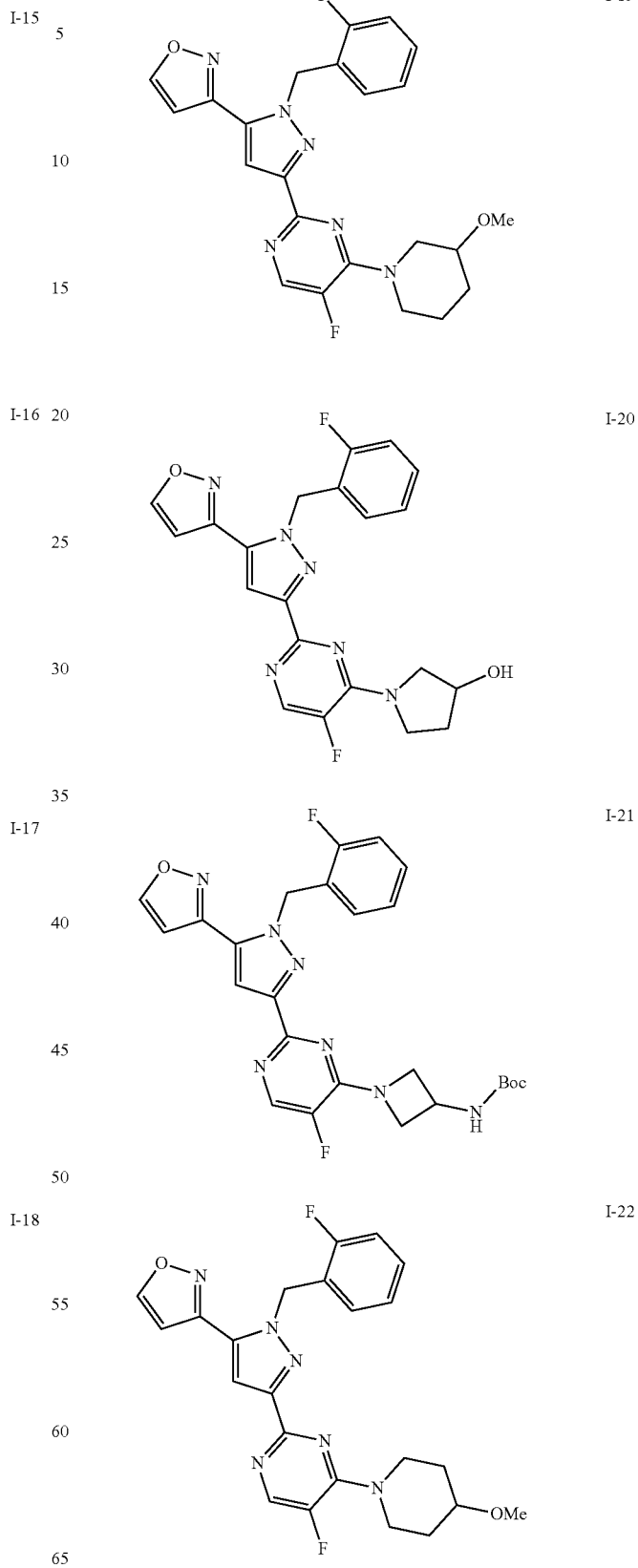
I-19
I-20
I-21
I-22

TABLE 1A-continued
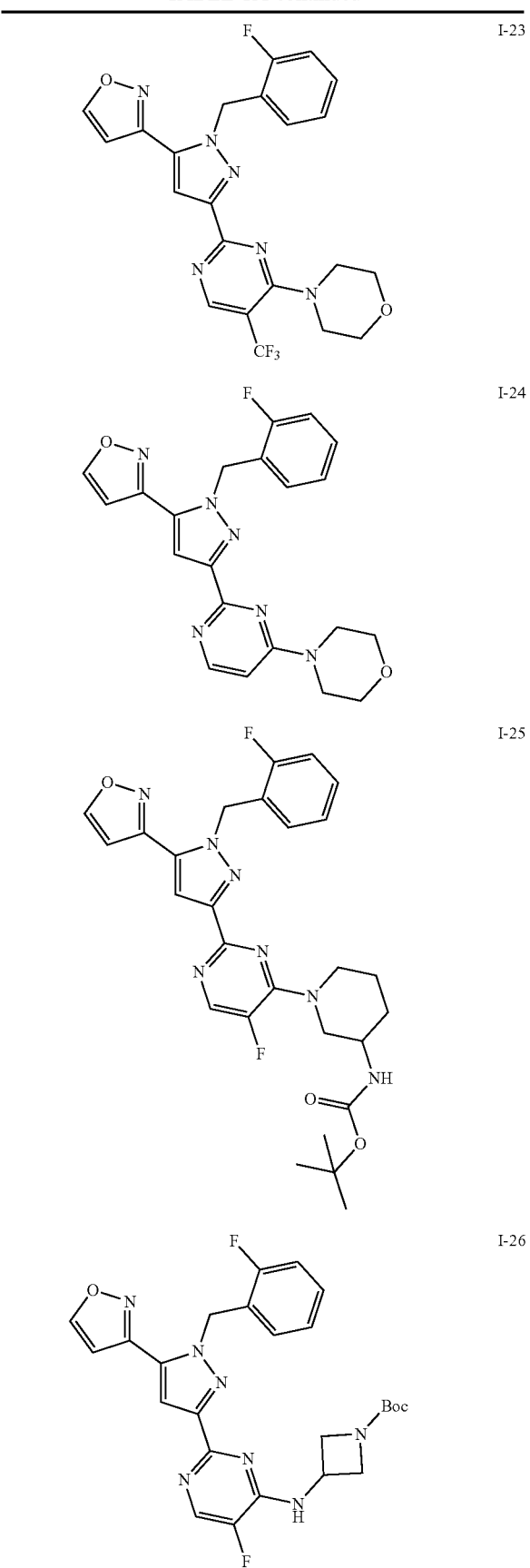
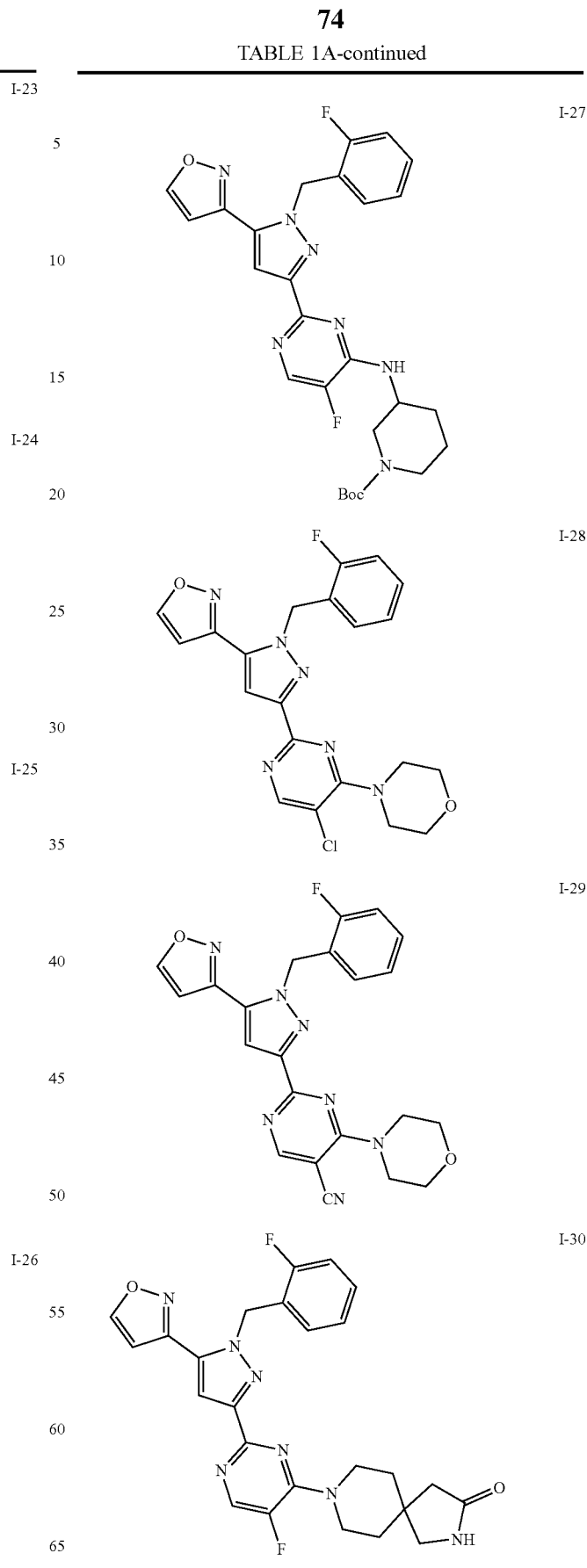

TABLE 1A-continued
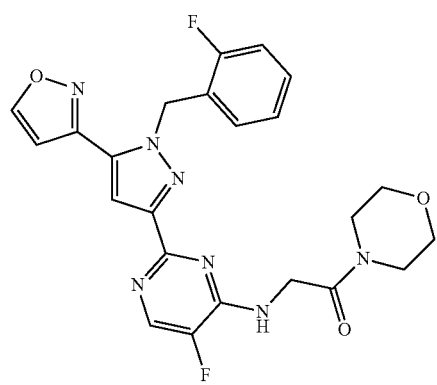 [SMILES: O=C(CNc1nc(-c2cc(-c3ccon3)n(Cc3ccccc3F)n2)ncc1F)N1CCOCC1]
I-31
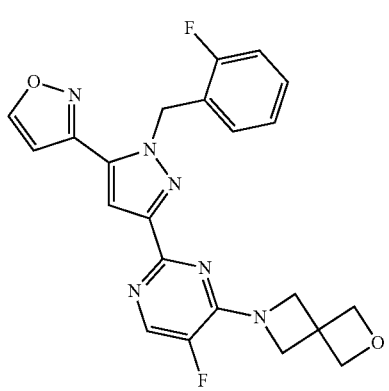 [SMILES: Fc1ccccc1Cn1nc(-c2ncc(F)c(N3CC4(COC4)C3)n2)cc1-c1ccon1]
I-32
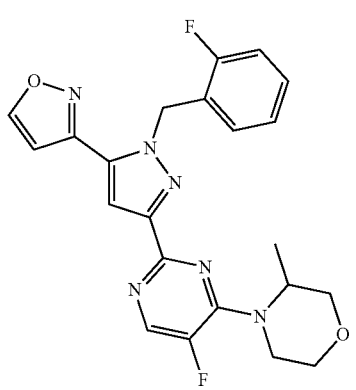 [SMILES: CC1COCCN1c1nc(-c2cc(-c3ccon3)n(Cc3ccccc3F)n2)ncc1F]
I-33
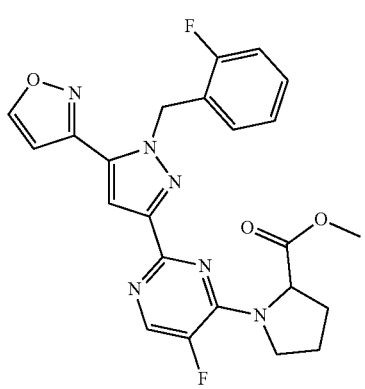 [SMILES: COC(=O)C1CCCN1c1nc(-c2cc(-c3ccon3)n(Cc3ccccc3F)n2)ncc1F]
I-34
TABLE 1A-continued
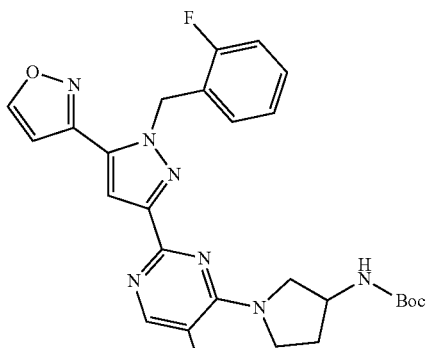
I-35
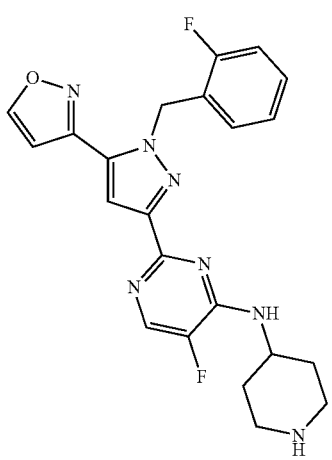 [SMILES: Fc1ccccc1Cn1nc(-c2ncc(F)c(NC3CCNCC3)n2)cc1-c1ccon1]
I-36
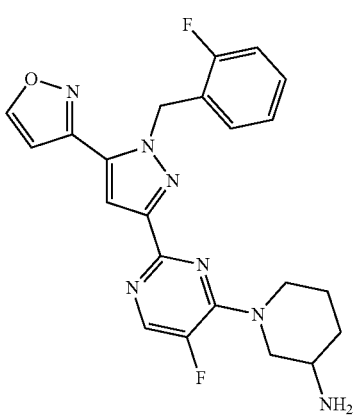 [SMILES: NC1CCCN(c2nc(-c3cc(-c4ccon4)n(Cc4ccccc4F)n3)ncc2F)C1]
I-37
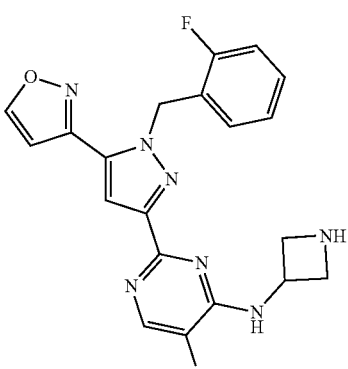
I-38

TABLE 1A-continued
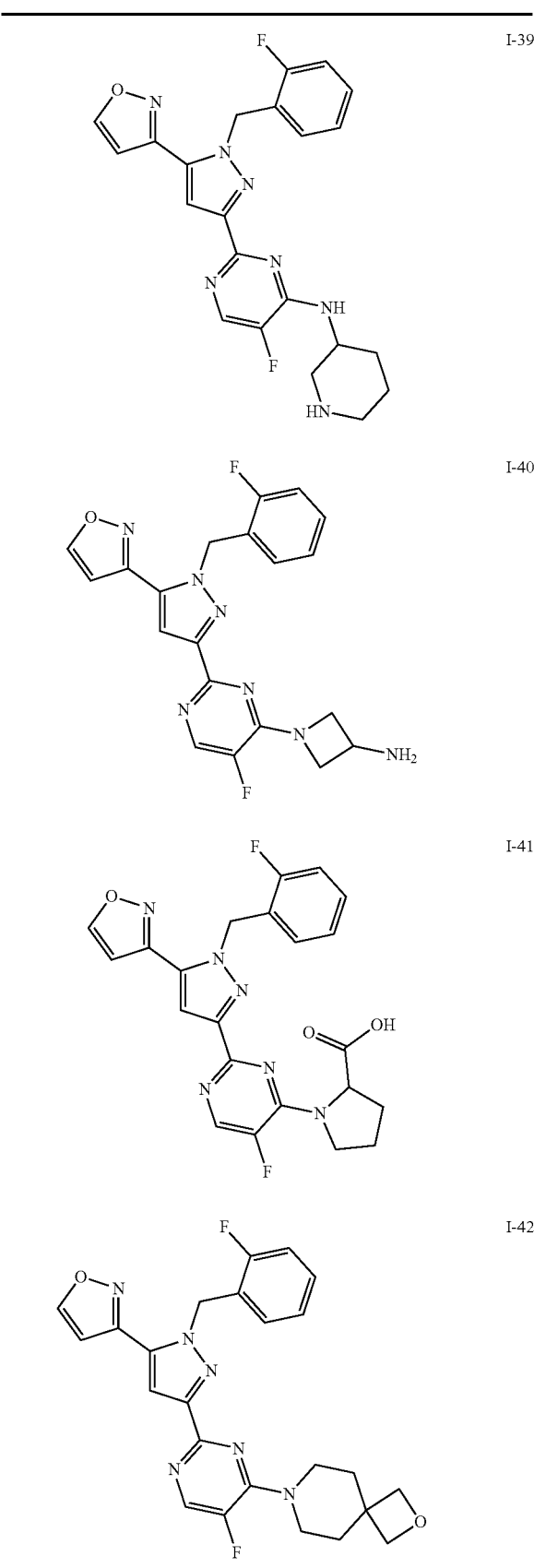
I-39
I-40
I-41
I-42
TABLE 1A-continued
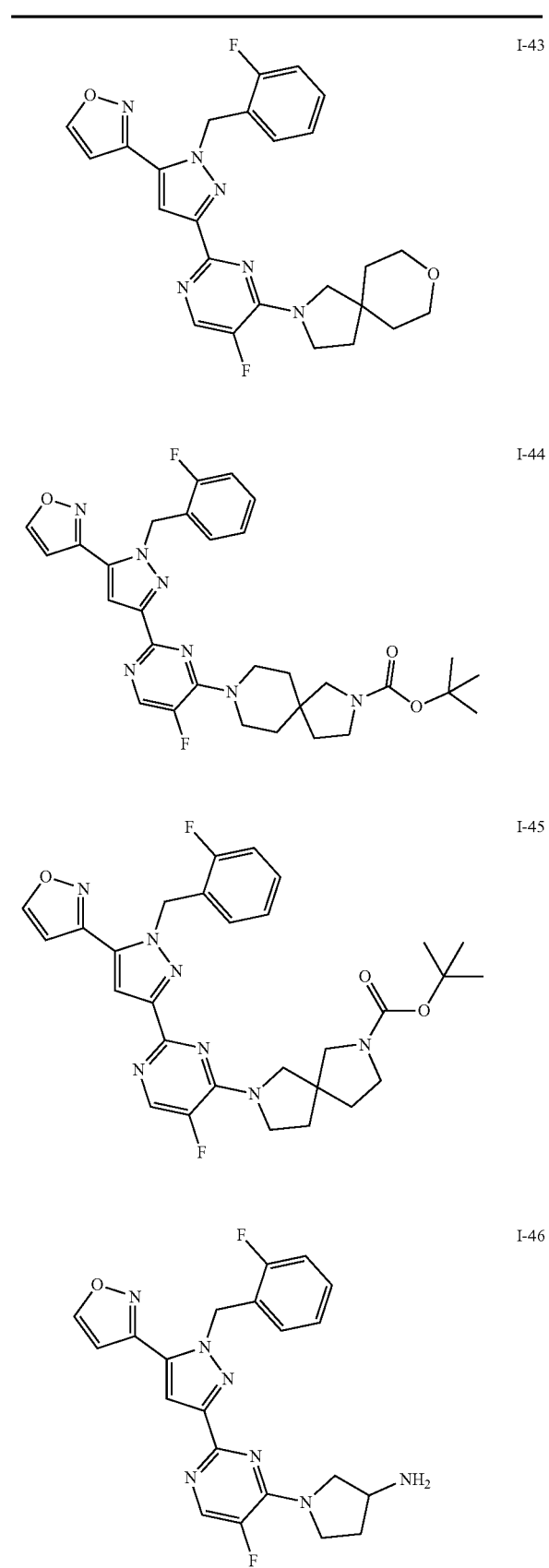
I-43
I-44
I-45
I-46

TABLE 1A-continued
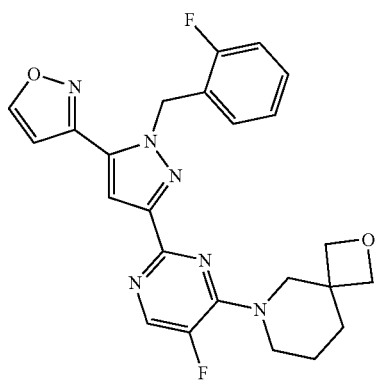 [SMILES: Fc1ccccc1Cn1nc(-c2ncc(F)c(N3CCCC4(COC4)C3)n2)cc1-c1ccon1]
I-47
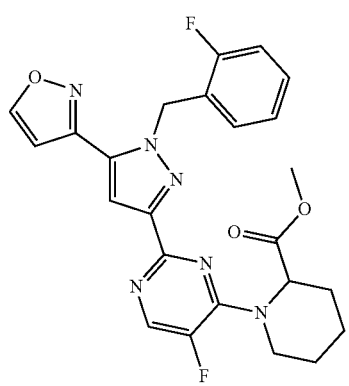 [SMILES: COC(=O)C1CCCCN1c1nc(-c2cc(-c3ccon3)n(Cc3ccccc3F)n2)ncc1F]
I-48
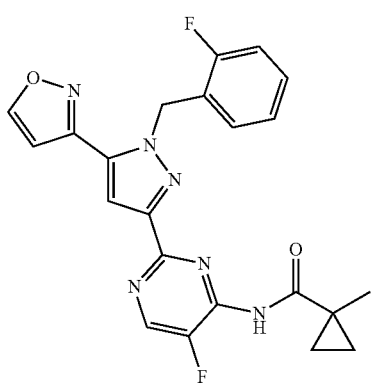 [SMILES: CC1(C(=O)Nc2nc(-c3cc(-c4ccon4)n(Cc4ccccc4F)n3)ncc2F)CC1]
I-49
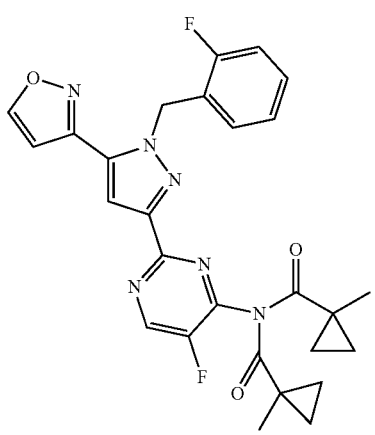 [SMILES: CC1(C(=O)N(C(=O)C2(C)CC2)c2nc(-c3cc(-c4ccon4)n(Cc4ccccc4F)n3)ncc2F)CC1]
I-50
TABLE 1A-continued
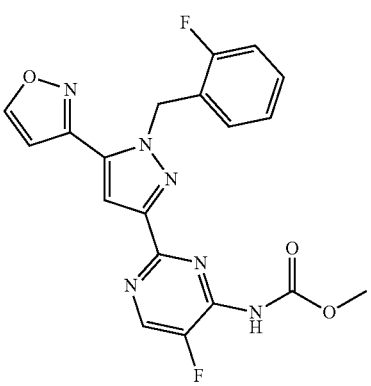 [SMILES: COC(=O)Nc1nc(-c2cc(-c3ccon3)n(Cc3ccccc3F)n2)ncc1F]
I-51
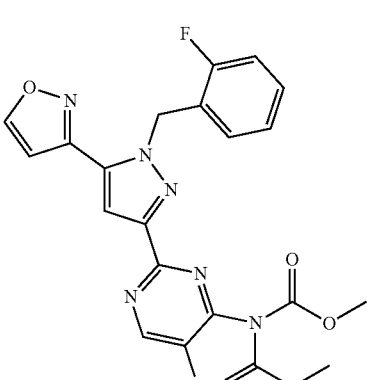
I-52
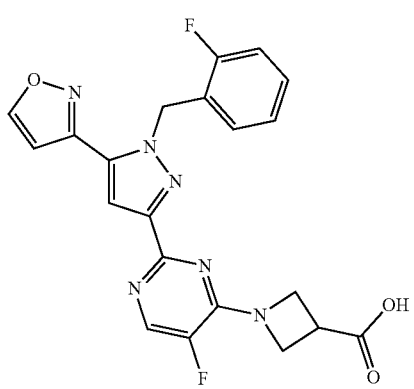 [SMILES: O=C(O)C1CN(c2nc(-c3cc(-c4ccon4)n(Cc4ccccc4F)n3)ncc2F)C1]
I-53
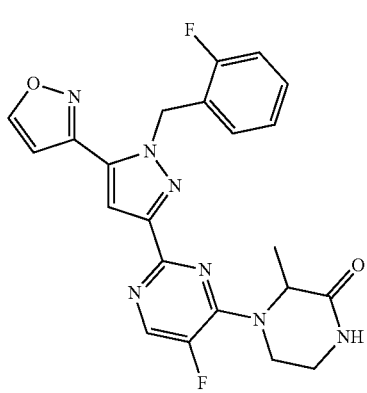 [SMILES: CC1C(=O)NCCN1c1nc(-c2cc(-c3ccon3)n(Cc3ccccc3F)n2)ncc1F]
I-54

TABLE 1A-continued
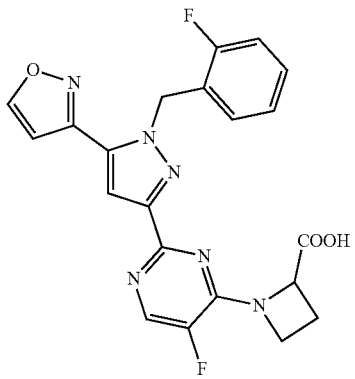 [SMILES: O=C(O)C1CCN1c1nc(-c2cc(-c3ccon3)n(Cc3ccccc3F)n2)ncc1F]
I-55
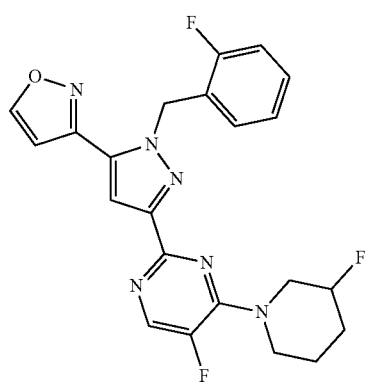 [SMILES: Fc1ccccc1Cn1nc(-c2ncc(F)c(N3CCCC(F)C3)n2)cc1-c1ccon1]
I-56
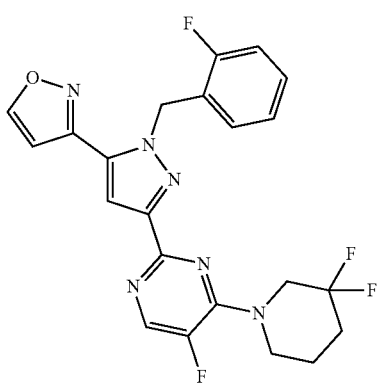 [SMILES: Fc1ccccc1Cn1nc(-c2ncc(F)c(N3CCCC(F)(F)C3)n2)cc1-c1ccon1]
I-57
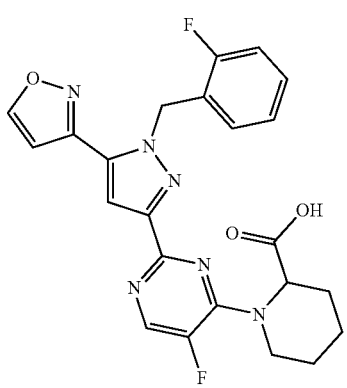 [SMILES: O=C(O)C1CCCCN1c1nc(-c2cc(-c3ccon3)n(Cc3ccccc3F)n2)ncc1F]
I-58
TABLE 1A-continued
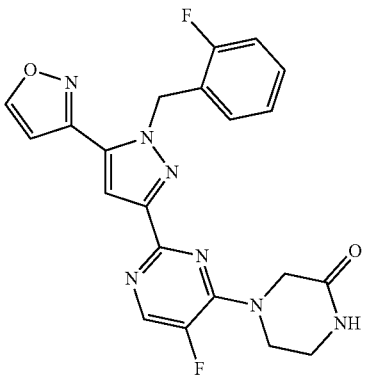 [SMILES: O=C1CN(c2nc(-c3cc(-c4ccon4)n(Cc4ccccc4F)n3)ncc2F)CCN1]
I-59
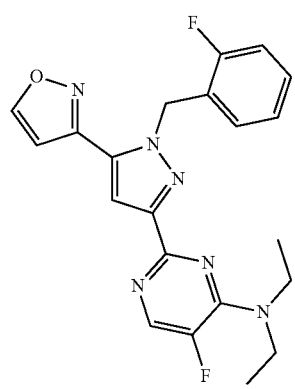 [SMILES: CCN(CC)c1nc(-c2cc(-c3ccon3)n(Cc3ccccc3F)n2)ncc1F]
I-60
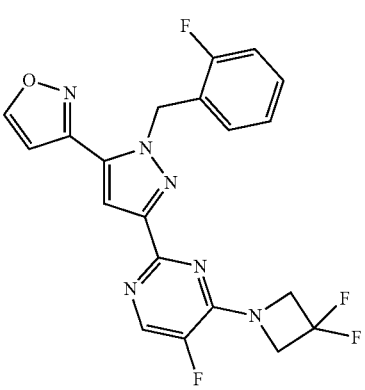 [SMILES: Fc1ccccc1Cn1nc(-c2ncc(F)c(N3CC(F)(F)C3)n2)cc1-c1ccon1]
I-61
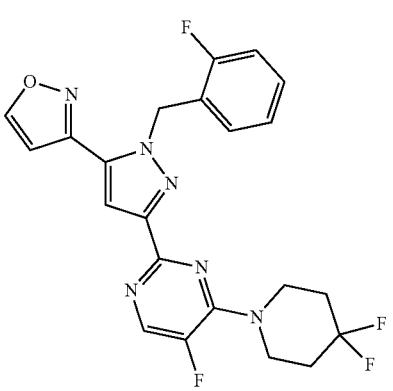 [SMILES: Fc1ccccc1Cn1nc(-c2ncc(F)c(N3CCC(F)(F)CC3)n2)cc1-c1ccon1]
I-62

TABLE 1A-continued
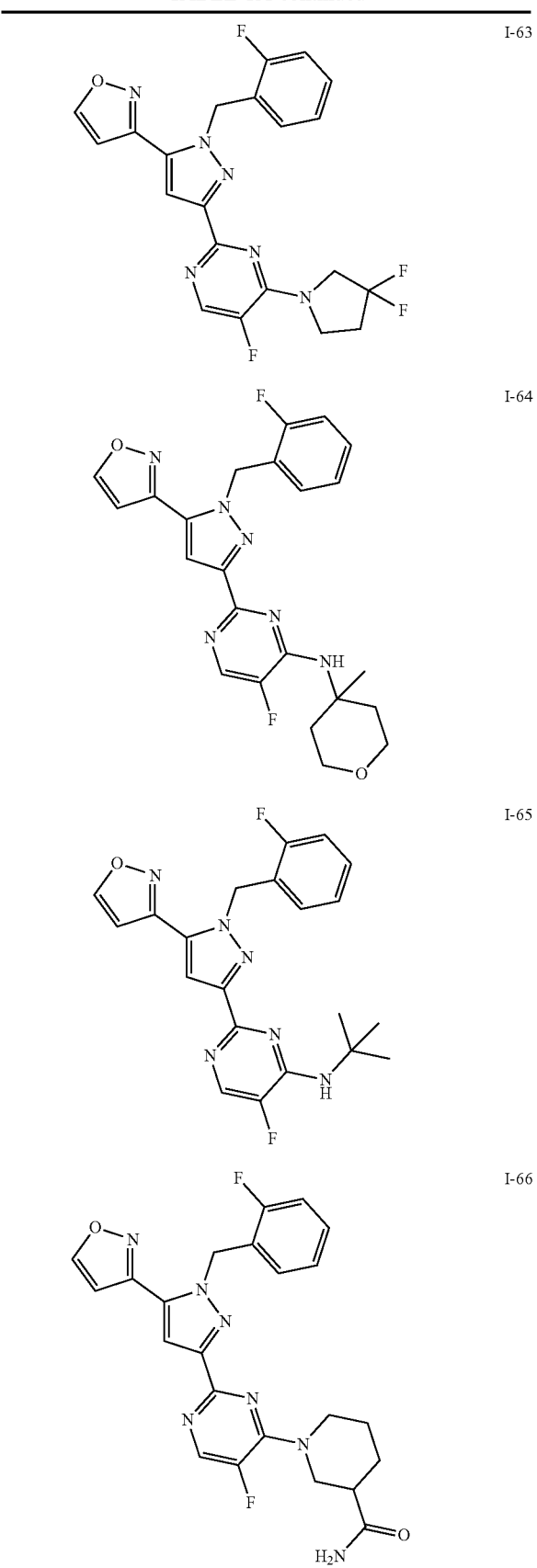
I-63
I-64
I-65
I-66
TABLE 1A-continued
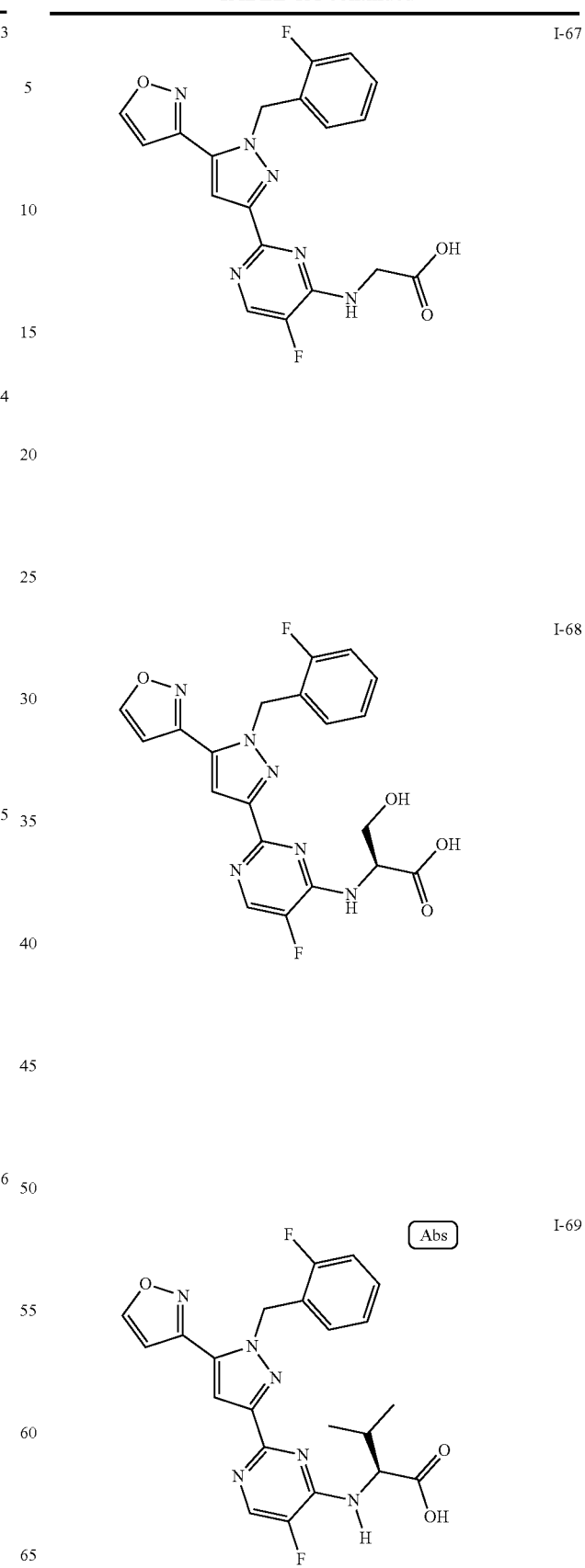
I-67
I-68
I-69

TABLE 1A-continued
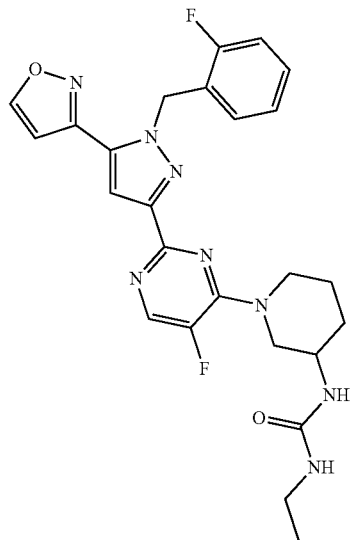 [SMILES: CCNC(=O)NC1CCCN(c2nc(-c3cc(-c4ccon4)n(Cc4ccccc4F)n3)ncc2F)C1]
I-70
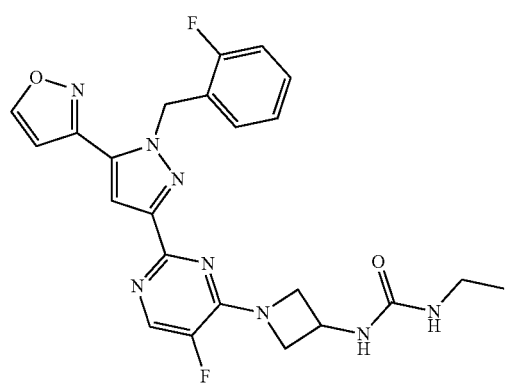 [SMILES: CCNC(=O)NC1CN(c2nc(-c3cc(-c4ccon4)n(Cc4ccccc4F)n3)ncc2F)C1]
I-71
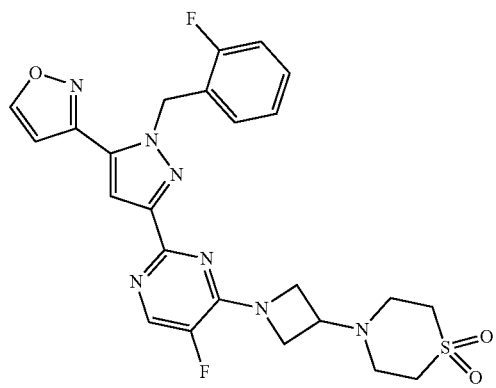 [SMILES: O=S1(=O)CCN(C2CN(c3nc(-c4cc(-c5ccon5)n(Cc5ccccc5F)n4)ncc3F)C2)CC1]
I-72
TABLE 1A-continued
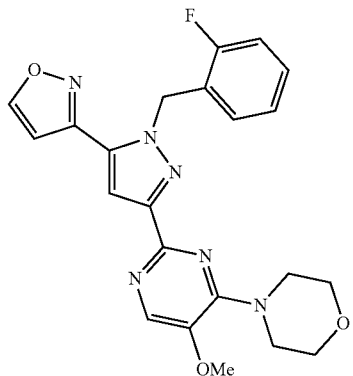
I-73
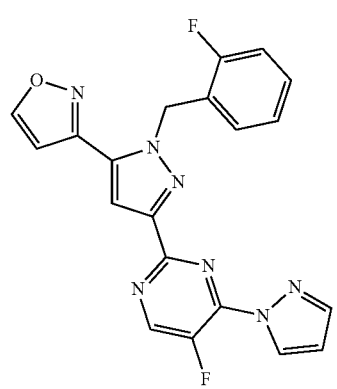 [SMILES: Fc1ccccc1Cn1nc(-c2ncc(F)c(-n3cccn3)n2)cc1-c1ccon1]
I-74
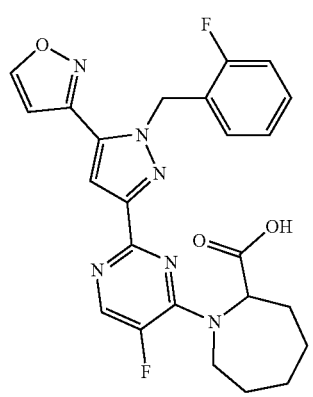 [SMILES: O=C(O)C1CCCCCN1c1nc(-c2cc(-c3ccon3)n(Cc3ccccc3F)n2)ncc1F]
I-75
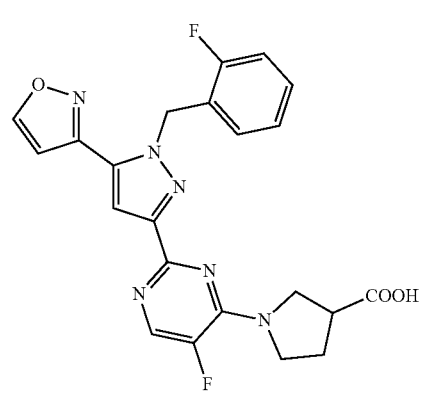 [SMILES: O=C(O)C1CCN(c2nc(-c3cc(-c4ccon4)n(Cc4ccccc4F)n3)ncc2F)C1]
I-76

TABLE 1A-continued
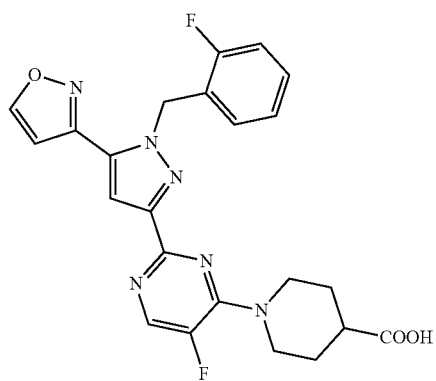 [SMILES: O=C(O)C1CCN(c2nc(-c3cc(-c4ccon4)n(Cc4ccccc4F)n3)ncc2F)CC1] I-77
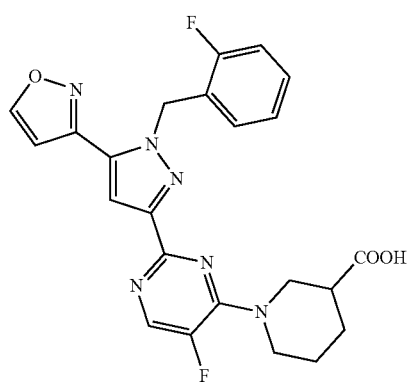 [SMILES: O=C(O)C1CCCN(c2nc(-c3cc(-c4ccon4)n(Cc4ccccc4F)n3)ncc2F)C1] I-78
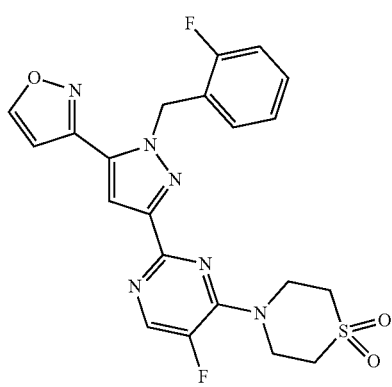 [SMILES: O=S1(=O)CCN(c2nc(-c3cc(-c4ccon4)n(Cc4ccccc4F)n3)ncc2F)CC1] I-79
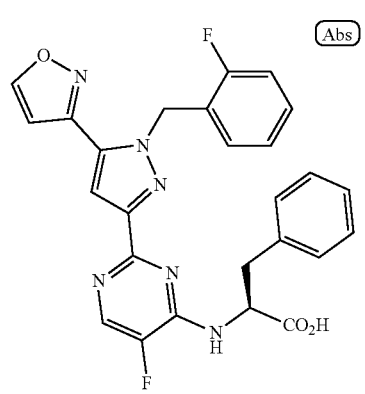 [SMILES: O=C(O)[C@H](Cc1ccccc1)Nc1nc(-c2cc(-c3ccon3)n(Cc3ccccc3F)n2)ncc1F] I-80
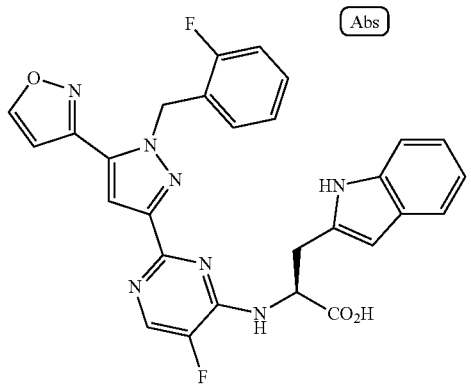 [SMILES: O=C(O)[C@H](Cc1cc2ccccc2[nH]1)Nc1nc(-c2cc(-c3ccon3)n(Cc3ccccc3F)n2)ncc1F] I-81
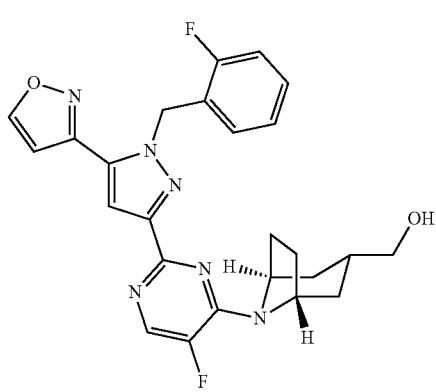 [SMILES: OCC1C[C@H]2CC[C@@H](C1)N2c1nc(-c2cc(-c3ccon3)n(Cc3ccccc3F)n2)ncc1F] I-82
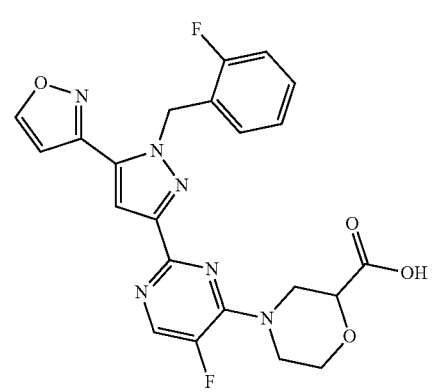 [SMILES: O=C(O)C1CN(c2nc(-c3cc(-c4ccon4)n(Cc4ccccc4F)n3)ncc2F)CCO1] I-83
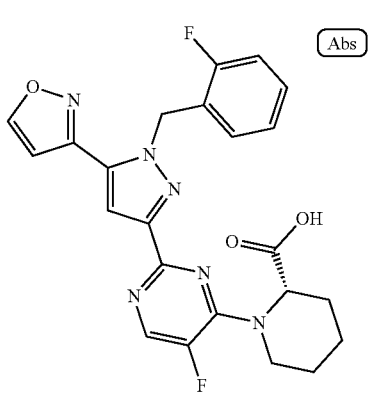 [SMILES: O=C(O)[C@@H]1CCCCN1c1nc(-c2cc(-c3ccon3)n(Cc3ccccc3F)n2)ncc1F] I-84

TABLE 1A-continued
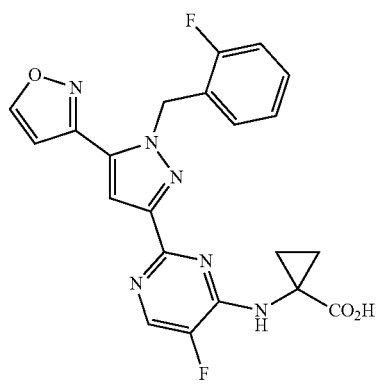 [SMILES: O=C(O)C1(Nc2nc(-c3cc(-c4ccon4)n(Cc4ccccc4F)n3)ncc2F)CC1]
I-85
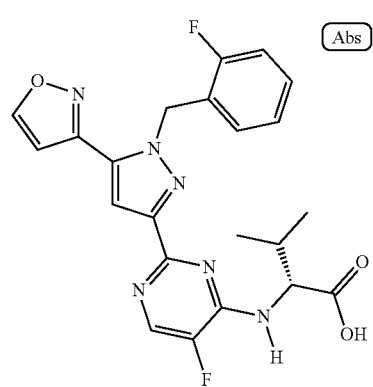 [SMILES: CC(C)[C@@H](Nc1nc(-c2cc(-c3ccon3)n(Cc3ccccc3F)n2)ncc1F)C(=O)O]
I-86
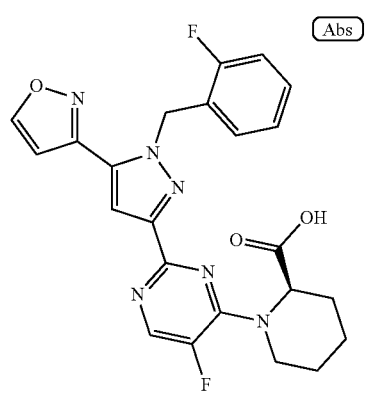 [SMILES: O=C(O)[C@H]1CCCCN1c1nc(-c2cc(-c3ccon3)n(Cc3ccccc3F)n2)ncc1F]
I-87
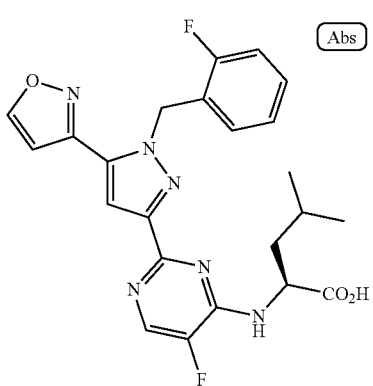 [SMILES: CC(C)C[C@H](Nc1nc(-c2cc(-c3ccon3)n(Cc3ccccc3F)n2)ncc1F)C(=O)O]
I-88
TABLE 1A-continued
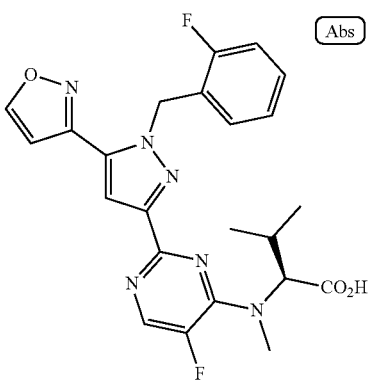 [SMILES: CC(C)[C@@H](C(=O)O)N(C)c1nc(-c2cc(-c3ccon3)n(Cc3ccccc3F)n2)ncc1F]
I-89
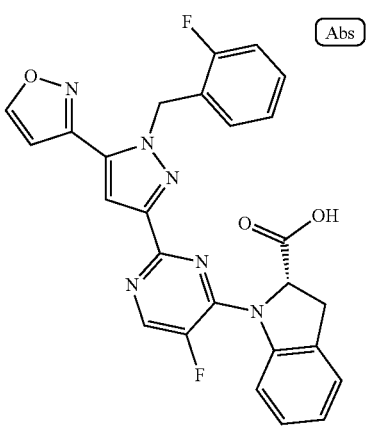 [SMILES: O=C(O)[C@@H]1Cc2ccccc2N1c1nc(-c2cc(-c3ccon3)n(Cc3ccccc3F)n2)ncc1F]
I-90
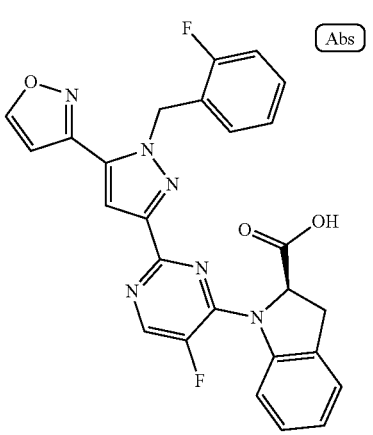 [SMILES: O=C(O)[C@H]1Cc2ccccc2N1c1nc(-c2cc(-c3ccon3)n(Cc3ccccc3F)n2)ncc1F]
I-91
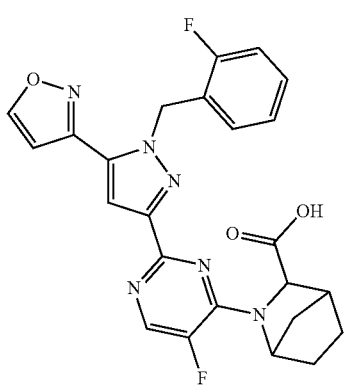 [SMILES: O=C(O)C1C2CCC(C2)N1c1nc(-c2cc(-c3ccon3)n(Cc3ccccc3F)n2)ncc1F]
I-92

TABLE 1A-continued
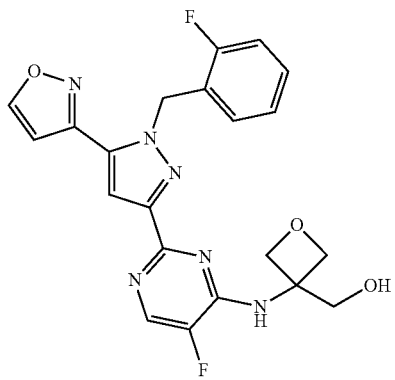 [SMILES: OCC1(Nc2nc(-c3cc(-c4ccon4)n(Cc4ccccc4F)n3)ncc2F)COC1]
I-93
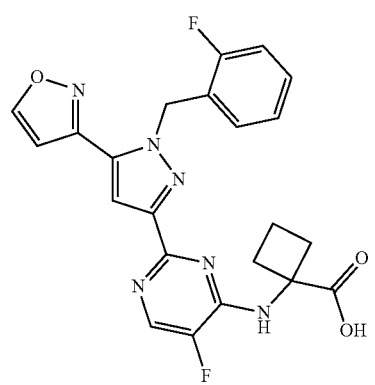 [SMILES: O=C(O)C1(Nc2nc(-c3cc(-c4ccon4)n(Cc4ccccc4F)n3)ncc2F)CCC1]
I-94
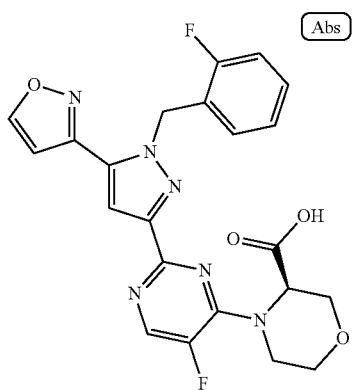 [SMILES: O=C(O)[C@H]1COCCN1c1nc(-c2cc(-c3ccon3)n(Cc3ccccc3F)n2)ncc1F]
I-95 [Abs]
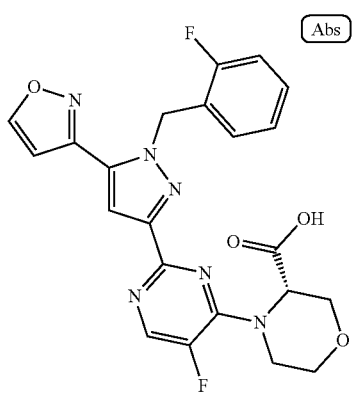 [SMILES: O=C(O)[C@@H]1COCCN1c1nc(-c2cc(-c3ccon3)n(Cc3ccccc3F)n2)ncc1F]
I-96 [Abs]
TABLE 1A-continued
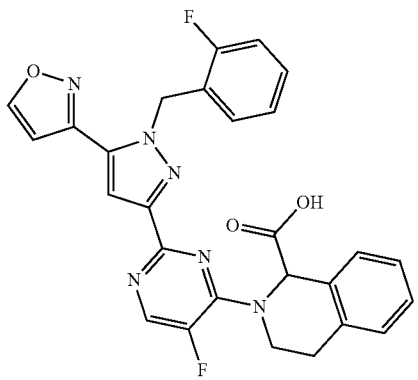 [SMILES: O=C(O)C1c2ccccc2CCN1c1nc(-c2cc(-c3ccon3)n(Cc3ccccc3F)n2)ncc1F]
I-97
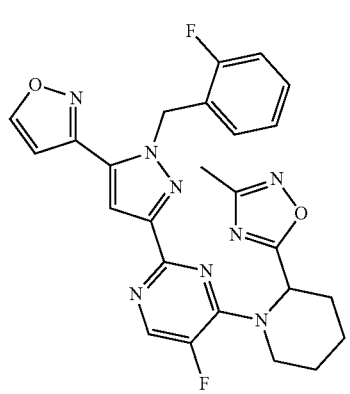 [SMILES: Cc1noc(C2CCCCN2c2nc(-c3cc(-c4ccon4)n(Cc4ccccc4F)n3)ncc2F)n1]
I-98
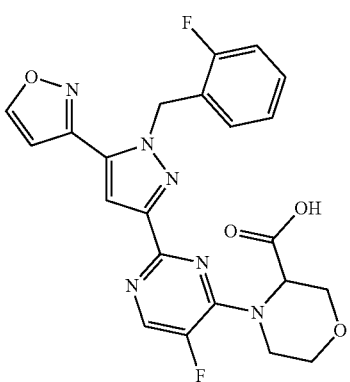 [SMILES: O=C(O)C1COCCN1c1nc(-c2cc(-c3ccon3)n(Cc3ccccc3F)n2)ncc1F]
I-99
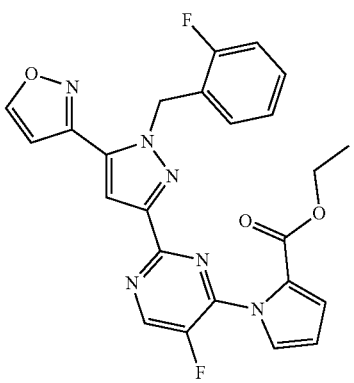 [SMILES: CCOC(=O)c1cccn1-c1nc(-c2cc(-c3ccon3)n(Cc3ccccc3F)n2)ncc1F]
I-100

TABLE 1A-continued
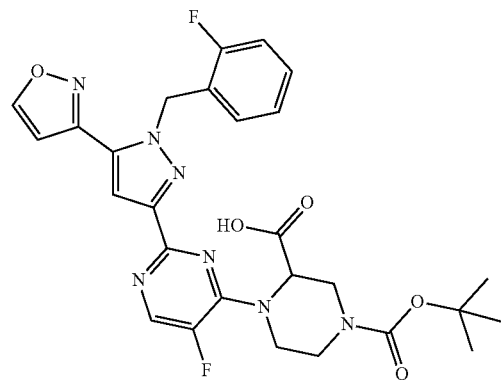 [SMILES: CC(C)(C)OC(=O)N1CCN(c2nc(-c3cc(-c4ccon4)n(Cc4ccccc4F)n3)ncc2F)C(C(=O)O)C1]
I-101
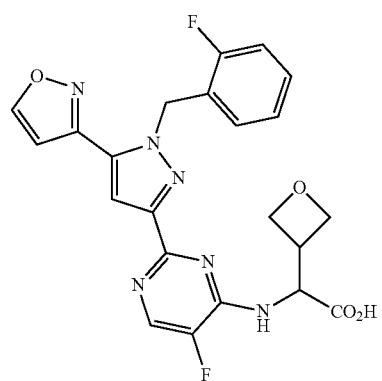 [SMILES: O=C(O)C(Nc1nc(-c2cc(-c3ccon3)n(Cc3ccccc3F)n2)ncc1F)C1COC1]
I-102
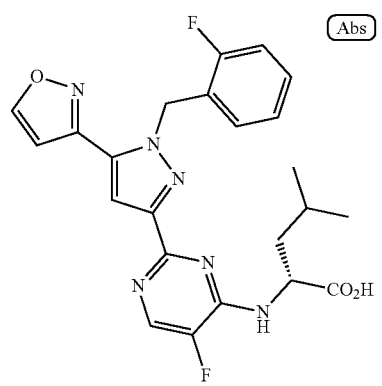 [SMILES: CC(C)C[C@@H](Nc1nc(-c2cc(-c3ccon3)n(Cc3ccccc3F)n2)ncc1F)C(=O)O]
I-103
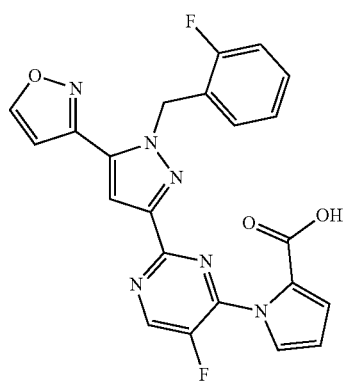 [SMILES: O=C(O)c1cccn1-c1nc(-c2cc(-c3ccon3)n(Cc3ccccc3F)n2)ncc1F]
I-104
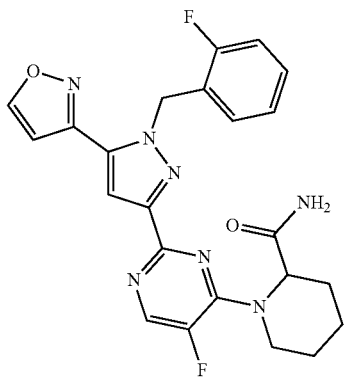 [SMILES: NC(=O)C1CCCCN1c1nc(-c2cc(-c3ccon3)n(Cc3ccccc3F)n2)ncc1F]
I-105
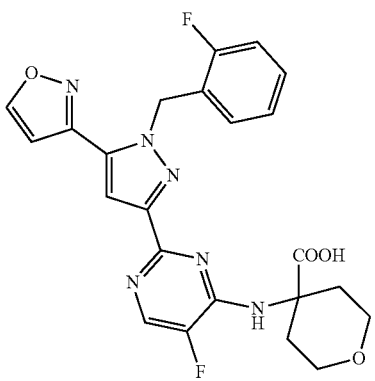 [SMILES: O=C(O)C1(Nc2nc(-c3cc(-c4ccon4)n(Cc4ccccc4F)n3)ncc2F)CCOCC1]
I-106
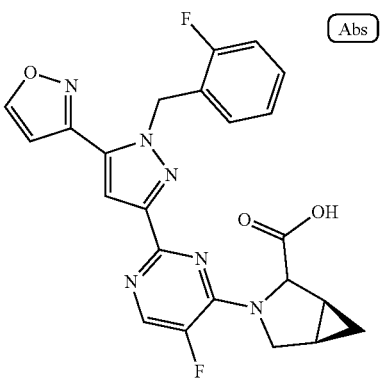 [SMILES: O=C(O)C1[C@H]2C[C@H]2CN1c1nc(-c2cc(-c3ccon3)n(Cc3ccccc3F)n2)ncc1F]
I-107
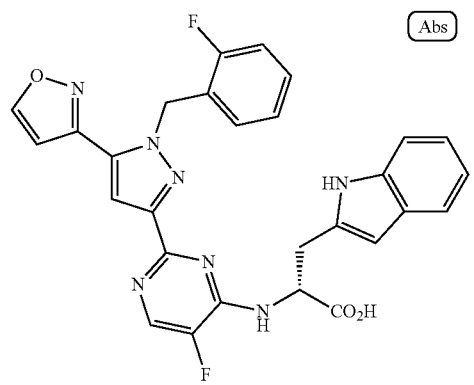 [SMILES: O=C(O)[C@@H](Cc1cc2ccccc2[nH]1)Nc1nc(-c2cc(-c3ccon3)n(Cc3ccccc3F)n2)ncc1F]
I-108

TABLE 1A-continued
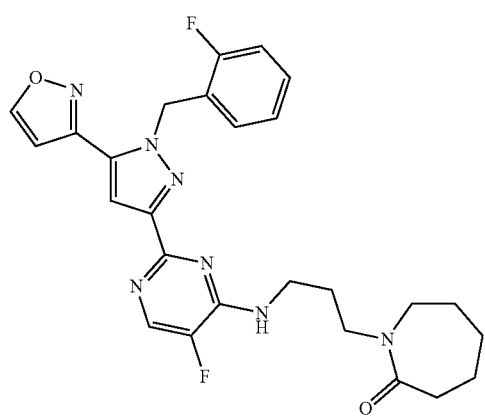 [SMILES: O=C1CCCCCN1CCCNc1nc(-c2cc(-c3ccon3)n(Cc3ccccc3F)n2)ncc1F]
I-109
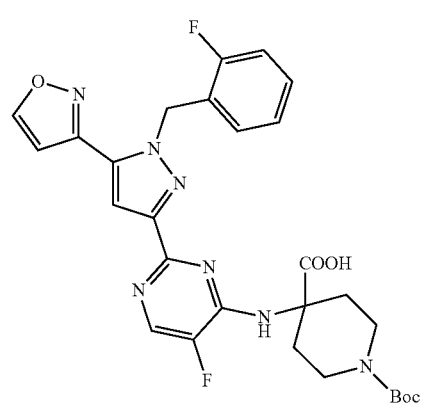 [SMILES: CC(C)(C)OC(=O)N1CCC(Nc2nc(-c3cc(-c4ccon4)n(Cc4ccccc4F)n3)ncc2F)(C(=O)O)CC1]
I-110
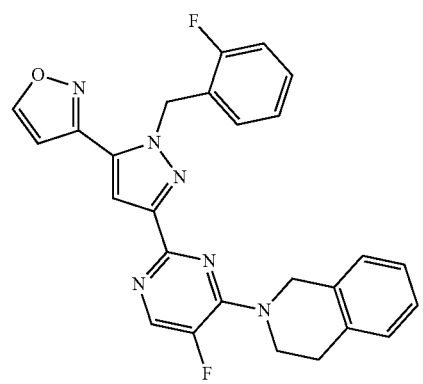 [SMILES: Fc1ccccc1Cn1nc(-c2ncc(F)c(N3CCc4ccccc4C3)n2)cc1-c1ccon1]
I-111
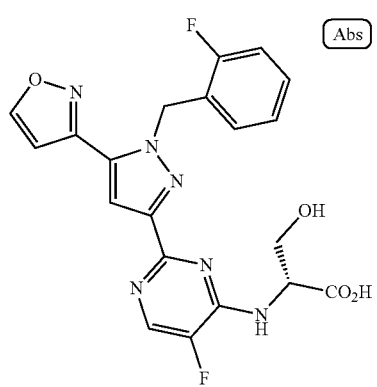 [SMILES: O=C(O)[C@@H](CO)Nc1nc(-c2cc(-c3ccon3)n(Cc3ccccc3F)n2)ncc1F]
I-112
TABLE 1A-continued
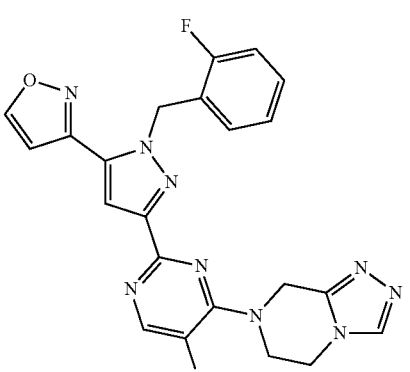
I-113
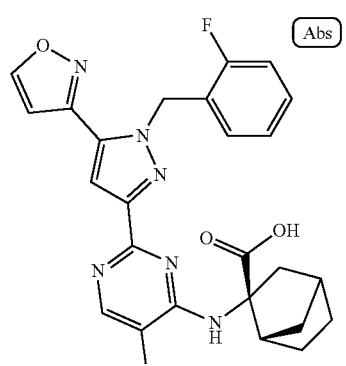
I-114
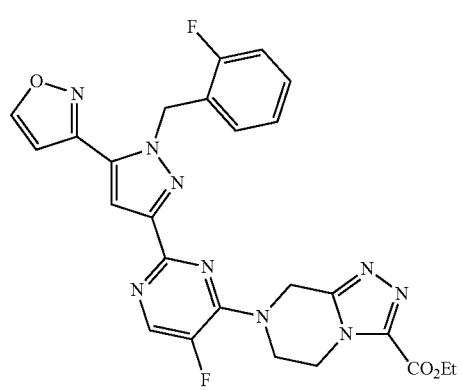 [SMILES: CCOC(=O)c1nnc2n1CCN(c1nc(-c3cc(-c4ccon4)n(Cc4ccccc4F)n3)ncc1F)C2]
I-115
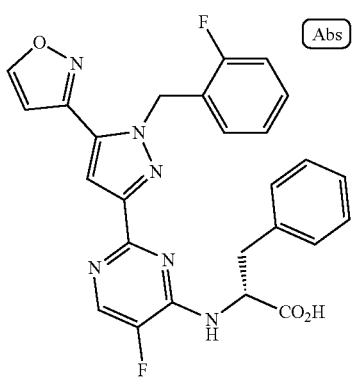 [SMILES: O=C(O)[C@@H](Cc1ccccc1)Nc1nc(-c2cc(-c3ccon3)n(Cc3ccccc3F)n2)ncc1F]
I-116

TABLE 1A-continued
I-117 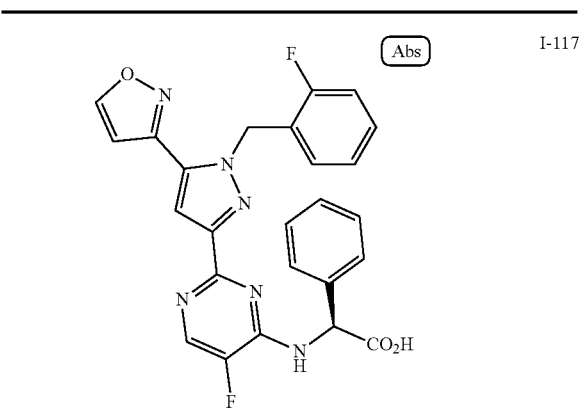
I-118 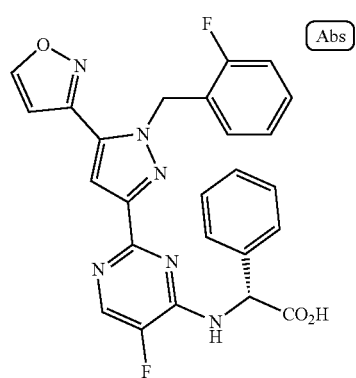 [SMILES: O=C(O)[C@H](Nc1nc(-c2cc(-c3ccon3)n(Cc3ccccc3F)n2)ncc1F)c1ccccc1]
I-119 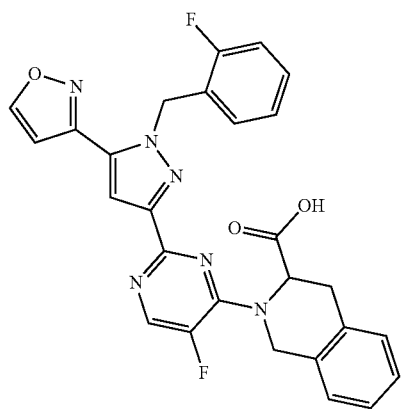 [SMILES: O=C(O)C1Cc2ccccc2CN1c1nc(-c2cc(-c3ccon3)n(Cc3ccccc3F)n2)ncc1F]
I-120 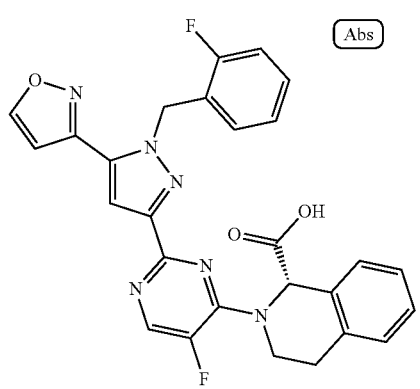 [SMILES: O=C(O)[C@@H]1c2ccccc2CCN1c1nc(-c2cc(-c3ccon3)n(Cc3ccccc3F)n2)ncc1F]
TABLE 1A-continued
I-121 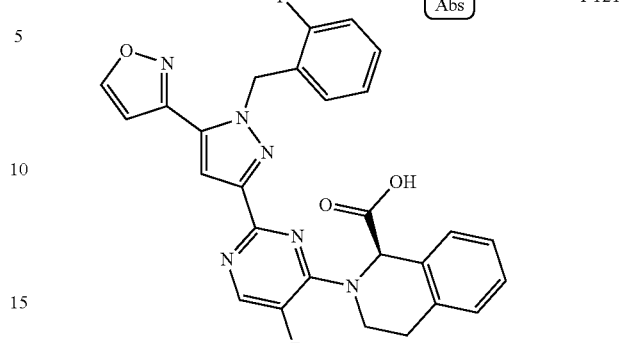
I-122 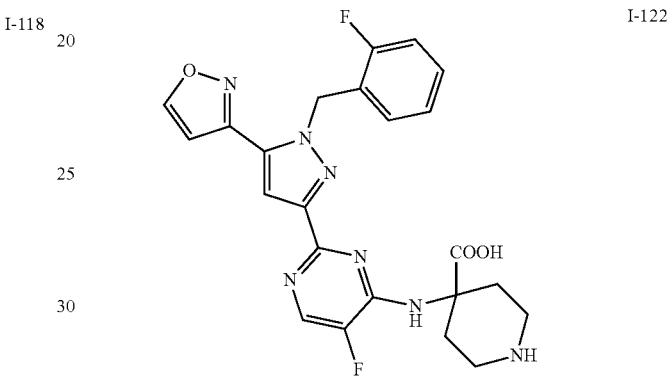
I-123 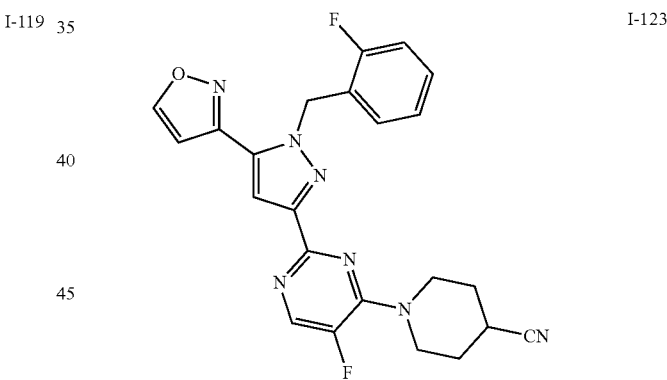
I-124 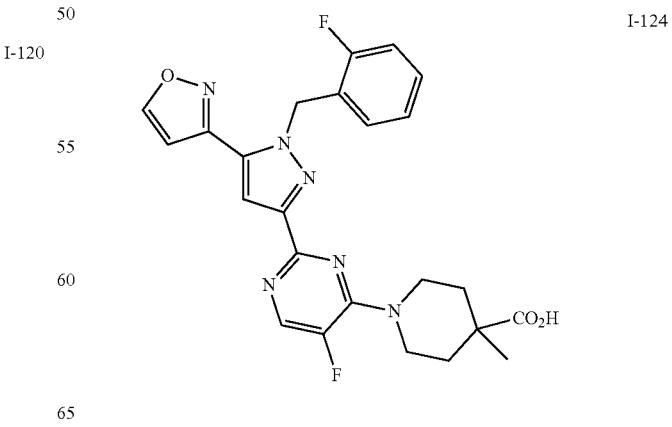

TABLE 1A-continued
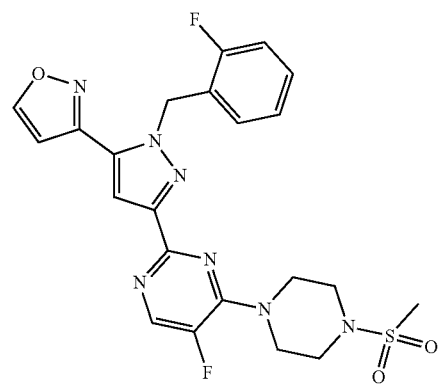 [SMILES: CS(=O)(=O)N1CCN(c2nc(-c3cc(-c4ccon4)n(Cc4ccccc4F)n3)ncc2F)CC1]
I-125
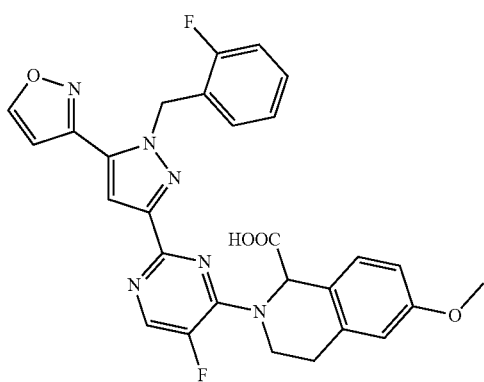 [SMILES: COc1ccc2c(c1)CCN(c1nc(-c3cc(-c4ccon4)n(Cc4ccccc4F)n3)ncc1F)C2C(=O)O]
I-126
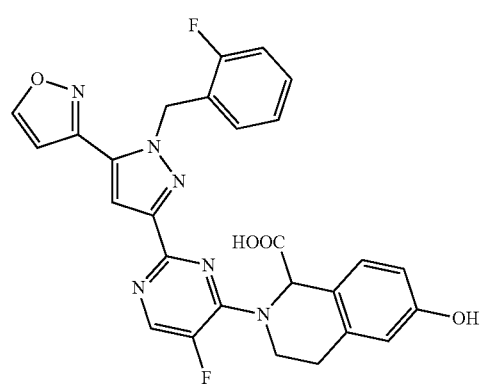 [SMILES: O=C(O)C1c2ccc(O)cc2CCN1c1nc(-c2cc(-c3ccon3)n(Cc3ccccc3F)n2)ncc1F]
I-127
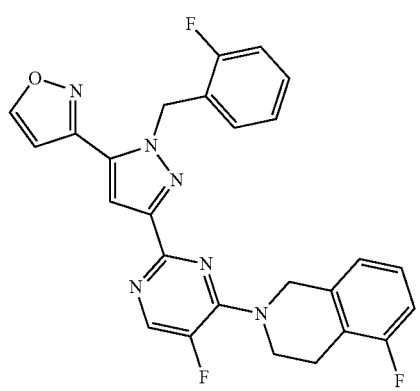 [SMILES: Fc1ccccc1Cn1nc(-c2ncc(F)c(N3CCc4c(F)cccc4C3)n2)cc1-c1ccon1]
I-128
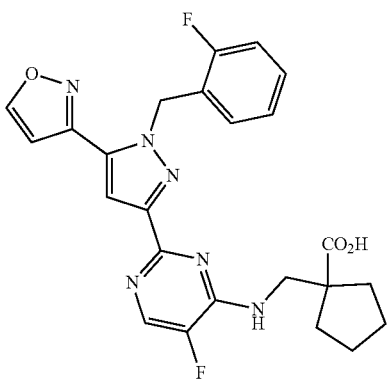 [SMILES: O=C(O)C1(CNc2nc(-c3cc(-c4ccon4)n(Cc4ccccc4F)n3)ncc2F)CCCC1]
I-129
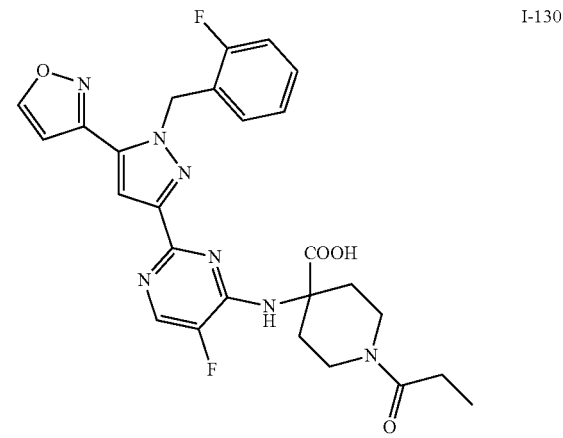
I-130
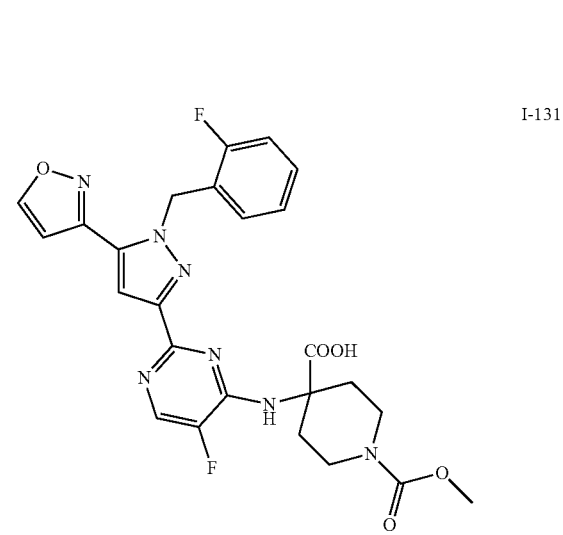
I-131

TABLE 1A-continued
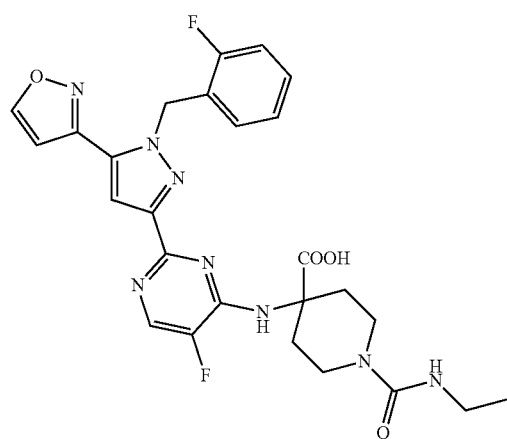 [SMILES: CCNC(=O)N1CCC(Nc2nc(-c3cc(-c4ccon4)n(Cc4ccccc4F)n3)ncc2F)(C(=O)O)CC1]
I-132
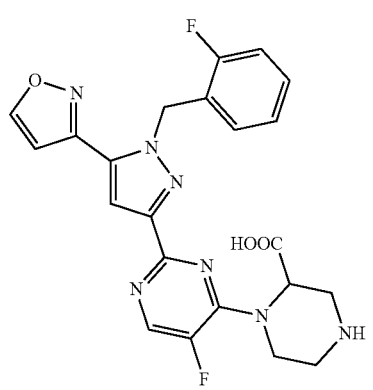 [SMILES: O=C(O)C1CNCCN1c1nc(-c2cc(-c3ccon3)n(Cc3ccccc3F)n2)ncc1F]
I-133
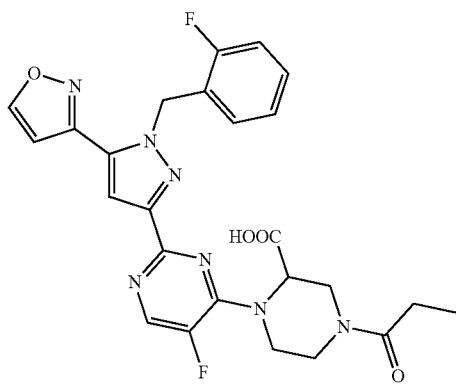 [SMILES: CCC(=O)N1CCN(c2nc(-c3cc(-c4ccon4)n(Cc4ccccc4F)n3)ncc2F)C(C(=O)O)C1]
I-134
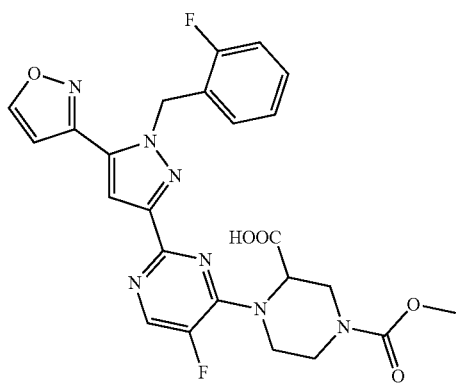 [SMILES: COC(=O)N1CCN(c2nc(-c3cc(-c4ccon4)n(Cc4ccccc4F)n3)ncc2F)C(C(=O)O)C1]
I-135
TABLE 1A-continued
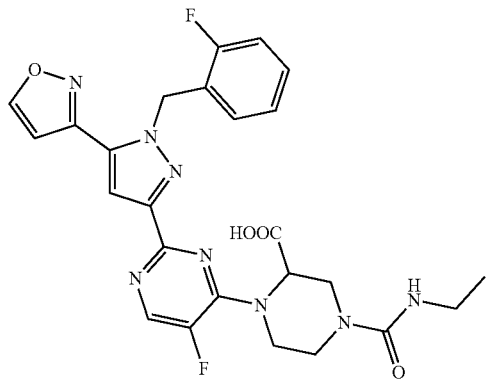 [SMILES: CCNC(=O)N1CCN(c2nc(-c3cc(-c4ccon4)n(Cc4ccccc4F)n3)ncc2F)C(C(=O)O)C1]
I-136
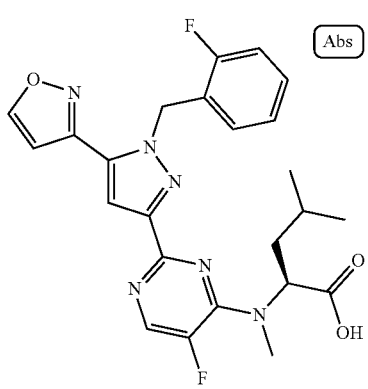 [SMILES: CC(C)C[C@@H](C(=O)O)N(C)c1nc(-c2cc(-c3ccon3)n(Cc3ccccc3F)n2)ncc1F]
I-137
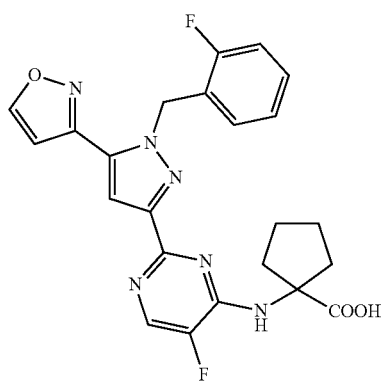 [SMILES: O=C(O)C1(Nc2nc(-c3cc(-c4ccon4)n(Cc4ccccc4F)n3)ncc2F)CCCC1]
I-138
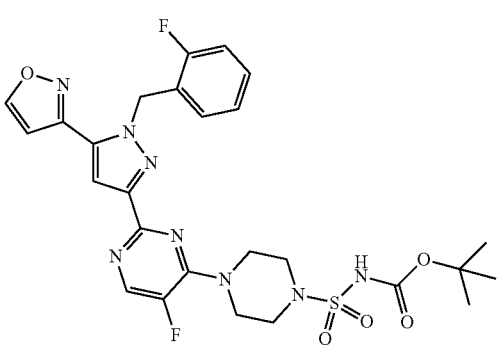 [SMILES: CC(C)(C)OC(=O)NS(=O)(=O)N1CCN(c2nc(-c3cc(-c4ccon4)n(Cc4ccccc4F)n3)ncc2F)CC1]
I-139

TABLE 1A-continued
I-140
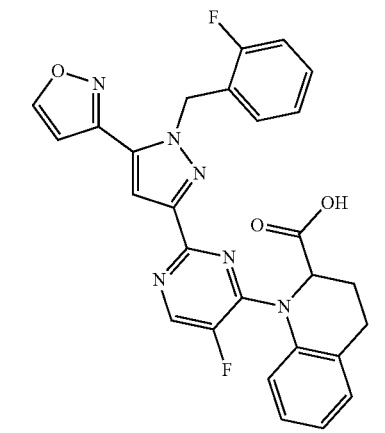 [SMILES: O=C(O)C1CCc2ccccc2N1c1nc(-c2cc(-c3ccon3)n(Cc3ccccc3F)n2)ncc1F]
I-141
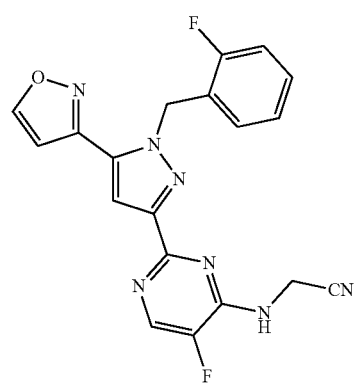 [SMILES: N#CCNc1nc(-c2cc(-c3ccon3)n(Cc3ccccc3F)n2)ncc1F]
I-142
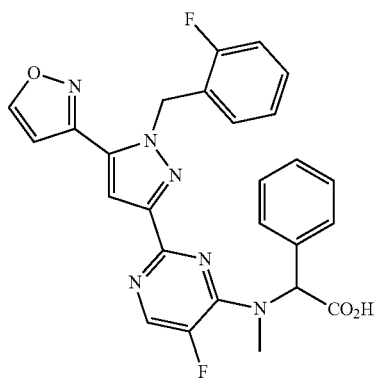 [SMILES: CN(c1nc(-c2cc(-c3ccon3)n(Cc3ccccc3F)n2)ncc1F)C(C(=O)O)c1ccccc1]
I-143
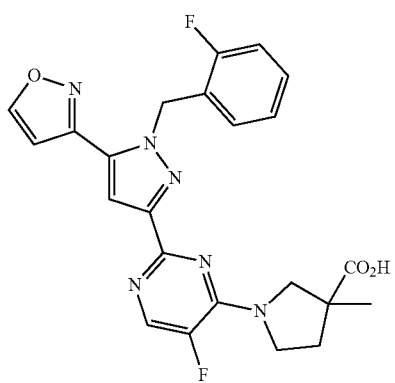 [SMILES: CC1(C(=O)O)CCN(c2nc(-c3cc(-c4ccon4)n(Cc4ccccc4F)n3)ncc2F)C1]
TABLE 1A-continued
I-144
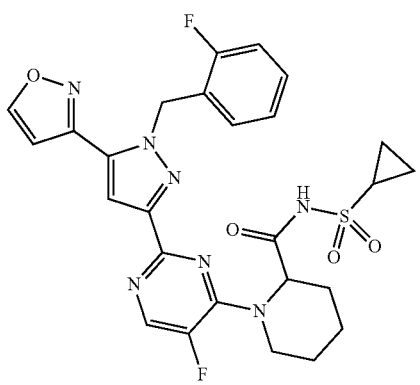 [SMILES: O=C(NS(=O)(=O)C1CC1)C1CCCCN1c1nc(-c2cc(-c3ccon3)n(Cc3ccccc3F)n2)ncc1F]
I-145
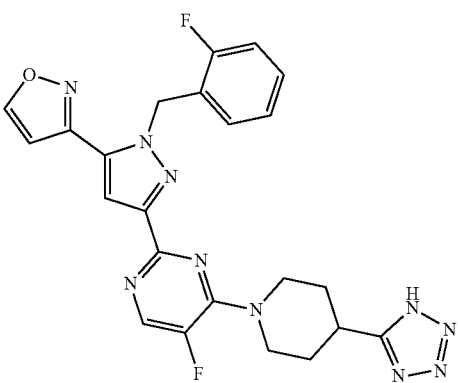 [SMILES: Fc1ccccc1Cn1nc(-c2ncc(F)c(N3CCC(c4nnn[nH]4)CC3)n2)cc1-c1ccon1]
I-146
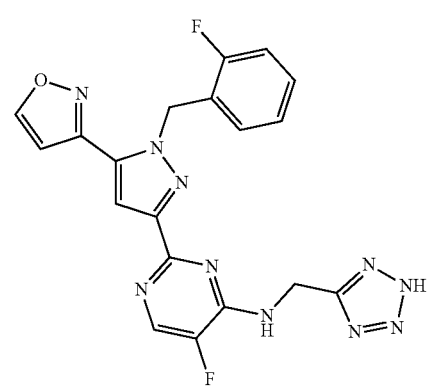 [SMILES: Fc1ccccc1Cn1nc(-c2ncc(F)c(NCc3nn[nH]n3)n2)cc1-c1ccon1]
I-147
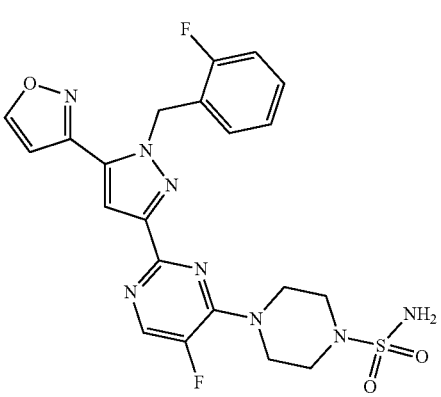 [SMILES: NS(=O)(=O)N1CCN(c2nc(-c3cc(-c4ccon4)n(Cc4ccccc4F)n3)ncc2F)CC1]

TABLE 1A-continued
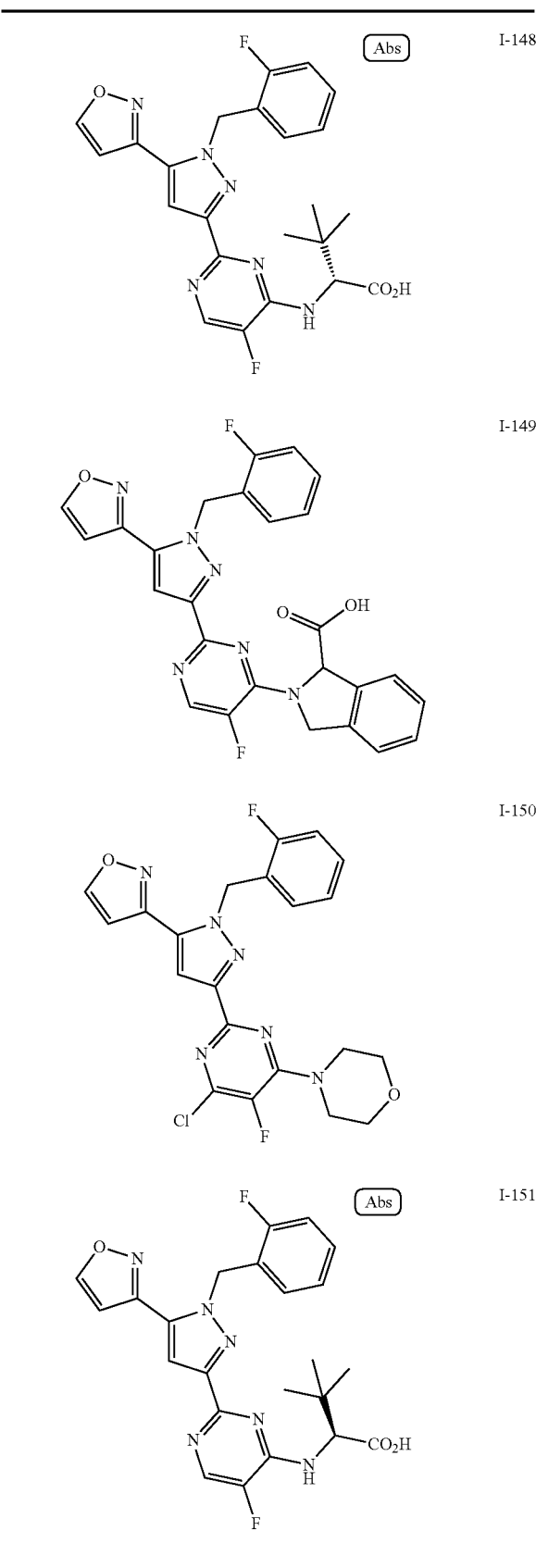
I-148
I-149
I-150
I-151
TABLE 1A-continued
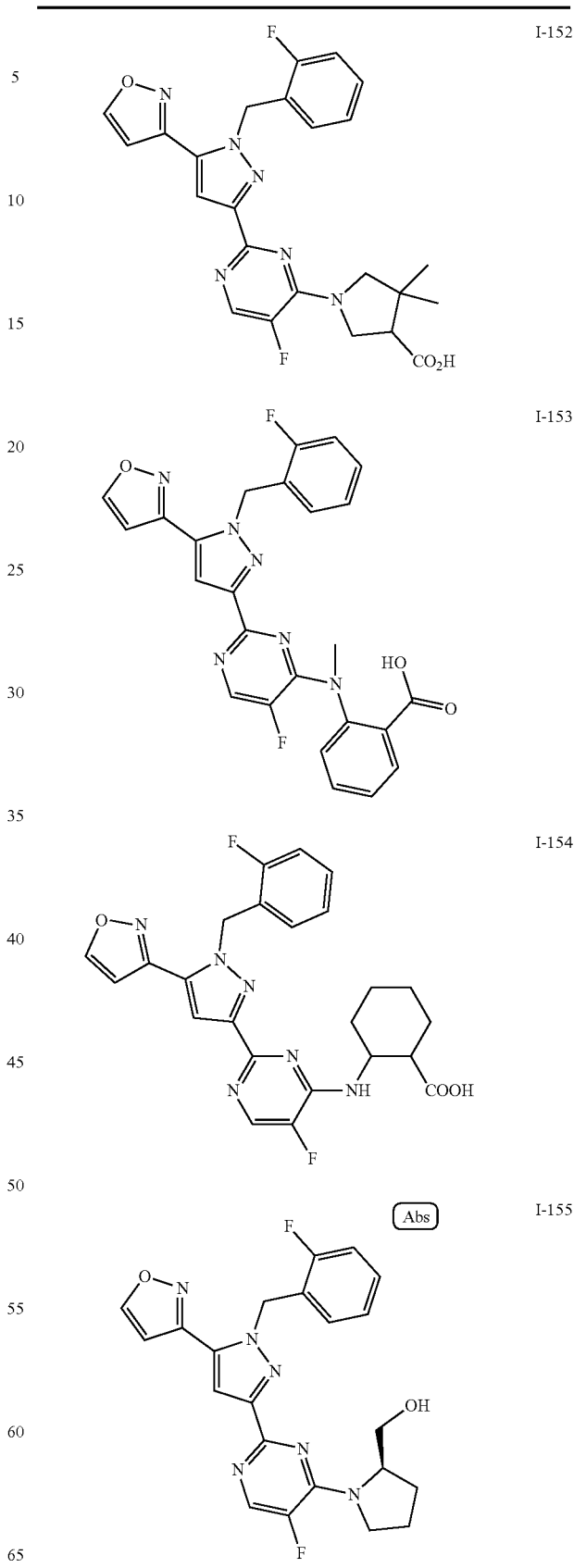
I-152
I-153
I-154
I-155

TABLE 1A-continued
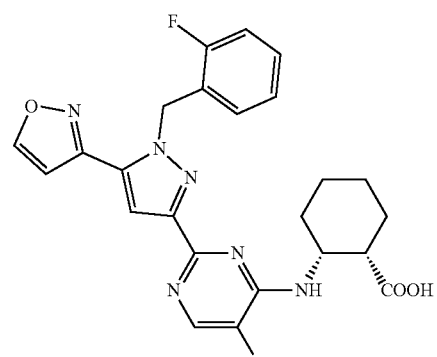
I-156
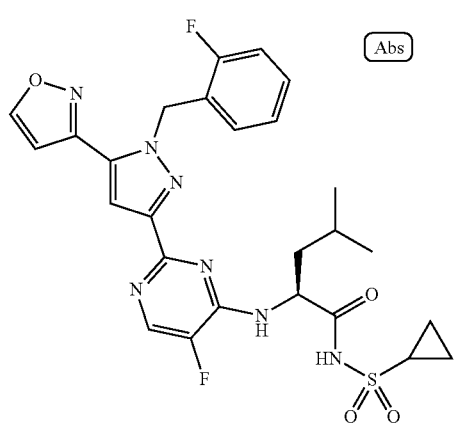 [SMILES: CC(C)C[C@H](Nc1nc(-c2cc(-c3ccon3)n(Cc3ccccc3F)n2)ncc1F)C(=O)NS(=O)(=O)C1CC1]
I-157 [Abs]
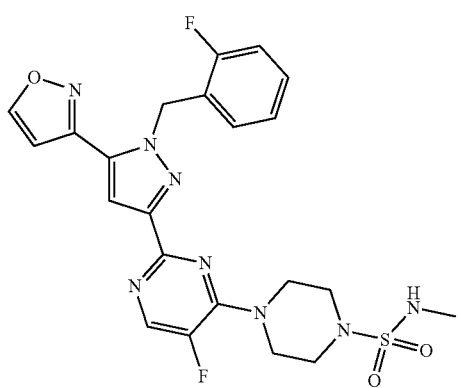 [SMILES: CNS(=O)(=O)N1CCN(c2nc(-c3cc(-c4ccon4)n(Cc4ccccc4F)n3)ncc2F)CC1]
I-158
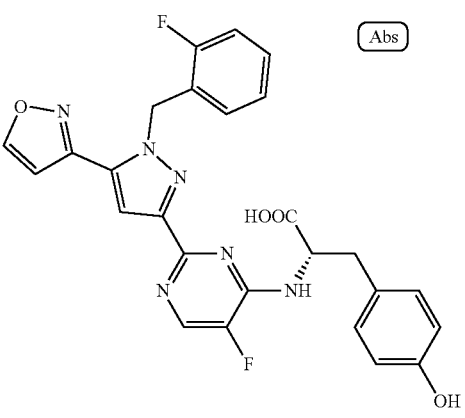 [SMILES: O=C(O)[C@H](Cc1ccc(O)cc1)Nc1nc(-c2cc(-c3ccon3)n(Cc3ccccc3F)n2)ncc1F]
I-159 [Abs]
TABLE 1A-continued
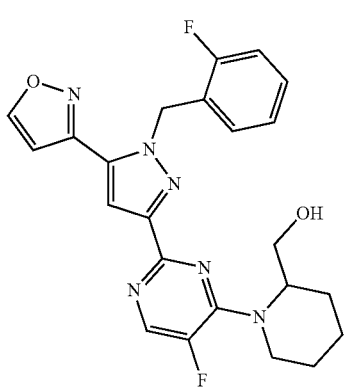 [SMILES: OCC1CCCCN1c1nc(-c2cc(-c3ccon3)n(Cc3ccccc3F)n2)ncc1F]
I-160
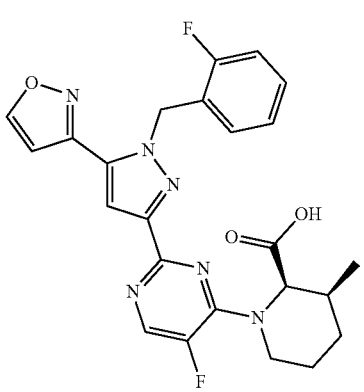 [SMILES: C[C@H]1CCCN(c2nc(-c3cc(-c4ccon4)n(Cc4ccccc4F)n3)ncc2F)[C@H]1C(=O)O]
I-161
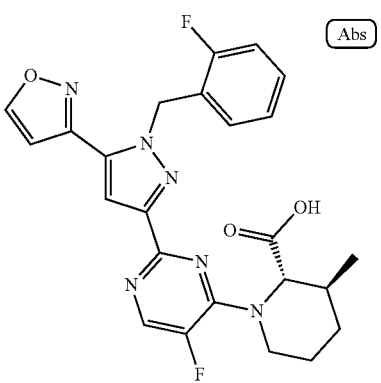 [SMILES: C[C@H]1CCCN(c2nc(-c3cc(-c4ccon4)n(Cc4ccccc4F)n3)ncc2F)[C@@H]1C(=O)O]
I-162 [Abs]
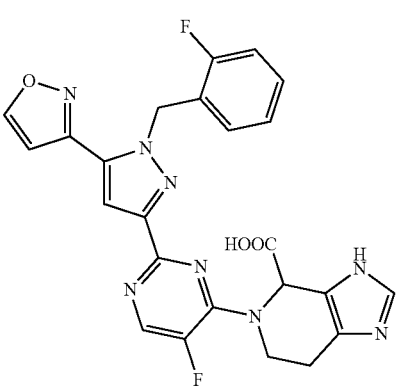 [SMILES: O=C(O)C1c2[nH]cnc2CCN1c1nc(-c2cc(-c3ccon3)n(Cc3ccccc3F)n2)ncc1F]
I-163

TABLE 1A-continued
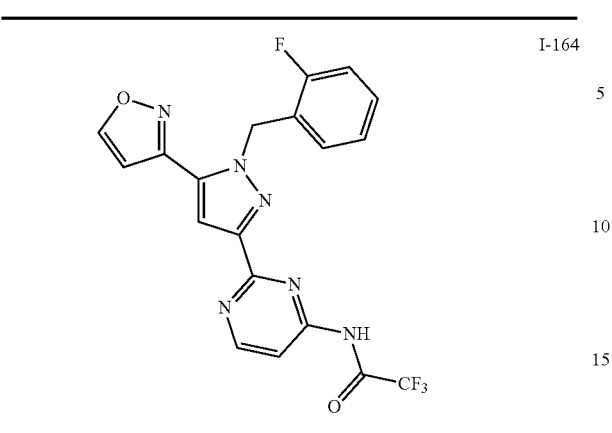
I-164
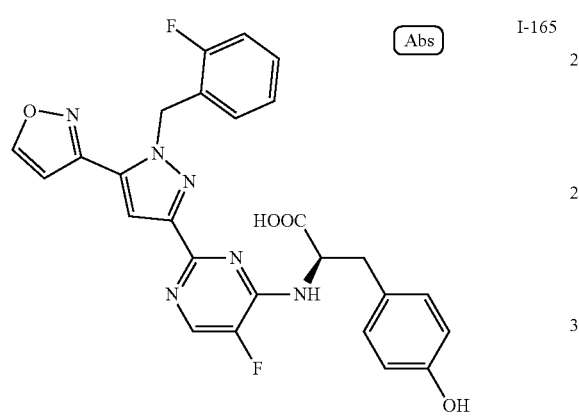
I-165
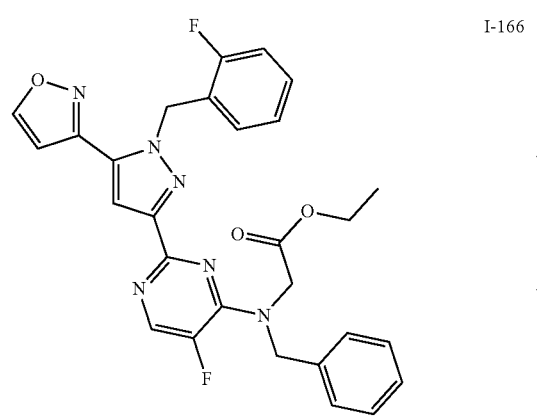
I-166
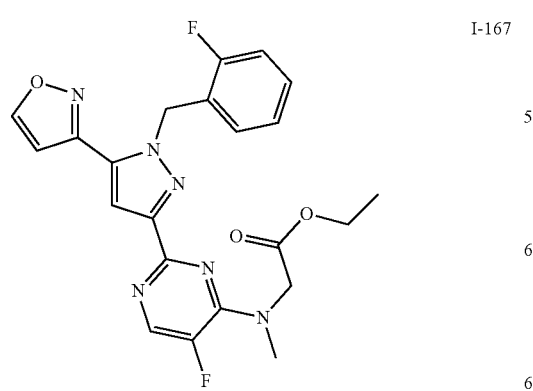
I-167
TABLE 1A-continued
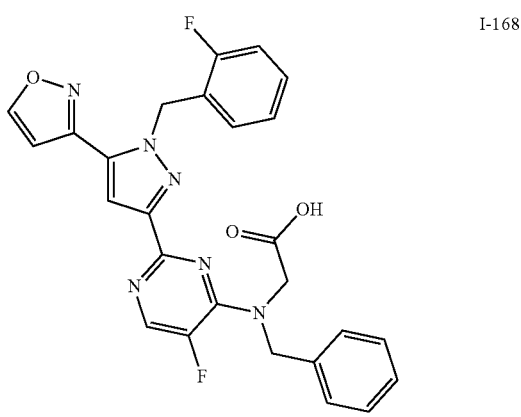
I-168
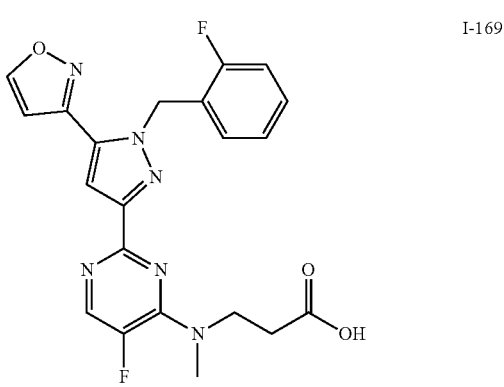
I-169
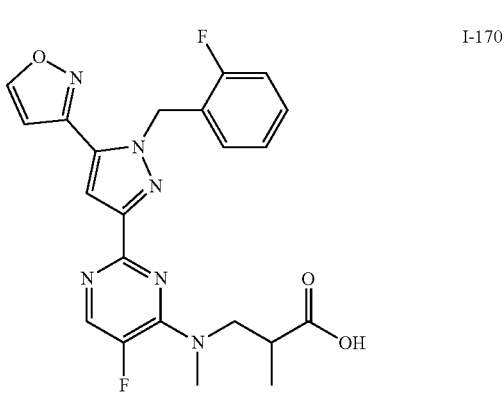
I-170
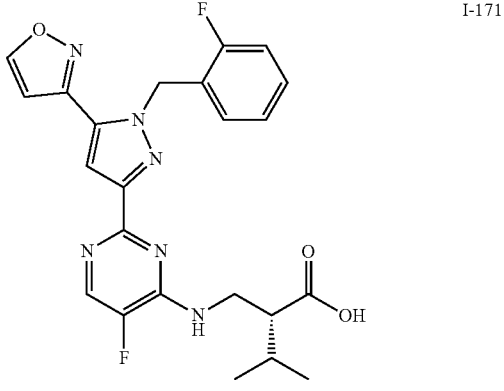
I-171

TABLE 1A-continued
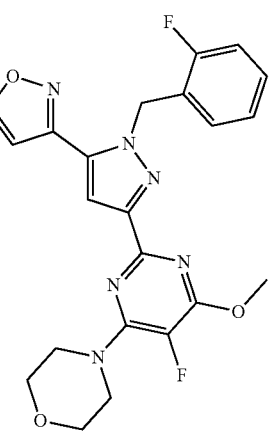
I-172
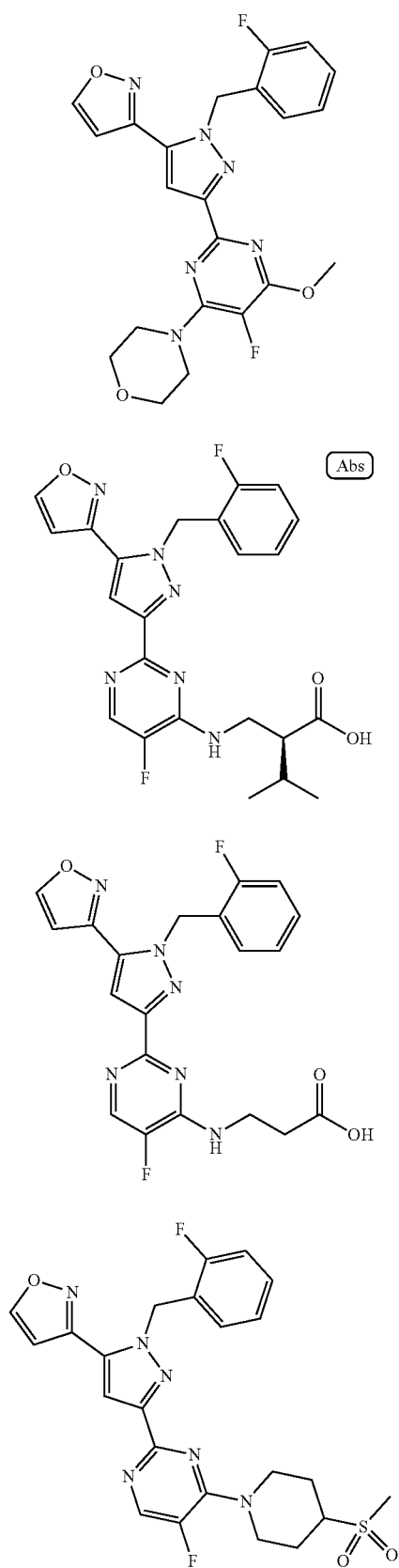
I-173
I-174
I-175
TABLE 1A-continued
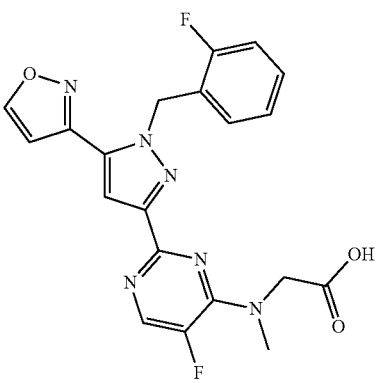 [SMILES: CN(CC(=O)O)c1nc(-c2cc(-c3ccon3)n(Cc3ccccc3F)n2)ncc1F]
I-176
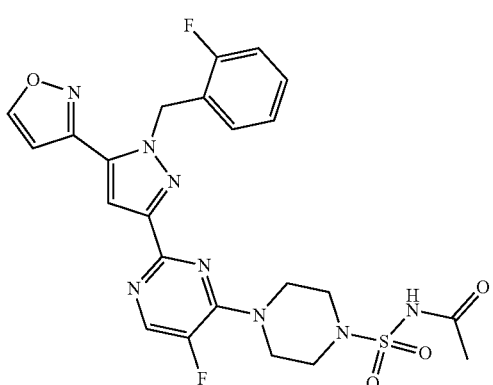 [SMILES: CC(=O)NS(=O)(=O)N1CCN(c2nc(-c3cc(-c4ccon4)n(Cc4ccccc4F)n3)ncc2F)CC1]
I-177
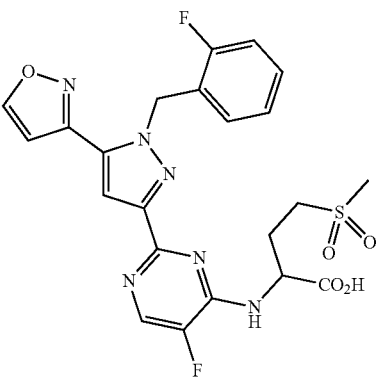 [SMILES: CS(=O)(=O)CCC(Nc1nc(-c2cc(-c3ccon3)n(Cc3ccccc3F)n2)ncc1F)C(=O)O]
I-178
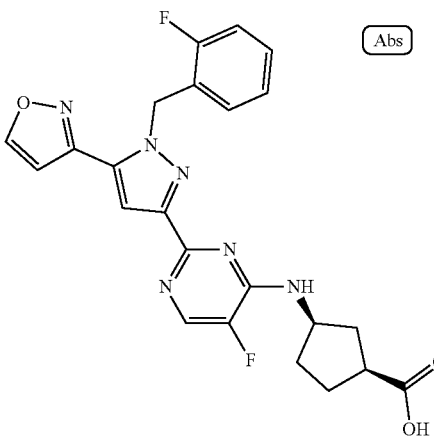
I-179

TABLE 1A-continued
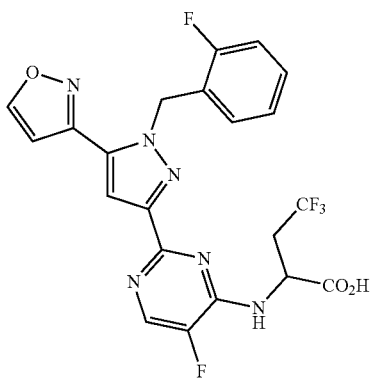 [SMILES: O=C(O)C(CC(F)(F)F)Nc1nc(-c2cc(-c3ccon3)n(Cc3ccccc3F)n2)ncc1F]
I-180
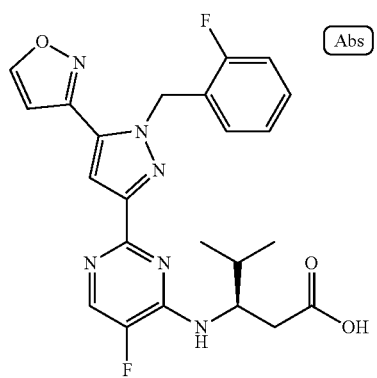 [SMILES: CC(C)[C@@H](CC(=O)O)Nc1nc(-c2cc(-c3ccon3)n(Cc3ccccc3F)n2)ncc1F]
I-181
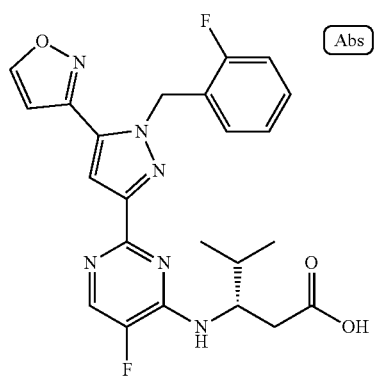 [SMILES: CC(C)[C@H](CC(=O)O)Nc1nc(-c2cc(-c3ccon3)n(Cc3ccccc3F)n2)ncc1F]
I-182
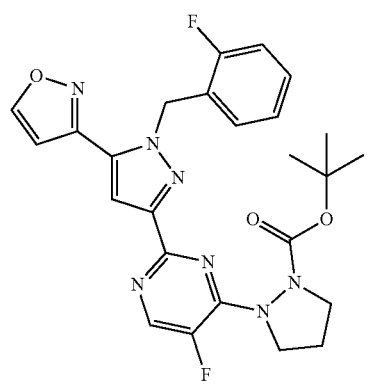 [SMILES: CC(C)(C)OC(=O)N1CCCN1c1nc(-c2cc(-c3ccon3)n(Cc3ccccc3F)n2)ncc1F]
I-183
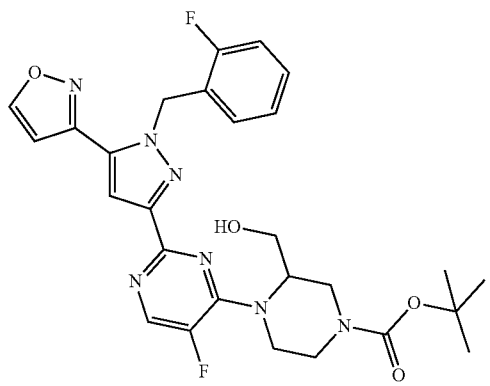 [SMILES: CC(C)(C)OC(=O)N1CCN(c2nc(-c3cc(-c4ccon4)n(Cc4ccccc4F)n3)ncc2F)C(CO)C1]
I-184
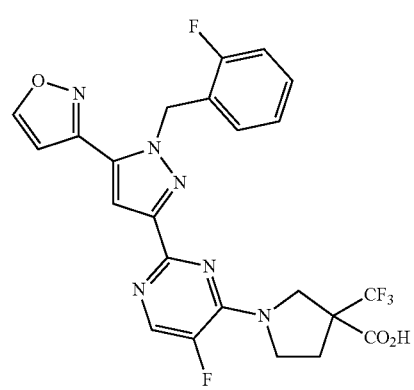 [SMILES: O=C(O)C1(C(F)(F)F)CCN(c2nc(-c3cc(-c4ccon4)n(Cc4ccccc4F)n3)ncc2F)C1]
I-185
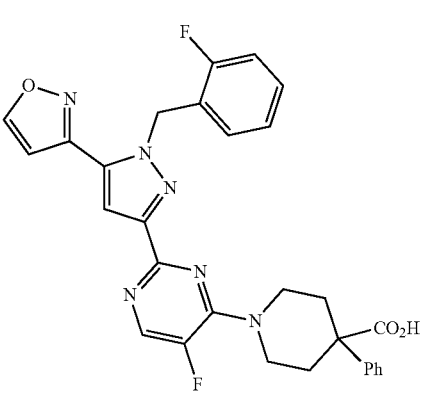 [SMILES: O=C(O)C1(c2ccccc2)CCN(c2nc(-c3cc(-c4ccon4)n(Cc4ccccc4F)n3)ncc2F)CC1]
I-186
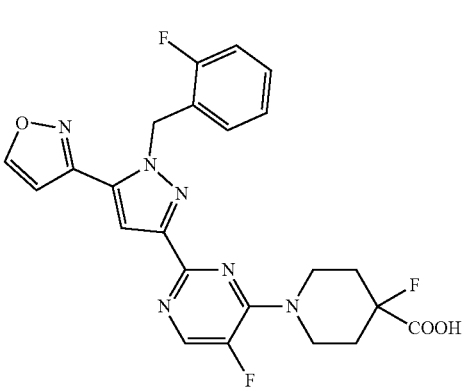 [SMILES: O=C(O)C1(F)CCN(c2nc(-c3cc(-c4ccon4)n(Cc4ccccc4F)n3)ncc2F)CC1]
I-188

TABLE 1A-continued
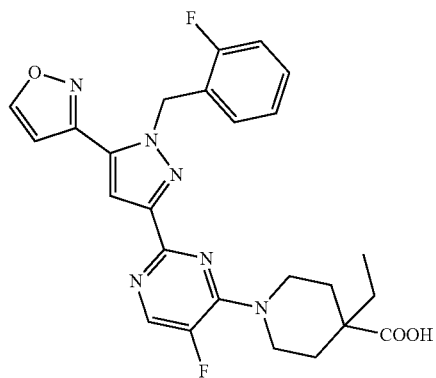 [SMILES: CCC1(C(=O)O)CCN(c2nc(-c3cc(-c4ccon4)n(Cc4ccccc4F)n3)ncc2F)CC1] I-189
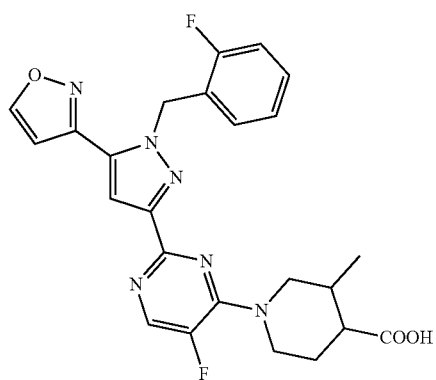 [SMILES: CC1CN(c2nc(-c3cc(-c4ccon4)n(Cc4ccccc4F)n3)ncc2F)CCC1C(=O)O] I-190
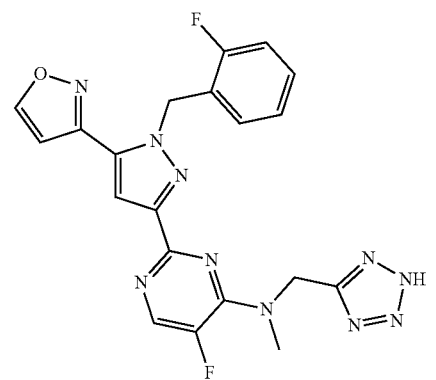 [SMILES: CN(Cc1nn[nH]n1)c1nc(-c2cc(-c3ccon3)n(Cc3ccccc3F)n2)ncc1F] I-191
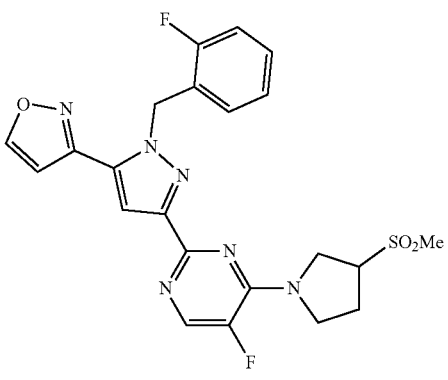 [SMILES: CS(=O)(=O)C1CCN(c2nc(-c3cc(-c4ccon4)n(Cc4ccccc4F)n3)ncc2F)C1] I-192
TABLE 1A-continued
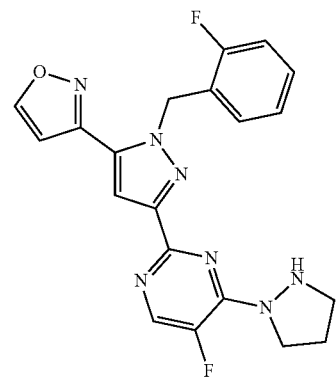 [SMILES: Fc1ccccc1Cn1nc(-c2ncc(F)c(N3CCCN3)n2)cc1-c1ccon1] I-193
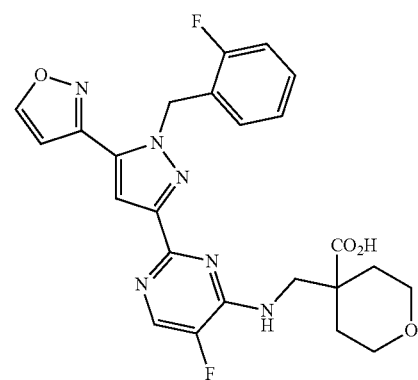 [SMILES: O=C(O)C1(CNc2nc(-c3cc(-c4ccon4)n(Cc4ccccc4F)n3)ncc2F)CCOCC1] I-194
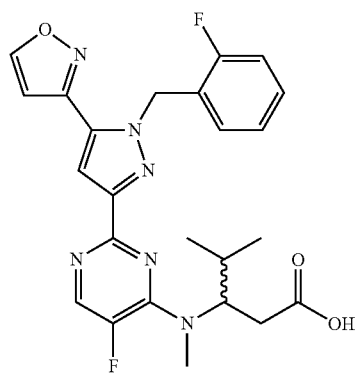 [SMILES: CC(C)C(CC(=O)O)N(C)c1nc(-c2cc(-c3ccon3)n(Cc3ccccc3F)n2)ncc1F] I-195
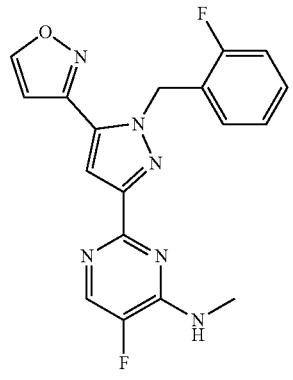 [SMILES: CNc1nc(-c2cc(-c3ccon3)n(Cc3ccccc3F)n2)ncc1F] I-196

TABLE 1A-continued
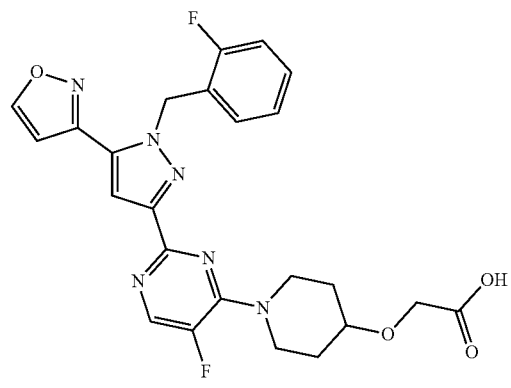 [SMILES: O=C(O)COC1CCN(c2nc(-c3cc(-c4ccon4)n(Cc4ccccc4F)n3)ncc2F)CC1]
I-197
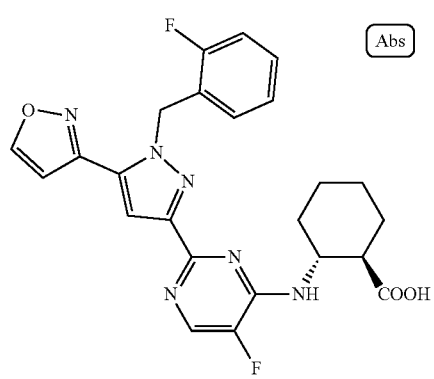 [SMILES: O=C(O)[C@@H]1CCCC[C@H]1Nc1nc(-c2cc(-c3ccon3)n(Cc3ccccc3F)n2)ncc1F]
I-198
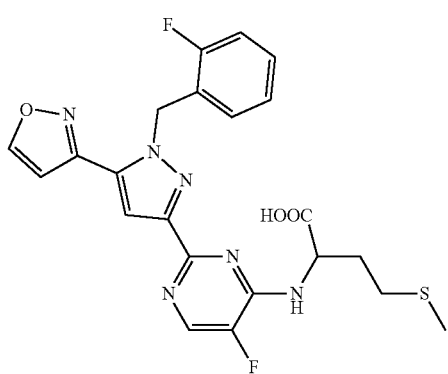 [SMILES: CSCCC(Nc1nc(-c2cc(-c3ccon3)n(Cc3ccccc3F)n2)ncc1F)C(=O)O]
I-199
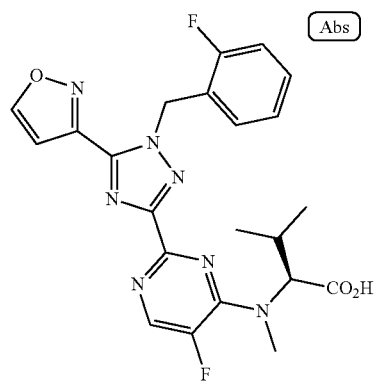 [SMILES: CC(C)[C@@H](C(=O)O)N(C)c1nc(-c2nc(-c3ccon3)n(Cc3ccccc3F)n2)ncc1F]
I-200
TABLE 1A-continued
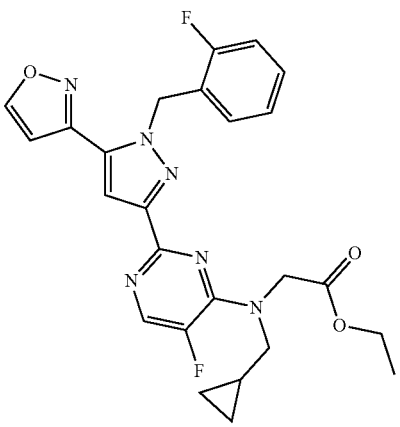 [SMILES: CCOC(=O)CN(CC1CC1)c1nc(-c2cc(-c3ccon3)n(Cc3ccccc3F)n2)ncc1F]
I-201
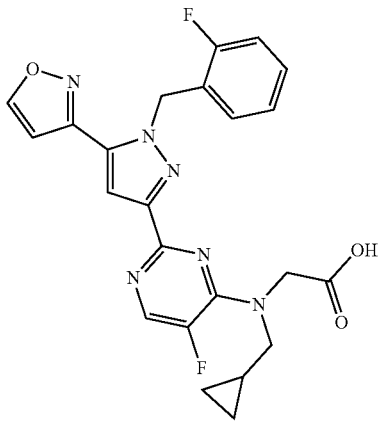 [SMILES: O=C(O)CN(CC1CC1)c1nc(-c2cc(-c3ccon3)n(Cc3ccccc3F)n2)ncc1F]
I-202
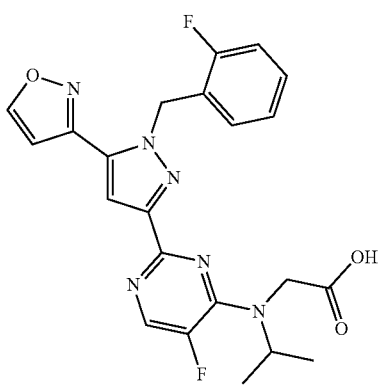 [SMILES: CC(C)N(CC(=O)O)c1nc(-c2cc(-c3ccon3)n(Cc3ccccc3F)n2)ncc1F]
I-203
I-204

TABLE 1A-continued
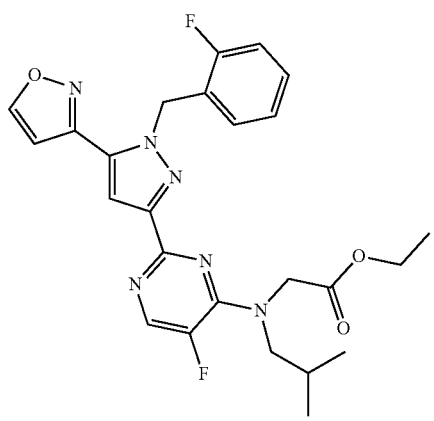 [SMILES: CCOC(=O)CN(CC(C)C)c1nc(-c2cc(-c3ccon3)n(Cc3ccccc3F)n2)ncc1F]
I-205
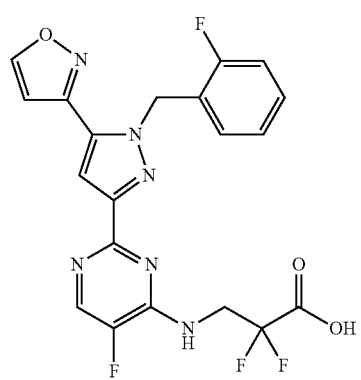 [SMILES: O=C(O)C(F)(F)CNc1nc(-c2cc(-c3ccon3)n(Cc3ccccc3F)n2)ncc1F]
I-206
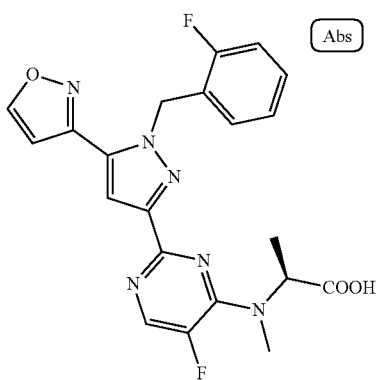 [SMILES: C[C@@H](C(=O)O)N(C)c1nc(-c2cc(-c3ccon3)n(Cc3ccccc3F)n2)ncc1F]
I-207
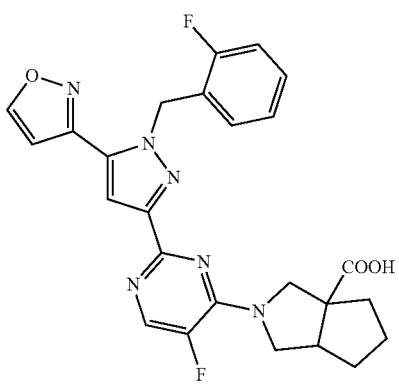 [SMILES: O=C(O)C12CCCC1CN(c1nc(-c3cc(-c4ccon4)n(Cc4ccccc4F)n3)ncc1F)C2]
I-208
TABLE 1A-continued
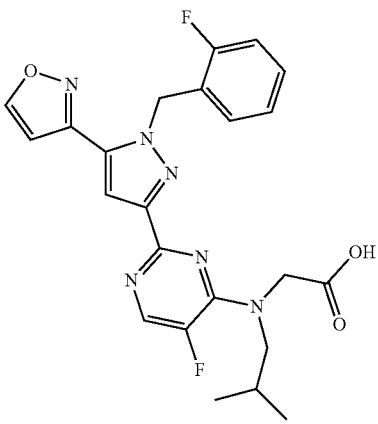 [SMILES: CC(C)CN(CC(=O)O)c1nc(-c2cc(-c3ccon3)n(Cc3ccccc3F)n2)ncc1F]
I-209
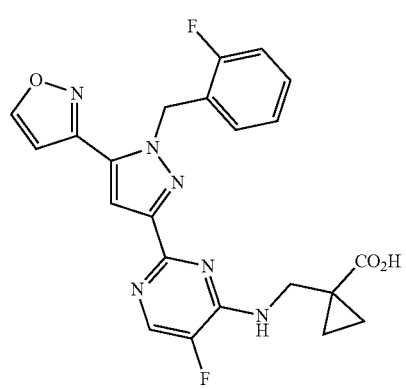 [SMILES: O=C(O)C1(CNc2nc(-c3cc(-c4ccon4)n(Cc4ccccc4F)n3)ncc2F)CC1]
I-210
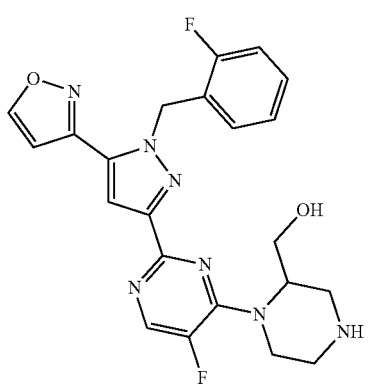 [SMILES: OCC1CNCCN1c1nc(-c2cc(-c3ccon3)n(Cc3ccccc3F)n2)ncc1F]
I-211
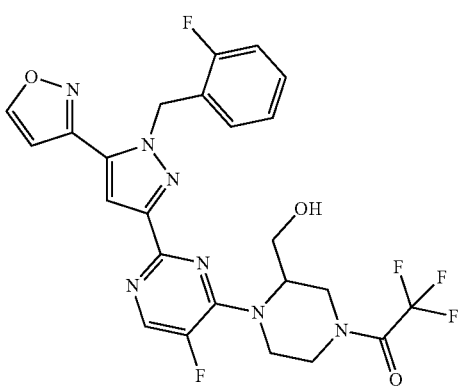 [SMILES: O=C(N1CCN(c2nc(-c3cc(-c4ccon4)n(Cc4ccccc4F)n3)ncc2F)C(CO)C1)C(F)(F)F]
I-212

TABLE 1A-continued
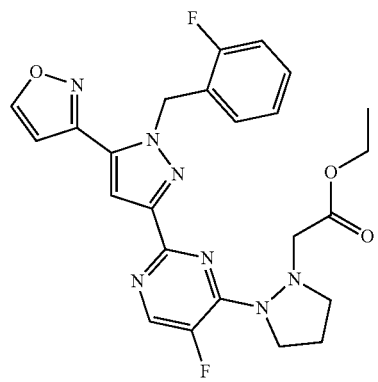 [SMILES: CCOC(=O)CN1CCCN1c1nc(-c2cc(-c3ccon3)n(Cc3ccccc3F)n2)ncc1F]
I-213
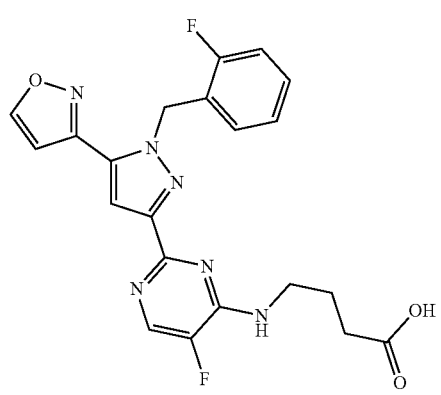 [SMILES: O=C(O)CCCNc1nc(-c2cc(-c3ccon3)n(Cc3ccccc3F)n2)ncc1F]
I-214
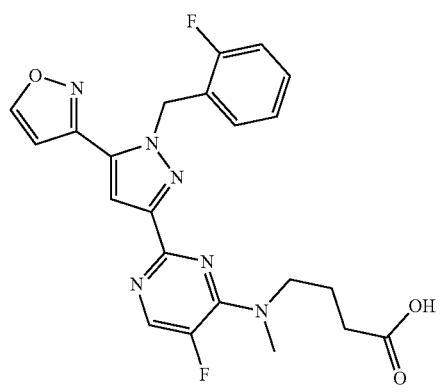 [SMILES: CN(CCCC(=O)O)c1nc(-c2cc(-c3ccon3)n(Cc3ccccc3F)n2)ncc1F]
I-215
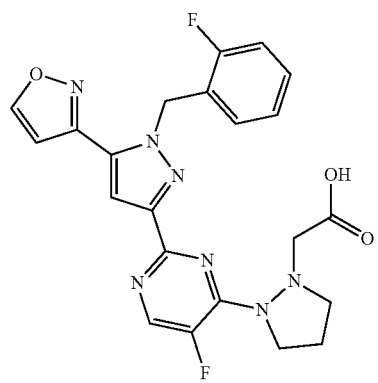 [SMILES: O=C(O)CN1CCCN1c1nc(-c2cc(-c3ccon3)n(Cc3ccccc3F)n2)ncc1F]
I-216
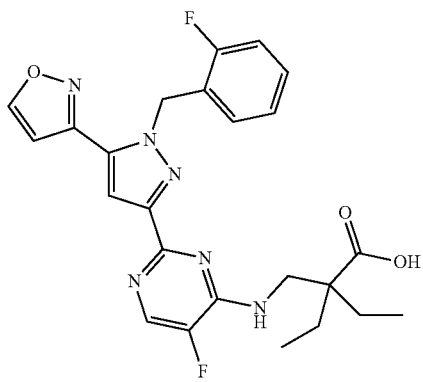 [SMILES: CCC(CC)(CNc1nc(-c2cc(-c3ccon3)n(Cc3ccccc3F)n2)ncc1F)C(=O)O]
I-217
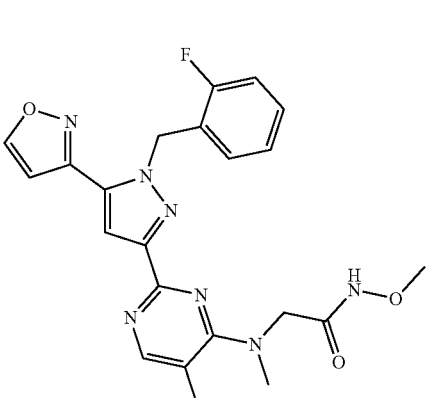
I-218
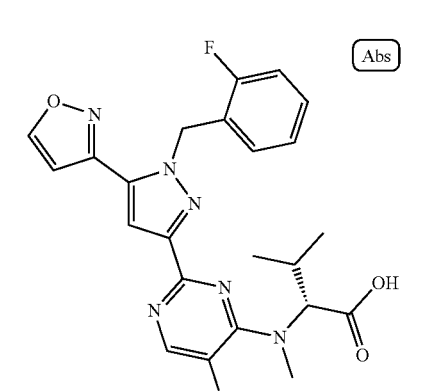
I-219
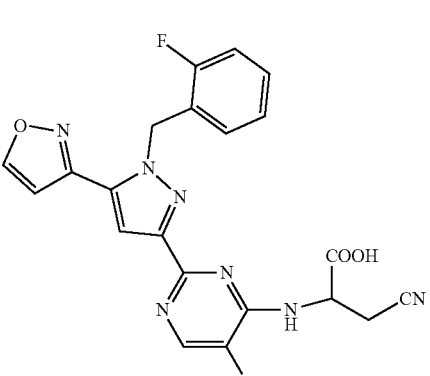
I-220

TABLE 1A-continued
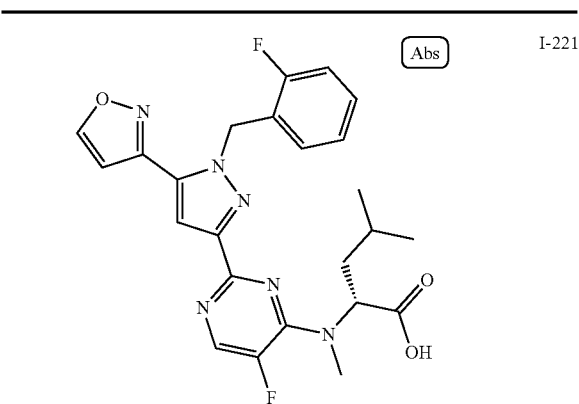
I-221
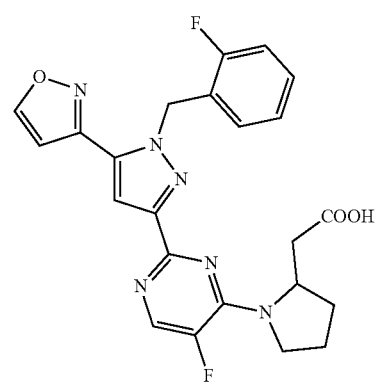 [SMILES: O=C(O)CC1CCCN1c1nc(-c2cc(-c3ccon3)n(Cc3ccccc3F)n2)ncc1F]
I-222
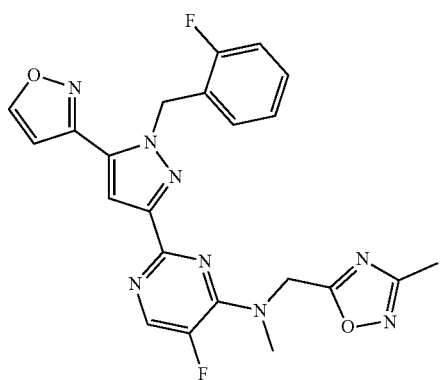 [SMILES: Cc1noc(CN(C)c2nc(-c3cc(-c4ccon4)n(Cc4ccccc4F)n3)ncc2F)n1]
I-223
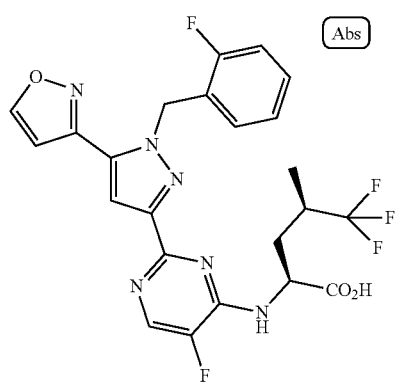 [SMILES: C[C@H](C[C@H](Nc1nc(-c2cc(-c3ccon3)n(Cc3ccccc3F)n2)ncc1F)C(=O)O)C(F)(F)F]
I-224
TABLE 1A-continued
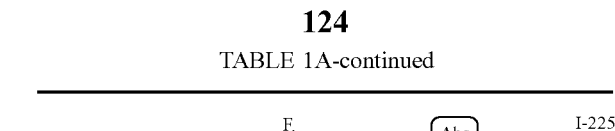
I-225
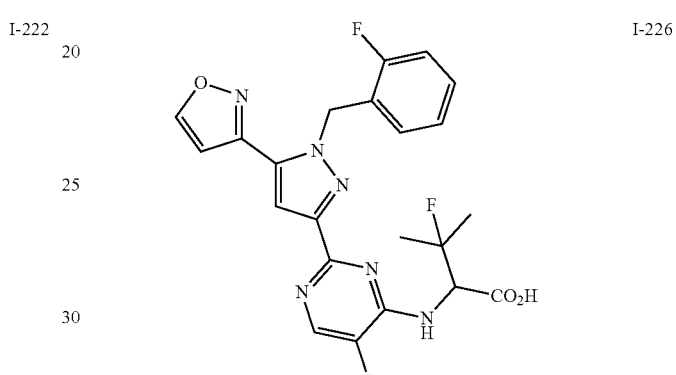
I-226
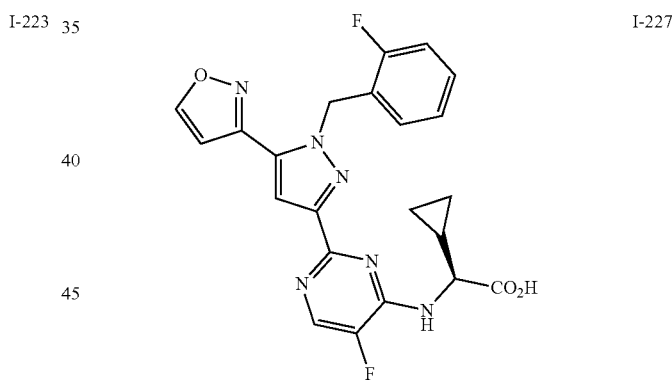
I-227
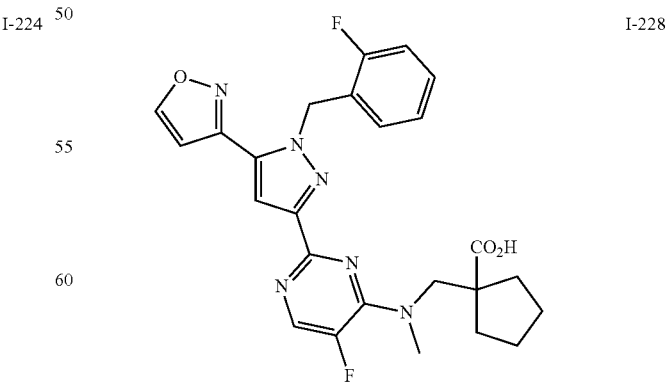
I-228

TABLE 1A-continued
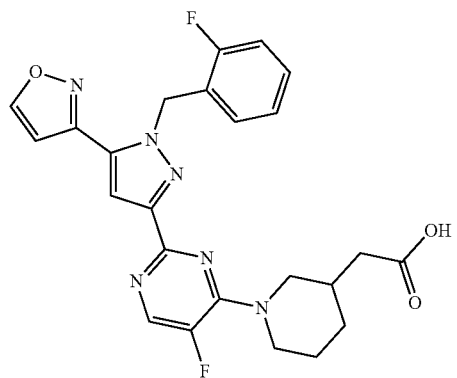 [SMILES: O=C(O)CC1CCCN(c2nc(-c3cc(-c4ccon4)n(Cc4ccccc4F)n3)ncc2F)C1]
I-229
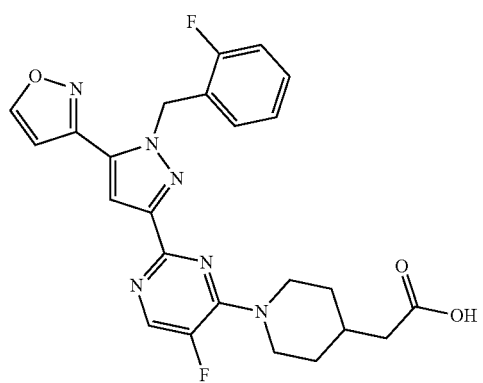 [SMILES: O=C(O)CC1CCN(c2nc(-c3cc(-c4ccon4)n(Cc4ccccc4F)n3)ncc2F)CC1]
I-230
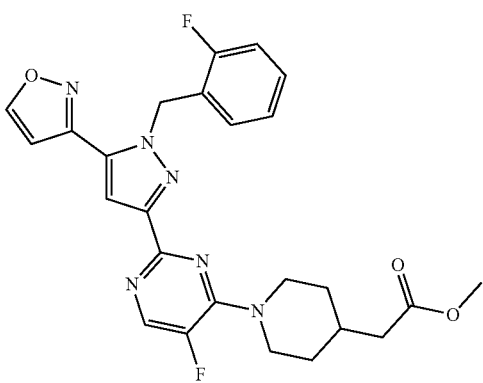 [SMILES: COC(=O)CC1CCN(c2nc(-c3cc(-c4ccon4)n(Cc4ccccc4F)n3)ncc2F)CC1]
I-231
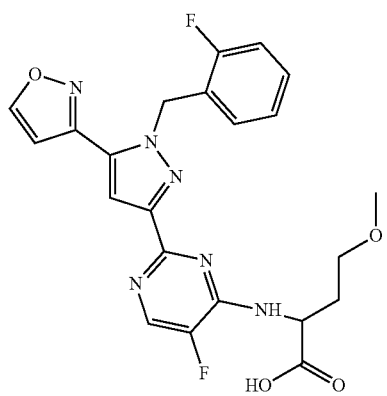 [SMILES: COCCC(Nc1nc(-c2cc(-c3ccon3)n(Cc3ccccc3F)n2)ncc1F)C(=O)O]
I-232
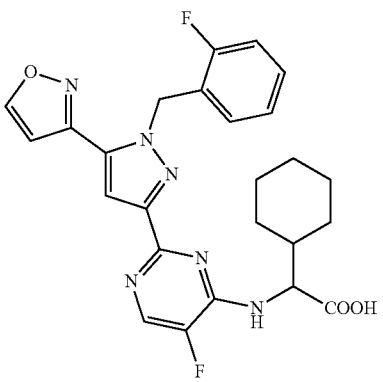 [SMILES: O=C(O)C(Nc1nc(-c2cc(-c3ccon3)n(Cc3ccccc3F)n2)ncc1F)C1CCCCC1]
I-233
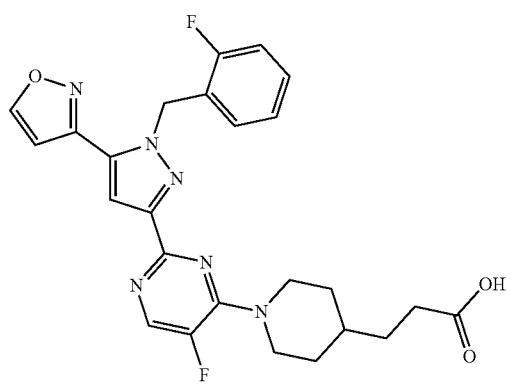 [SMILES: O=C(O)CCC1CCN(c2nc(-c3cc(-c4ccon4)n(Cc4ccccc4F)n3)ncc2F)CC1]
I-234
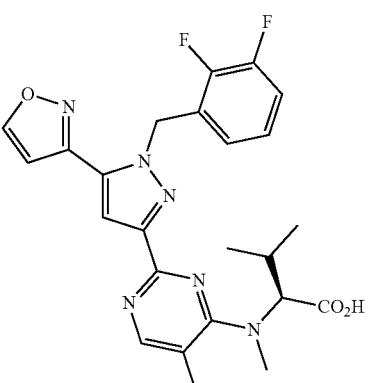
I-235
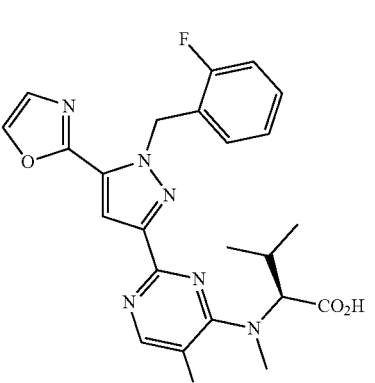
I-236

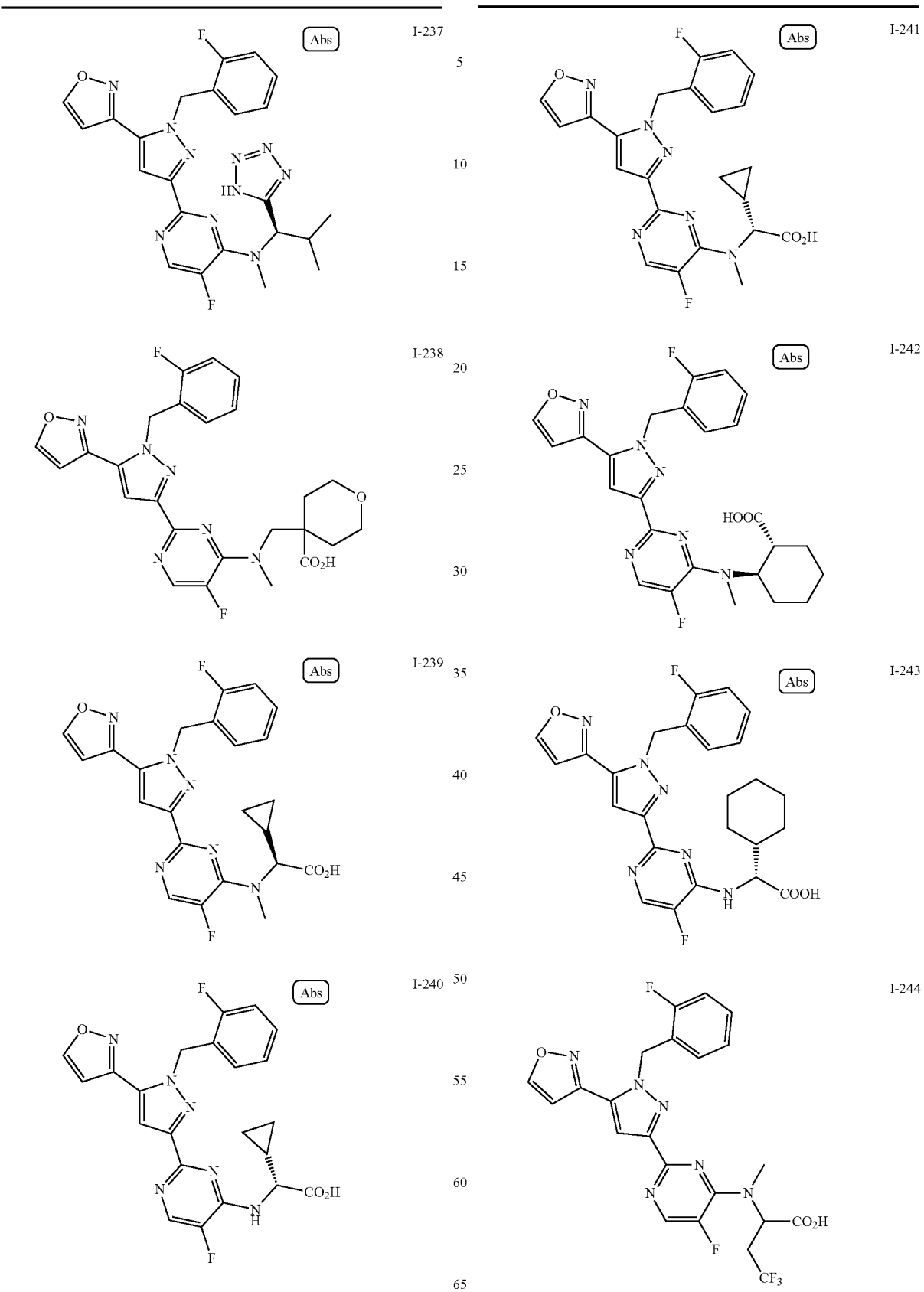

TABLE 1A-continued
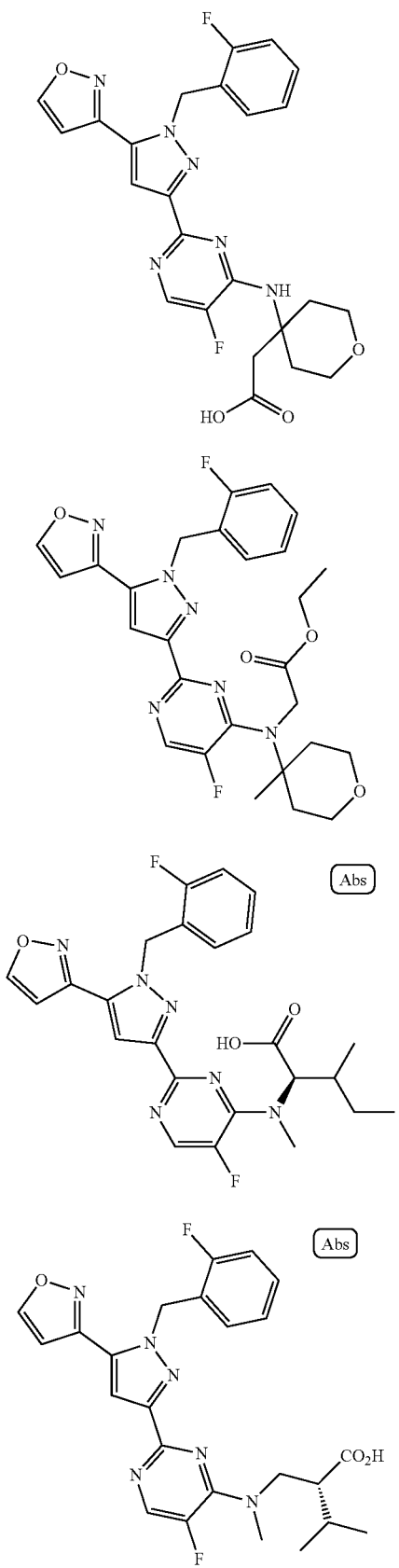
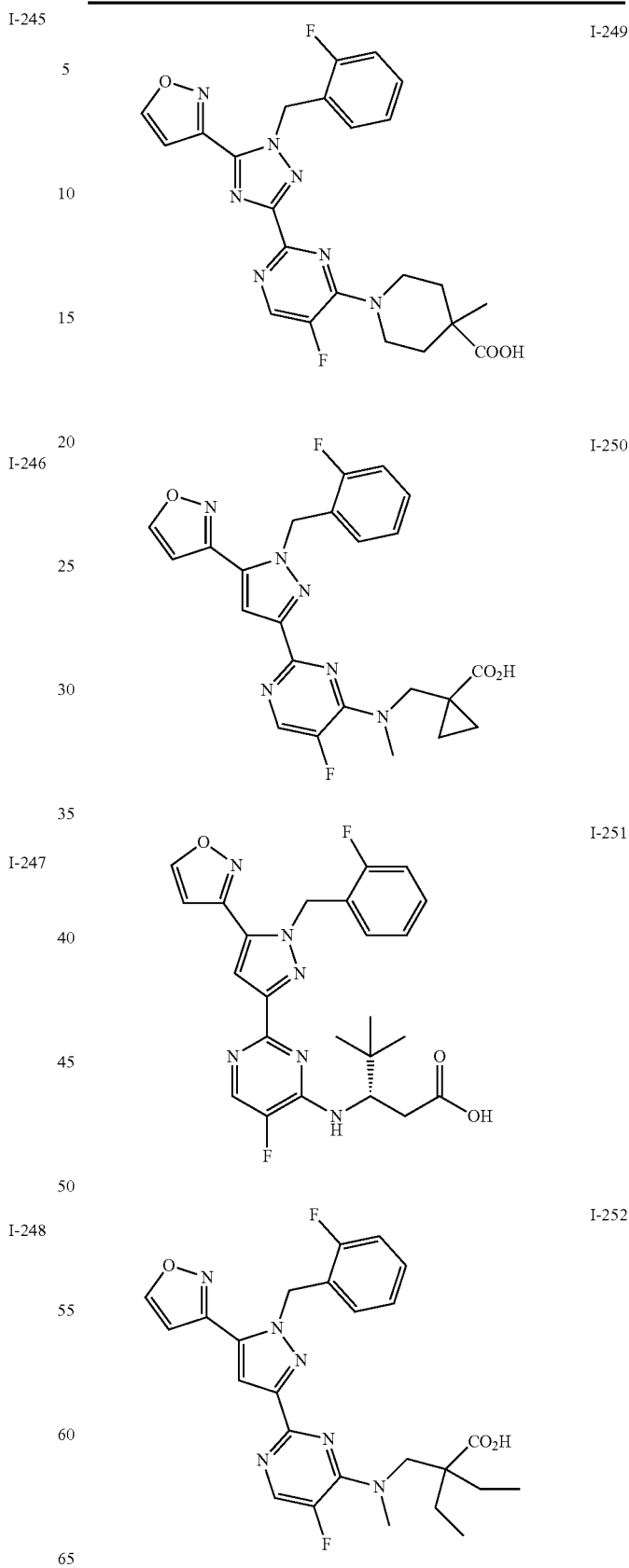

TABLE 1A-continued
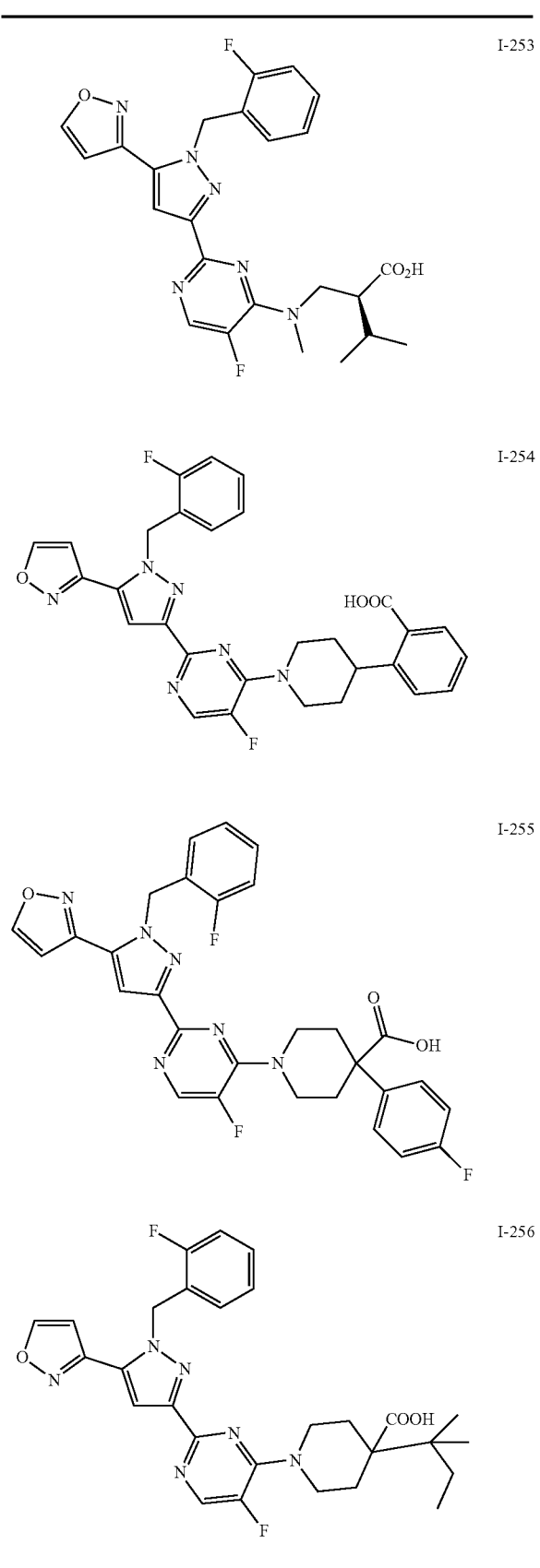
I-253
I-254
I-255
I-256
TABLE 1A-continued
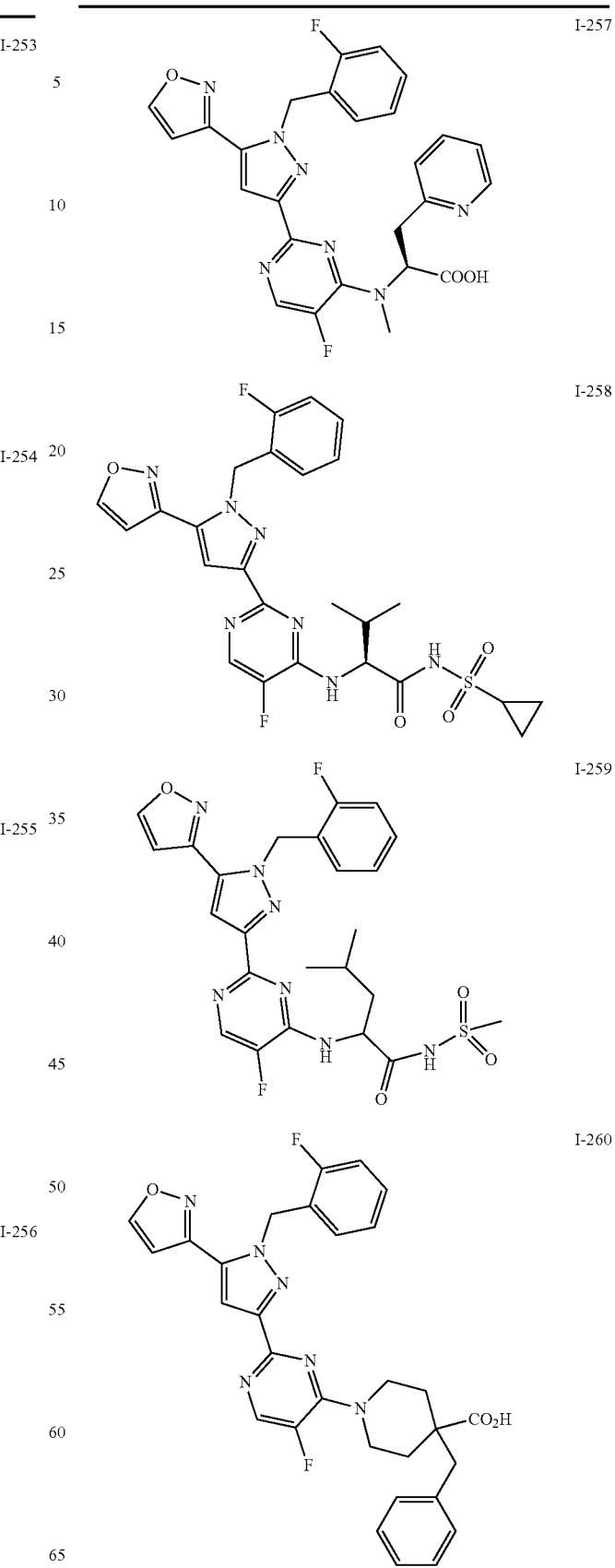
I-257
I-258
I-259
I-260

TABLE 1A-continued
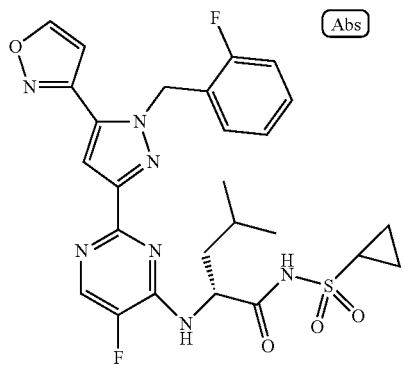 [SMILES: CC(C)C[C@@H](Nc1nc(-c2cc(-c3ccon3)n(Cc3ccccc3F)n2)ncc1F)C(=O)NS(=O)(=O)C1CC1]
I-261
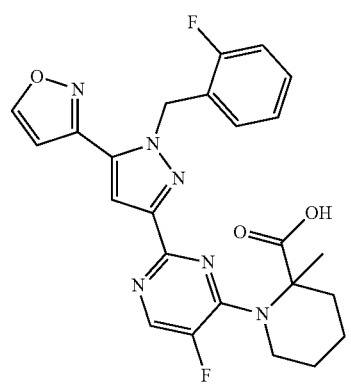 [SMILES: CC1(C(=O)O)CCCCN1c1nc(-c2cc(-c3ccon3)n(Cc3ccccc3F)n2)ncc1F]
I-262
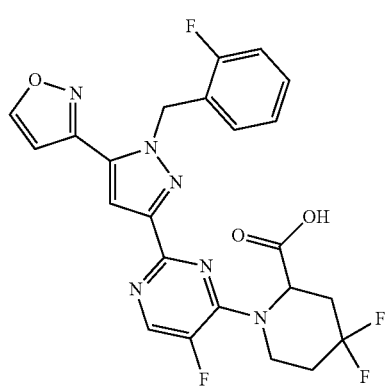 [SMILES: O=C(O)C1CC(F)(F)CCN1c1nc(-c2cc(-c3ccon3)n(Cc3ccccc3F)n2)ncc1F]
I-263
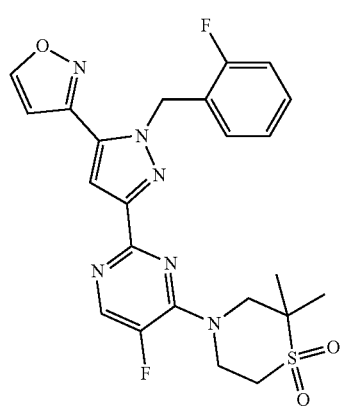 [SMILES: CC1(C)CN(c2nc(-c3cc(-c4ccon4)n(Cc4ccccc4F)n3)ncc2F)CCS1(=O)=O]
I-264
TABLE 1A-continued
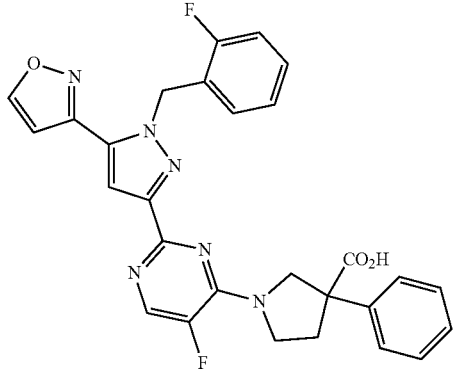 [SMILES: O=C(O)C1(c2ccccc2)CCN(c2nc(-c3cc(-c4ccon4)n(Cc4ccccc4F)n3)ncc2F)C1]
I-265
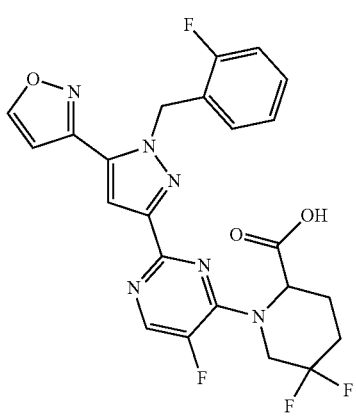 [SMILES: O=C(O)C1CCC(F)(F)CN1c1nc(-c2cc(-c3ccon3)n(Cc3ccccc3F)n2)ncc1F]
I-266
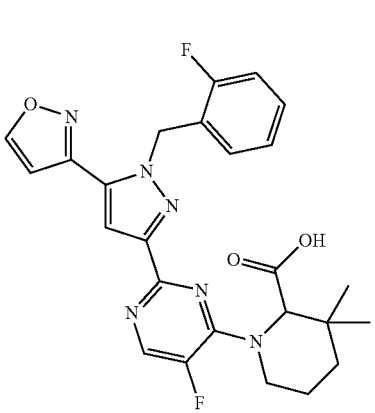 [SMILES: CC1(C)CCCN(c2nc(-c3cc(-c4ccon4)n(Cc4ccccc4F)n3)ncc2F)C1C(=O)O]
I-267
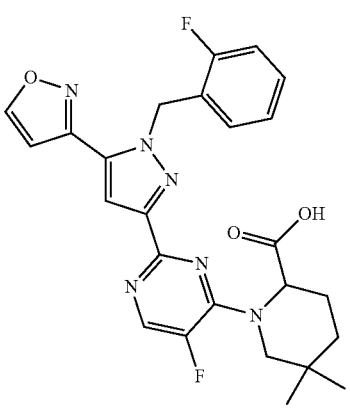 [SMILES: CC1(C)CCC(C(=O)O)N(c2nc(-c3cc(-c4ccon4)n(Cc4ccccc4F)n3)ncc2F)C1]
I-268

TABLE 1A-continued
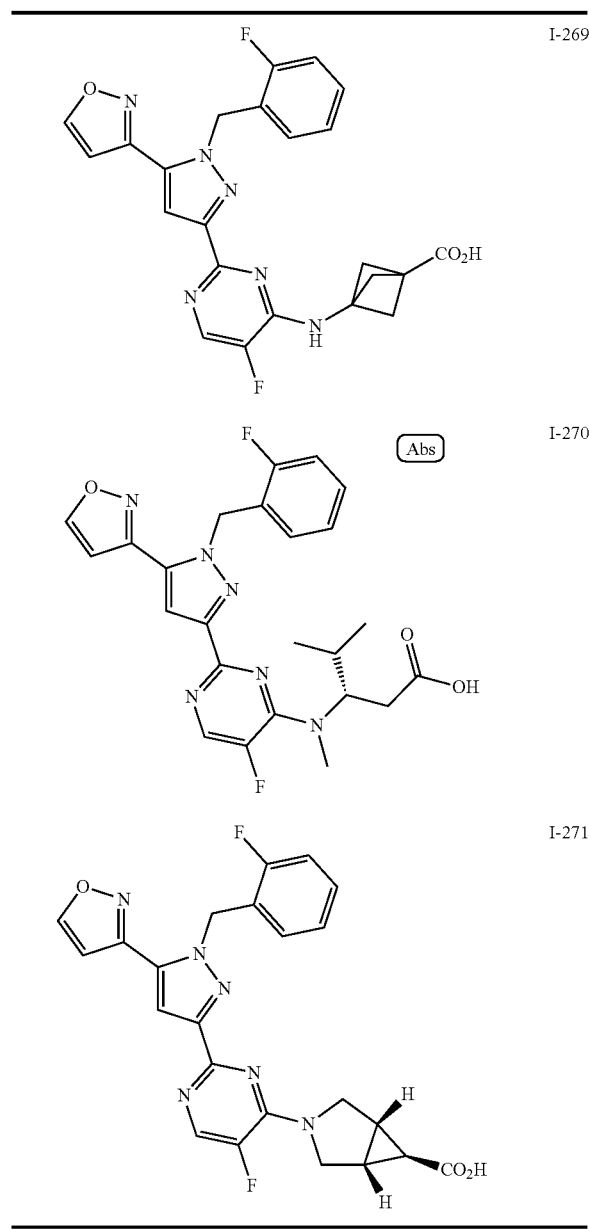
TABLE 1B
TABLE 1B-continued
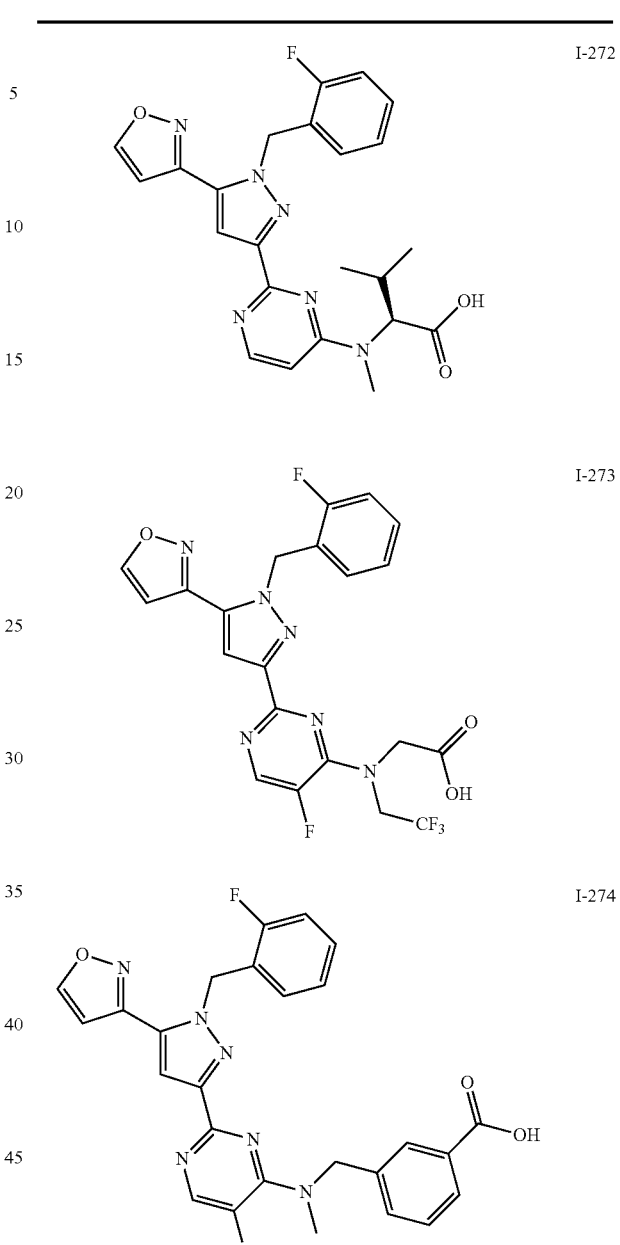
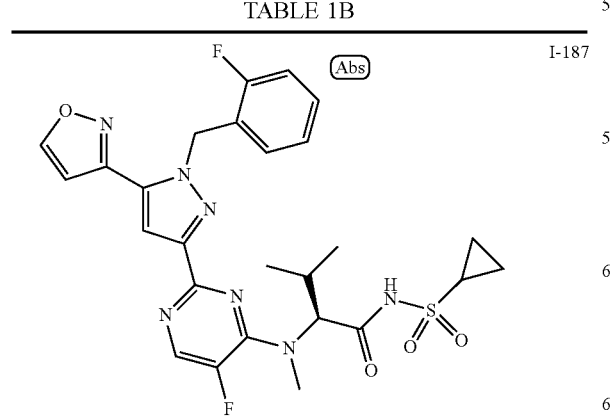
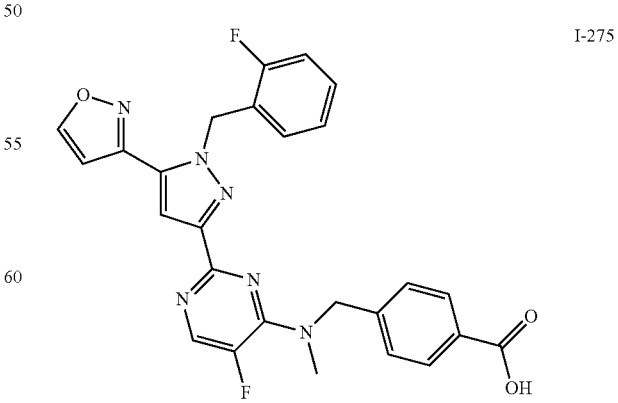

TABLE 1B-continued
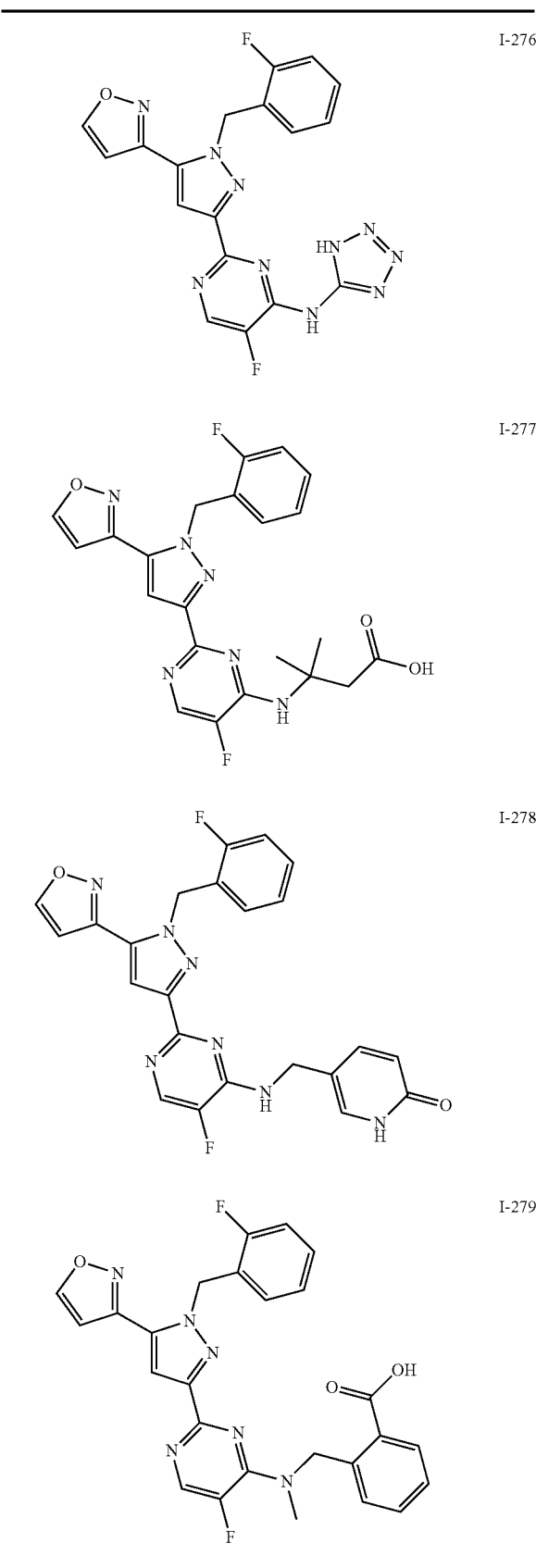
I-276
I-277
I-278
I-279
TABLE 1B-continued
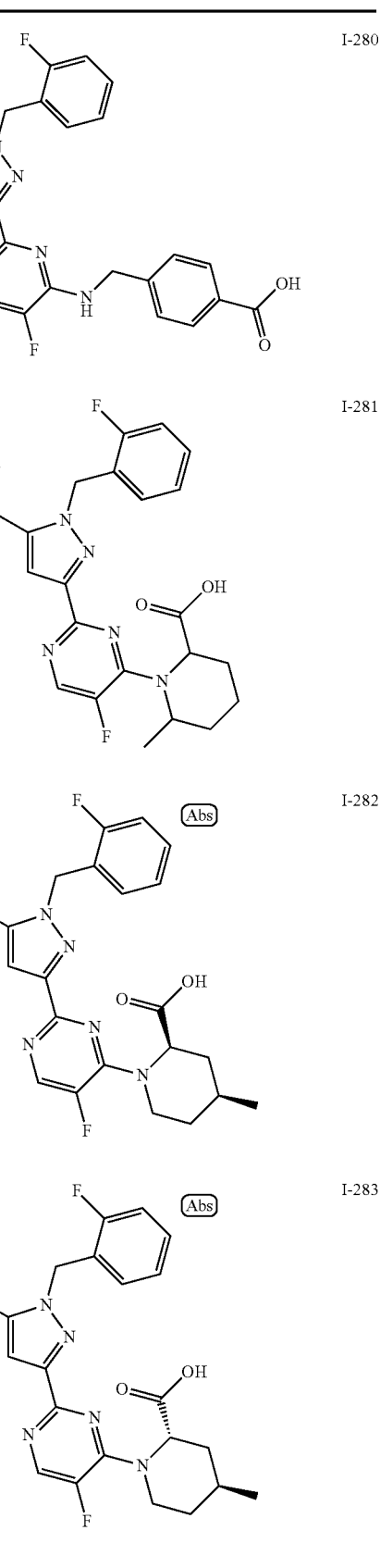
I-280
I-281
I-282
I-283

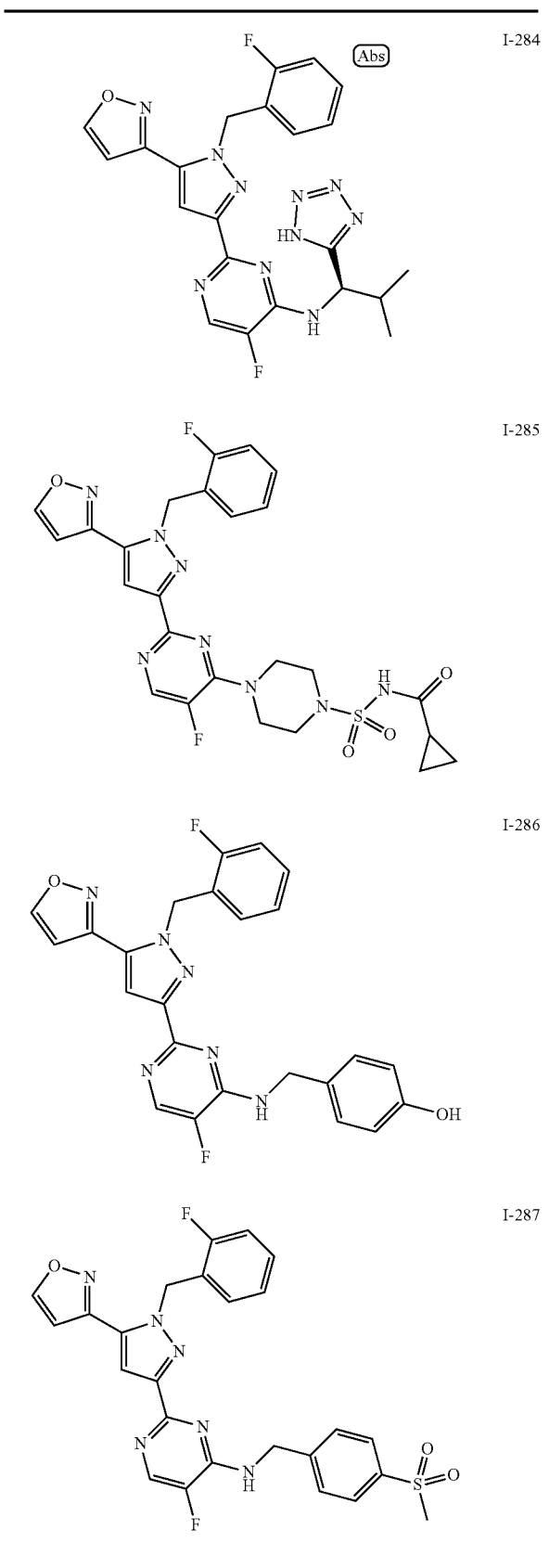
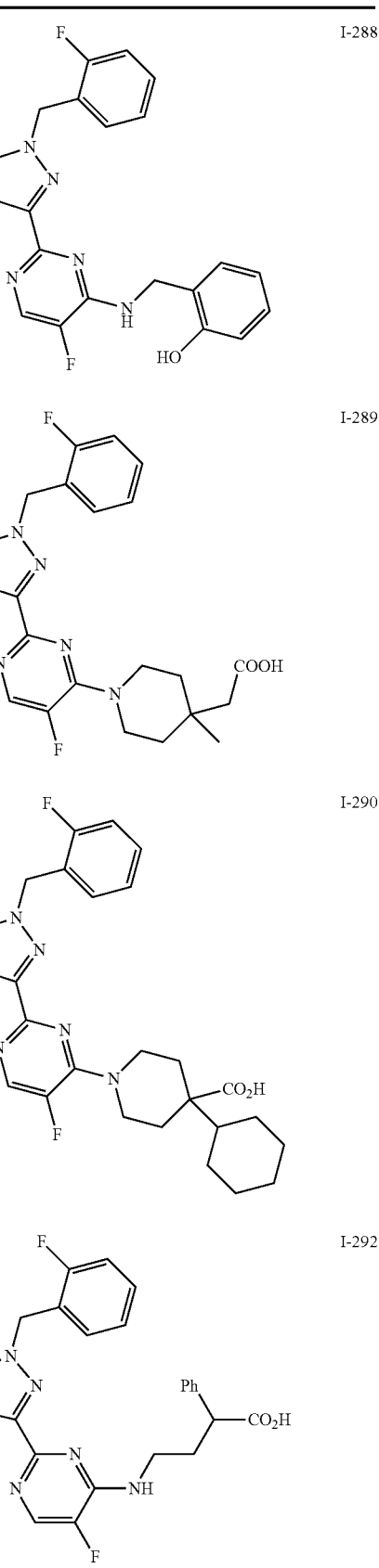

141
TABLE 1B-continued
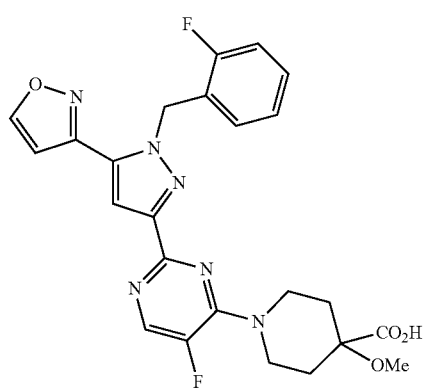 [SMILES: COC1(C(=O)O)CCN(c2nc(-c3cc(-c4ccon4)n(Cc4ccccc4F)n3)ncc2F)CC1]
I-293
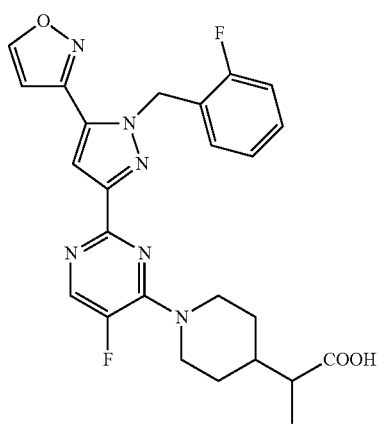 [SMILES: CC(C(=O)O)C1CCN(c2nc(-c3cc(-c4ccon4)n(Cc4ccccc4F)n3)ncc2F)CC1]
I-294
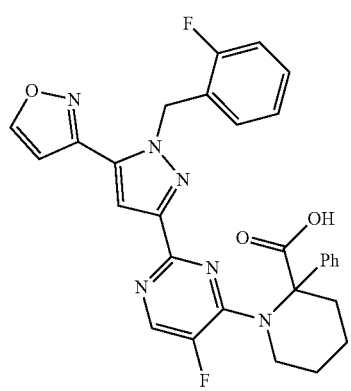 [SMILES: O=C(O)C1(c2ccccc2)CCCCN1c1nc(-c2cc(-c3ccon3)n(Cc3ccccc3F)n2)ncc1F]
I-291
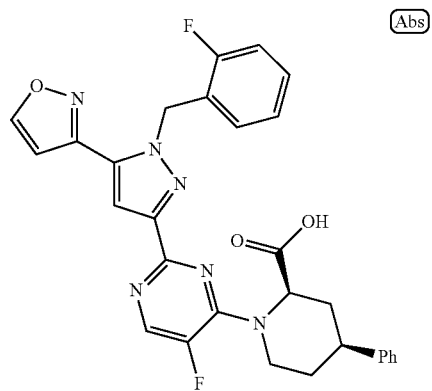 [SMILES: O=C(O)[C@H]1C[C@@H](c2ccccc2)CCN1c1nc(-c2cc(-c3ccon3)n(Cc3ccccc3F)n2)ncc1F]
I-295 [Abs]
142
TABLE 1B-continued
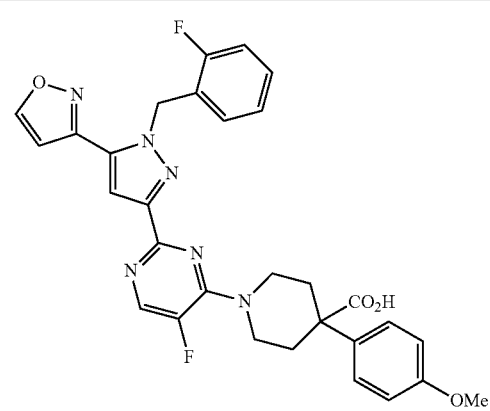 [SMILES: COc1ccc(C2(C(=O)O)CCN(c3nc(-c4cc(-c5ccon5)n(Cc5ccccc5F)n4)ncc3F)CC2)cc1]
I-296
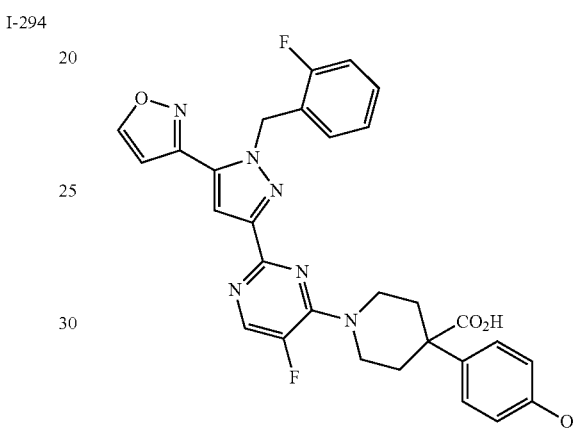
I-297
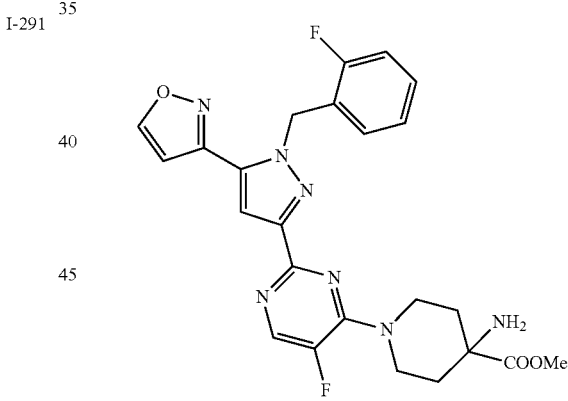
I-298
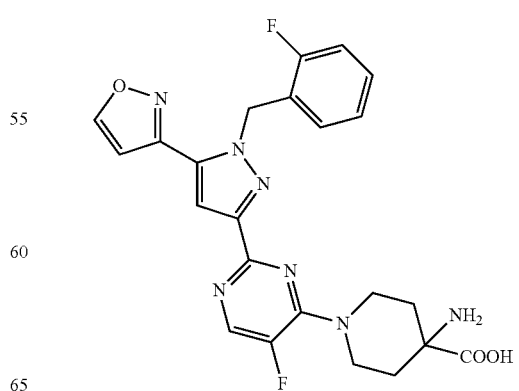
I-299

TABLE 1B-continued
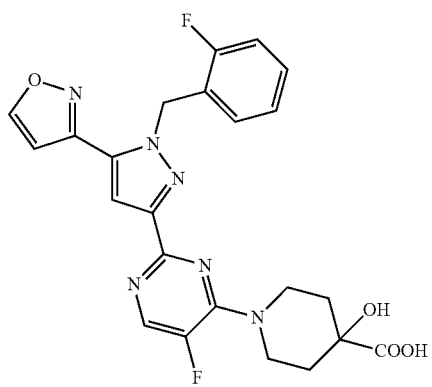 [SMILES: O=C(O)C1(O)CCN(c2nc(-c3cc(-c4ccon4)n(Cc4ccccc4F)n3)ncc2F)CC1]
I-300
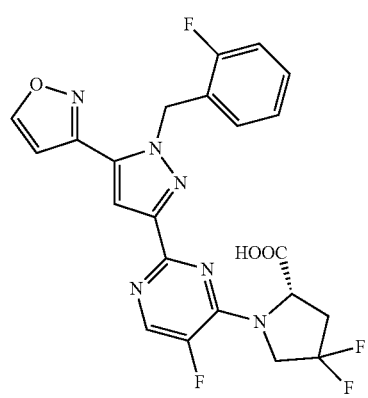 [SMILES: O=C(O)[C@@H]1CC(F)(F)CN1c1nc(-c2cc(-c3ccon3)n(Cc3ccccc3F)n2)ncc1F]
I-301
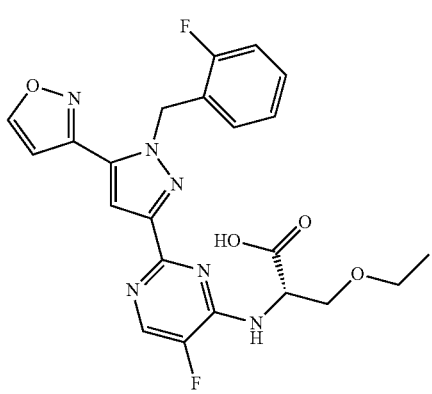 [SMILES: CCOC[C@H](Nc1nc(-c2cc(-c3ccon3)n(Cc3ccccc3F)n2)ncc1F)C(=O)O]
I-302
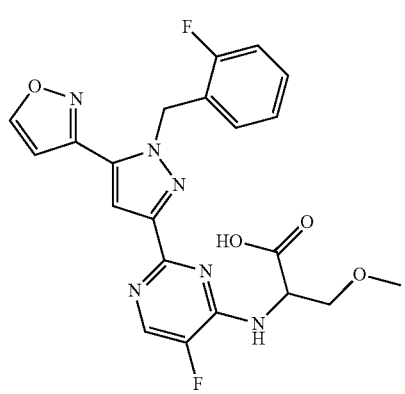 [SMILES: COCC(Nc1nc(-c2cc(-c3ccon3)n(Cc3ccccc3F)n2)ncc1F)C(=O)O]
I-303
TABLE 1B-continued
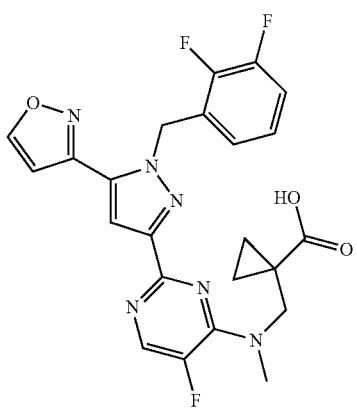 [SMILES: CN(CC1(C(=O)O)CC1)c1nc(-c2cc(-c3ccon3)n(Cc3cccc(F)c3F)n2)ncc1F]
I-304
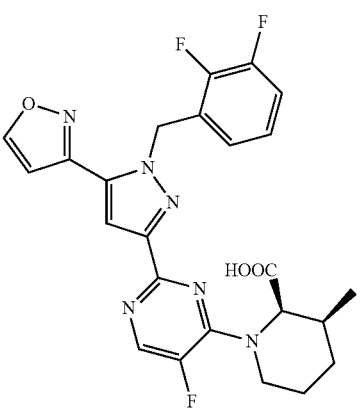 [SMILES: C[C@H]1CCCN(c2nc(-c3cc(-c4ccon4)n(Cc4cccc(F)c4F)n3)ncc2F)[C@H]1C(=O)O]
I-305
TABLE 1C
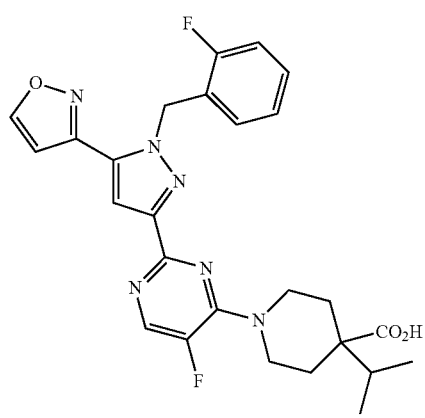 [SMILES: CC(C)C1(C(=O)O)CCN(c2nc(-c3cc(-c4ccon4)n(Cc4ccccc4F)n3)ncc2F)CC1]
I-306

TABLE 1C-continued
| | |
|---|---|
| 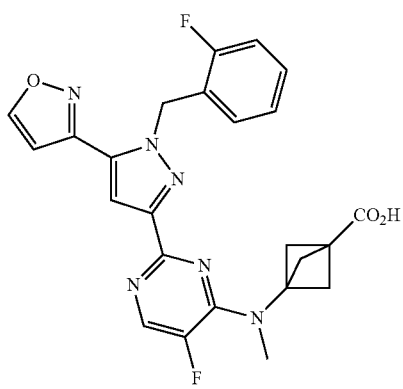 [SMILES: CN(c1nc(-c2cc(-c3ccon3)n(Cc3ccccc3F)n2)ncc1F)C12CC(C(=O)O)(C1)C2] I-307 | 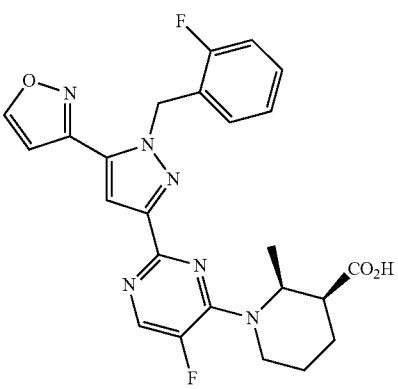 I-311 |
| 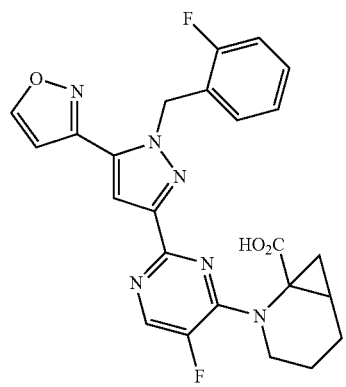 [SMILES: O=C(O)C12CC1CCCN2c1nc(-c2cc(-c3ccon3)n(Cc3ccccc3F)n2)ncc1F] I-308 | 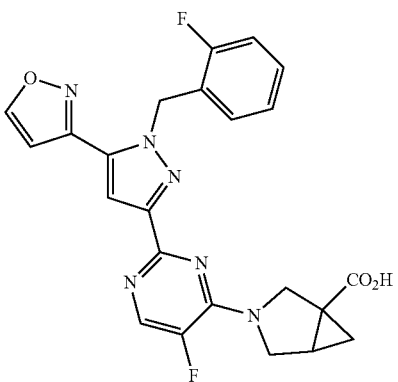 I-312 |
| 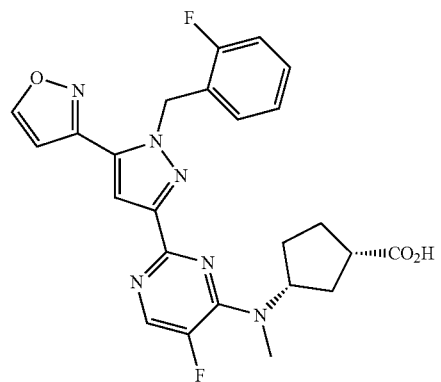 [SMILES: CN(c1nc(-c2cc(-c3ccon3)n(Cc3ccccc3F)n2)ncc1F)[C@@H]1CC[C@H](C(=O)O)C1] I-309 | 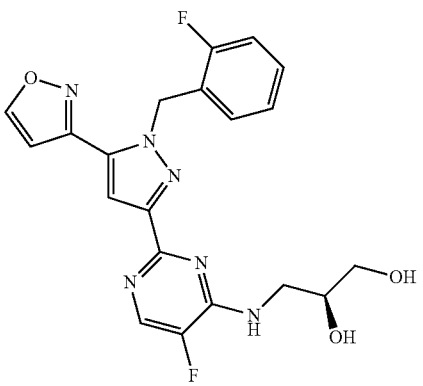 I-313 |
| 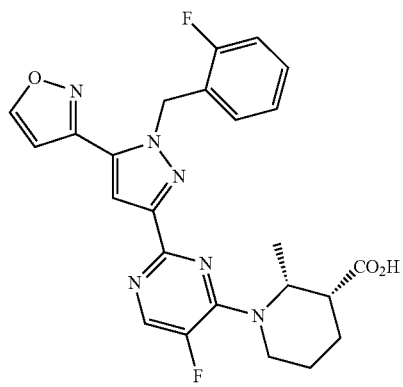 [SMILES: C[C@@H]1[C@H](C(=O)O)CCCN1c1nc(-c2cc(-c3ccon3)n(Cc3ccccc3F)n2)ncc1F] I-310 | 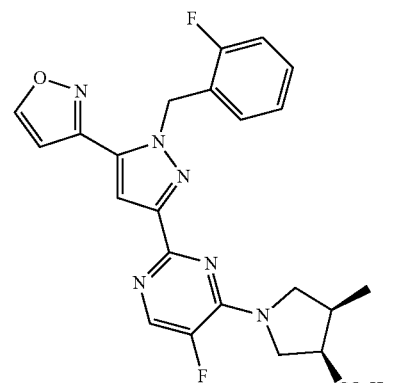 I-314 |

TABLE 1C-continued
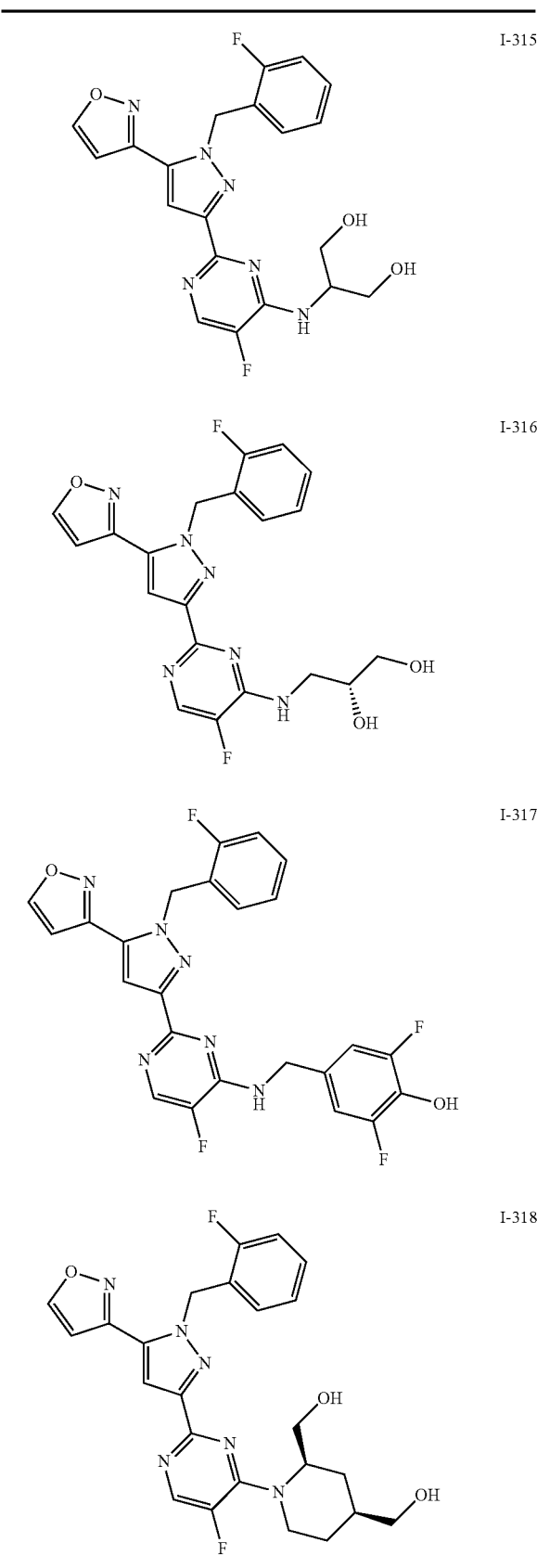
I-315
I-316
I-317
I-318
TABLE 1C-continued
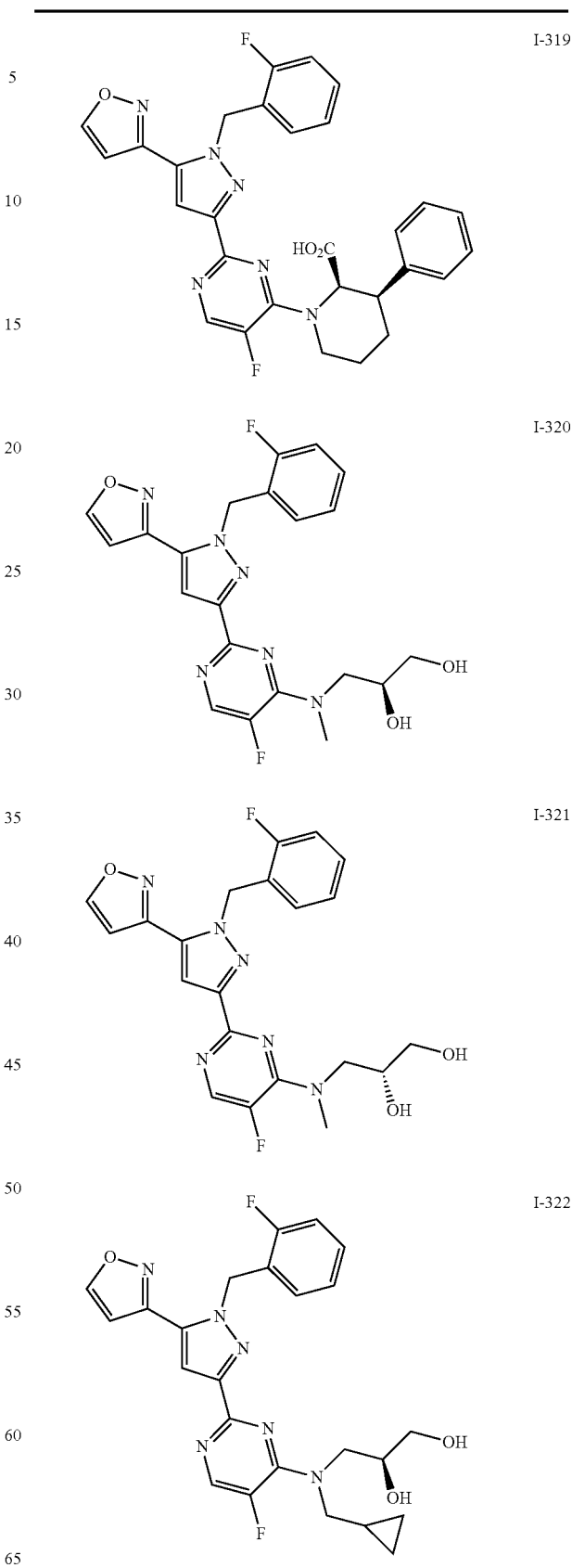
I-319
I-320
I-321
I-322

TABLE 1C-continued
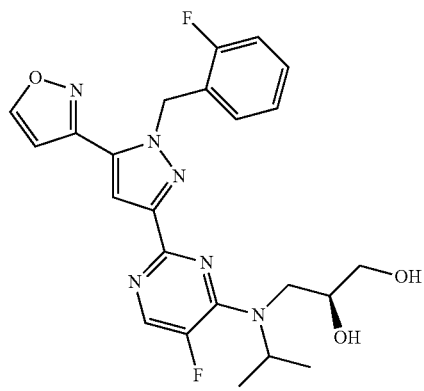 [SMILES: CC(C)N(C[C@H](O)CO)c1nc(-c2cc(-c3ccon3)n(Cc3ccccc3F)n2)ncc1F]
I-323
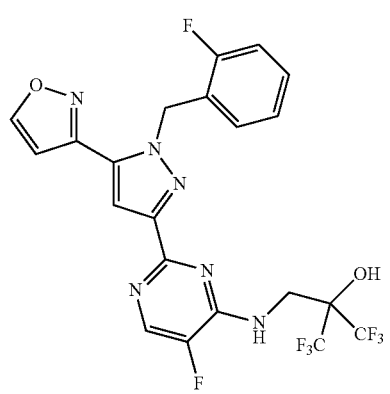 [SMILES: OC(CNc1nc(-c2cc(-c3ccon3)n(Cc3ccccc3F)n2)ncc1F)(C(F)(F)F)C(F)(F)F]
I-324
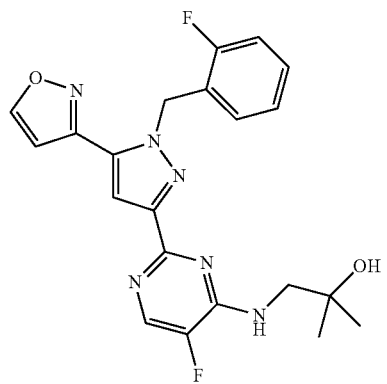 [SMILES: CC(C)(O)CNc1nc(-c2cc(-c3ccon3)n(Cc3ccccc3F)n2)ncc1F]
I-325
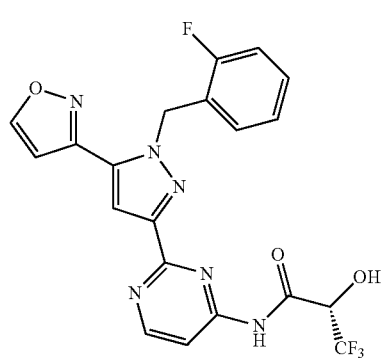 [SMILES: O=C(Nc1ccnc(-c2cc(-c3ccon3)n(Cc3ccccc3F)n2)n1)[C@H](O)C(F)(F)F]
I-326
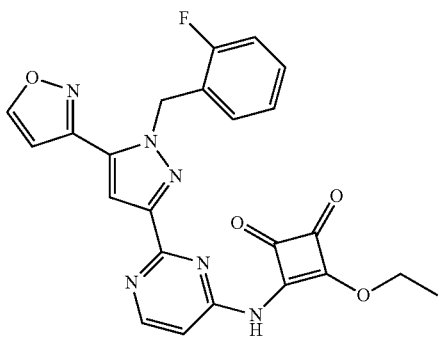 [SMILES: CCOc1c(Nc2ccnc(-c3cc(-c4ccon4)n(Cc4ccccc4F)n3)n2)c(=O)c1=O]
I-327
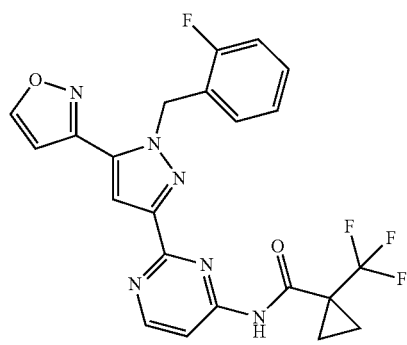 [SMILES: O=C(Nc1ccnc(-c2cc(-c3ccon3)n(Cc3ccccc3F)n2)n1)C1(C(F)(F)F)CC1]
I-328
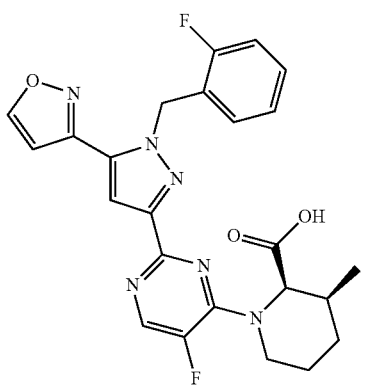 [SMILES: C[C@H]1CCCN(c2nc(-c3cc(-c4ccon4)n(Cc4ccccc4F)n3)ncc2F)[C@H]1C(=O)O]
I-329
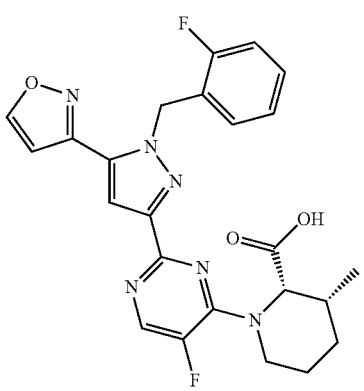 [SMILES: C[C@@H]1CCCN(c2nc(-c3cc(-c4ccon4)n(Cc4ccccc4F)n3)ncc2F)[C@@H]1C(=O)O]
I-330

TABLE 1C-continued
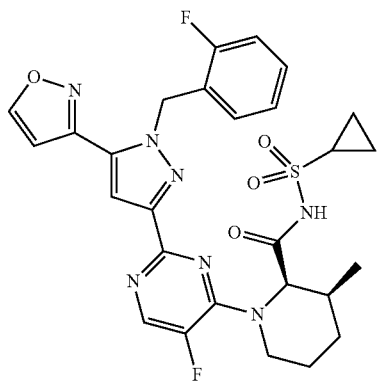 [SMILES: C[C@H]1CCCN(c2nc(-c3cc(-c4ccon4)n(Cc4ccccc4F)n3)ncc2F)[C@H]1C(=O)NS(=O)(=O)C1CC1]
I-331
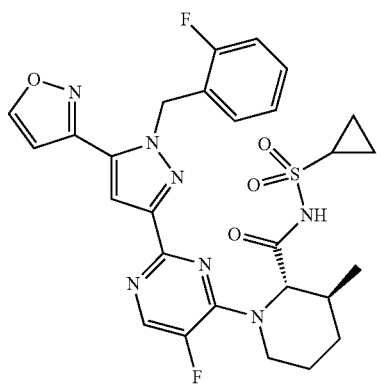 [SMILES: C[C@H]1CCCN(c2nc(-c3cc(-c4ccon4)n(Cc4ccccc4F)n3)ncc2F)[C@@H]1C(=O)NS(=O)(=O)C1CC1]
I-332
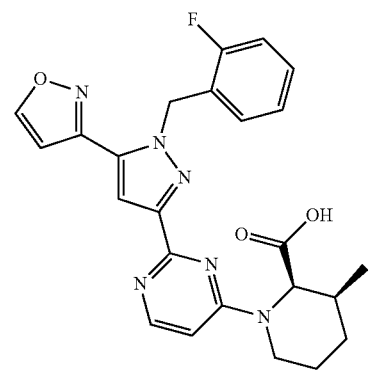 [SMILES: C[C@H]1CCCN(c2ccnc(-c3cc(-c4ccon4)n(Cc4ccccc4F)n3)n2)[C@H]1C(=O)O]
I-333
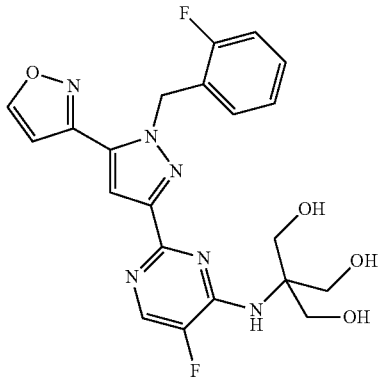 [SMILES: OCC(CO)(CO)Nc1nc(-c2cc(-c3ccon3)n(Cc3ccccc3F)n2)ncc1F]
I-334
TABLE 1C-continued
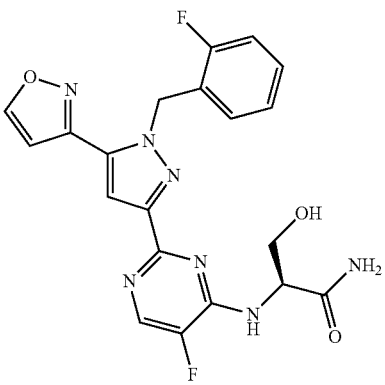 [SMILES: NC(=O)[C@H](CO)Nc1nc(-c2cc(-c3ccon3)n(Cc3ccccc3F)n2)ncc1F]
I-335
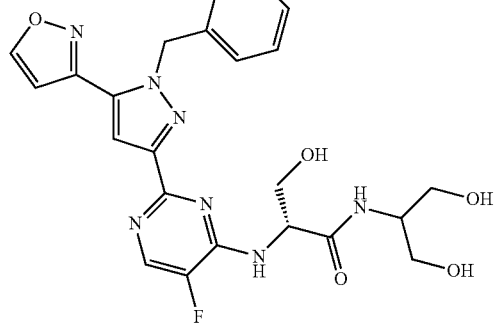
I-336
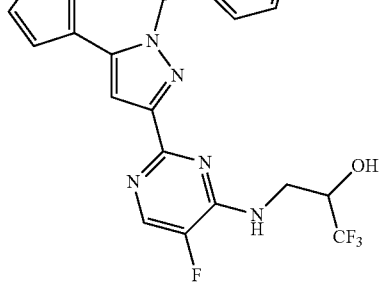
I-337
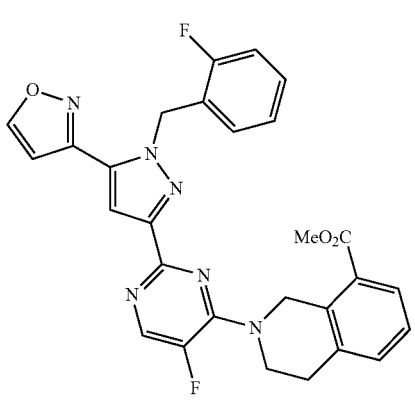 [SMILES: COC(=O)c1cccc2c1CN(c1nc(-c3cc(-c4ccon4)n(Cc4ccccc4F)n3)ncc1F)CC2]
I-338

TABLE 1C-continued
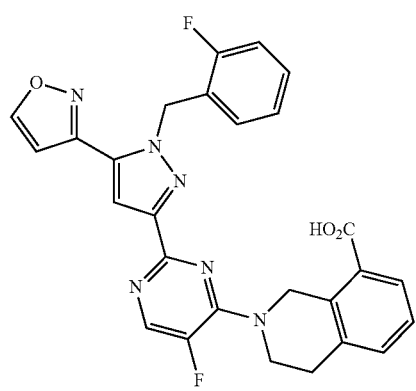 [SMILES: O=C(O)c1cccc2c1CN(c1nc(-c3cc(-c4ccon4)n(Cc4ccccc4F)n3)ncc1F)CC2]
I-339
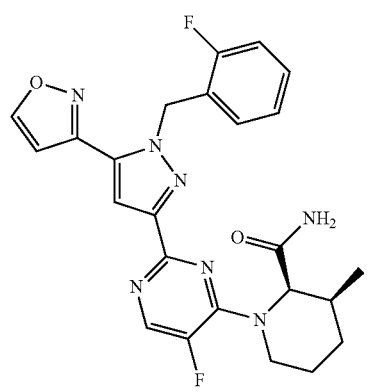 [SMILES: C[C@H]1CCCN(c2nc(-c3cc(-c4ccon4)n(Cc4ccccc4F)n3)ncc2F)[C@H]1C(N)=O]
I-340
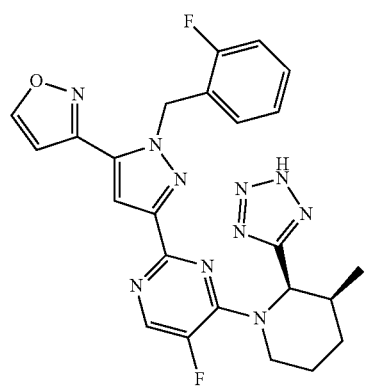 [SMILES: C[C@H]1CCCN(c2nc(-c3cc(-c4ccon4)n(Cc4ccccc4F)n3)ncc2F)[C@H]1c1nn[nH]n1]
I-341
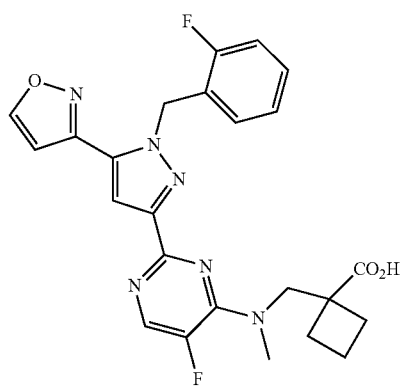 [SMILES: CN(CC1(C(=O)O)CCC1)c1nc(-c2cc(-c3ccon3)n(Cc3ccccc3F)n2)ncc1F]
I-342
TABLE 1C-continued
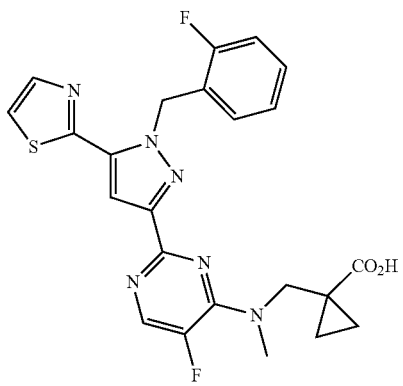 [SMILES: CN(CC1(C(=O)O)CC1)c1nc(-c2cc(-c3nccs3)n(Cc3ccccc3F)n2)ncc1F]
I-343
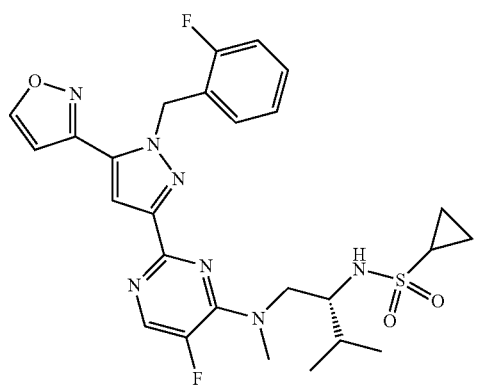 [SMILES: CC(C)[C@H](CN(C)c1nc(-c2cc(-c3ccon3)n(Cc3ccccc3F)n2)ncc1F)NS(=O)(=O)C1CC1]
I-344
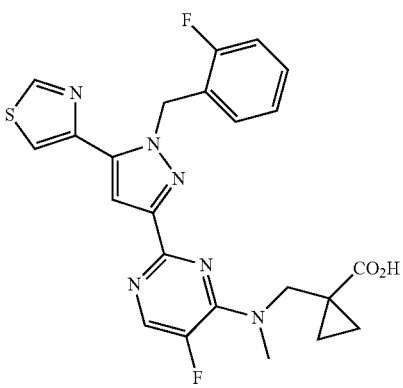 [SMILES: CN(CC1(C(=O)O)CC1)c1nc(-c2cc(-c3cscn3)n(Cc3ccccc3F)n2)ncc1F]
I-345
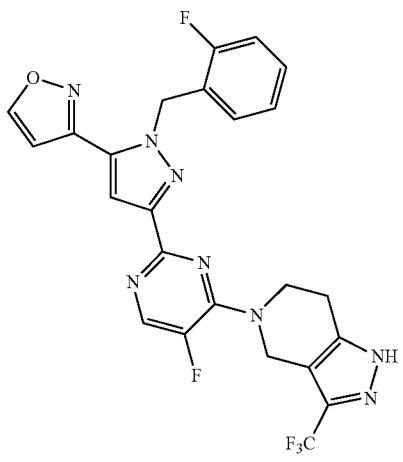 [SMILES: Fc1ccccc1Cn1nc(-c2ncc(F)c(N3CCc4[nH]nc(C(F)(F)F)c4C3)n2)cc1-c1ccon1]
I-346

TABLE 1C-continued
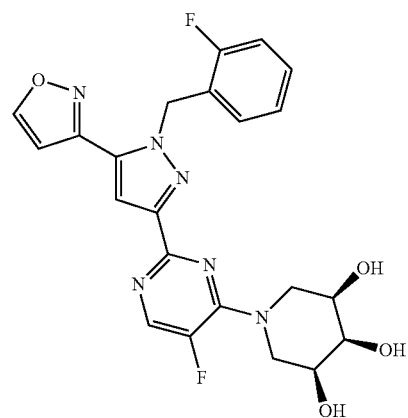 [SMILES: O[C@@H]1[C@H](O)CN(c2nc(-c3cc(-c4ccon4)n(Cc4ccccc4F)n3)ncc2F)C[C@@H]1O]
I-347
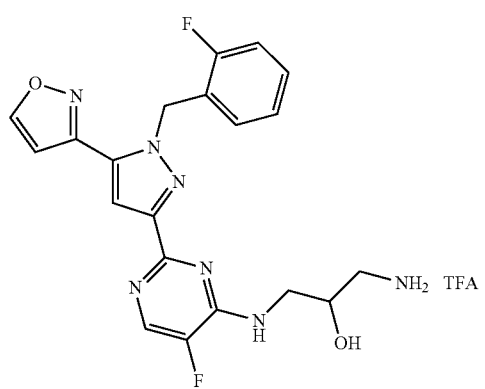 [SMILES: NCC(O)CNc1nc(-c2cc(-c3ccon3)n(Cc3ccccc3F)n2)ncc1F]
I-348
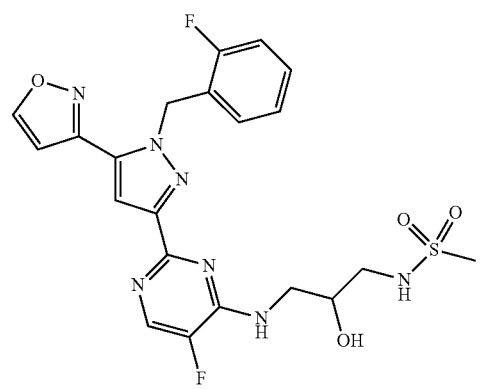 [SMILES: CS(=O)(=O)NCC(O)CNc1nc(-c2cc(-c3ccon3)n(Cc3ccccc3F)n2)ncc1F]
I-349
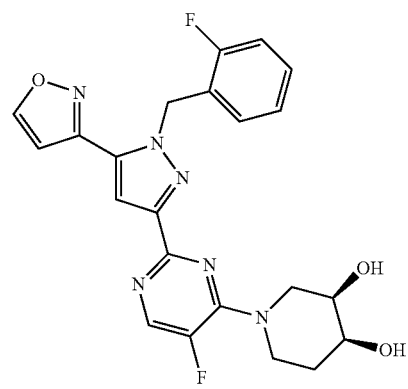 [SMILES: O[C@@H]1CN(c2nc(-c3cc(-c4ccon4)n(Cc4ccccc4F)n3)ncc2F)CC[C@@H]1O]
I-350
TABLE 1C-continued
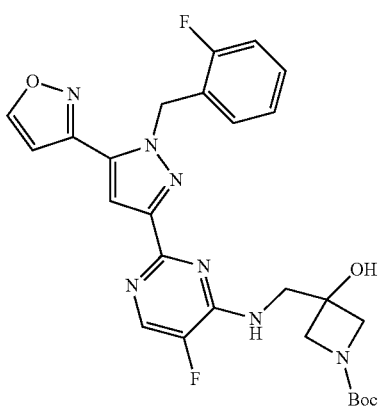 [SMILES: CC(C)(C)OC(=O)N1CC(O)(CNc2nc(-c3cc(-c4ccon4)n(Cc4ccccc4F)n3)ncc2F)C1]
I-351
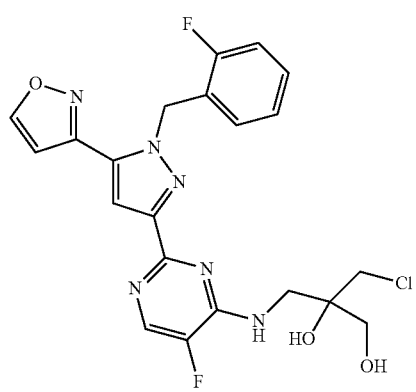 [SMILES: OCC(O)(CCl)CNc1nc(-c2cc(-c3ccon3)n(Cc3ccccc3F)n2)ncc1F]
I-352
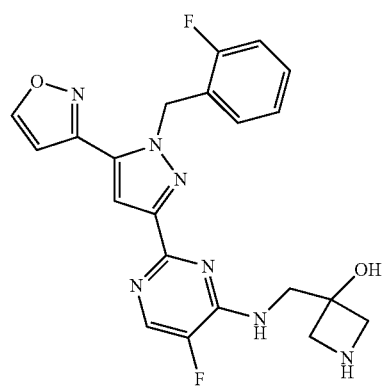 [SMILES: OC1(CNc2nc(-c3cc(-c4ccon4)n(Cc4ccccc4F)n3)ncc2F)CNC1]
I-353
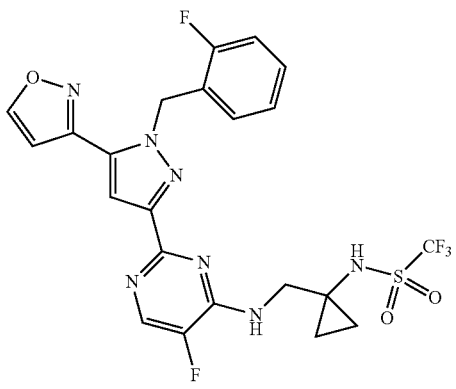 [SMILES: O=S(=O)(NC1(CNc2nc(-c3cc(-c4ccon4)n(Cc4ccccc4F)n3)ncc2F)CC1)C(F)(F)F]
I-354

TABLE 1C-continued
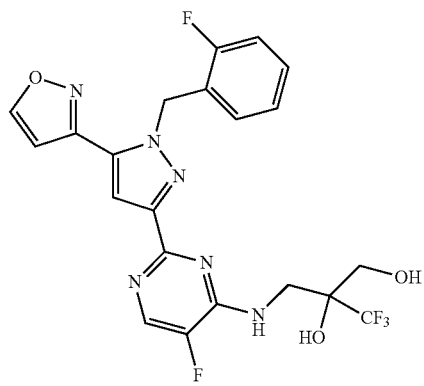 [SMILES: OCC(O)(CNc1nc(-c2cc(-c3ccon3)n(Cc3ccccc3F)n2)ncc1F)C(F)(F)F] I-355
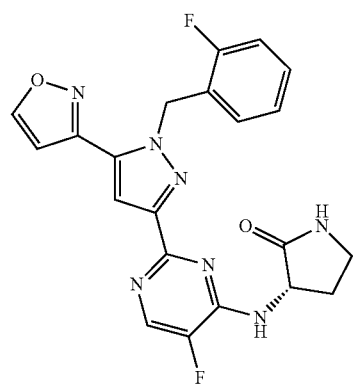 [SMILES: O=C1NCC[C@@H]1Nc1nc(-c2cc(-c3ccon3)n(Cc3ccccc3F)n2)ncc1F] I-356
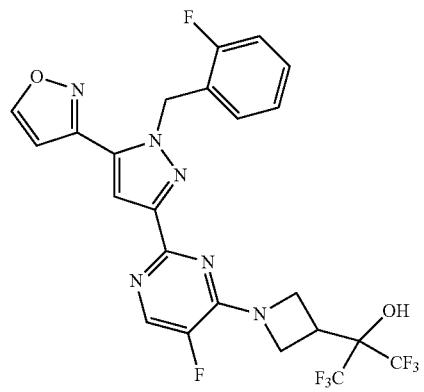 [SMILES: OC(C1CN(c2nc(-c3cc(-c4ccon4)n(Cc4ccccc4F)n3)ncc2F)C1)(C(F)(F)F)C(F)(F)F] I-357
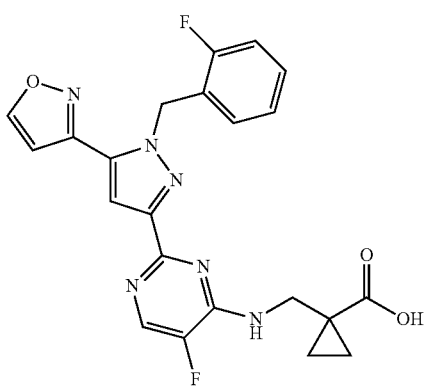 [SMILES: O=C(O)C1(CNc2nc(-c3cc(-c4ccon4)n(Cc4ccccc4F)n3)ncc2F)CC1] I-358
TABLE 1C-continued
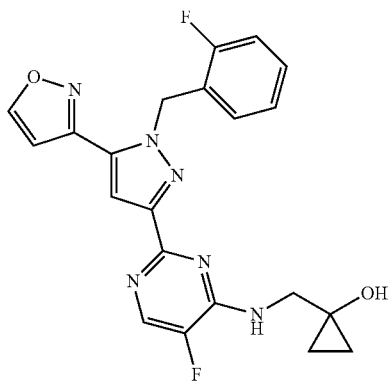 [SMILES: OC1(CNc2nc(-c3cc(-c4ccon4)n(Cc4ccccc4F)n3)ncc2F)CC1] I-359
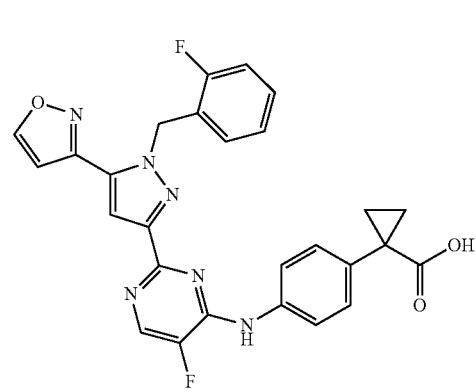 [SMILES: O=C(O)C1(c2ccc(Nc3nc(-c4cc(-c5ccon5)n(Cc5ccccc5F)n4)ncc3F)cc2)CC1] I-360
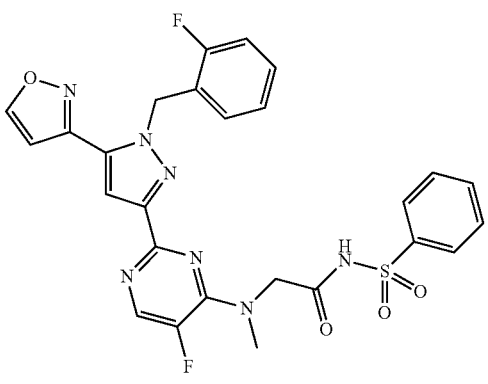 [SMILES: CN(CC(=O)NS(=O)(=O)c1ccccc1)c1nc(-c2cc(-c3ccon3)n(Cc3ccccc3F)n2)ncc1F] I-361
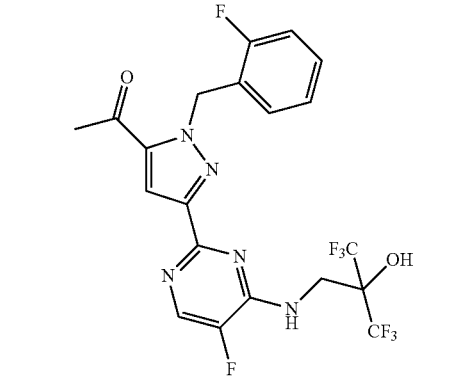 [SMILES: CC(=O)c1cc(-c2ncc(F)c(NCC(O)(C(F)(F)F)C(F)(F)F)n2)nn1Cc1ccccc1F] I-362

TABLE 1C-continued
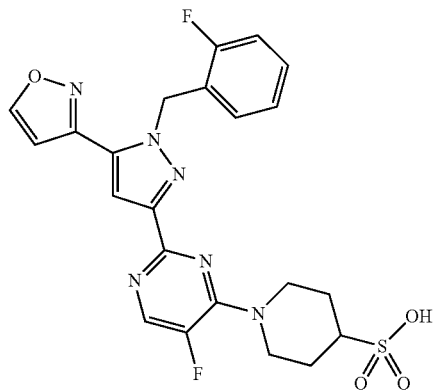 [SMILES: O=S(=O)(O)C1CCN(c2nc(-c3cc(-c4ccon4)n(Cc4ccccc4F)n3)ncc2F)CC1]
I-363
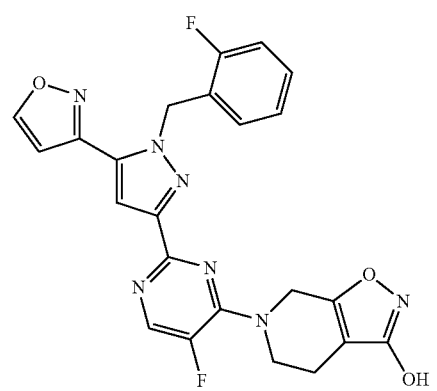 [SMILES: Oc1noc2c1CCN(c1nc(-c3cc(-c4ccon4)n(Cc4ccccc4F)n3)ncc1F)C2]
I-364
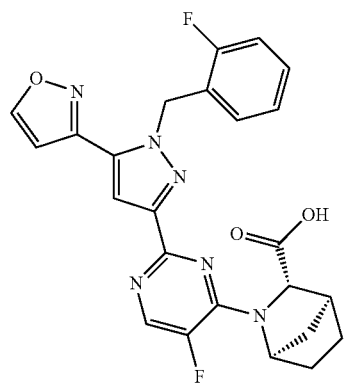 [SMILES: O=C(O)[C@@H]1[C@H]2CC[C@H](C2)N1c1nc(-c2cc(-c3ccon3)n(Cc3ccccc3F)n2)ncc1F]
I-365
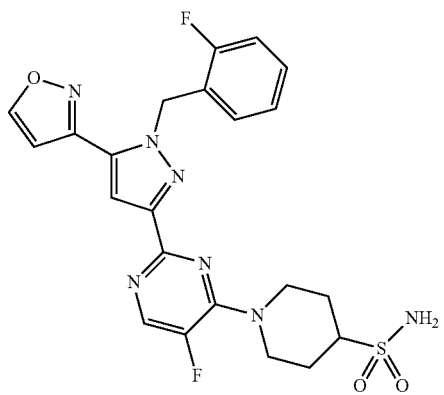 [SMILES: NS(=O)(=O)C1CCN(c2nc(-c3cc(-c4ccon4)n(Cc4ccccc4F)n3)ncc2F)CC1]
I-366
TABLE 1C-continued
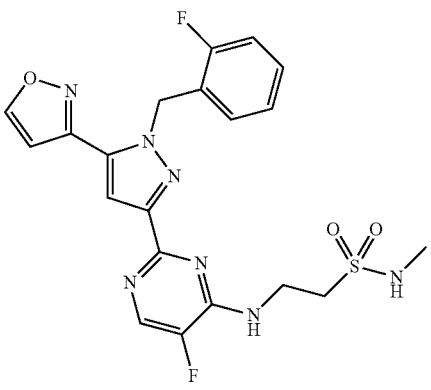 [SMILES: CNS(=O)(=O)CCNc1nc(-c2cc(-c3ccon3)n(Cc3ccccc3F)n2)ncc1F]
I-367
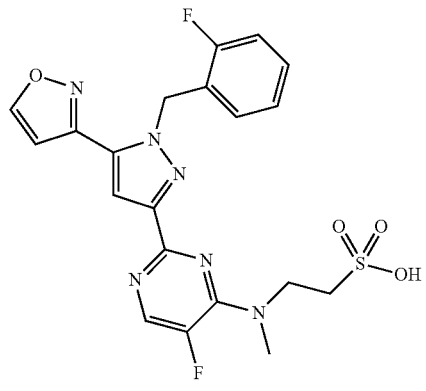 [SMILES: CN(CCS(=O)(=O)O)c1nc(-c2cc(-c3ccon3)n(Cc3ccccc3F)n2)ncc1F]
I-368
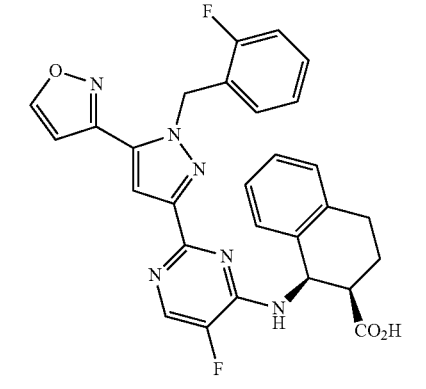 [SMILES: O=C(O)[C@@H]1CCc2ccccc2[C@@H]1Nc1nc(-c2cc(-c3ccon3)n(Cc3ccccc3F)n2)ncc1F]
I-369
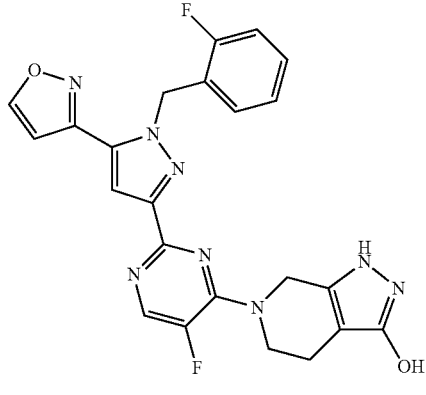 [SMILES: Oc1n[nH]c2c1CCN(c1nc(-c3cc(-c4ccon4)n(Cc4ccccc4F)n3)ncc1F)C2]
I-370

TABLE 1C-continued
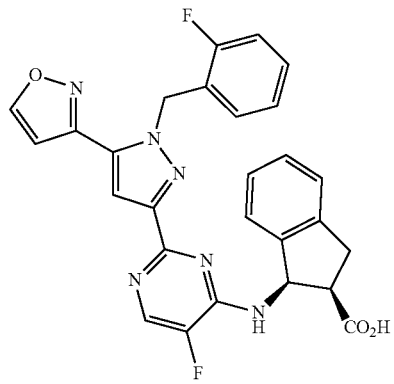 [SMILES: O=C(O)[C@@H]1Cc2ccccc2[C@@H]1Nc1nc(-c2cc(-c3ccon3)n(Cc3ccccc3F)n2)ncc1F]
I-371
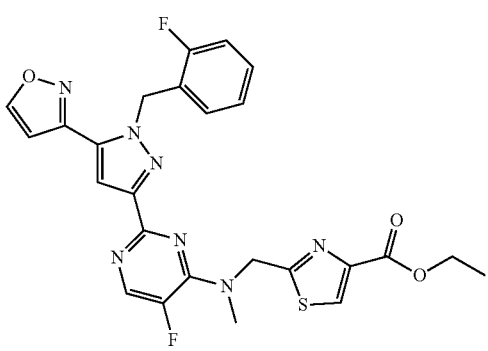 [SMILES: CCOC(=O)c1csc(CN(C)c2nc(-c3cc(-c4ccon4)n(Cc4ccccc4F)n3)ncc2F)n1]
I-372
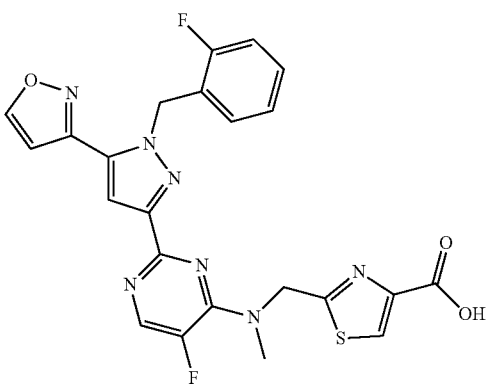 [SMILES: CN(Cc1nc(C(=O)O)cs1)c1nc(-c2cc(-c3ccon3)n(Cc3ccccc3F)n2)ncc1F]
I-373
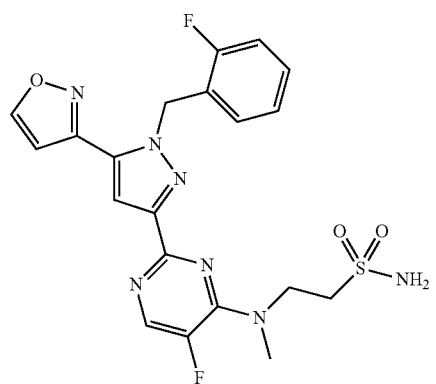 [SMILES: CN(CCS(N)(=O)=O)c1nc(-c2cc(-c3ccon3)n(Cc3ccccc3F)n2)ncc1F]
I-374
TABLE 1C-continued
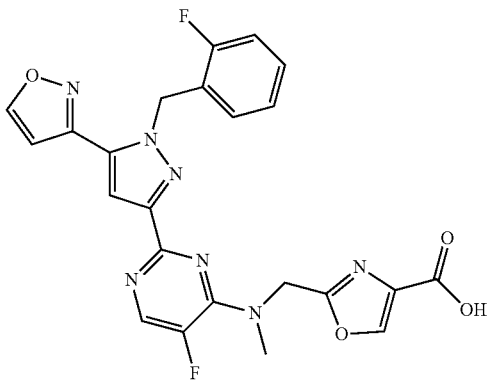 [SMILES: CN(Cc1nc(C(=O)O)co1)c1nc(-c2cc(-c3ccon3)n(Cc3ccccc3F)n2)ncc1F]
I-375
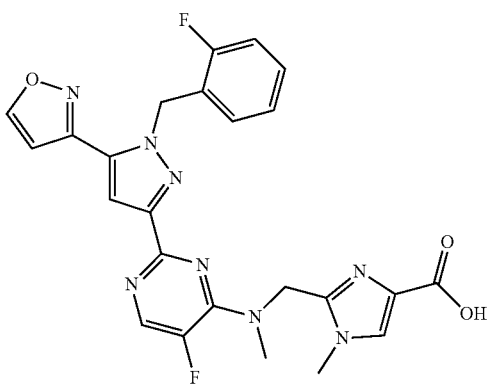 [SMILES: CN(Cc1nc(C(=O)O)cn1C)c1nc(-c2cc(-c3ccon3)n(Cc3ccccc3F)n2)ncc1F]
I-376
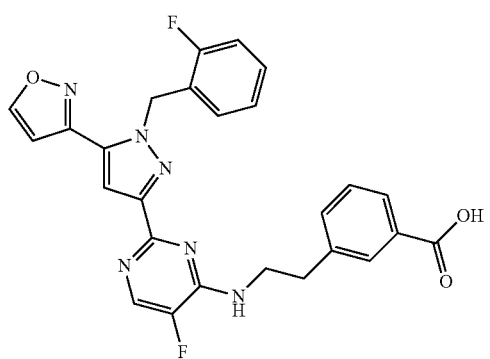 [SMILES: O=C(O)c1cccc(CCNc2nc(-c3cc(-c4ccon4)n(Cc4ccccc4F)n3)ncc2F)c1]
I-377
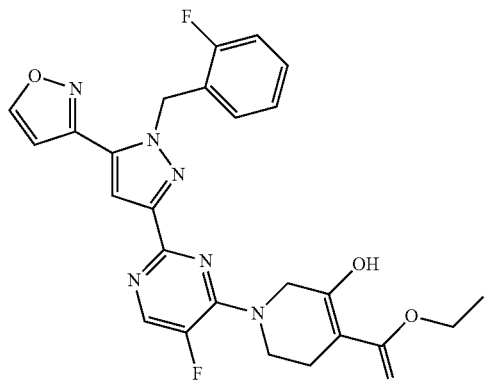
I-378

TABLE 1C-continued
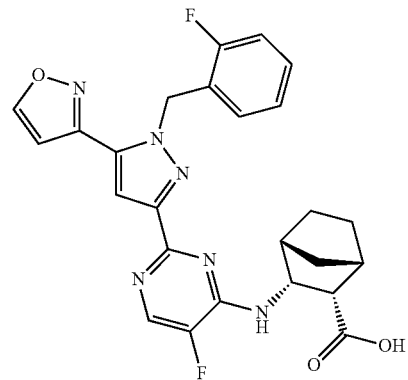 [SMILES: O=C(O)[C@H]1[C@H]2CC[C@H](C2)[C@H]1Nc1nc(-c2cc(-c3ccon3)n(Cc3ccccc3F)n2)ncc1F]
I-379
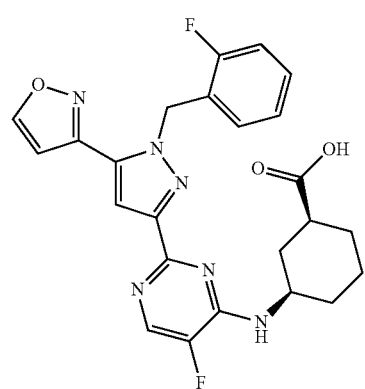 [SMILES: O=C(O)[C@H]1CCC[C@@H](Nc2nc(-c3cc(-c4ccon4)n(Cc4ccccc4F)n3)ncc2F)C1]
I-380
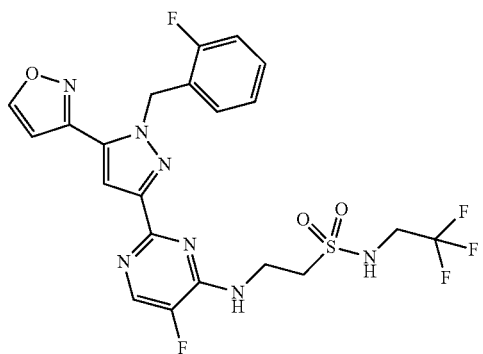 [SMILES: O=S(=O)(CCNc1nc(-c2cc(-c3ccon3)n(Cc3ccccc3F)n2)ncc1F)NCC(F)(F)F]
I-381
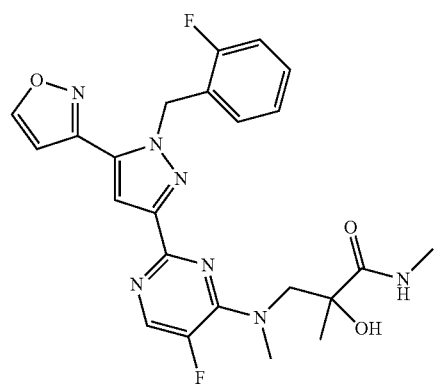 [SMILES: CNC(=O)C(C)(O)CN(C)c1nc(-c2cc(-c3ccon3)n(Cc3ccccc3F)n2)ncc1F]
I-382
TABLE 1C-continued
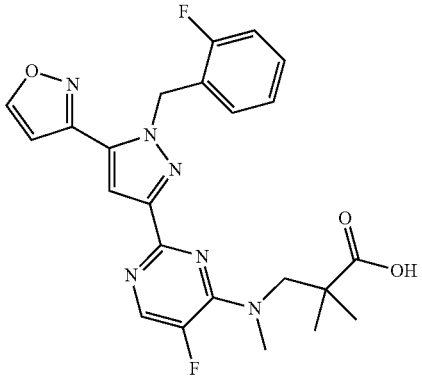 [SMILES: CN(CC(C)(C)C(=O)O)c1nc(-c2cc(-c3ccon3)n(Cc3ccccc3F)n2)ncc1F]
I-383
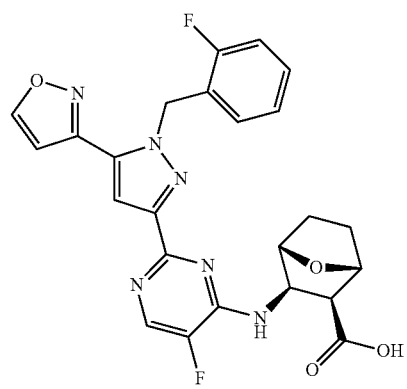 [SMILES: O=C(O)[C@H]1[C@@H](Nc2nc(-c3cc(-c4ccon4)n(Cc4ccccc4F)n3)ncc2F)[C@@H]2CC[C@H]1O2]
I-384
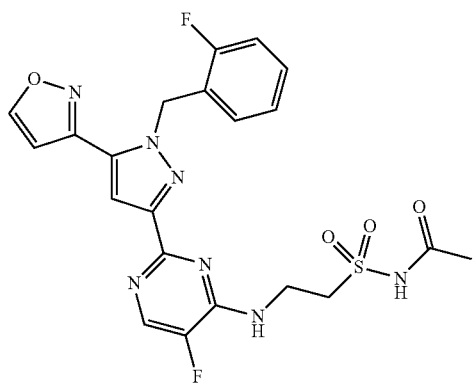 [SMILES: CC(=O)NS(=O)(=O)CCNc1nc(-c2cc(-c3ccon3)n(Cc3ccccc3F)n2)ncc1F]
I-385
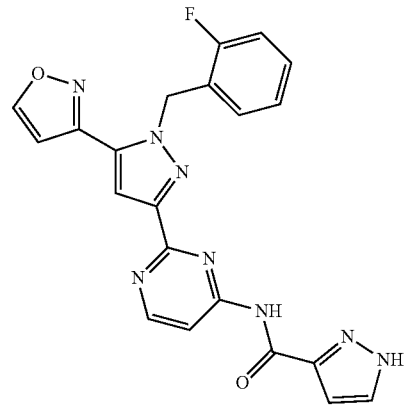 [SMILES: O=C(Nc1ccnc(-c2cc(-c3ccon3)n(Cc3ccccc3F)n2)n1)c1cc[nH]n1]
I-386

TABLE 1C-continued
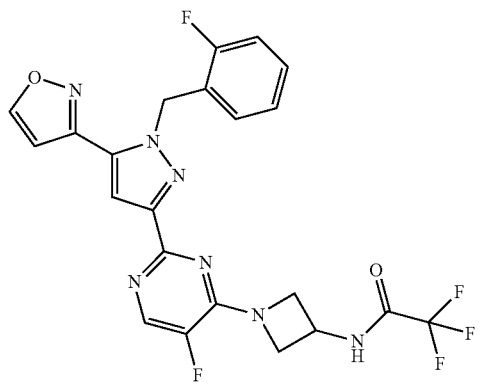 [SMILES: O=C(NC1CN(c2nc(-c3cc(-c4ccon4)n(Cc4ccccc4F)n3)ncc2F)C1)C(F)(F)F]
I-387
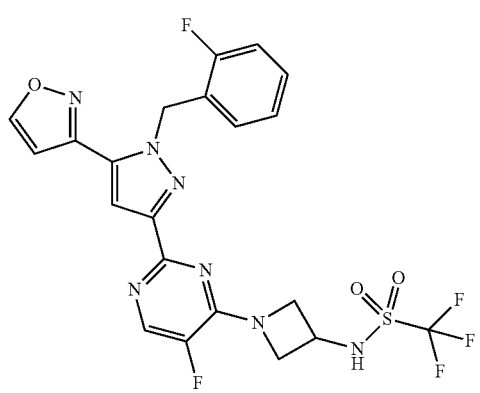 [SMILES: O=S(=O)(NC1CN(c2nc(-c3cc(-c4ccon4)n(Cc4ccccc4F)n3)ncc2F)C1)C(F)(F)F]
I-388
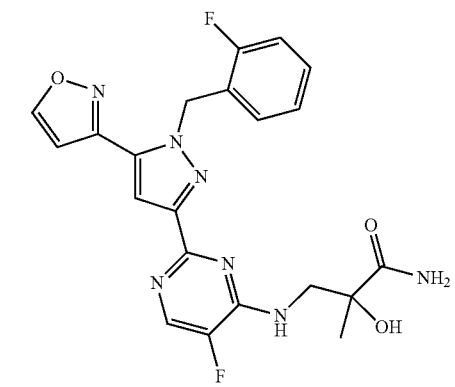 [SMILES: CC(O)(CNc1nc(-c2cc(-c3ccon3)n(Cc3ccccc3F)n2)ncc1F)C(N)=O]
I-389
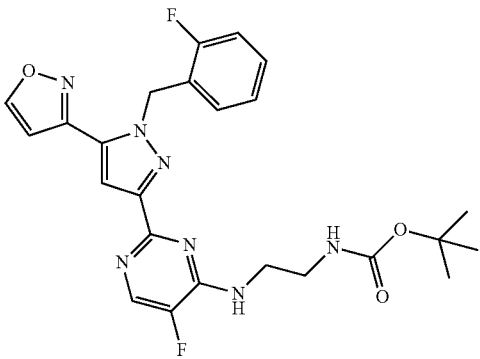 [SMILES: CC(C)(C)OC(=O)NCCNc1nc(-c2cc(-c3ccon3)n(Cc3ccccc3F)n2)ncc1F]
I-390
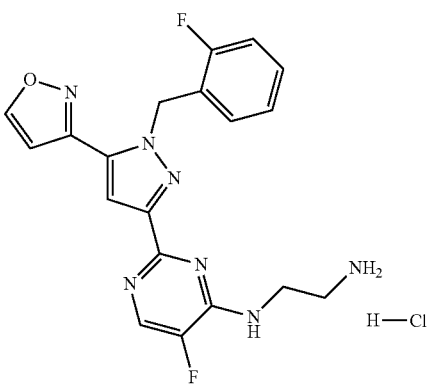
I-391
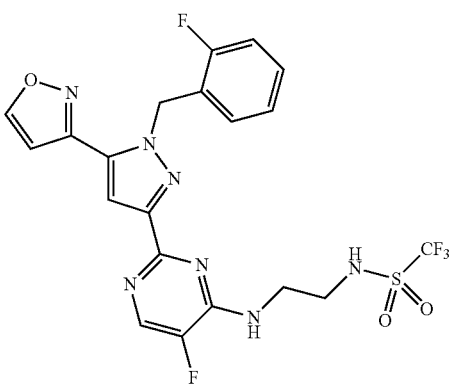 [SMILES: O=S(=O)(NCCNc1nc(-c2cc(-c3ccon3)n(Cc3ccccc3F)n2)ncc1F)C(F)(F)F]
I-392
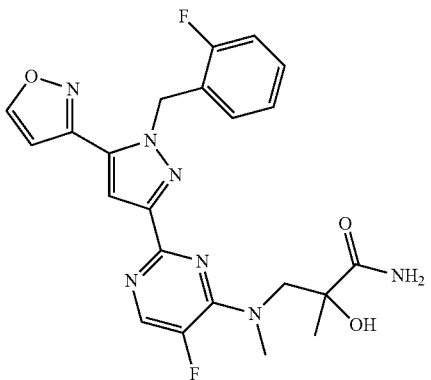 [SMILES: CN(CC(C)(O)C(N)=O)c1nc(-c2cc(-c3ccon3)n(Cc3ccccc3F)n2)ncc1F]
I-393
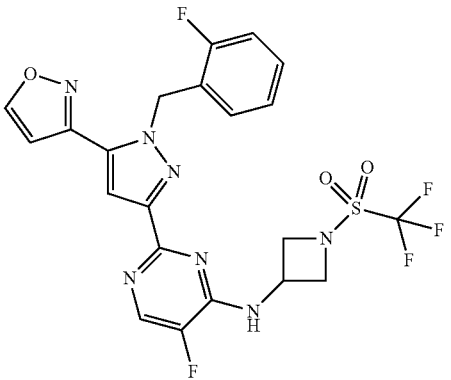 [SMILES: O=S(=O)(N1CC(Nc2nc(-c3cc(-c4ccon4)n(Cc4ccccc4F)n3)ncc2F)C1)C(F)(F)F]
I-394

TABLE 1C-continued
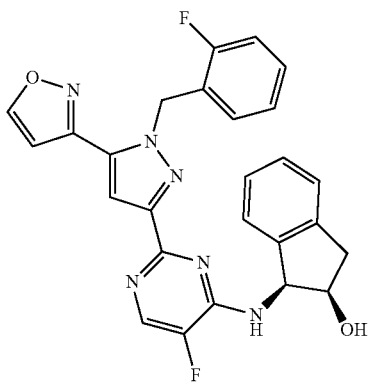 [SMILES: O[C@@H]1Cc2ccccc2[C@@H]1Nc1nc(-c2cc(-c3ccon3)n(Cc3ccccc3F)n2)ncc1F] I-395
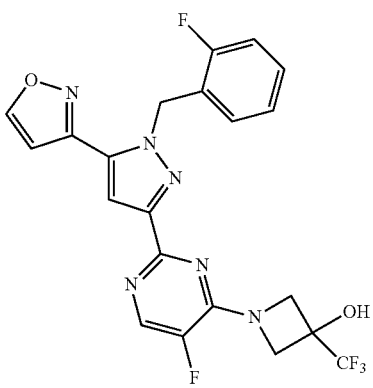 [SMILES: OC1(C(F)(F)F)CN(c2nc(-c3cc(-c4ccon4)n(Cc4ccccc4F)n3)ncc2F)C1] I-396
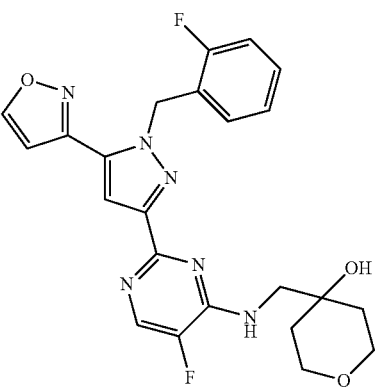 [SMILES: OC1(CNc2nc(-c3cc(-c4ccon4)n(Cc4ccccc4F)n3)ncc2F)CCOCC1] I-397
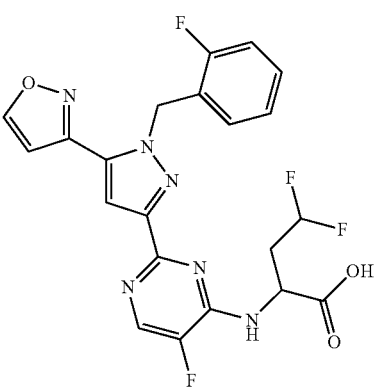 [SMILES: O=C(O)C(CC(F)F)Nc1nc(-c2cc(-c3ccon3)n(Cc3ccccc3F)n2)ncc1F] I-398
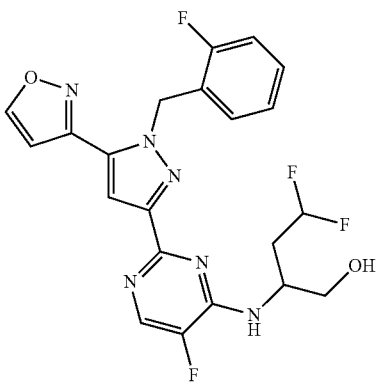 [SMILES: OCC(CC(F)F)Nc1nc(-c2cc(-c3ccon3)n(Cc3ccccc3F)n2)ncc1F] I-399
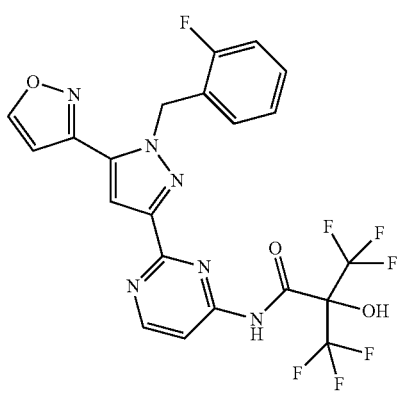 [SMILES: O=C(Nc1ccnc(-c2cc(-c3ccon3)n(Cc3ccccc3F)n2)n1)C(O)(C(F)(F)F)C(F)(F)F] I-400
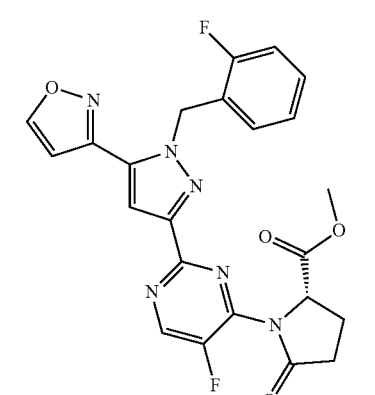 I-401
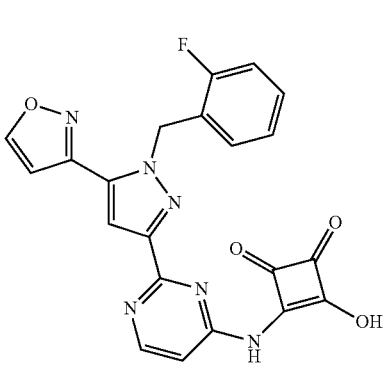 [SMILES: O=c1c(O)c(Nc2ccnc(-c3cc(-c4ccon4)n(Cc4ccccc4F)n3)n2)c1=O] I-402

TABLE 1C-continued
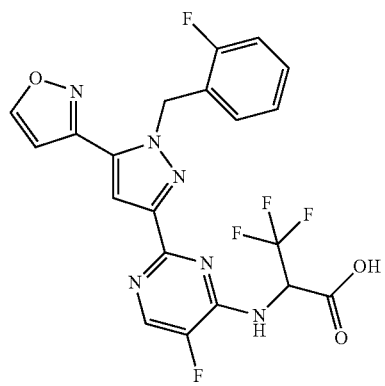 [SMILES: O=C(O)C(Nc1nc(-c2cc(-c3ccon3)n(Cc3ccccc3F)n2)ncc1F)C(F)(F)F]
I-403
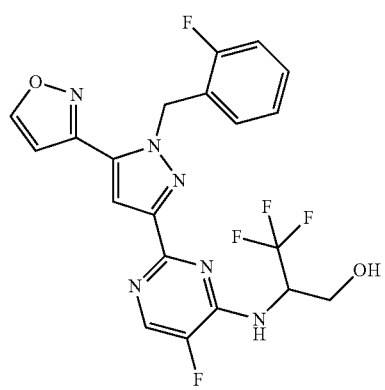 [SMILES: OCC(Nc1nc(-c2cc(-c3ccon3)n(Cc3ccccc3F)n2)ncc1F)C(F)(F)F]
I-404
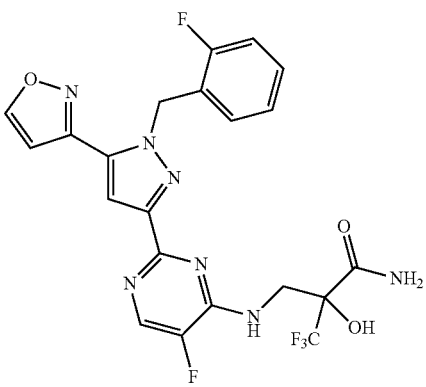
I-405
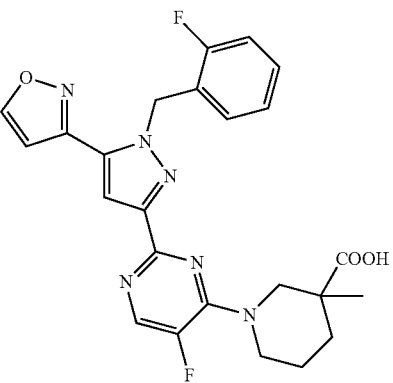 [SMILES: CC1(C(=O)O)CCCN(c2nc(-c3cc(-c4ccon4)n(Cc4ccccc4F)n3)ncc2F)C1]
I-406
TABLE 1C-continued
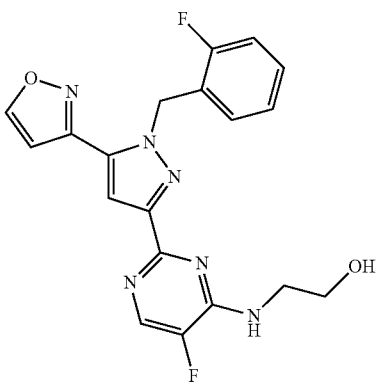 [SMILES: OCCNc1nc(-c2cc(-c3ccon3)n(Cc3ccccc3F)n2)ncc1F]
I-407
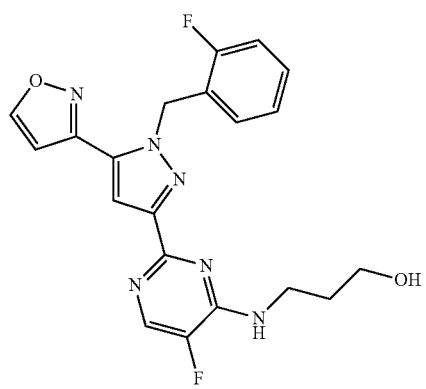 [SMILES: OCCCNc1nc(-c2cc(-c3ccon3)n(Cc3ccccc3F)n2)ncc1F]
I-408
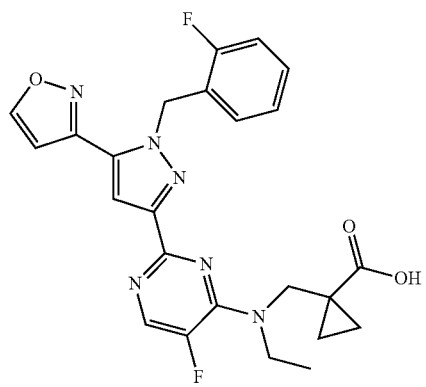 [SMILES: CCN(CC1(C(=O)O)CC1)c1nc(-c2cc(-c3ccon3)n(Cc3ccccc3F)n2)ncc1F]
I-409
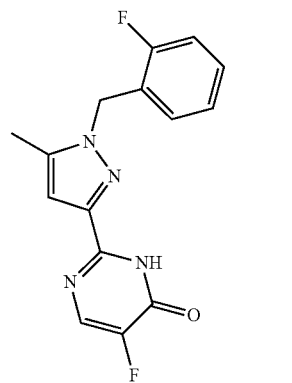 [SMILES: Cc1cc(-c2ncc(F)c(=O)[nH]2)nn1Cc1ccccc1F]
I-410

TABLE 1C-continued
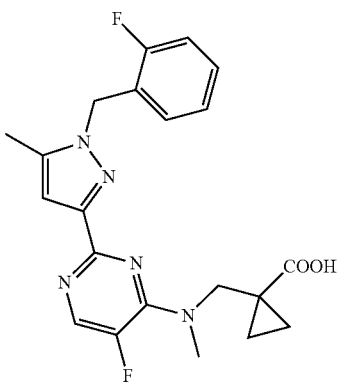 [SMILES: Cc1cc(-c2ncc(F)c(N(C)CC3(C(=O)O)CC3)n2)nn1Cc1ccccc1F]
I-411
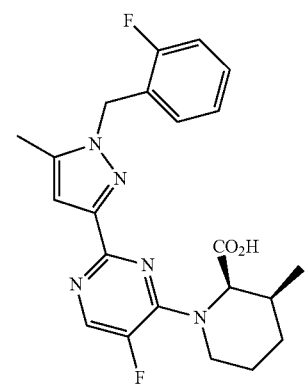
I-412
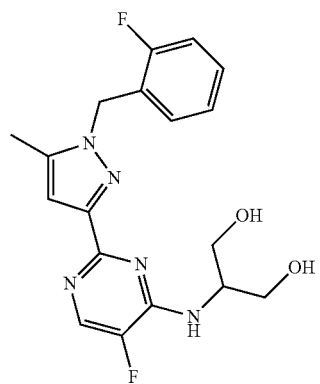 [SMILES: Cc1cc(-c2ncc(F)c(NC(CO)CO)n2)nn1Cc1ccccc1F]
I-413
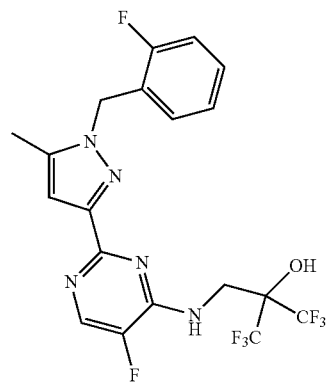 [SMILES: Cc1cc(-c2ncc(F)c(NCC(O)(C(F)(F)F)C(F)(F)F)n2)nn1Cc1ccccc1F]
I-414
TABLE 1C-continued
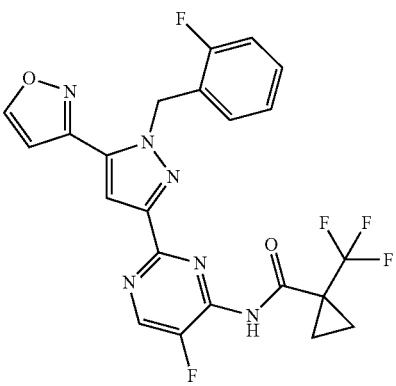 [SMILES: O=C(Nc1nc(-c2cc(-c3ccon3)n(Cc3ccccc3F)n2)ncc1F)C1(C(F)(F)F)CC1]
I-415
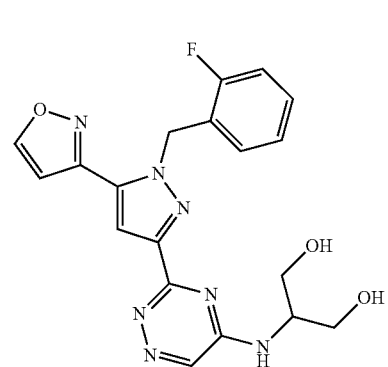 [SMILES: OCC(CO)Nc1cnnc(-c2cc(-c3ccon3)n(Cc3ccccc3F)n2)n1]
I-416
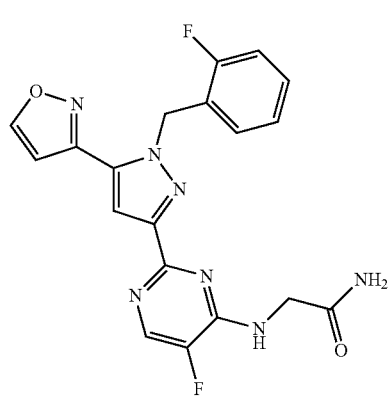 [SMILES: NC(=O)CNc1nc(-c2cc(-c3ccon3)n(Cc3ccccc3F)n2)ncc1F]
I-417
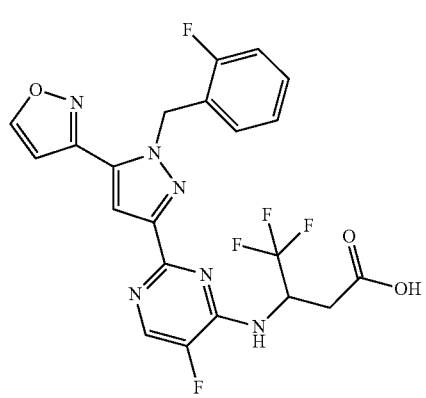 [SMILES: O=C(O)CC(Nc1nc(-c2cc(-c3ccon3)n(Cc3ccccc3F)n2)ncc1F)C(F)(F)F]
I-418

TABLE 1C-continued
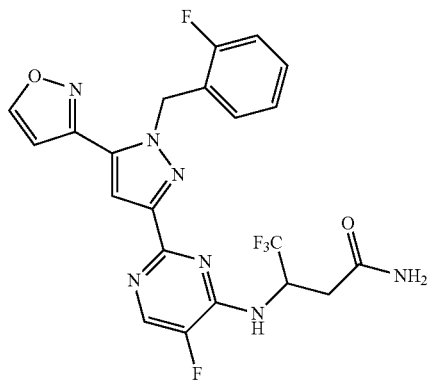 [SMILES: NC(=O)CC(Nc1nc(-c2cc(-c3ccon3)n(Cc3ccccc3F)n2)ncc1F)C(F)(F)F]
I-419
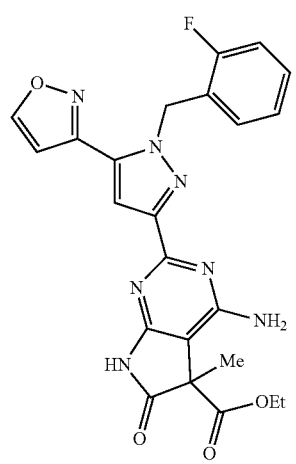 [SMILES: CCOC(=O)C1(C)C(=O)Nc2nc(-c3cc(-c4ccon4)n(Cc4ccccc4F)n3)nc(N)c21]
I-420
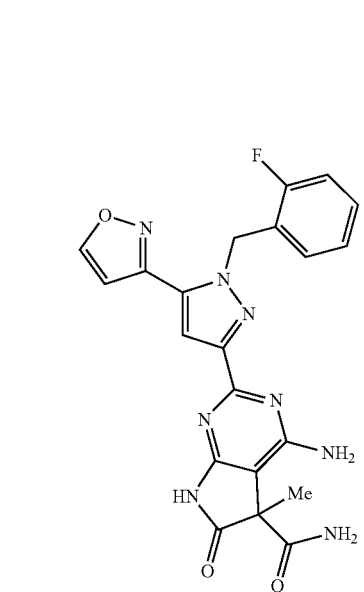
I-421
TABLE 1C-continued
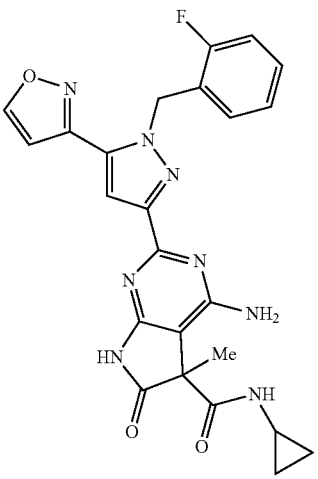 [SMILES: CC1(C(=O)NC2CC2)C(=O)Nc2nc(-c3cc(-c4ccon4)n(Cc4ccccc4F)n3)nc(N)c21]
I-422
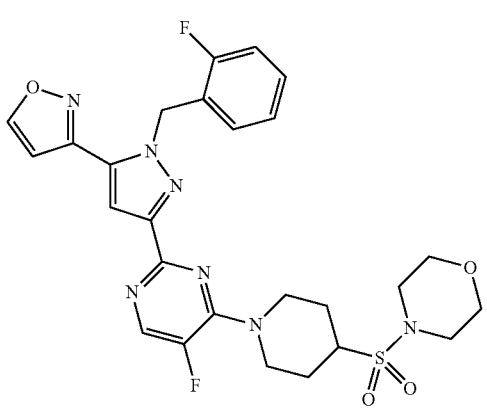 [SMILES: O=S(=O)(C1CCN(c2nc(-c3cc(-c4ccon4)n(Cc4ccccc4F)n3)ncc2F)CC1)N1CCOCC1]
I-423
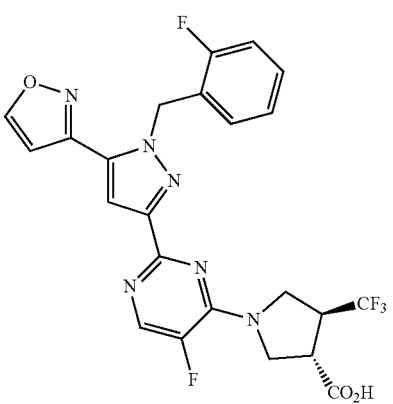 [SMILES: O=C(O)[C@@H]1CN(c2nc(-c3cc(-c4ccon4)n(Cc4ccccc4F)n3)ncc2F)C[C@H]1C(F)(F)F]
I-424
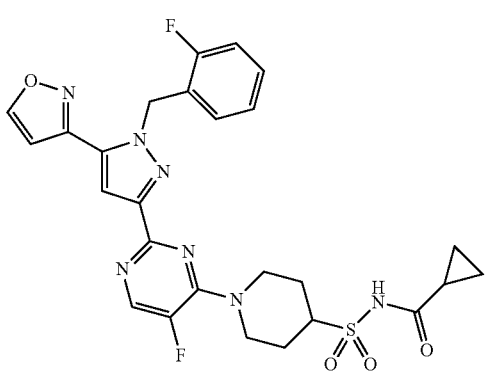 [SMILES: O=C(NS(=O)(=O)C1CCN(c2nc(-c3cc(-c4ccon4)n(Cc4ccccc4F)n3)ncc2F)CC1)C1CC1]
I-425

TABLE 1C-continued
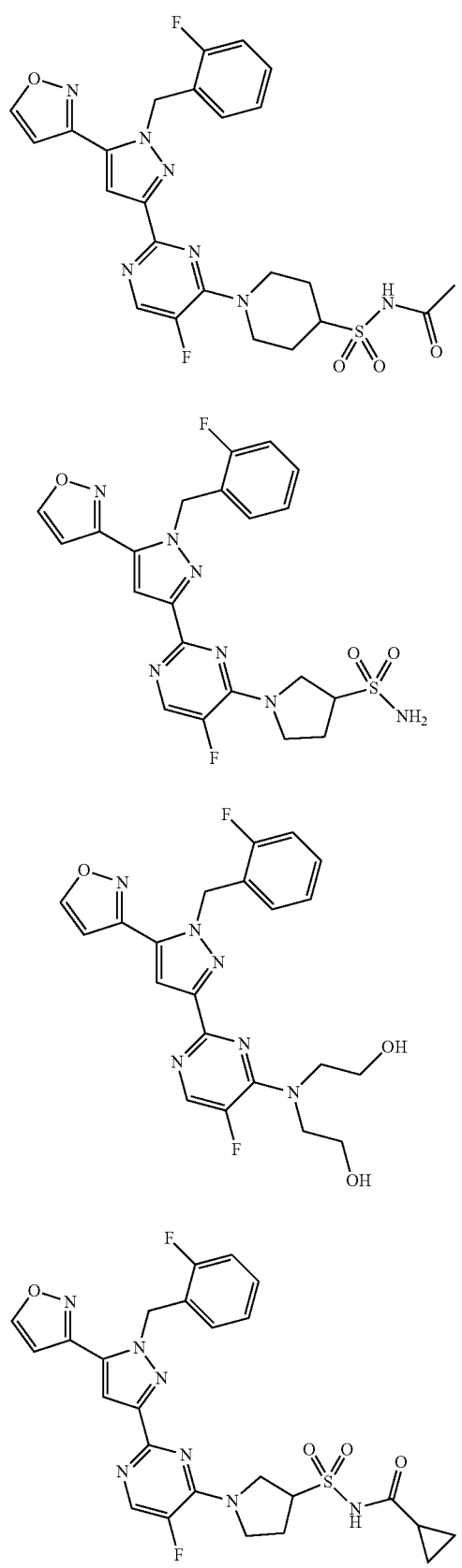
I-426
I-427
I-428
I-429
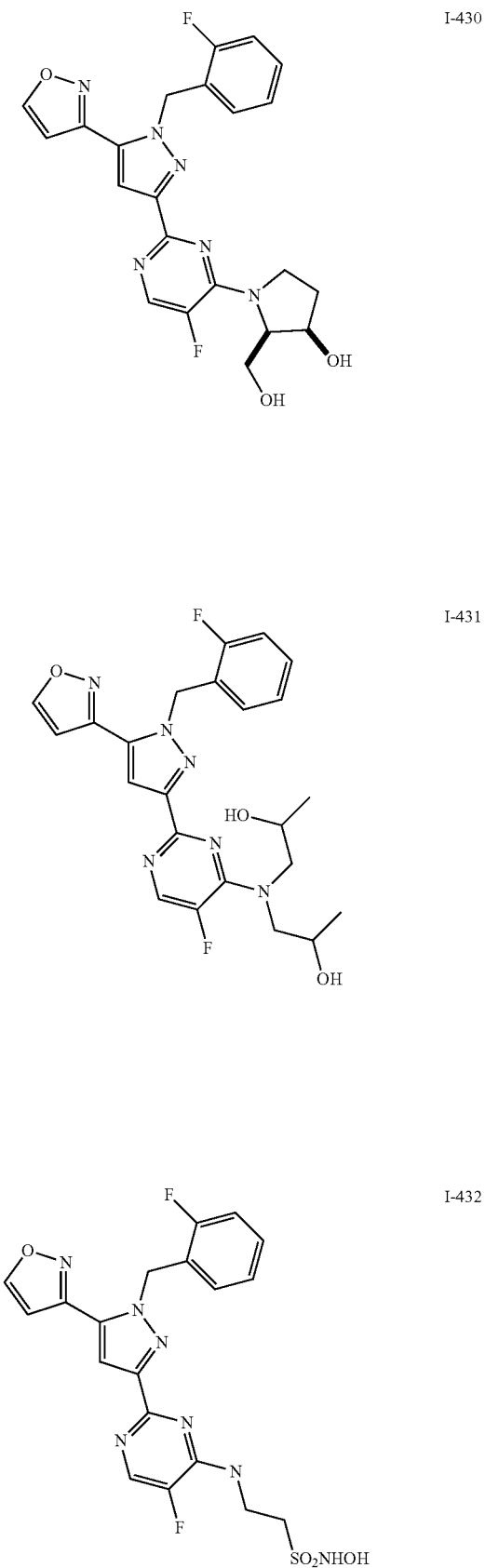
I-430
I-431
I-432

TABLE 1C-continued
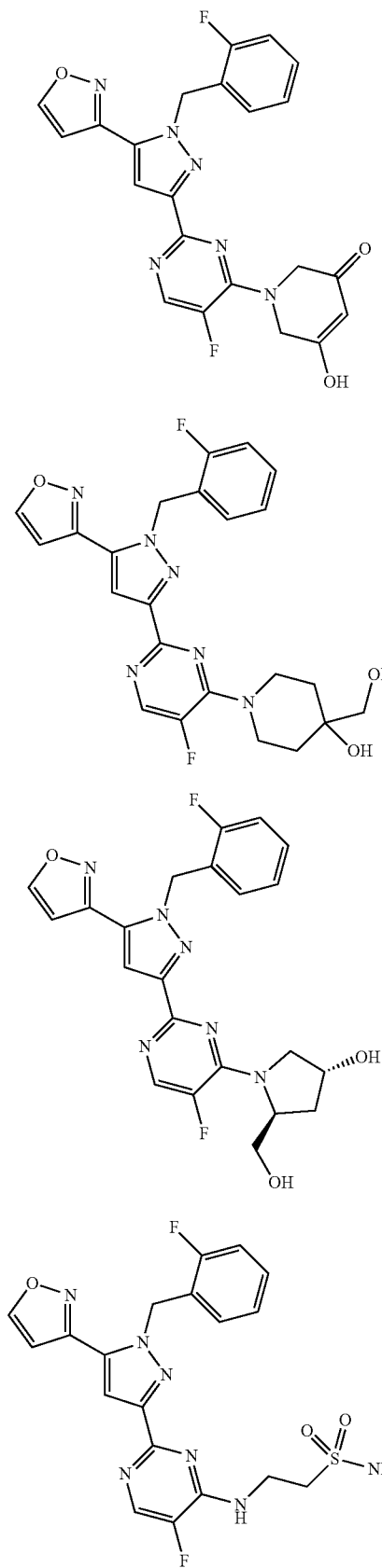
I-433
I-434
I-435
I-436
TABLE 1C-continued
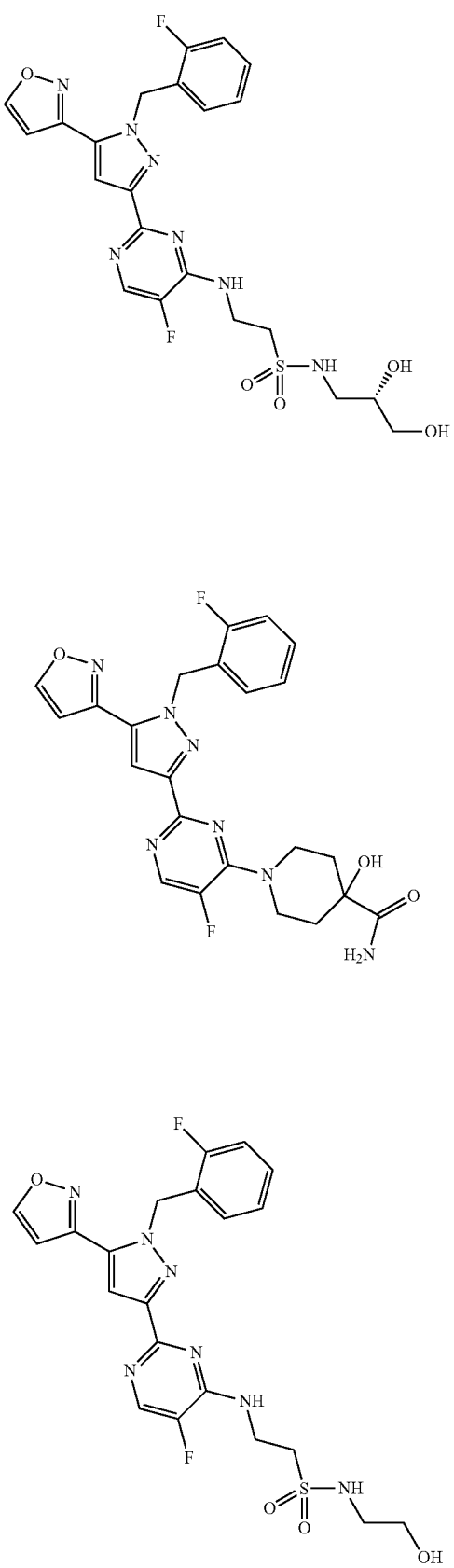
I-437
I-438
I-439

TABLE 1C-continued
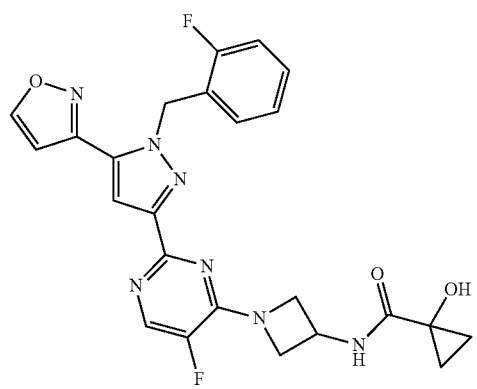 [SMILES: O=C(NC1CN(c2nc(-c3cc(-c4ccon4)n(Cc4ccccc4F)n3)ncc2F)C1)C1(O)CC1]
I-440
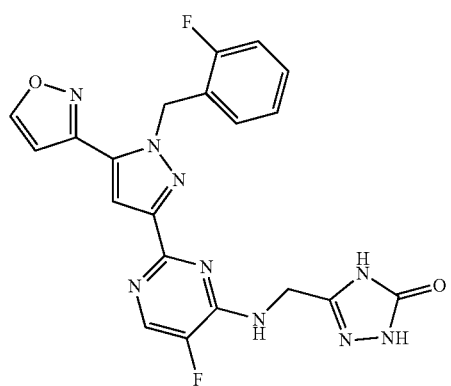 [SMILES: O=c1[nH]nc(CNc2nc(-c3cc(-c4ccon4)n(Cc4ccccc4F)n3)ncc2F)[nH]1]
I-441
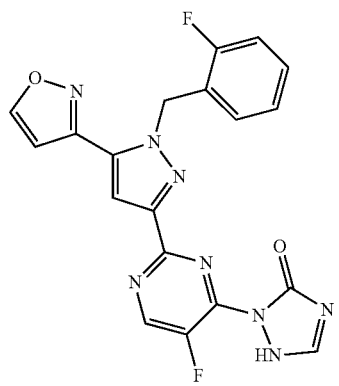 [SMILES: O=c1nc[nH]n1-c1nc(-c2cc(-c3ccon3)n(Cc3ccccc3F)n2)ncc1F]
I-442
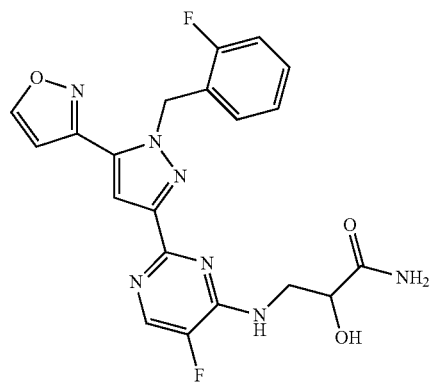 [SMILES: NC(=O)C(O)CNc1nc(-c2cc(-c3ccon3)n(Cc3ccccc3F)n2)ncc1F]
I-443
TABLE 1C-continued
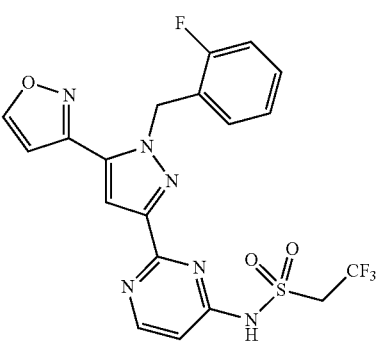 [SMILES: O=S(=O)(CC(F)(F)F)Nc1ccnc(-c2cc(-c3ccon3)n(Cc3ccccc3F)n2)n1]
I-444
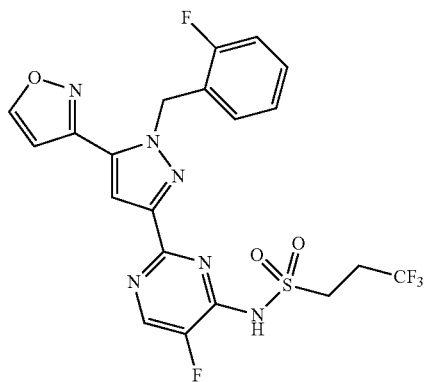 [SMILES: O=S(=O)(CCC(F)(F)F)Nc1nc(-c2cc(-c3ccon3)n(Cc3ccccc3F)n2)ncc1F]
I-445
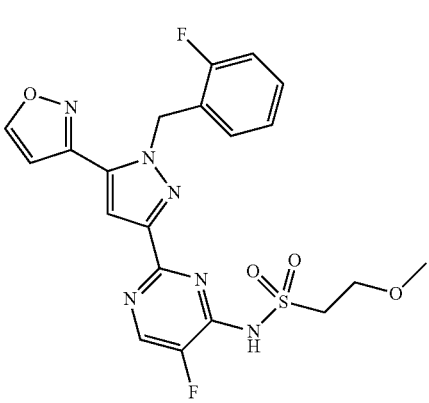 [SMILES: COCCS(=O)(=O)Nc1nc(-c2cc(-c3ccon3)n(Cc3ccccc3F)n2)ncc1F]
I-446
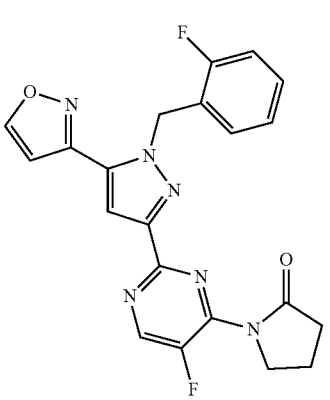 [SMILES: O=C1CCCN1c1nc(-c2cc(-c3ccon3)n(Cc3ccccc3F)n2)ncc1F]
I-447

TABLE 1C-continued
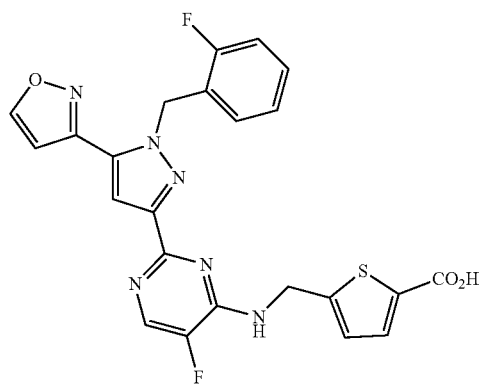 [SMILES: O=C(O)c1ccc(CNc2nc(-c3cc(-c4ccon4)n(Cc4ccccc4F)n3)ncc2F)s1]
I-448
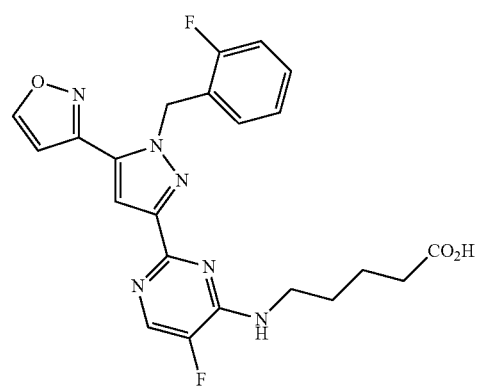 [SMILES: O=C(O)CCCCNc1nc(-c2cc(-c3ccon3)n(Cc3ccccc3F)n2)ncc1F]
I-449
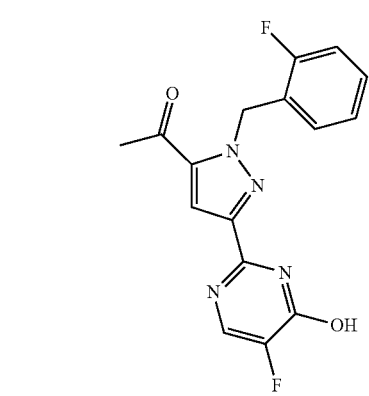 [SMILES: CC(=O)c1cc(-c2ncc(F)c(O)n2)nn1Cc1ccccc1F]
I-450
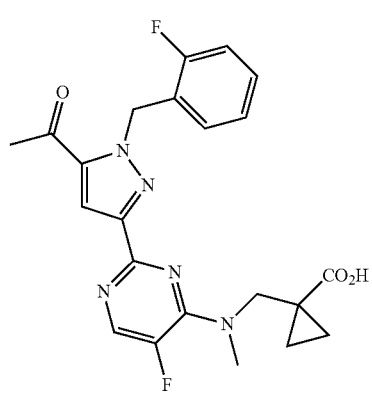 [SMILES: CC(=O)c1cc(-c2ncc(F)c(N(C)CC3(C(=O)O)CC3)n2)nn1Cc1ccccc1F]
I-451
TABLE 1C-continued
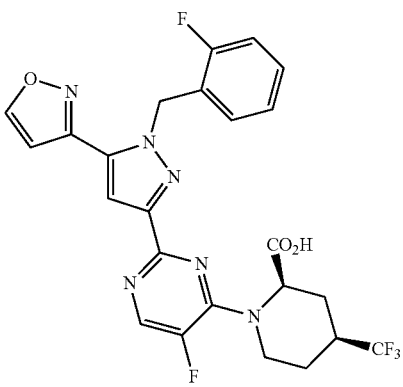 [SMILES: O=C(O)[C@H]1C[C@@H](C(F)(F)F)CCN1c1nc(-c2cc(-c3ccon3)n(Cc3ccccc3F)n2)ncc1F]
I-452
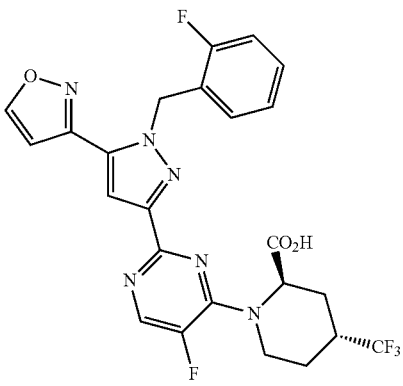 [SMILES: O=C(O)[C@H]1C[C@H](C(F)(F)F)CCN1c1nc(-c2cc(-c3ccon3)n(Cc3ccccc3F)n2)ncc1F]
I-453
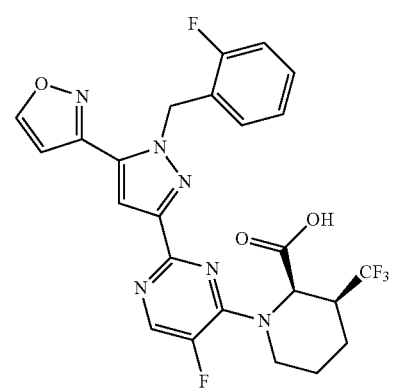 [SMILES: O=C(O)[C@H]1[C@@H](C(F)(F)F)CCCN1c1nc(-c2cc(-c3ccon3)n(Cc3ccccc3F)n2)ncc1F]
I-454
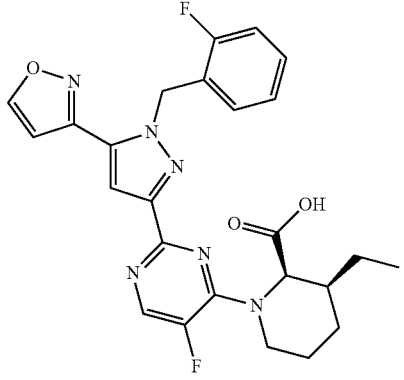 [SMILES: CC[C@H]1CCCN(c2nc(-c3cc(-c4ccon4)n(Cc4ccccc4F)n3)ncc2F)[C@H]1C(=O)O]
I-455

TABLE ID
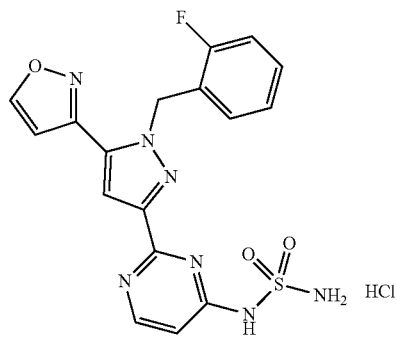 [SMILES: NS(=O)(=O)Nc1ccnc(-c2cc(-c3ccon3)n(Cc3ccccc3F)n2)n1 ; Cl]
I-456
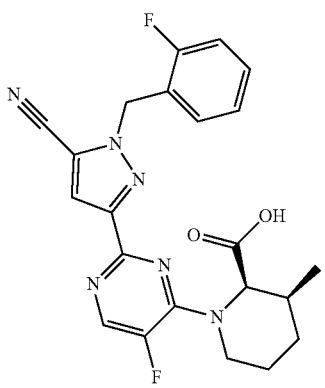 [SMILES: C[C@H]1CCCN(c2nc(-c3cc(C#N)n(Cc4ccccc4F)n3)ncc2F)[C@H]1C(=O)O]
I-457
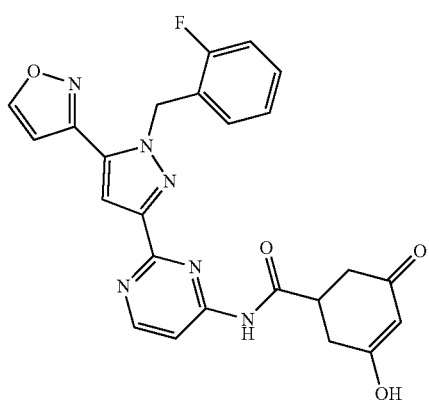 [SMILES: O=C1C=C(O)CC(C(=O)Nc2ccnc(-c3cc(-c4ccon4)n(Cc4ccccc4F)n3)n2)C1]
I-458
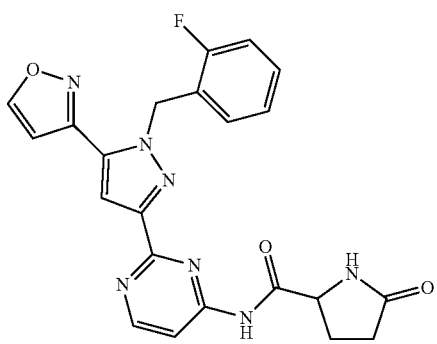 [SMILES: O=C1CCC(C(=O)Nc2ccnc(-c3cc(-c4ccon4)n(Cc4ccccc4F)n3)n2)N1]
I-459

TABLE ID-continued
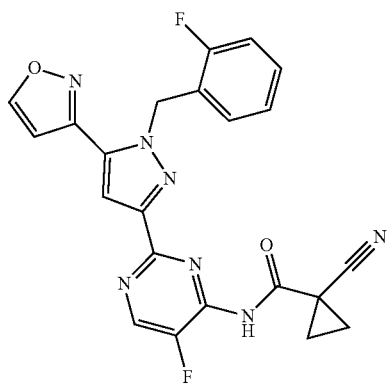 [SMILES: N#CC1(C(=O)Nc2nc(-c3cc(-c4ccon4)n(Cc4ccccc4F)n3)ncc2F)CC1]
I-460
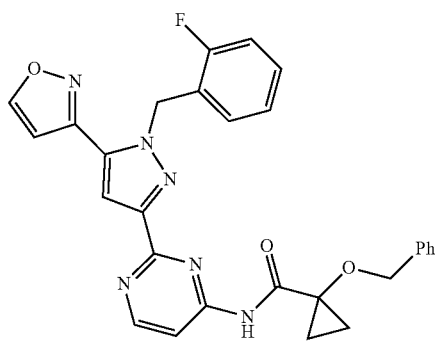 [SMILES: O=C(Nc1ccnc(-c2cc(-c3ccon3)n(Cc3ccccc3F)n2)n1)C1(OCc2ccccc2)CC1]
I-461
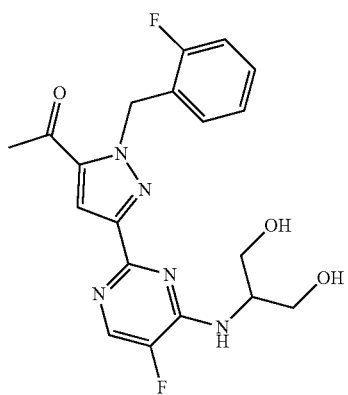
I-462
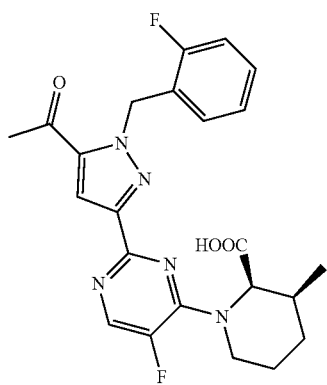 [SMILES: CC(=O)c1cc(-c2ncc(F)c(N3CCC[C@H](C)[C@@H]3C(=O)O)n2)nn1Cc1ccccc1F]
I-463

TABLE ID-continued
I-464
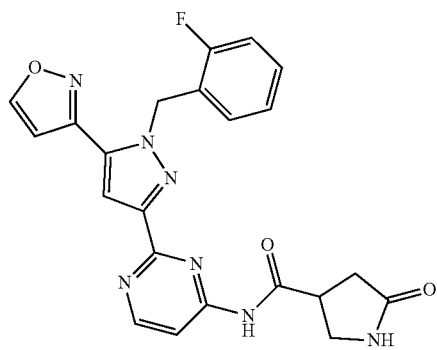 [SMILES: O=C1CC(C(=O)Nc2ccnc(-c3cc(-c4ccon4)n(Cc4ccccc4F)n3)n2)CN1]
I-465
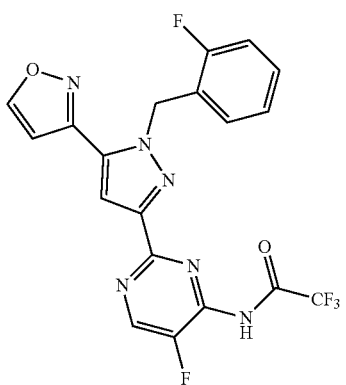 [SMILES: O=C(Nc1nc(-c2cc(-c3ccon3)n(Cc3ccccc3F)n2)ncc1F)C(F)(F)F]
I-466
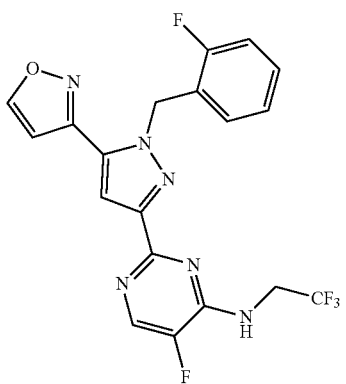 [SMILES: Fc1ccccc1Cn1nc(-c2ncc(F)c(NCC(F)(F)F)n2)cc1-c1ccon1]
I-467
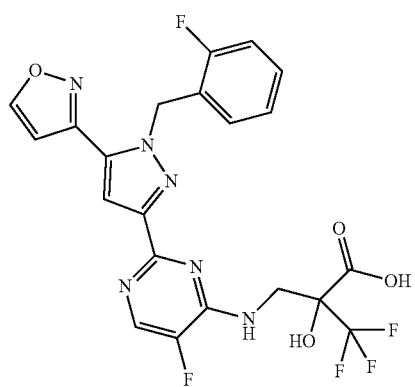 [SMILES: O=C(O)C(O)(CNc1nc(-c2cc(-c3ccon3)n(Cc3ccccc3F)n2)ncc1F)C(F)(F)F]

TABLE ID-continued
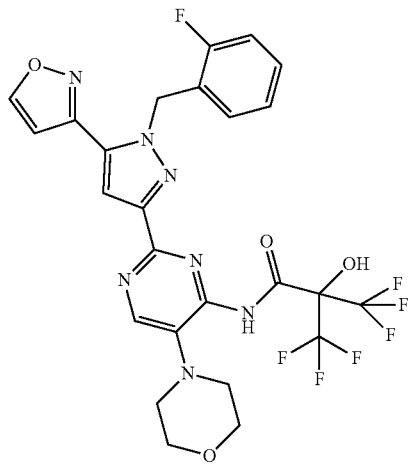 [SMILES: O=C(Nc1nc(-c2cc(-c3ccon3)n(Cc3ccccc3F)n2)ncc1N1CCOCC1)C(O)(C(F)(F)F)C(F)(F)F]
I-468
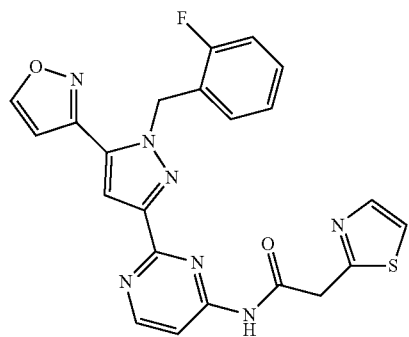 [SMILES: O=C(Cc1nccs1)Nc1ccnc(-c2cc(-c3ccon3)n(Cc3ccccc3F)n2)n1]
I-469
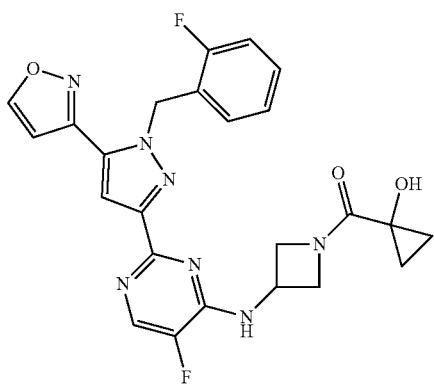 [SMILES: O=C(N1CC(Nc2nc(-c3cc(-c4ccon4)n(Cc4ccccc4F)n3)ncc2F)C1)C1(O)CC1]
I-470
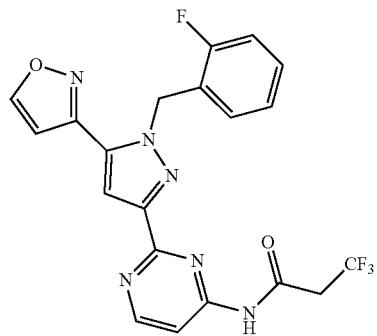 [SMILES: O=C(CC(F)(F)F)Nc1ccnc(-c2cc(-c3ccon3)n(Cc3ccccc3F)n2)n1]
I-471

TABLE ID-continued
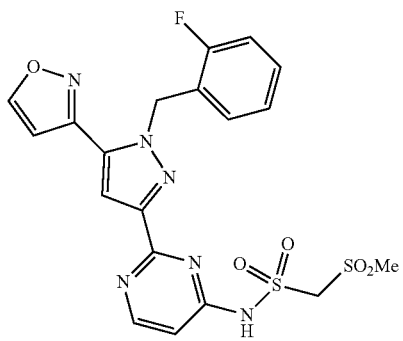 [SMILES: CS(=O)(=O)CS(=O)(=O)Nc1ccnc(-c2cc(-c3ccon3)n(Cc3ccccc3F)n2)n1]
I-472
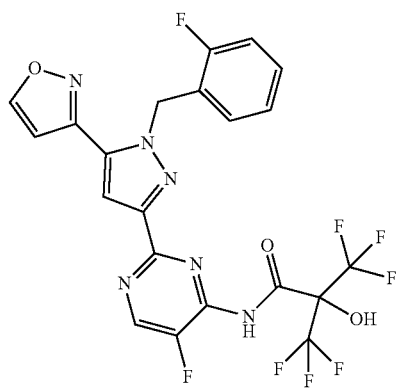 [SMILES: O=C(Nc1nc(-c2cc(-c3ccon3)n(Cc3ccccc3F)n2)ncc1F)C(O)(C(F)(F)F)C(F)(F)F]
I-473
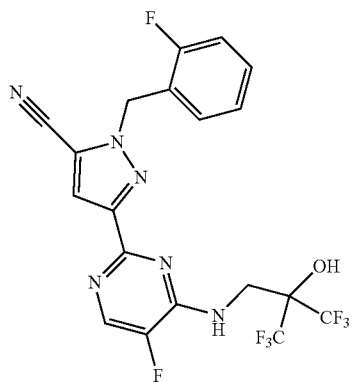 [SMILES: N#Cc1cc(-c2ncc(F)c(NCC(O)(C(F)(F)F)C(F)(F)F)n2)nn1Cc1ccccc1F]
I-474
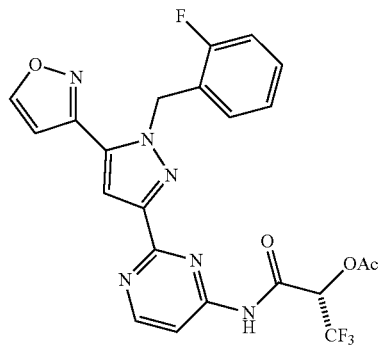 [SMILES: CC(=O)O[C@@H](C(=O)Nc1ccnc(-c2cc(-c3ccon3)n(Cc3ccccc3F)n2)n1)C(F)(F)F]
I-475

TABLE ID-continued
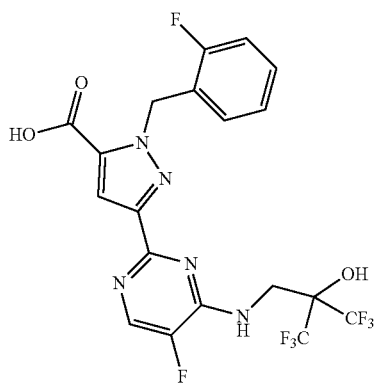 [SMILES: O=C(O)c1cc(-c2ncc(F)c(NCC(O)(C(F)(F)F)C(F)(F)F)n2)nn1Cc1ccccc1F]
I-476
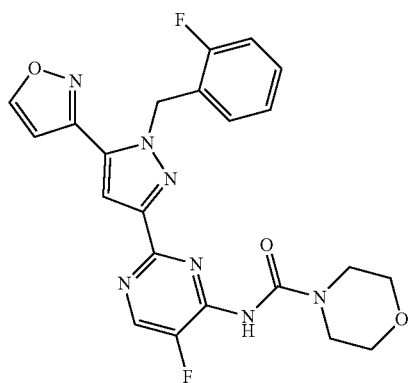 [SMILES: O=C(Nc1nc(-c2cc(-c3ccon3)n(Cc3ccccc3F)n2)ncc1F)N1CCOCC1]
I-477
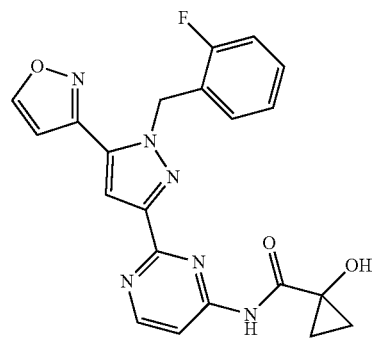 [SMILES: O=C(Nc1ccnc(-c2cc(-c3ccon3)n(Cc3ccccc3F)n2)n1)C1(O)CC1]
I-478
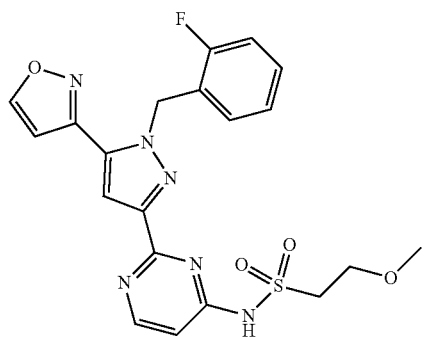 [SMILES: COCCS(=O)(=O)Nc1ccnc(-c2cc(-c3ccon3)n(Cc3ccccc3F)n2)n1]
I-479

TABLE ID-continued
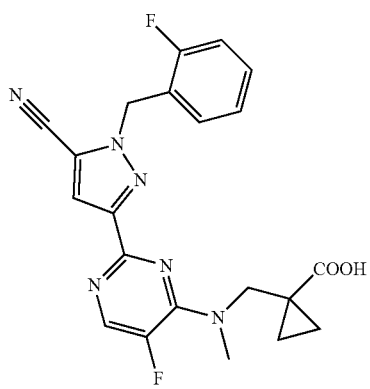 [SMILES: CN(CC1(C(=O)O)CC1)c1nc(-c2cc(C#N)n(Cc3ccccc3F)n2)ncc1F]
I-480
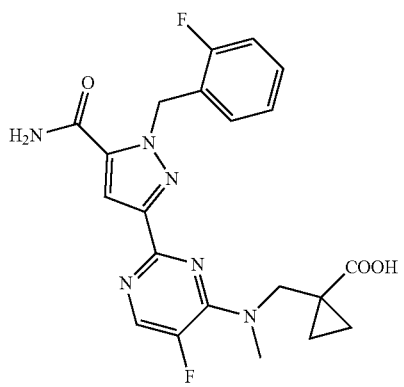 [SMILES: CN(CC1(C(=O)O)CC1)c1nc(-c2cc(C(N)=O)n(Cc3ccccc3F)n2)ncc1F]
I-481
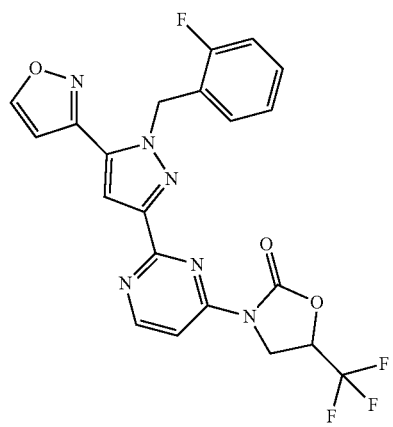 [SMILES: O=C1OC(C(F)(F)F)CN1c1ccnc(-c2cc(-c3ccon3)n(Cc3ccccc3F)n2)n1]
I-482
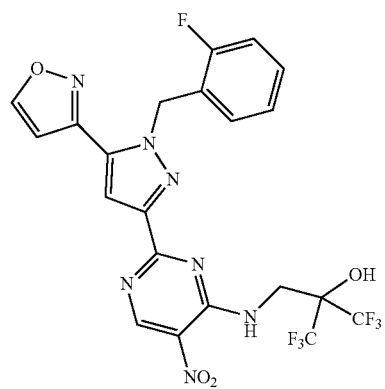
I-483

TABLE ID-continued
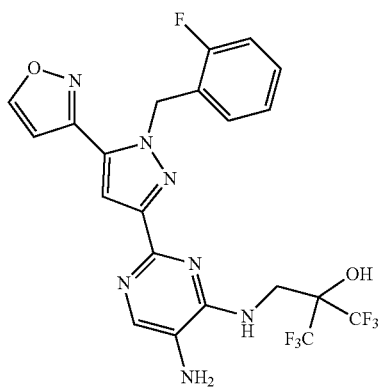 [SMILES: O=[N+]([O-])c1cnc(-c2cc(-c3ccon3)n(Cc3ccccc3F)n2)nc1NCC(O)(C(F)(F)F)C(F)(F)F]
I-484
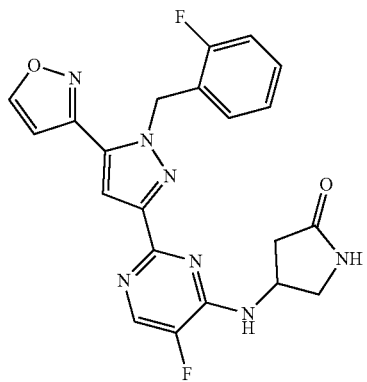 [SMILES: O=C1CC(Nc2nc(-c3cc(-c4ccon4)n(Cc4ccccc4F)n3)ncc2F)CN1]
I-485
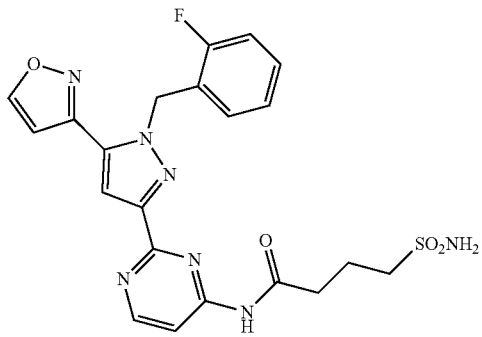 [SMILES: NS(=O)(=O)CCCC(=O)Nc1ccnc(-c2cc(-c3ccon3)n(Cc3ccccc3F)n2)n1]
I-486
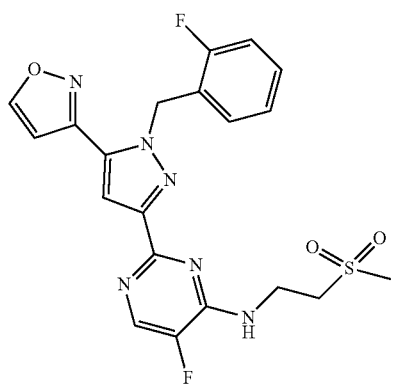 [SMILES: CS(=O)(=O)CCNc1nc(-c2cc(-c3ccon3)n(Cc3ccccc3F)n2)ncc1F]
I-487

TABLE ID-continued
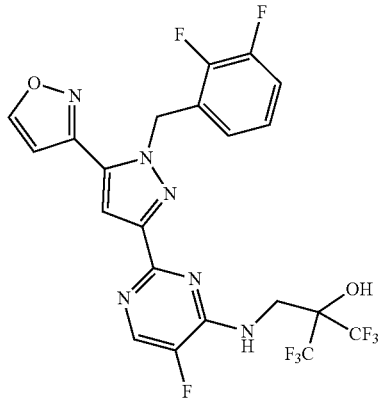 [SMILES: OC(CNc1nc(-c2cc(-c3ccon3)n(Cc3cccc(F)c3F)n2)ncc1F)(C(F)(F)F)C(F)(F)F]
I-488
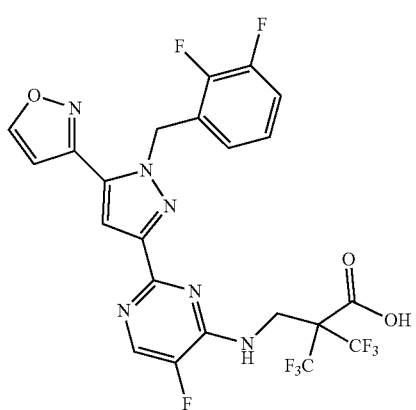 [SMILES: O=C(O)C(CNc1nc(-c2cc(-c3ccon3)n(Cc3cccc(F)c3F)n2)ncc1F)(C(F)(F)F)C(F)(F)F]
I-489
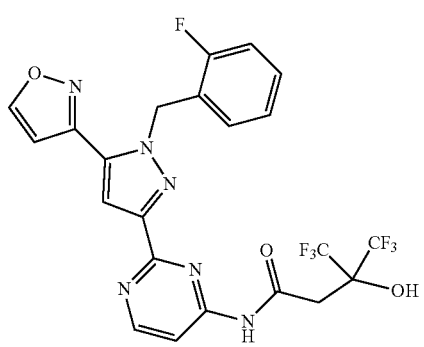 [SMILES: O=C(CC(O)(C(F)(F)F)C(F)(F)F)Nc1ccnc(-c2cc(-c3ccon3)n(Cc3ccccc3F)n2)n1]
I-490
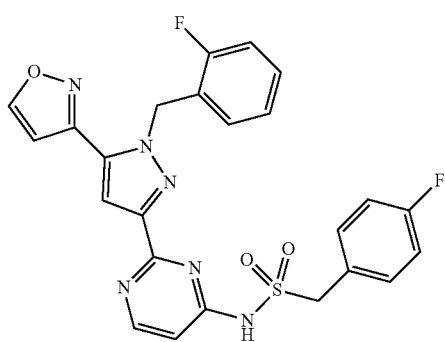 [SMILES: O=S(=O)(Cc1ccc(F)cc1)Nc1ccnc(-c2cc(-c3ccon3)n(Cc3ccccc3F)n2)n1]
I-491

TABLE ID-continued
I-492
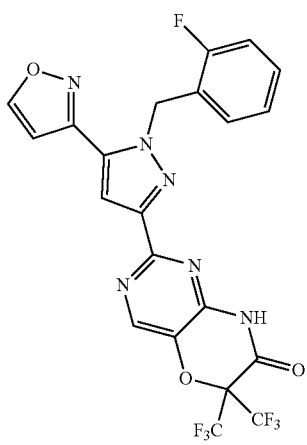 [SMILES: O=C1Nc2nc(-c3cc(-c4ccon4)n(Cc4ccccc4F)n3)ncc2OC1(C(F)(F)F)C(F)(F)F]
I-493
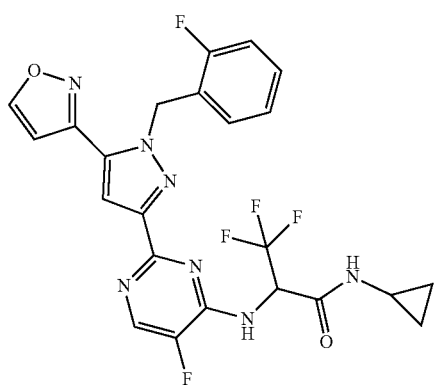 [SMILES: O=C(NC1CC1)C(Nc1nc(-c2cc(-c3ccon3)n(Cc3ccccc3F)n2)ncc1F)C(F)(F)F]
I-494
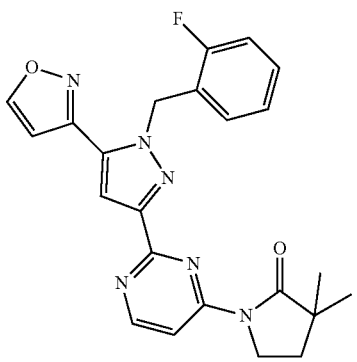 [SMILES: CC1(C)CCN(c2ccnc(-c3cc(-c4ccon4)n(Cc4ccccc4F)n3)n2)C1=O]
I-495
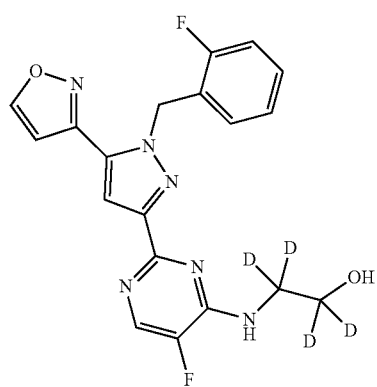 [SMILES: [2H]C([2H])(O)C([2H])([2H])Nc1nc(-c2cc(-c3ccon3)n(Cc3ccccc3F)n2)ncc1F]

TABLE ID-continued
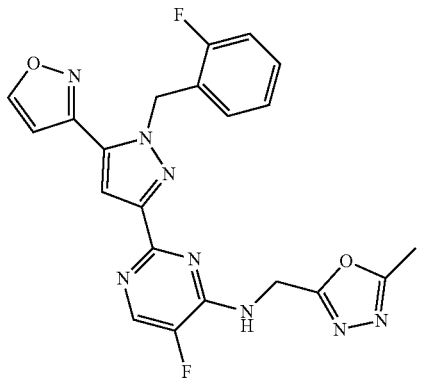 [SMILES: Cc1nnc(CNc2nc(-c3cc(-c4ccon4)n(Cc4ccccc4F)n3)ncc2F)o1]
I-496
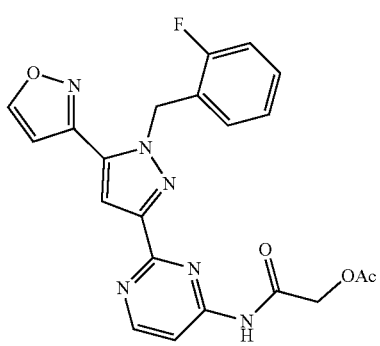 [SMILES: CC(=O)OCC(=O)Nc1ccnc(-c2cc(-c3ccon3)n(Cc3ccccc3F)n2)n1]
I-497
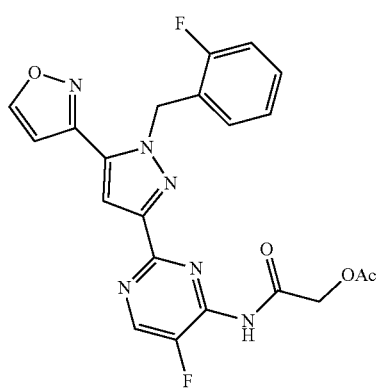 [SMILES: CC(=O)OCC(=O)Nc1nc(-c2cc(-c3ccon3)n(Cc3ccccc3F)n2)ncc1F]
I-498
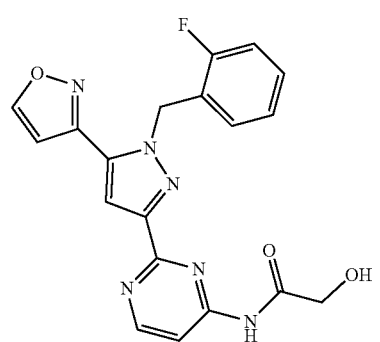 [SMILES: O=C(CO)Nc1ccnc(-c2cc(-c3ccon3)n(Cc3ccccc3F)n2)n1]
I-499

TABLE ID-continued
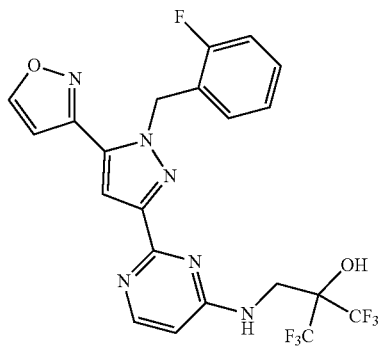 [SMILES: OC(CNc1ccnc(-c2cc(-c3ccon3)n(Cc3ccccc3F)n2)n1)(C(F)(F)F)C(F)(F)F]
I-500
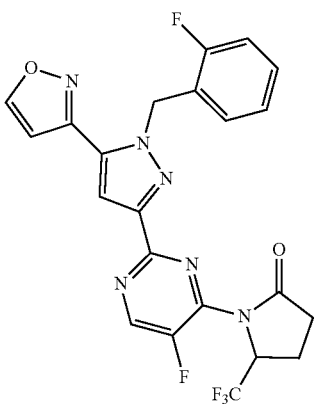 [SMILES: O=C1CCC(C(F)(F)F)N1c1nc(-c2cc(-c3ccon3)n(Cc3ccccc3F)n2)ncc1F]
I-501
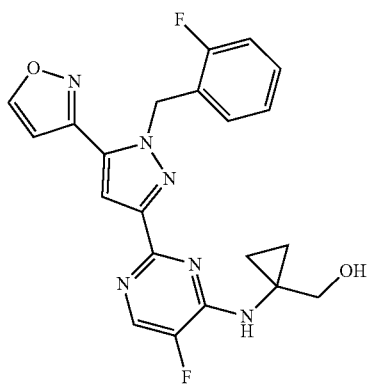 [SMILES: OCC1(Nc2nc(-c3cc(-c4ccon4)n(Cc4ccccc4F)n3)ncc2F)CC1]
I-502
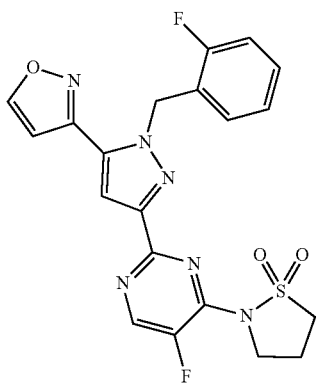 [SMILES: O=S1(=O)CCCN1c1nc(-c2cc(-c3ccon3)n(Cc3ccccc3F)n2)ncc1F]
I-503

TABLE ID-continued
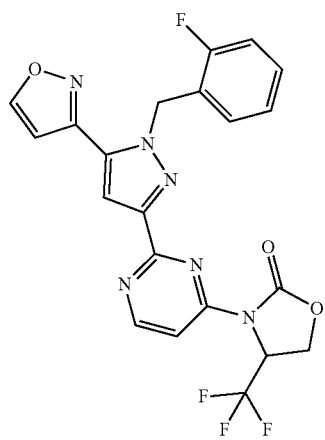 [SMILES: O=C1OCC(C(F)(F)F)N1c1ccnc(-c2cc(-c3ccon3)n(Cc3ccccc3F)n2)n1]
I-504
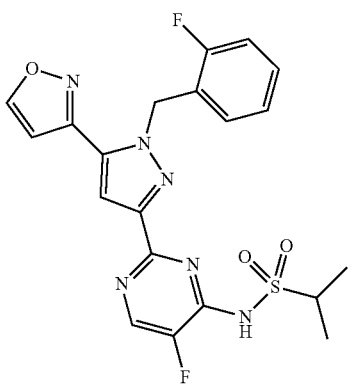 [SMILES: CC(C)S(=O)(=O)Nc1nc(-c2cc(-c3ccon3)n(Cc3ccccc3F)n2)ncc1F]
I-505
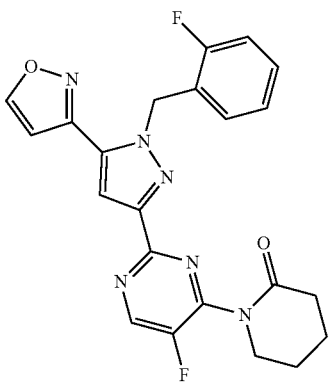 [SMILES: O=C1CCCCN1c1nc(-c2cc(-c3ccon3)n(Cc3ccccc3F)n2)ncc1F]
I-506
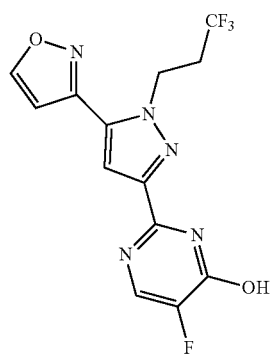 [SMILES: Oc1nc(-c2cc(-c3ccon3)n(CCC(F)(F)F)n2)ncc1F]
I-507

TABLE ID-continued
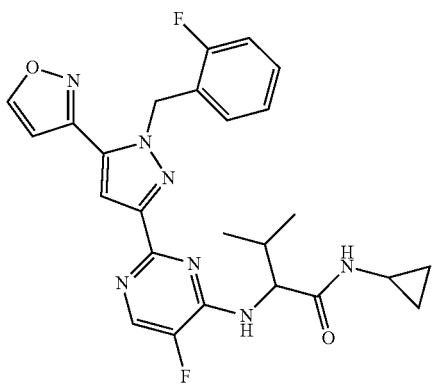 [SMILES: CC(C)C(Nc1nc(-c2cc(-c3ccon3)n(Cc3ccccc3F)n2)ncc1F)C(=O)NC1CC1]
I-508
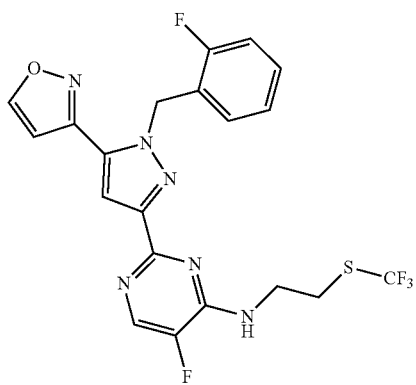 [SMILES: Fc1ccccc1Cn1nc(-c2ncc(F)c(NCCSC(F)(F)F)n2)cc1-c1ccon1]
I-509
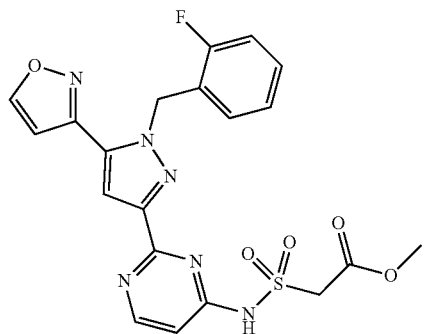 [SMILES: COC(=O)CS(=O)(=O)Nc1ccnc(-c2cc(-c3ccon3)n(Cc3ccccc3F)n2)n1]
I-510
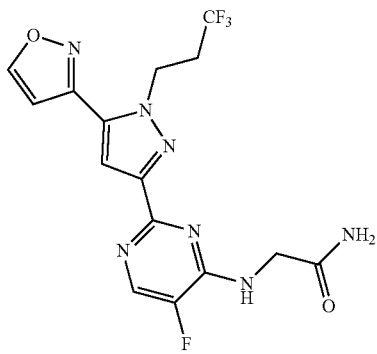 [SMILES: NC(=O)CNc1nc(-c2cc(-c3ccon3)n(CCC(F)(F)F)n2)ncc1F]
I-511

TABLE ID-continued
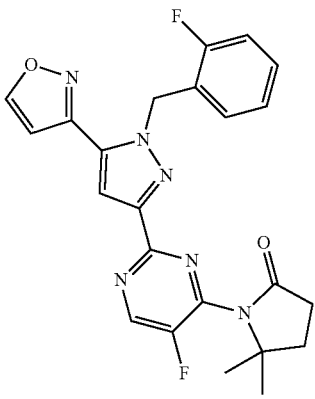 [SMILES: CC1(C)CCC(=O)N1c1nc(-c2cc(-c3ccon3)n(Cc3ccccc3F)n2)ncc1F]
I-512
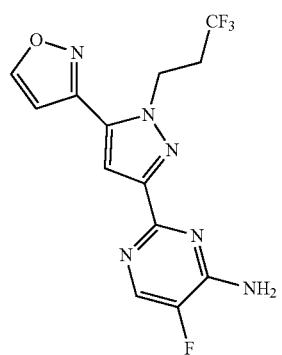 [SMILES: Nc1nc(-c2cc(-c3ccon3)n(CCC(F)(F)F)n2)ncc1F]
I-513
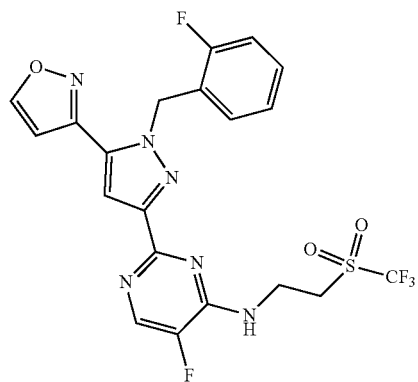 [SMILES: O=S(=O)(CCNc1nc(-c2cc(-c3ccon3)n(Cc3ccccc3F)n2)ncc1F)C(F)(F)F]
I-514
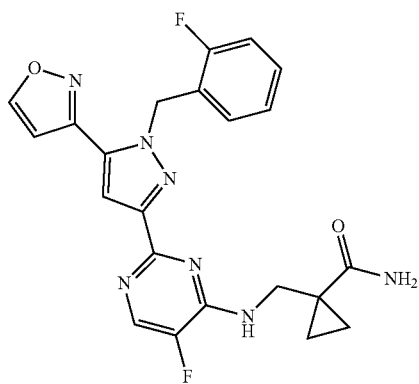 [SMILES: NC(=O)C1(CNc2nc(-c3cc(-c4ccon4)n(Cc4ccccc4F)n3)ncc2F)CC1]
I-515

TABLE ID-continued
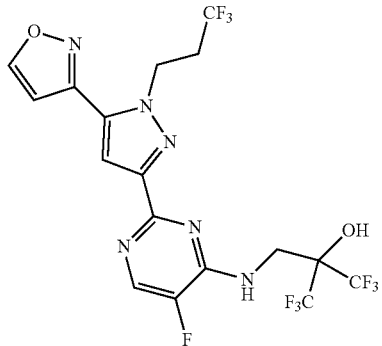 [SMILES: OC(CNc1nc(-c2cc(-c3ccon3)n(CCC(F)(F)F)n2)ncc1F)(C(F)(F)F)C(F)(F)F]
I-516
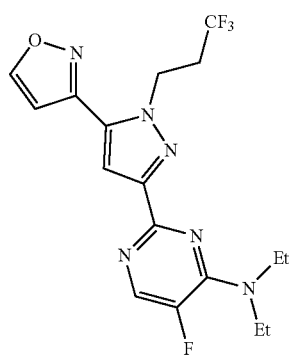 [SMILES: CCN(CC)c1nc(-c2cc(-c3ccon3)n(CCC(F)(F)F)n2)ncc1F]
I-517
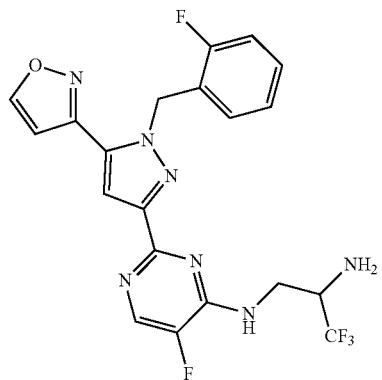 [SMILES: NC(CNc1nc(-c2cc(-c3ccon3)n(Cc3ccccc3F)n2)ncc1F)C(F)(F)F]
I-518
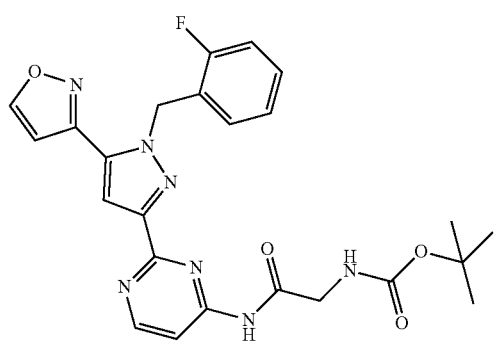 [SMILES: CC(C)(C)OC(=O)NCC(=O)Nc1ccnc(-c2cc(-c3ccon3)n(Cc3ccccc3F)n2)n1]
I-519

TABLE ID-continued
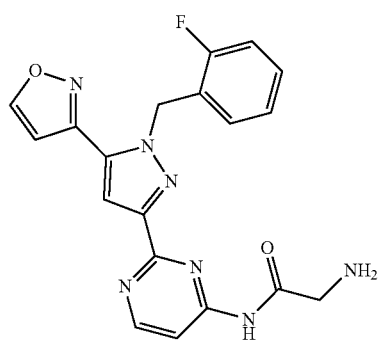 [SMILES: NCC(=O)Nc1ccnc(-c2cc(-c3ccon3)n(Cc3ccccc3F)n2)n1]
I-520
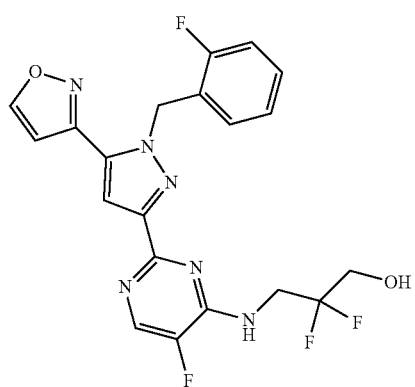 [SMILES: OCC(F)(F)CNc1nc(-c2cc(-c3ccon3)n(Cc3ccccc3F)n2)ncc1F]
I-521
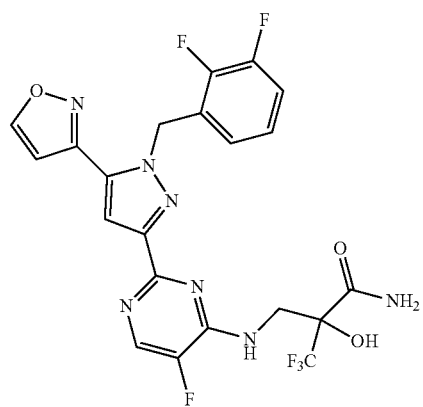 [SMILES: NC(=O)C(O)(CNc1nc(-c2cc(-c3ccon3)n(Cc3cccc(F)c3F)n2)ncc1F)C(F)(F)F]
I-522
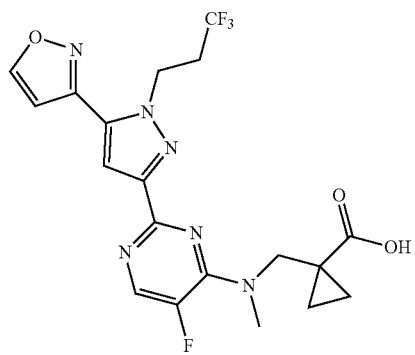 [SMILES: CN(CC1(C(=O)O)CC1)c1nc(-c2cc(-c3ccon3)n(CCC(F)(F)F)n2)ncc1F]
I-523

TABLE ID-continued
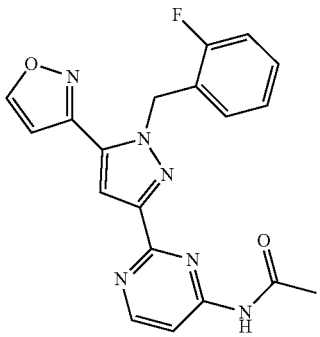 [SMILES: CC(=O)Nc1ccnc(-c2cc(-c3ccon3)n(Cc3ccccc3F)n2)n1]
I-524
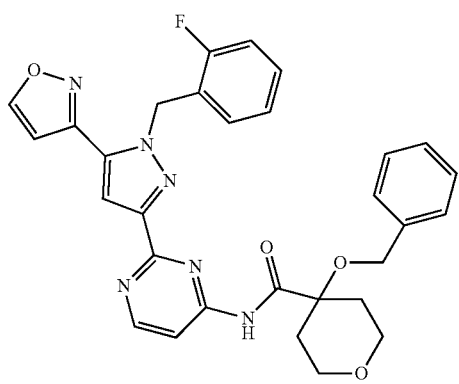 [SMILES: O=C(Nc1ccnc(-c2cc(-c3ccon3)n(Cc3ccccc3F)n2)n1)C1(OCc2ccccc2)CCOCC1]
I-525
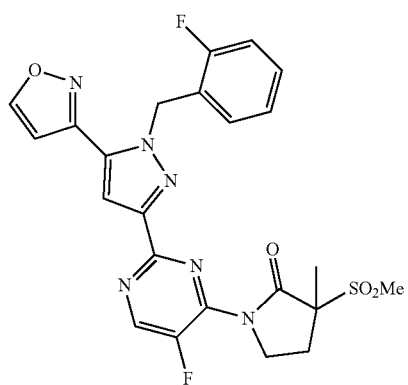 [SMILES: CC1(S(C)(=O)=O)CCN(c2nc(-c3cc(-c4ccon4)n(Cc4ccccc4F)n3)ncc2F)C1=O]
I-526
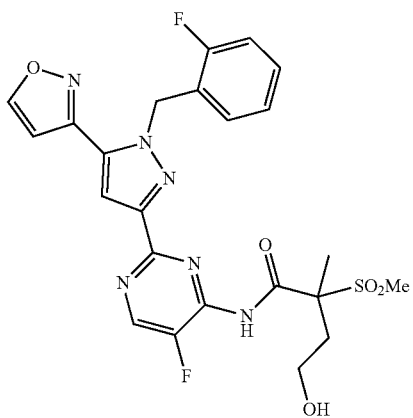 [SMILES: CC(CCO)(C(=O)Nc1nc(-c2cc(-c3ccon3)n(Cc3ccccc3F)n2)ncc1F)S(C)(=O)=O]
I-527

TABLE ID-continued
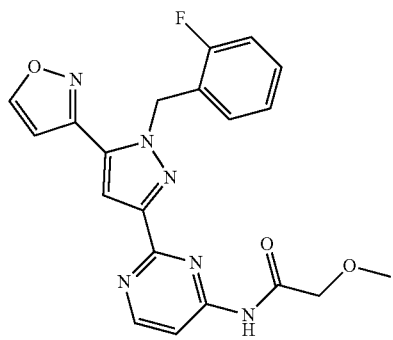 [SMILES: COCC(=O)Nc1ccnc(-c2cc(-c3ccon3)n(Cc3ccccc3F)n2)n1]
I-528
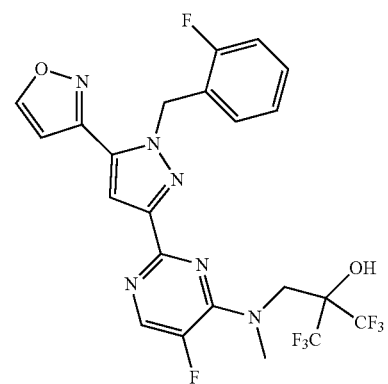 [SMILES: CN(CC(O)(C(F)(F)F)C(F)(F)F)c1nc(-c2cc(-c3ccon3)n(Cc3ccccc3F)n2)ncc1F]
I-529
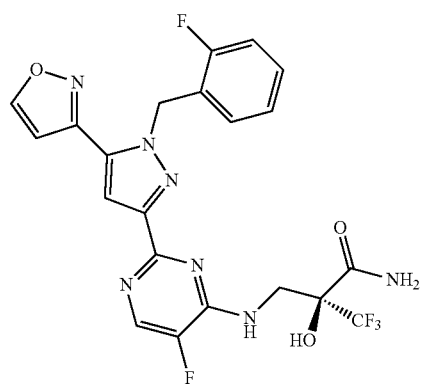 [SMILES: NC(=O)[C@@](O)(CNc1nc(-c2cc(-c3ccon3)n(Cc3ccccc3F)n2)ncc1F)C(F)(F)F]
I-530
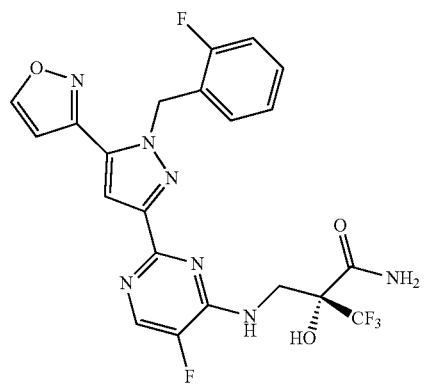 [SMILES: NC(=O)[C@](O)(CNc1nc(-c2cc(-c3ccon3)n(Cc3ccccc3F)n2)ncc1F)C(F)(F)F]
I-531

TABLE ID-continued
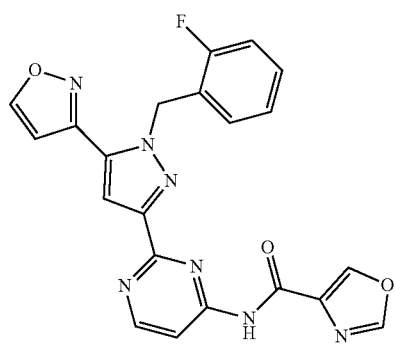 [SMILES: O=C(Nc1ccnc(-c2cc(-c3ccon3)n(Cc3ccccc3F)n2)n1)c1cocn1]
I-532
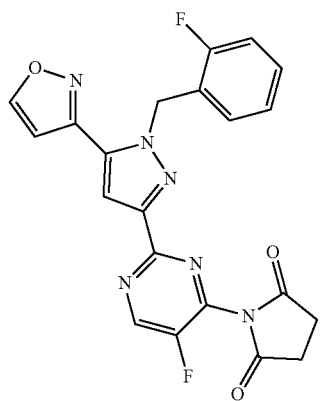 [SMILES: O=C1CCC(=O)N1c1nc(-c2cc(-c3ccon3)n(Cc3ccccc3F)n2)ncc1F]
I-533
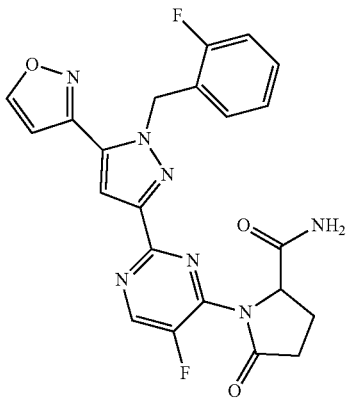 [SMILES: NC(=O)C1CCC(=O)N1c1nc(-c2cc(-c3ccon3)n(Cc3ccccc3F)n2)ncc1F]
I-534
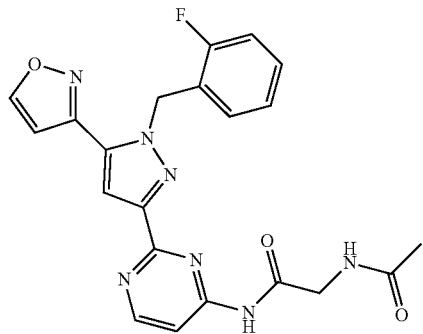 [SMILES: CC(=O)NCC(=O)Nc1ccnc(-c2cc(-c3ccon3)n(Cc3ccccc3F)n2)n1]
I-535

TABLE ID-continued
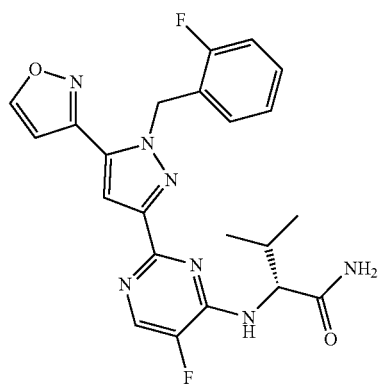 [SMILES: CC(C)[C@@H](Nc1nc(-c2cc(-c3ccon3)n(Cc3ccccc3F)n2)ncc1F)C(N)=O]
I-536
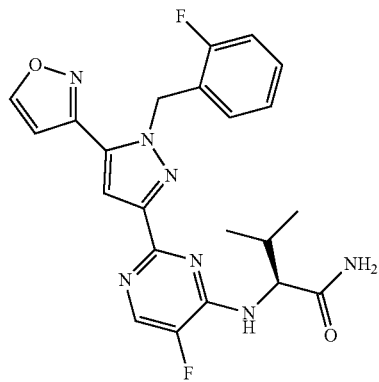 [SMILES: CC(C)[C@H](Nc1nc(-c2cc(-c3ccon3)n(Cc3ccccc3F)n2)ncc1F)C(N)=O]
I-537
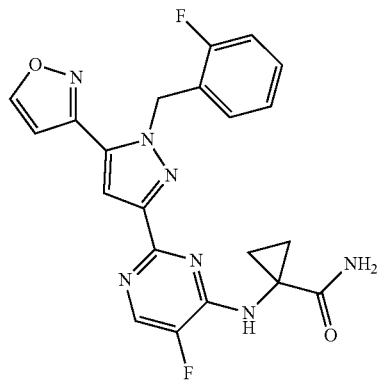 [SMILES: NC(=O)C1(Nc2nc(-c3cc(-c4ccon4)n(Cc4ccccc4F)n3)ncc2F)CC1]
I-538
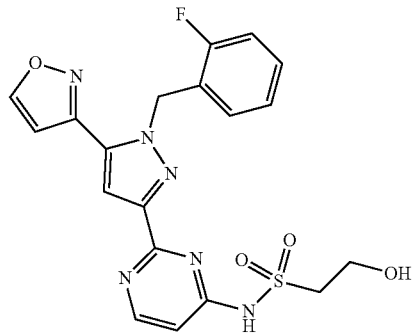 [SMILES: O=S(=O)(CCO)Nc1ccnc(-c2cc(-c3ccon3)n(Cc3ccccc3F)n2)n1]
I-539

TABLE ID-continued
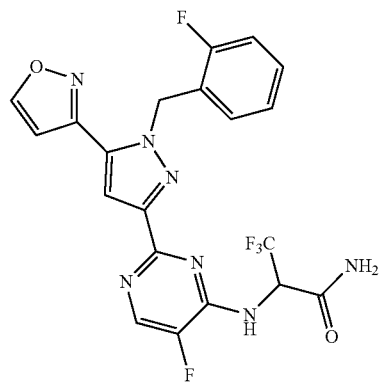 [SMILES: NC(=O)C(Nc1nc(-c2cc(-c3ccon3)n(Cc3ccccc3F)n2)ncc1F)C(F)(F)F]
I-540
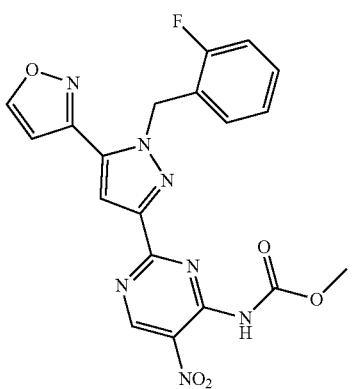
I-541
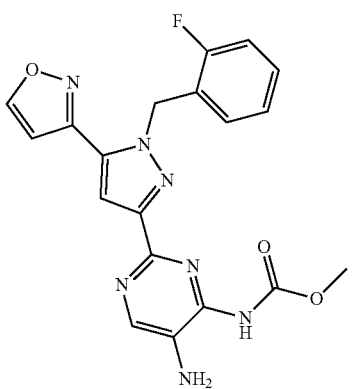 [SMILES: COC(=O)Nc1nc(-c2cc(-c3ccon3)n(Cc3ccccc3F)n2)ncc1[N+](=O)[O-]]
I-542
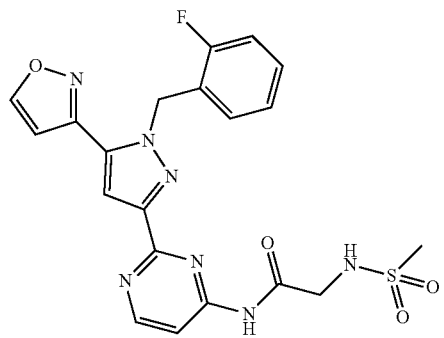 [SMILES: CS(=O)(=O)NCC(=O)Nc1ccnc(-c2cc(-c3ccon3)n(Cc3ccccc3F)n2)n1]
I-543

TABLE ID-continued
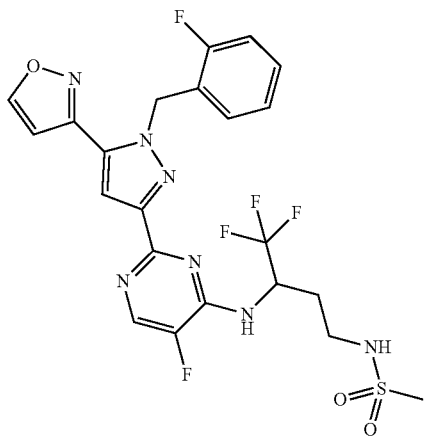 [SMILES: CS(=O)(=O)NCCC(Nc1nc(-c2cc(-c3ccon3)n(Cc3ccccc3F)n2)ncc1F)C(F)(F)F]
I-544
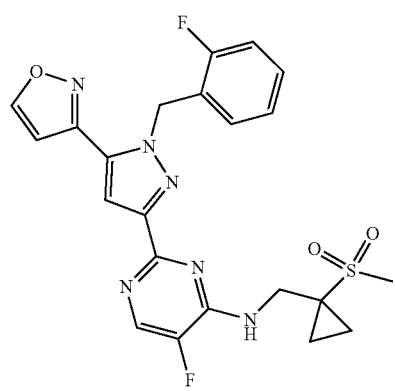 [SMILES: CS(=O)(=O)C1(CNc2nc(-c3cc(-c4ccon4)n(Cc4ccccc4F)n3)ncc2F)CC1]
I-545
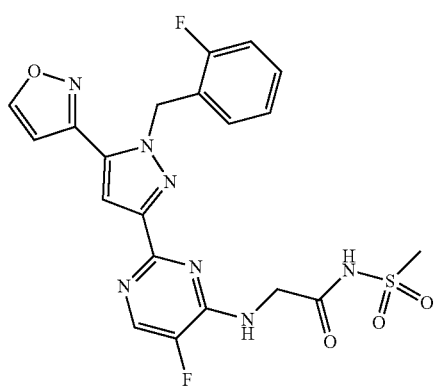 [SMILES: CS(=O)(=O)NC(=O)CNc1nc(-c2cc(-c3ccon3)n(Cc3ccccc3F)n2)ncc1F]
I-546
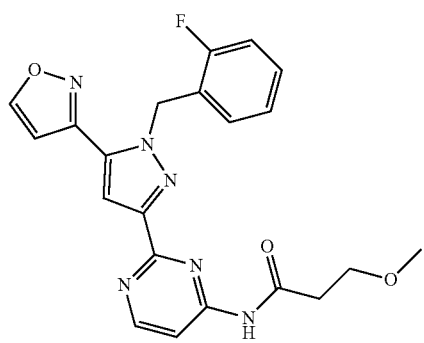 [SMILES: COCCC(=O)Nc1ccnc(-c2cc(-c3ccon3)n(Cc3ccccc3F)n2)n1]
I-547

TABLE ID-continued
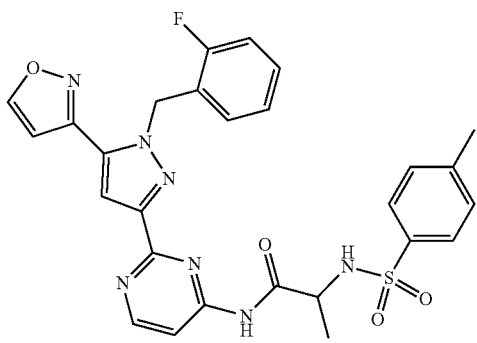 [SMILES: Cc1ccc(S(=O)(=O)NC(C)C(=O)Nc2ccnc(-c3cc(-c4ccon4)n(Cc4ccccc4F)n3)n2)cc1]
I-548
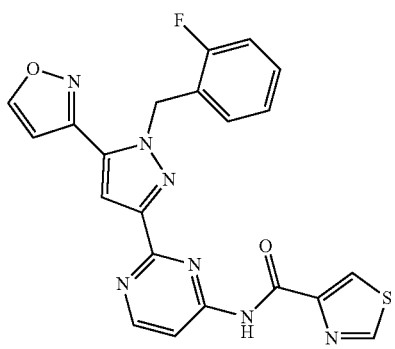 [SMILES: O=C(Nc1ccnc(-c2cc(-c3ccon3)n(Cc3ccccc3F)n2)n1)c1cscn1]
I-549
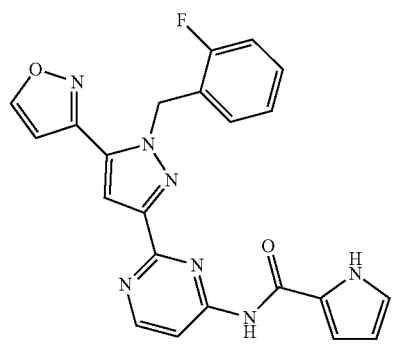 [SMILES: O=C(Nc1ccnc(-c2cc(-c3ccon3)n(Cc3ccccc3F)n2)n1)c1ccc[nH]1]
I-550
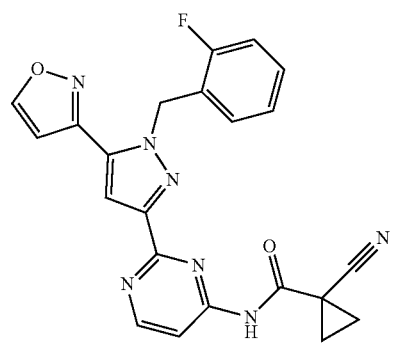 [SMILES: N#CC1(C(=O)Nc2ccnc(-c3cc(-c4ccon4)n(Cc4ccccc4F)n3)n2)CC1]
I-551

TABLE ID-continued
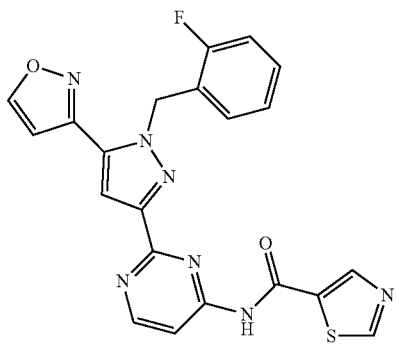 [SMILES: O=C(Nc1ccnc(-c2cc(-c3ccon3)n(Cc3ccccc3F)n2)n1)c1cncs1]
I-552
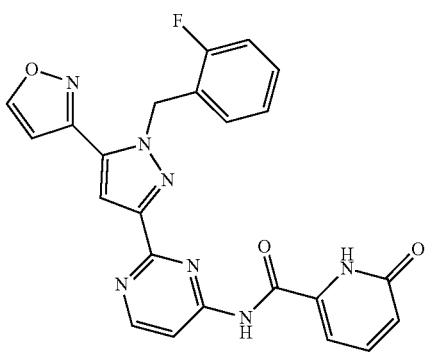 [SMILES: O=C(Nc1ccnc(-c2cc(-c3ccon3)n(Cc3ccccc3F)n2)n1)c1cccc(=O)[nH]1]
I-553
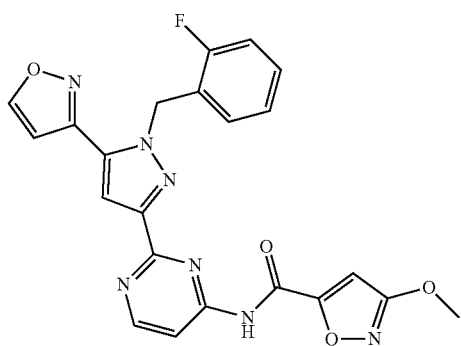 [SMILES: COc1cc(C(=O)Nc2ccnc(-c3cc(-c4ccon4)n(Cc4ccccc4F)n3)n2)on1]
I-554
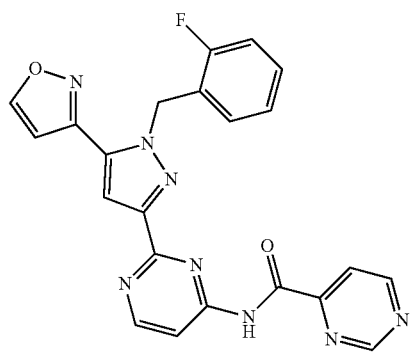 [SMILES: O=C(Nc1ccnc(-c2cc(-c3ccon3)n(Cc3ccccc3F)n2)n1)c1ccncn1]
I-555

TABLE 1D-continued
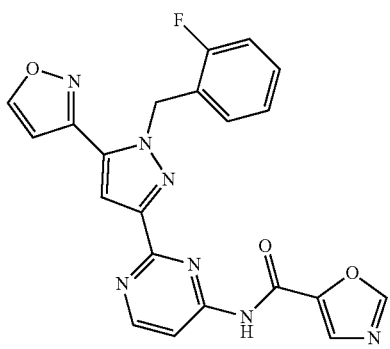 [SMILES: O=C(Nc1ccnc(-c2cc(-c3ccon3)n(Cc3ccccc3F)n2)n1)c1cnco1]
I-556
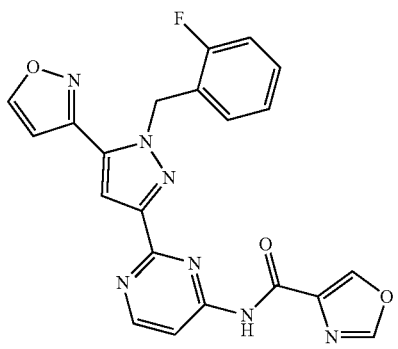 [SMILES: O=C(Nc1ccnc(-c2cc(-c3ccon3)n(Cc3ccccc3F)n2)n1)c1cocn1]
I-557
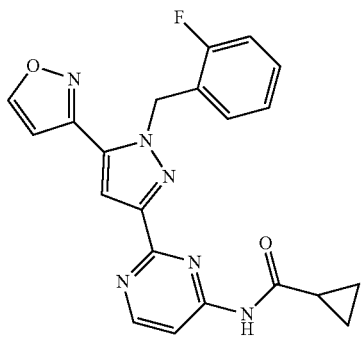 [SMILES: O=C(Nc1ccnc(-c2cc(-c3ccon3)n(Cc3ccccc3F)n2)n1)C1CC1]
I-558
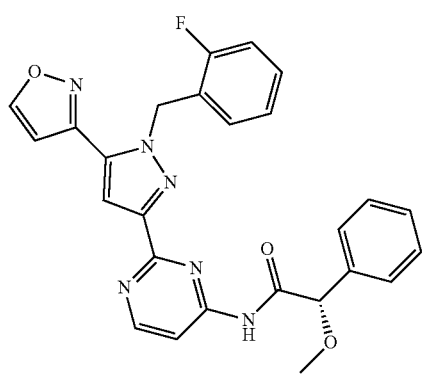 [SMILES: CO[C@H](C(=O)Nc1ccnc(-c2cc(-c3ccon3)n(Cc3ccccc3F)n2)n1)c1ccccc1]
I-559

TABLE ID-continued
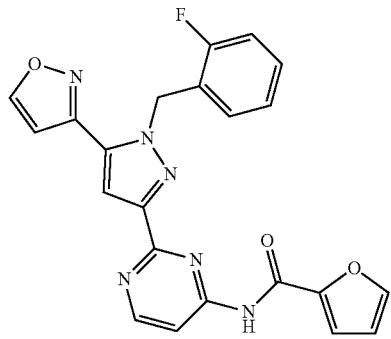 [SMILES: O=C(Nc1ccnc(-c2cc(-c3ccon3)n(Cc3ccccc3F)n2)n1)c1ccco1]
I-560
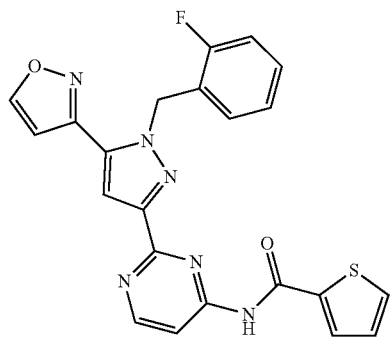 [SMILES: O=C(Nc1ccnc(-c2cc(-c3ccon3)n(Cc3ccccc3F)n2)n1)c1cccs1]
I-561
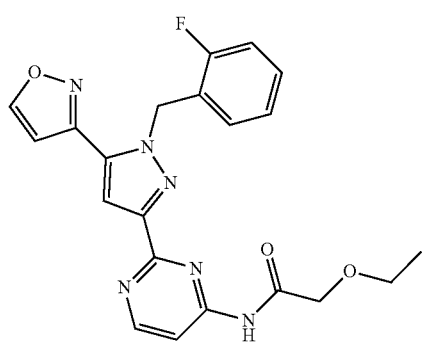
I-562
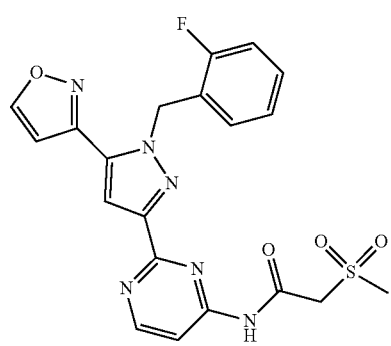 [SMILES: CS(=O)(=O)CC(=O)Nc1ccnc(-c2cc(-c3ccon3)n(Cc3ccccc3F)n2)n1]
I-563

TABLE ID-continued
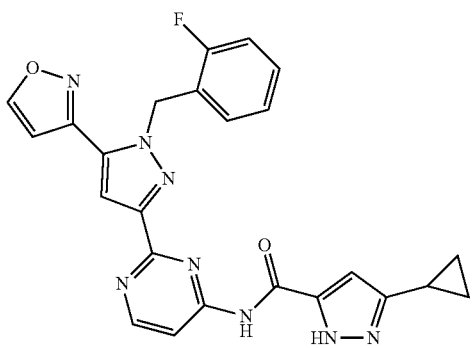 [SMILES: O=C(Nc1ccnc(-c2cc(-c3ccon3)n(Cc3ccccc3F)n2)n1)c1cc(C2CC2)n[nH]1]
I-564
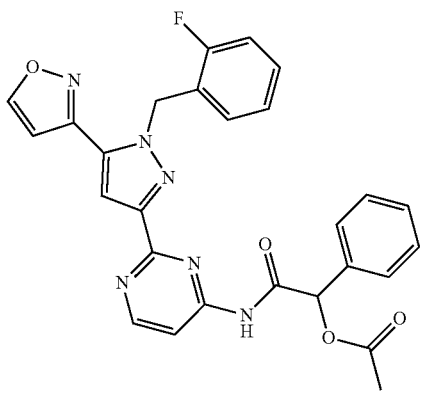 [SMILES: CC(=O)OC(C(=O)Nc1ccnc(-c2cc(-c3ccon3)n(Cc3ccccc3F)n2)n1)c1ccccc1]
I-565
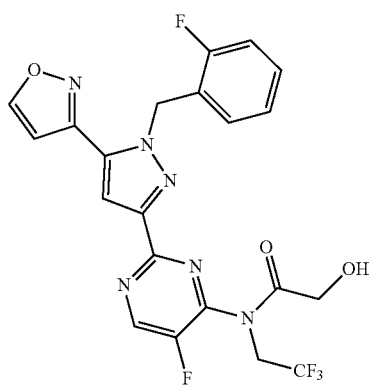 [SMILES: O=C(CO)N(CC(F)(F)F)c1nc(-c2cc(-c3ccon3)n(Cc3ccccc3F)n2)ncc1F]
I-566
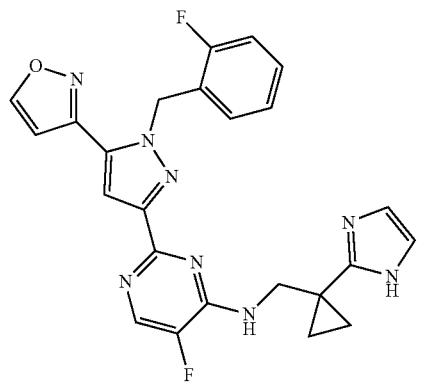 [SMILES: Fc1ccccc1Cn1nc(-c2ncc(F)c(NCC3(c4ncc[nH]4)CC3)n2)cc1-c1ccon1]
I-567

TABLE ID-continued
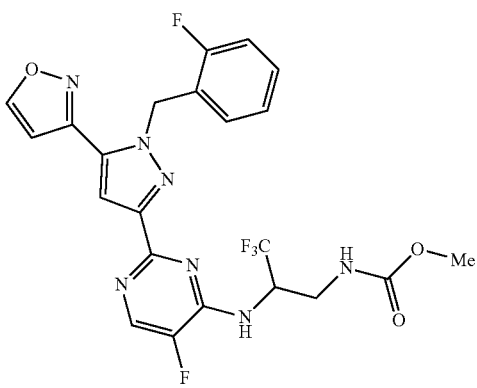 [SMILES: COC(=O)NCC(Nc1nc(-c2cc(-c3ccon3)n(Cc3ccccc3F)n2)ncc1F)C(F)(F)F]
I-568
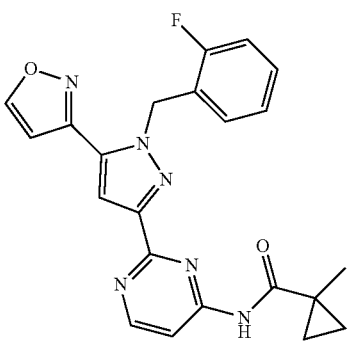 [SMILES: CC1(C(=O)Nc2ccnc(-c3cc(-c4ccon4)n(Cc4ccccc4F)n3)n2)CC1]
I-569
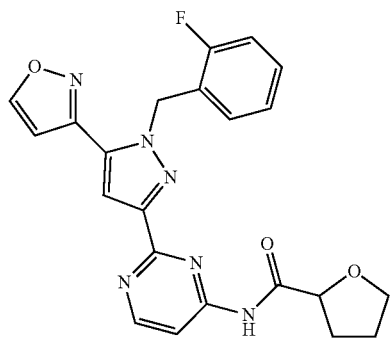 [SMILES: O=C(Nc1ccnc(-c2cc(-c3ccon3)n(Cc3ccccc3F)n2)n1)C1CCCO1]
I-570
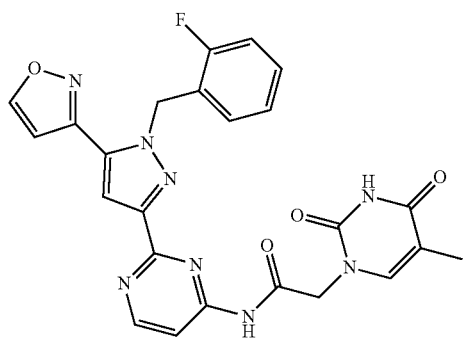 [SMILES: Cc1cn(CC(=O)Nc2ccnc(-c3cc(-c4ccon4)n(Cc4ccccc4F)n3)n2)c(=O)[nH]c1=O]
I-571

TABLE ID-continued
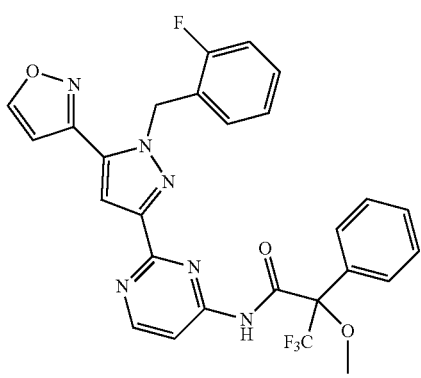 [SMILES: COC(C(=O)Nc1ccnc(-c2cc(-c3ccon3)n(Cc3ccccc3F)n2)n1)(c1ccccc1)C(F)(F)F]
I-572
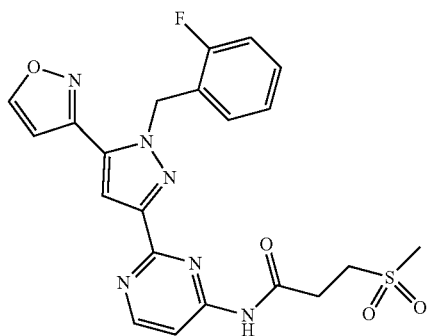 [SMILES: CS(=O)(=O)CCC(=O)Nc1ccnc(-c2cc(-c3ccon3)n(Cc3ccccc3F)n2)n1]
I-573
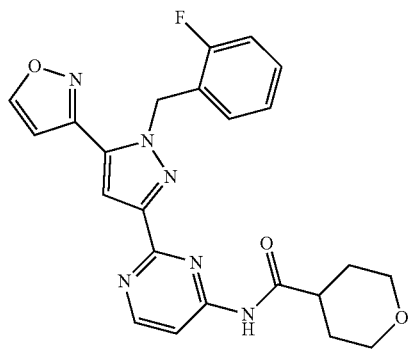 [SMILES: O=C(Nc1ccnc(-c2cc(-c3ccon3)n(Cc3ccccc3F)n2)n1)C1CCOCC1]
I-574
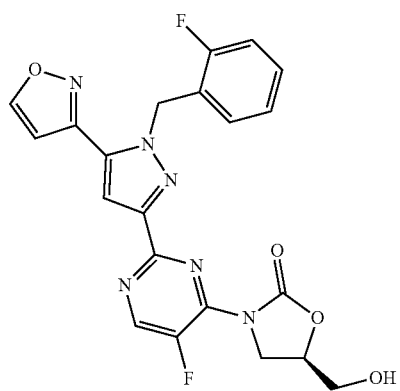 [SMILES: O=C1O[C@@H](CO)CN1c1nc(-c2cc(-c3ccon3)n(Cc3ccccc3F)n2)ncc1F]
I-575

TABLE ID-continued
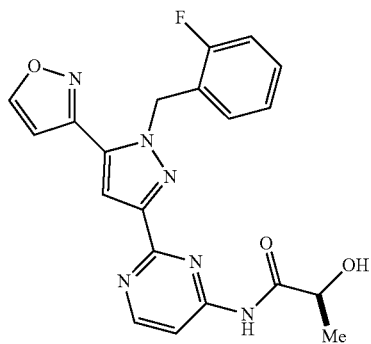 [SMILES: C[C@H](O)C(=O)Nc1ccnc(-c2cc(-c3ccon3)n(Cc3ccccc3F)n2)n1]
I-576
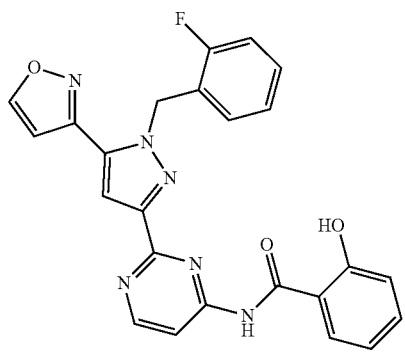 [SMILES: O=C(Nc1ccnc(-c2cc(-c3ccon3)n(Cc3ccccc3F)n2)n1)c1ccccc1O]
I-577
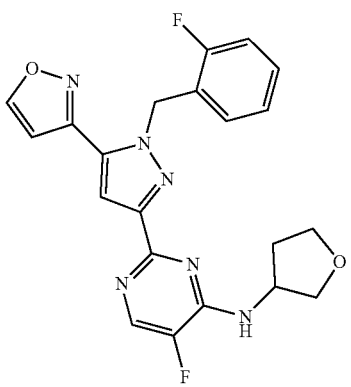 [SMILES: Fc1ccccc1Cn1nc(-c2ncc(F)c(NC3CCOC3)n2)cc1-c1ccon1]
I-578
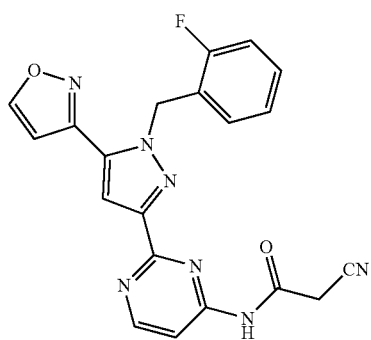 [SMILES: N#CCC(=O)Nc1ccnc(-c2cc(-c3ccon3)n(Cc3ccccc3F)n2)n1]
I-579

TABLE ID-continued
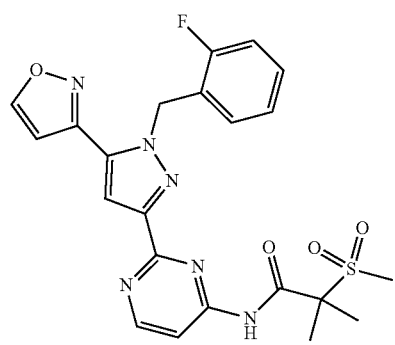 [SMILES: CC(C)(C(=O)Nc1ccnc(-c2cc(-c3ccon3)n(Cc3ccccc3F)n2)n1)S(C)(=O)=O]
I-580
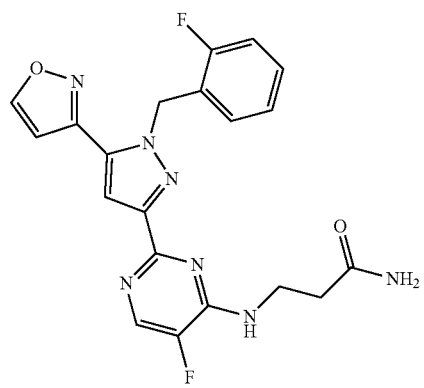 [SMILES: NC(=O)CCNc1nc(-c2cc(-c3ccon3)n(Cc3ccccc3F)n2)ncc1F]
I-581
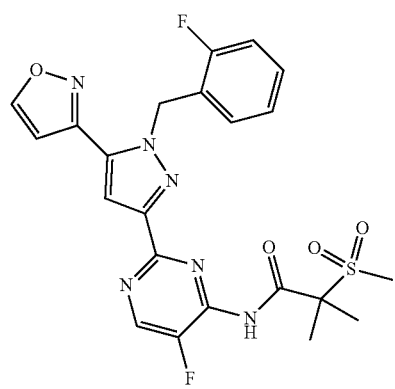 [SMILES: CC(C)(C(=O)Nc1nc(-c2cc(-c3ccon3)n(Cc3ccccc3F)n2)ncc1F)S(C)(=O)=O]
I-582
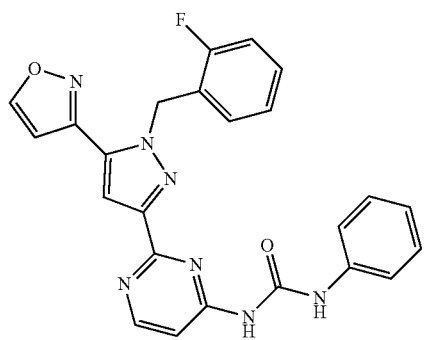 [SMILES: O=C(Nc1ccccc1)Nc1ccnc(-c2cc(-c3ccon3)n(Cc3ccccc3F)n2)n1]
I-583

TABLE ID-continued
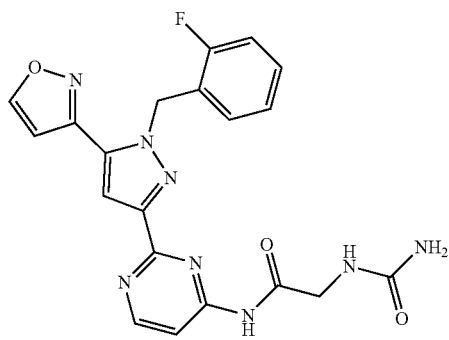 [SMILES: NC(=O)NCC(=O)Nc1ccnc(-c2cc(-c3ccon3)n(Cc3ccccc3F)n2)n1]
I-584
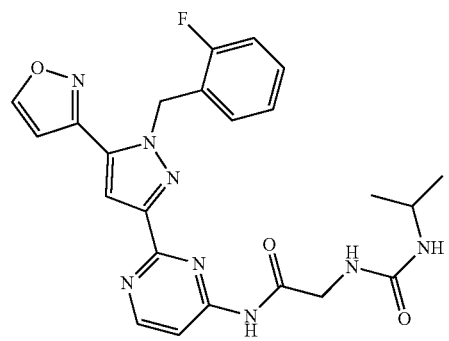 [SMILES: CC(C)NC(=O)NCC(=O)Nc1ccnc(-c2cc(-c3ccon3)n(Cc3ccccc3F)n2)n1]
I-585
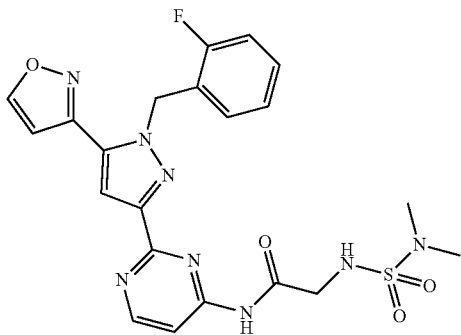 [SMILES: CN(C)S(=O)(=O)NCC(=O)Nc1ccnc(-c2cc(-c3ccon3)n(Cc3ccccc3F)n2)n1]
I-586
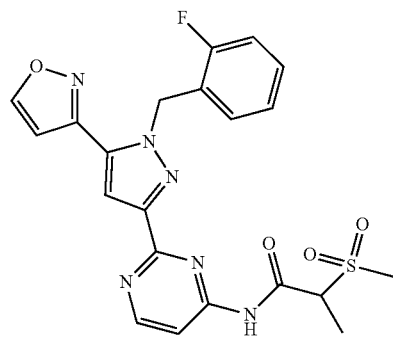 [SMILES: CC(C(=O)Nc1ccnc(-c2cc(-c3ccon3)n(Cc3ccccc3F)n2)n1)S(C)(=O)=O]
I-587

TABLE ID-continued
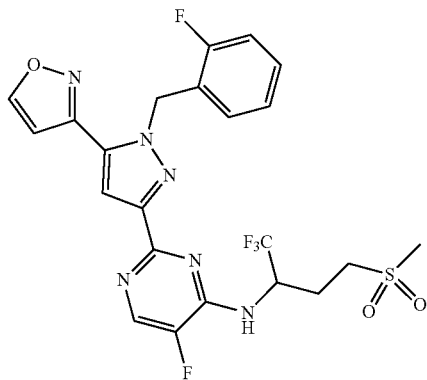 [SMILES: CS(=O)(=O)CCC(Nc1nc(-c2cc(-c3ccon3)n(Cc3ccccc3F)n2)ncc1F)C(F)(F)F]
I-588
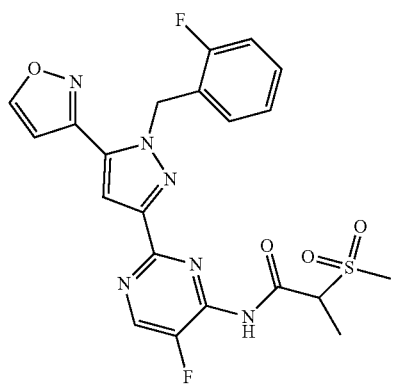 [SMILES: CC(C(=O)Nc1nc(-c2cc(-c3ccon3)n(Cc3ccccc3F)n2)ncc1F)S(C)(=O)=O]
I-589
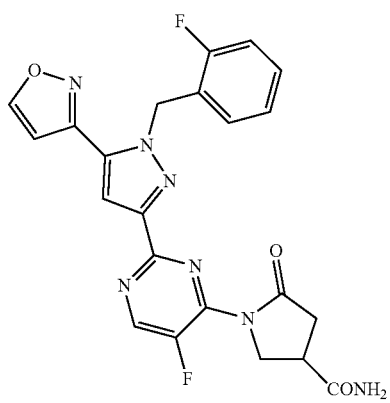 [SMILES: NC(=O)C1CC(=O)N(c2nc(-c3cc(-c4ccon4)n(Cc4ccccc4F)n3)ncc2F)C1]
I-590
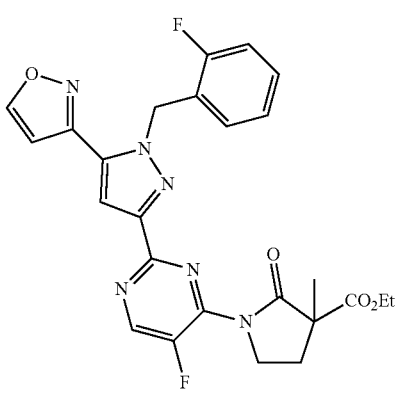 [SMILES: CCOC(=O)C1(C)CCN(c2nc(-c3cc(-c4ccon4)n(Cc4ccccc4F)n3)ncc2F)C1=O]
I-591

TABLE ID-continued
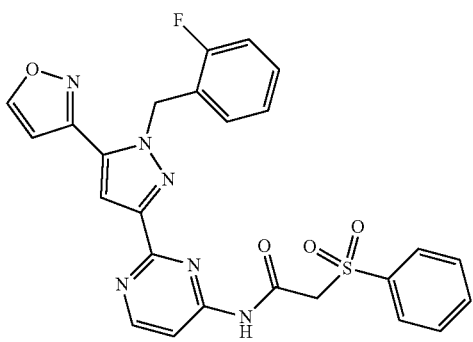 [SMILES: O=C(CS(=O)(=O)c1ccccc1)Nc1ccnc(-c2cc(-c3ccon3)n(Cc3ccccc3F)n2)n1]
I-592
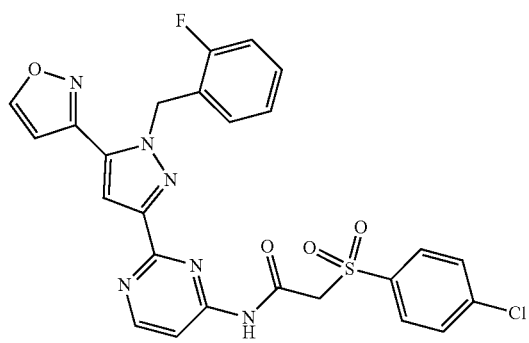 [SMILES: O=C(CS(=O)(=O)c1ccc(Cl)cc1)Nc1ccnc(-c2cc(-c3ccon3)n(Cc3ccccc3F)n2)n1]
I-593
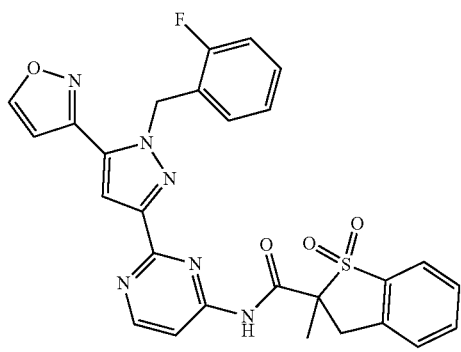 [SMILES: CC1(C(=O)Nc2ccnc(-c3cc(-c4ccon4)n(Cc4ccccc4F)n3)n2)Cc2ccccc2S1(=O)=O]
I-594
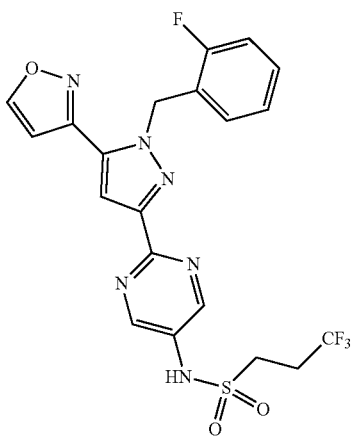 [SMILES: O=S(=O)(CCC(F)(F)F)Nc1cnc(-c2cc(-c3ccon3)n(Cc3ccccc3F)n2)nc1]
I-595

TABLE ID-continued
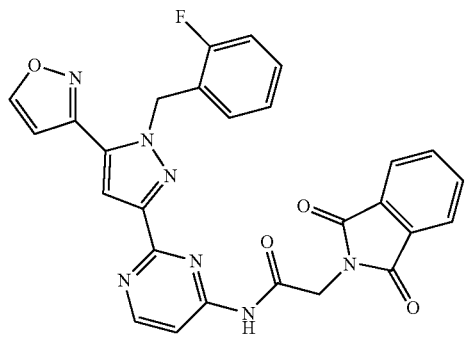 [SMILES: O=C(CN1C(=O)c2ccccc2C1=O)Nc1ccnc(-c2cc(-c3ccon3)n(Cc3ccccc3F)n2)n1]
I-596
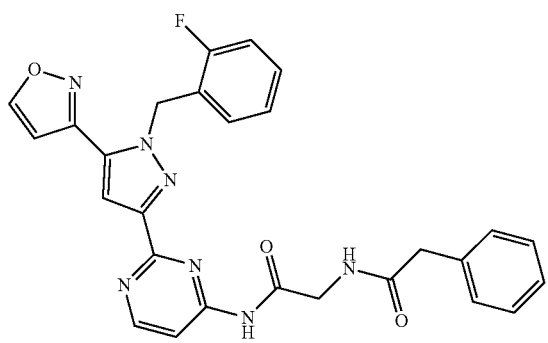 [SMILES: O=C(Cc1ccccc1)NCC(=O)Nc1ccnc(-c2cc(-c3ccon3)n(Cc3ccccc3F)n2)n1]
I-597
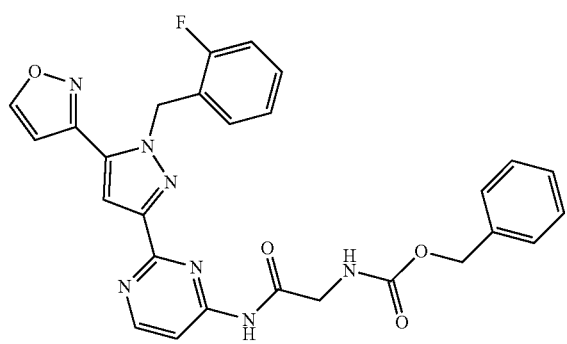 [SMILES: O=C(CNC(=O)OCc1ccccc1)Nc1ccnc(-c2cc(-c3ccon3)n(Cc3ccccc3F)n2)n1]
I-598
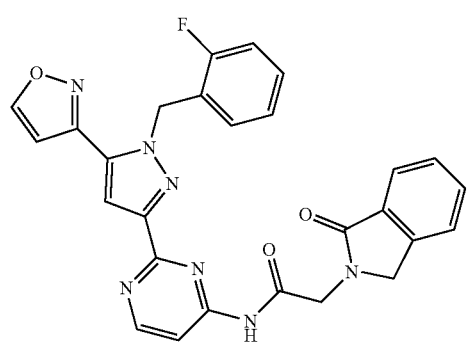 [SMILES: O=C(CN1Cc2ccccc2C1=O)Nc1ccnc(-c2cc(-c3ccon3)n(Cc3ccccc3F)n2)n1]
I-599

TABLE ID-continued
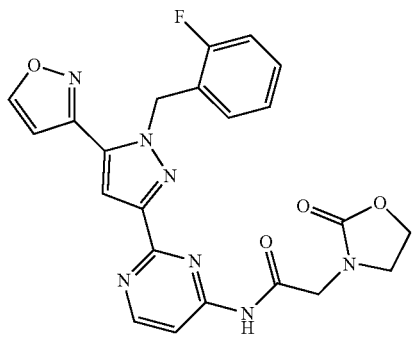 [SMILES: O=C(CN1CCOC1=O)Nc1ccnc(-c2cc(-c3ccon3)n(Cc3ccccc3F)n2)n1]
I-600
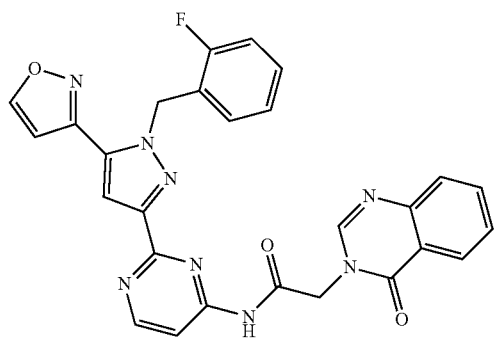 [SMILES: O=C(Cn1cnc2ccccc2c1=O)Nc1ccnc(-c2cc(-c3ccon3)n(Cc3ccccc3F)n2)n1]
I-601
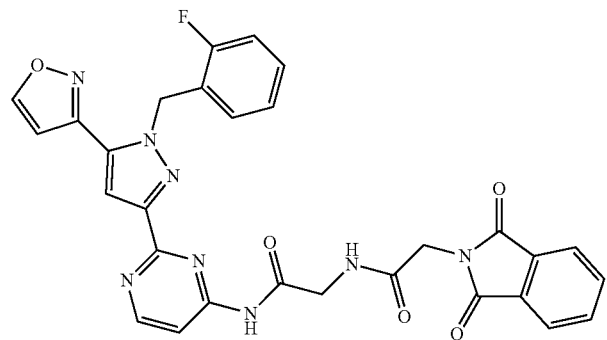 [SMILES: O=C(CN1C(=O)c2ccccc2C1=O)NCC(=O)Nc1ccnc(-c2cc(-c3ccon3)n(Cc3ccccc3F)n2)n1]
I-602
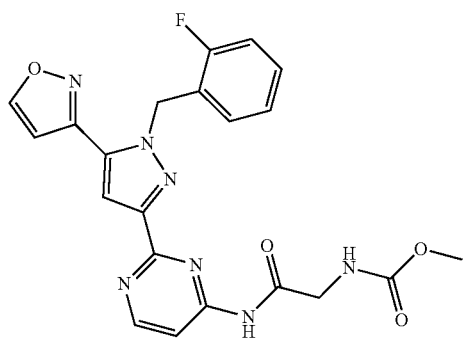 [SMILES: COC(=O)NCC(=O)Nc1ccnc(-c2cc(-c3ccon3)n(Cc3ccccc3F)n2)n1]
I-603

TABLE ID-continued
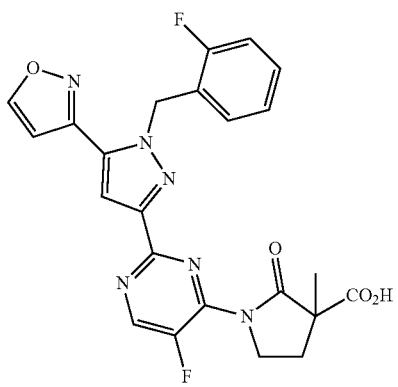 [SMILES: CC1(C(=O)O)CCN(c2nc(-c3cc(-c4ccon4)n(Cc4ccccc4F)n3)ncc2F)C1=O]
I-604
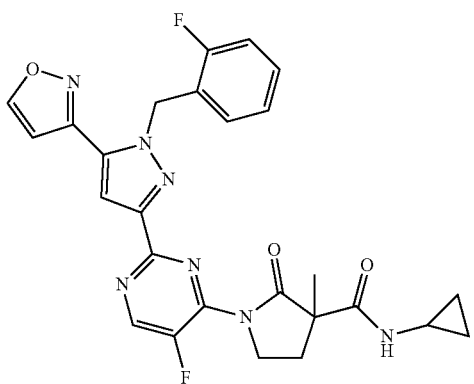 [SMILES: CC1(C(=O)NC2CC2)CCN(c2nc(-c3cc(-c4ccon4)n(Cc4ccccc4F)n3)ncc2F)C1=O]
I-605
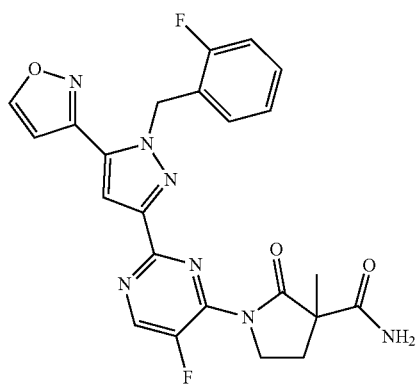 [SMILES: CC1(C(N)=O)CCN(c2nc(-c3cc(-c4ccon4)n(Cc4ccccc4F)n3)ncc2F)C1=O]
I-606
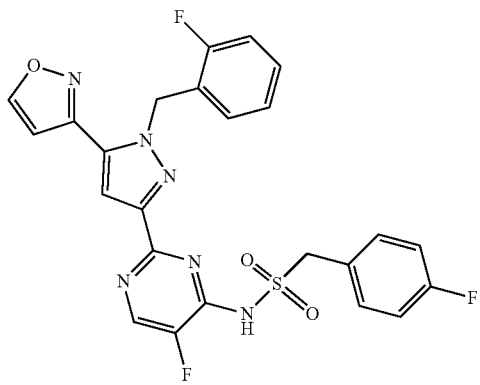 [SMILES: O=S(=O)(Cc1ccc(F)cc1)Nc1nc(-c2cc(-c3ccon3)n(Cc3ccccc3F)n2)ncc1F]
I-607

TABLE ID-continued
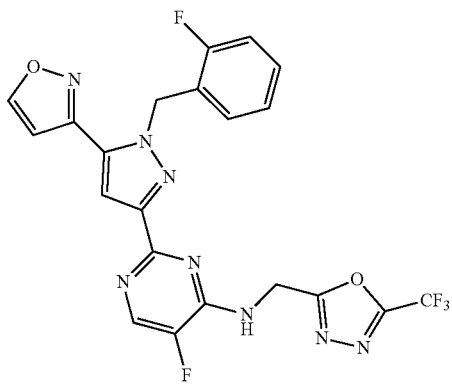 [SMILES: Fc1ccccc1Cn1nc(-c2ncc(F)c(NCc3nnc(C(F)(F)F)o3)n2)cc1-c1ccon1]
I-608
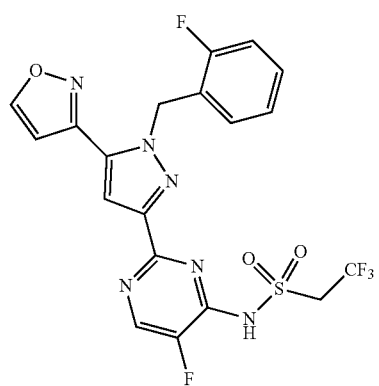 [SMILES: O=S(=O)(CC(F)(F)F)Nc1nc(-c2cc(-c3ccon3)n(Cc3ccccc3F)n2)ncc1F]
I-609
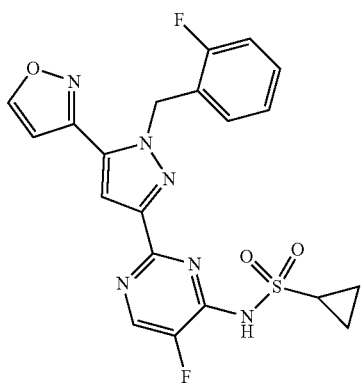 [SMILES: O=S(=O)(Nc1nc(-c2cc(-c3ccon3)n(Cc3ccccc3F)n2)ncc1F)C1CC1]
I-610
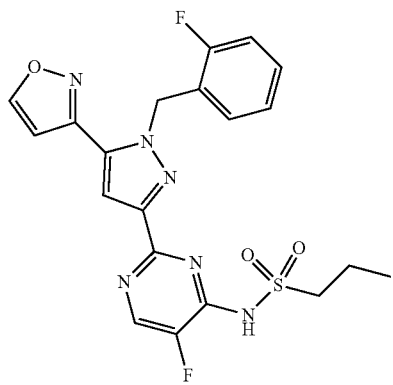 [SMILES: CCCS(=O)(=O)Nc1nc(-c2cc(-c3ccon3)n(Cc3ccccc3F)n2)ncc1F]
I-611

TABLE ID-continued
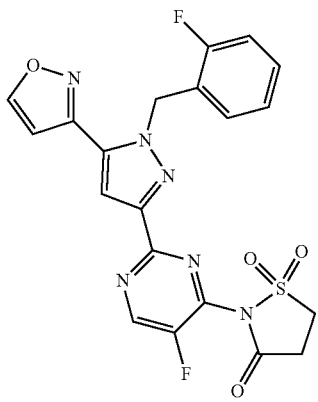 [SMILES: O=C1CCS(=O)(=O)N1c1nc(-c2cc(-c3ccon3)n(Cc3ccccc3F)n2)ncc1F]
I-612
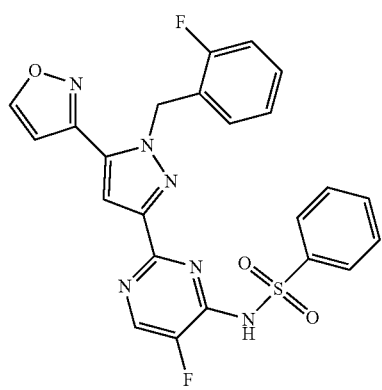 [SMILES: O=S(=O)(Nc1nc(-c2cc(-c3ccon3)n(Cc3ccccc3F)n2)ncc1F)c1ccccc1]
I-613
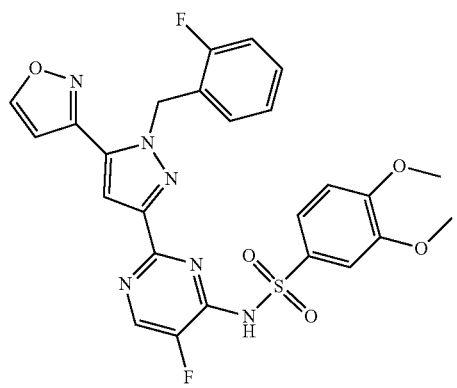 [SMILES: COc1ccc(S(=O)(=O)Nc2nc(-c3cc(-c4ccon4)n(Cc4ccccc4F)n3)ncc2F)cc1OC]
I-614
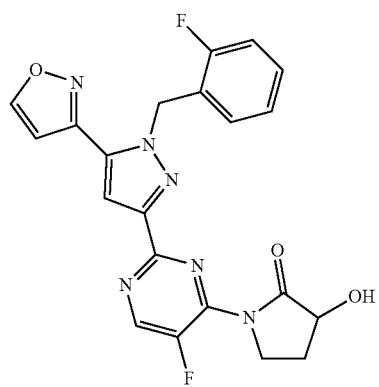 [SMILES: O=C1C(O)CCN1c1nc(-c2cc(-c3ccon3)n(Cc3ccccc3F)n2)ncc1F]
I-615

TABLE ID-continued
I-616
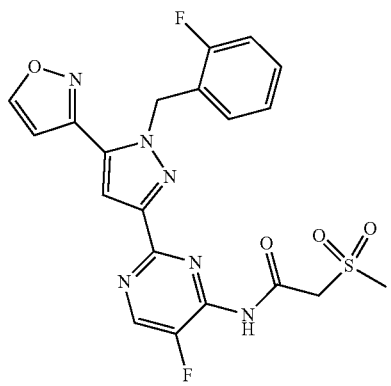 [SMILES: CS(=O)(=O)CC(=O)Nc1nc(-c2cc(-c3ccon3)n(Cc3ccccc3F)n2)ncc1F]
I-617
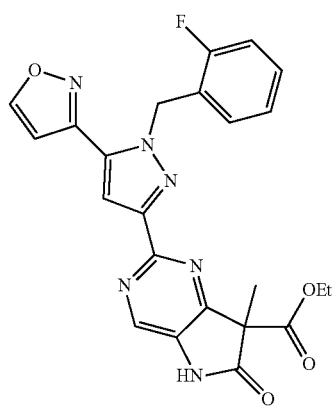 [SMILES: CCOC(=O)C1(C)C(=O)Nc2cnc(-c3cc(-c4ccon4)n(Cc4ccccc4F)n3)nc21]
I-618
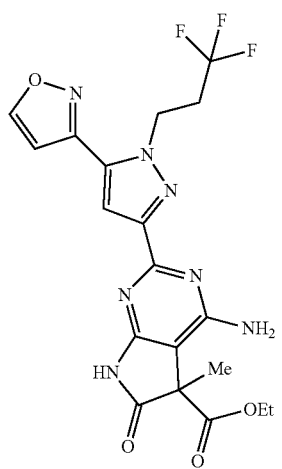 [SMILES: CCOC(=O)C1(C)C(=O)Nc2nc(-c3cc(-c4ccon4)n(CCC(F)(F)F)n3)nc(N)c21]

TABLE ID-continued
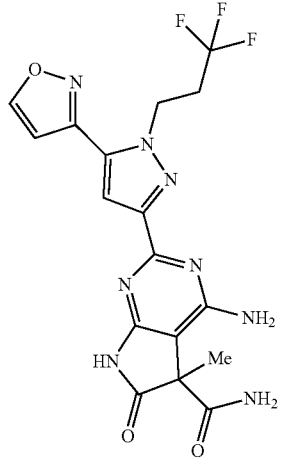 [SMILES: CC1(C(N)=O)C(=O)Nc2nc(-c3cc(-c4ccon4)n(CCC(F)(F)F)n3)nc(N)c21]
I-619
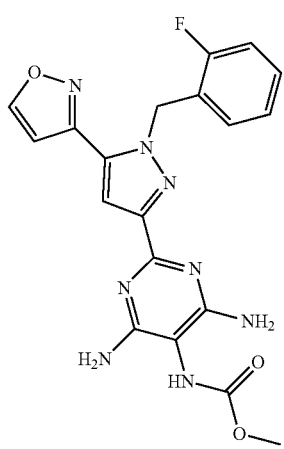 [SMILES: COC(=O)Nc1c(N)nc(-c2cc(-c3ccon3)n(Cc3ccccc3F)n2)nc1N]
I-620
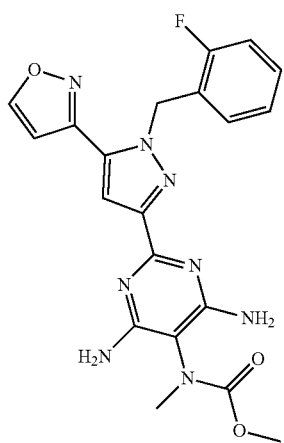 [SMILES: COC(=O)N(C)c1c(N)nc(-c2cc(-c3ccon3)n(Cc3ccccc3F)n2)nc1N]
I-621

TABLE ID-continued
I-622
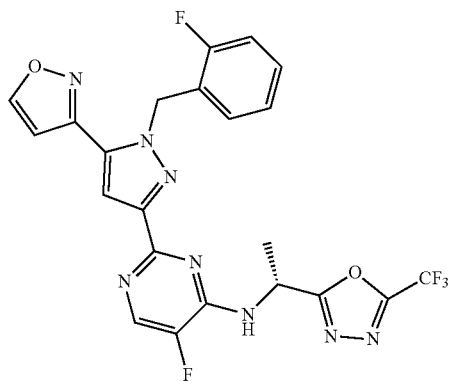 [SMILES: C[C@@H](Nc1nc(-c2cc(-c3ccon3)n(Cc3ccccc3F)n2)ncc1F)c1nnc(C(F)(F)F)o1]
I-623
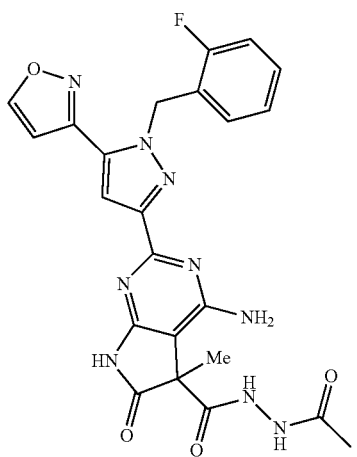 [SMILES: CC(=O)NNC(=O)C1(C)C(=O)Nc2nc(-c3cc(-c4ccon4)n(Cc4ccccc4F)n3)nc(N)c21]
I-624
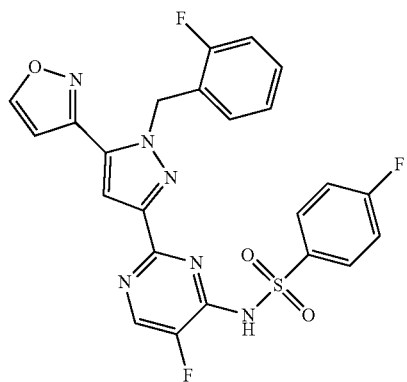 [SMILES: O=S(=O)(Nc1nc(-c2cc(-c3ccon3)n(Cc3ccccc3F)n2)ncc1F)c1ccc(F)cc1]
I-625
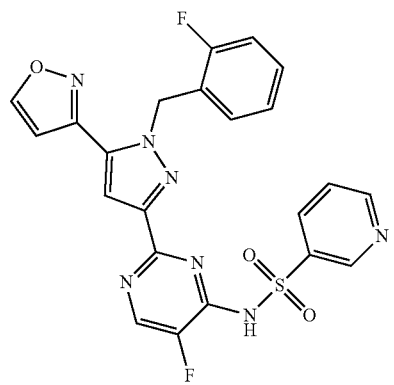 [SMILES: O=S(=O)(Nc1nc(-c2cc(-c3ccon3)n(Cc3ccccc3F)n2)ncc1F)c1cccnc1]

TABLE ID-continued
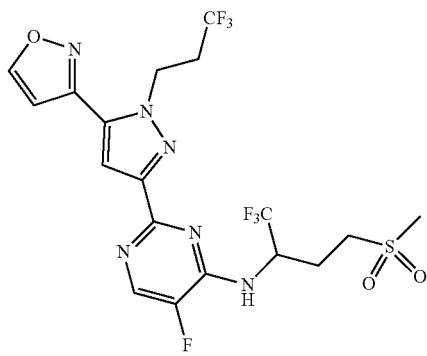 [SMILES: CS(=O)(=O)CCC(Nc1nc(-c2cc(-c3ccon3)n(CCC(F)(F)F)n2)ncc1F)C(F)(F)F]
I-626
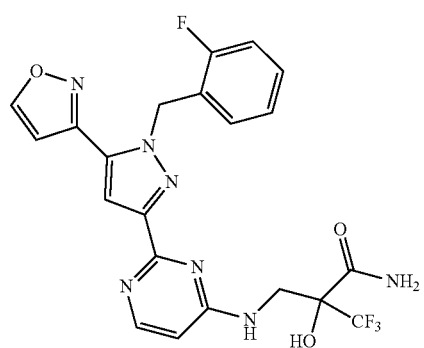 [SMILES: NC(=O)C(O)(CNc1ccnc(-c2cc(-c3ccon3)n(Cc3ccccc3F)n2)n1)C(F)(F)F]
I-627
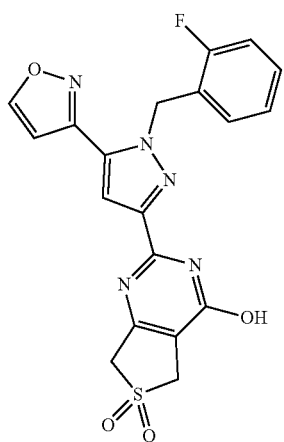 [SMILES: O=S1(=O)Cc2nc(-c3cc(-c4ccon4)n(Cc4ccccc4F)n3)nc(O)c2C1]
I-628
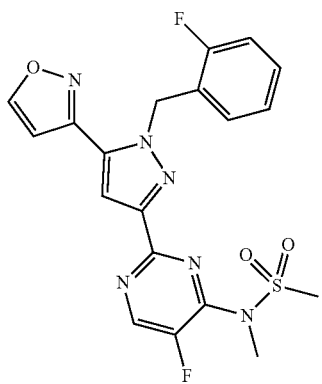 [SMILES: CN(c1nc(-c2cc(-c3ccon3)n(Cc3ccccc3F)n2)ncc1F)S(C)(=O)=O]
I-629

TABLE ID-continued
I-630
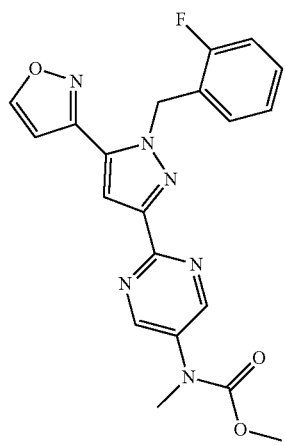 [SMILES: COC(=O)N(C)c1cnc(-c2cc(-c3ccon3)n(Cc3ccccc3F)n2)nc1]
I-631
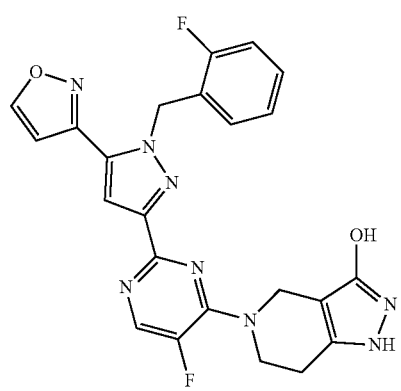 [SMILES: Oc1n[nH]c2c1CN(c1nc(-c3cc(-c4ccon4)n(Cc4ccccc4F)n3)ncc1F)CC2]
I-632
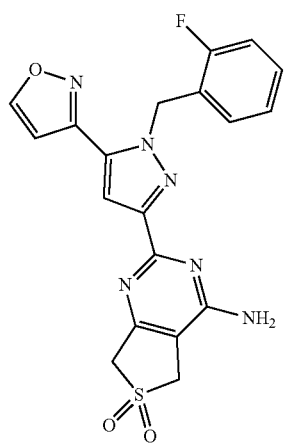 [SMILES: Nc1nc(-c2cc(-c3ccon3)n(Cc3ccccc3F)n2)nc2c1CS(=O)(=O)C2]

TABLE ID-continued

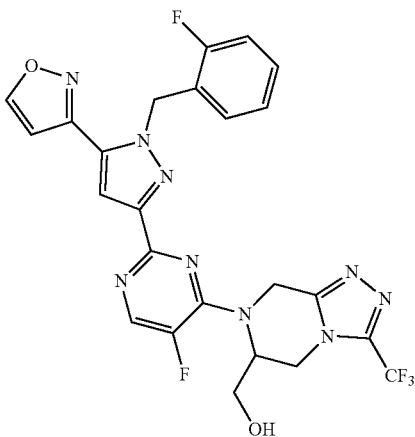 [SMILES: OCC1Cn2c(nnc2C(F)(F)F)CN1c1nc(-c2cc(-c3ccon3)n(Cc3ccccc3F)n2)ncc1F]
I-633

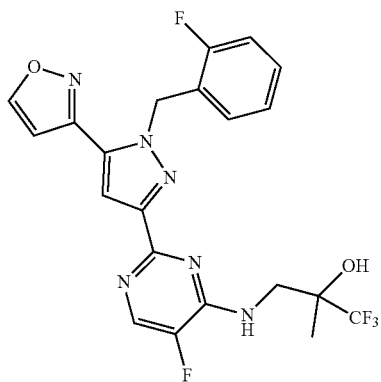 [SMILES: CC(O)(CNc1nc(-c2cc(-c3ccon3)n(Cc3ccccc3F)n2)ncc1F)C(F)(F)F]
I-634

Methods of Preparing the Compounds

The compounds of Formulae I to XI may be prepared according to the schemes and examples depicted and described below. Unless otherwise specified, the starting materials and various intermediates may be obtained from commercial sources, prepared from commercially available compounds or prepared using well-known synthetic methods. Another aspect of the present invention is a process for preparing the compounds of Formula I as disclosed herein.

General synthetic procedures for the compounds of this invention are described below. The synthetic schemes are presented as examples and do not limit the scope of the invention in any way.

General Procedure A

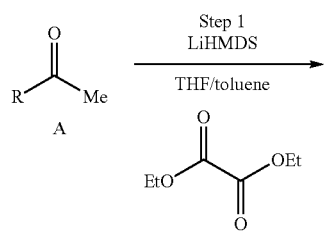

-continued

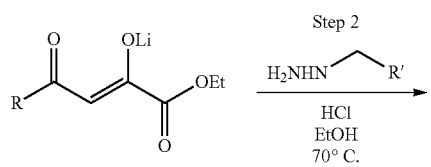

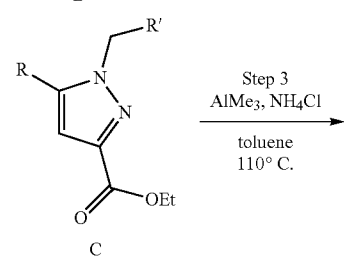

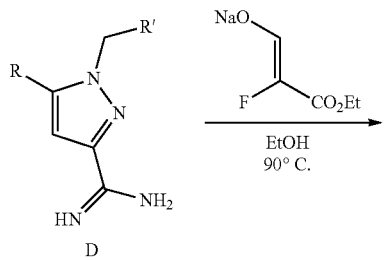

-continued

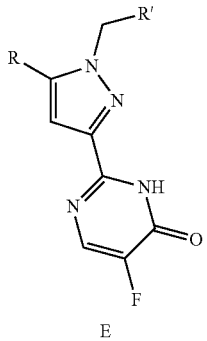

E

Step 1:
Dione Enolate Formation:

To a solution of ketone A in THF cooled to −78° C., LiHMDS (e.g., 0.9 equiv, 1.0 M in toluene) was added dropwise via syringe. The reaction was allowed to warm to 0° C., then charged with diethyl oxalate (1.2 equiv). At this time, the reaction was warmed to room temperature and stirred at that temperature until judged complete (e.g., using either TLC or LC/MS analysis). Once the reaction was complete (reaction time was typically 45 minutes), the product dione enolate B was used "as-is" in Step 2, i.e., the cyclization step, without any further purification.

Step 2:
Pyrazole Formation:

Dione enolate B was diluted with ethanol and consecutively charged with HCl (e.g., 3 equiv, 1.25 M solution in ethanol) and arylhydrazine hydrate (e.g., 1.15 equiv). The reaction mixture was heated to 70° C. and stirred at this temperature until cyclization was deemed complete (e.g., by LC/MS analysis, typically 30 minutes). Once complete, the reaction mixture was treated carefully with solid sodium bicarbonate (e.g., 4 equiv) and diluted with dichloromethane and water. Layers were separated, and aqueous layer was further diluted with water before extraction with dichloromethane (3×). The combined organics were washed with brine, dried over MgSO$_4$, filtered, and concentrated in vacuo. The resulting pyrazole C was then purified by SiO$_2$ chromatography using an appropriate gradient of EtOAc in hexanes.

Step 3:
Amidine Formation:

To a suspension of NH$_4$Cl (e.g., 5 equiv) in toluene cooled to 0° C. was added AlMe$_3$ (e.g., 5 equiv, 2.0M solution in toluene) dropwise via syringe. The reaction was allowed to warm to room temperature, and stirred at this temperature until no more bubbling was observed. Pyrazole C was added in 1 portion to the reaction mixture, heated to 110° C., and stirred at this temperature until judged complete (e.g., using either TLC or LC/MS analysis). Once complete, the reaction was cooled, treated with excess methanol, and stirred vigorously for 1 hour at room temperature. The thick slurry was filtered, and the resulting solid cake was washed with methanol. The filtrate was concentrated in vacuo, and the resulting solids were re-suspended in an ethyl acetate: isopropyl alcohol=5:1 solvent mixture. The reaction was further treated with saturated sodium carbonate solution, and stirred for 10 minutes before the layers are separated. The aqueous layer was extracted with the ethyl acetate:isopropyl alcohol=5:1 solvent mixture (3×), and the combined organics were washed with brine. The organics were further dried over MgSO$_4$, filtered, and the solvent removed in vacuo. The product amidine D was used as-is in subsequent steps without further purification.

Step 4:
Pyrimidone Formation:

Amidine D was suspended in ethanol, and stirred vigorously at 23° C. to encourage full solvation. The reaction was further treated with sodium 3-ethoxy-2-fluoro-3-oxoprop-1-en-1-olate (e.g., 3 equiv.), and the flask was equipped with a reflux condenser. The reaction was placed into a pre-heated oil bath maintained at 90° C. and stirred until full consumption of starting material was observed on the LC/MS (reaction times were typically 1 h). The contents were cooled to 23° C., and the reaction mixture acidified with HCl (e.g., 3 equiv., 1.25M solution in EtOH). The mixture was stirred for 30 minutes, and the majority of the solvent was removed in vacuo. Contents were re-suspended in ether and water (1:1 mixture), and the resulting slurry was stirred for 20 min. The suspension was vacuum filtered, and the solid cake was rinsed with additional water and ether and dried on high vacuum overnight. The resulting pyrimidone E was used as-is in subsequent steps without further purification.

General Procedure B

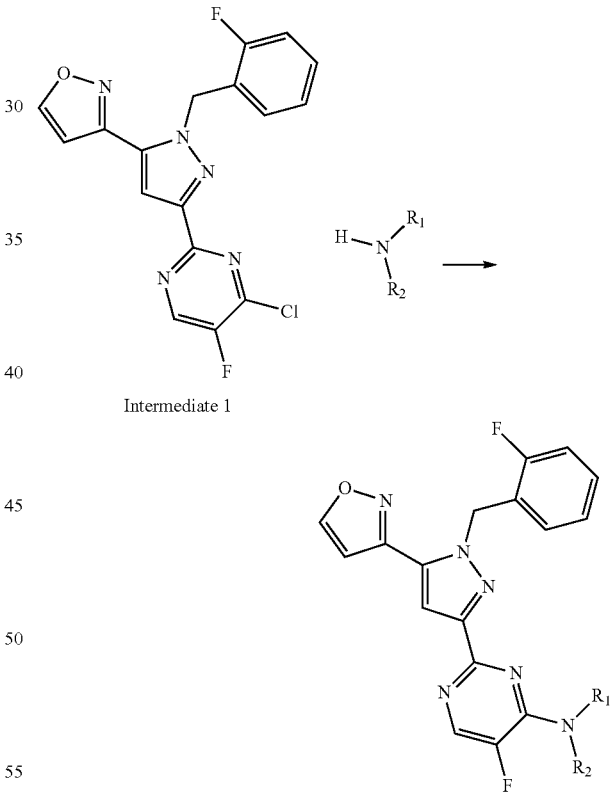

Intermediate 1

A solution of amino nucleophile (3 equiv.), triethylamine (10 equiv.), and Intermediate 1 (1 equiv.) was stirred in dioxane and water (2:1 ratio) at 90° C. until complete consumption of starting material was observed by LC/MS. The solution was diluted with aqueous 1N hydrochloric acid and dichloromethane. The layers were then separated and the aqueous layer was extracted with dichloromethane. The organics were combined, dried over magnesium sulfate, filtered, and the solvent was removed in vacuo. Purification yielded the desired product.

General Procedure C

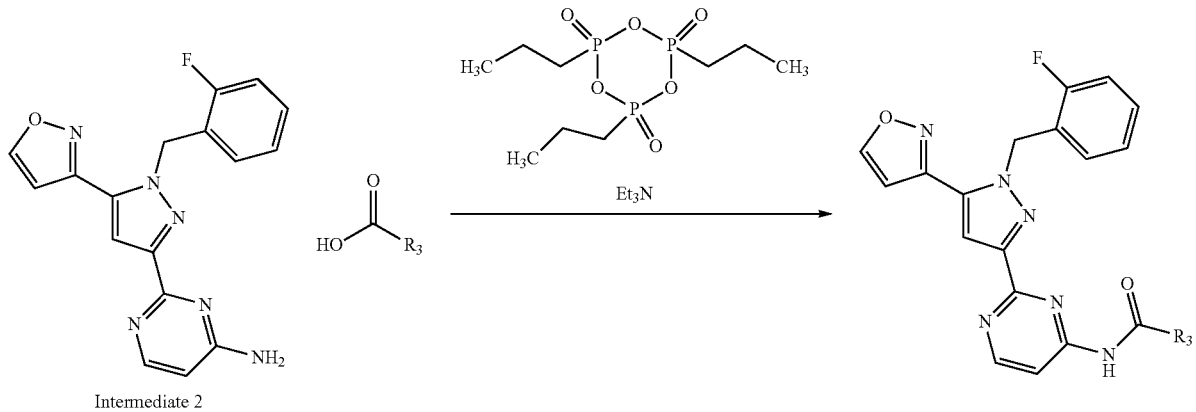

A mixture of Intermediate 2 (this intermediate was described in previously published patent application WO2012/3405 A1; 1 equivalent) and carboxylic acid (1.1 equivalent) in N,N-dimethylformamide was treated with triethylamine (4 equivalent) followed by a 50% in ethyl acetate solution of propylphosphonic anhydride (T3P, 1.4 equivalent). The reaction was heated to 80° C. for 24 h, after which the reaction was diluted with water and 1N hydrochloric acid solution. Contents were extracted with dichloromethane, then ethyl acetate. The combined organic layers were dried over sodium sulfate, filtered, and concentrated in vacuo. Purification yielded the desired product.

Pharmaceutically Acceptable Salts of the Invention.

The phrase "pharmaceutically acceptable salt," as used herein, refers to pharmaceutically acceptable organic or inorganic salts of a compound of Formula I or Formula I'. The pharmaceutically acceptable salts of a compound of Formula I or Formula I' are used in medicine. Salts that are not pharmaceutically acceptable may, however, be useful in the preparation of a compound of Formula I or Formula I' or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from the compounds with inorganic acids, organic acids or bases. In some embodiments, the salts can be prepared in situ during the final isolation and purification of the compounds. In other embodiments the salts can be prepared from the free form of the compound in a separate synthetic step.

When a compound of Formula I or Formula I' is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N.sup.1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of Formula I or Formula I' is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.

Pharmaceutical Compositions and Methods of Administration.

The compounds herein disclosed, and their pharmaceutically acceptable salts thereof may be formulated as pharmaceutical compositions or "formulations".

A typical formulation is prepared by mixing a compound of Formula I or Formula I', or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I and Formula I' is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I and Formula I' or pharmaceutical composition thereof) or aid in the manufacturing of the pharmaceutical product (i.e., medicament).

The formulations may be prepared using conventional dissolution and mixing procedures. For example, the bulk drug substance (i.e., a compound of Formula I and Formula I', a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula I and Formula I' or a pharmaceutically acceptable salt thereof is typically formulated into pharmaceutical dosage forms to provide an easily controllable dosage of the drug and to enable patient compliance with the prescribed regimen. Pharmaceutical formulations of a compound of Formula I and Formula I', or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula I and Formula I' will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, tretralose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, $21^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(–)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semipermeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolat. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e. g., Explotab™ CLV), microcrystalline cellulose (e. g., Avicel™), microcrystalline silicified cellulose (e. g., ProSolv™) and croscarmellose sodium (e. g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. Nos. 6,419,952, 6,342,249, 5,324,280, 4,672,850, 4,627,850, 4,203,440, and 3,995,631.

As further noted above, the agents described herein may be provided in the form of microparticulates, generally ranging in size from about 10 μm to about 2 mm (including, for example, from about 100 μm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet-and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 μm) can be designed using polymers able to be degraded in vivo (e.g. biodegradable polyalkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I and Formula I' that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound of Formula I and Formula I' in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of a compound of Formula I and Formula I' contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylceluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I and Formula I' may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I and Formula I' include Tween™-60, Span™-80, cetostearyl alcohol, benzyl alcohol, myristyl alcohol, glyceryl monostearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula I and Formula I' or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert or accept Formula I and Formula I'n the veterinary art and are compatible with the active ingredient. These veterinary compositions may be administered parenterally, orally or by any other desired route.

Therapeutic Methods

In a third aspect, the invention relates to the treatment of certain disorders by using sGC stimulators, either alone or in combination, or their pharmaceutically acceptable salts or pharmaceutical compositions comprising them, in a patient in need thereof.

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO or an increase in the concentration of cGMP might be desirable. The diseases that can be treated include but are not limited to pulmonary hypertension, arterial hypertension, heart failure, atherosclerosis, inflammation, thrombosis, renal fibrosis and failure, liver cirrhosis, erectile dysfunction, female sexual disorders, disorders related to diabetes, ocular disorders and other related cardiovascular disorders.

Increased concentration of cGMP leads to vasodilation, inhibition of platelet aggregation and adhesion, anti-hypertensive effects, anti-remodeling effects, anti-apoptotic effects, anti-inflammatory effects and neuronal signal transmission effects. Thus, sGC stimulators may be used to treat and/or prevent a range of diseases and disorders, including but not limited to a peripheral, pulmonary, hepatic, liver, cardiac or cerebralvascular/endothelial disorders or conditions, a urogenital-gynecological or sexual disorder or condition, a thromboembolic disease, an ischemic disease, a fibrotic disorder, a topical or skin disorder, a pulmonary or respiratory disorder, a renal or hepatic disorder, a metabolic disorder, atherosclerosis, or a lipid related disorder.

In other embodiments, the compounds here disclosed are sGC stimulators that may be useful in the prevention and/or treatment of diseases and disorders characterized by undesirable reduced bioavailability of and/or sensitivity to NO, such as those associated with conditions of oxidative stress or nitrosative stress.

Throughout this disclosure, the terms "hypertension", "arterial hypertension" or "high blood pressure (HBP)" are used interchangeable and refer to an extremely common and highly preventable chronic condition in which blood pressure (BP) in the arteries is higher than normal. If not properly controlled, it represents a significant risk factor for several serious cardiovascular and renal conditions. Hypertension may be a primary disease, called "essential hypertension" or "idiopathic hypertension", or it may be caused by other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension. Hypertension is an extremely common comorbid condition in diabetes, affecting ~20-60% of patients with diabetes, depending on obesity, ethnicity, and age. This type of hypertension is herein referred to as "diabetic hypertension". In type 2 diabetes, hypertension is often present as part of the metabolic syndrome of insulin resistance also including central obesity and dyslipidemia. In type 1 diabetes, hypertension may reflect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

As used herein "heart failure" is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neurohormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness, edema of the feet, ankles and legs, rapid weight gain, chronic cough, including that producing mucus or blood. Depending on its clinical presentation, heart failure is classified as de novo, transient or chronic. Acute heart failure, i.e. the rapid or gradual onset of symptoms requiring urgent therapy, may develop de novo or as a result of chronic heart failure becoming decompensated. Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease (COPD), peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, nonvoluntary loss of at least 6% of body weight over a period of six months.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertriglyceridemia" involves elevated levels of triglycerides). "Hyperlipoproteinemia" refers to elevated levels of lipoproteins (usually LDL unless otherwise specified).

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or brain. PVD can result from atherosclerosis, inflammatory processes leading to stenosis, an embolism, or thrombus formation. It causes either acute or chronic "ischemia (lack of blood supply)". Often PVD is a term used to refer to atherosclerotic blockages found in the lower extremity. PVD also includes a subset of diseases classified as microvascular diseases resulting from episodal narrowing of the arteries (e.g., "Raynaud's phenomenon"), or widening thereof (erythromelalgia), i.e. vascular spasms.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen, and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin.

A "stroke", or cerebrovascular accident (CVA), is the rapid loss of brain function(s) due to disturbance in the blood supply to the brain. This can be due to "ischemia" (lack of blood flow) caused by blockage (thrombosis, arterial embolism), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Ischemia" is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism).

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

As used herein, the term "bronchoconstriction" is used to define the constriction of the airways in the lungs due to the tightening of surrounding smooth muscle, with consequent coughing, wheezing, and shortness of breath. The condition has a number of causes, the most common being as well as asthma. Exercise and allergies can bring on the symptoms in an otherwise asymptomatic individual. Other conditions such as chronic obstructive pulmonary disease (COPD) can also present with bronchoconstriction.

Specific diseases of disorders which may be treated and/or prevented by administering an sGC stimulator of the invention, include but are not limited to: hypertension (e.g., diabetic hypertension, arterial hypertension, pulmonary hypertension, resistant hypertension, peripheral artery disease, etc), heart failure (e.g., left ventricular diastolic dysfunction (LVDD) and left ventricular systolic dysfunction (LVSD), sleep apnea associated with heart failure), arteriosclerotic disease (e.g., atherosclerosis), thromboembolic disorders (e.g., chronic thromboembolic pulmonary hypertension, thrombosis, stroke, embolism, pulmonary embolism), Alzheimer's disease, renal diseases (e.g., renal fibrosis, ischemic renal disease, renal failure, renal insufficiency, chronic kidney disease), hepatic disease (e.g., liver fibrosis or cirrhosis), respiratory disease (e.g., pulmonary fibrosis, asthma, chronic obstructive pulmonary disease, interstitial lung disease), sexual disorders (e.g., erectile dysfunction, male and female sexual dysfunction, vaginal atrophy), sickle cell anemia, neuro inflammatory diseases or disorders and metabolic disorders (e.g., lipid related disorders).

The compounds of Formula I and Formula I' as well as pharmaceutically acceptable salts thereof, as stimulators of sGC, are useful in the prevention and/or treatment of the following types of diseases, conditions and disorders which can benefit from sGC stimulation:

(1) Peripheral, pulmonary, hepatic, kidney, cardiac or cerebral vascular/endothelial disorders/conditions or diseases otherwise related to circulation:

disorders related to high blood pressure and decreased coronary blood flow such as increased acute and chronic coronary blood pressure, arterial hypertension and vascular disorder resulting from cardiac and renal complications (e.g. heart disease, stroke, cerebral ischemia, renal failure); resistant hypertension, diabetic hypertension, congestive heart failure; diastolic or systolic dysfunction; coronary insufficiency; arrhythmias; reduction of ventricular preload; cardiac hypertrophy; heart failure/cardiorenal syndrome; portal hypertension; endothelial dysfunction or injury;

thromboembolic disorders and ischemias such as myocardial infarction, stroke, transient ischemic attacks (TIAs); obstructive thromboanginitis; stable or unstable angina pectoris; coronary spasms, variant angina, Prinzmetal's angina; prevention of restenosis after thrombolysis therapies; thrombogenic disoders;

Alzheimer's disease; Parkinson's disease; dementia; vascular cognitive impairment; cerebral vasospasm; traumatic brain injury;

peripheral arterial disease, peripheral occlusive arterial disease; peripheral vascular disease; hypertonia; Raynaud's syndrome or phenomenon, critical limb ischemia, vasculitis; peripheral embolism; intermittent claudication; vaso-occlusive crisis; Duchene's and Becker muscular dystrophies; microcirculation abnormalities; control of vascular leakage or permeability;

shock; sepsis; cardiogenic shock; control of leukocyte activation; inhibition or modulation of platelet aggregation;

pulmonary/respiratory conditions such as pulmonary hypertension, pulmonary arterial hypertension, and associated pulmonary vascular remodeling (e.g. localized thrombosis and right heart hypertrophy); pulmonary hypertonia; primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; cystic fibrosis; bronchoconstriction or pulmonary bronchoconstriction; acute respiratory distress syndrome; lung fibrosis, lung transplant;

pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venooclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), connective tissue disease, lupus, schistosomiasis, sarcoidosis, chronic obstructive pulmonary disease, asthma, emphysema, chronic bronchitis, pulmonary capillary hemangiomatosis; histiocytosis X, lymphangiomatosis and compressed pulmonary vessels (such as due to adenopathy, tumor or fibrosing mediastinitis);

arterosclerotic diseases or conditions such as atherosclerosis (e.g., associated with endothelial injury, platelet and monocyte adhesion and aggregation, smooth muscle proliferation and migration); restenosis (e.g. developed after thrombolysis therapies, percutaneous transluminal angioplasties (PTAs), percutaneous transluminal coronary angioplasties (PTCAs) and bypass); inflammation;

cardiovascular disease associated with metabolic syndrome (e.g., obesity, dyslipidemia, diabetes, high blood pressure); lipid related disorders such as dyslipidemia, hypercholesterolemia, hypertriglyceridemia, sitosterolemia, fatty liver disease, and hepatitis; preeclamsia; polycystic kidney disease progression; subcutaneous fat; obesity;

liver cirrhosis, associated with chronic liver disease, hepatic fibrosis, hepatic stellate cell activation, hepatic fibrous collagen and total collagen accumulation; liver disease of necro-inflammatory and/or of immunological origin; andurogenital system disorders, such as renal fibrosis and renal failure resulting from chronic kidney diseases or insufficiency (e.g. due to accumulation/deposition and tissue injury, progressive sclerosis, glomerulonephritis); prostate hypertrophy systemic sclerosis; cardiac interstitial fibrosis; cardiac remodeling and fibrosis; cardiac hypertrophy;

(2) ischemia, reperfusion damage; ischemia/reperfusion associated with organ transplant, lung transplant, pulmonary transplant, cardiac transplant; conserving blood substituents in trauma patients;

(3) sexual, gynecologicaland urological disorders of conditions: erectile dysfunction; impotence; premature ejaculation; female sexual dysfunction (e.g., female sexual arousal dysfunction, hypoactive sexual arousal disorder), vaginal atrophy, dyspaneuria, atrophic vaginitis; benign prostatic hyperplasia (BPH) or hypertrophy or enlargement, bladder outlet obstruction; bladder pain syndrome (BPS), interstitial cystitis (IC), overactive bladder, neurogenic bladder and incontinence; diabetic nephropathy;

(4) ocular diseases or disorders: glaucoma, retinopathy, diabetic retinopathy, blepharitis, dry eye syndrome, Sjögren's Syndrome;

(5) hearing diseases or disorders: hearing impairment, partial or total hearing loss; partial or total deafness; tinnitus; noise-induced hearing loss;

(6) topical or skin disorders or conditions: dermal fibrosis, scleroderma, skin fibrosis;

(7) wound healing: for instance in diabetics; microvascular perfusion improvement (e.g., following injury, to counteract the inflammatory response in perioperative care), anal fissures, diabetic ulcers; and (8) other diseases or conditions: cancer metastasis, osteoporosis, gastroparesis; functional dyspepsia; diabetic complications, diseases associated with endothelial dysfunction, and neurologic disorders associated with decreased nitric oxide production.

In other embodiments of the invention, the compounds of Formula I and Formula I' as well as pharmaceutically acceptable salts thereof are useful in the prevention and/or treatment of the following types of diseases, conditions and disorders which can benefit from sGC stimulation:

hypertension, resistant hypertension, diabetic hypertension, pulmonary hypertension (PH), pulmonary arterial hypertension, PH associated with COPD, chronic airflow obstruction, asthma or pulmonary fibrosis, thrombosis, embolism, thromboembolic disorders, Alzheimer's disease, atherosclerosis, right heart hypertrophy, heart failure, diastolic dysfunction, systolic dysfunction, sleep apnea associated with heart failure, liver cirrhosis, renal fibrosis, renal failure resulting from chronic kidney diseases or insufficiency, metabolic disorder, dyslipidemia, hypercholesterolemia, hypertriglyceridemia, sitosterolemia, fatty liver disease, hepatitis, erectile dysfunction, female sexual dysfunction, female sexual arousal dysfunction and vaginal atrophy.

In some embodiments, the invention relates to a method of treating a disease, health condition or disorder in a subject, comprising administering a therapeutically effective amount of a compound of any of the above depicted Formulae, or a pharmaceutically acceptable salt thereof, to the subject in need of treatment, wherein the disease, health condition or disorder is selected from one of the diseases listed above.

In other embodiments the disease, health condition or disorder is selected from a peripheral, pulmonary, hepatic, kidney, cardiac or cerebral vascular/endothelial disorder or condition, or a disease otherwise related to circulation selected from: increased acute and chronic coronary blood pressure, arterial hypertension and vascular disorder resulting from cardiac and renal complications, heart disease, stroke, cerebral ischemia, renal failure; resistant hypertension, diabetic hypertension, congestive heart failure; diastolic or systolic dysfunction; coronary insufficiency; arrhythmias; reduction of ventricular preload; cardiac hypertrophy; heart failure/cardiorenal syndrome; portal hypertension; endothelial dysfunction or injury; myocardial infarction; stroke or transient ischemic attacks (TIAs); obstructive thromboanginitis; stable or unstable angina pectoris; coronary spasms, variant angina, Prinzmetal's angina; restenosis as a result of thrombolysis therapies and thrombogenic disoders.

In still other embodiments, the disease, health condition or disorder is selected from a peripheral vascular/endothelial disorder or condition or a disease otherwise related to circulation selected from: peripheral arterial disease, peripheral occlusive arterial disease; peripheral vascular disease; hypertonias; Raynaud's syndrome or phenomenon; critical limb ischemia; vasculitis; peripheral embolism; intermittent claudication; vaso-occlusive crisis; Duchene's and Becker muscular dystrophies; microcirculation abnormalities; and vascular leakage or permeability issues.

In further embodiments, the disease, health condition or disorder is a pulmonary disorder or condition or a disease otherwise related to circulation selected from: pulmonary hypertension; pulmonary arterial hypertension and associated pulmonary vascular remodeling; localized thrombosis; right heart hypertrophy; pulmonary hypertonia; primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; cystic fibrosis; bronchoconstriction or pulmonary bronchoconstriction; acute respiratory distress syndrome; lung fibrosis and lung transplant. In some of these embodiments, the pulmonary hypertension is pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, coagulation disorders, chronic thromboembolism; pulmonary embolism, due to tumor, parasites or foreign material; connective tissue disease, lupus, schistosomiasis, sarcoidosis, chronic obstructive pulmonary disease, asthma, emphysema, chronic bronchitis, pulmonary capillary hemangiomatosis; histiocytosis X; lymphangiomatosis and compressed pulmonary vessels due to adenopathy, tumor or fibrosing mediastinitis.

In still other embodiments, the health condition or disorder is a vascular or endothelial disorder or condition or a disease otherwise related to circulation selected from: arterosclerotic diseases; atherosclerosis, atherosclerosis associated with endothelial injury, atherosclerosis associated with platelet and monocyte adhesion and aggregation, atherosclerosis associated with smooth muscle proliferation and migration; restenosis, restenosis developed after thrombolysis therapies; restenosis developed after percutaneous transluminal angioplasties; restensosis developed after percutaneous transluminal coronary angioplasties and bypass; inflammation; cardiovascular disease associated with metabolic syndrome, obesity, dyslipidemia, diabetes or high blood pressure; lipid related disorders, dyslipidemia, hypercholesterolemia, hypertriglyceridemia, sitosterolemia, fatty liver disease, and hepatitis; preeclamsia; polycystic kidney disease progression; and subcutaneous fat.

In yet other embodiments, the disease, health condition or disorder selected from liver cirrhosis, liver cirrhosis associated with chronic liver disease, hepatic fibrosis, hepatic stellate cell activation, hepatic fibrous collagen and total collagen accumulation; and liver disease of necro-inflammatory or of immunological origin.

In further embodiments, the disease, health condition or disorder is a urogenital system disorder selected from renal fibrosis; renal failure resulting from chronic kidney diseases or insufficiency; renal failure due to accumulation or deposition and tissue injury, progressive sclerosis or glomerulonephritis; and prostatic hypertrophy.

In further embodiments, the disease, health condition or disorder is systemic sclerosis.

In further embodiments, the disease, health condition or disorder is a cardiac disorder selected from cardiac interstitial fibrosis; cardiac remodeling and fibrosis and cardiac hypertrophy.

In further embodiments, the disease, health condition or disorder is a CNS disorder or condition selected from Alzheimer's disease; Parkinson's disease; dementia; vascular cognitive impairment; cerebral vasospasm; and traumatic brain injury.

In further embodiments, the disease, health condition or disorder is selected from ischemia, reperfusion damage; ischemia/reperfusion associated with organ transplant, lung transplant, pulmonary transplant or cardiac transplant; conserving blood substituents in trauma patients.

In further embodiments, the disease, health condition or disorder is a sexual, gynecological or urological disorder of condition selected from erectile dysfunction; impotence; premature ejaculation; female sexual dysfunction; female sexual arousal dysfunction; hypoactive sexual arousal disorder; vaginal atrophy, dyspaneuria, atrophic vaginitis; benign prostatic hyperplasia (BPH) or hypertrophy or enlargement; bladder outlet obstruction; bladder pain syndrome (BPS); interstitial cystitis (IC); overactive bladder, neurogenic bladder and incontinence; diabetic nephropathy.

In further embodiments, the disease, health condition or disorder is selected from vaginal atrophy, dyspaneuria and atrophic vaginitis.

In further embodiments, the disease, health condition or disorder is selected from benign prostatic hyperplasia (BPH) or hypertrophy or enlargement; bladder outlet obstruction; bladder pain syndrome (BPS); interstitial cystitis (IC); overactive bladder, neurogenic bladder and incontinence.

In further embodiments, the disease, health condition or disorder is a sexual, condition selected from erectile dysfunction; impotence; premature ejaculation; female sexual dysfunction; female sexual arousal dysfunction and hypoactive sexual arousal disorder.

In further embodiments, the disease or disorder is diabetic nephropathy.

In further embodiments, the disease, health condition or disorder is Duchene's and Becker muscular dystrophies.

In further embodiments, the disease is an ocular diseases or disorder selected from glaucoma, retinopathy, diabetic retinopathy, blepharitis, dry eye syndrome and Sjögren's Syndrome.

In further embodiments, the disease is a hearing diseases or disorder selected from hearing impairment, partial or total hearing loss; partial or total deafness; tinnitus; and noise-induced hearing loss.

In further embodiments, the disease is a topical or skin disorders or condition selected from dermal fibrosis, scleroderma and skin fibrosis.

In further embodiments, the treatment involves wound healing; wound healing in diabetics; improvement of microvascular perfusion; improvement of microvascular perfusion issues following injury; treatment of anal fissures; and treatment of diabetic ulcers.

In further embodiments, the disease or condition is selected from cancer metastasis; osteoporosis; gastroparesis; functional dyspepsia; diabetic complications; diseases associated with endothelial dysfunction and neurologic disorders associated with decreased nitric oxide production.

In another embodiment, compounds of the invention can be delivered in the form of implanted devices, such as stents. A stent is a mesh 'tube' inserted into a natural passage/conduit in the body to prevent or counteract a disease-induced, localized flow constriction. The term may also refer to a tube used to temporarily hold such a natural conduit open to allow access for surgery.

A drug-eluting stent (DES) is a peripheral or coronary stent (a scaffold) placed into narrowed, diseased peripheral or coronary arteries that slowly releases a drug to block cell proliferation, usually smooth muscle cell proliferation. This prevents fibrosis that, together with clots (thrombus), could otherwise block the stented artery, a process called restenosis. The stent is usually placed within the peripheral or coronary artery by an Interventional cardiologist or Interventional Radiologist during an angioplasty procedure. Drugs commonly used in DES in order to block cell proliferation include paclitaxel or rapamycin analogues In some embodiments of the invention, a sGC stimulator of the invention can be delivered by means of a drug-eluting stent coated with said sGC stimulator. A drug-eluting stent coated with a sGC stimulator of the invention may be useful in the prevention of stent restenosis and thrombosis during percutaneous coronary interventions. A drug-eluting stent coated with a sGC stimulator of the invention may be able to prevent smooth cell proliferation as well as to assist re-vascularization and re-generation of the endothelial tissue of the artery in which the stent is inserted.

An alternative to percutaneous coronary intervention for the treatment of intractable angina due to coronary artery occlusive disease is the procedure named Coronary Artery Bypass Grafting (CABG). CABG provides only palliation of an ongoing process that is further complicated by the rapid development of graft atherosclerosis. The saphenous vein graft is the most commonly used conduit in CABG surgery. The long-term clinical success of venous CABG is hampered for three main reasons: accelerated graft atherosclerosis, incomplete endothelialization and thrombosis.

In some embodiments, a sGC stimulator of the invention can be used for the prevention of saphenous graft failure during CABG. Compounds of the invention may assist the process of endothelialization and help prevent thrombosis. In this indication, the sGC stimulator is delivered locally in the form of a gel.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound of Formula I and Formula I', or a pharmaceutically acceptable salt thereof, to the subject in need of the treatment. Alternatively, the invention provides the use of a compound of Formula I and Formula I', or a pharmaceutically acceptable salt thereof, in the treatment of one of these diseases, conditions and disorders in a subject in need of the treatment. The invention further provides a method of making or manufacturing a medicament useful for treating one of these diseases, conditions and disorders comprising using a compound of Formula I and Formula I', or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, feces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernable symptoms) of said condition (i.e. "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of an sGC, cGMP and/or NO mediated condition. In other embodiments the terms "treat", "treatment" and "treating" refer to the inhibition of the progression of an sGC, cGMP and/or NO mediated condition, either physically by, e.g., stabilization of a discernable symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g. a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I and Formula I' or a pharmaceutically acceptable salt thereof and a second amount of an additional suitable therapeutic agent.

In one embodiment of this invention, a compound of Formula I and Formula I' and the additional therapeutic agent are each administered in an effective amount (i.e., each in an amount which would be therapeutically effective if administered alone). In another embodiment, the compound of Formula I and Formula I' and the additional therapeutic agent are each administered in an amount which alone does not provide a therapeutic effect (a sub-therapeutic dose). In yet another embodiment, the compound of Formula I and Formula I' can be administered in an effective amount, while the additional therapeutic agent is administered in a sub-therapeutic dose. In still another embodiment, the compound of Formula I and Formula I' can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Formula I and Formula I' and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I and Formula I' and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of this disclosure, either administered separately or in the same pharmaceutical composition include, but are not limited to:

(1) Endothelium-derived releasing factor (EDRF);
(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatrate®-SR, Imdur®, Ismo®, Isordil®, Isordil®, Titradose®, Monoket®), FK 409 (NOR-3); FR 144420 (NOR-4); 3-morpholinosydnonimine; Linsidomine chlorohydrate ("SIN-1"); S-nitroso-N-acetylpenicillamine ("SNAP"); AZD3582 (CI-NOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), S-nitrosoglutathione (GSNO), Sodium Nitroprusside, S-nitrosoglutathione mono-ethyl-ester (GSNO-ester), 6-(2-hydroxy-1-methyl-nitro sohydrazino)-N-methyl-1-hexanamine (NOC-9) or diethylamine NONOate. Nitric oxide donors are also as disclosed in U.S. Pat. Nos. 5,155,137, 5,366,997, 5,405,919, 5,650,442, 5,700,830, 5,632,981, 6,290,981, 5,691,423 5,721,365, 5,714,511, 6,511,911, and 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;

(3) Other substances that enhance cGMP concentrations such as protoporphyrin IX, arachidonic acid and phenyl hydrazine derivatives;

(4) Nitric Oxide Synthase substrates: for example, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluormethyl) propylguanidine; and others reviewed in Cali et al. (2005, Current Topics in Medicinal Chemistry 5:721-736) and disclosed in the references cited therein;

(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g. 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schafer et al., Journal of Thrombosis and Homeostasis 2005; Volume 3, Supplement 1: abstract number P1487);

(6) NO independent heme-independent sGC activators, including, but not limited to: BAY 58-2667 (see patent publication DE19943635)

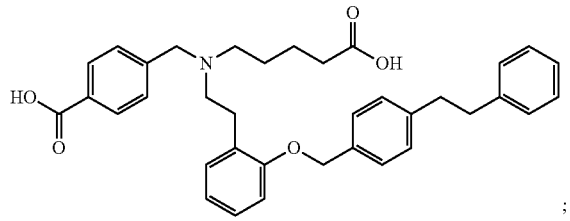 [SMILES: O=C(O)CCCCN(CCc1ccccc1OCc1ccc(CCc2ccccc2)cc1)Cc1ccc(C(=O)O)cc1]

HMR-1766 (ataciguat sodium, see patent publication WO2000002851)

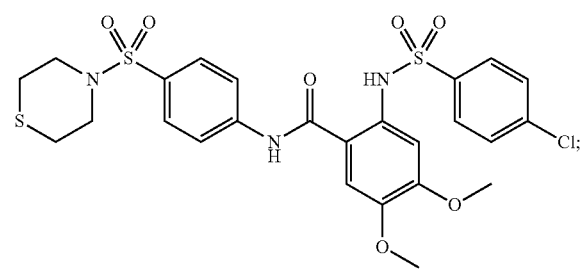 [SMILES: COc1cc(NS(=O)(=O)c2ccc(Cl)cc2)c(C(=O)Nc2ccc(S(=O)(=O)N3CCSCC3)cc2)cc1OC]

S 3448
(2-(4-chloro-phenylsulfonylamino)-4,5-dimethoxy-N-(4-(thiomorpholine-4-sulfonyl)-phenyl)-benzamide (see patent publications DE19830430 and WO2000002851)

and
HMR-1069 (Sanofi-Aventis).

(7) Heme-dependent sGC stimulators including, but not limited to:

YC-1 (see patent publications EP667345 and DE19744026)

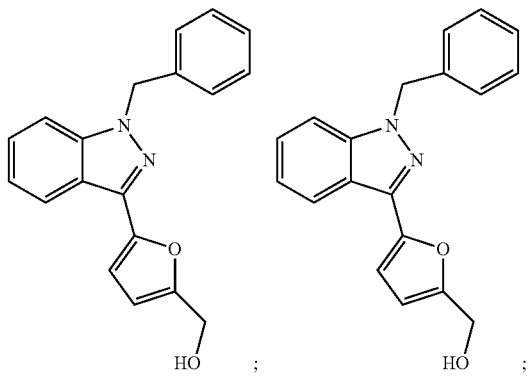 [SMILES: OCc1ccc(-c2nn(Cc3ccccc3)c3ccccc23)o1 ; OCc1ccc(-c2nn(Cc3ccccc3)c3ccccc23)o1]

Riociguat (BAY 63-2521, Adempas, commercial product, described in DE19834044)

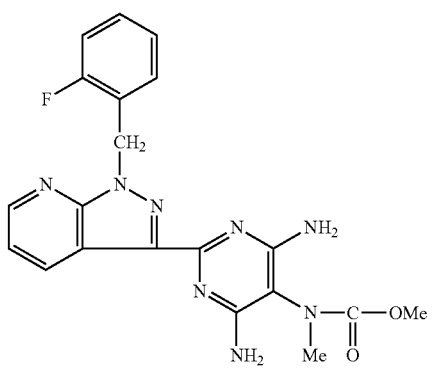 [SMILES: COC(=O)N(C)c1c(N)nc(-c2nn(Cc3ccccc3F)c3ncccc23)nc1N]

Neliciguat (BAY 60-4552, described in WO 2003095451)

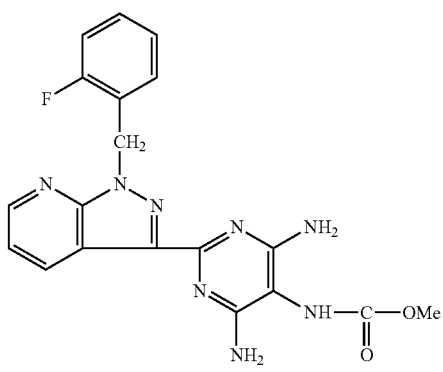 [SMILES: COC(=O)Nc1c(N)nc(-c2nn(Cc3ccccc3F)c3ncccc23)nc1N]

Vericiguat (BAY 1021189, clinical backup to Riociguat), BAY 41-2272 (described in DE19834047 and DE19942809)

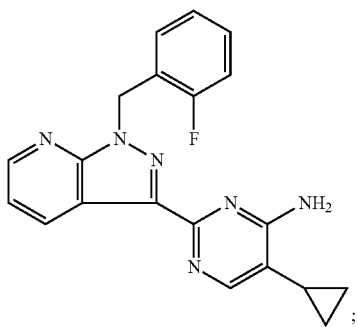 [SMILES: Nc1nc(-c2nn(Cc3ccccc3F)c3ncccc23)ncc1C1CC1]

BAY 41-8543 (described in DE19834044)

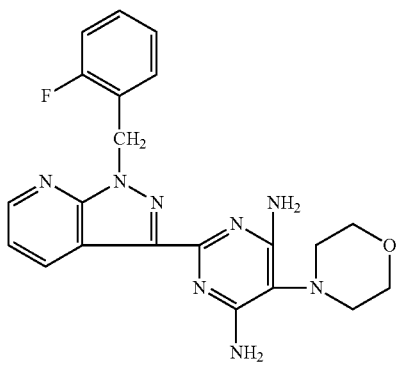 [SMILES: Nc1nc(-c2nn(Cc3ccccc3F)c3ncccc23)nc(N)c1N1CCOCC1]

Etriciguat (described in WO 2003086407)

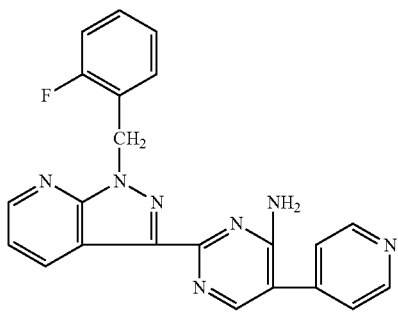 [SMILES: Nc1nc(-c2nn(Cc3ccccc3F)c3ncccc23)ncc1-c1ccncc1]

CFM-1571 (see patent publication WO2000027394)

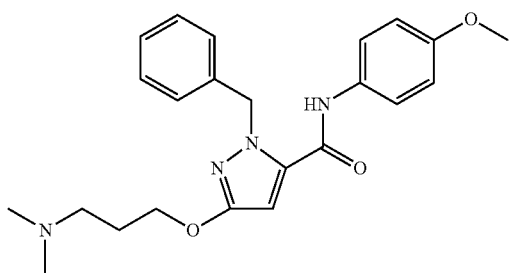

A-344905, its acrylamide analogue A-350619 and the aminopyrimidine analogue A-778935.

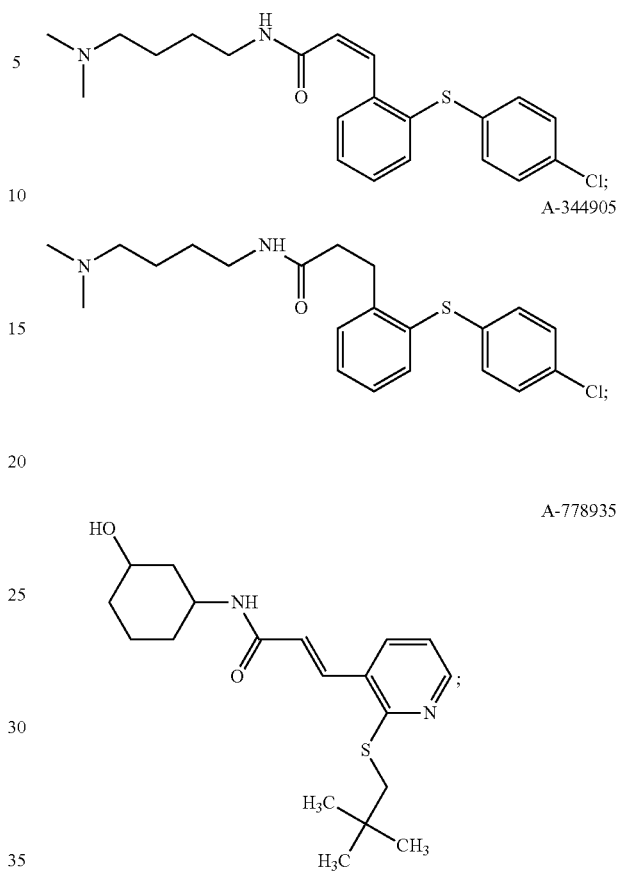

Compounds disclosed in one of publications: US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds disclosed in Tetrahedron Letters (2003), 44(48): 8661-8663.

(8) Compounds that inhibit the degradation of cGMP, such as:
PDE5 inhibitors, such as, for example, Sildenafil (Viagra®) and other related agents such as Avanafil, Lodenafil, Mirodenafil, Sildenafil citrate (Revatio®), Tadalafil (Cialis® or Adcirca®), Vardenafil (Levitra®) and Udenafil; Alprostadil; and Dipyridamole;

(9) Calcium channel blockers such as:
Dihydropyridine calcium channel blockers: Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Diltiazem, Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas), Isradipine (Lomir);

Phenylalkylamine calcium channel blockers: Verapamil (Calan, Isoptin)

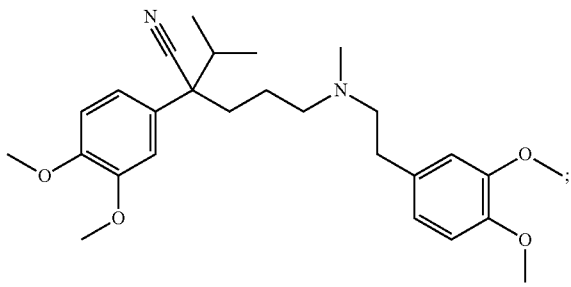

Gallopamil (Procorum, D600);
Benzothiazepines: Diltiazem (Cardizem);

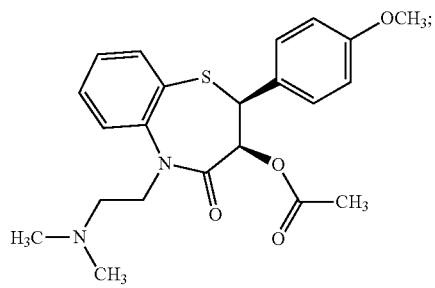 [SMILES: COc1ccc([C@@H]2Sc3ccccc3N(CCN(C)C)C(=O)[C@@H]2OC(C)=O)cc1]

Nonselective calcium channel inhibitors such as: mibefradil, bepridil and fluspirilene, fendiline;

(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S; dual/nonselective endothelin antagonist Actelion-1, that entered clinical trials in 2008;

(11) Prostacyclin derivatives or analogues: for instance prostacyclin (prostaglandin $I_2$), Epoprostenol (synthetic prostacyclin, marketed as Flolan®); Treprostinil (Remodulin®), Iloprost (Ilomedin®), Iloprost (marketed as Ventavis®); oral and inhaled forms of Remodulin® that are under development; Beraprost, an oral prostanoid available in Japan and South Korea;

(12) Antihyperlipidemics such as: bile acid sequestrants (e.g., Cholestyramine, Colestipol, Colestilan and Colesevelam); statins such as Atorvastatin, Simvastatin, Lovastatin, Fluvastatin, Pitavastatin, Rosuvastatin and Pravastatin; cholesterol absorption inhibitors such as Ezetimibe; other lipid lowering agents such as Icosapent ethyl ester, Omega-3-acid ethyl esters, Reducol; fibric acid derivatives such as Clofibrate, Bezafibrate, Clinofibrate, Gemfibrozil, Ronifibrate, Binifibrate, Fenofirate, Ciprofibrate, Choline fenofibrate; nicotinic acid derivatives such as Acipimox and Niacin; also combinations of statins, niacin, intestinal cholesterol absorption-inhibiting supplements (ezetimibe and others) and fibrates; antiplatelet therapies such as Clopidogrel bisulfate;

(13) Anticoagulants, such as the following types:
Coumarines (Vitamin K antagonists): Warfarin® (Coumadin) mostly used in the US and UK; Acenocoumarol® and Phenprocoumon®, mainly used in other countries; Phenindione®;
Heparin and derivative substances such as: Heparin; low molecular weight heparin, Fondaparinux and Idraparinux;

Direct thrombin inhibitors such as: Argatroban, Lepirudin, Bivalirudin and Dabigatran; Ximelagatran (Exanta®), not approved in the US;
Tissue plasminogen activators, used to dissolve clots and unblock arteries, such as Alteplase;

(14) Antiplatelet drugs: for instance thienopyridines such as Lopidogrel and Ticlopidine; Dipyridamole; Aspirin;

(15) ACE inhibitors, for example the following types:
Sulfhydryl-containing agents such as Captopril (trade name Capoten®), the first ACE inhibitor and Zofenopril;
Dicarboxylate-containing agents such as Enalapril (Vasotec/Renitec®); Ramipril (Altace/Tritace/Ramace/Ramiwin®); Quinapril (Accupril®), Perindopril (Coversyl/Aceon®); Lisinopril (Lisodur/Lopril/Novatec/Prinivil/Zestril®) and Benazepril (Lotensin®);
Phosphonate-containing agents such as: Fosinopril;
Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;
Other ACE inhibitors such as Alacepril, Delapril, Cilazapril, Imidapril, Trandolapril, Temocapril, Moexipril, Spirapril,

(16) Supplemental oxygen therapy;

(17) Beta blockers, such as the following types:
Non-selective agents: Alprenolol®, Bucindolol®, Carteolol®, Carvedilol® (has additional α-blocking activity), Labetalol® (has additional α-blocking activity), Nadolol®, Penbutolol® (has intrinsic sympathomimetic activity), Pindolol® (has intrinsic sympathomimetic activity), Oxprenonol, Acebutolol, Sotalol, Mepindolol, Celiprolol, Arotinolol, Tertatolol, Amosulalol, Nipradilol, Propranolol® and Timolol®;
$β_1$-Selective agents: Acebutolol® (has intrinsic sympathomimetic activity), Atenolol®, Betaxolol®, Bisoprolol®, Celiprolol®, Dobutamine hydrochloride, Irsogladine maleate, Carvedilol, Talinolol, Esmolol®, Metoprolol® and Nebivolol®;
$β_2$-Selective agents: Butaxamine® (weak α-adrenergic agonist activity);

(18) Antiarrhythmic agents such as the following types:
Type I (sodium channel blockers): Quinidine, Lidocaine, Phenytoin, Propafenone
Type III (potassium channel blockers): Amiodarone, Dofetilide, Sotalol
Type V: Adenosine, Digoxin

(19) Diuretics such as: Thiazide diuretics, e.g., Chlorothiazide, Chlorthalidone, and Hydrochlorothiazide, Bendroflumethiazide, Cyclopenthiazide, Methyclothiazide, Polythiazide, Quinethazone, Xipamide, Metolazone, Indapamide, Cicletanine; Loop diuretics, such as Furosemide and Toresamide; potassium-sparing diuretics such as Amiloride, Spironolactone, Canrenoate potassium, Eplerenone and Triamterene; combinations of these agents; other diuretics such as Acetazolamid and Carperitide (20a) Direct-acting vasodilators such as Hydralazine hydrochloride, Diazoxide, Sodium nitroprusside, Cadralazine; other vasodilators such as Isosorbide dinitrate and Isosorbide 5-mononitrate;

(20b) Exogenous vasodilators such as:
Adenocard®, an adenosine agonist, primarily used as an anti-arrhythmic;

Alpha blockers (which block the vasoconstricting effect of adrenaline): Alpha-1-adrenoceptor antagonists such as Prazosin, Indoramin, Urapidil, Bunazosin, Terazosin, Doxazosin Atrial natriuretic peptide (ANP);

Ethanol;

Histamine-inducers, which complement proteins C3a, C4a and C5a work by triggering histamine release from mast cells and basophil granulocytes;

Tetrahydrocannabinol (THC), major active chemical in marijuana which has minor vasodilatory effects;

Papaverine, an alkaloid found in the opium poppy *Papaver somniferum*; b

(21) Bronchodilators: there are two major types of bronchodilator, $\beta_2$ agonists and anticholinergics, exemplified below:

$\beta_2$ agonists: Salbutamol® or albuterol (common brand name: Ventolin) and Terbutaline® are short acting $\beta_2$ agonists for rapid relief of COPD symptoms. Long acting $\beta_2$ agonists (LABAs) such as Salmeterol® and Formoterol®;

anticholinergics: Ipratropium® is the most widely prescribed short acting anticholinergic drug. Tiotropium® is the most commonly prescribed long-acting anticholinergic drug in COPD;

Theophylline®, a bronchodilator and phosphodiesterase inhibitor;

(22) Corticosteroids: such as beclomethasone, methylprednisolone, betamethasone, prednisone, prenisolone, triamcinolone, dexamethasone, fluticasone, flunisolide and hydrocortisone, and corticosteroid analogs such as budesonide

(23) Dietary supplements such as, for example: omega-3 oils; folid acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Testosterone transdermal patch; Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;

(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WO0178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

(25) Immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

(26) Non-steroidal anti-asthmatics such as $\beta$2-agonists (e.g., terbutaline, metaproterenol, fenoterol, isoetharine, albuterol, salmeterol, bitolterol and pirbuterol) and $\beta$2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);

(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

(28) Cyclooxygenase-2 (COX-2) inhibitors such as celecoxib (Celebrex®), rofecoxib (Vioxx®), valdecoxib, etoricoxib, parecoxib and lumiracoxib; (opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and

(29) Anti-diabetic agents such as insulin and insulin mimetics, sulfonylureas (e.g., Glyburide, Glybenclamide, Glipizide, Gliclazide, Gliquidone, Glimepiride, Meglinatide, Tolbutamide, Chlorpropamide, Acetohexamide, Tolazamide), biguanides, e.g., metformin (Glucophage®), $\alpha$-glucosidase inhibitors (such as Acarbose, Epalrestat, Voglibose, Miglitol), thiazolidinone compounds, e.g., rosiglitazone (Avandia®), troglitazone (Rezulin®), ciglitazone, pioglitazone (Actos®) and englitazone; insulin sensitizers such as Pioglitazone and Rosiglitazone; Insulin secretagogues such as Repaglinide, Nateglinide and Mitiglinide; Incretin mimetics such as Exanatide and Liraglutide; Amylin analogues such as Pramlintide; glucose lowering agents such as Chromiumm picolinate (optinally combined with biotin); dipeptidyl peptidase IV inhibitors such as Sitagliptin, Vildagliptin, Saxagliptin, Alogliptin and Linagliptin; vaccines currently being developed for the treatment of diabetes; AVE-0277, Alum-GAD, BHT-3021, IBC-VS01; cytokine targeted therapies in development for the treatment of diabetes such as Anakinra, Canakinumab, Diacerein, Gevokizumab, LY-2189102, MABP-1, GIT-027; drugs in development for the treatment of diabetes:

| | Drugs in development for the treatment of diabetes | | |
|---|---|---|---|
| Dapagliflozin | AstraZeneca/ Bristol-Myers Squibb | SGLT-2 Inhibitors | Recommended Approval |
| Alogliptin benzoate/metformin hydrochloride | Takeda | Insulin Sensitizers/ Dipeptidyl Peptidase IV (CD26; DPP-IV; DP-IV) Inhibitors | Pre-Registered |
| Anagliptin | Kowa/Sanwa | Dipeptidyl Peptidase IV (CD26; DPP-IV; DP-IV) Inhibitors | Pre-Registered |

-continued

Drugs in development for the treatment of diabetes

| | | | |
|---|---|---|---|
| Dapagliflozin | AstraZeneca/ Bristol-Myers Squibb | SGLT-2 Inhibitors | Recommended Approval |
| Insulin degludec | Novo Nordisk | | Pre-Registered |
| Insulin degludec/insulin aspart | Novo Nordisk | | Pre-Registered |
| Insulin human (rDNA origin) inhalation powder | MannKind | | Pre-Registered |
| Lixisenatide | Sanofi | Insulin Secretagogues/GLP-1 Receptor Agonists | Pre-Registered |
| Recombinant human insulin | Biodel | | Pre-Registered |
| Teneligliptin | Mitsubishi Tanabe Pharma | Dipeptidyl Peptidase IV (CD26; DPP-IV; DP-IV) Inhibitors | Pre-Registered |
| AVE-0277 | Andromeda Biotech/ Teva | | Phase III |
| Albiglutide | GlaxoSmithKline | GLP-1 Receptor Agonists | Phase III |
| Aleglitazar | Roche | PPARalpha Agonists/ PPARgamma Agonists | Phase III |
| Atorvastatin calcium/glimebiride | GlaxoSmithKline | K(ATP) Channel Blockers/Dipeptidyl Peptidase IV (CD26; DPP-IV; DP-IV) Inhibitors/HMG-CoA Reductase/Inhibitors/ TNFSF6 Expression Inhibitors | Phase III |
| BYK-324677 | Nycomed | | Phase III |
| Balaglitazone | Dr. Reddy's Laboratories | Insulin Sensitizers/ PPARgamma Partial Agonists | Phase III |
| CSG-452 | Chugai Pharmaceutical | SGLT-2 Inhibitors | Phase III |
| Canagliflozin | Johnson & Johnson/ Mitsubishi Tanabe Pharma | SGLT-2 Inhibitors | Phase III |
| Canagliflozin/metformin hydrochloride | Johnson & Johnson | SGLT-2 Inhibitors/ Insulin Sensitizers | Phase III |
| Dabagliflozin/Metformin hydrochloride | AstraZeneca/ Bristol-Myers Squibb | SGLT-2 Inhibitors/ Insulin Sensitizers | Phase III |
| Dulaglutide | Lilly | Insulin Secretagogues/GLP-1 Receptor Agonists | Phase III |
| Empagliflozin | Boehringer Ingelheim/ Lilly | SGLT-2 Inhibitors | Phase III |
| Empagliflozin/linaglibtin | Boehringer Ingelheim/ Lilly | SGLT-2 Inhibitors/ Dipeptidyl Peptidase IV (CD26; DPP-IV; DP-IV) Inhibitors | Phase III |
| Gemigliptin | LG Life Sciences | Dipeptidyl Peptidase IV (CD26; DPP-IV; DP-IV) Inhibitors | Phase III |
| Hepatic-directed vesicle insulin | Diasome Pharmaceuticals | | Phase III |
| Human isophane insulin | Wockhardt | | Phase III |
| IN-105 | Biocon | | Phase III |
| Insulin degludec/liraglutide | Novo Nordisk | Insulin Secretagogues/GLP-1 Receptor Agonists | Phase III |
| Insulin glargine | Sanofi | | Phase III |
| Ipragliflozin L-proline | Astellas Pharma/ Kotobuki | SGLT-2 Inhibitors | Phase III |
| LY-2605541 | Lilly | | Phase III |
| LY-2963016 | Lilly | | Phase III |
| Lixisenatide/Insulin glargine | Sanofi | Insulin Secretagogues/GLP-1 Receptor Agonists | Phase III |
| Lobeglitazone sulfate | Chong Kun Dang Pharm (CKD Pharm) | PPARalpha Agonists/ PPARgamma Agonists/ Insulin Sensitizers | Phase III |
| Luseogliflozin | Taisho | SGLT-2 Inhibitors | Phase III |
| Otelixizumab | Tolerx | Anti-CD3 | Phase III |
| Ranolazine | Gilead | Sodium Channel Blockers | Phase III |

-continued

Drugs in development for the treatment of diabetes

| | AstraZeneca/ | | Recommended |
|---|---|---|---|
| Dapagliflozin | Bristol-Myers Squibb | SGLT-2 Inhibitors | Approval |
| Recombinant human insulin | National Institute of Health Sciences | | Phase III |
| Sitagliptin phosphate monohydrate/pioglitazone hydrochloride | Merck & Co. | PPARgamma Agonists/ Insulin Sensitizers/ Dipeptidyl Peptidase IV (CD26; DPP-IV; DP-IV) Inhibitors | Phase III |
| Sitagliptin/atorvastatin calcium | Merck & Co. | Dipeptidyl Peptidase IV (CD26; DPP-IV; DP-IV) Inhibitors/ HMG-CoA Reductase Inhibitors/TNFSF6 Expression Inhibitors | Phase III |
| TAK-875 | Takeda | Free Fatty Acid Receptor 1 (FFAR1; GPR40) Agonists/ Insulin Secretagogues | Phase III |
| TT-401 | 7TM Pharma | Cannabinoid CB1 Antagonists | Phase I |
| TT-401 | Transition Therapeutics | | Phase I |
| ZYH-2 | Cadila Healthcare (d/b/a Zydus Cadila) | PPARalpha Ligands/ PPARgamma Ligands | Phase I |
| ZYO-1 | Cadila Healthcare (d/b/a Zydus Cadila) | Cannabinoid CB1 Antagonists | Phase I |
| 701645 | Cellonis Biotechnologies | | Phase I |
| 701499 | Cellonis Biotechnologies | | Phase I |
| 743300 | University of California, San Francisco | | Phase I |
| 448661 | University of Pittsburgh | | Phase I |
| AD-1 | National Institute Pharma Res Dev | | Clinical |
| Colesevelam hydrochloride | Daiichi Sankyo | Bile Acid Sequestrants | Clinical |
| DBPR-108 | National Health Research Institutes/ ScinoPharm | | IND Filed |
| Nodlin | Biolaxy | | IND Filed |
| PSN-491 | Prosidion | Glucose-Dependent Insulinotropic Receptor (GDIR, GPR119) Agonists/ Dipeptidyl Peptidase IV (CD26; DPP-IV; DP-IV) Inhibitors | IND Filed |
| Tolimidone | Melior Discovery | Lyn Kinase Activators | IND Filed |
| ZYD-1 | Cadila Healthcare (d/b/a Zydus Cadila) | GLP-1 Receptor Agonists | IND Filed |
| ZYOG-1 | Cadila Healthcare (d/b/a Zydus Cadila) | GLP-1 Receptor Agonists | IND Filed |

(30) HDL cholesterol-increasing agents such as Anacetrapib, MK-524A, CER-001, DRL-17822, Dalcetrapib, JTT-302, RVX-000222, TA-8995;

(31) Antiobesity drugs such as Methamphetamine hydrochloride, Amfepramone hydrochloride (Tenuate®), Phentermine (Ionamin®), Benzfetamine hydrochloride (Didrex®), Phendimetrazine tartrate (Bontril®, Prelu-2®, Plegine®), Mazindol (Sanorex®), Orlistat (Xenical®), Sibutramine hydrochloride monohydrate (Meridia®, Reductil®), Rimonabant (Acomplia®), Amfepramone, Chromium picolinate, RM-493, TZP-301; combination such as Phentermine/Topiramate, Bupropion/Naltrexone, Sibutramine/Metformin, Bupropion SR/Zonisamide SR, Salmeterol, xinafoate/fluticasone propionate; Lorcaserin hydrochloride, Phentermine/topiramate, Bupropion/naltrexone, Cetilistat, Exenatide, KI-0803, Liraglutide, Metformin hydrochloride, Sibutramine/Metformin, 876167, ALS-L-1023, Bupropion SR/Zonisamide SR, CORT-108297, Canagliflozin, Chromium picolinate, GSK-1521498, LY-377604, Metreleptin, Obinepitide, P-57AS3, PSN-821, Salmeterol xinafoate/fluticasone propionate, Sodium tungstate, Somatropin (recombinant), TM-30339, TTP-435, Tesamorelin, Tesofensine, Velneperit, Zonisamide, BMS-830216, ALB-127158, AP-1030, ATHX-105, AZD-2820, AZD-8329, Beloranib hemioxalate, CP-404, HPP-404, ISIS-FGFR4Rx, Insulinotropin, KD-3010PF, 05212389, PP-1420, PSN-842, Peptide YY3-36, Resveratrol, S-234462; S-234462, Sobetirome, TM-38837, Tetrahydrocannabivarin, ZYO-1, beta-Lapachone;

(32) Angiotensin receptor blockers such as Losartan, Valsartan, Candesartan cilexetil, Eprosaran, Irbesartan, Telmisartan, Olmesartran medoxomil, Azilsartan medoxomil;
(33) Renin inhibitors such as Aliskiren hemifumirate;
(34) Centrally acting alpha-2-adrenoceptor agonists such as Methyldopa, Clonidine, Guanfacine;
(35) Adrenergic neuron blockers such as Guanethidine, Guanadrel;
(36) Imidazoline I-1 receptor agonists such as Rimenidine dihydrogen phosphate and Moxonidine hydrochloride hydrate;
(37) Aldosterone antagonists such as Spironolactone and Eplerenone
(38) Potassium channel activators such as Pinacidil
(39) Dopamine D1 agonists such as Fenoldopam mesilate; Other dopamine agonists such as Ibopamine, Dopexamine and Docarpamine;
(40) 5-HT2 antagonists such as Ketanserin;
(41) Drugs that are currently being developed for the treatment of arterial hypertension:

| Drugs in development for the treatment of hypertension | | | |
|---|---|---|---|
| Azilsartan | Takeda | Angiotensin AT1 Antagonists/ Angiotensin AT2 Antagonists/Insulin Sensitizers | Registered |
| Amlodipine besylate/irbesartan | Dainippon Sumitomo Pharma | Angiotensin AT1 Antagonists/Calcium Channel Blockers | Pre-Registered |
| Azilsartan/amlodipine besilate | Takeda | Angiotensin AT1 Antagonists/Insulin Sensitizers/Calcium Channel Blockers | Phase III |
| Cilnidipine/valsartan | Ajinomoto/ Mochida | Angiotensin AT1 Antagonists/Calcium Channel Blockers | Phase III |
| Fimasartan | Boryung | Angiotensin AT1 Antagonists | Phase III |
| Irbesartan/atorvastatin | Hanmi | Angiotensin AT1 Antagonists/Dipeptidyl Peptidase IV (CD26; DPP-IV; DP-IV) Inhibitors/HMG-CoA Reductase Inhibitors/ TNFSF6 Expression Inhibitors | Phase III |
| Irbesartan/trichlormethiazide | Shionogi | Angiotensin AT1 Antagonists | Phase III |
| Losartan potassium/hydrochlorothiazide/amlodipine besylate | Merck & Co. | Angiotensin AT1 Antagonists/Calcium Channel Blockers | Phase III |
| Pratosartan | Boryung | Angiotensin AT1 Antagonists | Phase III |
| ACT-280778 | Actelion | | Phase II |
| Amiloride hydrochloride/spironolactone | Hemodynamic Therapeutics | Mineralocorticoid Receptor (MR) Antagonists/Na+/H+ Exchanger (NHE) Inhibitors/Epithelial Sodium Channels (ENaC) Blockers/ K(V)1.5 Channel Blockers/K(V)4.3 Channel Blockers | Phase II |
| Angiotensin vaccine/CoVaccine HT | BTG | | Phase II |
| CYT006-AngQb | Cytos Biotechnology | Anti-Angiotensin II | Phase II |
| Cholecalciferol | Emory University | | Phase II |
| Cobiprostone | Sucampo Pharmaceuticals | ClC-2 Channel Activators | Phase II |
| INT-001 | IntelGenx | | Phase II |
| LCZ-696 | Novartis | Angiotensin AT1 Antagonists/Neprilysin (Enkephalinase, Neutral Endopeptidase, NEP) Inhibitors | Phase II |
| LFF-269 | Novartis | | Phase II |
| Octreotide acetate | Chiasma | Growth Hormone Release Inhibitors/ Somatostatin Agonists | Phase II |
| PL-3994 | Palatin Technologies | Atrial Natriuretic Peptide A (NPR1; Guanylate Cyclase A) Receptor Agonists | Phase II |

| Drugs in development for the treatment of hypertension | | | |
|---|---|---|---|
| Rostafuroxine | Sigma-Tau | | Phase II |
| SLx-2101 | NT Life Sciences | Phosphodiesterase V (PDE5A) Inhibitors | Phase II |
| TBC-3711 | Encysive Pharmaceuticals | Endothelin ETA Receptor Antagonists | Phase II |
| Udenafil | Dong-A/Falk Pharma | Phosphodiesterase V (PDE5A) Inhibitors | Phase II |
| Atorvastatin calcium/losartan potassium | HanAll BioPharma | Angiotensin AT1 Antagonists/Dipeptidyl Peptidase IV (CD26; DPP-IV; DP-IV) Inhibitors/HMG-CoA Reductase Inhibitors/ TNFSF6 Expression Inhibitors | Phase I |
| BIA-5-1058 | BIAL | Dopamine beta-monooxygenase Inhibitors | Phase I |
| CS-3150 | Daiichi Sankyo | | Phase I |
| DSP-9599 | Dainippon Sumitomo Pharma | Renin Inhibitors | Phase I |
| MK-1597 | Actelion/Merck & Co. | Renin Inhibitors | Phase I |
| MK-4618 | Merck & Co. | | Phase I |
| MK-5478 | Merck & Co. | | Phase I |
| MK-7145 | Merck & Co. | | Phase I |
| MK-8266 | Merck & Co. | | Phase I |
| MK-8457 | Merck & Co. | | Phase I |
| MP-157 | Mitsubishi Tanabe Pharma | Angiotensin AT2 Agonists | Phase I |
| MT-3995 | Mitsubishi Tanabe Pharma | Mineralocorticoid Receptor (MR) Antagonists | Phase I |
| Mirodenafil hydrochloride | SK Chemicals | Phosphodiesterase V (PDE5A) Inhibitors | Phase I |
| NV-04 | Novogen | Antioxidants | Phase I |
| Nifedipine/Candesartan cilexetil | Bayer | Angiotensin AT1 Antagonists/Calcium Channel Blockers/ Antioxidants | Phase I |
| QGC-001 | Quantum Genomics | Glutamyl Aminopeptidase (Aminopeptidase A) Inhibitors | Phase I |
| RDX-5791 | Ardelyx | Na+/H+ Exchanger type 3 (NHE-3) Inhibitors | Phase I |
| TAK-272 | Takeda | Renin Inhibitors | Phase I |
| TAK-591 | Takeda | Angiotensin AT2 Antagonists | Phase I |
| VTP-27999 | Vitae Pharmaceuticals | Renin Inhibitors | Phase I |
| Vasomera | PhaseBio | VPAC2 (VIP2) Agonists | Phase I |

(42) Vasopressin antagonists such as Tolvaptan;
(43) Calcium channel sensitizers such as Levosimendan or activators such as Nicorandil;
(44) PDE-3 inhibitors such as Amrinone, Milrinone, Enoximone, Vesnarinone, Pimobendan, Olprinone;
(45) Adenylate cyclase activators such as Colforsin dapropate hydrochloride;
(46) Positive inotropic agents such as Digoxin and Metildigoxin; metabolic cardiotonic agents such as Ubidecarenone; brain naturetic peptides such as Nesiritide;

(47) Drugs that are currently in development for the treatment of heart failure:

| Drugs in development for the treatment of heart failure | | | |
|---|---|---|---|
| Bucindolol hydrochloride | ARCA | beta-Adrenoceptor Antagonists | Pre-Registered |
| Aliskiren hemifumarate | Novartis | Renin Inhibitors | Phase III |
| Ferric carboxymaltose | Vifor | | Phase III |
| LCZ-696 | Novartis | Angiotensin AT1 Antagonists/ Neprilysin (Enkephalinase, Neutral | Phase III |

| Drugs in development for the treatment of heart failure | | | |
|---|---|---|---|
| | | Endopeptidase, NEP) Inhibitors | |
| Neuregulin-1 | Zensun | | Phase III |
| Olmesartan medoxomil | Tohoku University | Angiotensin AT1 Antagonists | Phase III |
| C3BS-CQR-1 | Cardio3 BioSciences | | Phase II/III |
| MyoCell | Bioheart | | Phase II/III |
| Serelaxin | Novartis | | Phase II/III |
| AAV1/SERCA2a | AmpliPhi Biosciences/ Celladon/Mount Sinai School of Medicine | | Phase II |
| Albiglutide | GlaxoSmithKline | GLP-1 Receptor Agonists | Phase II |
| Allogeneic mesenchymal precursor cells | Mesoblast | | Phase II |
| AlsterMACS | Miltenyi Biotec | | Phase II |
| BAY-94-8862 | Bayer | Mineralocorticoid Receptor (MR) Antagonists | Phase II |
| COR-1 | Corimmun | | Phase II |
| CXL-1020 | Cardioxyl Pharmaceuticals | Nitric Oxide Donors | Phase II |
| Cenderitide | Nile Therapeutics | Guanylate Cyclase Activators | Phase II |
| Endometrial regenerative cells | ERCell/Medistem | | Phase II |
| JNJ-39588146 | Johnson & Johnson | | Phase II |
| Omecamtiv mecarbil | Amgen/ Cytokinetics | Cardiac Myosin Activators | Phase II |
| PL-3994 | Palatin Technologies | Atrial Natriuretic Peptide A (NPR1; Guanylate Cyclase A) Receptor Agonists | Phase II |
| Remestemcel-L | Osiris | | Phase II |
| TRV-120027 | Trevena | Angiotensin AT1 Receptor Ligands | Phase II |
| Urocortin 2 | Neurocrine Biosciences | CRF2 Agonists | Phase II |
| AAV6-CMV-SERCA2a | Imperial College | | Phase I/II |
| Anakinra | National Institutes of Health (NIH) | IL-1 Receptor Antagonists | Phase I/II |
| LipiCell | Bioheart/Instituto de Medicina Regenerativa | | Phase I/II |
| ALD-201 | Cytomedix/Texas Heart Institute | | Phase I |
| BAY-1021189/Vericiguat | Bayer | | Phase II |
| BAY-1067197 | Bayer | Adenine Receptor Agonists | Phase I |
| BAY-86-8050 | Bayer | Drugs Acting on Vasopressin (AVP) Receptors | Phase I |
| BIA-5-1058 | BIAL | Dopamine beta-monooxygenase Inhibitors | Phase I |
| CSCs | University of Louisville | | Phase I |
| Calcitonin gene related peptide | VasoGenix | | Phase I |
| JVS-100 | Juventas Therapeutics | | Phase I |
| MyoCell SDF-1 | Bioheart | | Phase I |
| Myoblast | Advanced Cell Technology (ACT) | | Phase I |
| RO-1160367 | Serodus | 5-HT4 Antagonists | Phase I |
| Recombinant human glial growth factor 2 | Acorda/Vanderbilt University | | Phase I |
| [18F]LMI-1195 | Lantheus Medical Imaging | | Phase I |
| 677950 | Kyoto Prefectural University of Medicine | | Phase I |

(48) Drugs currently in development for the treatment of pulmonary hypertension:

| Drugs in development for the treatment of pulmonary hypertension | | | |
|---|---|---|---|
| Imatinib mesylate | Novartis | Breast Cancer-Resistant Protein (BCRP; ABCG2) Inhibitors/Abl Kinase Inhibitors/Angiogenesis Inhibitors/Bcr-Abl Kinase Inhibitors/CSF1R (c-FMS) Inhibitors/KIT (C-KIT) Inhibitors/Apoptosis Inducers/PDGFRalpha Inhibitors/PDGFRbeta Inhibitors/Inhibitors of Signal Transduction Pathways | Pre-Registered |
| Treprostinil diethanolamine | United Therapeutics | Prostacyclin Analogs | Pre-Registered |
| GSK-1325760A | GlaxoSmithKline | | Phase III |
| Macitentan | Actelion | Endothelin ETA Receptor Antagonists/Endothelin ETB Receptor Antagonists | Phase III |
| Riociguat/Adempas | Bayer | Guanylate Cyclase Activators | Approved 2013 |
| Selexipag | Actelion/Nippon Shinyaku | Prostanoid IP Agonists | Phase III |
| Udenafil | Dong-A | Phosphodiesterase V (PDE5A) Inhibitors | Phase III |
| L-Citrulline | Nat Heart, Lung, and Blood Institute/Vanderbilt University | | Phase II/III |
| BQ-123 | Brigham & Women's Hospital | Endothelin ETA Receptor Antagonists | Phase II |
| Cicletanine | Gilead | | Phase II |
| Fasudil hydrochloride | Asahi Kasei | Rho Kinase Inhibitors/Calcium Sensitizers | Phase II |
| Nilotinib hydrochloride monohydrate | Novartis | Bcr-Abl Kinase Inhibitors/Apoptosis Inducers/Inhibitors of Signal Transduction Pathways | Phase II |
| PRX-08066 | Clinical Data | 5-HT2B Antagonists | Phase II |
| Terguride | ErgoNex Pharma | 5-HT2A Antagonists/5-HT2B Antagonists/Dopamine Autoreceptor Agonists/Dopamine D2 Receptor Partial Agonists/Prolactin Secretion Inhibitors | Phase II |
| Tezosentan disodium | Actelion | Endothelin ETA Receptor Antagonists/Endothelin ETB Receptor Antagonists | Phase II |
| Anakinra | Virginia Commonwealth University (VCU) | IL-1 Receptor Antagonists | Phase I/II |
| Simvastatin | Imperial College | HDL-Cholesterol Increasing Agents/HMG-CoA Reductase Inhibitors | Phase I/II |
| 99mTC-PulmoBind | Montreal Heart Institute (MHI) | | Phase I |
| APD-811 | Arena | Prostanoid IP Agonists | Phase I |
| Sorafenib | Bayer | Raf kinase B Inhibitors/Raf kinase C Inhibitors/Angiogenesis Inhibitors/Flt3 (FLK2/STK1) Inhibitors/VEGFR-1 (Flt-1) Inhibitors/KIT (C-KIT) Inhibitors/VEGFR-2 (FLK-1/KDR) Inhibitors/VEGFR-3 (FLT4) Inhibitors/PDGFRbeta Inhibitors/RET Inhibitors/Inhibitors of Signal Transduction Pathways | Phase I |
| Triplelastat | Proteo Biotech | Elastase Inhibitors | Phase I |

(49) Drugs in current development for the treatment of female sexual dysfunction:

| Drugs in active development for the treatment of female sexual dysfunction | | | |
|---|---|---|---|
| Alprostadil | Apricus Biosciences/VIVUS | | Phase III |
| Prasterone | EndoCeutics/Monash University | HSD11B1 Expression Inhibitors | Phase III |
| Testosterone transdermal gel | BioSante | Androgen Receptor Agonists | Phase III |
| Bremelanotide | Palatin Technologies | Melanocortin MC3 Receptor Agonists/Melanocortin | Phase II |

Drugs in active development for the treatment of female sexual dysfunction

| | | | |
|---|---|---|---|
| Pill-Plus | Pantarhei Bioscience | MC4 Receptor Agonists | Phase II |
| Testosterone MDTS | Acrux | Androgen Receptor Agonists | Phase II |
| Estradiol/testosterone | BioSante | Estrogen Receptor (ER) Agonists/ Androgen Receptor Agonists | Phase I |
| LGD-2941 | Ligand | Selective Androgen Receptor Modulators (SARM) | Phase I |
| Lidocaine/heparin | Urigen | | Phase I |
| OnabotulinumtoxinA | Allergan | | Phase I |

(50) Drugs used for the treatment of erectile dysfunction such as Alprostadil, Aviptadil, Phentolamine mesilate, Weige, Alprostadil;

(51) Drugs currently in development for the treatment of male sexual dysfunction:

Drugs in active development for the treatment of erectile dysfunction

| | | | |
|---|---|---|---|
| Fluvastatin sodium | Novartis | Apoptosis Inducers/ HMG-CoA Reductase Inhibitors | Phase III |
| Lodenafil carbonate | Cristalia | Phosphodiesterase V (PDE5A) Inhibitors | Phase III |
| EFLA-400 | Chonbuk National University Hospital | | Phase II/III |
| Apomorphine hydrochloride | Vectura | Dopamine D2 Agonists | Phase II |
| LY-900010 | Lilly | Phosphodiesterase V (PDE5A) Inhibitors/ Selective Androgen Receptor Modulators (SARM) | Phase II |
| Nitroglycerin | Futura Medical | | Phase II |
| RX-10100 | Rexahn | Drugs Acting on Dopaminergic Transmission/ Drugs Acting on Serotonergic Transmission | Phase II |
| YHD-1023 | Yuhan | | Phase II |
| INT-007 | IntelGenx | | Phase I |
| LY-2452473 | Lilly | Selective Androgen Receptor Modulators (SARM) | Phase I |
| hMaxi-K | Albert Einstein College of Medicine/Ion Channel Innovations/ Mount Sinai | | Phase I |

Drugs in active development for the treatment of erectile dysfunction

| | | | |
|---|---|---|---|
| KH-204 | School of Medicine KMSI | | Clinical |

(51) Drugs in development for the treatment of sleep apnea:

Drugs in development for the treatment of sleep apnea

| | | | |
|---|---|---|---|
| CX-1739 | Cortex | AMPA Receptor Modulators | Phase II |
| Phentermine/topiramate | VIVUS | AMPA Antagonists/ Kainate Antagonists/ Sodium Channel Blockers/ Carbonic Anhydrase Type II Inhibitors | Phase II |
| AVE-0118 | Sanofi | Potassium Channel Blockers | Phase I |
| Suvorexant | Merck & Co. | Orexin Receptor Antagonists | Phase I |

(52) Drugs currently in development for the treatment of metabolic syndrome:

Antihyperlipidemic drugs under active development for the treatment of patients with metabolic syndrome

| | | | |
|---|---|---|---|
| GFT-505 | Genfit | PPARalpha Agonists/ PPARdelta Agonists | Phase II |
| MBX-8025 | Metabolex | PPARdelta Agonists | Phase II |
| Pitavastatin calcium | Kowa | APOA1 Expression Enhancers/ HMG-CoA Reductase Inhibitors/ SPP1 (Osteopontin) Expression Inhibitors | Phase I |

(53) Antiobesity drugs:

Drugs marketed for the treatment of obesity

| | | | |
|---|---|---|---|
| Methamphetamine hydrochloride (Desoxyn) | Abbott | Noradrenergic, alpha- and beta-adrenoceptor agonist | 1943 (U.S.) |
| Amfepramone hydrochloride (Tenuate) | Sanofi | Noradrenergic release stimulant | 1959 (U.S.) |
| Phentermine (Ionamin) | UCB Celltech | Noradrenergic release stimulant | 1959 (U.S.) |
| Benzfetamine hydrochloride (Didrex) | Pfizer | Noradrenergic release stimulant | 1960 (U.S.) |
| Phendimetrazine tartrate (Bontril, Prelu-2, Plegine) | Pfizer | Noradrenergic release stimulant | 1961 (U.S.) |
| Mazindol (Sanorex) | Novartis | Noradrenergic reuptake inhibitor | 1973 (U.S.) |

| Drugs marketed for the treatment of obesity | | | |
|---|---|---|---|
| Orlistat (Xenical) | Roche | Pancreatic lipase inhibitor | 1998 (New Zealand) |

(54) Drugs used for the treatment of Alzheimer's disease: e.g., cholinesterase inhibitors prescribed for mild to moderate Alzheimer's disease, including Razadyne® (galantamine), Exelon® (rivastigmine), and Aricept® (donepezil), Cognex® (tacrine); Namenda® (memantine), an N-methyl D-aspartate (NMDA) antagonist, and Aricept®, prescribed to treat moderate to severe Alzheimer's disease; vitamin E (an anti-oxidant).

(55) Antidepressants: tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®); SNRIs (e.g., venlafaxine and reboxetine); dopaminergic antidepressants (e.g., bupropion and amineptine).

(56) Neuroprotective agents: e.g., memantine, L-dopa, bromocriptine, pergolide, talipexol, pramipexol, cabergoline, neuroprotective agents currently under investigation including anti-apoptotic drugs (CEP 1347 and CTCT346), lazaroids, bioenergetics, antiglutamatergic agents and dopamine receptors. Other clinically evaluated neuroprotective agents are, e.g., the monoamine oxidase B inhibitors selegiline and rasagiline, dopamine agonists, and the complex I mitochondrial fortifier coenzyme Q10.

(57) Antipsychotic medications: e.g., ziprasidone (Geodon™), risperidone (Risperdal™), and olanzapine (Zyprexa™).

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

Example 1: Syntheses of the Compounds of Table 1A, Table 1B, Table 1C and Table 1D General Procedure a

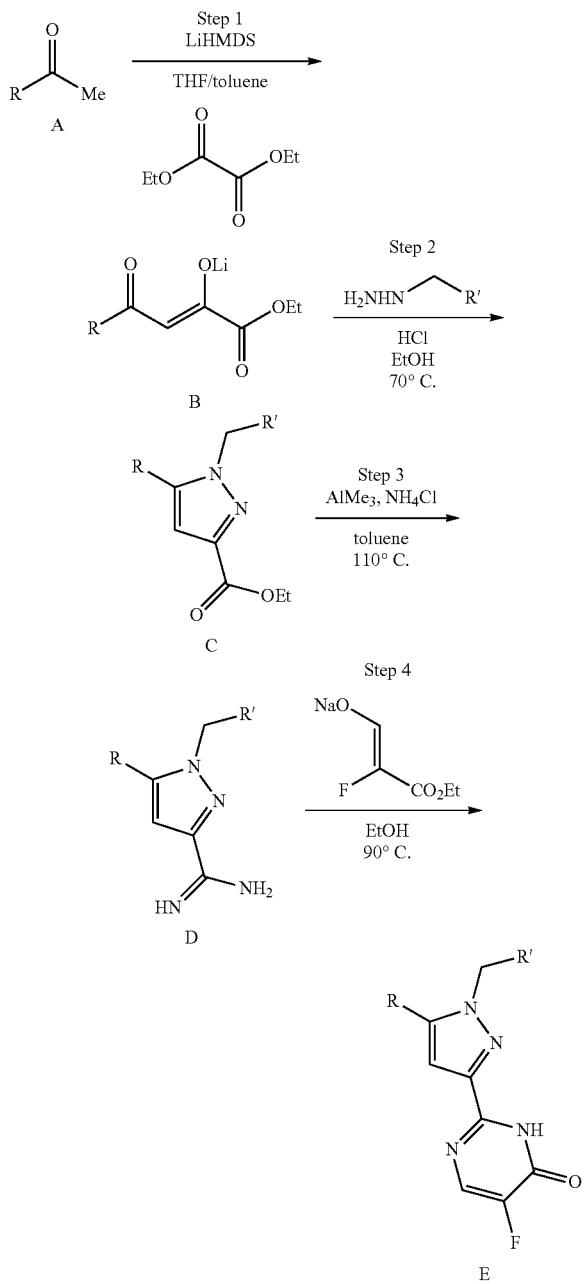

Step 1:
Dione Enolate Formation:
To a solution of ketone A in THF cooled to −78° C., LiHMDS (e.g., 0.9 equiv, 1.0 M in toluene) was added dropwise via syringe. The reaction was allowed to warm to 0° C., then charged with diethyl oxalate (1.2 equiv). At this time, the reaction was warmed to room temperature and stirred at that temperature until judged complete (e.g., using either TLC or LC/MS analysis). Once the reaction was complete (reaction time was typically 45 minutes), the product dione enolate B was used "as-is" in Step 2, i.e., the cyclization step, without any further purification.

Step 2:
Pyrazole Formation:
Dione enolate B was diluted with ethanol and consecutively charged with HCl (e.g., 3 equiv, 1.25 M solution in ethanol) and arylhydrazine hydrate (e.g., 1.15 equiv). The reaction mixture was heated to 70° C. and stirred at this temperature until cyclization was deemed complete (e.g., by LC/MS analysis, typically 30 minutes). Once complete, the reaction mixture was treated carefully with solid sodium bicarbonate (e.g., 4 equiv) and diluted with dichloromethane and water. Layers were separated, and aqueous layer was further diluted with water before extraction with dichloromethane (3×). The combined organics were washed with brine, dried over MgSO$_4$, filtered, and concentrated in vacuo. The resulting pyrazole C was then purified by SiO$_2$ chromatography using an appropriate gradient of EtOAc in hexanes.

Step 3:
Amidine Formation:
To a suspension of NH$_4$Cl (e.g., 5 equiv) in toluene cooled to 0° C. was added AlMe$_3$ (e.g., 5 equiv, 2.0M solution in toluene) dropwise via syringe. The reaction was allowed to warm to room temperature, and stirred at this temperature until no more bubbling was observed. Pyrazole C was added in 1 portion to the reaction mixture, heated to 110° C., and stirred at this temperature until judged complete (e.g., using either TLC or LC/MS analysis). Once complete, the reaction was cooled, treated with excess methanol, and stirred vigorously for 1 hour at room temperature. The thick slurry was filtered, and the resulting solid cake was washed with methanol. The filtrate was concentrated in vacuo, and the resulting solids were re-suspended in an ethyl acetate:isopropyl alcohol=5:1 solvent mixture. The reaction was further treated with saturated sodium carbonate solution, and stirred for 10 minutes before the layers are separated. The aqueous layer was extracted with the ethyl acetate:isopropyl alcohol=5:1 solvent mixture (3×), and the combined organics were washed with brine. The organics were further dried over MgSO$_4$, filtered, and the solvent removed in vacuo. The product amidine D was used as-is in subsequent steps without further purification.

Step 4:
Pyrimidone Formation:
Amidine D was suspended in ethanol, and stirred vigorously at 23° C. to encourage full solvation. The reaction was further treated with sodium 3-ethoxy-2-fluoro-3-oxoprop-1-en-1-olate (e.g., 3 equiv.), and the flask was equipped with a reflux condenser. The reaction was placed into a pre-heated oil bath maintained at 90° C. and stirred until full consumption of starting material was observed on the LC/MS (reaction times were typically 1 h). The contents were cooled to 23° C., and the reaction mixture acidified with HCl (e.g., 3 equiv., 1.25M solution in EtOH). The mixture was stirred for 30 minutes, and the majority of the solvent was removed in vacuo. Contents were re-suspended in ether and water (1:1 mixture), and the resulting slurry was stirred for 20 min. The suspension was vacuum filtered, and the solid cake was rinsed with additional water and ether and dried on high vacuum overnight. The resulting pyrimidone E was used as-is in subsequent steps without further purification.

General Procedure B

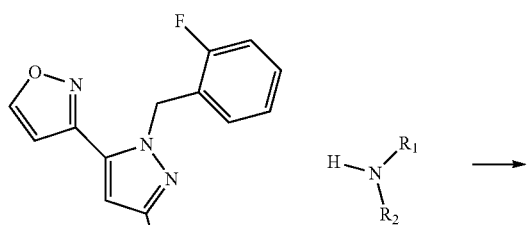

Intermediate 1

A solution of amino nucleophile (3 equiv.), triethylamine (10 equiv.), and Intermediate 1 (1 equiv.) was stirred in dioxane and water (2:1 ratio) at 90° C. until complete consumption of starting material was observed by LC/MS. The solution was diluted with aqueous 1N hydrochloric acid and dichloromethane. The layers were then separated and the aqueous layer was extracted with dichloromethane. The organics were combined, dried over magnesium sulfate, filtered, and the solvent was removed in vacuo. Purification yielded the desired product.

General Procedure C

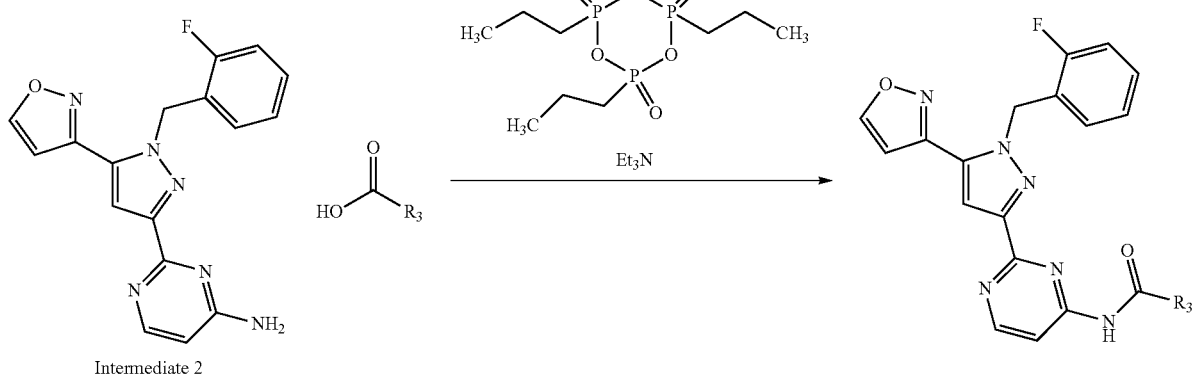

Intermediate 2

A mixture of Intermediate 2 (this intermediate was described in previously published patent application WO2012/3405 A1; 1 equivalent) and carboxylic acid (1.1 equivalent) in N,N-dimethylformamide was treated with triethylamine (4 equivalent) followed by a 50% in ethyl acetate solution of propylphosphonic anhydride (T3P, 1.4 equivalent). The reaction was heated to 80° C. for 24 h, after which the reaction was diluted with water and 1N hydrochloric acid solution. Contents were extracted with dichloromethane, then ethyl acetate. The combined organic layers were dried over sodium sulfate, filtered, and concentrated in vacuo. Purification yielded the desired product.

Synthesis of Intermediate 1

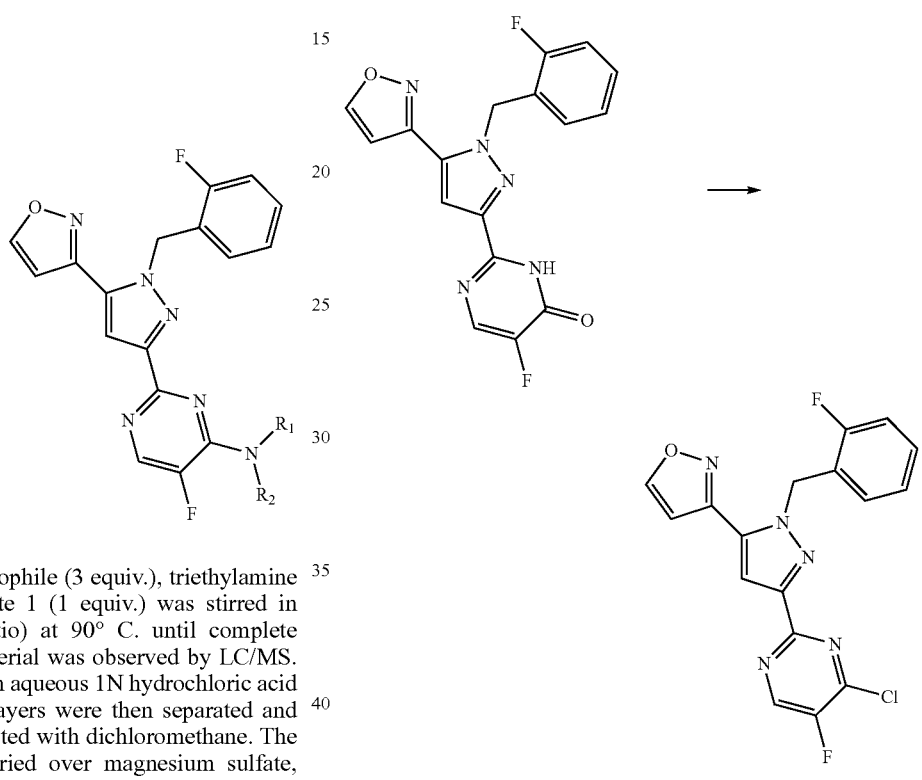

Intermediate 1

A suspension of 5-fluoro-2-(1-(2-fluorobenzyl)-5-(isoxazol-3-yl)-1H-pyrazol-3-yl)-pyrimidin-4-ol (generated via general procedure A, using 1-(isoxazol-3-yl)ethanone in step 1 and 2-fluorobenzylhydrazine in step 2, 11.5 g, 32.4 mmol, 1 equiv.) in phosphoryl trichloride (60.3 mL, 647 mmol, 20 equiv.) was heated at 60° C. for 3 h. The solution was cooled to 23° C., and poured portionwise over the course of 15 min into ice water (800 mL) with stirring. After completion of addition, contents were stirred for an additional 15 min, and diluted with dichloromethane (500 mL). The layers were separated and the aqueous layer was extracted with dichloromethane (2×200 mL). The organics were dried over magnesium sulfate, filtered, and the solvent was removed in vacuo to yield Intermediate 1 (12.5 g, 103% yield) as a tan solid.

$^1$H NMR (500 MHz, DMSO-d$_6$) δ 9.11 (d, 1H), 9.04 (s, 1H), 7.71-7.68 (m, 1H), 7.37-7.30 (m, 2H), 7.25-7.20 (m, 1H), 7.12 (t, 1H), 6.92 (td, 1H), 5.95 (s, 2H).

Compound I-248

A mixture of Intermediate 1 (48 mg, 1 equiv.), (R)-3-methyl-2-((methylamino)methyl) butanoic acid, (99 mg, TFA salt, 3 equiv.), and triethylamine (0.177 mL, 10 equiv.) was heated to 100° C. as a solution in dioxane/water (2:1) for 20 h, following General Procedure B The contents were treated with 3N HCl, and partitioned between a 1:1 mixture of dichloromethane and water. The layers were separated, and the aqueous layer was treated with a small amount of sodium chloride. The aqueous layer was then extracted with dichloromethane (×3), and the organic portions were combined and washed with brine. The mixture was dried over MgSO$_4$, filtered, and concentrated in vacuo. The crude material was purified via silica gel chromatography utilizing a 0-10% methanol/dichloromethane gradient to deliver the desired compound, Compound I-248 (20 mg, 93%) as an off-white solid.

$^1$H-NMR (500 MHz, MeOD) δ 8.74 (d, 1H), 8.09 (d, 1H), 7.38 (s, 1H), 7.29-7.23 (m, 1H), 7.10-7.05 (m, 1H), 7.02 (td, 1H), 6.87-6.83 (m, 1H), 6.83 (d, 1H), 5.98-5.89 (m, 2H), 4.15 (dd, 1H), 3.81 (dd, 1H), 3.33 (d, 3H), 2.72-2.65 (m, 1H), 1.94 (dq, 1H), 1.09 (d, 3H), 1.01 (d, 3H).

Compound I-250

The title compound was prepared following general procedure B, except 1-((methylamino)methyl) cyclopropanecarboxylic acid (as the TFA salt) was the amine reactant, contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-250 (40 mg, 54%) as an off-white solid.

$^1$H-NMR (500 MHz, MeOD) δ 8.74 (d, 1H), 8.07 (d, 1H), 7.36 (s, 1H), 7.29-7.23 (m, 1H), 7.11-7.05 (m, 1H), 7.03 (td, 1H), 6.88 (d, 1H), 6.85 (td, 1H), 5.93 (s, 2H), 4.14 (s, 2H), 3.35 (d, 3H), 1.30-1.25 (m, 2H), 1.07-1.03 (m, 2H).

Compound I-252

The title compound was prepared following general procedure B, except 2-ethyl-2-((methylamino)methyl)butanoic acid (as the TFA salt) was the amine reactant, contents were heated at 100° C. for 20 h, and the aqueous layer during workup was treated with sodium chloride. The crude material was purified via silica gel chromatography utilizing a 0-10% methanol/dichloromethane gradient to deliver the desired compound, Compound I-252 (33 mg, 39%) as a white solid.

$^1$H-NMR (500 MHz, CD$_3$OD) δ 8.80 (d, 1H), 8.25 (d, 1H), 7.50 (s, 1H), 7.32-7.26 (m, 1H), 7.12-7.06 (m, 1H), 7.04 (t, 1H), 6.94 (t, 1H), 6.91 (d, 1H), 5.97 (s, 2H), 4.20 (s, 2H), 3.46 (d, 3H), 1.86-1.77 (m, 2H), 1.68 (dq, 2H), 0.91 (t, 6H).

Compound I-253

The title compound was prepared following general procedure B, except (S)-3-methyl-2-((methylamino)methyl)butanoic acid (as the TFA salt) was the amine reactant, contents were heated at 100° C. for 20 h, and the aqueous layer during workup was treated with sodium chloride. The crude material was purified via silica gel chromatography utilizing a 0-10% methanol/dichloromethane gradient to deliver the desired compound, Compound I-253 (26 mg, 64%) as a white solid.

$^1$H-NMR (500 MHz, CD$_3$OD) δ 8.74 (d, 1H), 8.08 (d, 1H), 7.37 (s, 1H), 7.28-7.22 (m, 1H), 7.10-7.05 (m, 1H), 7.02 (t, 1H), 6.84 (t, 1H), 6.82 (d, 1H), 5.97-5.88 (m, 2H), 4.15 (dd, 1H), 3.79 (dd, 1H), 3.32 (d, 3H), 2.70-2.64 (m, 1H), 1.93 (dq, 1H), 1.08 (d, 3H), 1.01 (d, 3H).

Compound I-260

The title compound was prepared following general procedure B, except 4-benzylpiperidine-4-carboxylic acid was the amine reactant, contents were heated to 100° C. for 20 h, and the aqueous layer during workup was treated with sodium chloride. The crude material was purified via silica gel chromatography utilizing a 0-10% methanol/dichloromethane gradient to deliver the desired, Compound I-260 (26 mg, 64%) as a white solid.

$^1$H-NMR (500 MHz, CD$_3$OD) δ 8.74 (d, 1H), 8.11 (d, 1H), 7.41 (s, 1H), 7.29-7.22 (m, 3H), 7.22-7.15 (m, 3H), 7.11-7.06 (m, 1H), 7.05-7.00 (m, 1H), 6.91 (d, 1H), 6.84-6.79 (m, 1H), 5.96 (s, 2H), 4.57 (d, 2H), 3.29-3.23 (m, 2H), 2.90 (s, 2H), 2.19 (d, 2H), 1.68-1.61 (m, 2H).

Compound I-262

The title compound was prepared following general procedure B, except ethyl 2-methylpiperidine-2-carboxylate was the amine reactant, contents were heated to 100° C. for 19 h, and the aqueous layer during workup was treated with sodium chloride. The crude material was purified via reverse phase HPLC utilizing a 5-75% acetonitrile/water gradient to deliver the desired compound, Compound I-262 (1.1 mg, 8%) as a white solid.

$^1$H-NMR (500 MHz, CD$_3$OD) δ 8.82 (d, 1H), 8.33 (d, 1H), 7.47 (s, 1H), 7.32-7.26 (m, 1H), 7.12-7.07 (m, 1H), 7.05 (t, 1H), 6.92 (t, 1H), 6.88 (d, 1H), 6.03-5.95 (m, 2H), 4.32-4.24 (m, 1H), 3.63 (dt, 1H), 2.14 (ddd, 1H), 2.01-1.79 (m, 5H), 1.76 (s, 3H).

Compound I-265

The title compound was prepared following general procedure B, except 3-phenylpyrrolidine-3-carboxylic acid was the amine reactant, contents were heated to 100° C. for 24 h, and the aqueous layer during workup was treated with sodium chloride. The crude material was purified via silica gel chromatography utilizing a 0-10% methanol/dichloromethane gradient to deliver the desired compound, Compound I-265 (29 mg, 45%) as an off-white solid.

$^1$H-NMR (500 MHz, CD$_3$OD) δ 8.74 (d, 1H), 8.11 (d, 1H), 7.51-7.44 (m, 3H), 7.40-7.36 (m, 2H), 7.32-7.23 (m, 2H), 7.12-7.06 (m, 1H), 7.03 (t, 1H), 6.92 (s, 1H), 6.81 (t, 1H), 5.96 (s, 2H), 4.03-3.96 (m, 1H), 3.91 (d, 1H), 3.87 (br. s., 1H), 3.07-3.00 (m, 1H), 2.41-2.32 (m, 1H).

Compound I-267

The title compound was prepared following general procedure B, except 3,3-dimethylpiperidine-2-carboxylic acid (as the HCl salt) was the amine reactant, contents were heated to 100° C. for 18 h, and the aqueous layer during workup was treated with sodium chloride. The crude material was purified via silica gel chromatography utilizing a 0-10% methanol/dichloromethane gradient to deliver the desired compound, Compound I-267 (15 mg, 17%) as a white solid.

¹H-NMR (500 MHz, CD₃OD) δ 8.81 (d, 1H), 8.35 (d, 1H), 7.57 (s, 1H), 7.32-7.26 (m, 1H), 7.12-7.07 (m, 1H), 7.04 (t, 1H), 6.94-6.90 (m, 2H), 5.99 (s, 2H), 4.99 (s, 1H), 4.62 (d, 1H), 3.86 (td, 1H), 2.07-1.96 (m, 1H), 1.95-1.87 (m, 1H), 1.81-1.75 (m, 1H), 1.50 (d, 1H), 1.22 (s, 3H), 1.17 (s, 3H).

Compound I-269

The title compound was prepared following general procedure B, except 3-aminobicyclo[1.1.1]pentane-1-carboxylic acid (as the TFA salt) was the amine reactant, contents were heated at 100° C. for 18 h, and the aqueous layer during workup was treated with sodium chloride.

The crude material was purified via silica gel chromatography utilizing a 0-10% methanol/dichloromethane gradient to deliver the desired compound, Compound I-269 (11 mg, 16%) as a white solid.

¹H-NMR (500 MHz, CD₃OD δ 8.76 (d, 1H), 8.08 (d, 1H), 7.36 (s, 1H), 7.30-7.23 (m, 1H), 7.12-7.06 (m, 1H), 7.04 (t, 1H), 6.96 (d, 1H), 6.91 (t, 1H), 5.94 (s, 2H), 2.53 (s, 6H).

Compound I-80

The title compound was prepared following general procedure B, except L-phenylalanine was the amine reactant and the contents were heated to 90° C. for 48 h as a solution in THF/water (2:1). The contents were concentrated in vacuo, and the crude material was purified via reverse phase HPLC utilizing a 5-75% acetonitrile/water gradient to deliver the desired product, Compound I-80 (1.3 mg, 4%) as a white solid.

¹H-NMR (500 MHz, CD₃ODMeOD) δ 8.81 (s, 1H), 8.20 (d, 1H), 7.51-7.48 (m, 1H), 7.34-7.26 (m, 3H), 7.22 (t, 2H), 7.17-7.03 (m, 3H), 6.96 (s, 1H), 6.90 (t, 1H), 6.00 (s, 2H), 5.36-5.29 (m, 1H), 3.48 (d, 1H), 3.24-3.18 (m, 1H).

Compound I-81

The title compound was prepared following general procedure B, except L-tryptophan was the amine reactant and the contents were heated at 90° C. for 48 h as a solution in THF/water (2:1). The contents were concentrated in vacuo, and the residue was purified via reverse phase HPLC utilizing a 5-75% acetonitrile/water gradient to deliver the desired compound, Compound I-81 (7.3 mg, 18%) as a brown solid.

¹H-NMR (500 MHz, CD₃OD) δ 8.86-8.83 (m, 1H), 8.16 (d, 1H), 7.69 (d, 1H), 7.33-7.27 (m, 1H), 7.16 (d, 1H), 7.13-7.04 (m, 4H), 7.01-6.96 (m, 1H), 6.95-6.88 (m, 3H), 5.96 (s, 2H), 5.51 (dd, 1H), 3.74-3.67 (m, 1H), 3.30-3.25 (m, 1H).

Compound I-85

The title compound was prepared following general procedure B, except 1-aminocyclopropanecarboxylic acid was the amine reactant and the contents were heated at 90° C. for 48 h as a solution in THF/water (2:1). The contents were concentrated in vacuo, and the residue was purified via reverse phase HPLC utilizing a 5-95% acetonitrile/water gradient to deliver the desired compound, Compound I-85 (7.3 mg, 18%) as a clear oil.

¹H-NMR (500 MHz, CD₃OD) δ 8.83 (d, 1H), 8.38 (d, 1H), 7.47 (s, 1H), 7.34-7.28 (m, 1H), 7.13-7.04 (m, 2H), 6.99-6.95 (m, 2H), 6.02 (s, 2H), 1.84-1.79 (m, 2H), 1.43-1.38 (m, 2H).

Compound I-93

The title compound was prepared following general procedure B, except (3-aminooxetan-3-yl)methanol was the amine reactant and the contents were heated at 170° C. for 15 min in the microwave as a solution in THF/water (2:1). The contents were concentrated in vacuo, and the residue was purified via reverse phase HPLC utilizing a 5-75% acetonitrile/water gradient to deliver the desired compound, Compound I-93 (0.6 mg, 4%) as a clear oil.

¹H-NMR (500 MHz, CD₃OD) δ 8.85 (d, 1H), 8.55 (s, 1H), 7.69 (s, 1H), 7.32-7.37 (m, 1H), 7.09-7.17 (m, 3H), 6.97 (d, 1H), 6.01 (s, 2H), 5.00 (s, 2H), 3.76 (q, 4H).

Compound I-102

The title compound was prepared following general procedure B, except methyl 2-amino-2-(oxetan-3-yl)acetate was the amine reactant and the contents were heated at 100° C. for 42 h as a solution in THF/water (2:1). The contents were concentrated in vacuo, and the residue was purified via reverse phase HPLC utilizing a 5-75% acetonitrile/water gradient to deliver the desired compound, Compound I-102 (0.6 mg, 2%) as a clear oil.

¹H-NMR (500 MHz, CD₃OD) δ 8.80 (d, 1H), 8.30 (d, 1H), 7.50 (s, 1H), 7.32-7.27 (m, 1H), 7.12-7.03 (m, 2H), 6.92 (t, 1H), 6.89 (d, 1H), 5.99 (s, 2H), 5.23 (d, 1H), 4.65 (t, 1H), 4.31 (t, 1H), 3.83-3.74 (m, 2H), 3.02 (dtd, 1H).

Compound I-109

The title compound was prepared following general procedure B, except no amine reactant was used, DBU was used in place of triethylamine, and the contents were heated at 100° C. for 18 h as a solution in THF/water (2:1). The contents were concentrated in vacuo, and the residue was purified via reverse phase HPLC utilizing a 5-75% acetonitrile/water gradient to deliver the desired compound, Compound I-109 (7 mg, 35%) as a clear oil.

¹H-NMR (500 MHz, CD₃OD) δ 8.84 (d, 1H), 8.26 (d, 1H), 7.67 (s, 1H), 7.25-7.28 (m, 1H), 7.14-7.05 (m, 2H), 7.02 (d, 1H), 7.01-6.97 (m, 1H), 6.03 (s, 2H), 3.79 (t, 2H), 3.56-3.47 (m, 4H), 2.56-2.50 (m, 2H), 1.99 (quintet, 2H), 1.80-1.73 (m, 2H), 1.72-1.61 (m, 4H).

Compound I-108

The title compound was prepared following general procedure B, except D-tryptophan was the amine reactant and the contents were heated at 100° C. for 18 h as a solution in THF/water (2:1). The contents were treated with 3N HCl solution, solvent was removed in vacuo, and the resulting solid was washed with H₂O, then purified via reverse phase HPLC utilizing a 5-75% acetonitrile/water gradient to deliver the desired compound, Compound I-108 (3.5 mg, 16%) as a clear oil.

¹H-NMR (500 MHz, CD₃OD) δ 8.85 (d, 1H), 8.16 (d, 1H), 7.69 (d, 1H), 7.33-7.27 (m, 1H), 7.17 (d, 1H), 7.13-7.05 (m, 4H), 7.01-6.96 (m, 1H), 6.95-6.89 (m, 3H), 5.97 (s, 2H), 5.50 (dd, 1H), 3.70 (dd, 1H), 3.28 (d, 1H).

Compound I-116

The title compound was prepared following general procedure B, except D-phenylalanine was the amine reactant and the contents were heated to 100° C. for 18 h as a solution in THF/water (2:1). The contents were treated with 3N HCl solution, solvent was removed in vacuo, and the resulting residue was purified via reverse phase HPLC utilizing a 5-75% acetonitrile/water gradient to deliver the desired compound, Compound I-116 (25 mg, 61%) as a solid.

¹H-NMR (500 MHz, CD₃OD, MeOD) δ 8.77 (s, 1H), 8.13 (d, 1H), 7.43 (s, 1H), 7.31 (d, 2H), 7.28-7.18 (m, 3H), 7.16-7.11 (m, 1H), 7.09-7.03 (m, 1H), 7.01 (t, 1H), 6.91 (s, 1H), 6.85 (t, 1H), 5.94 (s, 2H), 5.26 (dd, 1H), 3.45 (dd, 1H), 3.19 (dd, 1H).

Compound I-117

The title compound was prepared following general procedure B, except L-phenylglycine was the amine reactant and the contents were heated to 100° C. for 18 h as a solution in THF/water (2:1). The contents were treated with 3N HCl solution, solvent was removed in vacuo, and the resulting solid was purified via reverse phase HPLC utilizing a 5-75% acetonitrile/water gradient to deliver the desired compound, Compound I-117 (26 mg, 63%) as a solid.

$^1$H-NMR (500 MHz, CD$_3$OD) δ 8.81 (s, 1H), 8.29 (d, 1H), 7.61 (d, 2H), 7.52 (s, 1H), 7.46-7.36 (m, 3H), 7.27 (q, 1H), 7.10-7.05 (m, 1H), 7.03 (t, 1H), 6.95-6.90 (m, 2H), 6.02 (s, 1H), 5.97 (s, 2H).

Compound I-118

The title compound was prepared following general procedure B, except D-phenylglycine was the amine reactant and the contents were heated to 100° C. for 18 h as a solution in THF/water (2:1). The contents were treated with 3N HCl solution, solvent was removed in vacuo, and the resulting solid was purified via reverse phase HPLC utilizing a 5-75% acetonitrile/water gradient to deliver the desired compound, Compound I-118 (22 mg, 53%) as a solid.

$^1$H-NMR (500 MHz, CD$_3$OD) δ 8.81 (s, 1H), 8.30 (d, 1H), 7.60 (d, 2H), 7.53 (s, 1H), 7.46-7.37 (m, 3H), 7.28 (q, 1H), 7.11-7.06 (m, 1H), 7.04 (t, 1H), 6.96-6.91 (m, 2H), 6.02 (s, 1H), 5.99 (s, 2H).

Compound I-142

The title compound was prepared following general procedure B, except N-methyl phenylglycine was the amine reactant and the contents were heated to 100° C. for 18 h as a solution in THF/water (2:1). The contents were treated with 3N HCl solution, solvent was removed in vacuo, and the resulting solid was purified via reverse phase HPLC utilizing a 5-75% acetonitrile/water gradient to deliver the desired compound (15 mg, 52%) as a solid.

$^1$H-NMR (500 MHz, MeOD) δ 8.80 (d, 1H), 8.45-8.39 (m, 1H), 7.58-7.55 (m, 1H), 7.50-7.44 (m, 5H), 7.34-7.27 (m, 1H), 7.14-7.04 (m, 2H), 7.00-6.94 (m, 1H), 6.90 (d, 1H), 6.61-6.55 (m, 1H), 6.02 (s, 2H), 3.25-3.20 (m, 3H).

Compound I-120

The title compound was prepared following general procedure B, except 1-(aminomethyl)cyclopropanecarboxylic acid was the amine reactant, contents were heated at 100° C. for 22 h, and the aqueous layer during workup was treated with sodium chloride. The crude material was purified via silica gel chromatography utilizing a 0-10% methanol/dichloromethane gradient to deliver the desired compound, Compound I-120 (20 mg, 42%) as a white solid.

$^1$H-NMR (500 MHz, CD$_3$OD) δ 8.75 (d, 1H), 8.05 (d, 1H), 7.39 (s, 1H), 7.30-7.24 (m, 1H), 7.12-7.06 (m, 1H), 7.03 (t, 1H), 6.89 (d, 1H), 6.84 (t, 1H), 5.95 (s, 2H), 3.88 (s, 2H), 1.25-1.20 (m, 2H), 1.15-1.10 (m, 2H).

Compound I-207

The title compound was prepared following general procedure B, except N-methyl-L-alanine was the amine reactant, contents were heated to 100° C. for 22 h, and the aqueous layer during workup was treated with sodium chloride. The crude material was purified via silica gel chromatography utilizing a 0-10% methanol/dichloromethane gradient to deliver the desired compound, Compound I-207 (20 mg, 57%) as a white solid.

$^1$H-NMR (500 MHz, CD$_3$OD) δ 8.74 (d, 1H), 8.16 (d, 1H), 7.40 (s, 1H), 7.29-7.23 (m, 1H), 7.11-7.05 (m, 1H), 7.02 (t, 1H), 6.87 (d, 1H), 6.82 (t, 1H), 5.94 (s, 2H), 5.10 (q, 1H), 3.33 (d, 3H), 1.59 (d, 3H).

Compound I-217

The title compound was prepared following general procedure B, except 2-(aminomethyl)-2-ethylbutanoic acid was the amine reactant, contents were heated to 100° C. for 22 h, and the aqueous layer during workup was treated with sodium chloride. The crude material was purified via silica gel chromatography utilizing a 0-10% methanol/dichloromethane gradient to deliver the desired compound, Compound I-217 (20 mg, 50%) as a clear oil.

$^1$H-NMR (500 MHz, CD$_3$OD) δ 8.76-8.72 (m, 1H), 8.07-8.03 (m, 1H), 7.42-7.39 (m, 1H), 7.29-7.22 (m, 1H), 7.11-7.04 (m, 1H), 7.02 (t, 1H), 6.89-6.81 (m, 2H), 5.94 (s, 2H), 3.91 (s, 2H), 1.68 (q, 4H), 0.98-0.90 (t, 6H).

Compound I-224 and Compound I-225

The title compounds were prepared following general procedure B, except 2-amino-5,5,5-trifluoro-4-methylpentanoic acid was the amine reactant, contents were heated to 100° C. for 18 h, and the aqueous layer during workup was treated with sodium chloride. The crude material was purified via reverse phase HPLC utilizing a 5-75% acetonitrile/water gradient to deliver the desired diastereomers, Compound I-224 (3.3 mg, 7%, eluting first on the LCMS) as a white solid and Compound I-225 (2 mg, 5%, eluting second on the LCMS) as a white solid.

$^1$H-NMR for Compound I-224 (500 MHz, CD$_3$OD) δ 8.75 (d, 1H), 8.15 (d, 1H), 7.38 (s, 1H), 7.29-7.24 (m, 1H), 7.11-7.06 (m, 1H), 7.03 (t, 1H), 6.86 (d, 1H), 6.83 (t, 1H), 5.95 (s, 2H), 4.94 (t, 1H), 2.60 (dd, 1H), 2.45-2.38 (m, 1H), 1.96-1.89 (m, 1H), 1.25 (d, 3H).

$^1$H-NMR for Compound I-225 (500 MHz, CD$_3$OD) δ 8.81 (d, 1H), 8.34 (d, 1H), 7.58 (s, 1H), 7.33-7.27 (m, 1H), 7.13-7.08 (m, 1H), 7.06 (t, 1H), 6.99-6.92 (m, 2H), 6.01 (s, 2H), 5.26 (dd, 1H), 2.53-2.42 (m, 1H), 2.42-2.33 (m, 1H), 2.13 (ddd, 1H), 1.24 (d, 3H).

Compound I-226

The title compound was prepared following general procedure B, except 2-amino-3-fluoro-3-methylbutanoic acid was the amine reactant, contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-226 (11 mg, 42%) as a white solid.

$^1$H-NMR (500 MHz, CD$_3$OD) δ 8.75 (d, 1H), 8.16 (d, 1H), 7.44 (s, 1H), 7.30-7.22 (m, 1H), 7.11-7.06 (m, 1H), 7.02 (t, 1H), 6.90 (d, 1H), 6.81 (t, 1H), 5.95 (s, 2H), 5.13 (d, 1H), 1.65-1.58 (m, 3H), 1.58-1.51 (m, 3H).

Compound I-227

The title compound was prepared following general procedure B, except (S)-2-amino-2-cyclopropylacetic acid was the amine reactant, contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-227 (21 mg, 86%) as a white solid.

$^1$H-NMR (500 MHz, MeOD) δ 8.74 (d, 1H), 8.10 (d, 1H), 7.37 (s, 1H), 7.28-7.22 (m, 1H), 7.11-7.05 (m, 1H), 7.02 (t, 1H), 6.85 (d, 1H), 6.82 (t, 1H), 5.93 (s, 2H), 3.96 (d, 1H), 1.38-1.28 (m, 1H), 0.75-0.64 (m, 3H), 0.53-0.47 (m, 1H).

Compound I-239

The title compound was prepared following general procedure B, except (S)—N-methyl-2-amino-2-cyclopropylacetic acid was the amine reactant, contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-239 (4 mg, 20%) as a white solid.

$^1$H-NMR (500 MHz, CD$_3$OD) δ 8.75 (d, 1H), 8.16 (d, 1H), 7.39 (s, 1H), 7.26 (ddd, 1H), 7.08 (ddd, 1H), 7.04-7.00 (m, 1H), 6.86 (d, 1H), 6.82 (td, 1H), 5.94 (s, 2H), 4.19 (d, 1H), 3.48 (d, 3H), 1.53-1.44 (m, 1H), 0.91-0.83 (m, 1H), 0.76-0.64 (m, 2H), 0.44 (dq, 1H).

Compound I-240

The title compound was prepared following general procedure B, except (R)-2-amino-2-cyclopropylacetic acid was the amine reactant, contents were heated to 100° C. for 2 h, and the aqueous layer during workup was treated with sodium chloride. The crude material was purified via silica gel chromatography utilizing a 0-10% methanol/dichloromethane gradient to deliver the desired compound, Compound I-240 (46 mg, 93%) as a white solid.

$^1$H-NMR (500 MHz, CD$_3$OD) δ 8.74 (d, 1H), 8.10 (d, 1H), 7.36 (s, 1H), 7.28-7.22 (m, 1H), 7.07 (ddd, 1H), 7.01 (td, 1H), 6.84 (d, 1H), 6.81 (td, 1H), 5.93 (s, 2H), 3.96 (d, 1H), 1.38-1.30 (m, 1H), 0.74-0.65 (m, 3H), 0.52-0.47 (m, 1H).

Compound I-241

The title compound was prepared following general procedure B, except (R)—N-methyl-2-amino-2-cyclopropylacetic acid (as the TFA salt) was the amine reactant, contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-241 (20 mg, 93%) as a white solid.

$^1$H-NMR (500 MHz, CD$_3$OD) δ 8.74 (d, 1H), 8.15 (d, 1H), 7.38 (s, 1H), 7.28-7.22 (m, 1H), 7.10-7.04 (m, 1H), 7.04-6.99 (m, 1H), 6.85 (d, 1H), 6.82 (t, 1H), 5.93 (s, 2H), 4.18 (d, 1H), 3.48 (d, 3H), 1.53-1.44 (m, 1H), 0.91-0.82 (m, 1H), 0.76-0.64 (m, 2H), 0.48-0.41 (m, 1H).

Compound I-90

The title compound was prepared following general procedure B, except (S)-indoline-2-carboxylic acid was the amine reactant (1 equiv.), and the contents were heated at 90° C. for 12 h as a solution in THF/water (1:1), followed by heating at 125° C. for 15 min in the microwave. The contents extracted with ethyl acetate during workup. The crude material was purified via by reverse phase HPLC using 5 to 95% acetonitrile in water spiked with 0.1% trifluoroacetic acid to afford the desired compound, Compound I-90 (3.9 mg, 15% yield) as an off-white solid.

$^1$H-NMR (500 MHz, DMSO-d$_6$) δ (ppm): 9.10-9.21 (d, 1H), 8.61-8.75 (m, 1H), 8.47-8.57 (d, 1H), 7.49-7.58 (s, 1H), 7.33-7.41 (m, 1H), 7.22-7.33 (m, 4H), 7.10-7.20 (m, 2H), 6.98-7.10 (m, 1H), 5.95 (s, 2H), 5.39-5.53 (m, 1H), 3.64-3.74 (dd, 1H), 3.20-3.32 (dd, 2H).

Compound I-91

The title compound was prepared following general procedure B, except (R)-indoline-2-carboxylic acid was the amine reactant (1 equiv.), and the contents were heated to 90° C. for 12 h as a solution in THF/water (1:1), followed by heating at 125° C. for 15 min in the microwave. Contents extracted with ethyl acetate during workup. The crude material was purified via reverse phase HPLC using a 5-95% acetonitrile in water gradient (in 0.1% TFA) to deliver the desired compound, Compound I-91 Compound obtained following usual procedure (1.9 mg, 7%).

$^1$H NMR (500 MHz, CD$_3$CN) δ (ppm): 8.68-8.75 (d, 1H), 8.35-8.49 (m, 2H), 7.42-7.49 (m, 1H), 7.27-7.41 (m, 3H), 7.05-7.24 (m, 4H), 6.91-6.96 (m, 1H), 5.97 (s, 2H), 5.38-5.48 (m, 1H), 3.65-3.79 (dd, 1H), 3.31-3.44 (dd, 1H).

Compound I-114

Purification was achieved by reverse phase HPLC using 5-75% acetonitrile in water over 30 minutes (spiked with 0.1% trifluoroacetic acid) to afford the desired compound (1.6 mg, 4% yield) as a clear oil. Only the later running diastereomer (Compound I-114) was purified from this reaction mixture.

$^1$H NMR (500 MHz, 500 MHz, CD$_3$CN) δ (ppm): 8.85 (s, 1H), 8.33 (d, 1H), 7.40-7.48 (m, 1H), 7.28-7.38 (m, 1H), 7.04-7.19 (m, 2H), 6.90-7.00 (m, 2H), 6.03 (s, 2H), 3.13-3.17 (m, 1H), 2.47-2.59 (m, 1H), 2.36-2.42 (m, 1H), 2.03-2.17 (m, 1H), 1.77-1.85 (m, 1H), 1.65-1.74 (m, 2H), 1.49-1.60 (m, 2H), 1.38-1.47 (m, 1H).

Compound I-107

The title compound was prepared following general procedure B, except (1S,2S,5R)-3-azabicyclo[3.1.0]hexane-2-carboxylic acid was the amine reactant (1 equiv.), 3 equivalents of triethyl amine was used, and the contents were heated to 70° C. for 14 h as a solution in THF/water (10:1). Contents extracted with ethyl acetate during workup, dried, filtered, and concentrated to deliver the desired compound. Compound I-107 (38.3 mg, 100% yield) was obtained as a light-tan solid. No purification was necessary for this compound.

$^1$H NMR (500 MHz, CD$_3$OD) δ ppm: 8.79 (s, 1H), 8.23 (d, 1H), 7.36-7.46 (br. s, 1H), 7.25-7.31 (m, 1H), 7.06-7.12 (m, 1H), 7.01-7.06 (m, 1H), 6.83-6.90 (m, 2H, 2 shifts overlapping), 5.96 (s, 2H), 4.18 (dd, 1H), 4.02-4.08 (m, 1H), 1.93-2.02 (m, 1H), 0.83-0.93 (m, 4H).

Compound I-129

Purification was achieved by silica gel chromatography using 1 to 10% methanol in dichloromethane over 30 minutes to afford Compound I-129 (21.7 mg, 57% yield) as a white solid.

$^1$H NMR (400 MHz, CDCl$_3$) δ (ppm): 8.45-8.57 (m, 2H, 2 shifts isochronous) 7.40-7.48 (m, 3H), 7.24-7.40 (m, 1H), 6.93-7.09 (m, 2H), 6.58-6.68 (m, 1H), 5.90 (s, 2H), 3.74-3.90 (m, 2H), 1.99-2.20 (m, 2H), 1.70-1.89 (m, 4H), 1.55-1.69 (m, 2H).

Compound I-124

The title compound was prepared following general procedure B, except 4-methylpiperidine-4-carboxylic acid (as the HCl salt) was the amine reactant (1.1 equiv.), 4 equivalents of triethyl amine was used, and the contents were heated to 80° C. for 18 h as a solution in THF/water (10:1). Contents extracted with ethyl acetate during workup. The crude material was purified via silica gel chromatography utilizing a 1-10% methanol/dichloromethane gradient over 30 minutes to deliver the desired compound, Compound I-124 as an off-white solid (36.1 mg, 95% yield).

$^1$H NMR (400 MHz, CDCl$_3$) δ (ppm): 8.49 (s, 1H), 8.16-8.28 (d, 1H), 7.35-7.44 (m, 1H), 7.17-7.26 (m, 1H), 6.95-7.10 (m, 2H), 6.87 (m, 1H), 6.62 (s, 1H), 6.00 (s, 2H), 4.34-4.48 (m, 1H), 3.36-3.48 (m, 1H), 2.36-2.41 (m, 1H), 1.58-1.68 (m, 1H), 1.34 (s, 3H), 0.71-0.81 (m, 4H).

Compound I-143

The title compound was prepared following general procedure B, except 3-methylpyrrolidine-3-carboxylic acid was the amine reactant (1.05 equiv.), 4 equivalents of triethyl amine was used, and the contents were heated to 80° C. for 4 h as a solution in THF/water (10:1). Contents extracted with ethyl acetate during workup. The crude material was purified via silica gel chromatography utilizing a 1-10% methanol/dichloromethane gradient over 30 minutes to deliver the desired compound, Compound I-143 as a white solid (18.9 mg, 48% yield).

$^1$H NMR (500 MHz, CDCl$_3$) δ (ppm): 8.45 (s, 1H), 8.12-8.19 (d, 1H), 7.30 (s, 1H), 7.27 (s, 1H), 7.14-7.22 (m, 1H), 6.98-7.05 (m, 1H), 6.93-6.98 (m, 1H), 6.80-6.87 (m, 1H), 6.57 (d, 1H), 5.96 (s, 2H), 4.24-4.36 (m, 1H), 3.84-4.00 (m, 2H), 3.59-3.70 (m, 1H), 2.45-2.58 (m, 1H), 1.84-2.00 (m, 1H), 1.47 (s, 3H).

Compound I-152

The title compound was prepared following general procedure B, except 4,4-Dimethyl-pyrrolidine-3-carboxylic acid was the amine reactant (1.05 equiv.), 4 equivalents of triethyl amine was used, and the contents were heated to 90° C. for 14 h as a solution in THF/water (10:1). Contents extracted with ethyl acetate during workup. The crude material was purified via silica gel chromatography utilizing a 1-7% methanol/dichloromethane gradient over 30 minutes to deliver the desired compound, Compound I-152 as an off-white solid (14.3 mg, 37% yield).

$^1$H NMR (400 MHz, CDCl$_3$) δ (ppm): 8.45 (s, 1H), 8.05-8.20 (d, 1H), 7.29-7.34 (m, 1H), 7.14-7.25 (m, 1H), 6.91-7.08 (m, 2H), 6.79-6.87 (m, 1H), 6.56-6.63 (m, 1H), 5.96 (s, 2H), 4.01-4.23 (m, 2H), 3.71-3.87 (dd, 1H), 3.53-3.65 (dd, 1H), 2.85-2.97 (m, 1H), 1.34 (s, 3H), 1.15 (s, 3H).

Compound I-186

The title compound was prepared following general procedure B, except 4-phenylpiperidine-4-carboxylic acid (as the HCl salt) was the amine reactant (1.05 equiv.), 4 equivalents of triethyl amine was used, and the contents were heated to 70° C. for 24 h as a solution in THF/water (10:1). Contents extracted with ethyl acetate during workup. The crude material was purified via silica gel chromatography utilizing a 4-7% methanol/dichloromethane gradient over 40 minutes to deliver the desired compound, Compound I-186 as a white solid (22.3 mg, 51% yield).

$^1$H NMR (400 MHz, CDCl$_3$) δ (ppm): 8.46 (s, 1H), 8.19 (d, 1H), 7.44-7.49 (m, 2H, 2 shifts overlapping), 7.36-7.41 (m, 2H), 7.29-7.34 (m, 2H), 7.16-7.22 (m, 2H), 6.99-7.05 (m, 1H), 6.93-6.98 (m, 1H), 6.81-6.86 (m, 1H), 6.59 (m, 1H), 5.97 (s, 2H), 4.50-4.58 (m, 2H), 3.42-3.50 (m, 2H), 2.69-2.75 (m, 2H), 2.07-2.14 (m, 2H).

Compound I-194

This compound was prepared following the general procedure B described above, except 4-(aminomethyl)tetrahydro-2H-pyran-4-carboxylic acid was the amine reactant (1.05 equiv.), 4 equivalents of triethyl amine was used, and the contents were heated at 70° C. for 6 h as a solution in THF/water (10:1), followed by heating at 90° C. for 12 h. Contents extracted with ethyl acetate during workup. and purification was achieved by silica gel chromatography using 4 to 7% methanol in dichloromethane over 40 minutes to deliver the desired compound, Compound I-194 ((26.8 mg, 66% yield) as a white solid $^1$H NMR (500 MHz, CDCl$_3$) δ (ppm): 8.46 (s, 1H), 8.10 (d, 1H), 7.28 (s, 1H), 7.18-7.24 (m, 1H), 6.94-7.07 (m, 3H), 6.58 (d, 1H), 5.95 (s, 2H), 5.50-5.57 (m, 1H), 3.86-3.94 (m, 2H), 3.79-3.85 (m, 2H), 3.51-3.60 (m, 2H), 2.12-2.20 (m, 2H), 1.53-1.62 (m, 2H).

Compound I-228

The title compound was prepared in 4 steps:

Step 1: 1-((4-methylphenylsulfonamido)methyl)cyclopentanecarboxylic Acid

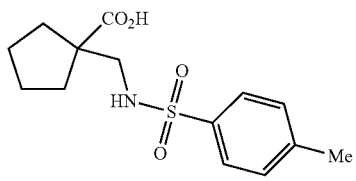 [SMILES: Cc1ccc(S(=O)(=O)NCC2(C(=O)O)CCCC2)cc1]

A slurry of 1-(aminomethyl)cyclopentanecarboxylic acid (316 mg, 1.0 equiv.), p-toluenesulfonyl chloride (505 mg, 1.2 equiv) and 1M aqueous sodium hydroxide solution (6.62 mL, 3.0 equiv.) was heated in water (10 mL) at 90° C. for 1 hour, after which the reaction mixture was cooled to 0° C. and acidified by the addition of 3M aqueous hydrochloric acid solution. The resulting white precipitate was filtered then washed successively with water and ethanol to afford 1-((4-methylphenylsulfonamido)methyl)cyclopentanecarboxylic acid (383 mg, 58% yield) as a white solid.

$^1$H-NMR (500 MHz, DMSO-d$_6$) δ (ppm): 12.14-12.38 (s, 1H), 7.64-7.75 (d, 2H), 7.47-7.56 (t, 1H), 7.33-7.45 (d, 2H), 2.79-2.90 (d, 2H), 2.38 (s, 3H), 1.81-1.95 (m, 2H), 1.47-1.65 (m, 6H).

Step 2: 1-((N,4-dimethylphenylsulfonamido)methyl)cyclopentanecarboxylic Acid

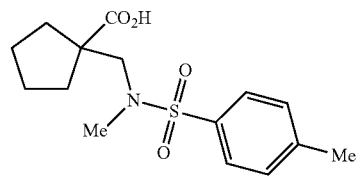 [SMILES: Cc1ccc(S(=O)(=O)N(C)CC2(C(=O)O)CCCC2)cc1]

A solution of 1-((4-methylphenylsulfonamido)methyl)cyclopentanecarboxylic acid (383 mg, 1.0 equiv.), iodomethane (0.254 mL, 3.15 equiv.), and 1M aqueous sodium hydroxide solution (5.15 mL, 4.0 equiv.) in water (5 mL) was heated to 75° C. for 1.5 hours, after which LCMS analysis indicated that the reaction was complete. The reaction mixture was cooled to room temperature, washed with dichloromethane (3×30 mL), acidified by the addition of 3M aqueous hydrochloric acid solution, extracted with diethyl ether (3×30 mL), dried (sodium sulfate), filtered, and concentrated to afford 1-((N,4-dimethylphenylsulfonamido)methyl)cyclopentanecarboxylic acid (343 mg, 86% yield) as a yellow-gold solid. No purification was necessary.

$^1$H NMR (500 MHz, CDCl$_3$) δ (ppm): 7.59-7.73 (d, 2H), 7.30-7.41 (d, 2H), 3.24-3.39 (s, 2H), 2.71 (s, 3H), 2.45 (s, 3H), 2.06-2.22 (m, 2H), 1.69-1.88 (m, 6H).

Step 3: 1-((methylamino)methyl)cyclopentanecarboxylic Acid Hydrobromide

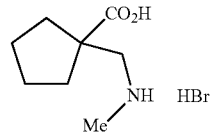

A solution of 1-((N,4-dimethylphenylsulfonamido)methyl)cyclopentanecarboxylic acid (343 mg, 1.0 equiv.) was heated in a 33% glacial acetic acid solution of hydrogen bromide (6.0 mL, 30 equiv.) for 2 hours at 75° C. The reaction was then cooled to room temperature, diluted in water (10 mL), and washed with diethyl ether (3×40 mL). The aqueous layer was concentrated to dryness and the resulting solid was recrystallized in acetone to afford 1-((methylamino)methyl)cyclopentanecarboxylic acid hydrobromide (127 mg, 48% yield) as a crystalline white solid.

$^1$H-NMR (500 MHz, DMSO-d$_6$) δ (ppm): 12.76-13.15 (s, 1H), 8.12-8.39 (m, 2H), 2.98-3.11 (m, 2H), 2.55 (s, 3H), 1.86-2.01 (m, 2H), 1.62 (m, 6H).

Step 4: Compound I-228

The title compound was prepared following general procedure B, except 1-((methylamino)methyl)cyclopentanecarboxylic acid (as the HBr salt) was the amine reactant (1.3 equiv.), 4 equivalents of triethyl amine was used, and the contents were heated at 90° C. for 6 h as a solution in THF/water (10:1). Contents were extracted with ethyl acetate during workup. Purification was achieved by silica gel chromatography using 2 to 5% methanol in dichloromethane over 40 minutes. The desired compound was obtained as a white solid (13.4 mg, 45% yield).

$^1$H NMR (400 MHz, CDCl$_3$) δ (ppm): 8.44 (s, 1H), 8.08 (d, 1H), 7.29 (s, 1H), 7.15-7.25 (m, 1H), 6.95-7.08 (m, 3H), 6.55-6.58 (m, 1H), 5.95 (s, 2H), 4.02 (s, 2H), 3.35 (d, 3H), 2.18-2.29 (m, 2H), 1.57-1.79 (m, 6H).

Compound I-238

The title compound was prepared in 4 steps:

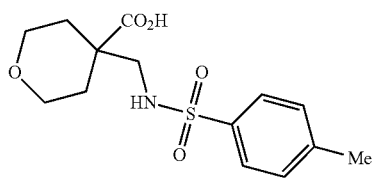 [SMILES: Cc1ccc(S(=O)(=O)NCC2(C(=O)O)CCOCC2)cc1]

Step 1: 4-((4-methylphenylsulfonamido)methyl)tetrahydro-2H-pyran-4-carboxylic Acid A slurry of 4-(aminomethyl)tetrahydro-2H-pyran-4-carboxylic acid (500 mg, 1.0 equiv.), p-toluenesulfonyl chloride (719 mg, 1.2 equiv.) and 1M aqueous sodium hydroxide solution (9.4 mL, 3.0 equiv.) was heated at 90° C. for 1 hour after which the reaction mixture was cooled to 0° C. and acidified by the addition of 3M aqueous hydrochloric acid solution. The resulting white precipitate was filtered then washed successively with water and ethanol to afford 4-((4-methylphenylsulfonamido)methyl)tetrahydro-2H-pyran-4-carboxylic acid (840 mg, 85% yield) as a white solid. No purification was necessary.

$^1$H-NMR (400 MHz, DMSO-d$_6$) δ (ppm): 12.6 (br. s, 1H), 7.68 (d, 2H), 7.66 (t, 1H), 7.39 (d, 2H), 3.63-3.72 (m, 2H), 3.27-3.32 (m, 2H), 2.81 (d, 2H), 2.38 (s, 3H), 1.76-1.85 (m, 2H), 1.33-1.46 (m, 2H).

Step 2: 4-((N,4-dimethylphenylsulfonamido)methyl)tetrahydro-2H-pyran-4-carboxylic Acid

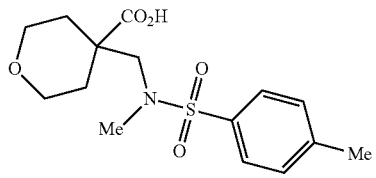 [SMILES: Cc1ccc(S(=O)(=O)N(C)CC2(C(=O)O)CCOCC2)cc1]

A suspension of 4-((4-methylphenylsulfonamido)methyl)tetrahydro-2H-pyran-4-carboxylic acid (840 mg, 1.0 equiv.) in 1M aqueous sodium hydroxide solution (10.7 mL, 4.0 equiv.) and iodomethane (0.528 mL, 3.15 equiv.) was heated to 100° C. for two hours after which the reaction mixture was diluted in 3M aqueous hydrochloric acid solution, extracted with dichloromethane (3×30 mL), dried (sodium sulfate), filtered and concentrated to afford 4-((N,4-dimethylphenylsulfonamido)methyl)tetrahydro-2H-pyran-4-carboxylic acid (197 mg, 22% yield) as a creme-colored solid. No purification was necessary.

$^1$H NMR (500 MHz, CDCl$_3$) δ (ppm): 7.63-7.72 (d, 2H), 7.31-7.39 (d, 2H), 3.87-3.97 (m, 2H), 3.50-3.61 (m, 2H), 3.25 (s, 2H), 2.76 (s, 3H), 2.45 (s, 3H), 2.13-2.23 (m, 2H), 1.62-1.74 (m, 2H).

Step 3: 4-((methylamino)methyl)tetrahydro-2H-pyran-4-carboxylic Acid Hydrobromide

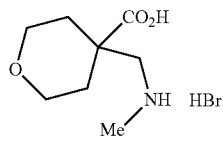 [SMILES: CNCC1(C(=O)O)CCOCC1 ; Br]

A solution of 4-((N,4-dimethylphenylsulfonamido)methyl)tetrahydro-2H-pyran-4-carboxylic acid (197 mg, 1.0 equiv.) was heated in a 33% glacial acetic acid solution of hydrogen bromide (1 mL, 31 equiv.) at 85° C. for 3 hours, after which LCMS analysis indicated that the starting material had been consumed. After cooling the reaction mixture to room temperature, water was added, and the reaction mixture was washed with diethyl ether (3×30 mL). The water layer was concentrated to dryness, and the resulting solid was recrystallized from acetone to afford 4-((methylamino)methyl)tetrahydro-2H-pyran-4-carboxylic acid hydrobromide (54.8 mg, 36% yield) as a white solid.

$^1$H NMR (500 MHz, D$_2$O) δ (ppm): 3.71-3.89 (m, 2H), 3.50-3.64 (m, 2H), 3.17 (s, 2H), 2.66 (s, 3H), 1.96-2.09 (m, 2H), 1.48-1.66 (m, 2H).

Step 4: Compound I-238

This compound was prepared following general procedure B, with the exception that 4-((methylamino)methyl)tetrahydro-2H-pyran-4-carboxylic acid (as the HBr salt) was the amine reactant (1.05 equiv.), 4 equivalents of triethyl amine was used, and the reaction was conducted in dioxane/water (3:1) at 90° C. for 18 hours. Contents extracted with ethyl acetate during workup. and the purification was achieved by silica gel chromatography using 2 to 7% methanol in dichloromethane over 40 minutes to deliver the desired compound, Compound I-238, as a white solid (31.0 mg, 43% yield) following the procedure described for above.

$^1$H NMR (400 MHz, CDCl$_3$) δ (ppm): 8.47 (s, 1H), 8.06 (d, 1H), 7.31 (s, 1H), 7.23-7.27 (m, 1H), 7.22 (br. s, 1H), 7.00-7.09 (m, 3H), 6.59 (d, 1H), 5.96 (s, 2H), 3.83-3.95 (m, 4H), 3.47-3.56 (m, 2H), 3.40 (d, 3H), 2.20-2.26 (m, 2H), 1.51-1.64 (m, 2H).

Compound I-244

The title compound was prepared in 4 steps:

Step 1: 4,4,4-trifluoro-2-(4-methylphenylsulfonamido)butanoic Acid

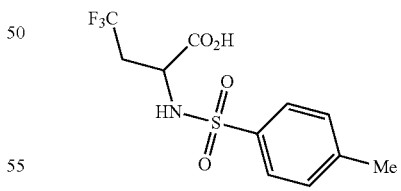

A slurry of 2-amino-4,4,4-trifluorobutanoic acid (300 mg, 1.0 equiv.), p-toluenesulfonyl chloride (437 mg, 1.2 equiv.) and 1M aqueous sodium hydroxide solution (5.73 ml, 3.0 equiv.) was heated in water (4 mL) at 90° C. for 1 hour, after the reaction mixture was cooled to 0° C., and acidified by the addition of 3M aqueous hydrochloric acid solution, extracted with dichloromethane (3×40 mL), dried (sodium sulfate), filtered and concentrated to afford 4,4,4-trifluoro-2-(4-methylphenylsulfonamido)butanoic acid (175 mg, 29% yield) as a white solid.

¹H NMR (500 MHz, CDCl₃) δ (ppm): 7.71-7.80 (d, 2H), 7.28 (d, 2H, isochronous with chloroform), 5.72-5.91 (br. s, 1H), 4.16-4.29 (m, 1H), 2.64-2.76 (m, 1H), 2.52-2.63 (m, 1H), 2.43 (s, 3H).

Step 2: 2-(N, 4-dimethylphenylsulfonamido)-4,4,4-trifluorobutanoic Acid

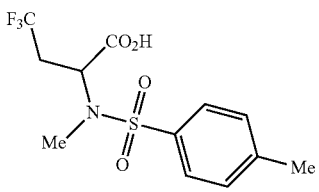 [SMILES: Cc1ccc(S(=O)(=O)N(C)C(CC(F)(F)F)C(=O)O)cc1]

A mixture of 4,4,4-trifluoro-2-(4-methylphenylsulfonamido)butanoic acid (175 mg, 1.0 equiv.) and iodomethane (146 μL, 3.15 equiv.) in 1M aqueous sodium hydroxide solution (2.81 mL, 4.0 equiv.) was heated at 85° C. for 2.5 hour after which LCMS analysis indicated the presence of the desired product and the methyl ester of the desired product. The reaction mixture was acidified with 3M hydrochloric acid solution, extracted with dichloromethane (3×30 mL), dried (sodium sulfate), filtered and concentrated to a residue. This residue was reconstituted in tetrahydrofuran (2 mL), then treated with 1M aqueous sodium hydroxide solution (0.5 mL). After 30 minutes of stirring at room temperature, the reaction mixture was acidified with 3M hydrochloric acid solution, extracted with dichloromethane (3×30 mL), dried (sodium sulfate), and concentrated to afford 2-(N,4-dimethylphenylsulfonamido)-4,4,4-trifluorobutanoic acid (66 mg, 36% yield) as a gum with about 90% purity by ¹H NMR. Used as is in the next step without further purification.

¹H NMR (500 MHz, CDCl₃) δ (ppm): 7.60-7.70 (d, 2H), 7.19 (d, 2H), 4.90-4.99 (m, 1H), 2.75-2.89 (m, 1H), 2.66-2.72 (s, 3H), 2.30-2.44 (m, 1H), 2.29 (s, 3H).

Step 3: 4,4,4-trifluoro-2-(methylamino)butanoic Acid Hydrobromide

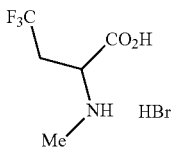

A solution of 2-(N,4-dimethylphenylsulfonamido)-4,4,4-trifluorobutanoic acid (66 mg, 1.0 equiv.) in a 33% glacial acetic acid solution of hydrogen bromide (1.0 mL, 91 equiv.) was heated to 85° C. for 2 hours. Starting material still remained. Allowed to stir at 60° C. for 72 hours after which the deprotection was nearly complete. The reaction mixture was diluted in water, washed with diethyl ether (3×30 mL), and the the water layer was concentrated to dryness. This crude material was used as is in the next step without any purification.

Step 4: Compound I-244

This compound was prepared following the procedure B described above with the exception that 4,4,4-trifluoro-2-(methylamino)butanoic acid (as the HBr salt) was the amine reactant (1.2 equiv.), 4 equivalents of triethyl amine was used and the reaction was conducted in dioxane/water (3:1) at 90° C. for 5 days. The crude material was purified via silica gel chromatography utilizing a 2-10% methanol/dichloromethane gradient over 40 minutes to deliver the desired compound, Compound I-244 (24.7 mg, 32% yield) as a tan solid.

¹H NMR (500 MHz, CDCl₃) δ (ppm): 8.77 (s, 1H), 8.21 (d, 1H), 7.41 (m, 1H), 7.24-7.33 (m, 1H), 6.07-7.13 (m, 1H), 7.02-7.07 (m, 1H), 6.90 (d, 1H), 6.82-6.88 (m, 1H), 5.97 (s, 2H), 3.38-3.46 (m, 2H), 3.33-3.36 (m, 1H), 3.03-3.19 (m, 3H).

Compound I-94

Compound was prepared following general procedure B, with the exception that methyl 1-aminocyclobutanecarboxylate was the amine reactant, 5 equivalents of triethylamine was used, the reaction was heated at 90° C. as a solution in THF/water (10:1) for 14 h, followed by heating at 170° C. for 10 minutes in the microwave. The contents were then treated with water and solid 1N HCl and dried in vacuo. The crude material was purified via preparative reverse-phase HPLC to afford the desired compound, Compound I-94 (0.30 mg, 1.5% yield) as a white solid.

¹H NMR (500 MHz, METHANOL-d4) δ (ppm): 8.81 (d, 1H), 8.23 (d, 1H), 7.34 (s, 1H), 7.25-7.31 (m, 1H), 7.01-7.13 (m, 2H), 6.86-6.94 (m, 2H), 5.97 (s, 2H), 2.89 (ddd, 2H), 2.45-2.54 (m, 2H), 2.07-2.14 (m, 1H), 1.95-2.03 (m, 1H).

Compound I-138

This compound was prepared as above with the exception that methyl 1-aminocyclopentanecarboxylate (as the HCl salt) was the amine reactant, the mixture was heated for 5 hours at 140° C. in DMA (Volume: 142 μl) to give the ester. The reaction then allowed to stir at room temperature (23° C.) for 16 hrs. Sodium hydroxide (14.2 mg) was added and reaction and heated at 40 for 1 hr, then cooled, water added, reaction neutralized with 1N HCl and extracted with ethyl acetate (3 times). The organics were combined and dried, purified via reverse phase preparative HPLC to afford the desired compound, Compound I-138 (0.5 mg, 1.5% yield).

¹H NMR (500 MHz, METHANOL-d4) δ (ppm): 8.84 (s, 1H), 8.29 (d, 1H), 7.40 (s, 1H), 7.28-7.35 (m, 1H), 7.04-7.16 (m, 2H), 6.91-7.00 (m, 2H), 6.01 (s, 2H), 2.50-2.62 (m, 3H), 2.17-2.26 (m, 2H), 1.90 (br. s., 3H).

Compound I-156

A mixture of Intermediate 1 (30.8 mg), (1S,2R)-2-aminocyclopentanecarboxylic acid (31.9 mg, 3 equiv.) and triethylamine (115 μl, 10 equiv.) were heated to 80° C. for 16 hours in a 10:1 mixture of THF/Water. Contents were concentrated in vacuo, and purified via Preparative reverse-phase HPLC to afford the desired compound, Compound I-156, as a white solid (6.2 mg, 16% yield).

¹H NMR (500 MHz, CDCl₃) δ (ppm): 8.52 (s, 1H), 8.46 (br. s., 1H), 7.44 (br. s., 2H), 7.22-7.27 (m, 1H), 7.15 (t, 1H), 7.00-7.09 (m, 2H), 6.66 (s, 1H), 5.94 (s, 2H), 4.88 (br. s., 1H), 3.13-3.21 (m, 1H), 2.23 (d, 1H), 2.15 (br. s., 2H), 1.85-2.03 (m, 2H), 1.76 (d, 1H).

Compound I-154

The title compound was prepared following general procedure B, except cis-2-aminocyclohexanecarboxylic acid was the amine reactant and the mixture was heated at 80° C. for 24 h as a solution in THF/water (10:1). Contents were concentrated in vacuo, and purified via reverse phase HPLC to deliver the desired compound, Compound I-154 (8.5 mg, 26% yield) as a white solid.

¹H NMR (500 MHz, CDCl₃) δ ppm: 8.62 (d, 1H), 8.53 (d, 1H), 7.79 (br. s., 1H), 7.45 (s, 1H), 7.19-7.27 (m, 2H), 7.00-7.10 (m, 2H), 6.67 (s, 1H), 5.94 (s, 2H), 4.58 (br. s., 1H), 2.94 (d, 1H), 2.33 (d, 1H), 1.87 (br. s., 2H), 1.81 (d, 1H), 1.61-1.74 (m, 2H), 1.36-1.57 (m, 2H).

Compound I-159

The title compound was prepared following general procedure B, except 3-(4-Hydroxyphenyl)-L-alanine was the amine reactant and the mixture was heated at 80° C. for 18 h as a solution in THF/water (10:1). Contents were concentrated in vacuo, and purified via reverse phase HPLC to deliver the desired compound, Compound I-159 as a brown oil.

$^1$H NMR (500 MHz, CD$_3$OD) δ ppm: 8.82 (d, 1H), 8.22 (d, 1H), 7.52 (s, 1H), 7.25-7.33 (m, 1H), 7.02-7.15 (m, 4H), 6.97 (d, 1H), 6.92 (t, 1H), 6.64 (d, 2H), 6.00 (s, 2H), 5.29 (dd, 1H), 3.40 (dd, 1H), 3.09 (dd, 1H).

Compound I-165

The title compound was prepared following general procedure B, except 3-(4-Hydroxyphenyl)-D-alanine was the amine reactant and the mixture was heated at 80° C. for 90 h as a solution in THF/water (10:1). Contents were concentrated in vacuo, and purified via reverse phase HPLC to deliver the desired compound, Compound I-165 (4.7 mg, 13% yield) as a brown oil.

$^1$H NMR (500 MHz, CD$_3$OD) δ ppm: 8.82 (d, 1H), 8.24 (d, 1H), 7.53 (s, 1H), 7.26-7.38 (m, 1H), 7.13 (d, 2H), 7.04-7.11 (m, 2H), 6.98 (d, 1H), 6.93 (t, 1H), 6.64 (d, 2H), 6.01 (s, 2H), 5.30 (dd, 1H), 3.41 (dd, 1H), 3.09 (dd, 1H).

Compound I-179

The title compound was prepared following general procedure B, except (1S,3R)-3-aminocyclopentanecarboxylic acid was the amine reactant and the mixture was heated at 80° C. for 48 h as a solution in THF/water (10:1). Contents were concentrated in vacuo, and purified via reverse phase HPLC to deliver the desired compound, Compound I-179 (1.7 mg, 5% yield).

$^1$H NMR (400 MHz, CD$_3$OD) δ ppm: 8.83 (d, 1H), 8.23 (d, 1H), 7.67 (s, 1H), 7.26-7.35 (m, 1H), 7.12 (d, 1H), 7.05-7.10 (m, 1H), 7.01 (d, 1H), 6.94-7.00 (m, 1H), 6.03 (s, 2H), 2.96-3.06 (m, 1H), 2.42-2.54 (m, 1H), 2.21 (td, 1H), 1.97-2.15 (m, 4H), 1.80-1.96 (m, 1H).

Compound I-188

The title compound was prepared following general procedure B, except 4-Fluoro-4-piperidinecarboxylic acid (as the HCl salt) was the amine reactant and the mixture was heated at 80° C. for 8 h as a solution in THF/water (10:1) followed by stirring at 23° C. for an additional 8 h. Contents were concentrated in vacuo, and purified via reverse phase HPLC to deliver the desired compound, Compound I-188 (7 mg, 18% yield) as a white solid.

$^1$H NMR (500 MHz, CD$_3$OD) δ ppm: 8.81 (d, 1H), 8.32 (d, 1H), 7.63 (s, 1H), 7.26-7.33 (m, 1H), 7.03-7.14 (m, 2H), 6.91-6.98 (m, 2H), 6.01 (s, 2H), 4.82 (br. s., 1H), 3.59-3.73 (m, 2H), 2.26-2.41 (m, 2H), 2.16-2.23 (m, 2H), 0.10 (m, 1H).

Compound I-199

The title compound was prepared following general procedure B, except (S)-2-Amino-4-(methylmercapto)butyric acid was the amine reactant and the mixture was heated at 80° C. for 16 h as a solution in THF/water (10:1). Contents were concentrated in vacuo, and purified via reverse phase HPLC to deliver the desired compound, Compound I-199 (4 mg, 9% yield) as a white solid.

$^1$H NMR (500 MHz, CD$_3$OD) δ ppm: 8.82 (d, 1H), 8.34 (d, 1H), 7.58 (s, 1H), 7.27-7.34 (m, 1H), 7.04-7.14 (m, 2H), 6.93-7.00 (m, 2H), 6.02 (s, 2H), 5.24 (dd, 1H), 2.59-2.79 (m, 2H), 2.36-2.46 (m, 1H), 2.22-2.31 (m, 1H), 2.12 (s, 3H).

Compound I-192

The title compound was prepared following general procedure B, except 3-(Methanesulfonyl)pyrrolidine was the amine reactant and the mixture was heated at 80° C. for 48 h as a solution in THF/water (10:1). Contents acidified with 1N hydrochloric acid, concentrated in vacuo, and purified via reverse phase HPLC to deliver the desired compound, Compound I-192 (6.3 mg, 18% yield) as a white solid.

$^1$H NMR (500 MHz, CD$_3$OD) δ ppm: 8.81 (d, 1H), 8.30 (d, 1H), 7.61 (s, 1H), 7.30 (ddd, 1H), 7.03-7.14 (m, 2H), 6.88-6.98 (m, 2H), 6.01 (s, 2H), 4.41-4.54 (m, 1H), 4.27-4.38 (m, 1H), 4.06-4.27 (m, 3H), 3.11 (s, 3H), 2.52-2.68 (m, 2H).

Compound I-220

The title compound was prepared following general procedure B, except β-cyano-L-alanine was the amine reactant and the mixture was heated at 80° C. for 18 h as a solution in THF/water (10:1). Contents concentrated in vacuo, and purified via reverse phase HPLC to deliver the desired compound, Compound I-220 (2.5 mg, 8% yield) as a white solid.

$^1$H NMR (500 MHz, CD$_3$OD) δ ppm: 8.79 (d, 1H), 8.30 (d, 1H), 7.52 (s, 1H), 7.25-7.31 (m, 1H), 7.02-7.13 (m, 2H), 6.86-6.95 (m, 2H), 5.99 (s, 2H), 5.34 (dd, 1H), 3.15-3.25 (m, 2H).

Compound I-198

The title compound was prepared following general procedure B, except trans-2-aminocyclohexanecarboxylic acid was the amine reactant and the mixture was heated at 80° C. for 16 h as a solution in THF/water (10:1). Contents acidified with 1N hydrochloric acid solution, and the solids were filtered, re-suspended in dichloromethane, and filtered to deliver the desired compound, Compound I-198 (14.5 mg, 31% yield) as a white solid.

$^1$H NMR (500 MHz, METHANOL-d4) δ ppm: 8.75 (d, 1H), 8.00 (d, 1H), 7.42 (s, 1H), 7.23-7.29 (m, 1H), 7.05-7.11 (m, 1H), 7.02 (t, 1H), 6.89-6.92 (m, 1H), 6.81 (t, 1H), 5.95 (s, 2H), 4.58 (td, 1H), 2.56 (td, 1H), 1.98-2.14 (m, 2H), 1.78-1.90 (m, 2H), 1.67 (qd, 1H), 1.48-1.61 (m, 1H), 1.28-1.47 (m, 2H).

Compound I-208

The title compound was prepared following general procedure B, except octahydrocyclopenta[c]pyrrole-3a-carboxylic acid (4 equiv.) was the amine reactant and the mixture was heated at 80° C. for 5 h as a solution in THF/water (10:1). Contents were blown dry with nitrogen, and the crude mixture was re-suspended in methanol and filtered to deliver the desired compound, Compound I-208 (37 mg, 93% yield).

$^1$H NMR (500 MHz, METHANOL-d4) δ ppm: 8.74 (d, 1H), 8.06-8.13 (m, 1H), 7.39-7.45 (m, 1H), 7.26 (m, 1H), 7.09 (m, 1H), 7.02 (d, 1H), 6.91 (d, 1H), 6.82 (m, 1H), 5.96 (s., 2H), 4.40 (d, 1H), 4.06 (m, 1H), 3.79 (d, 2H), 3.06 (br. s., 1H), 2.31 (m, 1H), 2.11 (m, 1H), 1.90 (m, 2H), 1.64 (m, 1H), 1.30 (m, 1H)

Compound I-233

The title compound was prepared following general procedure B, except methyl L-cyclohexylglycine methyl ester (as the HCl salt) was the amine reactant, and the contents were heated to 90° C. as a solution in THF/water (10:1) for 16 h. Contents cooled, treated with solid sodium hydroxide, and stirred at 23° C. for 2 h. The organic solvent was removed from the reaction mixture, upon completion and the precipitate was filtered to furnish desired compound, Compound I-233 as a white solid (26.0 mg, 0.047 mmol, 70.7% yield).

$^1$H NMR (500 MHz, METHANOL-d4) δ ppm: 9.08 (d, 1H), 8.12 (d, 1H), 7.42 (s, 1H), 7.29-7.35 (m, 1H), 7.25 (d, 1H), 7.18-7.24 (m, 1H), 7.09 (t, 1H), 6.93 (t, 1H), 6.77 (d, 1H), 5.82-5.92 (dd, 2H), 4.17 (br. s, 1H), 3.30 (s., 1H), 1.79-1.91 (m, 2H), 1.50-1.69 (m, 3H), 0.89-1.24 (m, 5H).

Compound I-243

A mixture of Intermediate 1 (25 mg, (S)-methyl 2-amino-2-cyclohexylacetate hydrochloride (41.7 mg, 3 equiv.) and triethylamine (93 µl, 10 equiv), was heated at 90° C. for 16 hours in a mixture of THF/water. The reaction mixture was cooled, NaOH (5.35 mg, 2 equiv) was added, and the mixture stirred at room temperature for 2 hours. The organic solvent was removed, and the resulting precipitate was filtered to furnish (R)-2-cyclohexyl-2-((5-fluoro-2-(1-(2-fluorobenzyl)-5-(isoxazol-3-yl)-1H-pyrazol-3-yl)pyrimidin-4-yl)amino)acetic acid as a white solid (26.0 mg, 0.047 mmol, 70.7% yield).

$^1$H NMR (500 MHz, METHANOL-d4) δ ppm: 8.75 (d, 1H), 8.11 (d, 1H), 7.41 (s, 1H), 7.23-7.29 (m, 1H), 7.00-7.11 (m, 1H), 7.02 (t, 1H), 6.88 (d, 1H), 6.83 (t, 1H), 5.95 (s, 2H), 4.73 (d, 1H), 1.97-2.04 (m, 1H), 1.88 (t, 2H), 1.80 (d, 2H), 1.70 (d, 1H), 1.17-1.39 (m, 5H). The title compound was also prepared following general procedure B, except methyl D-cyclohexylglycine methyl ester (as the HCl salt) was the amine reactant (1 equiv.), and the contents were heated to 90° C. for 16 h as a solution in THF/water (10:1). Contents cooled, treated with solid sodium hydroxide, and stirred at 23° C. for 18 h. Contents concentrated in vacuo, and purified via reverse phase HPLC to deliver the desired compound, Compound I-243 (1 mg, 3% yield) as a white solid.

Compound I-242

The title compound was prepared in 4 steps:

Step 1: Trans-2-(4-methylphenylsulfonamido)cyclohexanecarboxylic Acid

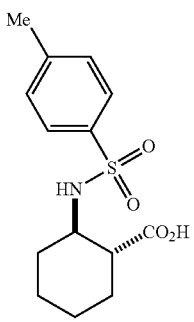

A slurry of trans-2-aminocyclohexanecarboxylic acid (318 mg, 1.0 equiv.), p-toluenesulfonyl chloride (508 mg, 1.2 equiv.) and 1M aqueous sodium hydroxide solution (6.7 mL, 3.0 equiv) was heated in water (5 mL) at 90° C. for 1 hour. The reaction mixture was cooled to 0° C., and acidified by the addition of 3M aqueous hydrochloric acid solution. The resulting white precipitate was filtered and washed successively with water then ethanol to afford racemic trans-2-(4-methylphenylsulfonamido)cyclohexanecarboxylic acid as a white solid (179.6 mg, 27% yield).

$^1$H NMR (400 MHz, CDCl$_3$) δ (ppm): 7.73 (d, 2H), 7.27 (d, 2H), 4.98-5.16 (m, 1H), 3.24-3.46 (br. s, 1H), 2.39 (s, 3H), 2.23-2.34 (m, 1H), 1.87-2.03 (m, 2H), 1.58-1.78 (m, 2H), 1.42-1.58 (m, 1H), 1.08-1.35 (m, 3H).

Step 2: Synthesis of trans-2-(N,4-dimethylphenylsulfonamido)cyclohexanecarboxylic Acid

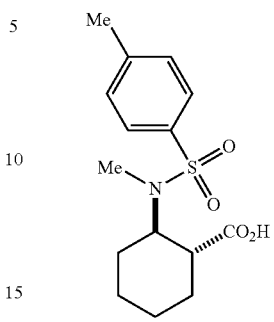

A solution of trans-2-(4-methylphenylsulfonamido)cyclohexanecarboxylic acid (187 mg, 0.629 mmol), iodomethane (0.124 mL, 3.0 equiv) and 1M aqueous sodium hydroxide solution (2.52 mL, 4.0 equiv) solution in water (5 mL) was heated at 75° C. for 1.5 hours, after which the reaction mixture was cooled to room temperature, washed with dichloromethane (2×30 mL), acidified by the addition of 3M aqueous hydrochloric acid solution, extracted with dichloromethane (3×30 mL), dried (sodium sulfate), filtered, and concentrated to afford the crude N-methyl amino acid product. Purification was achieved using silica gel chromatography with 2 to 5% methanol in dichloromethane as the eluent over 40 minutes. This afforded trans-2-(N,4-dimethylphenylsulfonamido)cyclohexanecarboxylic acid as a white foam (130 mg, 66% yield).

$^1$H NMR (500 MHz, CDCl$_3$) δ (ppm): 7.69-7.76 (d, 2H), 7.28 (d, 2H), 4.03-4.16 (m, 1H), 2.78 (s, 3H), 2.49-2.61 (m, 1H), 2.43 (s, 3H), 2.02-2.13 (m, 1H), 1.73-1.84 (m, 2H), 1.63-1.73 (m, 1H), 1.55-1.63 (m, 1H), 1.35-1.45 (m, 2H), 1.10-1.22 (m, 1H).

Step 3: trans-2-(methylamino)cyclohexanecarboxylic Acid Hydrobromide

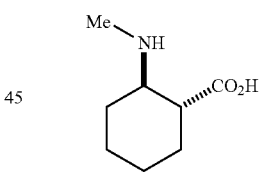

To a vial containing trans-2-(N,4-dimethylphenylsulfonamido)cyclohexanecarboxylic acid (130 mg, 1.0 equiv) was added a 33% glacial acetic acid solution of hydrogen bromide (1.2 ml, 53 equiv). The suspension was heated at 85° C. for 2.5 hours after which it was diluted in water and washed with diethyl ether (2×30 mL), then concentrated to a gold foamy residue. Recrystallization of this material from acetone afforded trans-2 (methylamino)cyclohexanecarboxylic acid hydrobromide as a cream-colored solid (54.4 mg, 55% yield).

$^1$H NMR (500 MHz, D$_2$O) δ (ppm): 3.24-3.37 (m, 1H), 2.65 (s, 3H), 2.47-2.60 (m, 1H), 2.06-2.20 (m, 2H), 1.76-1.84 (m, 1H), 1.15-1.51 (m, 5H).

Step 4: Compound I-242

The title compound was prepared following general procedure B, except trans-2(methylamino) cyclohexanecarboxylic acid (as the HBr salt) was the amine reactant, and the contents were heated to 85° C. for 18 h as a solution in THF/water (10:1). Contents cooled, concentrated in vacuo, and purified via reverse phase HPLC to deliver the desired compound, Compound I-242 (1 mg, 3% yield) as a white solid.

$^1$H NMR (500 MHz, METHANOL-d4) δ ppm: 8.75 (d, 1H), 8.09 (d, 1H), 7.38 (s, 1H), 7.23-7.30 (m, 1H), 7.06-7.11 (m, 1H), 7.00-7.05 (m, 1H), 6.89 (d, 1H), 6.83 (t, 1H), 5.94 (s, 2H), 3.16-3.24 (m, 3H), 2.79 (br. s., 1H), 2.08 (d, 1H), 1.86-1.97 (m, 2H), 1.81 (d, 2H), 1.45-1.70 (m, 2H), 1.34 (dt, 1H)

Compound I-31

The title compound was prepared following general procedure B, except 2-amino-1-morpholinoethanone (5 equiv.) was the amine reactant, 3 equivalents of triethylamine was used, and the contents were heated to 80° C. for 1 h as a solution in THF. Solvent was removed in vacuo, and contents were taken up in ethyl acetate. The organic layer was washed with 1N hydrochloric acid solution, water, and brine, dried over sodium sulfate, filtered, and concentrated in vacuo. The crude material was purified via silica gel chromatography utilizing a 0 to 100% ethyl acetate/hexane gradient to deliver the desired compound, Compound I-31 (4.7 mg, 23% yield).

$^1$H NMR (500 MHz, CDCl$_3$) δ 8.44-8.52 (m, 1H), 8.14-8.25 (m, 1H), 7.19-7.27 (m, 1H), 6.97-7.12 (m, 2H), 6.83-6.91 (m, 1H), 6.61-6.66 (m, 1H), 6.00 (s, 2H), 4.39-4.47 (m, 2H), 3.71-3.82 (m, 7H), 3.56-3.63 (m, 2H).

Compound I-33

The title compound was prepared following general procedure B, except 3-methylmorpholine was the amine reactant, 5 equivalents of triethylamine was used, and the contents were heated to 60° C. for 18 h as a solution in THF, followed by 80° C. for 18 h. Solvent was removed in vacuo, and contents were taken up in ethyl acetate. The organic layer was washed with 1N hydrochloric acid, water, and brine, dried over sodium sulfate, filtered, and concentrated in vacuo. The crude material was purified via silica gel chromatography utilizing a 0-5% methanol/dichloromethane gradient to deliver the desired compound, Compound I-33 (8 mg, 41% yield).

$^1$H NMR (500 MHz, CDCl$_3$) δ 8.48 (m, 1H), 8.22 (m, 1H), 7.31 (s, 1H), 7.1822 (m, 1H), 6.99 (s, 2H), 6.87 (m, 1H), 6.61 (d, 1H), 5.98 (s, 2H), 4.69 (m, 1H), 4.37 (m, 1H), 4.05 (m, 1H), 3.83 (m, 2H), 3.69 (m, 1H), 3.4752 (m, 1H), 1.45 (d, 3H).

Compound I-34

The title compound was prepared following general procedure B, except methyl pyrrolidine-2-carboxylate was the amine reactant, 2 equivalents of triethylamine was used, and the contents were heated to 60° C. for 18 h as a solution in THF. Solvent was removed in vacuo, and contents were taken up in ethyl acetate. The organic layer was washed with 1N hydrochloric acid solution, water, and brine, dried over sodium sulfate, filtered, and concentrated in vacuo. The crude material was purified via silica gel chromatography utilizing a 0-5% methanol/dichloromethane gradient to deliver the desired compound, Compound I-34 (10.6 mg, 57% yield).

$^1$H NMR (500 MHz, CDCl$_3$) δ 8.47 (m, 1H), 8.20 (m, 1H), 8.17.29 (s, 1H), 7.21 (m, 1H), 7.04 (m, 1H), 6.98 (m, 1H), 6.87 (m, 1H), 6.59 (dm, 1H), 5.98 (m, 2H), 4.76 (m, 1H), 4.05 (m, 1H), 3.94 (m, 1H), 3.73 (s, 3H), 2.35 (m, 1H), 2.17 (m, 3H).

Compound I-35

The title compound was prepared following general procedure B, except tert-butyl pyrrolidin-3-ylcarbamate was the amine reactant (5 equiv.), 3 equivalents of triethylamine was used, and the contents were heated to 80° C. for 1 h as a solution in THF. Solvent was removed in vacuo, and contents were purified via silica gel chromatography utilizing a 0-100% ethyl acetate/hexanes gradient to deliver the desired compound, Compound I-35 (30 mg, 68% yield).

$^1$H NMR (500 MHz, CDCl$_3$) δ 8.44-8.48 (m, 1H), 8.14-8.19 (m, 1H), 7.32 (s, 1H), 7.17-7.24 (m, 1H), 6.95-7.08 (m, 2H), 6.82-6.89 (m, 1H), 6.57-6.63 (m, 1H), 5.99 (s, 2H), 4.72-4.79 (m, 1H), 4.32-4.43 (m, 1H), 4.00-4.07 (m, 1H), 3.86-3.95 (m, 2H), 3.68-3.75 (m, 1H), 2.23-2.33 (m, 1H), 1.96-2.05 (m, 1H), 1.48 (s, 9H).

Compound I-41

The title compound was prepared following general procedure B, except methyl pyrrolidine-2-carboxylate was the amine reactant, 2 equivalents of triethylamine was used, and the contents were heated to 60° C. for 18 h as a solution in THF. Solvent was removed in vacuo, and contents were taken up in ethyl acetate. The organic layer was washed with 1N hydrochloric acid solution, water, and brine, dried over sodium sulfate, filtered, and concentrated in vacuo. The crude material was purified via silica gel chromatography utilizing a 0-5% methanol/dichloromethane gradient to deliver the desired compound, Compound I-41 (4 mg, 22% yield).

$^1$H NMR (500 MHz, CDCl$_3$) δ 8.44-8.49 (m, 1H), 8.19-8.26 (m, 1H), 7.34-7.39 (m, 1H), 7.18-7.25 (m, 1H), 6.92-7.10 (m, 3H), 6.74-6.80 (m, 1H), 5.95-6.00 (m, 2H), 4.45-4.51 (m, 2H), 2.42-2.51 (m, 3H), 2.16-2.23 (m, 4H).

Compound I-46

The title compound was prepared by treating a solution of Compound I-35 in dichloromethane with an equal volume of trifluroacetic acid. After stirring at 23° C. for 1 h, solvent was removed under a stream of nitrogen, and contents were dried under vacuum for 18 h to deliver the desired compound, Compound I-46 (29 mg) as a solid.

$^1$H NMR (500 MHz, CD$_3$OD) δ 8.83-8.87 (m, 1H), 8.37-8.42 (m, 1H), 7.59-7.63 (m, 1H), 7.29-7.37 (m, 1H), 7.05-7.16 (m, 2H), 6.94-7.02 (m, 2H), 6.04 (s, 2H), 4.13-4.33 (m, 5H), 2.53-2.64 (m, 1H), 2.27-2.39 (m, 1H).

Compound I-48

The title compound was prepared following general procedure B, except methyl piperidine-2-carboxylate was the amine reactant, 2 equivalents of triethylamine was used, and the contents were heated to 60° C. for 18 h as a solution in THF. Solvent was removed in vacuo, and contents were taken up in ethyl acetate. The organic layer was washed with 1N hydrochloric acid solution, water, and brine, dried over sodium sulfate, filtered, and concentrated in vacuo. The crude material was purified via reverse phase HPLC to deliver the desired compound, Compound I-48 (3.7 mg, 18% yield).

$^1$H NMR (400 MHz, CDCl$_3$) δ 8.46-8.50 (m, 1H), 8.37-8.44 (m, 1H), 7.32-7.37 (m, 1H), 7.17-7.23 (m, 1H), 6.97-7.09 (m, 3H), 6.59-6.62 (m, 1H), 5.91 (s, 2H), 5.46-5.57 (m, 1H), 4.54-4.67 (m, 1H), 3.75 (s, 3H), 3.38-3.47 (m, 1H), 2.34-2.45 (m, 1H), 1.78-1.89 (m, 3H), 1.61-1.72 (m, 1H), 1.45-1.55 (m, 1H).

Compound I-53

The title compound was prepared following general procedure B, except azetidine-3-carboxylic acid was the amine reactant (5 equiv.), 3 equivalents of triethylamine was used, and the contents were heated to 75° C. for 18 h as a solution in THF. Solvent was removed under a stream of nitrogen. Product isolated via reverse phase HPLC to deliver the desired compound, Compound I-53 (15.4 mg, 88% yield).

$^1$H NMR (500 MHz, METHANOL-d$_4$) δ 8.81-8.85 (m, 1H), 8.22-8.27 (m, 1H), 7.55-7.59 (m, 1H), 7.29-7.36 (m,

1H), 7.05-7.16 (m, 2H), 6.93-6.99 (m, 2H), 5.99-6.05 (m, 2H), 4.65-4.84 (m, 4H), 3.75-3.84 (m, 1H).

Compound I-54

The title compound was prepared following general procedure B, except 3-methylpiperazin-2-one was the amine reactant (5 equiv.), 3 equivalents of triethylamine was used, and the contents were heated to 75° C. for 18 h as a solution in THF. Solvent was removed under a stream of nitrogen. Product isolated via reverse phase HPLC to deliver the desired compound, Compound I-54 (1.4 mg, 8% yield).

$^1$H NMR (500 MHz, CDCl$_3$) δ 8.53-8.55 (m, 1H), 8.49-8.53 (m, 1H), 7.43-7.48 (m, 1H), 7.31-7.37 (m, 1H), 7.24-7.28 (m, 1H), 7.09-7.14 (m, 1H), 7.02-7.08 (m, 2H), 6.67-6.70 (m, 1H), 5.97 (s, 2H), 5.34-5.47 (m, 1H), 4.89-4.95 (m, 1H), 3.62-3.78 (m, 2H), 3.50-3.60 (m, 1H), 1.70 (d, 3H).

Compound I-55

The title compound was prepared following general procedure B, except azetidine-2-carboxylic acid (5 equiv.) was the amine reactant, 5 equivalents of triethylamine was used, and the contents were heated to 75° C. for 18 h as a solution in THF. Solvent was removed in vacuo, and contents were purified via reverse phase HPLC to deliver the desired compound, Compound I-55 (1.3 mg, 2% yield).

$^1$H NMR (500 MHz, CD$_3$OD) δ 8.82 (s, 1H), 8.23-8.29 (m, 1H), 7.40-7.52 (m, 1H), 7.28-7.35 (m, 1H), 7.04-7.16 (m, 2H), 6.93 (br. s., 2H), 5.98-6.03 (m, 2H), 5.23-5.36 (m, 1H), 4.42-4.67 (m, 2H), 2.92-3.07 (m, 1H), 2.50-2.62 (m, 1H).

Compound I-56

The title compound was prepared following general procedure B, except 3-fluoropiperidine (5 equiv.) was the amine reactant, 5 equivalents of triethylamine was used, and the contents were heated to 75° C. for 18 h as a solution in THF. Solvent was removed in vacuo, and contents were purified via reverse phase HPLC to deliver the desired compound, Compound I-56 (1.3 mg, 2% yield).

$^1$H NMR (500 MHz, CHLOROFORM-d) δ 8.52-8.56 (m, 1H), 8.45-8.50 (m, 1H), 7.49-7.54 (m, 1H), 7.24-7.28 (m, 1H), 7.13-7.20 (m, 1H), 7.01-7.11 (m, 2H), 6.68 (s, 1H), 5.95 (s, 2H), 4.85-5.03 (m, 1H), 4.56-4.81 (m, 2H), 3.71-3.89 (m, 1H), 3.47-3.60 (m, 1H), 1.75-2.26 (m, 4H).

Compound I-57

The title compound was prepared following general procedure B, except 3,3-difluoropiperidine (5 equiv.) was the amine reactant, 5 equivalents of triethylamine was used, and the contents were heated to 75° C. for 18 h as a solution in THF. Solvent was removed in vacuo, and contents were purified via reverse phase HPLC to deliver the desired compound, Compound I-57 (4.5 mg, 5% yield).

$^1$H NMR (500 MHz, CDCl$_3$) δ 8.52-8.55 (m, 1H), 8.47-8.52 (m, 1H), 7.40-7.45 (m, 1H), 7.24-7.28 (m, 1H), 7.11-7.17 (m, 1H), 7.02-7.10 (m, 2H), 6.65-6.68 (m, 1H), 5.93-5.98 (m, 2H), 4.20-4.30 (m, 2H), 4.00-4.08 (m, 2H), 2.16-2.27 (m, 2H), 1.96-2.05 (m, 2H).

Compound I-58

A solution of Compound I-48 was dissolved in THF, and an aqueous solution of lithium hydroxide (3 equiv.) was added. The solution was stirred at 25° C. for 18 h. Contents were concentrated and the remaining aqueous layer was acidified with 1N hydrochloric acid solution which resulted in a white precipitate. The aqueous layer was extracted with ethyl acetate, and the combined organic layers were washed with water and brine. Contents dried over sodium sulfate, filtered, and concentrated to deliver the desired compound, Compound I-58 (29 mg, 100% yield).

$^1$H NMR (400 MHz, CD$_3$OD) δ 8.75 (m, 1H), 8.20 (m, 1H), 7.42 (m, 1H), 7.26 (m, 1H), 6.98-7.11 (m, 2H), 6.84 (m, 2H), 5.95 (s, 2H), 5.47 (m, 1H), 4.52 (m, 1H), 3.44 (m, 1H), 2.31-2.40 (m, 1H), 1.93 (m, 1H), 1.81 (m, 2H), 1.68 (m, 1H), 1.54 (m, 1H).

Compound I-59

The title compound was prepared following general procedure B, except piperazin-2-one was the amine reactant (5 equiv.), 5 equivalents of triethylamine was used, and the contents were heated to 75° C. for 18 h as a solution in THF. Solvent was removed under a stream of nitrogen and contents were purified via reverse phase HPLC to deliver the desired compound, Compound I-59 (1.6 mg, 2% yield).

$^1$H NMR (500 MHz, CDCl$_3$') δ 8.51-8.54 (m, 1H), 8.45-8.49 (m, 1H), 7.69-7.73 (m, 1H), 7.23-7.27 (m, 1H), 7.03-7.09 (m, 3H), 6.69-6.73 (m, 2H), 6.00-6.03 (m, 2H), 4.70-4.73 (m, 2H), 4.26-4.32 (m, 2H), 3.64-3.69 (m, 2H).

Compound I-60

The title compound was prepared following general procedure B, except triethylamine was the amine reactant (2 equiv.), and the contents were heated to 60° C. for 18 h as a solution in THF. Solvent was removed in vacuo, and contents were taken up in ethyl acetate. The organic layer was washed with 1N hydrochloric acid solution, water, and brine, dried over sodium sulfate, filtered, and concentrated in vacuo. The crude material was purified via reverse phase HPLC to deliver the desired compound, Compound I-60 (1.9 mg, 11% yield).

$^1$H NMR (400 MHz, CD$_3$OD) δ 8.77-8.81 (m, 1H), 8.17-8.22 (m, 1H), 7.48-7.52 (m, 1H), 7.23-7.32 (m, 1H), 7.01-7.13 (m, 2H), 6.89-6.98 (m, 2H), 5.96-6.01 (m, 2H), 3.81-3.90 (m, 4H), 1.34 (s, 6H).

Compound I-66

The title compound was prepared following general procedure B, except piperidine-3-carboxamide was the amine reactant (5 equiv.), 8 equivalents of triethylamine was used, and the contents were heated to 75° C. for 18 h as a solution in THF. Solvent was removed and crude material was purified via reverse phase HPLC to deliver the desired compound, Compound I-66 (7 mg, 36% yield).

$^1$H NMR (500 MHz, CDCl$_3$) δ 8.51-8.55 (m, 1H), 8.25-8.31 (m, 1H), 7.47-7.52 (m, 1H), 7.22-7.27 (m, 1H), 7.09-7.16 (m, 1H), 7.00-7.09 (m, 2H), 6.83-6.90 (m, 1H), 6.67-6.72 (m, 1H), 6.17-6.22 (m, 1H), 5.90-5.95 (m, 2H), 4.52-4.60 (m, 1H), 4.30-4.43 (m, 1H), 3.81-3.90 (m, 1H), 3.60-3.69 (m, 1H), 2.69-2.81 (m, 1H), 2.05-2.13 (m, 2H), 1.92-2.00 (m, 1H), 1.69-1.81 (m, 1H).

Compound I-75

The title compound was prepared following general procedure B, except methyl azepane-2-carboxylate was the amine reactant (1.5 equiv.), potassium carbonate (4 equiv.) was used instead of triethylamine, and the contents were heated to 150° C. for 10 min in the microwave as a solution in NMP. The resulting mixture was filtered to remove the solid potassium carbonate, and concentrated in vacuo. The crude material was purified via reverse phase HPLC using a 20-70% acetonitrile/water (with 0.1% TFA) gradient to deliver the desired compound, Compound I-75 (1 mg, 3% yield).

$^1$H NMR (500 MHz, CDCl$_3$) δ 8.83 (m, 1H), 8.33 (m, 1H), 7.48 (m, 1H), 7.31 (m, 1H), 7.10 (m, 2H), 6.91 (m, 2H), 6.01 (s, 2H), 5.04 (m, 1H), 4.18 (m, 1H), 3.73 (m, 1H), 2.58 (m, 1H), 2.04 (m, 3H), 1.92 (m, 1H), 1.79 (m, 1H), 1.53 (m, 2H).

Compound I-82

The title compound was prepared following general procedure B, except (1R,3S,5S)-8-azabicyclo[3.2.1]octan-3-yl-methanol (as the HCl salt) was the amine reactant (3.5 equiv.), 5 equivalents of triethylamine was used, and the contents were heated to 120° C. for 30 min in the microwave as a solution in NMP. The resulting mixture was purified via reverse phase HPLC to deliver the desired compound, Compound I-82 (10.8 mg, 42% yield).

$^1$H NMR (500 MHz, METHANOL-$d_4$) δ 8.82-8.86 (m, 1H), 8.25-8.29 (m, 1H), 7.62-7.66 (m, 1H), 7.30-7.36 (m, 1H), 7.05-7.15 (m, 2H), 6.92-7.02 (m, 2H), 6.00-6.06 (m, 2H), 3.66-3.72 (m, 2H), 2.10-2.40 (m, 4H), 1.78-2.07 (m, 5H).

Compound I-83

The title compound was prepared following general procedure B, except morpholine-2-carboxylic acid (as the HCl salt) was the amine reactant (2 equiv.), Hunig's base (3 equiv.) was used in place of triethylamine, and contents were heated to 120° C. for 30 min in the microwave as a solution in NMP. The resulting mixture was purified via reverse phase HPLC using a 0-95% acetonitrile/water (with 0.1% TFA) gradient to deliver the desired compound, Compound I-83 (10.8 mg, 42% yield) as a clear glass.

$^1$H NMR (500 MHz, METHANOL-$d_4$) δ 8.81-8.85 (m, 1H), 8.35-8.44 (m, 1H), 7.64 (s, 1H), 7.26-7.35 (m, 1H), 7.04-7.14 (m, 2H), 6.97 (d, 2H), 6.02 (s, 2H), 4.73 (m, 1H), 4.46 (m, 2H), 4.14-4.20 (m, 1H), 3.97 (m, 1H), 3.89 (d, 2H).

Compound I-87

The title compound was prepared following general procedure B, except (R)-piperidine-2-carboxylic acid (4 equiv.) was the amine reactant, 5 equivalents of triethylamine was used, and the contents were heated to 90° C. for 18 h as a solution in THF/water (9:1). Solvent was removed under a stream of nitrogen, and the crude material was purified via reverse phase HPLC using a 20-51% acetonitrile/water (in 0.1% TFA) gradient to deliver the desired compound, Compound I-87 (12 mg, 48% yield).

$^1$H NMR (500 MHz, METHANOL-$d_4$) δ 8.79-8.83 (m, 1H), 8.34-8.39 (m, 1H), 7.60 (s, 1H), 7.27-7.35 (m, 1H), 7.03-7.15 (m, 2H), 6.90-6.98 (m, 2H), 6.02 (s, 2H), 4.61-4.83 (m, 1H), 3.43-3.58 (m, 1H), 2.43-2.51 (m, 1H), 1.69-2.02 (m, 5H), 1.55-1.69 (m, 1H).

Compound I-84

The title compound was prepared following general procedure B, except (S)-piperidine-2-carboxylic acid (4 equiv.) was the amine reactant, 5 equivalents of triethylamine was used, and the contents were heated to 90° C. for 18 h as a solution in THF/water (9:1). Solvent was removed under a stream of nitrogen, and the crude material was purified via reverse phase HPLC using a 20-51% acetonitrile/water (in 0.1% TFA) gradient to deliver the desired compound, Compound I-84 (9.6 mg, 39% yield).

$^1$H NMR (500 MHz, METHANOL-$d_4$) δ 8.79-8.83 (m, 1H), 8.31-8.36 (m, 1H), 7.54-7.58 (m, 1H), 7.27-7.34 (m, 1H), 7.04-7.15 (m, 2H), 6.89-6.97 (m, 2H), 6.01 (s, 2H), 5.65 (br. s., 1H), 4.58-4.80 (m, 1H), 3.42-3.57 (m, 1H), 2.41-2.50 (m, 1H), 1.67-2.02 (m, 4H), 1.55-1.66 (m, 1H).

Compound I-95

The title compound was prepared following general procedure B, except (R)-morpholine-3-carboxylic acid (4 equiv.) was the amine reactant, Hunig's base (5 equiv.) was used instead of triethylamine, and the contents were heated to 90° C. for 18 h as a solution in THF/water (9:1). Solvent was removed under a stream of nitrogen, and the crude material was purified via reverse phase HPLC using a 20-51% acetonitrile/water (in 0.1% TFA) gradient to deliver the desired compound, Compound I-95 (19 mg, 76% yield).

$^1$H NMR (500 MHz, CD$_3$OD) δ 8.81 (d, 1H), 8.39 (d, 1H), 7.57 (s, 1H), 7.26-7.34 (m, 1H), 7.02-7.16 (m, 2H), 6.93 (d, 2H), 6.00 (s, 2H), 5.26-5.59 (m, 1H), 4.55 (d, 2H), 4.04 (s, 1H), 3.93 (dd, 1H), 3.62-3.80 (m, 2H).

Compound I-96

The title compound was prepared following general procedure B, except (S)-morpholine-3-carboxylic acid (4 equiv.) was the amine reactant, Hunig's base (5 equiv.) was used instead of triethylamine, and the contents were heated to 90° C. for 18 h as a solution in THF/water (9:1). Solvent was removed under a stream of nitrogen, and the crude material was purified via reverse phase HPLC using a 20-51% acetonitrile/water (in 0.1% TFA) gradient to deliver the desired compound, Compound I-96 (8 mg, 31% yield).

$^1$H NMR (500 MHz, METHANOL-$d_4$) δ 8.81 (s, 1H), 8.34-8.42 (m, 1H), 7.51-7.59 (m, 1H), 7.27-7.35 (m, 1H), 7.02-7.15 (m, 2H), 6.94 (s, 2H), 6.01 (s, 2H), 5.37-5.54 (m, 1H), 4.56 (d, 2H), 4.01-4.09 (m, 1H), 3.89-3.96 (m, 1H), 3.61-3.81 (s, 2H).

Compound I-97

The title compound was prepared following general procedure B, except 1,2,3,4-tetrahydroisoquinoline-1-carboxylic acid (4 equiv.) was the amine reactant, Hunig's base (5 equiv.) was used instead of triethylamine, and the contents were heated to 90° C. for 18 h as a solution in THF/water (9:1). Solvent was removed under a stream of nitrogen, and contents were taken up in ethyl acetate. The organic layer was washed with 1N hydrochloric acid solution, water, and brine, dried over sodium sulfate, filtered, and concentrated in vacuo. The crude material was purified via reverse phase HPLC to deliver the desired compound, Compound I-97 (3.4 mg, 12% yield) as a solid.

$^1$H NMR (500 MHz, METHANOL-$d_4$) δ 8.84-8.89 (m, 1H), 8.42-8.49 (m, 1H), 7.62-7.69 (m, 2H), 7.30-7.40 (m, 4H), 7.06-7.16 (m, 2H), 6.97 (m, 2H), 6.12-6.18 (m, 1H), 6.05 (s, 2H), 4.48-4.58 (m, 1H), 4.14-4.23 (m, 2H), 3.05-3.15 (m, 1H).

Compound I-98

The title compound was prepared following general procedure B, except 3-methyl-5-(piperidin-2-yl)-1,2,4-oxadiazole (4 equiv.) was the amine reactant, Hunig's base (5 equiv.) was used instead of triethylamine, and the contents were heated to 90° C. for 18 h as a solution in THF/water (9:1). Solvent was removed under a stream of nitrogen, and contents were taken up in ethyl acetate. The organic layer was washed with 1N hydrochloric acid solution, water, and brine, dried over sodium sulfate, filtered, and concentrated in vacuo. The crude material was purified via reverse phase HPLC to deliver the desired compound, Compound I-98 (5.3 mg, 20% yield) as a solid.

$^1$H NMR (500 MHz, METHANOL-$d_4$) δ 8.77-8.83 (m, 1H), 8.37-8.45 (m, 1H), 7.54 (s, 1H), 7.26-7.36 (m, 1H), 7.03-7.17 (m, 2H), 6.93 (s, 2H), 6.48-6.55 (m, 1H), 6.00 (s, 2H), 4.60-4.75 (m, 1H), 3.45-3.55 (m, 1H), 2.49-2.58 (m, 1H), 2.38 (s, 3H), 2.15-2.27 (m, 1H), 1.74-1.94 (m, 3H), 1.59-1.73 (m, 1H).

Compound I-99

The title compound was prepared following general procedure B, except methyl morpholine-3-carboxylate (4 equiv.) was the amine reactant, Hunig's base (3 equiv.) was used instead of triethylamine, and the contents were heated to 120° C. for 2 h as a solution in NMP. Solvent was removed and the crude material was purified via reverse phase HPLC to deliver the desired compound, Compound I-99 (7 mg, 25% yield) as a solid.

$^1$H NMR (400 MHz, CD$_3$OD) δ 8.71-8.75 (m, 1H), 8.21-8.26 (m, 1H), 7.39-7.43 (m, 1H), 7.19-7.29 (m, 1H), 6.97-7.12 (m, 2H), 6.85-6.88 (m, 1H), 6.75-6.82 (m, 1H), 5.90-5.95 (m, 2H), 5.20-5.31 (m, 1H), 4.45 (s, 1H), 3.93-4.01 (m, 1H), 3.82-3.93 (m, 2H), 3.66-3.75 (m, 2H).

Compound I-105

The title compound was prepared following general procedure B, except piperidine-2-carboxamide (4 equiv.) was the amine reactant, 6 equivalents of triethylamine was used, and the contents were heated to 60° C. for 48 h as a solution in THF/water (9:1). Solvent was removed under a stream of nitrogen, and the crude material was purified via reverse phase HPLC using a 20-51% acetonitrile/water (in 0.1% TFA) gradient to deliver the desired compound, Compound I-105 (12 mg, 48% yield) as a solid.

$^1$H NMR (500 MHz, METHANOL-$d_4$) δ 8.80-8.87 (m, 1H), 8.35-8.41 (m, 1H), 7.58-7.65 (m, 1H), 7.28-7.36 (m, 1H), 7.05-7.16 (m, 2H), 6.91-7.02 (m, 2H), 6.03 (s, 2H), 5.53-5.61 (m, 1H), 4.65-4.77 (m, 1H), 3.56-3.69 (m, 1H), 2.37-2.46 (m, 1H), 1.62-2.07 (m, 6H).

Compound I-106

The title compound was prepared following general procedure B, except 4-aminotetrahydro-2H-pyran-4-carboxylic acid (3.5 equiv.) was the amine reactant, 5 equivalents of triethylamine was used, and the contents were heated to 200° C. for 10 min in the microwave as a solution in NMP. The reaction mixture was diluted with water and filtered. The filtrate was basified to pH 10 with 3N sodium hydroxide solution, and extracted with dichloromethane. The filtrate was then acidified to pH 1 with 1N hydrochloric acid solution and extracted with dichloromethane. The organic layer was concentrated in vacuo, and the crude material was purified via reverse phase HPLC to deliver the desired compound, Compound I-106 (2.3 mg, 9% yield) as a solid.

$^1$H NMR (500 MHz, METHANOL-$d_4$) δ 8.81-8.87 (m, 1H), 8.31-8.35 (m, 1H), 7.38-7.41 (m, 1H), 7.25-7.34 (m, 1H), 7.04-7.15 (m, 2H), 6.89-6.98 (m, 2H), 6.01 (s, 2H), 3.87-3.96 (m, 2H), 3.76-3.87 (m, 2H), 2.36-2.45 (m, 2H), 2.23-2.33 (m, 2H).

Compound I-110

The title compound was prepared following general procedure B, except 4-amino-1-(tert-butoxycarbonyl)piperidine-4-carboxylic acid (3 equiv.) was the amine reactant, 5 equivalents of triethylamine was used, and the contents were heated to 120° C. for 18 h as a solution in DMSO. Without workup, the crude material was purified via reverse phase HPLC to deliver the desired compound, Compound I-110 (8.2 mg, 26% yield) as a solid.

$^1$H NMR (500 MHz, METHANOL-$d_4$) δ 8.83 (s, 1H), 8.31-8.36 (m, 1H), 7.39 (s, 1H), 7.26-7.36 (m, 1H), 7.02-7.14 (m, 2H), 6.91 (s, 2H), 6.00 (s, 2H), 3.75-3.88 (m, 2H), 3.36-3.49 (m, 2H), 2.29 (br. s., 4H), 1.50 (s, 9H).

Compound I-111

The title compound was prepared following general procedure B, except 1,2,3,4-tetrahydroisoquinoline (2.5 equiv.) was the amine reactant, no triethylamine was used, and the contents were heated to 120° C. for 18 h as a solution in THF. Solvent was removed under a stream of nitrogen, and the crude material was purified via reverse phase HPLC using a 20-51% acetonitrile/water (in 0.1% TFA) gradient to deliver the desired compound, Compound I-111 (13.9 mg, 55% yield) as a solid.

$^1$H NMR (500 MHz, METHANOL-$d_4$) δ 8.82-8.86 (m, 1H), 8.28-8.34 (m, 1H), 7.68-7.73 (m, 1H), 7.24-7.35 (m, 6H), 6.93-7.15 (m, 5H), 6.00-6.06 (m, 2H), 5.24 (s, 2H), 4.27-4.33 (m, 2H), 3.10-3.16 (m, 2H).

Compound I-122

In a 25 ml flask was dissolved Compound I-110 (0056 g, 0.096 mmol) in DCM (Volume: 2 ml), and TFA (2 mL, 26.0 mmol). After stirring for 3 h at room temperature, the reaction was complete. The solvent was removed in vacuo to give pure product, Compound I-122 (13.9 mg, 55% yield) as a white solid.

$^1$H NMR (500 MHz, METHANOL-$d_4$) δ 8.78-8.86 (m, 1H), 8.30-8.38 (m, 1H), 7.26-7.38 (m, 2H), 7.01-7.15 (m, 2H), 6.84-6.96 (m, 2H), 5.97 (s, 2H), 3.36-3.51 (m, 4H), 2.50-2.67 (m, 4H).

Compound I-126

The title compound was prepared following general procedure B, except 6-methoxy-1,2,3,4-tetrahydroisoquinoline-1-carboxylic acid (3 equiv.) was the amine reactant, no triethylamine was used, and the contents were heated to 120° C. for 18 h as a solution in DMSO. The reaction mixture was filtered, and directly purified via reverse phase HPLC to deliver the desired compound, Compound I-126 (11 mg, 38% yield) as a solid.

$^1$H NMR (500 MHz, METHANOL-$d_4$) δ 8.82-8.85 (m, 1H), 8.33-8.37 (m, 1H), 7.53-7.59 (m, 2H), 7.27-7.34 (m, 1H), 7.10 (m, 2H), 6.86-6.97 (m, 4H), 5.01 (s, 2H), 5.96 (m, 1H), 4.35-4.45 (m, 1H), 4.04-4.15 (m, 1H), 3.84 (s, 3H), 3.04 (m, 2H).

Compound I-127

The title compound was prepared following general procedure B, except 6-hydroxy-1,2,3,4-tetrahydroisoquinoline-1-carboxylic acid (3 equiv.) was the amine reactant, no triethylamine was used, and the contents were heated to 120° C. for 18 h as a solution in DMSO. The reaction mixture was filtered, and directly purified via reverse phase HPLC to deliver the desired compound, Compound I-127 (5.2 mg, 18% yield) as a solid.

$^1$H NMR (500 MHz, METHANOL-$d_4$) δ 8.83-8.87 (m, 1H), 8.37-8.42 (m, 1H), 7.57-7.63 (m, 1H), 7.42-7.48 (m, 1H), 7.28-7.36 (m, 1H), 7.05-7.16 (m, 2H), 6.90-7.00 (m, 2H), 6.71-6.80 (m, 2H), 6.02 (s, 2H), 5.94-5.99 (m, 1H), 4.42-4.51 (m, 1H), 3.99-4.13 (m, 1H), 3.16-3.27 (m, 2H), 2.94-3.02 (m, 1H).

Compound I-128

The title compound was prepared following general procedure B, except 5-fluoro-1,2,3,4-tetrahydroisoquinoline-1-carboxylic acid (3 equiv.) was the amine reactant, no triethylamine was used, and the contents were heated to 60° C. for 18 h as a solution in DMSO, followed by heating to 120° C. for 1 h. The reaction mixture was filtered, and directly purified via reverse phase HPLC to deliver the desired compound, Compound I-128 (5.7 mg, 20% yield) as a solid.

$^1$H NMR (500 MHz, $CD_3OD$) δ 8.83 (m, 1H), 8.31 (m, 1H), 7.68 (m, 1H), 7.28 (m, 2H), 7.03 (m, 6H), 6.02 (s, 2H), 5.21 (s, 2H), 4.27 (m, 2H), 3.08 (m, 2H).

Compound I-130

A solution of Compound I-122 (as the TFA salt) in dichloromethane was treated with triethylamine (2 equiv.) and propionyl chloride (1.1 equiv.) at 25° C. Reaction was stirred at 25° C. for 18 h. A slurry remained, so contents treated with 5 drops of NMP (contents go clear), and 1 additional equivalents of both propionyl chloride and triethylamine. Contents were then stirred at 25° C. for 18 h. Solvent was removed in vacuo and the crude material was purified via reverse phase HPLC to deliver the desired compound, Compound I-130 (5.5 mg, 47% yield) as a solid.

$^1$H NMR (500 MHz, METHANOL-$d_4$) δ 8.82-8.86 (m, 1H), 8.33-8.38 (m, 1H), 7.38-7.42 (m, 1H), 7.28-7.36 (m, 1H), 7.05-7.15 (m, 2H), 6.89-6.99 (m, 2H), 6.00 (s, 2H), 4.04-4.13 (m, 1H), 3.82-3.92 (m, 1H), 3.55-3.64 (m, 1H), 3.44-3.52 (m, 1H), 2.21-2.52 (m, 7H), 1.16 (t, 3H).

Compound I-131

A solution of Compound I-122 (as the TFA salt) in dichloromethane was treated with triethylamine (2 equiv.)

and methyl carbonochloridate (1.1 equiv.) at 25° C. Reaction was stirred at 25° C. for 18 h. A slurry remained, so contents treated with 5 drops of NMP (contents go clear), and 1 additional equivalents of both methyl carbonochloridate and triethylamine. Contents were then stirred at 25° C. for 18 h. Solvent was removed in vacuo and the crude material was purified via reverse phase HPLC to deliver the desired compound, Compound I-131 (3.8 mg, 32% yield) as a solid.

$^1$H NMR (500 MHz, METHANOL-$d_4$) δ 8.81-8.86 (m, 1H), 8.30-8.37 (m, 1H), 7.39 (s, 1H), 7.26-7.34 (m, 1H), 7.04-7.15 (m, 2H), 6.93 (m, 2H), 6.00 (s, 2H), 3.88 (m, 2H), 3.73 (s, 3H), 3.42-3.52 (m, 2H), 2.28-2.34 (br.s., 4H).

Compound I-132

A solution of Compound I-122 (as the TFA salt) in dichloromethane was treated with triethylamine (2 equiv.) and ethyl isocyanate (1.1 equiv.) at 25° C. Reaction was stirred at 25° C. for 18 h. A slurry remained, so contents treated with 5 drops of NMP (contents go clear), and 1 additional equivalents of both ethyl isocyanate and triethylamine. Contents were then stirred at 25° C. for 18 h. Solvent was removed in vacuo and the crude material was purified via reverse phase HPLC to deliver the desired compound, Compound I-132 (5.9 mg, 49% yield) as a solid.

$^1$H NMR (500 MHz, METHANOL-$d_4$) δ 8.83-8.86 (m, 1H), 8.32-8.37 (m, 1H), 7.38-7.41 (m, 1H), 7.28-7.34 (m, 1H), 7.05-7.15 (m, 2H), 6.89-6.99 (m, 2H), 6.00 (s, 2H), 3.74-3.83 (m, 2H), 3.37-3.45 (m, 2H), 3.19-3.26 (m, 2H), 2.30 (s, 4H), 1.14 (s, 3H).

Compound I-153

The title compound was prepared following general procedure B, except 2-(methylamino)benzoic acid was the amine reactant, 5 equivalents of triethylamine was used, and the contents were heated to 120° C. for 12 h as a solution in THF. Solvent was removed under vacuum and the crude material was purified via reverse phase HPLC to deliver the desired compound, Compound I-153 (5.5 mg, 40% yield) as a solid.

$^1$H NMR (500 MHz, METHANOL-$d_4$) δ 8.80-8.85 (m, 1H), 8.12-8.21 (m, 2H), 7.71-7.78 (m, 1H), 7.53-7.64 (m, 3H), 7.28-7.36 (m, 1H), 7.06-7.17 (m, 2H), 6.91-7.02 (m, 2H), 6.04 (s, 2H), 3.72 (s, 3H).

Compound I-161 and Compound I-162

The title compounds were prepared following general procedure B, except 3-methylpiperidine-2-carboxylic acid was the amine reactant, Hunig's base (5 equiv.) was used instead of triethylamine, and the contents were heated to 120° C. for 18 h as a solution in THF/water (5:1). Solvent was removed under vacuum and the crude material was purified via reverse phase HPLC to deliver the desired compounds, Compound I-161 (cis, racemic, 5.1 mg, 20% yield) as a solid and Compound I-162 (trans, racemic, 1.3 mg, 5%) as a solid.

$^1$H NMR (400 MHz, CD$_3$OD) Compound I-161 δ 8.77-8.80 (m, 1H), 8.30-8.34 (m, 1H), 7.52-7.56 (m, 1H), 7.23-7.32 (m, 2H), 6.99-7.12 (m, 2H), 6.87-6.94 (m, 2H), 5.98 (s, 2H), 5.24-5.30 (m, 1H), 4.50-4.61 (m, 1H), 3.72-3.83 (m, 1H), 2.09-2.21 (m, 1H), 1.91-2.00 (m, 1H), 1.72-1.81 (m, 2H), 1.48-1.62 (m, 1H), 1.22 (d, J=7.43 Hz, 3H).

$^1$H NMR (400 MHz, CD$_3$OD) Compound I-162 δ 8.78-8.80 (m, 1H), 8.31-8.35 (m, 1H), 7.55-7.58 (m, 1H), 7.24-7.32 (m, 1H), 7.01-7.12 (m, 2H), 6.87-6.96 (m, 2H), 5.99 (s, 2H), 5.29-5.39 (m, 1H), 3.44-3.57 (m, 1H), 2.67-2.75 (m, 1H), 1.78-2.03 (m, 3H), 1.54-1.72 (m, 2H), 1.19 (d, 3H).

Compound I-197

The title compound was prepared following general procedure B, except 2-(piperidin-4-yloxy)acetic acid was the amine reactant, Hunig's base (5 equiv.) was used instead of triethylamine, and the contents were heated to 100° C. for 18 h as a solution in THF/water (10:1). Solvent was removed in vacuo and the crude material was purified via reverse phase HPLC to deliver the desired compound, Compound I-197 (3 mg, 11% yield) as a solid.

$^1$H NMR (500 MHz, METHANOL-$d_4$) δ 8.80-8.84 (m, 1H), 8.24-8.30 (m, 1H), 7.57-7.64 (m, 1H), 7.29-7.35 (m, 1H), 7.05-7.16 (m, 2H), 6.92-7.01 (m, 2H), 6.00-6.05 (m, 2H), 4.28-4.36 (m, 2H), 4.23 (s, 2H), 3.97-4.05 (m, 2H), 3.82-3.89 (m, 1H), 2.05-2.16 (m, 2H), 1.87-1.95 (m, 2H).

Compound I-214

The title compound was prepared following general procedure B, except 4-aminobutanoic acid was the amine reactant, and the contents were stirred for 14 h. The crude material was purified via silica gel chromatography utilizing a 0-10% methanol/dichloromethane gradient to deliver the desired compound, Compound I-214 (20 mg, 57% yield) as a white solid.

$^1$H-NMR (400 MHz, DMSO-$d_6$) δ 12.09 (bs, 1H), 9.08 (d, 1H), 8.21 (d, 1H), 8.19 (bs, 1H), 7.55 (s, 1H), 7.33-7.27 (m, 1H), 7.21-7.18 (m, 2H), 7.08 (ddd, 1H), 6.82 (t, 1H), 5.88 (s, 2H), 3.50 (dd, 2H), 2.30 (dd, 2H), 1.86-1.79 (m, 2H).

Compound I-215

The title compound was prepared following general procedure B, except 4-(methylamino)butanoic acid was the amine reactant. The crude material was purified via silica gel chromatography utilizing a 0-10% methanol/dichloromethane gradient to deliver the desired compound, Compound I-215 (31 mg, 81% yield) as a solid.

$^1$H-NMR (400 MHz, DMSO-$d_6$) δ 9.10 (d, 1H), 8.35 (d, 1H), 7.67 (s, 1H), 7.33-7.28 (m, 1H), 7.22-7.18 (m, 2H), 7.08 (t, 1H), 6.86 (t, 1H), 5.90 (s, 2H), 1.88 (t, 2H), 3.30 (d, 3H), 2.30 (t, 2H), 1.90-1.82 (m, 2H).

Compound I-219

The title compound was prepared following general procedure B, except N-methyl-D-valine was the amine reactant. The crude material was purified via silica gel chromatography utilizing a 0-10% methanol/dichloromethane gradient to deliver the desired compound, Compound I-219 (17 mg, 43% yield) as a solid.

$^1$H-NMR (400 MHz, CD$_3$OD) δ 8.74 (d, 1H), 8.17 (d, 1H), 7.41 (s, 1H), 7.27-7.22 (m, 1H), 7.09-6.98 (m, 2H), 6.87 (d, 1H), 6.81 (t, 1H), 5.93 (s, 2H), 4.71 (d, 1H), 3.31 (s, 3H), 2.51-2.43 (m, 1H), 1.14 (d, 3H), 0.96 (d, 3H).

Compound I-221

The title compound was prepared following general procedure B, except N-methyl-D-leucine was the amine reactant. The crude material was purified via silica gel chromatography utilizing a 0-10% methanol/dichloromethane gradient to deliver the desired compound, Compound I-221 (31 mg, 76% yield) as a solid.

$^1$H-NMR (400 MHz, DMSO-$d_6$) δ 12.86 (bs, 1H), 9.07 (d, 1H), 8.29 (d, 1H), 7.44 (s, 1H), 7.32-7.27 (m, 1H), 7.20-7.15 (m, 1H), 7.16 (d, 1H), 7.08-7.05 (m, 1H), 6.85 (t, 1H), 5.83 (dd, 2H), 3.12 (d, 3H), 3.05-3.00 (m, 1H), 1.91-1.82 (m, 1H), 1.76-1.68 (m, 1H), 1.51-1.47 (m, 1H), 0.89 (d, 3H), 0.85 (d, 3H).

Compound I-185

The title compound was prepared following general procedure B, except 3-(trifluoromethyl)pyrrolidine-3-carboxylic acid was the amine reactant. The crude material was purified via silica gel chromatography utilizing a 0-10% methanol/dichloromethane gradient to deliver the desired compound, Compound I-185 (51 mg, 87% yield) as a solid.

$^1$H-NMR (400 MHz, DMSO-$d_6$) δ 9.05 (d, 1H), 8.29 (d, 1H), 7.53 (s, 1H), 7.29 (q, 1H), 7.24 (d, 1H), 7.21-7.16 (m,

1H), 7.07 (t, 1H), 6.78 (t, 1H), 5.88 (s, 2H), 4.29 (d, 1H), 3.98 (d, 1H), 3.95-3.75 (m, 2H), 2.64-2.37 (m, 2H).

Compound I-180

The title compound was prepared following general procedure B, except 2-amino-4,4,4-trifluorobutanoic acid was the amine reactant. The crude material was purified via silica gel chromatography utilizing a 0-10% methanol/dichloromethane gradient to deliver the desired compound, Compound I-180 (24 mg, 58% yield) as a solid.

$^1$H-NMR (400 MHz, DMSO-$d_6$) δ 13.29 (bs, 1H), 9.07 (d, 1H), 8.26 (d, 1H), 8.15-8.12 (m, 1H), 7.39 (s, 1H), 7.28 (q, 1H), 7.18 (t, 1H), 7.15 (s, 1H), 7.07 (t, 1H), 6.83 (t, 1H), 5.84 (s, 2H), 4.95-4.92 (m, 1H), 3.03-2.94 (m, 2H).

Compound I-178

The title compound was prepared following general procedure B, except 2-amino-4-(methylsulfonyl)butanoic acid was the amine reactant. The crude material was purified via silica gel chromatography utilizing a 0-10% methanol/dichloromethane gradient to deliver the desired compound, Compound I-178 (6 mg, 14% yield) as a solid.

H$^1$ NMR (400 MHz, CD$_3$OD) δ 8.78 (d, 1H), 8.29 (d, 1H), 7.57 (s, 1H), 7.29-7.23 (m, 1H), 7.10-7.04 (m, 1H), 7.03 (t, 1H), 6.91 (d, 1H), 6.89 (t, 1H), 5.98 (s, 2H), 5.24 (dd, 1H), 3.38-3.25 (m, 1H), 3.22-3.16 (m, 1H), 2.29 (s, 3H), 2.67-2.58 (m, 1H), 2.47-2.38 (m, 1H).

Compound I-72

This compound was prepared following the procedure described above for Compound I-71, except the reaction solvent was THF and the work up was carried out with DCM and brine (22 mg, 31%).

$^1$H-NMR (400 MHz, DMSO-$d_6$) δ 9.06 (d, 1H), 8.23 (d, 1H), 7.48 (s, 1H), 7.33-7.27 (m, 1H), 7.23-7.17 (m, 2H), 7.08-7.03 (m, 1H), 6.77-6.73 (m, 1H), 5.86 (s, 2H), 4.33-4.24 (m, 2H), 4.11-4.03 (m, 2H), 3.60-3.55 (m, 1H), 3.14-3.07 (m, 2H), 2.85-2.78 (m, 2H).

Compound I-103

The title compound was prepared following general procedure B, except D-leucine was the amine reactant. The crude material was purified via silica gel chromatography utilizing a 0-10% methanol/dichloromethane gradient to deliver the desired compound, Compound I-103 (18 mg, 46% yield) as a solid.

$^1$H-NMR (400 MHz, DMSO-$d_6$) δ 12.67 (bs, 1H), 9.07 (d, 1H), 8.23 (d, 1H), 8.04 (d, 1H), 7.39 (s, 1H), 7.28 (dd, 1H), 7.20-7.14 (m, 1H), 7.14 (d, 1H), 7.07 (t, 1H), 6.84 (t, 1H), 5.89-5.80 (m, 2H), 4.74-4.64 (m, 1H), 1.86-1.79 (m, 1H), 1.70-1.58 (m, 2H), 0.90 (d, 3H), 0.67 (d, 3H).

Compound I-148

The title compound was prepared following general procedure B, except (R)-2-amino-3,3-dimethylbutanoic acid was the amine reactant. The crude material was purified via silica gel chromatography utilizing a 0-10% methanol/dichloromethane gradient to deliver the desired compound, Compound I-148 (33 mg, 83% yield) as a solid.

$^1$H-NMR (400 MHz, DMSO-$d_6$) δ 12.84 (br. s, 1H), 9.09 (d, 1H), 8.27 (d, 1H), 7.43-7.27 (m, 2H), 7.33-7.27 (m, 1H), 7.18 (t, 1H), 7.15 (d, 1H), 7.08 (t, 1H), 6.85 (t, 1H), 5.85 (s, 2H), 4.58 (d, 1H), 0.96 (s, 9H).

Compound I-151

The title compound was prepared following general procedure B, except (S)-2-amino-3,3-dimethylbutanoic acid was the amine reactant. The crude material was purified via silica gel chromatography utilizing a 0-10% methanol/dichloromethane gradient to deliver the desired compound, Compound I-151 (22 mg, 59% yield) as a solid.

$^1$H-NMR (400 MHz, DMSO-$d_6$) δ 12.84 (br. s, 1H), 9.09 (d, 1H), 8.27 (d, 1H), 7.43-7.27 (m, 2H), 7.33-7.27 (m, 1H), 7.18 (t, 1H), 7.15 (d, 1H), 7.08 (t, 1H), 6.85 (t, 1H), 5.85 (s, 2H), 4.58 (d, 1H), 0.96 (s, 9H).

Compound I-137

The title compound was prepared following general procedure B, except N-methyl-L-leucine was the amine reactant. The crude material was purified via silica gel chromatography utilizing a 0-10% methanol/dichloromethane gradient to deliver the desired compound, Compound I-137 (14 mg, 36% yield) as a solid.

$^1$H-NMR (400 MHz, CD$_3$OD) δ 8.79 (d, 1H), 8.34 (d, 1H), 7.52 (s, 1H), 7.27 (dd, 1H), 7.10-7.01 (m, 2H), 6.95-6.90 (m, 2H), 5.98 (s, 2H), 5.57-5.47 (m, 1H), 3.44 (d, 3H), 2.03-1.98 (m, 2H), 1.74-1.51 (m, 1H), 1.00 (d, 3H), 0.98 (d, 3H).

Compound I-115

The title compound was prepared following general procedure B, except ethyl 5,6,7,8-tetrahydro-[1,2,4]triazolo[4,3-a]pyrazine-3-carboxylate (4 equiv.) was the amine reactant, and the reaction was run in THF. The workup was carried out in dichloromethane and brine. The crude material was purified via silica gel chromatography utilizing a 0-10% methanol/dichloromethane gradient to deliver the desired compound, Compound I-115 (42 mg, 37% yield) as a solid.

$^1$H-NMR (400 MHz, CDCl3) δ 8.47 (d, 1H), 8.35 (d, 1H), 7.40 (s, 1H), 7.21-7.16 (m, 1H), 7.01 (t, 1H), 6.95 (t, 1H), 6.84 (t, 1H), 6.65 (d, 1H), 5.98 (s, 2H), 5.35 (s, 2H), 4.59 (t, 2H), 4.48 (q, 2H), 4.30 (t, 2H), 1.44 (t, 3H).

Compound I-16

Intermediate 1 (0.030 g, 0.080 mmol) was diluted with THF (2.0 ml) then charged with 3-(trifluoromethyl)-5,6,7,8-tetrahydro-[1,2,4]triazolo[4,3-a]pyrazine (0.031 g, 0.161 mmol). Reaction was heated to 50° C. and stirred for 1 hour. At this time, the LC/MS did not show product forming—therefore, at this time TEA (0.056 ml, 0.401 mmol) was added and the resulting reaction mixture was heated to 80° C. overnight. In the morning, clean reaction was detected by LC/MS. The crude reaction was concentrated and purified using SiO$_2$ chromatography employing a 0-50% (7:1 ACN/MeOH) in DCM gradient to deliver the desired material as a white solid (32 mg, 72%).

$^1$H-NMR (400 MHz, DMSO-$d_6$) δ 9.08 (d, 1H), 8.43 (d, 1H), 7.62 (s, 1H), 7.30 (dd, 1H), 7.23 (d, 1H), 7.19 (t, 1H), 7.07 (t, 1H), 6.81 (t, 1H), 5.89 (s, 2H), 5.24 (s, 2H), 4.33-4.25 (m, 4H).

Compound I-112

The title compound was prepared following general procedure B, except D-serine was the amine reactant and the reaction was run in THF/water. The crude material was purified via reverse phase HPLC to deliver the desired compound, Compound I-112 (4 mg, 15% yield) as a solid.

$^1$H-NMR (400 MHz, CD$_3$OD) δ 8.78 (d, 1H), 8.27 (dd, 1H), 7.51 (s, 1H), 7.29-7.23 (m, 1H), 7.07 (t, 1H), 7.02 (t, 1H), 6.92-6.91 (m, 1H), 6.88 (t, 1H), 5.97 (s, 2H), 5.13 (t, 1H), 4.09 (d, 2H).

Compound I-86

The title compound was prepared following general procedure B, except D-valine was the amine reactant and the reaction was run in THF/water. The crude material was purified via reverse phase HPLC to deliver the desired compound, Compound I-86 (2 mg, 7% yield) as a solid.

$^1$H-NMR (400 MHz, CD$_3$OD) δ 8.80 (d, 1H), 8.32 (d, 1H), 7.57 (s, 1H), 7.31-7.25 (m, 1H), 7.10-7.02 (m, 2H), 6.95 (s, 1H), 6.95-6.91 (m, 1H), 6.00 (s, 2H), 4.85 (d, 1H), 2.45-2.36 (m, 1H), 1.11 (d, 3H), 1.10 (d, 3H).

Compound I-88

The title compound was prepared following general procedure B, except L-leucine was the amine reactant and the reaction was run in THF/water. The crude material was purified via reverse phase HPLC to deliver the desired compound, Compound I-88 (3 mg, 10% yield) as a solid.

$^1$H-NMR (400 MHz, DMSO-d$_6$) δ 12.67 (bs, 1H), 9.07 (d, 1H), 8.23 (d, 1H), 8.04 (d, 1H), 7.39 (s, 1H), 7.28 (dd, 1H), 7.20-7.14 (m, 1H), 7.14 (d, 1H), 7.07 (t, 1H), 6.84 (t, 1H), 5.89-5.80 (m, 2H), 4.74-4.64 (m, 1H), 1.86-1.79 (m, 1H), 1.70-1.58 (m, 2H), 0.90 (d, 3H), 0.67 (d, 3H).

Compound I-67

The title compound was prepared following general procedure B, except glycine was the amine reactant and the reaction was run in THF/water. The crude material was purified via reverse phase HPLC to deliver the desired compound, Compound I-67 (8 mg, 33% yield) as a solid.

$^1$H-NMR (400 MHz, DMSO-d$_6$) δ 12.72 (bs, 1H), 9.07 (d, 1H), 8.25 (d, 1H), 8.14 (bs, 1H), 7.45 (s, 1H), 7.32-7.27 (m, 1H), 7.21-7.16 (m, 1H), 7.16 (d, 1H), 7.07 (t, 1H), 6.80 (t, 1H), 5.86 (s, 2H), 4.15 (d, 2H).

Compound I-69

The title compound was prepared following general procedure B, except L-valine was the amine reactant and the reaction was run in THF/water. The crude material was purified via reverse phase HPLC to deliver the desired compound, Compound I-69 (24 mg, 66% yield) as a solid.

$^1$H-NMR (400 MHz, CD$_3$OD) δ 8.80 (d, 1H), 8.32 (d, 1H), 7.57 (s, 1H), 7.31-7.25 (m, 1H), 7.10-7.02 (m, 2H), 6.95 (s, 1H), 6.95-6.91 (m, 1H), 6.00 (s, 2H), 4.85 (d, 1H), 2.45-2.36 (m, 1H), 1.11 (d, 3H), 1.10 (d, 3H).

Compound I-89

The title compound was prepared following general procedure B, except N-methyl-L-valine was the amine reactant and the reaction was run in THF/water. The crude material was purified via reverse phase HPLC to deliver the desired compound, Compound I-89 (22 mg, 76% yield) as a solid.

$^1$H-NMR (400 MHz, CD$_3$OD) δ 8.74 (d, 1H), 8.17 (d, 1H), 7.41 (s, 1H), 7.27-7.22 (m, 1H), 7.09-6.98 (m, 2H), 6.87 (d, 1H), 6.81 (t, 1H), 5.93 (s, 2H), 4.71 (d, 1H), 3.31 (s, 3H), 2.51-2.43 (m, 1H), 1.14 (d, 3H), 0.96 (d, 3H).

Compound I-79

The title compound was prepared following general procedure B, except thiomorpholine 1,1-dioxide was the amine reactant and the reaction was run in THF/water. The workup was carried out in dichloromethane and brine. The crude material was purified via reverse phase HPLC to deliver the desired compound, Compound I-79 (4 mg, 16% yield).

$^1$H-NMR (400 MHz, CDCl3) δ 8.47-8.45 (m, 1H), 8.33 (d, 1H), 7.24 (s, 1H), 7.19 (dd, 1H), 7.02 (t, 1H), 6.96 (t, 1H), 6.84 (t, 1H), 6.57 (d, 1H), 5.94 (s, 2H), 4.36 (dd, 2H), 3.19 (dd, 2H).

Compound I-68

The title compound was prepared following general procedure B, except L-serine was the amine reactant and the reaction was run in THF/water. The crude material was purified via reverse phase HPLC to deliver the desired compound, Compound I-68 (12 mg, 48% yield) as a solid.

$^1$H-NMR (400 MHz, CD$_3$OD) δ 8.78 (d, 1H), 8.27 (dd, 1H), 7.51 (s, 1H), 7.29-7.23 (m, 1H), 7.07 (t, 1H), 7.02 (t, 1H), 6.92-6.91 (m, 1H), 6.88 (t, 1H), 5.97 (s, 2H), 5.13 (t, 1H), 4.09 (d, 2H).

Compound I-65

The title compound was prepared following general procedure B, except tert-butylamine (50 equiv.) was the amine reactant and the reaction was heated to 60° C. for 48 h as a solution in THF. The reaction was concentrated in vacuo, and the crude material was purified via silica gel chromatography utilizing a 0-30% (7:1 acetonitrile/methanol) in dichloromethane gradient to deliver the desired compound, Compound I-65 (19 mg, 96% yield) as a solid $^1$H-NMR (400 MHz, CDCl3) δ 8.45 (d, 1H), 8.14 (d, 1H), 7.40 (bs, 1H), 7.21-7.16 (m, 1H), 7.03-6.91 (m, 3H), 6.61 (d, 1H), 5.93 (s, 2H), 1.58 (s, 9H).

Compound I-113

This compound was prepared by treating Compound I-115 with LiOH.H$_2$O in a 2:1:1 solvent mixture of THF:MeOH:water. Once decarboxylation was complete, the reaction was acidified using 1N HCl, and was then extracted (3 times) with dichloromethane. The organic portions were combined, dried (Na$_2$SO$_4$), filtered, and then concentrated. The crude material was purified via silica gel chromatography using a 0-10% MeOH in dichloromethane gradient to deliver the title compound, Compound I-113, as a white solid (5 mg, 5%).

$^1$H-NMR (400 MHz, DMSO-d$_6$) δ 9.07 (d, 1H), 8.50 (s, 1H), 8.41 (d, 1H), 7.61 (s, 1H), 7.32-7.28 (m, 1H), 7.24 (d, 1H), 7.19 (t, 1H), 7.07 (t, 1H), 6.81 (t, 1H), 5.89 (s, 2H), 5.14 (s, 2H), 4.28-4.16 (m, 4H).

Compound I-174

The title compound was prepared following general procedure B, except 3-aminopropanoic acid was the amine reactant, and contents were heated to 110° C. for 14 h as a solution in THF/water (10:1). The crude material was purified via reverse-phase prep-HPLC to deliver the desired compound, Compound I-174 (17 mg, 56%) as a white solid.

$^1$H NMR (500 MHz, CD$_3$OD) δ ppm 8.80 (br. s., 1H), 8.17 (br. s., 1H), 7.55 (s, 1H), 7.29 (d, 1H), 7.01-7.15 (m, 2H), 6.95 (br. s., 1H), 6.91 (d, 1H), 6.00 (br. s., 2H), 3.96 (t, 2H), 2.77 (t, 2H).

Compound I-169

The title compound was prepared following general procedure B, except 3-(methylamino)propanoic acid was the amine reactant, and contents were heated to 110° C. for 4 h as a solution in THF/water (10:1). Reaction was concentrated in vacuo, and the crude material was purified via reverse phase HPLC to deliver the desired compound, Compound I-169 (14 mg, 56% yield) as a solid.

$^1$H NMR (500 MHz, CD$_3$OD) δ ppm 8.71 (d, 1H), 8.17 (d, 1H), 7.48 (s, 1H), 7.19 (d, 1H), 6.89-7.05 (m, 2H), 6.84 (d, 2H), 5.90 (s, 2H), 4.05 (t, 2H), 3.42 (d, 3H), 2.71 (t, 2H).

Compound I-170

The title compound was prepared following general procedure B, except 2-methyl-3-(methylamino)propanoic acid was the amine reactant, and contents were heated to 110° C. for 18 h as a solution in THF/water (10:1). Reaction was concentrated in vacuo, and the crude material was purified via reverse phase HPLC to deliver the desired compound, Compound I-170 (13 mg, 51% yield) as a solid.

$^1$H NMR (500 MHz, CD$_3$OD) δ ppm 8.68 (d, 1H), 8.09 (d, 1H), 7.38 (s, 1H), 7.14-7.21 (m, 1H), 6.90-7.02 (m, 2H), 6.76-6.83 (m, 2H), 5.87 (s, 2H), 4.01 (dd, 1H), 3.77 (dd, 1H), 3.34 (d, 3H), 2.92 (m, 1H), 1.14 (d, 3H).

Compound I-171

The title compound was prepared following general procedure B, except (R)-2-(aminomethyl)-3-methylbutanoic acid was the amine reactant, and contents were heated to 110° C. for 18 h as a solution in THF/water (10:1). Reaction was concentrated in vacuo, methanol was added, and the crude material was purified via reverse phase HPLC to deliver the desired compound, Compound I-171 (15 mg, 57% yield) as a solid.

$^1$H NMR (500 MHz, METHANOL-d$_4$) δ ppm 8.86 (d, 1H), 8.29 (d, 1H), 7.60 (s, 1H), 7.33 (d, 1H), 7.06-7.17 (m, 2H), 6.99-7.05 (m, 1H), 6.95 (d, 1H), 6.04 (s, 2H), 3.93-4.08 (m, 2H), 2.71 (ddd, 1H), 2.10 (dq, 1H), 1.07-1.20 (m, 6H).

Compound I-173

The title compound was prepared following general procedure B, except (S)-2-(aminomethyl)-3-methylbutanoic acid was the amine reactant, and contents were heated to 110° C. for 18 h as a solution in THF/water (10:1). Reaction was concentrated in vacuo, and the crude material was purified via reverse phase HPLC to deliver the desired compound, Compound I-173 (18 mg, 68% yield) as a solid.

$^1$H NMR (500 MHz, CD$_3$OD) δ ppm 8.84 (d, 1H), 8.25 (d, 1H), 7.56 (s, 1H), 7.31 (d, 1H), 7.04-7.15 (m, 2H), 6.96-7.01 (m, 1H), 6.93 (d, 1H), 6.01 (s, 2H), 3.91-4.04 (m, 2H), 2.71 (dt, 1H), 2.04-2.14 (m, 1H), 1.14 (d, 3H), 1.10 (d, 3H).

Compound I-181

The title compound was prepared following general procedure B, except (R)-3-amino-4-methylpentanoic acid was the amine reactant, and contents were heated to 100° C. for 18 h as a solution in THF/water (10:1). Reaction was concentrated in vacuo, and the crude material was purified via reverse phase HPLC to deliver the desired compound, Compound I-181 (7 mg, 21% yield).

$^1$H NMR (500 MHz, CD$_3$OD) δ ppm 8.85 (d, 1H), 8.29 (d, 1H), 7.65 (s, 1H), 7.30-7.37 (m, 1H), 7.07-7.16 (m, 2H), 6.98-7.03 (m, 2H), 6.05 (s, 2H), 4.91-4.96 (m, 1H), 2.71-2.86 (m, 2H), 2.05-2.13 (m, 1H), 1.08 (dd, 6H).

Compound I-182

The title compound was prepared following general procedure B, except (S)-3-amino-4-methylpentanoic acid was the amine reactant, and contents were heated to 100° C. for 18 h as a solution in THF/water (10:1). Reaction was concentrated in vacuo, and the crude material was purified via reverse phase HPLC to deliver the desired compound, Compound I-182 (7 mg, 24% yield).

$^1$H NMR (500 MHz, CD$_3$OD) δ ppm 8.79-8.85 (m, 1H), 8.23-8.28 (m, 1H), 7.63 (d, 1H), 7.30 (br. s., 1H), 7.03-7.15 (m, 2H), 6.94-7.02 (m, 2H), 6.03 (br. s., 2H), 2.66-2.85 (m, 2H), 2.01-2.13 (m, 2H), 1.00-1.10 (m, 6H).

Compound I-195 and Compound I-196

The title compounds were prepared following general procedure B, except 4-methyl-3-(methylamino)pentanoic acid was the amine reactant, and contents were heated at 100° C. for 18 h as a solution in THF/water (10:1). Reaction was concentrated in vacuo, and the crude material was purified via reverse phase HPLC to deliver two compounds, Compound I-195 (5 mg, 16% yield), and Compound I-196 (12 mg, 41% yield).

$^1$H NMR for Compound I-195 (500 MHz, CD$_3$OD) δ ppm 8.82 (d, 1H), 8.28 (d, 1H), 7.57 (s, 1H), 7.29-7.34 (m, 1H), 7.05-7.15 (m, 2H), 6.93-6.98 (m, 2H), 6.02 (s, 2H), 2.92 (m, 2H), 2.75-2.82 (m, 3H), 2.10-2.19 (m, 2H), 1.13 (d, 3H) 1.00 (d, 3H).

$^1$H NMR for Compound I-196 (500 MHz, CD$_3$OD) δ ppm 8.83 (d, 1H), 8.21 (d, 1H), 7.64 (s, 1H), 7.29-7.35 (m, 1H), 7.05-7.14 (m, 2H), 6.95-7.01 (m, 2H), 6.03 (s, 2H), 3.27 (s, 3H).

Compound I-202

The title compound was prepared in 3 steps:

Step 1: Synthesis of (R)-methyl 3-((5-fluoro-2-(1-(2-fluorobenzyl)-5-(isoxazol-3-yl)-1H-pyrazol-3-yl)pyrimidin-4-yl)amino)-4-methylpentanoate To a stirred solution of Compound I-181 in ether/methanol (3:1) was added TMS-diazomethane (2 equiv.) slowly at 23° C. The mixture was stirred for 30 min, and the solvent was removed in vacuo. The crude material was purified via silica gel chromatography to deliver the desired intermediate, (R)-methyl 3-((5-fluoro-2-(1-(2-fluorobenzyl)-5-(isoxazol-3-yl)-1H-pyrazol-3-yl)pyrimidin-4-yl)amino)-4-methylpentanoate (58 mg, 56% yield).

Step 2: Synthesis of (R)-methyl 3-((5-fluoro-2-(1-(2-fluorobenzyl)-5-(isoxazol-3-yl)-1H-pyrazol-3-yl)pyrimidin-4-yl)(methyl)amino)-4-methylpentanoate To a 0° C. solution of (R)-methyl 3-((5-fluoro-2-(1-(2-fluorobenzyl)-5-(isoxazol-3-yl)-1H-pyrazol-3-yl)pyrimidin-4-yl)amino)-4-methylpentanoate in DMF was added sodium hydride (1.2 equiv.) followed by iodomethane (1.1 equiv.). The mixture was stirred and warmed to 23° C. Reaction quenched with water, and layers separated. Aqueous layer extracted with dichloromethane, and organic layer dried, filtered, and concentrated. Residue taken onto the next step without further purification.

Step 3: Synthesis of Compound I-202

To a stirred solution of (R)-methyl 3-((5-fluoro-2-(1-(2-fluorobenzyl)-5-(isoxazol-3-yl)-1H-pyrazol-3-yl)pyrimidin-4-yl)(methyl)amino)-4-methylpentanoate in THF/water/methanol (3:1:1) was added solid sodium hydroxide (3 equiv.). Contents stirred at 23° C. for 18 h. Solvent was removed in vacuo, and the crude material was purified via reverse phase HPLC to deliver Compound I-202 (0.5 mg, 12% yield) as a solid.

$^1$H NMR (500 MHz, CD$_3$OD) δ ppm 8.83 (d, 1H), 8.29 (d, 1H), 7.58 (s, 1H), 7.32 (dd, 2H), 7.06-7.15 (m, 1H), 6.93-6.99 (m, 2H), 6.02 (s, 2H), 2.90 (dd, 2H), 2.75-2.82 (m, 3H), 2.14 (m, 2H), 1.13 (d, 3H), 1.00 (d, 3H).

Compound I-206

The title compound was prepared following general procedure B, except 3-amino-2,2-difluoropropanoic acid was the amine reactant, and contents were heated to 110° C. for 18 h as a solution in dioxane/water (10:1). Reaction was concentrated in vacuo, methanol was added, and the crude material was purified via reverse phase HPLC to deliver the desired compound, Compound I-206 (20 mg, 22% yield).

$^1$H NMR (500 MHz, CD$_3$OD) δ ppm 8.78 (d, 1H), 8.22 (d, 1H), 7.61 (s, 1H), 7.25-7.31 (m, 1H), 7.07-7.12 (m, 1H), 7.05 (t, 1H), 6.96 (d, 1H), 6.89 (t, 1H), 6.00 (s, 2H), 4.35 (t, 2H).

Compound I-251

The title compound was prepared following general procedure B, except (S)-3-amino-4,4-dimethylpentanoic acid was the amine reactant, and contents were heated to 110° C. for 18 h as a solution in dioxane/water (10:1). Reaction was concentrated in vacuo, methanol was added, and the crude material was purified via reverse phase HPLC to deliver the desired compound, Compound I-251 (15 mg, 44% yield).

$^1$H NMR (500 MHz, CD$_3$OD) δ ppm 8.83 (d, 1H), 8.26 (d, 1H), 7.63 (s, 1H), 7.29-7.35 (m, 1H), 7.06-7.16 (m, 2H), 7.02 (d, 1H), 6.95-7.00 (m, 1H), 6.04 (s, 2H), 2.82-2.88 (m, 1H), 2.72 (dd, 2H), 1.08 (s, 9H).

Compound I-266

A solution of 5,5-difluoropiperidine-2-carboxylic acid (2.5-3.0 equivalents), triethylamine (8.0-10 equivalents) and Intermediate 1 was stirred in dioxane/water (2:1 ratio) at 100° C. until complete consumption of starting material by LC/MS, following general procedure B. The solution was poured into 1N HCl and extracted with dichloromethane. The organic phases were dried over sodium sulfate, filtered and concentrated in vacuo. Purification by silica gel chromatography (3-8% methanol/dichloromethane gradient) yielded the desired compound, Compound I-266, (29 mg, combined yield from 2 experiments) as an off-white solid.

$^1$H-NMR (400 MHz, CDCl$_3$) δ 8.46 (d, 1H), 8.25 (d, 1H), 7.36 (s, 1H), 7.20 (app. q, 1H), 7.03 (app. t, 1H), 6.96 (app. t, 1H), 6.69 (app. t, 1H), 6.58 (d, 1H), 6.22 (d, 1H), 6.08 (d, 1H), 5.95 (m, 1H), 4.59 (m, 1H), 3.53 (dd, 1H), 2.37 (br. d, 1H), 2.08 (m, 2H), 1.57 (m, 1H).

Compound I-263

The title compound was prepared in 4 steps:

Step 1: Synthesis of Tert-Butyl 4,4-difluoropiperidine-1-carboxylate

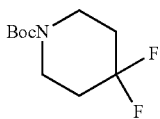

A suspension of 4,4-difluoropiperidine hydrochloride and triethylamine (2.2 equivalents) in dichloromethane was added to a solution of di-tert-butyl dicarbonate (1.1 equivalents) in dichloromethane slowly via a pipet (note: gas evolution was observed). The reaction was stirred at ambient temperature until complete consumption of starting material as indicated by NMR. The reaction mixture was diluted with dichloromethane and washed with half-saturated ammonium chloride solution. The organic layer was dried over sodium sulfate, filtered, and the solvent was removed in vacuo. Purification by silica gel chromatography (2% ethyl acetate/hexane) yielded tert-butyl 4,4-difluoropiperidine-1-carboxylate (73%).

Step 2: Synthesis of 1-(tert-butoxycarbonyl)-4,4-difluoropiperidine-2-carboxylic Acid

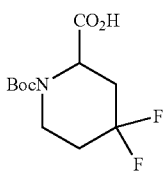

A 0.5 M solution of tert-butyl 4,4-difluoropiperidine-1-carboxylate, tetramethylethylenediamine (TMEDA, 1.0 equivalent) in anhydrous ether at −78° C. was treated dropwise with sec-butyllithium (1.2 equivalents) and stirred for 2 hours. Carbon dioxide gas was then introduced via bubbling for 2 min. The reaction was stirred at −78° C. for 10 min, warmed to ambient temperature and stirred for an additional hour. The resulting mixture was then quenched with water, acidified to pH 2 with 1N HCl and extracted with ethyl acetate. The combined organic layers were dried over sodium sulfate, filtered, and the solvent was removed in vacuo. Purification by silica gel chromatography (20-50% ethyl acetate/hexane gradient) yielded 1-(tert-butoxycarbonyl)-4,4-difluoropiperidine-2-carboxylic acid (87%).

Step 3: Synthesis of 2-carboxy-4,4-difluoropiperidinium Trifluoroacetate

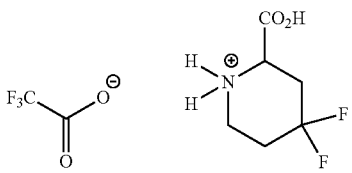 [SMILES: O=C([O-])C(F)(F)F ; O=C(O)C1CC(F)(F)CC[NH2+]1]

A solution of trifluoroacetic acid (20 equivalents) and 1-(tert-butoxycarbonyl)-4,4-difluoropiperidine-2-carboxylic acid was stirred in dichloromethane at ambient temperature until complete consumption of starting material by LC/MS. The reaction mixture was concentrated in vacuo to afford 2-carboxy-4,4-difluoropiperidinium trifluoroacetate (Intermediate WW) as a sticky pale orange solid (>99%) which was used without further manipulation.

Step 4: Synthesis of Compound I-263

The title compound was prepared following general procedure B, except 2-carboxy-4,4-difluoropiperidinium trifluoroacetate (2.4 equiv.) was the amine reactant, and contents were heated to 100° C. The crude material was purified via silica gel chromatography utilizing a 2-7% methanol/dichloromethane gradient to deliver the desired compound, Compound I-263 (26 mg, 56% yield) as an off-white solid.

$^1$H-NMR (400 MHz, acetone-$d_6$) δ 8.88 (s, 1H), 8.30 (d, 1H), 7.50 (s, 1H), 7.31 (app. q, 1H), 7.14 (app. t, 1H), 7.08 (app. t, 1H), 7.01 (s, 1H), 6.90 (app. t, 1H), 5.96 (s, 2H), 5.70 (br. d, 1H), 4.69 (br. d, 1H), 3.68 (app. t, 1H), 2.84 (m, 1H), 2.52 (m, 1H), 2.23 (m, 2H).

Compound I-247

A mixture of Intermediate-1 (26.0 mg), (2S)-3-methyl-2-(methylamino)pentanoic acid (0.030 g, 3 equiv and triethylamine (0.096 ml, 10 equiv) in a 10:1 mixture of THF/Water was heated at 85° C. for 16 hrs, following procedure B. The reaction was cooled, the solvent removed, and the resulting crude purified via preparative reverse-phase HPLC to afford the desired product, Compound I-247 as a solid (2.4 mg, 7.2% yield). d $^1$H NMR (500 MHz, CD$_3$OD) δ 8.80 (d, 1H), 8.32 (d, 1H), 7.51 (s, 1H), 7.26-7.32 (m, 1H), 7.02-7.13 (m, 2H), 6.92-6.95 (m, 1H), 6.91 (d, 1H), 5.99 (s, 2H), 5.49 (s, 1H), 3.44 (d, 3H), 2.03 (s, 1H), 1.03 (t, 3H), 0.98 (dd, 2H), 0.85-0.92 (m, 3H).

Compound I-255

A mixture of Intermediate-1 (36.0 mg), 4-isopropylpiperidine-4-carboxylic acid (3 equiv.), and TEA (10 equiv.), in a 10:1 mixture of THF/Water was heated at 90° C. for 3 hrs, following general procedure B. The reaction was cooled, the solvent removed, and the resulting crude to afford the desired product, Compound I-255, as a white solid (22 mg 49% yield)

$^1$H NMR (500 MHz, CHLOROFORM-d) δ ppm 8.49 (d, 1H), 8.35 (d, 1H), 7.64 (s, 1H), 7.48 (s, 1H), 7.20-7.25 (m, 1H), 7.05 (s, 1H), 7.01-7.05 (m, 3H), 6.67 (d, 1H), 5.98 (s, 2H), 4.80 (d, 2H), 3.72-3.79 (m, 1H), 3.23 (t, 2H), 2.35 (d, 3H), 1.80-1.92 (m, 2H), 1.62 (td, 2H), 1.41 (t, 1H), 0.97 (d, 6H)

Compound I-254

A mixture of Intermediate-1 (35.0 mg), 4 2-(piperidin-4-yl)benzoic acid (3 equiv.), and TEA (10 equiv.), in a 10:1 mixture of THF/Water was heated at 90° C. for 2 hrs. The reaction mixture was cooled, the solvent removed, and the mixture treated with 1N HCl and the resulting crude was purified via preparative reverse-phase HPLC to afford the desired product, Compound I-254, as a white solid (1 mg, 2% yield).

$^1$H NMR (500 MHz, CDCl$_3$) δ ppm 8.45 (d, 1H), 8.22 (d, 1H), 7.99 (dd, 1H), 7.51-7.56 (m, 1H), 7.39-7.44 (m, 2H), 7.32 (t, 1H), 7.17-7.24 (m, 1H), 6.95-7.09 (m, 2H), 6.86-6.93 (m, 1H), 6.61 (s, 1H), 5.98 (s, 2H), 4.90 (br. s., 2H), 3.94 (br. s., 1H), 3.21 (t, 2H), 2.03-2.09 (m, 2H), 1.80-1.90 (m, 2H)

Compound I-256

A mixture of Intermediate 1 (20.0 mg), 4-(tert-pentyl) piperidine-4-carboxylic acid (3 equiv., as the TFA salt), and TEA (10 equiv.), in a 10:1 mixture of THF/Water was heated at 90° C. for 2 hrs. The reaction was cooled, the organic solvent removed, 1N HCl added, and the resulting precipitate was filtered to afford the desired product, Compound I-256, as a white solid (13.4 mg, 47% yield).

$^1$H NMR (500 MHz, CDCl$_3$) δ ppm: 8.45 (d, 1H), 8.17 (d, 1H), 7.29 (s, 1H), 7.15-7.22 (m, 1H), 6.99-7.07 (m, 1H), 6.96 (t, 1H), 6.85 (t, 1H), 6.58 (d, 1H), 5.97 (s, 2H), 4.69 (d, 2H), 3.04 (t, 2H), 2.25 (d, 2H), 1.71 (td, 2H), 1.35-1.45 (m, 2H), 0.90-0.95 (m, 6H), 0.87 (t, 3H)

Compound I-258

To a solution of (S)-2-((5-fluoro-2-(1-(2-fluorobenzyl)-5-(isoxazol-3-yl)-1H-pyrazol-3-yl)pyrimidin-4-yl)amino)-3-methylbutanoic acid (Compound I-69, 0.040 g, 0.088 mmol) in DCM (1.8 ml) was added CDI (0.043 g, 0.264 mmol). The reaction was heated at 45° C. for 60 minutes. After this, DBU (0.013 ml, 0.088 mmol) and cyclopropanesulfonamide (0.053 g, 0.440 mmol) were added. Reaction was continued for an additional 40 minutes at the same temperature, until it was deemed to be complete. At this time, the reaction was quenched with 1N HCl. The layers were separated and the aqueous portion was extracted two times with DCM. The organic portions were combined, dried (Na$_2$SO4), filtered, and concentrated. The crude material was purified using silica chromatography 0-10% MeOH/DCM gradient to afford the desired compound, Compound I-258, as a white solid (10.8 mg, 80% yield).

$^1$H NMR (500 MHz, CHLOROFORM-d) δ ppm: 9.93 (br. s., 1H), 8.46 (d, 1H), 8.21 (d, 1H), 7.32 (s, 1H), 7.21-7.25 (m, 1H), 6.99-7.09 (m, 2H), 6.91-6.97 (m, 1H). 6.61 (d, 1H), 6.03-6.08 (m, 1H), 5.93-5.99 (m, 1H), 5.45 (d, 1H), 4.35 (t, 1H), 2.77-2.88 (m, 1H), 2.52-2.62 (m, 1H), 1.12-1.15 (m, 6H), 1.05-1.07 (m, 2H), 0.88-0.90 (m, 2H).

Compound I-259

To a solution of Compound I-88 in dichloromethane was added CDI (3 equiv.). Reaction heated to 45° C. for 30 min, after which DBU (1 equiv.) and methanesulfonamide (5 equiv.) were added. Reaction was heated for an additional 40 min until reaction was complete. At this time, the reaction was quenched with 1N hydrochloric acid solution. The layers were separated, and the aqueous portion was extracted with dichloromethane (2×). The organic portions were combined, dried (Na$_2$SO$_4$), filtered, and concentrated. The crude material was purified via silica gel chromatography utilizing a 0-10% methanol/dichloromethane gradient to deliver the desired compound, Compound I-259 (15.8 mg, 44% yield) as a white solid.

$^1$H NMR (500 MHz, CDCl$_3$) δ ppm 10.14 (br. s., 1H), 8.47 (d, 1H), 8.22 (d, 1H), 7.33 (s, 1H), 7.21-7.26 (m, 1H), 6.99-7.08 (m, 2H), 6.91-6.96 (m, 1H), 6.63 (d, 1H), 5.96-6.09 (m, 2H), 5.3 (br. s., 1H) 4.51-4.60 (m, 1H), 3.06-3.11 (m, 3H), 1.90-2.00 (m, 1H), 1.71-1.87 (m, 2H), 1.05 (d, 3H), 0.96-0.99 (m, 3H).

Compound I-261

To a solution of Compound I-103 in dichloromethane was added CDI (3 equiv.). Reaction was heated to 45° C. for 1.5 h, after which DBU (1 equiv.) and cyclopropanesulfonamide (5 equiv.) were added. Reaction was heated for an additional 40 minutes, until reaction was complete. The reaction was quenched with 1N hydrochloric acid solution, the layers were separated, and the aqueous portion was extracted with dichloromethane (2×). The organic portions were combined, dried (Na$_2$SO$_4$), filtered, and concentrated. The crude material was purified using silica gel chromatography utilizing a 0-10% methanol/dichloromethane gradient to deliver the desired compound, Compound I-261 (40 mg, 80% yield) as a solid.

$^1$H NMR (500 MHz, CDCl$_3$) δ ppm: 10.20 (br. s., 1H), 8.47 (s, 1H), 8.22 (br. s., 1H), 7.35 (s, 1H), 7.17-7.26 (m, 1H), 6.91-7.09 (m, 3H), 6.64 (s, 1H), 5.92-6.09 (m, 2H), 5.39 (br. s., 1H), 4.59-4.70 (m, 1H), 2.76-2.89 (m, 1H), 2.50-2.65 (m, 1H), 1.95 (dt, 1H), 1.69-1.86 (m, 2H), 1.04 (d, 2H), 0.98 (d, 3H), 0.85-0.95 (m, 3H), 0.74-0.83 (m, 1H).

Compound I-264

A mixture of Intermediate-1 (38.8 mg), 2,2-dimethylthiomorpholine 1,1-dioxide, (3 equiv.), and TEA (10 equiv.), in a 10:1 mixture of THF/Water was heated at 90° C. for 3 hrs, following general procedure B. The reaction was cooled, poured into a 1:1 mixture of 1N HCl and DCM, the organics extracted (three times) combined, dried, purified by silica chromatography utilizing a 0-10% methanol/dichloromethane gradient to deliver the desired compound, Compound I-264 (40 mg, 77% yield) as a white solid.

$^1$H NMR (500 MHz, CDCl$_3$) δ ppm 8.48 (d, 1H), 8.31 (d, 1H), 7.26 (s, 1H), 7.22 (q, 1H), 7.02-7.07 (m, 1H), 6.99 (t, 1H), 6.86-6.91 (m, 1H), 6.59 (d, 1H), 5.97 (s, 2H), 4.41 (br.s., 2H), 4.09 (br.s., 2H), 3.26 (t, 2H), 1.43 (s, 6H).

Compound I-270

A mixture of Intermediate-1 (313 mg), (S)-4-methyl-3-(methylamino)pentanoic acid (3 equiv.), and TEA (10 equiv.), in a 10:1 mixture of THF/Water was heated at 85° C. for 3 hrs, following procedure B. The reaction was cooled, poured into a 1:1 mixture of 1N HCl and DCM, the organics extracted (three times) combined, dried, purified via silica gel chromatography utilizing a 0-10% methanol/dichloromethane gradient to deliver the desired compound, Compound I-270 (56 mg, 14% yield) as a white solid.

$^1$H NMR (500 MHz, CDCl$_3$) δ ppm 8.48-8.53 (m, 1H), 8.31 (br. s., 1H), 7.39 (s, 1H), 7.20-7.26 (m, 1H), 7.13 (t, 1H), 6.99-7.05 (m, 2H), 6.66 (br. s., 1H), 5.86-5.94 (m, 2H), 3.19 (d, 3H), 2.85 (dd, 1H), 2.60-2.73 (m, 1H), 1.93-2.05 (m, 1H), 1.26 (s, 1H), 0.93 (d, 3H), 1.08 (d, 3H).

Compound I-271

A mixture of Intermediate 1 (313 mg), (1R,5S,6R)-3-azabicyclo[3.1.0]hexane-6-carboxylic acid (3 equiv.), and TEA (10 equiv.), in a 10:1 mixture of THF/Water was heated at 85° C. for 3 hrs, following general procedure B. The reaction was cooled, poured into a 1:1 mixture of 1N HCl and DCM, the organics extracted (three times) combined, dried, purified via silica gel chromatography utilizing a 0-10% methanol/dichloromethane gradient to deliver the desired compound, Compound I-271 (22 mg, 33% yield) as a white solid.

$^1$H NMR (500 MHz, CDCl$_3$) δ ppm: 8.49 (d, 1H), 8.35 (d, 1H), 7.45 (br. s., 1H), 7.23 (td, 1H), 7.05 (d, 1H), 7.01 (d, 2H), 6.63 (d, 1H), 5.97 (s, 2H), 4.32 (d, 2H), 3.95 (d, 2H), 2.40 (br. s., 2H, 1.65 (t, 1H), 0.97 (d, 1H).

Compound I-268

The title compound was prepared in 2 steps:

Step 1: Synthesis of 2-carboxy-5,5-dimethylpiperidinium Trifluoroacetate

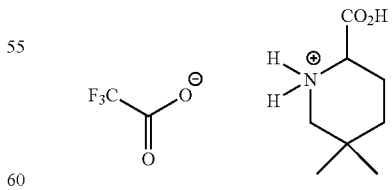

2-carboxy-5,5-dimethylpiperidinium trifluoroacetate was prepared as a white solid following the procedure for the synthesis of 2-carboxy-4,4-difluoropiperidinium trifluoroacetate, as described in the preparation of Compound I-263, with the exception of using 3,3-dimethylpiperidine hydrochloride in step 1.

Step 2: Synthesis of Compound I-268

The title compound was prepared following general procedure B, except 2-carboxy-5,5-dimethylpiperidinium trifluoroacetate was the amine reactant, and contents were heated to 100° C. The resulting solution was poured into water and acidified to pH 3 with aqueous 1N hydrochloric acid solution. The resulting precipitate was collected by vacuum filtration, washed with HCl solution (pH 3) and ether to deliver the desired compound, Compound I-268 (38 mg, 62% yield) as a white solid.

$^1$H-NMR (400 MHz, DMSO-d$_6$) δ 13.0 (br. s, 1H), 9.10 (d, 1H), 8.33 (d, 1H), 7.50 (s, 1H), 7.33 (app. q, 1H), 7.22 (m, 2H), 7.10 (app. t, 1H), 6.85 (app. t, 1H), 5.89 (s, 2H), 5.38 (m, 1H), 3.99 (m, 1H), 3.03 (m, 1H), 2.11 (m, 1H), 2.01 (m, 1H), 1.44 (br. d, 1H), 1.32 (td, 1H), 0.97 (s, 3H), 0.95 (s, 3H).

Compound I-245

A solution of methyl 2-(4-aminotetrahydro-2H-pyran-4-yl)acetate hydrochloride (3.0 equivalents), triethylamine (10 equivalents) and Intermediate 1 was stirred in dioxane/water (2:1 ratio) at 100° C. until complete consumption of starting material by LC/MS, following general procedure B. The solution was poured into water and acidified to pH 3 with 1N HCl and extracted with dichloromethane. The organic phases were dried over sodium sulfate, filtered and concentrated in vacuo. Purification by reverse-phase HPLC (20-65% acetonitrile in water with 0.1% trifluoroacetic acid, 20 minute gradient) yielded Compound I-245 (8.8 mg, 13%) as a white solid.

$^1$H-NMR (400 MHz, CD$_3$OD) δ 8.82 (d, 1H), 8.31 (d, 1H), 7.53 (s, 1H), 7.30 (app. q, 1H), 7.09 (m, 1H), 7.05 (app. t, 1H), 7.01 (d, 1H), 6.97 (app. t, 1H), 6.00 (s, 2H), 3.82 (dt, 2H), 3.74 (td, 2H), 3.20 (s, 2H), 2.65 (br. d, 2H), 2.06 (m, 2H).

Compound I-155

The title compound was prepared following general procedure B, except (R)-pyrrolidin-2-ylmethanol was the amine reactant, and contents were heated to 40° C. for 18 min as a solution in THF. The reaction was diluted with ethyl acetate and washed with water and brine. The organic phase was dried over Na$_2$SO$_4$, filtered, and concentrated in vacuo. The crude material was purified via silica gel chromatography utilizing a 20-60% ethyl acetate/hexanes gradient to deliver the desired compound, Compound I-155 (11 mg, 44% yield) as a white solid.

$^1$H-NMR (400 MHz, CDCl$_3$) δ 8.43 (d, 1H), 8.14 (d, 1H), 7.27 (s, 1H), 7.19 (m, 1H), 7.01 (app. t, 1H), 6.97 (app. t, 1H), 6.89 (app. t, 1H), 6.57 (d, 1H), 5.94 (s, 2H), 5.29 (br. s, 1H), 4.52 (m, 1H), 3.88 (m, 2H), 3.78 (m, 2H), 2.13 (m, 1H), 2.07-1.92 (m, 2H), 1.79 (m, 1H).

Compound I-160

The title compound was prepared following general procedure B, except piperidin-2-ylmethanol was the amine reactant, and contents were heated to 55° C. for 4 d as a solution in THF/DMSO (2:1). The reaction was diluted with ethyl acetate and washed with water and brine. The organic phase was dried over Na$_2$SO$_4$, filtered, and concentrated in vacuo. The crude material was purified via silica gel chromatography utilizing a 30-60% ethyl acetate/hexanes gradient to deliver the desired compound, Compound I-160 (9.6 mg, 70% yield) as a clear oil.

$^1$H-NMR (400 MHz, CDCl$_3$) δ 8.44 (d, 1H), 8.17 (d, 1H), 7.26 (s, 1H), 7.19 (m, 1H), 7.02 (app. t, 1H), 6.97 (app. t, 1H), 6.86 (app. t, 1H), 6.58 (d, 1H), 5.97 (d, 1H), 5.93 (d, 1H), 4.81 (m, 1H), 4.25 (m, 1H), 4.14 (m, 1H), 3.83 (br. s, 1H), 3.79 (m, 1H), 3.28 (m, 1H), 1.85-1.65 (m, 6H).

Compound I-183

The title compound was prepared following general procedure B, except tert-butyl pyrazolidine-1-carboxylate (1.1 equiv.) was the amine reactant, and contents were heated to 70° C. for 5 d as a solution in THF/DMSO (4:1). The reaction was poured into water and extracted with ethyl acetate. The organic phase was dried over Na$_2$SO$_4$, filtered, and concentrated in vacuo. The crude material was purified via silica gel chromatography utilizing a 20% ethyl acetate/hexanes gradient to deliver the desired compound, Compound I-183 (53 mg, 75% yield).

$^1$H-NMR (400 MHz, CDCl$_3$) δ 8.44 (d, 1H), 8.26 (d, 1H), 7.30 (s, 1H), 7.18 (m, 1H), 7.01 (app. t, 1H), 6.95 (app. t, 1H), 6.84 (app. t, 1H), 6.56 (d, 1H), 5.96 (s, 2H), 4.40-3.60 (br. m, 4H), 2.13 (app. quintet, 2H), 1.45 (s, 9H).

Compound I-193

A solution of trifluoroacetic acid (20 equivalents) and Compound I-183 was stirred in dichloromethane at ambient temperature until complete consumption of starting material by LC/MS. The solution was carefully poured into saturated sodium bicarbonate and dichloromethane. The layers were separated and the organic layer was dried over sodium sulfate, filtered, and the solvent was removed in vacuo to yield Compound I-193 (35 mg, 85%) as a white solid.

$^1$H-NMR (400 MHz, CDCl$_3$) δ 8.43 (d, 1H), 8.17 (d, 1H), 7.31 (s, 1H), 7.18 (m, 1H), 7.01 (app. t, 1H), 6.95 (app. t, 1H), 6.82 (app. t, 1H), 6.57 (d, 1H), 5.96 (s, 2H), 4.58 (br. s, 1H), 3.87 (m, 2H), 3.19 (app. t, 2H), 2.19 (app. quintet, 2H).

Compound I-213

A solution of ethyl bromoacetate (1.0 equivalent), N,N-diisopropylethylamine (1.5 equivalents) and Compound I-193 was stirred in dimethylformamide at ambient temperature until complete consumption of starting material by LC/MS. The solution was diluted with water and extracted with ethyl acetate. The combined organic layers were dried over sodium sulfate, filtered, and the solvent was removed in vacuo. Purification by silica gel chromatography (50% ethyl acetate/hexanes) yielded Compound I-213 (20 mg, 59%) as a clear oil.

$^1$H-NMR (400 MHz, CDCl$_3$) δ 8.44 (d, 1H), 8.21 (d, 1H), 7.32 (s, 1H), 7.17 (m, 1H), 7.01 (app. t, 1H), 6.95 (app. t, 1H), 6.83 (app. t, 1H), 6.57 (d, 1H), 5.96 (s, 2H), 4.22 (q, 2H), 3.98 (app. t, 2H), 3.70 (s, 2H), 3.28 (app. t, 2H), 2.25 (app. quintet, 2H), 1.28 (t, 3H).

Compound I-216

A solution of sodium hydroxide (3.0 N in water, 8.0 equivalents) and Compound I-213 was stirred in methanol at ambient temperature until complete consumption of starting material by LC/MS. The reaction mixture was concentrated, diluted with water and neutralized to pH 6-7 by addition of 1N HCl. Crude product was collected by vacuum filtration and purification by reverse-phase HPLC (5-95% acetonitrile in water with 0.1% trifluoroacetic acid, 20 minute gradient) yielded Compound I-216 (13 mg, 72%) as an off-white solid.

$^1$H-NMR (400 MHz, CD$_3$OD) δ 9.09 (d, 1H), 8.29 (d, 1H), 7.53 (s, 1H), 7.33 (m, 1H), 7.22 (m, 2H), 7.10 (app. t, 1H), 6.84 (app. t, 1H), 5.90 (s, 2H), 3.84 (m, 2H), 3.57 (s, 2H), 3.12 (m, 2H), 2.17 (app. quintet, 2H).

Compound I-222

A solution of 2-(pyrrolidin-2-yl)acetic acid hydrochloride (2.3 equivalents), triethylamine (10 equivalents) and Intermediate 1 was stirred in dioxane/water (2:1 ratio) at 100° C. until complete consumption of starting material by LC/MS following procedure B. The solution was diluted with water and neutralized to pH 3 by addition of 1N HCl. Resultant solid was collected by filtration and dried in vacuo to yield Compound I-222 (63 mg, 94%).

¹H-NMR (400 MHz, DMSO-d₆) δ 12.3 (s, 1H), 9.11 (d, 1H), 8.24 (d, 1H), 7.48 (s, 1H), 7.33 (m, 1H), 7.21 (m, 1H), 7.11 (m, 2H), 6.90 (m, 1H), 5.87 (s, 2H), 4.62 (m, 1H), 3.80 (m, 1H), 3.65 (m, 1H), 2.82 (m, 1H), 2.39 (m, 1H), 2.12-1.90 (m, 3H), 1.84 (m, 1H).

Compound I-184

Compound was obtained by General Procedure B, starting from Intermediate 1. Purification by silica gel chromatography (20-50% ethyl acetate/hexanes gradient) yielded Compound I-184 (62 mg, 81%) as a clear oil.

¹H-NMR (400 MHz, CDCl3) δ 8.45 (d, 1H), 8.22 (d, 1H), 7.27 (s, 1H), 7.19 (m, 1H), 7.02 (app. t, 1H), 6.97 (app. t, 1H), 6.87 (app. t, 1H), 6.59 (d, 1H), 5.97 (d, 1H), 5.93 (d, 1H), 4.76 (br. m, 1H), 4.34-3.96 (br. m, 3H), 3.96-3.74 (br. m, 2H), 3.50-3.10 (br. m, 4H), 1.49 (s, 9H).

Compound I-211 and Compound I-212

A solution of trifluoroacetic acid (20 equivalents) and Compound I-184 was stirred in dichloromethane at ambient temperature until complete consumption of starting material by LC/MS. The solution was carefully poured into saturated sodium bicarbonate and extracted with dichloromethane. The combined organic layers were dried over sodium sulfate, filtered, and the solvent was removed in vacuo. Purification by reverse-phase HPLC (5-75% acetonitrile in water with 0.1% trifluoroacetic acid, 20 minute gradient) yielded two products:

Compound I-211 (17 mg, 28% as TFA salt) as a clear oil.
¹H-NMR (400 MHz, CD₃OD) δ 8.79 (m, 1H), 8.35 (m, 1H), 7.52 (s, 1H), 7.28 (m, 1H), 7.10 (m, 1H), 7.04 (m, 1H), 6.90 (m, 1H), 6.85 (m, 1H), 5.97 (s, 2H), 5.08 (m, 1H), 4.91 (m, 1H), 4.09 (m, 1H), 4.01 (m, 1H), 3.85 (app. t, 1H), 3.71 (app. d, 1H), 3.52 (app. d, 1H), 3.45 (m, 1H), 3.40 (m, 1H).

Compound I-212 (19 mg, 32%) as a clear oil. ¹H-NMR (400 MHz, CD₃OD) δ 8.80 (s, 1H), 8.34 (d, 1H), 7.61 (d, 1H), 7.29 (m, 1H), 7.10 (app. t, 1H), 7.05 (app. t, 1H), 6.94 (m, 1H), 6.91 (app. t, 1H), 6.00 (s, 2H), 5.12-4.98 (m, 1H*), 4.82 (m, 1H), 4.59-4.32 (m, 1H*), 4.17 (m, 1H*), 3.93-3.58 (m, 4H*), 3.65-3.33 (m, 1H*). Sets of rotamer peaks (~0.5H each) seen for select protons marked with *.

Compound I-150

The title compound was prepared in 3 steps:
Step 1: Synthesis of 5-fluoro-2-(1-(2-fluorobenzyl)-5-(isoxazol-3-yl)-1H-pyrazol-3-yl)-6-hydroxypyrimidin-4(3H)-one (the Preparation of this Compound was Described in a Published Patent Application, WO2013/101830)

A mixture of 1-(2-fluorobenzyl)-5-(isoxazol-3-yl)-1H-pyrazole-3-carboximidamide, diethyl 2-fluoromalonate (1 equiv.) and DBU (1 equiv.) in ethanol was heated to 70° C. for 24 h. The mixture was concentrated under vacuum to give an oil. The oil was purified by column chromatography (0 to 20% dichloromethane in methanol) to give 5-fluoro-2-(1-(2-fluorobenzyl)-5-(isoxazol-3-yl)-1H-pyrazol-3-yl)-6-hydroxypyrimidin-4(3H)-one (145 mg, 100% yield) as a white solid.

¹H NMR (500 MHz, CD₃OD) δ ppm 8.81 (d, 1H), 7.42 (s, 1H), 7.26-7.36 (m, 1H) 7.05-7.18 (m, 2H), 6.97 (t, 1H), 6.92 (d, 1H), 5.97 (s, 2H).

Step 2: Synthesis of 3-(3-(4,6-dichloro-5-fluoropyrimidin-2-yl)-1-(2-fluorobenzyl)-1H-pyrazol-5-yl)isoxazole A mixture of 5-fluoro-2-(1-(2-fluorobenzyl)-5-(isoxazol-3-yl)-1H-pyrazol-3-yl)-6-hydroxypyrimidin-4(3H)-one (1 equiv.) and POCl₃ (40 equiv.) was heated to 70° C. for 24 h. The mixture was concentrated under vacuum to give a white solid. It was diluted in ethyl acetate and washed with water. The organic layer was dried, filtered and evaporated to give 3-(3-(4,6-dichloro-5-fluoropyrimidin-2-yl)-1-(2-fluorobenzyl)-1H-pyrazol-5-yl)isoxazole (61 mg, 38% yield) as a white solid.

¹H NMR (500 MHz, CDCl₃) δ ppm 8.40 (s, 1H) 7.37 (s, 1H) 7.10-7.18 (m, 1H) 6.88-7.00 (m, 2H) 6.76 (t, 1H) 6.53 (d, 1H) 5.96 (s, 2H).

Step 3: Synthesis of Compound I-150

A mixture of 3-(3-(4,6-dichloro-5-fluoropyrimidin-2-yl)-1-(2-fluorobenzyl)-1H-pyrazol-5-yl)isoxazole (1 equiv.), morpholine [1M in THF] (1 equiv.) and Hunig's base (1 equiv.) in THF was stirred at 23° C. for 24 h. The mixture was diluted in ethyl acetate and washed with 1N HCl solution. The organic layer was dried, filtered and evaporated to give a white solid. The solid was purified by column chromatography (0-100% ethyl acetate in hexanes) to deliver the desired compound, Compound I-150 (32 mg, 47% yield) as a white solid.

¹H NMR (500 MHz, CDCl₃) δ ppm 8.47 (d, 1H), 7.31-7.34 (m, 1H), 7.19-7.26 (m, 1H), 7.02-7.09 (m, 1H), 6.99 (t, 1H), 6.84 (t, 1H), 6.59 (d, 1H), 6.00 (s, 2H), 3.89-3.96 (m, 4H), 3.81-3.89 (m, 4H).

Compound I-172

This compound was prepared in two steps.
Step 1: Synthesis of 3-(3-(4-chloro-5-fluoro-6-methoxypyrimidin-2-yl)-1-(2-fluorobenzyl)-1H-pyrazol-5-yl)isoxazole To a suspension of 3-(3-(4,6-dichloro-5-fluoropyrimidin-2-yl)-1-(2-fluorobenzyl)-1H-pyrazol-5-yl)isoxazole (1 equiv.) in methanol was added sodium methoxide [0.5 M in methanol] (1 equiv.). The mixture was stirred at 23° C. for 4 h. The mixture was treated with HCl (4.0 M in dioxane, 1 equiv.). The mixture was concentrated under vacuum. The resulting solid was dissolved in ethyl acetate and washed with brine. The organic layer was dried, filtered and evaporated to give 3-(3-(4-chloro-5-fluoro-6-methoxypyrimidin-2-yl)-1-(2-fluorobenzyl)-1H-pyrazol-5-yl)isoxazole (42 mg, 85% yield) as a white solid.

¹H NMR (500 MHz, CD₃OD) δ ppm 8.67 (d, 1H), 7.45 (s, 1H), 7.16-7.21 (m, 1H), 6.97-7.04 (m, 1H), 6.94 (t, 1H), 6.83 (d, 1H), 6.74 (t, 1H), 5.88 (s, 2H), 4.12 (s, 3H).

Step 2: Synthesis of Compound I-172

A mixture of 3-(3-(4-chloro-5-fluoro-6-methoxypyrimidin-2-yl)-1-(2-fluorobenzyl)-1H-pyrazol-5-yl)isoxazole (1 equiv.), triethylamine (2 equiv.) and morpholine (2 equiv.) in THF was stirred at 100° C. for 24 h. The mixture was diluted in ethyl acetate and washed with water. The organic layer was dried, filtered and evaporated to give an oil. The oil was purified by column chromatography (0-100% ethyl acetate in hexanes) to give a light brown solid. The solid was rinsed with methanol to deliver the desired compound, Compound I-172 (19 mg, 41% yield) as a white solid.

¹H NMR (500 MHz, DMSO-d₆) δ ppm 9.08 (d, 1H), 7.56 (s, 1H), 7.29-7.36 (m, 1H), 7.18-7.26 (m, 2H), 7.09 (t, 1H), 6.72 (t, 1H), 5.92 (s, 2H), 4.01 (s, 3H), 3.72 (s, 8H).

Compound I-23

A suspension of 2-(1-(2-fluorobenzyl)-5-(isoxazol-3-yl)-1H-pyrazol-3-yl)-5-(trifluoromethyl) pyrimidin-4(3H)-one (this intermediate was described in a published patent application, WO2012/3405 A1) in phosphoryl trichloride (75 equiv.) was heated to 70° C. for 1 h. The phosphoryl trichloride was removed under a stream of nitrogen and the resulting crude intermediate was dissolved in tetrahydrofuran. Morpholine (30 equiv.) was added, and the solution was stirred at room temperature until the reaction was complete by LC/MS. The solution was poured into saturated aqueous ammonium chloride solution and dichloromethane. The layers were separated and the aqueous layer was extracted with dichloromethane. The organics were washed with saturated aqueous sodium chloride, dried over magnesium sulfate, filtered, and the solvent was removed in vacuo. The residue was suspended in diethyl ether and then resulting solid was filtered off to deliver the desired compound, Compound I-23 (6.5 mg, 69% yield) as a white solid.

$^1$H-NMR (400 MHz, CD$_3$OD) δ 8.77 (m, 1H), 8.66 (s, 1H), 7.57 (s, 1H), 7.31-7.26 (m, 1H), 7.12-7.02 (m, 2H), 6.94 (m, 1H), 6.84 (t, 1H), 5.99 (s, 2H), 3.85-3.81 (m, 8H).

Compound I-24

The title compound was synthesized according to the procedure described for Compound I-23, with the exception of using 2-(1-(2-fluorobenzyl)-5-(isoxazol-3-yl)-1H-pyrazol-3-yl) pyrimidin-4(3H)-one (this intermediate was described in previous patent application publication WO2012/3405 A1) as the starting pyrimidone. The final residue was suspended in diethyl ether and then the resulting solid was filtered off to deliver the desired compound, Compound I-24 (42 mg, quantitative yield) as a white solid.

$^1$H-NMR (400 MHz, CD$_3$OD) δ 8.74 (m, 1H), 8.21 (d, 1H), 7.46 (s, 1H), 7.27-7.22 (m, 1H), 7.10-6.99 (m, 2H), 6.89 (m, 1H), 6.79 (t, 1H), 6.70 (d, 1H), 5.95 (s, 2H), 3.77 (br s, 8H).

Compound I-28

The title compound was synthesized according to the procedure described for Compound I-23, with the exception of using 5-chloro-2-(1-(2-fluorobenzyl)-5-(isoxazol-3-yl)-1H-pyrazol-3-yl)pyrimidin-4(3H)-one (this intermediate was described in published patent application WO2012/3405 A1) as the starting pyrimidone. The final residue was suspended in diethyl ether and then resulting solid was filtered off to deliver the desired compound, Compound I-28 (7.5 mg, 32% yield) as a solid.

$^1$H-NMR (400 MHz, CDCl3) δ 8.44 (m, 1H), 8.38 (s, 1H), 7.30 (s, 1H), 7.21-7.15 (m, 1H), 7.03-6.98 (s, 1H), 6.95 (t, 1H), 6.82 (t, 1H), 6.57 (m, 1H), 5.95 (s, 2H), 3.85-3.81 (m, 8H).

Compound I-29

The title compound was synthesized according to the procedure described for Compound I-23, with the exception of using 2-(1-(2-fluorobenzyl)-5-(isoxazol-3-yl)-1H-pyrazol-3-yl)-6-oxo-1,6-dihydropyrimidine-5-carbonitrile (this intermediate was described in a previous patent application publication, WO2012/3405 A1) as the starting pyrimidone. The final residue was suspended in diethyl ether and then resulting solid was filtered off to deliver the desired compound, Compound I-29 (18 mg, 84% yield) as a white solid.

$^1$H-NMR (400 MHz, DMSO-d$_6$) δ 9.11 (m, 1H), 8.78 (s, 1H), 7.71 (s, 1H), 7.36-7.31 (m, 1H), 7.27-7.20 (m, 2H), 7.11 (t, 1H), 6.83 (t, 1H), 5.93 (s, 2H), 4.02-4.00 (m, 4H), 3.76-3.74 (m, 4H).

Compound I-73

The title compound was prepared in 2 steps:

Step 1: Synthesis of 2-(1-(2-fluorobenzyl)-5-(isoxazol-3-yl)-1H-pyrazol-3-yl)-5-methoxypyrimidin-4(3H)-one A solution of 1-(2-fluorobenzyl)-5-(isoxazol-3-yl)-1H-pyrazole-3-carboximidamide (1 equiv.), methyl 3-(dimethylamino)-2-methoxyacrylate (3.1 equiv.), and 1,8-diazabicycloundec-7-ene (2 equiv.) was stirred at 100° C. for 6 h. The reaction solution was diluted with dichloromethane and saturated ammonium chloride. The layers were separated and the aqueous layer was extracted with dichloromethane (2×). The organics were washed with saturated ammonium chloride and brine, dried over magnesium sulfate, filtered, and the solvent was remove in vacuo. Purification of the crude material via silica gel chromatography (0-5% methanol in dichloromethane gradient) provided 2-(1-(2-fluorobenzyl)-5-(isoxazol-3-yl)-1H-pyrazol-3-yl)-5-methoxypyrimidin-4-ol (49 mg, 35% yield) as a white solid.

$^1$H-NMR (400 MHz, CD$_3$OD) δ 8.77 (d, 1H), 7.58 (s, 1H), 7.38 (s, 1H), 7.29-7.24 (m, 1H), 7.10-7.02 (m, 2H), 6.92-6.85 (m, 2H), 5.96 (s, 2H), 3.87 (s, 3H).

Step 2: Synthesis of Compound I-73

The title compound was synthesized according to the procedure described for Compound I-23, with the exception of using 2-(1-(2-fluorobenzyl)-5-(isoxazol-3-yl)-1H-pyrazol-3-yl)-5-methoxypyrimidin-4(3H)-one as the starting pyrimidone. The final residue was suspended in diethyl ether and then resulting solid was filtered off to deliver the desired compound, Compound I-73 (50 mg, 86% yield) as a white solid.

$^1$H-NMR (400 MHz, DMSO-d$_6$) δ 9.08 (m, 1H), 8.11 (s, 1H), 7.51 (s, 1H), 7.35-7.29 (m, 1H), 7.24-7.20 (m, 2H), 7.10 (t, 1H), 6.79 (t, 1H), 5.89 (s, 2H), 3.88 (s, 3H), 3.75-3.71 (m, 8H).

Compound I-77

A solution of piperidine-4-carboxylic acid (3 equivalents), triethylamine (10 equivalents), and Intermediate 1 was stirred in tetrahydrofuran and water (1:1 ratio) at 100° C. until complete consumption of starting material by LC/MS, following general procedure B. The solution was diluted with aqueous 1N hydrochloric acid and ethyl acetate. The layers were separated and the aqueous layer was extracted with ethyl acetate and 5:1 dichloromethane/isopropyl alcohol. The organics were combined, dried over magnesium sulfate, filtered, and the solvent was removed in vacuo. Purification by reverse-phase HPLC (5-75% acetonitrile in water with 0.1% trifluoroacetic acid, 20 minute gradient) yielded Compound I-77 (11 mg, 44% yield) as a white solid.

$^1$H-NMR (400 MHz, CD$_3$OD) δ 8.79 (m, 1H), 8.23 (d, 1H), 7.57 (m, 1H), 7.31-7.26 (m, 1H), 7.12-7.03 (m, 2H), 6.96 (m, 1H), 6.90 (t, 1H), 5.99 (s, 2H), 4.70 (d, 2H), 3.51-3.45 (m, 2H), 2.79-2.74 (m, 1H), 2.15-2.11 (m, 2H), 1.90-1.80 (m, 2H).

Compound I-78

The title compound was prepared following general procedure B, except piperidine-3-carboxylic acid was the amine reactant, and contents were heated to 90° C. for 1.5 h as a solution in THF/water (1:1). The solution was diluted with 1N hydrochloric acid solution and ethyl acetate. The layers were separated and the aqueous layer was extracted with ethyl acetate and 5:1 dichloromethane/isopropyl alcohol. The organics were combined, dried over magnesium sulfate, filtered, and the solvent was removed in vacuo. The crude material was purified via reverse phase HPLC (5-75% acetonitrile in water with 0.1% trifluoroacetic acid, 20 minute gradient) to deliver the desired compound, Compound I-78 (7 mg, 28% yield) as a white solid.

$^1$H-NMR (400 MHz, CD$_3$OD) δ 8.81 (m, 1H), 8.28 (d, 1H), 7.60 (m, 1H), 7.33-7.27 (m, 1H), 7.13-7.04 (m, 2H), 6.97-6.92 (m, 2H), 6.01 (s, 2H), 4.52 (d, 1H), 4.31-4.26 (m, 1H), 4.00 (dd, 1H), 3.93-3.84 (m, 1H), 2.84-2.78 (m, 1H), 2.23-2.12 (m, 1H), 2.04-1.88 (m, 2H), 1.82-1.73 (m, 1H).

Compound I-76

The title compound was prepared following general procedure B, except pyrrolidine-3-carboxylic acid was the amine reactant, and contents were heated to 60° C. for 2.5 h as a solution in THF/water (1:1). The solution was diluted with 1N hydrochloric acid solution and ethyl acetate. The layers were separated and the aqueous layer was extracted with ethyl acetate and 5:1 dichloromethane/isopropyl alcohol. The organics were combined, dried over magnesium sulfate, and the solvent was removed in vacuo. The crude material was purified via reverse phase HPLC (5-75% acetonitrile in water with 0.1% trifluoroacetic acid, 20 minute gradient) to deliver the desired compound, Compound I-76 (11 mg, 45% yield) as a white solid.

$^1$H-NMR (400 MHz, CD$_3$OD) δ 8.83 (m, 1H), 8.29-8.27 (m, 1H), 7.63 (s, 1H), 7.33-7.29 (m, 1H), 7.13-7.05 (m, 2H), 6.99-6.96 (m, 2H), 6.03 (s, 2H), 4.23-4.03 (m, 5H), 2.34 (br s, 2H).

Compound I-92

The title compound was prepared following general procedure B, except 2-azabicyclo[2.2.1]heptane-3-carboxylic acid was the amine reactant, and contents were heated to 90° C. for 16 h as a solution in THF/water (10:1). Upon completion of the reaction, 3N hydrochloric acid solution was added and the solvent was removed in vacuo. The crude residue was brought up in water and the solid was filtered and rinsed with water to deliver the desired compound, Compound I-92 (12 mg, 47% yield) as a brown solid.

$^1$H-NMR (400 MHz, CD$_3$OD) exists as >3 diastereomers δ 8.80 (m, 1H), 8.25-8.16 (m, 1H), 7.32-7.28 (m, 2H), 7.12-7.03 (m, 2H), 6.97-6.83 (m, 2H), 6.00-5.96 (m, 2H), 4.51-4.36 (m, 1H), 2.99-2.90 (m, 1H), 2.25 (d, 1H), 1.94-1.57 (m, 6H).

Compound I-100

Sodium hydride (1.0 equivalent) and ethyl 1H-pyrrole-2-carboxylate (1 equivalent) were dissolved in tetrahydrofuran. After stirring for 15 minutes, 0.5 equivalents of pyrrolidine anion was added to a solution of Intermediate 1 (1.0 equivalent) in tetrahydrofuran at room temperature. After 5 minutes, an additional 0.5 equivalents of anion was added. The solution was stirred at room temperature for 45 minutes, 45° C. for 2 hours, and then 65° C. for 15 hours. An additional 1 equivalent of pyrrole anion was added, and after 1.5 hours at 65° C. the solution was diluted with saturated aqueous ammonium chloride solution and dichloromethane. The layers were separated and the aqueous layer was extracted with dichloromethane. The organics were dried over magnesium sulfate, filtered, and the solvent was removed in vacuo. Purification by silica gel chromatography (0-50% ethyl acetate in hexanes) provided Compound I-100 (16 mg, 42% yield) as a white solid.

$^1$H-NMR (400 MHz, CDCl$_3$) δ 8.71 (m, 1H), 8.45 (m, 1H), 7.40 (s, 1H), 7.33-7.32 (m, 1H), 7.22-7.14 (m, 2H), 7.04-6.95 (m, 2H), 6.84 (t, 1H), 6.57 (m, 1H), 6.43-6.41 (m, 1H), 6.00 (s, 2H), 4.23 (q, 2H), 1.25 (t, 3H).

Compound I-104

A solution of Compound I-100 (1 equivalent) in tetrahydrofuran, methanol, and water (3:1:1 ratio) was treated with lithium hydroxide hydrate (1.5 equivalents). The solution was stirred at room temperature for 45 minutes and 45° C. for 3 hours. The solution was diluted with ethyl acetate, aqueous 1N sodium hydroxide, and water. The layers were separated and the aqueous layer was acidified with aqueous 1N hydrochloric acid to pH ~1. The acidified aqueous layer was extracted with ethyl acetate, dried over magnesium sulfate, filtered, and the solvent was removed in vacuo. Purification by reverse-phase HPLC (5-75% acetonitrile in water w/0.1% trifluoroacetic acid, 20 minute gradient) provided Compound I-104 (1 mg, 6% yield) as a white solid.

$^1$H-NMR (400 MHz, CD$_3$OD) δ 8.83 (m, 1H), 8.77 (m, 1H), 7.59 (s, 1H), 7.47 (m, 1H), 7.31-7.25 (m, 1H), 7.16-7.03 (m, 3H), 6.94 (m, 1H), 6.87 (t, 1H), 6.48-6.46 (m, 1H), 6.00 (s, 2H).

Compound I-119

The title compound was prepared following general procedure B, except 1,2,3,4-tetrahydroisoquinoline-3-carboxylic acid (as the HCl salt) was the amine reactant, and the reaction heated as a solution in THF/water (10:1) for 16 h. The solvent was removed in vacuo and the residue brought up in water. The solid was filtered off and the filtrate was purified by reverse-phase HPLC (5-75% acetonitrile in water w/0.1% trifluoroacetic acid, 20 minute gradient) to deliver the desired compound, Compound I-119 (20 mg, 48% yield) as a white solid.

1H-NMR (400 MHz, CD$_3$OD) δ 8.80 (m, 1H), 8.33 (d, 1H), 7.55 (br s, 1H), 7.30-7.27 (m, 5H), 7.12-7.03 (m, 2H), 6.93 (s, 1H), 6.89 (t, 1H), 5.99 (s, 2H), 5.58 (br s, 1H), 5.21 (d, 1H), 5.10 (d, 1H), 3.42-3.40 (m, 2H).

Compound I-140

This was synthesized according to General Procedure B utilizing 1,2,3,4-tetrahydroquinoline-2-carboxylic acid and a 10:1 ratio of tetrahydrofuran:water as solvent. Following consumption of starting material, the solvent was removed in vacuo and the resulting residue was purified by reverse phase HPLC (5-75% acetonitrile in water w/0.1% TFA, 20 minute gradient) to provide Compound I-140 (9 mg, 22% yield) as an orange solid.

$^1$H-NMR (400 MHz, CD$_3$OD) δ 8.79 (m, 1H), 8.35 (d, 1H), 7.47 (s, 1H), 7.30-7.19 (m, 3H), 7.16-7.02 (m, 4H), 6.90-6.85 (m, 2H), 5.97 (s, 2H), 5.04 (t, 1H), 2.85-2.81 (m, 1H), 2.75-2.69 (m, 2H), 1.88-1.80 (m, 1H).

Compound I-120

The title compound was prepared following general procedure B, except (S)-1,2,3,4-tetrahydroisoquinoline-1-carboxylic acid was the amine reactant, and the reaction was heated to 80° C. for 2 h as a solution in THF/water (10:1). Following consumption of starting material, the solvent was removed in vacuo and the resulting residue was brought up in methanol, the solids were filtered off, and the filtrate was purified by reverse phase HPLC (5-75% acetonitrile in water w/0.1% TFA, 20 minute gradient) to deliver the desired compound, Compound I-120 (27 mg, 65% yield) as a white solid.

$^1$H-NMR (400 MHz, CD$_3$OD) δ 8.80 (m, 1H), 8.34 (d, 1H), 7.67-7.64 (m, 1H), 7.55 (s, 1H), 7.34-7.26 (m, 4H), 7.12-7.03 (m, 2H), 6.91 (t, 1H), 6.87 (s, 1H), 6.02 (s, 1H), 5.98 (s, 2H), 4.45-3.37 (m, 1H), 4.13-4.04 (m, 1H), 3.26-3.20 (m, 1H), 3.05 (dt, 1H).

Compound I-121

The title compound was prepared following general procedure B, except (R)-1,2,3,4-tetrahydroisoquinoline-1-carboxylic acid was the amine reactant, and the reaction was heated to 80° C. for 2 h as a solution in THF/water (10:1). Following consumption of starting material, the solvent was removed in vacuo and the resulting residue was brought up in methanol, the solids were filtered off, and the filtrate was purified by reverse-phase HPLC (5-75% acetonitrile in water w/0.1% TFA, 20 minute gradient) to deliver the desired compound, Compound I-121 (17 mg, 62% yield) as a white solid.

$^1$H-NMR (400 MHz, CD$_3$OD) δ 8.80 (m, 1H), 8.34 (d, 1H), 7.67-7.64 (m, 1H), 7.55 (s, 1H), 7.34-7.26 (m, 4H), 7.12-7.03 (m, 2H), 6.91 (t, 1H), 6.87 (s, 1H), 6.02 (s, 1H), 5.98 (s, 2H), 4.45-3.37 (m, 1H), 4.13-4.04 (m, 1H), 3.26-3.20 (m, 1H), 3.05 (dt, 1H).

Compound I-123

The title compound was prepared following general procedure B, except piperidine-4-carbonitrile was the amine reactant, and the reaction was heated to 80° C. for 2 h as a solution in THF/water (10:1). Following consumption of starting material, the reaction solution was diluted with dichloromethane and the solvent was dried over magnesium sulfate. After filtering and removing the solvent in vacuo, the crude material was purified by silica gel chromatography (0-70% ethyl acetate in hexanes) to deliver the desired compound, Compound I-123 (28 mg, 94% yield) as a white solid.

$^1$H-NMR (400 MHz, CD$_3$OD) δ 8.75 (m, 1H), 8.16 (d, 1H), 7.42 (s, 1H), 7.29-7.24 (m, 1H), 7.11-7.06 (m, 1H), 7.02 (t, 1H), 6.90 (m, 1H), 6.80 (t, 1H), 5.95 (s, 2H), 4.24-4.18 (m, 2H), 3.76-3.70 (m, 2H), 3.13 (tt, 1H), 2.08 (ddd, 2H), 1.96-1.87 (m, 2H).

Compound I-141

The title compound was prepared following general procedure B, except 2-aminoacetonitrile (as the HCl salt) was the amine reactant, and the reaction was heated to 90° C. as a solution in THF/water (10:1). After stirring for 15 h, an additional two equivalents of 2-aminoacetonitrile (as the HCl salt) was added and the solution was stirred for another 24 h at which point the solution was diluted with water and ethyl acetate. The layers were separated and the organic layer was washed with water. The organics were dried over magnesium sulfate, filtered, and the solvent was removed in vacuo. Methanol was added, and the resulting desired solid product was filtered off. The methanol filtrate contained dissolved product and was purified by reverse phase HPLC (5-75% acetonitrile in water, 0.1% trifluoroacetic acid, 20 minute gradient) to give additional product, which was combined with the filtered solids to deliver the desired compound, Compound I-141 (11 mg, 35% yield) as a tan solid.

$^1$H-NMR (400 MHz, DMSO-d$_6$) δ 9.11 (m, 1H), 8.43 (t, 1H), 8.36 (d, 1H), 7.61 (s, 1H), 7.36-7.30 (m, 1H), 7.25-7.20 (m, 2H), 7.11 (t, 1H), 6.86 (t, 1H), 5.90 (s, 2H), 4.55 (d, 2H).

Compound I-145

A suspension of sodium azide (1 equivalent), ammonium chloride (1 equivalent), and Compound I-141 (1 equivalent) in N,N-dimethylformamide was heated to 80° C. for 1 hour and then 110° C. for 16 hours. Additional ammonium chloride and sodium azide were added, and after 20 hours the solution was diluted with methanol and water. Purification by reverse-phase HPLC (5-75% acetonitrile in water with 0.1% trifluoroacetic acid, 20 minute gradient) provided Compound I-145 (6 mg, 43%) as a yellow solid.

$^1$H-NMR (400 MHz, DMSO-d$_6$) δ 9.10 (m, 1H), 8.37 (d, 1H), 7.59 (s, 1H), 7.35-7.30 (m, 1H), 7.25-7.20 (m, 2H), 7.10 (t, 1H), 6.81 (t, 1H), 5.90 (s, 2H), 3.93-3.91 (m, 4H), 3.28-3.26 (m, 4H), 2.91 (br s, 2H).

Compound I-139

To a 0° C. solution of 2-methylpropan-2-ol (165 equivalents) in dichloromethane was added sulfurisocyanatidic chloride (150 equivalents). The solution was maintained at 0° C. for 20 minutes, and then 3 equivalents of the resulting sulfonyl chloride was added to a room temperature solution of Compound I-4 (1 equivalent) and triethylamine (3 equivalents) in dichloromethane. The solution was maintained at room temperature for 30 minutes, at which point the solution was diluted with saturated aqueous sodium bicarbonate and ethyl acetate. The layers were separated and the aqueous layer was extracted with ethyl acetate. The organics were combined, dried over magnesium sulfate, filtered, and the solvent was removed in vacuo. Purification by silica gel chromatography (hexanes in ethyl acetate) gave Compound I-139 (8 mg, quantitative yield) as a tan solid.

$^1$H-NMR (400 MHz, CD$_3$OD) δ 8.76 (m, 1H), 8.21 (d, 1H), 7.46 (s, 1H), 7.29-7.24 (m, 1H), 7.12-7.07 (m, 1H), 7.02 (t, 1H), 6.91 (m, 1H), 6.80 (t, 1H), 5.96 (s, 2H), 4.02-3.99 (m, 4H), 3.49-3.47 (m, 2H), 1.46-1.43 (m, 9H).

Compound I-125

To a solution of Compound I-4 (1 equivalent) in dichloromethane was added triethylamine (2 equivalents) followed by methanesulfonyl chloride (1.5 equivalents). The solution was stirred at room temperature for 15 minutes and then diluted with water and ethyl acetate. The layers were separated and the organic layer was washed with water. The organics were dried over magnesium sulfate, filtered, and the solvent was removed in vacuo to Compound I-125 (8.5 mg, quantitative yield) as a tan solid.

$^1$H-NMR (400 MHz, DMSO-d$_6$) δ 9.06 (m, 1H), 8.34 (d, 1H), 7.56 (s, 1H), 7.32-7.27 (m, 1H), 7.22-7.17 (m, 2H), 7.07 (t, 1H), 6.78 (t, 1H), 5.87 (s, 2H), 3.90-3.88 (m, 4H), 3.25-3.22 (m, 4H), 2.88 (s, 3H).

Compound I-146

The title compound was prepared following general procedure B, (1H-tetrazol-5-yl)methanamine (as the HCl salt) was the amine reactant, and the reaction was heated to 90° C. for 3 h as a solution in dioxane/water (3:1). After workup, the organics were washed with water, dried over magnesium sulfate, filtered, and the solvent was removed in vacuo to deliver the desired compound, Compound I-146 (21 mg, 60% yield) as a white solid.

$^1$H-NMR (400 MHz, CD$_3$OD) δ 8.81 (m, 1H), 8.34 (d, 1H), 7.45 (s, 1H), 7.32-7.26 (m, 1H), 7.12-7.03 (m, 2H), 6.94-6.90 (m, 2H), 6.00 (s, 2H), 5.23 (s, 2H).

Compound I-147

A solution of Compound I-139 (1 equiv.) in dichloromethane and trifluoroacetic acid (200 equiv.) was stirred at 23° C. for 2 h, at which point the solvent was removed in vacuo and the residue was brought up in methanol. The solid product was filtered off. Purification of the filtrate by reverse phase HPLC (5-75% acetonitrile in water w/0.1% trifluoroacetic acid, 20 minute gradient) and combining with the previously filtered product delivered the desired compound, Compound I-147 (2.4 mg, 41% yield) as a white solid.

$^1$H-NMR (400 MHz, DMSO-d$_6$) δ 9.10 (m, 1H), 8.37 (d, 1H), 7.59 (s, 1H), 7.36-7.30 (m, 1H), 7.24-7.20 (m, 2H), 7.10 (t, 1H), 6.88 (s, 2H), 6.81 (t, 1H), 5.90 (s, 2H), 3.91-3.89 (m, 4H), 3.11-3.09 (m, 4H).

Compound I-149

The title compound was prepared following general procedure B, isoindoline-1-carboxylic acid was the amine reactant, and the reaction was heated to 80° C. for 1.5 h as a solution in THF/water (10:1). Upon completion by LC/MS, the solvent was removed under a stream of nitrogen and the resulting solid was brought up in methanol and water (5:1). The resulting solids were filtered off and the filtrate was purified by reverse-phase HPLC (5-75% acetonitrile in water w/0.1% trifluoroacetic acid, 20 minute gradient) to deliver the desired compound, Compound I-149 (14.5 mg, 54% yield) as a tan solid.

$^1$H-NMR (400 MHz, DMSO-d$_6$) δ 9.13 (br s, 1H), 8.39 (br s, 1H), 7.51 (br s, 2H), 7.45-7.39 (m, 2H), 7.36-7.31 (m, 1H), 7.27-7.21 (m, 1H), 7.14-7.05 (m, 2H), 6.96-6.75 (m, 2H), 6.03-5.82 (m, 3H), 5.23-5.07 (m, 2H).

Compound I-158

To a solution of Compound I-139 (1 equiv) in methanol was added (diazomethyl)trimethylsilane (~15 equiv) until the yellow color persisted. The solvent was removed under a stream of nitrogen to give an intermediate that was not isolated. Dichloromethane and trifluoroacetic acid (200 equivalents) were added, and after stirring at room temperature for 2 hours, the solvent was removed under a stream of nitrogen. Purification by silica gel chromatography (0-5% methanol in dichloromethane) provided Compound I-158 (2.1 mg, 31% yield) as a white solid.

$^1$H-NMR (400 MHz, CD$_3$OD) δ 8.74 (m, 1H), 8.19 (d, 1H), 7.44 (s, 1H), 7.28-7.22 (m, 1H), 7.10-7.05 (m, 1H), 7.01 (t, 1H), 6.90 (m, 1H), 6.78 (t, 1H), 5.94 (s, 2H), 4.01-3.98 (m, 4H), 2.66 (s, 3H).

Compound I-177

To a 0° C. solution of Compound I-147 (1 equivalent) and pyridine (100 equivalents) in dichloromethane was added acetyl chloride (5 equivalents). After five minutes, the solution was warmed to room temperature and maintained at that temperature for 1 hour. Additional acetyl chloride (5 equiv) was added and stirred at room temperature for 2.5 hours. The solution was then poured into saturated aqueous ammonium chloride and dichloromethane. The layers were separated and the aqueous layer was extracted with dichloromethane. The organics were dried over magnesium sulfate, filtered, and the solvent was removed in vacuo. Purification by reverse-phase HPLC (5-75% acetonitrile in water w/0.1% trifluoroacetic acid, 20 minute gradient) provided Compound I-177 (7.9 mg, 29% yield) as a yellow solid.

$^1$H-NMR (400 MHz, CD$_3$OD) δ 8.83 (m, 1H), 8.36 (d, 1H), 7.67 (s, 1H), 7.33-7.28 (m, 1H), 7.13-7.04 (m, 2H), 6.97-6.92 (m, 2H), 6.02 (s, 2H), 4.22-4.20 (m, 4H), 3.60-3.58 (m, 4H), 2.03 (s, 3H).

Compound I-175

The title compound was prepared following general procedure B, 4-(methylsulfonyl)piperidine was the amine reactant, and the reaction was heated to 80° C. for 1.5 h as a solution in THF. Upon completion by LC/MS, the solution was diluted with ethyl acetate and saturated aqueous ammonium chloride. The layers were separated and the organic layer was washed with additional ammonium chloride solution, dried over magnesium sulfate, filtered, and the solvent was removed in vacuo to deliver the desired compound, Compound I-175 (25 mg, 93% yield) as a yellow solid.

$^1$H-NMR (400 MHz, CDCl$_3$) δ 8.44 (m, 1H), 8.21 (d, 1H), 7.26 (s, 1H), 7.20-7.15 (m, 1H), 7.03-6.96 (m, 1H), 6.95 (t, 1H), 6.82 (t, 1H), 6.57 (m, 1H), 5.95 (s, 2H), 4.83 (d, 2H), 3.18-3.05 (m, 3H), 3.07 (s, 3H), 2.26 (d, 2H), 1.93 (qd, 2H).

Compound I-192

The title compound was prepared following general procedure B, N-methyl-1-(1H-tetrazol-5-yl)methanamine (as the HCl salt) was the amine reactant, and the reaction was heated to 90° C. for 1.5 h as a solution in dioxane/water (3:1). Following completion of the reaction as judged by LC/MS, the solution was diluted with 1 N hydrochloric acid solution and ethyl acetate. The layers were separated and the aqueous layer was extracted with dichloromethane. The organics were washed with water, dried over magnesium sulfate, filtered, and the solvent was removed in vacuo to deliver the desired compound, Compound I-192 (30 mg, 83%) as a white solid.

$^1$H-NMR (400 MHz, DMSO-d$_6$) δ 9.11 (m, 1H), 8.34 (d, 1H), 7.44 (s, 1H), 7.35-7.30 (m, 1H), 7.23-7.17 (m, 2H), 7.10 (t, 1H), 6.84 (t, 1H), 5.88 (s, 2H), 5.21 (s, 2H), 3.35 (m, 3H).

Compound I-201

The title compound was prepared following general procedure B, ethyl 2-((cyclopropylmethyl)amino)acetate was the amine reactant, and the reaction was heated to 90° C. for 16 h as a solution in dioxane. The crude material was purified via silica gel chromatography (0-70% ethyl acetate in hexanes) to deliver the desired compound, Compound I-201 (32 mg, 81% yield) as a clear oil.

$^1$H-NMR (400 MHz, CDCl$_3$) δ 8.43 (m, 1H), 8.17 (d, 1H), 7.21 (s, 1H), 7.19-7.13 (m, 1H), 7.01-6.92 (m, 2H), 6.81 (t, 1H), 6.54 (m, 1H), 5.92 (s, 2H), 4.37 (s, 2H), 4.17 (q, 2H), 3.63 (d, 2H), 1.21 (t, 3H), 1.15-1.09 (m, 1H), 0.59-0.54 (m, 2H), 0.31-0.26 (m, 2H).

Compound I-203

A solution of Compound I-201 (1 equivalent) in tetrahydrofuran, ethanol, and water (ratio 3:1:1) was treated with lithium hydroxide monohydrate (1.5 equivalents) and stirred at room temperature for 4 hours, at which point the solution was diluted with water and dichloromethane. The layers were separated and the aqueous layer was acidified to pH ~1. The acidified aqueous layer was extracted with dichloromethane, dried over magnesium sulfate, filtered, and the solvent was removed in vacuo to give Compound I-203 (18.5 mg, 65% yield) as a white solid.

$^1$H-NMR (400 MHz, CD$_3$OD) δ 8.76 (d, 1H), 8.15 (d, 1H), 7.36 (s, 1H), 7.29-7.24 (m, 1H), 7.10-7.01 (m, 2H), 6.86-6.82 (m, 2H), 5.94 (s, 2H), 4.47 (s, 2H), 3.96 (d, 2H), 1.22-1.15 (m, 1H), 0.59-0.55 (m, 2H), 0.38-0.34 (m, 2H).

Compound I-204

The title compound was prepared following general procedure B, 2-(isopropylamino)acetic acid was the amine reactant, and the reaction was heated to 100° C. for 16 h as a solution in dioxane/water (3:1). The crude material was purified via silica gel chromatography (0-10% methanol in dichloromethane) to deliver the desired compound, Compound I-204 (8 mg, 33% yield) as a white solid.

$^1$H-NMR (400 MHz, CDCl$_3$) δ 8.40 (br s, 1H), 8.11 (br s, 1H), 7.22 (s, 1H), 7.20-7.15 (m, 1H), 7.20-6.92 (m, 2H), 6.83 (br s, 1H), 6.60 (br s, 1H), 5.91 (br s, 2H), 4.75 (br s, 1H), 4.14 (br s, 2H), 1.29 (d, 6H).

Compound I-205

The title compound was prepared following general procedure B, ethyl 2-(isobutylamino)acetate was the amine reactant, and the reaction was heated to 90° C. for 44 h as a solution in dioxane. Following completion of the reaction as judged by LC/MS, the solution was diluted with water and dichloromethane. The layers were separated and the aqueous layer was extracted with dichloromethane. The organics were dried over magnesium sulfate, filtered, and the solvent was removed in vacuo. The crude material was purified via silica gel chromatography (0-50% ethyl acetate in hexanes) to deliver the desired compound, Compound I-205 (19 mg, 57% yield) as a yellow solid.

$^1$H-NMR (400 MHz, CDCl$_3$) δ 8.43 (m, 1H), 8.16 (d, 1H), 7.20-7.14 (m, 2H), 7.02-6.98 (m, 1H), 6.94 (t, 1H), 6.81 (t, 1H), 6.54 (m, 1H), 6.54 (m, 1H), 5.93 (s, 2H), 4.26 (s, 2H), 4.16 (q, 2H), 3.54 (d, 2H), 2.09-2.03 (m, 1H), 1.19 (t, 3H), 0.97 (d, 6H).

Compound I-209

A solution of Compound I-205 (1 equivalent) in tetrahydrofuran, ethanol, and water (ratio 3:1:1) was treated with lithium hydroxide monohydrate (2 equivalents) and stirred at room temperature until complete consumption of starting material as judged by LC/MS. The solution was diluted with water and diethyl ether. The layers were separated and the aqueous layer was acidified to pH ~1. The acidified aqueous layer was extracted with ethyl acetate, dried over magnesium sulfate, filtered, and the solvent was removed in vacuo to give Compound I-209 (13 mg, 86% yield) as a white solid.

$^1$H-NMR (400 MHz, CD$_3$OD) δ 8.76 (m, 1H), 8.15 (d, 1H), 7.36 (s, 1H), 7.29-7.24 (m, 1H), 7.10-7.01 (m, 2H), 6.86-6.82 (m, 2H), 5.92 (s, 2H), 4.38 (s, 2H), 3.61 (d, 2H), 2.15-2.08 (m, 1H), 1.00 (d, 6H).

Compound I-257

The title compound was prepared in 4 steps:

Step 1: Synthesis of (S)-2-(4-methylphenylsulfonamido)-3-(pyridin-2-yl)propanoic Acid

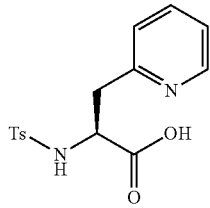 [SMILES: Cc1ccc(S(=O)(=O)N[C@@H](Cc2ccccn2)C(=O)O)cc1]

A suspension of (S)-2-amino-3-(pyridin-2-yl)propanoic acid, p-toluenesulfonyl chloride (1.2 equiv.) in water was treated with sodium hydroxide (1N solution, 3 equiv.). The reaction was stirred at 90° C. for 18 h. The resulting mixture was cooled to room temperature, neutralized to pH 6 with 1N HCl solution. Sodium chloride was added to saturate the solution which was then extracted with dichloromethane/iso-propanol (4:1 v/v). The combined organic phases were dried over sodium sulfate, filtered, and the solvent was removed in vacuo to afford (S)-2-(4-methylphenylsulfonamido)-3-(pyridin-2-yl)propanoic acid an off-white solid (35% yield).

Step 2: Synthesis of (S)-2-(N,4-dimethylphenylsulfonamido)-3-(pyridin-2-yl)propanoic Acid

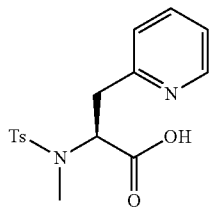 [SMILES: Cc1ccc(S(=O)(=O)N(C)[C@@H](Cc2ccccn2)C(=O)O)cc1]

A suspension of (S)-2-(4-methylphenylsulfonamido)-3-(pyridin-2-yl)propanoic acid and methyl iodide (3.2 equiv.) in 1N aqueous sodium hydroxide solution (4.0 equiv.) was heated at 100° C. for 6 h. The resulting mixture was cooled to room temperature, neutralized to pH 6 with 1N HCl solution and extracted with dichloromethane/iso-propanol (4:1 v/v). The combined organic phases were dried over sodium sulfate, filtered, and the solvent was removed in vacuo. Purification by silica gel chromatography (20-50% acetonitrile/methanol (7:1) in dichloromethane gradient) yielded (S)-2-(N,4-dimethylphenylsulfonamido)-3-(pyridin-2-yl) propanoic acid as a yellow foam solid (39% yield).

Step 3: Synthesis of (S)-2-(methylamino)-3-(pyridin-2-yl) propanoic Acid (as HBr Salt)

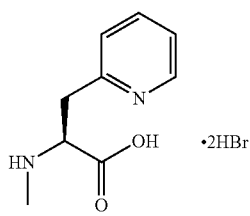

To (S)-2-(N,4-dimethylphenylsulfonamido)-3-(pyridin-2-yl)propanoic acid was added HBr (33 wt % in glacial acetic acid, 25 equiv.). The reaction was stirred at 85° C. for 6 h and then at 60° C. for 3 d. Additional amount of HBr solution (3.3 equiv.) was added and the resulting mixture was stirred at 85° C. for 6 h. The reaction was cooled to room temperature, diluted with water and washed with ether. The aqueous phase was concentrated in vacuo to afford crude (S)-2-(methylamino)-3-(pyridin-2-yl)propanoic acid dihydrobromide as a thick red oil (>99% yield) which was used in the next step without further manipulation.

Step 4: Synthesis of Compound I-257

The title compound was prepared following general procedure B, except (S)-2-(methylamino)-3-(pyridin-2-yl)propanoic acid (as the HBr salt) was the amine reactant, 1.1 equivalents of Intermediate 1 was used, and contents were heated to 100° C. The crude material was purified via reverse phase HPLC (20-75% acetonitrile in water with 0.1% trifluoroacetic acid, 20 minute gradient) to deliver the desired compound, Compound I-257 (123 mg, 73% yield) as a tan solid.

$^1$H-NMR (400 MHz, CD$_3$OD) d 8.81 (d, 1H), 8.49 (d, 1H), 8.24 (d, 1H), 8.13 (app. t, 1H), 7.88 (d, 1H), 7.58 (app. t, 1H), 7.42 (s, 1H), 7.29 (app. q, 1H), 7.11 (m, 1H), 7.06 (app. t, 1H), 6.90 (d, 1H), 6.89 (m, 1H), 6.01 (d, 1H), 5.97 (d, 1H), 5.65 (br. m, 1H), 3.88 (dd, 1H), 3.67 (dd, 1H), 3.35 (d, 3H).

$^1$H-NMR (400 MHz, CD$_3$OD) δ 8.81 (d, 1H), 8.49 (d, 1H), 8.24 (d, 1H), 8.13 (app. t, 1H), 7.88 (d, 1H), 7.58 (app. t, 1H), 7.42 (s, 1H), 7.29 (app. q, 1H), 7.11 (m, 1H), 7.06 (app. t, 1H), 6.90 (d, 1H), 6.89 (m, 1H), 6.01 (d, 1H), 5.97 (d, 1H), 5.65 (br. m, 1H), 3.88 (dd, 1H), 3.67 (dd, 1H), 3.35 (d, 3H).

Compound I-200

The title compound was synthesized in 8 steps:

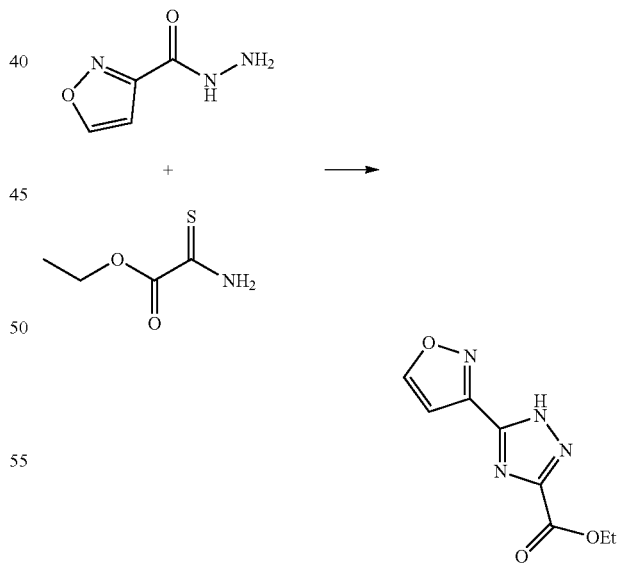

Step 1: Synthesis of ethyl 3-(isoxazol-3-yl)-1H-1,2,4-triazole-5-carboxylate

A suspension of isoxazole-3-carbohydrazide (1 equiv.), ethyl 2-amino-2-thioxoacetate (1 equiv.) and ammonium chloride (10 equiv.) in absolute ethanol in a sealed vial was heated at 110° C. for 7 d. The crude mixture was concentrated in vacuo. Water was added and the aqueous phase was extracted with ethyl acetate. The combined organic phases were dried over sodium sulfate, filtered, and the solvent was removed in vacuo. Purification via silica gel chromatography (10-20% acetonitrile/methanol (7:1) in dichloromethane gradient) yielded ethyl 3-(isoxazol-3-yl)-1H-1,2,4-triazole-5-carboxylate as an orange solid (24% yield).

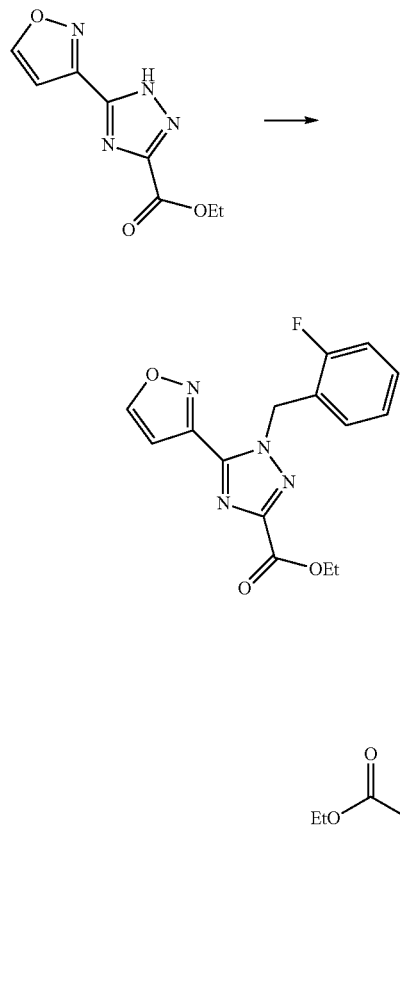

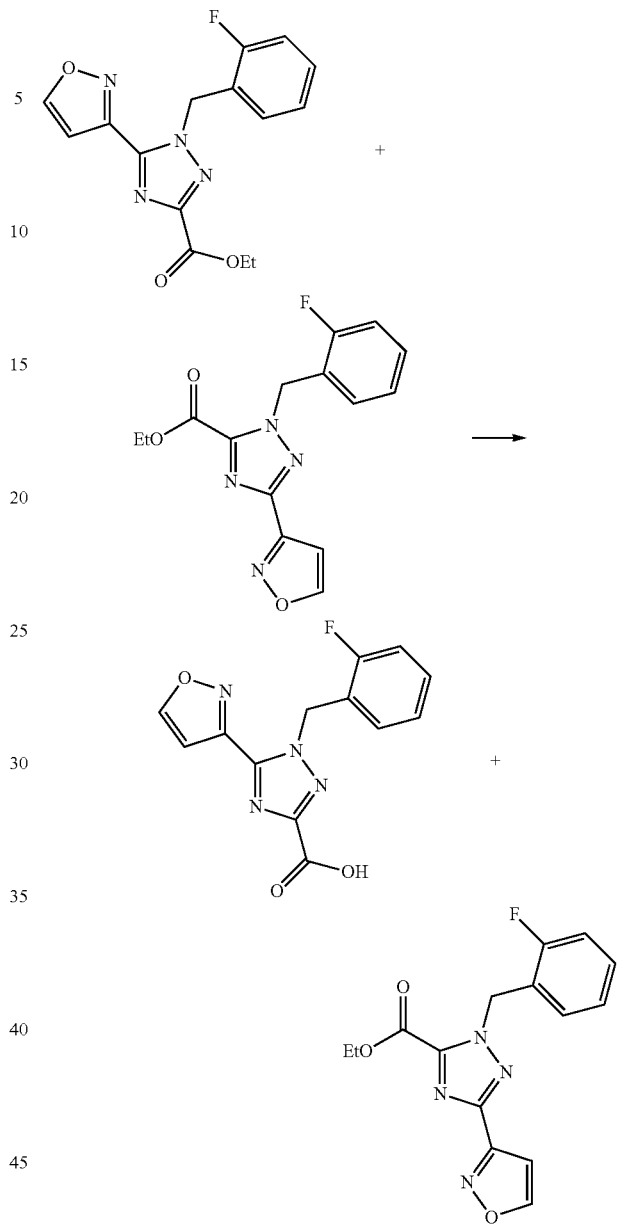

Step 2: Synthesis of ethyl 1-(2-fluorobenzyl)-5-(isoxazol-3-yl)-1H-1,2,4-triazole-3-carboxylate and ethyl 1-(2-fluorobenzyl)-3-(isoxazol-3-yl)-1H-1,2,4-triazole-5-carboxylate To ethyl 3-(isoxazol-3-yl)-1H-1,2,4-triazole-5-carboxylate in DMF was added sodium hydride (60 wt % in mineral oil, 1.2 equiv.). After 10 min, 2-fluorobenzyl bromide (1.2 equiv.) was added and the reaction was stirred for 2 h. Water was added and the resulting mixture was extracted with ethyl acetate. The combined organic phases were washed with water and brine, dried over sodium sulfate, filtered, and the solvent was removed in vacuo. Purification via silica gel chromatography (10-40% ethyl acetate/hexanes gradient) yielded ethyl 1-(2-fluorobenzyl)-5-(isoxazol-3-yl)-1H-1,2,4-triazole-3-carboxylate and ethyl 1-(2-fluorobenzyl)-3-(isoxazol-3-yl)-1H-1,2,4-triazole-5-carboxylate (63% yield, 42:58 ratio).

Step 3: Synthesis of 1-(2-fluorobenzyl)-5-(isoxazol-3-yl)-1H-1,2,4-triazole-3-carboxylic acid and 1-(2-fluorobenzyl)-3-(isoxazol-3-yl)-1H-1,2,4-triazole-5-carboxylic Acid To a solution of ethyl 1-(2-fluorobenzyl)-5-(isoxazol-3-yl)-1H-1,2,4-triazole-3-carboxylate and ethyl 1-(2-fluorobenzyl)-3-(isoxazol-3-yl)-1H-1,2,4-triazole-5-carboxylate in tetrahydrofuran/methanol/water (3:1:1 ratio) was added lithium hydroxide hydrate (1.5 equivalents). After 1 h, water and 1N HCl solution (50:8 ratio) were added and the resultant mixture was extracted with ethyl acetate. Note: Product was not completely soluble and was collected by vacuum filtration. The aqueous layer was extracted with dichloromethane/iso-propanol (4:1 v/v). The combined organic phases were concentrated in vacuo and triturated with ether to give additional product. The combined solids (88%, mixture of regioisomers) were used in the next step without further manipulation.

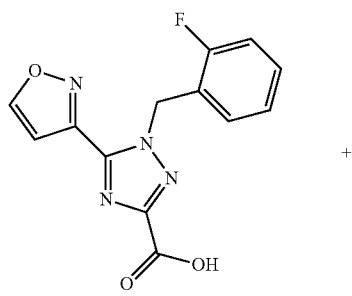

+

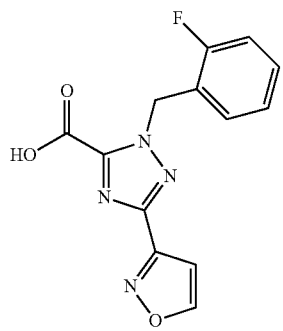

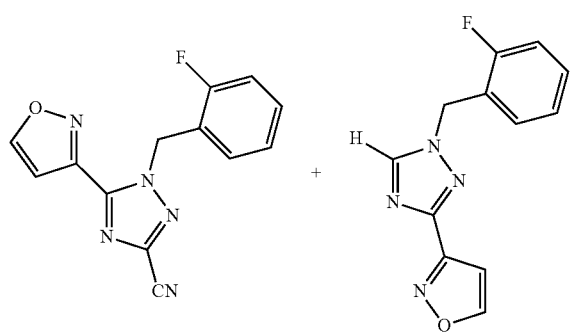

Step 4: Synthesis of 1-(2-fluorobenzyl)-5-(isoxazol-3-yl)-1H-1,2,4-triazole-3-carbonitrile To a suspension of 1-(2-fluorobenzyl)-5-(isoxazol-3-yl)-1H-1,2,4-triazole-3-carboxylic acid and 1-(2-fluorobenzyl)-3-(isoxazol-3-yl)-1H-1,2,4-triazole-5-carboxylic acid, 2-methylpropan-2-amine (2 equiv.), and triethylamine (2 equiv.) in ethyl acetate was added n-propylphosphonic anhydride (T3P, 50 wt % solution in ethyl acetate, 3 equiv.). The resultant yellow solution was heated at 65° C. for 2.5 h. The solvent was removed in vacuo. Phosphoryl trichloride (18 equiv.) was added and the resulting mixtures was stirred at 70° C. for 50 min. The reaction was quenched by carefully pouring into a mixture of water and ice, neutralized to pH 7 by addition of saturated sodium bicarbonate solution and extracted with dichloromethane. The combined organic phases were dried over sodium sulfate, filtered, and the solvent was removed in vacuo. Purification by silica gel chromatography (10-60% ethyl acetate/hexanes gradient) yielded 1-(2-fluorobenzyl)-5-(isoxazol-3-yl)-1H-1,2,4-triazole-3-carbonitrile (39% yield). Note: One of the regioisomers decarboxylated to form 3-(1-(2-fluorobenzyl)-1H-1,2,4-triazol-3-yl)isoxazole. The structural assignment is consistent with the nOe's observed. This side-reaction may have occurred during the saponification step (Step 3).

Step 5: Synthesis of 1-(2-fluorobenzyl)-5-(isoxazol-3-yl)-1H-1,2,4-triazole-3-carboximidamide A solution of 1-(2-fluorobenzyl)-5-(isoxazol-3-yl)-1H-1,2,4-triazole-3-carbonitrile in methanol was treated sodium methoxide (25 wt % solution in methanol, 5 equiv.) and stirred for 1 h. Ammonium chloride (10 equiv.) was added. After 18 h, the reaction mixture was concentrated in vacuo and partitioned between half-saturated sodium bicarbonate/1N sodium hydroxide solution (10:1 ratio) and ethyl acetate. The organic phases were dried over sodium sulfate, filtered, and the solvent was removed in vacuo to afford 1-(2-fluorobenzyl)-5-(isoxazol-3-yl)-1H-1,2,4-triazole-3-carboximidamide (>99% yield) which was used without further purification.

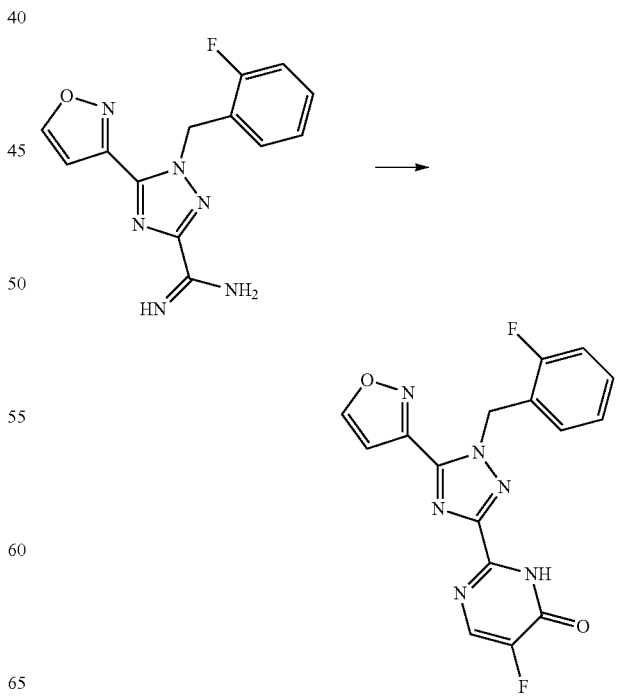

Step 6: Synthesis of 5-fluoro-2-(1-(2-fluorobenzyl)-5-(isoxazol-3-yl)-1H-1,2,4-triazol-3-yl) pyrimidin-4(3H)-one A suspension of 1-(2-fluorobenzyl)-5-(isoxazol-3-yl)-1H-1,2,4-triazole-3-carboximidamide was treated with sodium (Z)-3-ethoxy-2-fluoro-3-oxoprop-1-en-1-olate (3.0 equiv.) and heated at 90° C. for 1 h. After cooling to ambient temperature, the reaction mixture was neutralized by addition of HCl (1.25 M solution in ethanol). The resultant pale yellow suspension was stirred for 5 min and then concentrated in vacuo. The residue was partitioned between dichloromethane and water and the aqueous layer was back-extracted with dichloromethane. The combined organic phases were dried over sodium sulfate, filtered, and the solvent was removed in vacuo. Purification by silica gel chromatography (5-20% acetonitrile/methanol (7:1) in dichloromethane gradient) yielded 5-fluoro-2-(1-(2-fluorobenzyl)-5-(isoxazol-3-yl)-1H-1,2,4-triazol-3-yl)-pyrimidin-4(3H)-one (61 mg, 74% yield) as a pale yellow solid.

$^1$H-NMR (400 MHz, CD$_3$OD) δ 8.95 (d, 1H), 8.09 (d, 1H), 7.35 (app. q, 1H), 7.23 (app. t, 1H), 7.17 (d, 1H), 7.15 (m, 2H), 6.07 (s, 2H).

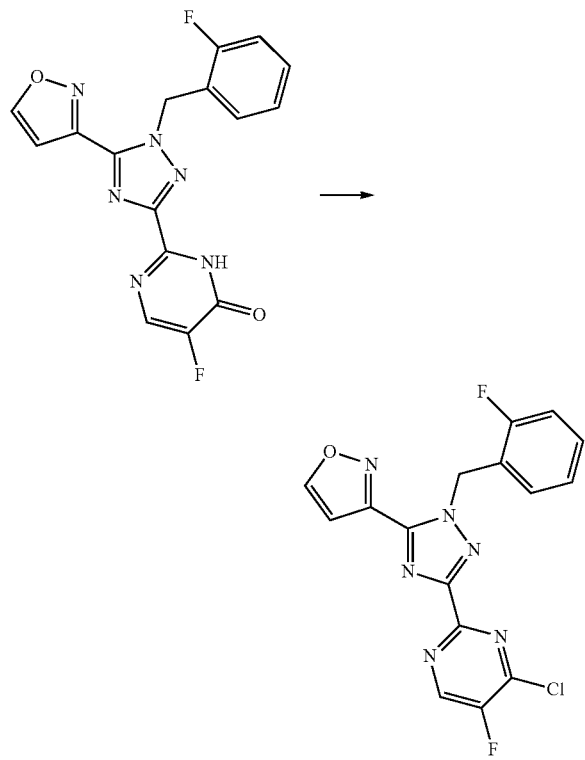

Step 7: Synthesis of 3-(3-(4-chloro-5-fluoropyrimidin-2-yl)-1-(2-fluorobenzyl)-1H-1,2,4-triazol-5-yl)isoxazole A suspension of 5-fluoro-2-(1-(2-fluorobenzyl)-5-(isoxazol-3-yl)-1H-1,2,4-triazol-3-yl) pyrimidin-4(3H)-one in phosphoryl trichloride (77 equiv.) was heated to 65° C. for 2 h. The reaction mixture was carefully poured into ice and stirred for 20 min. The resultant mixture was basicified to pH 8 by addition of saturated sodium bicarbonate and extracted with dichloromethane. The combined organic layers were dried over sodium sulfate, filtered, and the solvent was removed in vacuo to afford 3-(3-(4-chloro-5-fluoropyrimidin-2-yl)-1-(2-fluorobenzyl)-1H-1,2,4-triazol-5-yl)isoxazole as an off-white solid (>99% yield).

Step 8: Synthesis of Compound I-200

The title compound was prepared following general procedure B, except (S)-3-methyl-2-(methylamino)butanoic acid was the amine reactant, 3-(3-(4-chloro-5-fluoropyrimidin-2-yl)-1-(2-fluorobenzyl)-1H-1,2,4-triazol-5-yl)isoxazole was used in place of Intermediate 1, and contents were heated to 100° C. The crude material was purified via silica gel chromatography (20-50% (acetonitrile/methanol=7:1) in dichloromethane gradient) yielded impure product. The sample was re-purified by reverse phase HPLC (5-95% acetonitrile in water with 0.1% trifluoroacetic acid, 20 minute gradient) to deliver the desired compound, Compound I-200 (23 mg, 66% over two steps) as a white solid.

$^1$H-NMR (400 MHz, CDCl$_3$) δ 8.56 (d, 1H), 8.34 (d, 1H), 7.27 (app. q, 1H), 7.21 (app. t, 1H), 7.15 (d, 1H), 7.06 (m, 2H), 6.09 (d, 1H), 6.02 (d, 1H), 4.27 (d, 1H), 3.07 (d, 3H), 2.55 (m, 1H), 1.10 (d, 3H), 0.95 (d, 3H).

Compound I-249

The title compound was prepared following general procedure B, except 4-methylpiperidine-4-carboxylic acid (as the HCl salt) was the amine reactant, 3-(3-(4-chloro-5-fluoropyrimidin-2-yl)-1-(2-fluorobenzyl)-1H-1,2,4-triazol-5-yl)isoxazole (the synthesis of which is described in the procedure for Compound I-200) was used in place of Intermediate 1, and contents were heated to 100° C. for 19 h. The reaction was cooled and diluted with water, and neutralized with aqueous 1N HCl. The resulting solids were collected via vacuum filtration, washed with water, and dried in vacuo to deliver the desired compound, Compound I-249 (29 mg, 85% yield) as an off-white solid.

$^1$H-NMR (400 MHz, CDCl3) δ 8.54 (d, 1H), 8.22 (d, 1H), 7.24 (m, 1H), 7.17 (d, 1H), 7.07-7.00 (m, 3H), 6.08 (s, 2H), 4.41 (br. d, 2H), 3.38 (app. t, 2H), 2.28 (br. d, 2H), 1.59 (m, 2H), 1.31 (s, 3H).

Compound I-1

The title compound was prepared following general procedure B, except pyrrolidine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-1 (23 mg, 76% yield) as a solid.

$^1$H NMR (400 MHz, DMSO-d$_6$) δ ppm 9.08 (d, 1H), 8.20 (d, 1H), 7.52 (s, 1H), 7.30-7.40 (m, 1H), 7.18-7.28 (m, 2H), 7.10 (t, 1H), 6.82 (t, 1H), 5.89 (s, 2H), 3.65-3.70 (m, 4H), 1.92 (d, 4H).

Compound I-2

The title compound was prepared following general procedure B, except piperidine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-2 (25 mg, 80% yield) as a solid.

$^1$H NMR (400 MHz, DMSO-d$_6$) δ ppm 9.09 (s, 1H), 8.26 (d, 1H), 7.54 (s, 1H), 7.32 (s, 2H), 7.20-7.27 (m, 2H), 7.10 (t, 1H), 6.81 (t, 1H), 5.90 (s, 2H), 3.74-3.80 (m, 4H), 1.58-1.62 (m, 6H).

Compound I-3

The title compound was prepared following general procedure B, except morpholine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-3 (24 mg, 76% yield) as a solid.

$^1$H NMR (400 MHz, DMSO-d$_6$) δ ppm 9.08 (s, 1H), 8.33 (d, 1H), 7.57 (s, 1H), 7.32 (d, 2H), 7.20-7.27 (m, 2H), 7.10 (t, 2H), 6.81 (t, 1H), 5.90 (s, 2H), 3.79 (d, 4H), 3.74 (d, 4H).

Compound I-4

The title compound was prepared following general procedure B, except piperazine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-4 (20 mg, 64% yield) as a solid.

$^1$H NMR (400 MHz, DMSO-d$_6$) δ ppm 9.09 (s, 1H), 8.33 (d, 1H), 7.56 (s, 1H), 7.32 (s, 1H), 7.20-7.28 (m, 2H), 7.10 (t, 1H), 6.81 (t, 1H), 5.90 (s, 2H), 3.78-3.84 (m, 4H), 2.90-3.00 (m, 3H).

Compound I-5

The title compound was prepared following general procedure B, except N-methylpiperazine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-5 (23 mg, 71% yield) as a solid.

$^1$H NMR (400 MHz, DMSO-d$_6$) δ ppm 9.09 (s, 1H), 8.31 (d, 1H), 7.56 (s, 1H), 7.32 (s, 1H), 7.18-7.27 (m, 2H), 7.10 (t, 1H), 6.80 (s, 1H), 5.90 (s, 2H), 3.74-3.81 (m, 4H), 3.25-3.35 (s, 3H), 2.20-2.30 (m, 4H).

Compound I-6

The title compound was prepared following general procedure B, except 2-morpholinoethanamine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-6 (25 mg, 72% yield) as a gum.

$^1$H NMR (400 MHz, DMSO-d$_6$) δ ppm 9.09 (d, 1H), 8.17 (d, 1H), 7.59 (s, 1H), 7.48 (s, 1H), 7.28-7.38 (m, 1H), 7.17-7.26 (m, 2H), 7.10 (t, 1H), 6.86 (t, 1H), 5.88 (s, 2H), 3.56-3.62 (m, 4H), 3.48 (t, 4H), 2.44 (m, 2H), 2.29-2.40 (m, 2H).

Compound I-7

The title compound was prepared following general procedure B, except N,N-dimethylethane-1,2-diamine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-7 (24 mg, 76% yield) as a gum.

$^1$H NMR (400 MHz, DMSO-d$_6$) δ ppm 9.09 (d, 1H), 8.17 (d, 1H), 7.54 (s, 1H), 7.48 (s, 1H), 7.29-7.38 (m, 1H), 7.18-7.27 (m, 2H), 7.11 (t, 1H), 6.88 (t, 1H), 5.89 (s, 2H), 3.57 (q, 2H), 2.43-2.49 (m, 2H), 2.19 (s, 6H).

Compound I-9

The title compound was prepared following general procedure B, except cyclohexylamine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-9 (20 mg, 62% yield) as a solid.

$^1$H NMR (400 MHz, DMSO-d$_6$) δ ppm 9.09 (d, 1H), 8.14 (d, 1H), 7.51 (d, 1H), 7.45 (s, 1H), 7.33 (d, 1H), 7.18-7.28 (m, 2H), 7.10 (t, 1H), 6.85 (t, 1H), 5.88 (s, 2H), 4.03-4.08 (m, 1H), 1.89-1.92 (m, 2H), 1.72-1.76 (m, 2H), 1.63 (d, 2H), 1.32-1.43 (m, 4H).

Compound I-8

The title compound was prepared following general procedure B, except dimethylamine (7 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-8 (19 mg, 67% yield) as a solid.

$^1$H NMR (400 MHz, DMSO-d$_6$) δ ppm 9.09 (s, 1H), 8.18 (d, 1H), 7.52 (s, 1H), 7.39-7.45 (m, 1H), 7.18-7.27 (m, 2H), 7.10 (t, 1H), 6.82-6.88 (m, 1H), 5.90 (s, 2H), 3.24 (d, 6H).

Compound I-11

The title compound was prepared following general procedure B, except 2-methylpyrrolidine was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo, and the crude material was purified via silica gel chromatography, utilizing a 0-10% methanol/dichloromethane gradient to deliver the desired compound, Compound I-11 (16 mg, 51% yield) as a solid.

$^1$H NMR (400 MHz, DMSO-d$_6$) δ ppm 9.09 (d, 1H), 8.21 (d, 1H), 7.49 (s, 1H), 7.29-7.38 (m, 1H), 7.17-7.27 (m, 2H), 7.10 (t, 1H), 6.84 (t 1H), 5.92 (s, 2H), 4.40-4.48 (m, 1H), 3.75-3.90 (m, 1H), 3.56-3.69 (m, 1H), 2.00-2.07 (m, 2H), 1.93 (d, 1H), 1.65-1.73 (m, 1H), 1.23 (d, 3H).

Compound I-10

The title compound was prepared following general procedure B, except piperidin-4-ol was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo to deliver the desired compound, Compound I-10 (19 mg, 58% yield) as a solid.

$^1$H NMR (400 MHz, DMSO-d$_6$) δ ppm 9.08 (d, 1H), 8.27 (d, 1H), 7.54 (s, 1H), 7.21-7.39 (m, 3H), 7.10 (t, 1H), 6.81 (t, 1H), 5.90 (s, 2H), 4.78-4.84 (m, 1H), 4.18 (d, 2H), 3.74-3.79 (m, 1H), 3.37-3.47 (m, 2H), 1.81-8.89 (m, 2H), 1.40-1.54 (m, 2H).

Compound I-12

The title compound was prepared following general procedure B, except tert-butyl 4-aminopiperidine-1-carboxylate (1.5 equiv.) was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo, and the crude material was purified via silica gel chromatography, utilizing a 0-10% methanol/dichloromethane gradient to deliver the desired compound, Compound I-12 (36 mg, 90% yield) as a solid.

$^1$H NMR (400 MHz, DMSO-d$_6$) δ ppm 9.04-9.15 (m, 1H), 8.18 (d, 1H), 7.53-7.65 (m, 1H), 7.47 (s, 1H), 7.30-7.39 (m, 1H), 7.19-7.27 (m, 2H), 7.07-7.16 (m, 1H), 6.85 (t, 1H), 5.83-5.91 (m, 2H), 4.25 (d, 1H), 3.96 (d, 2H), 2.87-2.91 (m, 2H), 1.87 (d, 2H), 1.44-1.51 (m, 2H), 1.41 (s, 9H).

Compound I-13

The title compound was prepared following general procedure B, except (S)-pyrrolidin-2-ylmethanol was the amine reactant, no triethylamine was used, and contents were heated to 40° C. for 10 min as a solution in THF, then at 23° C. for 18 h. The reaction was cooled and diluted with ethyl acetate, and washed with water and brine. Solvent was removed in vacuo, and the crude material was purified via silica gel chromatography, utilizing a 0-10% methanol/dichloromethane gradient to deliver the desired compound, Compound I-13 (18 mg, 55% yield) as a solid.

$^1$H NMR (400 MHz, DMSO-d$_6$) δ ppm 9.09 (d, 1H), 8.21 (d, 1H), 7.49 (s, 1H), 7.28-7.37 (m, 1H), 7.18-7.26 (m, 2H), 7.10 (t, 1H), 6.83 (t, 1H), 5.85-5.93 (m, 2H), 4.86 (t, 1H), 4.32-4.39 (m, 1H), 3.74-3.79 (m, 1H), 3.62-3.69 (m, 1H), 3.52-3.59 (m, 1H), 3.44-3.50 (m, 1H), 1.98-2.04 (m, 2H), 1.91 (d, 2H).

Compound I-17

The title compound was prepared following general procedure B, except 3-methoxypyrrolidine (4 equiv.) was the amine reactant, 4 equivalents of triethylamine was used, and contents were heated to 40° C. for 1 h as a solution in THF. The reaction was cooled and diluted with ethyl acetate, and washed with water and brine. Solvent was removed in vacuo to deliver the desired compound, Compound I-17 (12 mg, 61% yield) as a solid.

$^1$H NMR (400 MHz, DMSO-d$_6$) δ ppm 9.09 (d, 1H), 8.23 (d, 1H), 7.53 (s, 1H), 7.29-7.40 (m, 1H), 7.18-7.28 (m, 2H), 7.10 (t, 1H), 6.82 (t, 1H), 5.90 (s, 2H), 4.03-4.12 (m, 1H), 3.70-3.87 (m, 3H), 3.66 (d, 1H), 3.28 (s, 3H), 1.96-2.15 (m, 2H).

Compound I-18

The title compound was prepared following general procedure B, except piperidin-3-ol (4 equiv.) was the amine reactant, no triethylamine was used, and contents were heated to 40° C. for 1 h as a solution in THF. The reaction was cooled and diluted with ethyl acetate, and washed with water and brine. Solvent was removed in vacuo to deliver the desired compound, Compound I-18 (14 mg, 72% yield) as a solid.

$^1$H NMR (400 MHz, DMSO-d$_6$) δ ppm 9.09 (d, 1H), 8.25 (d, 1H), 7.53 (s, 1H), 7.28-7.39 (m, 1H), 7.17-7.27 (m, 2H), 7.10 (t, 1H), 6.81 (t, 1H), 5.90 (s, 2H), 4.97 (d, 1H), 4.18 (d, 1H), 3.56-3.68 (m, 1H), 3.37-3.48 (m, 2H), 3.21 (dd, 1H), 1.73-1.96 (m, 2H), 1.43-1.58 (m, 2H).

Compound I-25

The title compound was prepared following general procedure B, except tert-butyl piperidin-3-ylcarbamate (4 equiv.) was the amine reactant, no triethylamine was used, and contents were heated to 40° C. for 1 h as a solution in THF. The reaction was cooled and diluted with ethyl acetate, and washed with water and brine. Solvent was removed in vacuo, and the crude material was purified via silica gel chromatography, utilizing a 0-10% methanol/dichloromethane gradient to deliver the desired compound, Compound I-25 (25 mg, 66% yield) as a solid.

$^1$H NMR (500 MHz, CD$_3$OD) δ ppm 8.75 (d, 1H), 8.16 (d, 1H), 7.58 (s, 1H), 7.23-7.38 (m, 1H), 7.08-7.17 (m, 1H), 7.05 (t, 1H), 6.95 (s, 1H), 6.84 (t, 1H), 6.78 (d, 1H), 5.98 (s, 2H), 4.40 (d, 1H), 4.13-4.24 (m, 1H), 3.69 (br. s., 1H), 3.56 (d, 1H), 3.35-3.42 (m, 1H), 2.00-2.09 (m, 1H), 1.91 (dd, 1H), 1.59-1.72 (m, 2H), 1.45 (s, 9H).

Compound I-26

The title compound was prepared following general procedure B, except tert-butyl 3-aminoazetidine-1-carboxylate (4 equiv.) was the amine reactant, 2 equivalents of triethylamine was used, and contents were heated to 40° C. for 1 h as a solution in THF, followed by heating to 75° C. until full consumption of starting material was observed on the LC/MS. The reaction was cooled and diluted with ethyl acetate, and washed with water and brine. Solvent was removed in vacuo, and the crude material was purified via silica gel chromatography, utilizing a 0-10% methanol/dichloromethane gradient to deliver the desired compound, Compound I-26 (24 mg, 67% yield) as a solid.

$^1$H NMR (400 MHz, DMSO-d$_6$) δ ppm 9.10 (d, 1H), 8.31 (d, 1H), 8.25 (d, 1H), 7.48-7.57 (m, 1H), 7.29-7.38 (m, 1H), 7.15-7.28 (m, 2H), 7.11 (t, 1H), 6.85 (t, 1H), 5.89 (s, 2H), 4.76-4.93 (m, 1H), 4.15-4.25 (m, 2H), 3.91 (dd, 2H), 1.39 (s, 9H).

Compound I-27

The title compound was prepared following general procedure B, except tert-butyl 3-aminopiperidine-1-carboxylate (4 equiv.) was the amine reactant, 2 equivalents of triethylamine was used, and contents were heated to 40° C. for 1 h as a solution in THF, followed by heating to 75° C. until full consumption of starting material was observed on the LC/MS. The reaction was cooled and diluted with ethyl acetate, and washed with water and brine. Solvent was removed in vacuo, and the crude material was purified via silica gel chromatography, utilizing a 0-10% methanol/dichloromethane gradient to deliver the desired compound, Compound I-27 (24 mg, 57% yield) as a solid.

$^1$H NMR (500 MHz, CD$_3$OD) δ ppm 8.78 (d, 1H), 8.15 (d, 1H), 7.58 (s, 1H), 7.25-7.33 (m, 1H), 7.08-7.17 (m, 1H), 7.05 (t, 1H), 6.95 (s, 1H), 6.84 (t, 1H), 6.78 (d, 1H), 5.98 (s, 2H), 4.40 (d, 1H), 4.18 (d, 1H), 3.69 (m, 1H), 3.56 (d, 1H), 3.39 (d, 1H), 1.99-2.08 (m, 1H), 1.91 (dd, 1H), 1.57-1.76 (m, 2H), 1.45 (s, 9H).

Compound I-19

The title compound was prepared following general procedure B, except 3-methoxypiperidine (4 equiv.) was the amine reactant, 2 equivalents of triethylamine was used, and contents were heated to 40° C. for 1 h as a solution in THF, followed by heating to 75° C. until full consumption of starting material was observed on the LC/MS. The reaction was cooled and filtered, and the solids were washed with ethyl acetate. The filtrate was collected and washed with water and brine. Solvent was removed in vacuo to deliver the desired compound, Compound I-19 (15 mg, 74% yield) as a solid.

$^1$H NMR (400 MHz, DMSO-d$_6$) δ ppm 9.06 (d, 1H), 8.23 (d, 1H), 7.49 (s, 1H), 7.25-7.35 (m, 1H), 7.13-7.24 (m, 2H), 7.07 (t, 1H), 6.78-6.87 (m, 1H), 5.86 (s, 2H), 3.91 (d, 1H), 3.62-3.81 (m, 3H), 3.34 (dd, 1H), 3.23 (s, 3H), 1.83-1.94 (m, 1H), 1.72-1.81 (m, 1H), 1.56-1.65 (m, 1H), 1.44-1.54 (m, 1H).

Compound I-20

The title compound was prepared following general procedure B, except pyrrolidin-3-ol (4 equiv.) was the amine reactant, no triethylamine was used, and contents were heated to 40° C. for 1 h as a solution in THF. The reaction was cooled and filtered, and the solids were washed with ethyl acetate. The filtrate was collected and washed with water and brine. Solvent was removed in vacuo to deliver the desired compound, Compound I-20 (10 mg, 53% yield) as a solid.

$^1$H NMR (400 MHz, DMSO-d$_6$) δ ppm 9.08 (d, 1H), 8.21 (d, 1H), 7.52 (s, 1H), 7.29-7.37 (m, 1H), 7.18-7.28 (m, 2H), 7.10 (t, 1H), 6.82 (t, 1H), 5.90 (s, 2H), 5.04 (d, 1H), 4.32-4.39 (m, 1H), 3.81 (d, 1H), 3.69-3.77 (m, 1H), 3.60-3.68 (m, 1H), 1.96-2.05 (m, 1H), 1.88-1.95 (m, 1H).

Compound I-21

The title compound was prepared following general procedure B, except tert-butyl azetidin-3-ylcarbamate (4 equiv.) was the amine reactant, no triethylamine was used, and contents were heated to 40° C. for 1 h as a solution in THF.

The reaction was cooled and filtered, and the solids were collected and dried in vacuo to deliver the desired compound, Compound I-21 (30 mg, 79% yield) as a solid.

$^1$H NMR (400 MHz, DMSO-d$_6$) δ ppm 9.08 (s, 1H), 8.25 (m, 1H), 7.62-7.66 (m, 2H), 7.51 (s, 1H), 7.29-7.34 (m, 1H), 7.15-7.27 (m, 2H), 7.07-7.14 (m, 1H), 6.79-6.84 (m, 1H), 5.90 (s, 2H), 4.35-4.44 (m, 2H), 4.01-4.12 (m, 2H), 3.84-3.90 (m, 1H), 1.39 (s, 9H).

Compound I-22

The title compound was prepared following general procedure B, except 4-methoxypiperidine (4 equiv.) was the amine reactant, no triethylamine was used, and contents were heated to 40° C. for 1 h as a solution in THF. The reaction was cooled and diluted with ethyl acetate, and washed with water and brine. Solvent was removed in vacuo to deliver the desired compound, Compound I-22 (15 mg, 74% yield) as a solid.

$^1$H NMR (400 MHz, DMSO-d$_6$) δ ppm 9.05 (d, 1H), 8.25 (d, 1H), 7.51 (s, 1H), 7.26-7.31 (m, 1H), 7.14-7.25 (m, 2H), 7.07 (t, 1H), 6.74-6.82 (m, 1H), 5.87 (s, 2H), 4.06-4.11 (m, 2H), 3.42-3.50 (m, 2H), 3.25 (s, 3H), 1.89-1.95 (m, 2H), 1.46-1.51 (m, 3H).

Compound I-64

The title compound was prepared following general procedure B, except 4-methyltetrahydro-2H-pyran-4-amine (as the HCl salt) (5 equiv.) was the amine reactant, 10 equivalents of Hunig's base was used in place of triethylamine, and contents were heated to 175° C. for 1 h in the microwave as a solution in THF/DMF (1:1). The reaction was cooled and diluted with ethyl acetate, and washed with water and brine. Solvent was removed in vacuo, and the crude material was purified via silica gel chromatography, utilizing a 5-90% ethyl acetate/hexanes gradient to deliver the desired compound, Compound I-64 (4 mg, 20% yield) as a solid.

$^1$H NMR (500 MHz, CD$_3$OD) δ ppm 8.74 (s, 1H), 8.05 (d, 1H), 7.19-7.33 (m, 2H), 6.97-7.12 (m, 2H), 6.79-6.93 (m, 2H), 5.92 (s, 2H), 3.67-3.81 (m, 4H), 2.49 (d, 2H), 1.77-1.91 (m, 2H), 1.63 (s, 3H).

Compound I-101

The title compound was prepared following general procedure B, except 4-(tert butoxycarbonyl)piperazine-2-carboxylic acid hydrate (4 equiv.) was the amine reactant, 5 equivalents of triethylamine was used, and contents were heated to 90° C. for 5 h as a solution in THF/water (9:1). Workup was carried out with ethyl acetate instead of dichloromethane. The crude material was purified via reverse phase HPLC to deliver the desired compound, Compound I-101 (12 mg, 26% yield) as a solid.

$^1$H NMR (500 MHz, DMSO-d$_6$) δ ppm 9.10 (d, 1H), 8.39 (d, 1H), 7.54 (s, 1H), 7.28-7.39 (m, 1H), 7.15-7.25 (m, 2H), 7.11 (t, 1H), 6.85 (t, 1H), 5.85-5.97 (m, 2H), 5.17 (br. s., 1H), 4.45 (d, 1H), 4.33 (br. s., 1H), 3.91-4.02 (m, 1H), 3.33-3.39 (m, 2H), 3.05-3.17 (m, 1H), 1.41 (s, 9H).

Compound I-163

The title compound was prepared following general procedure B, except 4,5,6,7-tetrahydro-3H-imidazo[4,5-c]pyridine-4-carboxylic acid (4 equiv.) was the amine reactant, 3 equivalents of triethylamine was used, and contents were heated to 175° C. for 10 min as a solution in NMP. Contents were diluted with diethyl ether, and the resulting precipitate was filtered and collected. The crude material was further purified via reverse phase HPLC to deliver the desired compound, Compound I-163 (5 mg, 15% yield) as a solid.

$^1$H NMR (500 MHz, methanol-d$_4$) δ ppm 9.03 (d, 1H), 8.82-8.89 (m, 1H), 8.58 (s, 1H), 7.58 (s, 1H), 7.28-7.37 (m, 1H), 7.11-7.18 (m, 1H), 7.02-7.10 (m, 1H), 6.94 (s, 1H), 6.83-6.92 (m, 1H), 6.01 (s, 2H), 5.12 (d, 1H), 5.00 (d, 1H), 4.55-4.64 (m, 1H), 3.43 (dd, 1H), 3.20 (d, 1H).

Compound I-189

The title compound was prepared following general procedure B, except 4-ethylpiperidine-4-carboxylic acid (as the HCl salt) was the amine reactant, 4 equivalents of triethylamine was used, and contents were heated to 40° C. for 18 h as a solution in THF. The reaction was incomplete, so additional amine reactant (3 equiv.), triethylamine (4 equiv.) and DMF (equivalent volume as THF) was introduced into the vessel, and the resulting mixture was heated to 85° C. for 18 h. The reaction was cooled and diluted with ethyl acetate, and washed with water and brine. Solvent was removed in vacuo, and the crude material was purified via reverse phase HPLC to deliver the desired compound, Compound I-189 as a solid.

$^1$H NMR (500 MHz, methanol-d$_4$) δ ppm 8.79 (d, 1H), 8.20 (d, 1H), 7.54 (s, 1H), 7.21-7.35 (m, 1H), 7.07-7.13 (m, 1H), 7.05 (t, 1H), 6.95 (d, 1H), 6.89 (t, 1H), 5.99 (s, 2H), 4.65 (d, 2H), 3.33-3.43 (m, 2H), 2.32 (d, 2H), 1.63-1.68 (m, 2H), 1.55-1.63 (m, 2H), 0.91 (t, 3H).

Compound I-190

The title compound was prepared following general procedure B, except 3-methylpiperidine-4-carboxylic acid was the amine reactant, 4 equivalents of triethylamine was used, and contents were heated to 40° C. for 18 h as a solution in THF. The reaction was incomplete, so additional amine reactant (3 equiv.), triethylamine (4 equiv.) and DMF (equivalent volume as THF) was introduced into the vessel, and the resulting mixture was heated to 85° C. for 18 h. The reaction was cooled and diluted with ethyl acetate, and washed with water and brine. Solvent was removed in vacuo, and the crude material was purified via reverse phase HPLC to deliver the desired compound, Compound I-190 as a solid.

$^1$H NMR (500 MHz, methanol-d$_4$) δ ppm 8.79 (d, 1H), 8.22-8.29 (m, 1H), 7.59 (s, 1H), 7.24-7.34 (m, 1H), 7.02-7.15 (m, 2H), 6.96-7.00 (m, 1H), 6.93 (t, 1H), 6.01 (m, 2H), 4.76 (d, 1H), 4.58 (d, 1H), 3.70 (dd, 1H), 3.52-3.58 (m, 1H), 2.87-2.94 (m, 1H), 2.45-2.54 (m, 1H), 2.00-2.11 (m, 1H), 1.90-1.99 (m, 1H), 1.02 (d, 3H).

Compound I-235

The title compound was prepared in 3 steps:

Step 1: Synthesis of 2-(1-(2,3-difluorobenzyl)-5-(isoxazol-3-yl)-1H-pyrazol-3-yl)-5-fluoropyrimidin-4(3H)-one The above compound was prepared following general procedure A, using 1-(isoxazol-3-yl)ethanone in step 1 and 2,3-difluorobenzylhydrazine in step 2.

Step 2: Preparation of 3-(3-(4-chloro-5-fluoropyrimidin-2-yl)-1-(2,3-difluorobenzyl)-1H-pyrazol-5-yl)isoxazole A suspension of 2-(1-(2,3-difluorobenzyl)-5-(isoxazol-3-yl)-1H-pyrazol-3-yl)-5-fluoropyrimidin-4(3H)-one in phosphoryl trichloride (47 equiv) was heated at 65° C. for 2 hour. The reaction mixture was carefully poured into ice and stirred for 20 min. The resultant mixture was basicified to pH 8 by addition of saturated sodium bicarbonate and extracted with dichloromethane. The combined organic layers were dried over sodium sulfate, filtered, and the solvent was removed in vacuo to afford 3-(3-(4-chloro-5-fluoropyrimidin-2-yl)-1-(2,3-difluorobenzyl)-1H-pyrazol-5-yl)isoxazole as a light yellow solid which was used in the next step without further manipulation.

Step 3: Synthesis of Compound I-235

A solution of (S)-3-methyl-2-(methylamino)butanoic acid (3.0 equivalents), triethylamine (10 equivalents). and 3-(3-(4-chloro-5-fluoropyrimidin-2-yl)-1-(2,3-difluorobenzyl) 1H-pyrazol-5-yl)isoxazole was stirred in dioxane/water (2:1 ratio) at 100° C. for 23 h, following general procedure B. The solution was diluted with water, neutralized to pH 3 by addition of 1N HCl and extracted with dichloromethane. The combined organic layers were dried over sodium sulfate, filtered, and the solvent was removed in vacuo. Purification by silica gel chromatography (0-10% acetonitrile/methanol (7:1) in dichloromethane gradient) yielded Compound I-235 (38 mg, 61% over 2 steps) as an off-white solid.

$^1$H-NMR (400 MHz, CDCl$_3$) δ 8.46 (d, 1H), 8.22 (d, 1H), 7.23 (s, 1H), 7.04 (dd, 1H), 6.92 (dd 1H), 6.77 (app. t, 1H), 6.58 (d, 1H), 5.99 (d, 1H), 5.94 (d, 1H), 4.27 (d, 1H), 3.24 (d, 3H), 2.52 (m, 1H), 1.11 (d, 3H), 0.94 (d, 3H).

Compound I-236

The title compound was prepared in 3 steps:

Step 1: Synthesis of 5-fluoro-2-(1-(2-fluorobenzyl)-5-(oxazol-2-yl)-1H-pyrazol-3-yl) pyrimidin-4(3H)-one The above compound was prepared following general procedure A, using 1-(oxazol-2-yl)ethanone in Step 1 and 2-fluorobenzylhydrazine in Step 2.

Step 2: Synthesis of 2-(3-(4-chloro-5-fluoropyrimidin-2-yl)-1-(2-fluorobenzyl)-1H-pyrazol-5-yl)oxazole The above compound was prepared following a process analogous to Step 2 of the synthesis of Compound I-235, using 5-fluoro-2-(1-(2-fluorobenzyl)-5-(oxazol-2-yl)-1H-pyrazol-3-yl)-pyrimidin-4(3H)-one as the starting pyrimidone.

Step 3: Synthesis of Compound I-236

The title compound was prepared following general procedure B, except (S)-3-methyl-2-(methylamino)butanoic acid was the amine reactant, 2-(3-(4-chloro-5-fluoropyrimidin-2-yl)-1-(2-fluorobenzyl)-1H-pyrazol-5-yl)oxazole was used in place of Intermediate 1, and contents were heated to 100° C. for 41 h. The crude material was purified via silica gel chromatography (0-20% (acetonitrile/methanol=7:1) in dichloromethane gradient) delivered the desired compound, Compound I-236 (8.9 mg, 49% over two steps) as an off-white solid.

$^1$H-NMR (400 MHz, CDCl$_3$) δ 8.25 (d, 1H), 7.70 (s, 1H), 7.46 (s, 1H), 7.24 (s, 1H), 7.21 (m 1H), 7.07-6.95 (m, 3H), 6.11 (d, 1H), 6.04 (d, 1H), 4.27 (d, 1H), 3.23 (d, 3H), 2.52 (m, 1H), 1.11 (d, 3H), 0.94 (d, 3H).

Compound I-36

Into a stirred solution of Compound I-12 dissolved in dichloromethane was added and equivalent volume of trifluoroacetic acid at 23° C. Contents stirred until full consumption of starting material was observed via LC/MS. The reaction was diluted with dichloromethane and quenched with saturated sodium bicarbonate solution. The layers were separated, and the organic layer was washed with saturated sodium bicarbonate solution, water, and brine. The organic layer was further dried over Na$_2$SO$_4$, filtered, and concentrated in vacuo to deliver the desired compound, Compound I-36 (19.5 mg, 75% yield) as a solid.

$^1$H NMR (500 MHz, CDCl$_3$) δ 8.46 (s, 1H), 8.15 (d, 1H), 7.27-7.30 (m, 1H), 7.13-7.23 (m, 1H), 7.00-7.09 (m, 1H), 6.91-7.00 (m, 1H), 6.81-6.90 (m, 1H), 6.54-6.62 (m, 1H), 5.95 (s, 2H), 5.19 (d, 1H), 4.26-4.40 (m, 1H), 3.23-3.35 (m, 2H), 3.03 (br. s, 1H), 2.92 (td, 2H), 2.10-2.20 (m, 2H), 1.59-1.77 (m, 2H).

Compound I-37

Into a stirred solution of Compound I-25 dissolved in dichloromethane was added and equivalent volume of trifluoroacetic acid at 23° C. Contents stirred until full consumption of starting material was observed via LC/MS. The reaction was diluted with dichloromethane and quenched with saturated sodium bicarbonate solution. The layers were separated, and the organic layer was washed with saturated sodium bicarbonate solution, water, and brine. The organic layer was further dried over Na$_2$SO$_4$, filtered, and concentrated in vacuo to deliver the desired compound, Compound I-37 (14 mg, 79% yield) as a solid.

$^1$H NMR (500 MHz, CDCl$_3$) δ 8.45 (d, 1H), 8.16 (d, 1H), 7.30 (s, 1H), 7.14-7.23 (m, 1H), 7.00-7.07 (m, 1H), 6.96 (td, 1H), 6.78-6.89 (m, 1H), 6.60 (d, 1H), 5.96 (s, 2H), 4.39-4.51 (m, 1H), 4.22-4.36 (m, 1H), 3.25 (ddd, 1H), 2.93-3.08 (m, 2H), 1.99-2.11 (m, 1H), 1.83-1.92 (m, 1H), 1.59-1.72 (m, 1H), 1.37-1.50 (m, 1H).

Compound I-38

Into a stirred solution of Compound I-26 dissolved in dichloromethane was added and equivalent volume of trifluoroacetic acid at 23° C. Contents stirred until full consumption of starting material was observed via LC/MS. The reaction was diluted with dichloromethane and quenched with saturated sodium bicarbonate solution. The layers were separated, and the organic layer was washed with saturated sodium bicarbonate solution, water, and brine. The organic layer was further dried over Na$_2$SO$_4$, filtered, and concentrated in vacuo to deliver the desired compound, Compound I-38 (11 mg, 55% yield) as a solid.

$^1$H NMR (500 MHz, CDCl$_3$) δ 8.46 (d, 1H), 8.16-8.22 (m, 1H), 7.30 (m, 1H), 7.17-7.25 (m, 2H), 7.00-7.09 (m, 1H), 6.91-6.98 (m, 1H), 6.85 (d, 1H), 6.56-6.68 (m, 1H), 5.96-6.03 (m, 1H), 5.95 (s, 2H), 4.94-5.01 (m, 1H), 4.39 (t, 2H), 3.99 (dd, 2H).

Compound I-39

Into a stirred solution of Compound I-27 dissolved in dichloromethane was added and equivalent volume of trifluoroacetic acid at 23° C. Contents stirred until full consumption of starting material was observed via LC/MS. The reaction was diluted with dichloromethane and quenched with saturated sodium bicarbonate solution. The layers were separated, and the organic layer was washed with saturated sodium bicarbonate solution, water, and brine. The organic layer was further dried over Na$_2$SO$_4$, filtered, and concentrated in vacuo to deliver the desired compound, Compound I-39 (12.2 mg, 69% yield) as a solid.

$^1$H NMR (500 MHz, CDCl$_3$) δ 8.45 (d, 1H), 8.13 (d, 1H), 7.35 (s, 1H), 7.14-7.24 (m, 1H), 6.99-7.08 (m, 1H), 6.92-6.99 (m, 1H), 6.79-6.89 (m, 1H), 6.64 (d, 1H), 5.97 (s, 2H), 5.55 (br. s., 1H), 4.34-4.49 (m, 1H), 3.29 (dd, 1H), 2.88-3.01 (m, 1H), 2.79-2.87 (m, 1H), 2.75 (dd, 1H), 1.90-2.02 (m, 1H), 1.77-1.88 (m, 1H), 1.58-1.76 (m, 2H).

Compound I-40

Into a stirred solution of Compound I-21 dissolved in dichloromethane was added and equivalent volume of trifluoroacetic acid at 23° C. Contents stirred until full consumption of starting material was observed via LC/MS. The reaction was diluted with dichloromethane and quenched with saturated sodium bicarbonate solution. The layers were separated, and the organic layer was washed with saturated sodium bicarbonate solution, water, and brine. The organic layer was further dried over Na$_2$SO$_4$, filtered, and concentrated in vacuo to deliver the desired compound, Compound I-40 (22 mg, 90% yield) as a solid.

$^1$H NMR (500 MHz, methanol-d$_4$) δ 8.73 (d, 1H), 8.06 (d, 1H), 7.37 (s, 1H), 7.19-7.30 (m, 1H), 7.04-7.11 (m, 1H), 7.00 (t, 1H), 6.86 (d, 1H), 6.77 (t, 1H), 5.93 (s, 2H), 4.58 (t, 2H), 4.13 (dd, 2H), 3.98-4.09 (m, 1H).

Compound I-133

Into a stirred solution of Compound I-101 dissolved in dichloromethane was added and equivalent volume of trifluoroacetic acid at 23° C. Contents stirred until full consumption of starting material was observed via LC/MS. The mixture was concentrated in vacuo, and the resulting gum was triturated with diethyl ether, filtered, and the solids were washed with diethyl ether. The solids were collected and dried in vacuo to deliver the desired compound, Compound I-133 (as the TFA salt, 100 mg, 83% yield) as a white solid.

$^1$H NMR (500 MHz, DMSO-d$_6$) δ 9.11 (s, 1H), 8.87 (s, 1H), 8.47 (d, 1H), 7.58 (s, 1H), 7.29-7.40 (m, 1H), 7.17-7.27 (m, 2H), 7.11 (t, 1H), 6.83 (t, 1H), 5.89 (s, 2H), 5.44-5.49 (m, 1H), 4.59-4.64 (m, 1H), 3.79 (d, 1H), 3.41-3.46 (m, 1H), 3.11-3.18 (m, 1H), 3.01-3.12 (m, 1H).

Compound I-30

The title compound was prepared following general procedure B, except 2,8-diazaspiro[4.5]decan-3-one (2 equiv.) was the amine reactant, no triethylamine was used, and contents were heated to 40° C. for 2 d as a solution in THF. The reaction was cooled, solvent was removed in vacuo, and the resulting solid was rinsed with 1N HCl solution to deliver the desired compound, Compound I-30 (57.8 mg, 83% yield) as a white solid.

$^1$H NMR (500 MHz, METHANOL-d$_4$) δ ppm 8.86 (s, 1H) 8.36 (d, 1H) 7.71 (s, 1H) 7.31-7.37 (m, 1H) 7.13 (dd, 2H) 6.99-7.04 (m, 2H) 6.06 (s, 2H) 4.32 (br. s., 2H) 4.13 (br. s., 2H) 3.37 (br. s., 2H) 2.42 (s, 2H) 1.95 (t, 4H).

Compound I-42

The title compound was prepared following general procedure B, except 2-oxa-7-azaspiro[3.5]nonane oxalate (2 equiv.) was the amine reactant, 8 equivalents of triethylamine was used, and contents were heated to 40° C. for 24 h as a solution in NMP. The reaction was cooled, diluted with ethyl acetate, and the mixture was rinsed with water. Contents were dried, filtered, and concentrated in vacuo. The crude material was purified via silica gel chromatography utilizing a 0-80% ethyl acetate/hexanes gradient to deliver the desired compound, Compound I-42 (42 mg, 52% yield) as a white solid.

$^1$H NMR (500 MHz, METHANOL-d$_4$) δ ppm 8.75 (s, 1H) 8.13 (d, 1H) 7.41 (s, 1H) 7.20-7.32 (m, 1H) 6.97-7.14 (m, 2H) 6.90 (s, 1H) 6.81 (t, 1H) 5.95 (s, 2H) 4.52 (s, 4H) 3.80-3.88 (m, 4H) 1.90-2.05 (m, 4H).

Compound I-43

The title compound was prepared following general procedure B, except 8-oxa-2-azaspiro[4.5]decane (2 equiv.) was the amine reactant, no triethylamine was used, and contents were heated to 40° C. for 24 h as a solution in THF. The reaction was cooled and concentrated to yield a solid, which was dissolved in ethyl acetate. The organic layer was washed with aqueous 1N HCl, dried, filtered, and concentrated in vacuo. The crude material was purified via silica gel chromatography utilizing a 0-100% ethyl acetate/hexanes gradient to deliver the desired compound, Compound I-42 (6.4 mg, 17% yield) as a white solid.

$^1$H NMR (500 MHz, METHANOL-d$_4$) δ ppm 8.77 (s, 1H) 8.09 (d, 1H) 7.44 (s, 1H) 7.25-7.33 (m, 1H) 7.11 (t, 1H) 7.05 (s, 1H) 6.93 (s, 1H) 6.82 (s, 1H) 5.98 (s, 2H) 3.92 (br. s., 2H) 3.71-3.84 (m, 6H) 2.00 (t, 2H) 1.64-1.75 (m, 4H).

Compound I-32

The title compound was prepared following general procedure B, except 2-oxa-6-azaspiro[3.3]heptane oxalate (2 equiv.) was the amine reactant, 6 equivalents of triethylamine was used, and contents were heated to 40° C. for 2 d as a solution in THF. The reaction was cooled and concentrated to yield a solid, which was dissolved in ethyl acetate. The organic layer was washed with 1N HCl solution, dried, filtered, and concentrated in vacuo to deliver the desired compound, Compound I-32 (19 mg, 33% yield) as a white solid.

$^1$H NMR (500 MHz, METHANOL-d$_4$) δ ppm 8.83 (s, 1H) 8.24 (br. s, 1H) 7.57 (br. s., 1H) 7.29-7.33 (m, 1H) 7.03-7.16 (m, 2H) 6.91-7.01 (m, 2H) 5.99-6.05 (m, 2H) 4.28-4.61 (m, 4H) 3.99 (s, 2H) 3.88 (s, 2H).

Compound I-47

The title compound was prepared following general procedure B, except 2-oxa-6-azaspiro[3.5]nonane oxalate (2 equiv.) was the amine reactant, 4 equivalents of triethylamine was used, and contents were heated to 40° C. for 2 h as a solution in NMP. The reaction was cooled and concentrated to yield a solid, which was dissolved in ethyl acetate. The organic layer was washed with water, dried, filtered, and concentrated in vacuo. The crude material was purified via silica gel chromatography utilizing a 0-100% ethyl acetate/hexanes gradient to deliver the desired compound, Compound I-47 (42.3 mg, 66% yield) as a white solid.

$^1$H NMR (400 MHz, METHANOL-d$_4$) δ ppm 8.67-8.76 (m, 1H) 8.12 (d, 1H) 7.40 (s, 1H) 7.19-7.28 (m, 1H) 7.02-7.10 (m, 1H) 6.99 (t, 1H) 6.88 (d, 1H) 6.79 (t, 1H) 5.89-5.95 (m, 2H) 4.38-4.49 (m, 4H) 4.05-4.10 (m, 2H) 3.71-3.79 (m, 2H) 1.92-1.98 (m, 2H) 1.58-1.68 (m, 2H).

Compound I-44

The title compound was prepared following general procedure B, except tert-butyl 2,8-diazaspiro[4.5]decane-2-carboxylate (2 equiv.) was the amine reactant, no triethylamine was used, and contents were heated to 40° C. for 2 d as a solution in THF. The reaction was cooled and diluted with ethyl acetate. The organic layer was washed with water, dried, filtered, and concentrated in vacuo. The crude material was purified via silica gel chromatography utilizing a 0-100% ethyl acetate/hexanes gradient to deliver the desired compound, Compound I-44 (51.6 mg, 67% yield) as a white solid.

$^1$H NMR (500 MHz, METHANOL-d$_4$) δ ppm 8.77 (s, 1H) 8.15 (d, 1H) 7.43 (s, 1H) 7.23-7.33 (m, 1H) 7.11 (t, 1H) 7.05 (t, 1H) 6.92 (s, 1H) 6.83 (t, 1H) 5.97 (s, 2H) 3.79-4.09 (m, 4H) 3.43-3.52 (m, 2H) 3.30 (s, 2H) 1.89 (t, 2H) 1.72 (br. s., 4H) 1.49 (s, 9H).

Compound I-45

The title compound was prepared following general procedure B, except tert-butyl 2,7-diazaspiro[4.4]nonane-2-carboxylate (2 equiv.) was the amine reactant, 1 equivalent of triethylamine was used, and contents were heated to 40° C. for 2 d as a solution in THF. The reaction was cooled and diluted with ethyl acetate. The organic layer was washed with water, dried, filtered, and concentrated in vacuo. The crude material was purified via silica gel chromatography utilizing a 0-100% ethyl acetate/hexanes gradient to deliver the desired compound, Compound I-45 (48.3 mg, 64% yield) as a white solid.

$^1$H NMR (500 MHz, METHANOL-d$_4$) δ ppm 8.75 (s, 1H) 8.04-8.13 (m, 1H) 7.40 (s, 1H) 7.24-7.32 (m, 1H) 7.10 (t, 1H) 7.03 (t, 1H) 6.89 (s, 1H) 6.82 (t, 1H) 5.96 (s, 2H) 3.85-3.98 (m, 2H) 3.69-3.82 (m, 2H) 3.49 (br. s., 2H) 3.30-3.43 (m, 4H) 1.48 (d, 9H).

Compound I-61

The title compound was prepared following general procedure B, except 3,3-difluoroazetidine (as the HCl salt, 1 equiv.) was the amine reactant, 2 equivalents of Hunig's base was used instead of triethylamine, and contents were heated to 40° C. for 3 h as a solution in NMP. The reaction was cooled and diluted with ethyl acetate. The organic layer was washed with water, dried, filtered, and concentrated in vacuo. The crude material was purified via silica gel chromatography utilizing a 0-30% ethyl acetate/hexanes gradient to deliver the desired compound, Compound I-61 (37 mg, 71% yield) as a white solid.

$^1$H NMR (400 MHz, CDCl$_3$) δ ppm 8.44 (d, 1H) 8.22 (d, 1H) 7.30 (s, 1H) 7.14-7.21 (m, 1H) 6.91-7.04 (m, 2H) 6.81 (t, 1H) 6.54-6.59 (m, 1H) 5.95 (s, 2H) 4.60-4.71 (m, 4H).

Compound I-62

The title compound was prepared following general procedure B, except 4,4-Difluoropiperidine (as the HCl salt, 1 equiv.) was the amine reactant, 2 equivalents of Hunig's base was used instead of triethylamine, and contents were heated to 40° C. for 3 h as a solution in NMP. The reaction was cooled and diluted with ethyl acetate. The organic layer was washed with water, dried, filtered, and concentrated in vacuo. The crude material was purified via silica gel chromatography utilizing a 0-30% ethyl acetate/hexanes gradient to deliver the desired compound, Compound I-62 (40.4 mg, 71% yield) as a white solid.

$^1$H NMR (400 MHz, CDCl$_3$) δ ppm 8.43 (d, 1H) 8.22 (d, 1H) 7.24-7.25 (m, 1H) 7.12-7.21 (m, 1H) 6.91-7.04 (m, 2H) 6.82 (t, 1H) 6.56 (d, 1H) 5.94 (s, 2H) 3.94-4.02 (m, 4H) 2.04-2.17 (m, 4H).

Compound I-63

The title compound was prepared following general procedure B, except 3,3-difluoro-pyrrolidine (as the HCl salt, 1 equiv.) was the amine reactant, 2 equivalents of Hunig's base was used instead of triethylamine, and contents were heated to 40° C. for 3 h as a solution in NMP. The reaction was cooled and diluted with ethyl acetate. The organic layer was washed with water, dried, filtered, and concentrated in vacuo. The crude material was purified via silica gel chromatography utilizing a 0-30% ethyl acetate/hexanes gradient to deliver the desired compound, Compound I-63 (41.5 mg, 71% yield) as a white solid.

$^1$H NMR (400 MHz, CDCl$_3$) δ ppm 8.43 (d, 1H) 8.19 (d, 1H) 7.29 (s, 1H) 7.11-7.22 (m, 1H) 6.90-7.04 (m, 2H) 6.78-6.87 (m, 1H) 6.56 (d, 1H) 5.94 (s, 2H) 3.98-4.18 (m, 4H) 2.40-2.54 (m, 2H).

Compound I-166

The title compound was prepared following general procedure B, except N-benzylglycine ethyl ester (1 equiv.) was the amine reactant, 2 equivalents of triethylamine was used, and contents were heated to 80° C. for 24 h as a solution in THF/water (10:1). The reaction was cooled and diluted with ethyl acetate. The organic layer was washed with saturated ammonium chloride solution, dried, filtered, and concentrated in vacuo. The crude material was purified via silica gel chromatography to deliver the desired compound, Compound I-166 (33 mg, 47%) as a white solid.

$^1$H NMR (400 MHz, CDCl$_3$) δ ppm 8.42 (d, 1H) 8.23 (d, 1H) 7.28-7.39 (m, 5H) 7.23 (d, 1H) 7.12-7.21 (m, 1H) 6.91-7.05 (m, 2H) 6.83 (t, 1H) 6.53 (d, 1H) 5.94 (s, 2H) 5.00 (s, 2H) 4.20-4.24 (m, 2H) 4.14-4.20 (m, 2H) 1.21 (t, 3H).

Compound I-167

The title compound was prepared following general procedure B, except ethyl N-methylaminoacetate (as the HCl salt, 1 equiv.) was the amine reactant, 2 equivalents of triethylamine was used, and contents were heated to 90° C. for 24 h as a solution in THF. The reaction was cooled and diluted with ethyl acetate and water. The layers were separated, and the the organic layer was dried, filtered, and concentrated in vacuo. The crude material was purified via silica gel chromatography utilizing a 0-100% ethyl acetate/ hexanes gradient to deliver the desired compound, Compound I-167 (77 mg, 79% yield) as a white solid.

$^1$H NMR (500 MHz, CDCl$_3$) δ ppm 8.46 (d, 1H) 8.22 (d, 1H) 7.28 (d, 1H) 7.15-7.25 (m, 1H) 6.95-7.06 (m, 2H) 6.81-6.89 (m, 1H) 6.58 (d, 1H) 5.95-6.00 (m, 1H) 4.35 (s, 2H) 4.23 (q, 2H) 3.43 (d, 3H) 1.25 (t, 3H).

Compound I-176

A mixture of Compound I-167 (70 mg, 1 equiv.) and sodium hydroxide [1.0 N aqueous solution] (770 µl, 5 eqiuv.) in THF (385 µl) and MeOH (385 µl) was stirred at rt for 24 h. The mixture was quenched with 1N HCl (5 equiv.). The white precipitate formed was collected by filtration, rinsed with a minimal amount of ether and dried to give Compound I-176 (52 mg, 79% yield) as a white solid.

$^1$H NMR (500 MHz, DMSO-d$_6$) δ ppm 9.11 (d, 1H) 8.34 (d, 1H) 7.54 (s, 1H) 7.30-7.37 (m, 1H) 7.19-7.25 (m, 2H) 7.11 (t, 1H) 6.86 (t, 1H) 5.90 (s, 2H) 4.41-4.45 (m, 2H) 3.32 (d, 3H).

Compound I-168

A mixture of Compound I-167 (30 mg, 1 equiv.) and sodium hydroxide [1.0 N aqueous solution] (57 µl, 1 equiv) in THF (141 µl) and MeOH (141 µl) was stirred at rt for 24 h. It was treated with 1N HCl (1 equiv.). The mixture was diluted in dichloromethane (100 ml) and washed with water (50 ml). The organic layer was dried, filtered and evaporated to give an oil. The oil was purified by column chromatography (0 to 10% methanol in dichloromethane) to give Compound I-168 (10 mg, 36% yield) as a white solid.

$^1$H NMR (400 MHz, METHANOL-d$_4$) δ ppm 8.74 (d, 1H) 8.20 (d, 1H) 7.33-7.43 (m, 5H) 7.22-7.32 (m, 3H) 6.99-7.13 (m, 3H) 6.84 (d, 2H) 5.95 (s, 2H) 5.05 (s, 2H).

Compound I-218

A mixture of Compound I-176 (48 mg, 1 equiv.), O-methylhydroxylamine hydrochloride (14 mg, 1.5 equiv), EDC (32 mg, 1.5 equiv.) and DMAP (21 mg, 1.5 equiv) in DMF (563 µl) was stirred at rt for 2 h. The mixture was diluted in ethyl acetate (100 ml) and washed with water (50 ml×3). The organic layer was dried, filtered and evaporated to give an oil. The oil was purified by column chromatography to give Compound I-218 (26 mg, 51% yield) as a white solid.

$^1$H NMR (500 MHz, METHANOL-d$_4$) δ ppm 8.63-8.68 (m, 1H) 8.08 (d, 1H) 7.30 (s, 1H) 7.13-7.20 (m, 1H) 6.96-7.02 (m, 1H) 6.92 (t, 1H) 6.77 (s, 1H) 6.71 (t, 1H) 5.85 (s, 2H) 4.17 (s, 2H) 3.55 (s, 3H) 3.30-3.34 (m, 3H).

Compound I-223

The title compound was prepared following general procedure B, except N-methyl-1-(3-methyl-1,2,4-oxadiazol-5-yl)methanamine (as the HCl salt, 1 equiv.) was the amine reactant, 4 equivalents of triethylamine was used, and contents were heated to 85° C. for 24 h as a solution in dioxane. The reaction was cooled and diluted with ethyl acetate. The the organic layer was washed with 1N HCl solution, dried, filtered, and concentrated in vacuo. The crude material was purified via silica gel chromatography utilizing a 0-100% ethyl acetate/hexanes gradient to deliver the desired compound, Compound I-223 (16.3 mg, 21% yield) as a white solid.

$^1$H NMR (500 MHz, CDCl$_3$) δ ppm 8.46 (d, 1H) 8.25 (d, 1H) 7.15-7.22 (m, 2H) 6.96 (t, 1H) 6.84 (t, 1H) 6.61 (d, 1H) 5.95 (s, 2H) 5.03 (s, 2H) 3.52 (d, 3H) 2.38 (s, 3H).

Compound I-14

2-(1-(2-fluorobenzyl)-5-(isoxazol-3-yl)-1H-pyrazol-3-yl)-5-nitropyrimidin-4-ol (1 equiv.) (this intermediated was in a previous patent: WO2012/3405 A1) (25 mg, 1 equiv.) was treated with POCl$_3$ (457 µl, 75 equiv.) and stirred at reflux for 1.5 h. Contents were concentrated in vacuo, and residue was azeotroped with toluene (×2). The residue was re-dissolved in THF (0.7 mL) and treated with morpholine (171 µl, 30 equiv.). The contents were heated to 40° C., and reaction stirred for 1.5 h. Residue was transferred to 1:1 mixture of ethyl acetate and water. The layers were separated, and the aqueous layer was extracted with ethyl acetate (×3). The organic portions were combined and washed with brine. The mixture was dried over MgSO$_4$, filtered, and concentrated in vacuo to deliver the desired Compound I-14 (30 mg, 97%) as a pale yellow solid.

$^1$H-NMR (400 MHz, CDCl$_3$) δ 8.47 (d, 1H), 8.36 (d, 1H), 8.09-8.16 (m, 1H), 7.69 (dd, 1H), 7.41 (d, 1H), 7.20 (t, 1H), 6.66-6.70 (m, 1H), 6.45 (d, 1H), 6.06 (s, 2H), 3.79-3.86 (m, 4H), 3.74 (m, 4H).

Compound I-15

A solution of Compound I-14 (30 mg, 1 equiv.) in methanol was treated with palladium on carbon (7 mg, 10% wt palladium, 0.1 equiv) and placed under at atmosphere of hydrogen. Contents were stirred for 2 h at 23° C. Contents were filtered over celite, and eluted with methanol. Contents were concentrated in vacuo, and the crude material was purified via silica gel chromatography utilizing a 0-70% (acetonitrile:methanol=7:1)/dichloromethane gradient to deliver the desired Compound I-15 (11.5 mg, 39%) as a white solid.

$^1$H-NMR (400 MHz, CDCl$_3$) δ 8.43 (d, 1H), 8.36 (d, 1H), 7.35 (d, 1H), 6.80 (t, 1H), 6.59-6.53 (m, 1H), 6.49-6.40 (m, 2H), 6.11 (dd, 1H), 5.93-5.82 (m, 2H), 3.87-3.76 (m, 4H), 3.72 (d, 4H).

Compound I-70

A solution of Compound I-37 in toluene was treated with ethyl isocyanate (3 equiv.) and heated to 90° C. for 20 min. The resulting precipitates were filtered and rinsed with toluene. The solids were collected and dried in vacuo to deliver the desired compound, Compound I-70 (7 mg, 36% yield) as a solid.

$^1$H NMR (500 MHz, DMSO-d$_6$) δ 9.09 (d, 1H), 8.27 (d, 1H), 7.77 (s, 1H), 7.30-7.36 (m, 1H), 7.14-7.27 (m, 2H), 7.07-7.12 (m, 1H), 6.83 (t, 1H), 5.94 (d, 1H), 5.91 (s, 2H), 5.76 (t, 1H), 4.17 (d, 1H), 3.94 (d, 1H), 3.69 (dt, 1H), 3.52 (t, 1H), 3.22 (dd, 1H), 3.02 (quin, 2H), 1.85 (d, 1H), 1.71-1.81 (m, 1H), 1.43-1.62 (m, 2H), 0.97 (t, 3H).

Compound I-71

A solution of Compound I-40 in toluene was treated with ethyl isocyanate (3 equiv.) and heated to 90° C. for 20 min. The resulting precipitates were filtered and rinsed with toluene. The solids were collected and dried in vacuo to deliver the desired compound, Compound I-71 (3 mg, 16% yield) as a solid.

$^1$H NMR (500 MHz, DMSO-d$_6$) δ 9.10 (d, 1H), 8.25 (d, 1H), 7.49-7.55 (m, 1H) 7.29-7.37 (m, 1H), 7.19-7.27 (m, 2H), 7.10 (t, 1H), 6.81 (t, 1H), 6.52-6.61 (m, 1H), 6.02 (t, 1H), 5.90 (s, 2H), 4.51-4.59 (m, 1H), 4.47 (m, 1H), 4.06 (d, 2H), 2.94-3.07 (m, 2H), 0.99 (t, 3H).

Compound I-136

A solution of Compound I-133 in dichloromethane was treated with ethyl isocyanate (1.1 equiv.) and triethylamine (2 equiv.), and stirred at 23° C. for 1 h. Solvent removed in vacuo, and residue re-suspended in diethyl ether. The resulting precipitates were filtered and rinsed with diethyl ether. The solids were collected and dried in vacuo to deliver the desired compound, Compound I-136 (2.9 mg, 28% yield) as a solid.

$^1$H NMR (500 MHz, DMSO-d$_6$) δ 9.09 (s, 1H), 8.26-8.39 (m, 1H), 7.52 (s, 1H) 7.32 (m, 1H), 7.17-7.27 (m, 2H), 7.10 (t, 1H), 6.78-6.88 (m, 1H), 6.63 (br.s., 1H), 5.90 (m, 2H), 4.90-5.19 (m, 1H) 4.43 (d, 1H), 4.30 (br.s., 1H), 3.91 (d, 1H), 3.48 (d, 1H), 3.22 (d, 1H), 2.99-3.05 (m, 3H), 1.01 (t, 3H).

Compound I-134

A solution of Compound I-133 in dichloromethane was treated with propionyl chloride (1.1 equiv.) and triethylamine (2 equiv.), and stirred at 23° C. for 1 h. Solvent removed in vacuo, and residue re-suspended in diethyl ether. The resulting precipitates were filtered and rinsed with diethyl ether. The solids were collected and dried in vacuo to deliver the desired compound, Compound I-134 (3.5 mg, 35% yield) as a solid.

$^1$H NMR (500 MHz, DMSO-d$_6$) δ 9.10 (s, 1H), 8.40 (d, 1H), 7.49-7.64 (m, 1H), 7.28-7.39 (m, 1H), 7.15-7.26 (m, 2H), 7.11 (t, 1H), 6.84 (br. s., 1H), 5.89 (s, 2H), 4.79 (d, 1H), 4.24-4.45 (m, 2H), 3.91 (d, 1H), 3.67 (br. s., 1H), 3.58 (d, 1H), 2.87-3.00 (m, 1H), 2.31-2.40 (m, 2H), 0.93-1.04 (m, 3H).

Compound I-135

A solution of Compound I-133 in dichloromethane was treated with methyl chloroformate (1.1 equiv.) and triethylamine (2 equiv.), and stirred at 23° C. for 1 h. Solvent removed in vacuo, and residue re-suspended in diethyl ether. The resulting precipitates were filtered and rinsed with diethyl ether. The solids were collected purified via reverse phase HPLC to deliver the desired compound, Compound I-135 (3.5 mg, 37% yield) as a solid.

$^1$H NMR (500 MHz, CD$_3$OD) δ 8.82 (s, 1H), 8.41 (d, 1H), 7.58 (s, 1H), 7.26-7.35 (m, 1H), 7.12 (t, 1H), 7.07 (t, 1H), 6.88-6.97 (m, 2H), 6.01 (s, 2H), 5.51 (br. s., 1H), 4.68 (d, 1H), 4.58 (br. s., 1H), 4.09 (d, 1H), 3.79-3.95 (m, 1H), 3.76 (s, 3H), 3.52-3.62 (m, 1H), 3.35-3.45 (m, 1H).

Compound I-49 and Compound I-50

A solution of 1-methylcyclopropanecarboxylic acid (141 mg, 10 equiv.) in dichloromethane (1 mL) was treated with oxalyl chloride (0.11 mL, 9 equiv.), and contents were stirred until no more bubbling was observed. The resulting solution was then added portionwise over 5 minutes to a cooled (0° C.) solution of 5-fluoro-2-(1-(2-fluorobenzyl)-5-(isoxazol-3-yl)-1H-pyrazol-3-yl)-pyrimidin-4-amine (1 equiv, 50 mg this intermediate was described in a previous patent application publication, WO2012/3405 A1) in dichloromethane (0.35 mL) and pyridine (0.35 mL). The mixture was heated to 60° C. and stirred for 24 h. The reaction mixture was diluted with ethyl acetate and washed with saturated aqueous ammonium chloride solution. The layers were separated, and the aqueous layer was extracted with ethyl acetate (×3) and dichloromethane (×1). The organic portions were combined and washed with brine. The mixture was dried over MgSO$_4$, filtered, and concentrated in vacuo. The crude material was purified via silica gel chromatography utilizing a 0-60% ethyl acetate/hexanes gradient to deliver the desired Compound I-49 (18.5 mg, 30%) as a white solid, along with I-50 (16.2 mg, 22%) as a clear oil.

Compound I-49 H$^1$ NMR (400 MHz, CDCl$_3$) δ 8.57 (d, 1H), 8.43 (d, 1H), 8.01 (s, 1H), 7.38 (s, 1H), 7.22-7.13 (m, 1H), 7.00 (t, 1H), 6.98-6.90 (m, 1H), 6.78 (t, 1H), 6.57 (d, 1H), 5.99 (s, 2H), 1.48 (s, 3H), 1.38-1.32 (m, 2H), 0.79-0.73 (m, 2H).

Compound I-50 H$^1$ NMR (400 MHz, CDCl$_3$) δ 8.64 (d, 1H), 8.47-8.44 (m, 1H), 7.28 (s, 1H), 7.22-7.15 (m, 1H), 7.02 (d, 1H), 6.97 (t, 1H), 6.93-6.87 (m, 1H), 6.55-6.53 (m, 1H), 5.95 (s, 2H), 1.53-1.48 (m, 4H), 1.22 (s, 6H), 0.85-0.79 (m, 4H).

Compound I-51 and Compound I-52

A solution of 5-fluoro-2-(1-(2-fluorobenzyl)-5-(isoxazol-3-yl)-1H-pyrazol-3-yl)-pyrimidin-4-amine (1 equiv, this intermediate in a previous patent application publication; WO2012/3405 A1) (see above) (50 mg, 1 equiv.) in THF (0.7 mL) was cooled to 0° C. and treated with LiHMDS (0.16 mL, 1.1 equiv., 1M solution) and stirred for 20 minutes. The reaction was then treated with methyl chloroformate (44 µL, 4 equiv.). The reaction mixture was stirred at 0° C. for 20 minutes, then warmed to 23° C., over 1 h. The reaction was diluted with ethyl acetate and quenched with saturated aqueous ammonium chloride solution. The layers were separated, and the aqueous layer was extracted with ethyl acetate (twice) and dichloromethane (three times). The organic portions were combined and washed with brine. The mixture was dried over MgSO$_4$, filtered, and concentrated in vacuo. The crude material was purified via silica gel chromatography utilizing a 0-100% ethyl acetate/hexanes gradient to deliver the desired Compound I-51 (5.3 mg, 9%) as an off-white solid, along with Compound I-52 (13.1 mg, 20%) as a white solid.

Compound I-51 $^1$H-NMR (500 MHz, CDCl$_3$) δ 8.56 (s, 1H), 8.45 (s, 1H), 7.41 (s, 1H), 7.38 (s, 1H), 7.19 (m, 1H), 7.02 (t, 1H), 6.95 (m, 1H), 6.81 (m, 1H), 6.61 (s, 1H), 6.00 (s, 2H), 3.87 (s, 3H).

Compound I-52 $^1$H-NMR (500 MHz, CDCl$_3$) δ 8.77 (s., 1H), 8.47 (s, 1H), 7.40 (s, 1H), 7.21 (m, 1H), 7.07-6.93 (m, 2H), 6.84 (m, 1H), 6.59 (s, 1H), 6.02 (s, 2H), 3.83 (s, 6H).

Compound I-144

In a small vial, Compound I-58 (0.022 g, 0.047 mmol) was diluted with DCM (Volume: 2.0 ml) then charged with CDI (28 mg, 0.173 mmol). The reaction mixture was then heated to 45° C. until complete consumption of starting acid was noted by LC/MS. At this time, cyclopropanesulfonamide (22.86 mg, 0.189 mmol) and DBU (7.11 μl, 0.047 mmol) were added and the reaction was heated for an additional 30 minutes. At this time, the reaction was quenched with 1N HCl, then diluted with DCM. The layers were separated and the aqueous portion was extracted an addition two times with DCM. The organic portions were combined, dried (Na$_2$SO4), filtered, and concentrated. The crude material was purified using SiO$_2$ chromatography employing a 0-10% MeOH/DCM gradient to deliver the desired acyl sulfonamide, Compound I-144 (16 mg, 54% yield).

$^1$H-NMR (400 MHz, CDCl$_3$) δ 10.62 (bs, 1H), 8.43 (d, 1H), 8.23 (d, 1H), 7.45 (s, 1H), 7.19 (dd, 1H), 7.03-6.95 (m, 2H), 6.85 (t, 1H), 6.69 (s, 1H), 5.96 (dd, 2H), 4.20-4.12 (m, 1H), 2.87-2.79 (m, 1H), 2.30-2.24 (m, 1H), 2.02-1.92 (m, 1H), 1.86-1.70 (m, 4H), 1.30-0.86 (m, 6H).

Compound I-157

The title compound was prepared using the same procedure described for Compound I-144, with the exception of using Compound I-88 as the starting carboxylic acid. Purification via silica gel chromatography delivered the desired compound, Compound I-157 (10 mg, 55% yield) as a solid.

$^1$H-NMR (400 MHz, CD$_3$OD) δ 8.76 (d, 1H), 8.18 (d, 1H), 7.55 (s, 1H), 7.25 (dd, 1H), 7.07 (t, 1H), 7.00 (t, 1H), 6.92 (d, 1H), 6.81 (t, 1H), 5.96 (dd, 2H), 4.66-4.62 (m, 1H), 2.88-2.83 (m, 1H), 1.93-1.83 (m, 2H), 1.31-1.27 (m, 2H), 1.16-1.10 (m, 1H), 1.04 (d, 3H), 0.97 (d, 3H), 0.92-0.78 (m, 2H).

Compound I-187

The title compound was prepared using the same procedure described for Compound I-144, with the exception of using Compound I-89 as the starting carboxylic acid. Purification via silica gel chromatography delivered the desired compound, Compound I-187 (33 mg, 80% yield) as a solid.

$^1$H-NMR (400 MHz, DMSO-d$_6$) δ 11.92 (s, 1H), 9.09 (d, 1H), 8.33 (d, 1H), 7.55 (s, 1H), 7.29 (dd, 1H), 7.18 (t, 1H), 7.12 (d, 1H), 7.07 (t, 1H), 6.84 (t, 1H), 5.87 (s, 2H), 4.50 (d, 1H), 3.19 (d, 3H), 2.95-2.87 (m, 1H), 2.42-2.35 (m, 1H), 1.05 (d, 3H), 1.02-0.94 (m, 2H), 0.89 (d, 3H), 0.87-0.83 (m, 2H).

Compound I-272

The title compound was prepared following general procedure B, except (S)-3-methyl-2-(methylamino)butanoic acid was the amine reactant, 3-(3-(4-chloropyrimidin-2-yl)-1-(2-fluorobenzyl)-1H-pyrazol-5-yl)isoxazole (synthesis described in procedure towards Compound I-24) was used in place of Intermediate 1, and the contents were heated to 110° C. for 72 h. The crude material was purified via silica gel chromatography utilizing a 0-10% methanol/dichloromethane gradient to deliver the desired compound, Compound I-272 (4 mg, 8% yield) as a solid.

$^1$H-NMR (400 MHz, DMSO-d$_6$) δ 12.98 (bs, 1H), 9.07 (s, 1H), 8.24 (bs, 2H), 7.48 (bs, 1H), 7.30 (dd, 1H), 7.19 (t, 1H), 7.07 (t, 1H), 6.84 (bs, 1H), 6.60 (bs, 1H), 5.86 (s, 2H), 5.24 (bs, 1H), 2.94 (bs, 3H), 2.30 (bs, 1H), 1.02 (d, 3H), 0.77 (d, 3H).

Compound I-74

Intermediate 1 was dissolved in THF and cooled to 0° C. In a separate vial, 1H-pyrazole (1 equiv.) was diluted with THF then charged with sodium hydride (60% in dispersion oil, 1 equiv.) to generate the sodium salt. The contents were allowed to stir for 15 min. At this time, the sodium salt was added portion-wise to the solution of Intermediate 1. Once starting material was consumed as observed on the LC/MS, the reaction was quenched with aqueous 1N HCl and the mixture was extracted with dichloromethane (three times). The organic portions were combined dried, filtered, and concentrated. The crude material was then purified using a 0-10% methanol/dichloromethane gradient to deliver the desired compound, Compound I-74 (41 mg, 72% yield).

$^1$H-NMR (400 MHz, DMSO-d$_6$) δ 9.10 (t, 1H), 9.03 (dd, 1H), 8.80-8.79 (m, 1H), 8.02-8.00 (m, 1H), 7.81 (d, 1H), 7.34-7.28 (m, 1H), 7.24 (t, 1H), 7.23-7.18 (m, 1H), 7.09 (t, 1H), 6.88 (t, 1H), 6.72-6.70 (m, 1H), 5.93 (s, 2H).

Compound I-273

This compound was synthesized according to the general procedure B using 2-((2,2,2-trifluoroethyl)amino)acetic acid hydrochloride. Following complete consumption of starting material, the solution was diluted with aqueous 1N sodium hydroxide until pH ~10. Diethyl ether was added and the layers were separated. The aqueous layer was acidified with aqueous 1N hydrochloric acid until pH ~2. Ethyl acetate was added, and the layers were again separated. The aqueous layer was extracted with ethyl acetate and the combined organics were dried over magnesium sulfate, filtered, and the solvent was removed under vacuum. Purification by silica gel chromatography (0-15% methanol in dichloromethane) provided compound I-273 (6 mg, 23%) as a white solid.

$^1$H-NMR (400 MHz, CD$_3$OD) δ 8.73 (m, 1H), 8.27 (d, 1H), 7.40 (s, 1H), 7.27-7.22 (m, 1H), 7.09-6.99 (m, 2H), 6.87-6.86 (m, 1H), 6.80 (t, 1H), 5.94 (s, 2H), 4.61-4.55 (m, 2H), 4.45 (s, 2H).

Compound I-274

The title compound was prepared following general procedure B, except 3-((methylamino)methyl)benzoic acid (as the HCl salt) was the amine reactant, and contents were heated to 90° C. for 2 h as a solution in dioxane. Ethyl acetate was used as the extraction solvent during workup. The crude compound Compound I-274 (20 mg, 68% yield) was isolated as a white solid that did not require additional purification.

$^1$H-NMR (400 MHz, CD$_3$OD) δ 8.76 (m, 1H), 8.29 (d, 1H), 8.08 (s, 1H), 7.97 (d, 1H), 7.65-7.63 (m, 1H), 7.54 (s, 1H), 7.48 (t, 1H), 7.30-7.24 (m, 1H), 7.10-7.01 (m, 2H), 6.94-6.88 (m, 2H), 5.99 (s, 2H), 5.16 (s, 2H), 3.48 (d, 3H).

Compound I-275

The title compound was prepared following general procedure B, except 4-((methylamino)methyl)benzoic acid (as the HCl salt) was the amine reactant. Ethyl acetate was used as the extraction solvent during workup. The crude compound Compound I-275 (17 mg, 63% yield) was isolated as a white solid that did not require additional purification.

$^1$H-NMR (400 MHz, DMSO-$d_6$) δ 12.88 (br s, 1H), 9.05 (m, 1H), 8.25 (d, 1H), 7.87 (d, 2H), 7.48 (s, 1H), 7.44 (d, 2H), 7.32-7.27 (m, 1H), 7.21-7.19 (m, 2H), 7.07 (t, 1H), 6.83 (t, 1H), 5.86 (s, 2H), 4.95 (s, 2H), 3.24 (d, 3H).

Compound I-276

This compound was synthesized according to the general procedure B using 1H-tetrazol-5-amine and dioxane as solvent. The crude residue was suspended in dichloromethane and filtered. The filtrate was purified by silica gel chromatography (0-10% methanol in dichloromethane) to provide compound I-276 (0.4 mg, 2% yield) as a white film.

$^1$H-NMR (400 MHz, CD$_3$OD) δ 8.75 (m, 1H), 8.42 (d, 1H), 7.48 (s, 1H), 7.29-7.24 (m, 1H), 7.11-7.06 (m, 1H), 7.05-7.01 (m, 1H), 6.89-6.83 (m, 2H), 5.97 (s, 2H).

Compound I-277

This compound was synthesized according to the general procedure B using 3-amino-3-methylbutanoic acid and contents were heated to 80 C for 68 h. Purification by silica gel chromatography (0-10% methanol in dichloromethane) provided compound I-277 (1.3 mg, 5% yield) as a white film.

$^1$H-NMR (400 MHz, CD$_3$OD) δ 8.74 (m, 1H), 8.02 (d, 1H), 7.34 (d, 1H), 7.27-7.22 (m, 1H), 7.09-7.00 (m, 2H), 6.89-6.83 (m, 2H), 5.93 (s, 2H), 3.03 (s, 2H), 1.66 (s, 6H).

Compound I-278

This compound was synthesized according to the general procedure B using 5-(aminomethyl)pyridin-2(1H)-one and contents were stirred at 90° C. for 40 h. The crude reaction mixture was diluted with 1N aqueous hydrochloric acid and ethyl acetate. The layers were separated and the aqueous layer was concentrated under vacuum. Purification by reverse phase HPLC (20-50% acetonitrile in water w/0.1% TFA, 20 min gradient) provided compound I-278 (13 mg, 35% yield) as a tan solid.

$^1$H-NMR (400 MHz, CD$_3$OD) δ 8.82 (s, 1H), 8.28 (d, 1H), 7.73-7.64 (m, 3H), 7.32-7.26 (m, 1H), 7.11-7.03 (m, 2H), 6.99-6.95 (m, 2H), 6.54 (d, 1H), 6.01 (s, 2H), 4.73 (s, 2H).

Compound I-279

This compound was synthesized according to the general procedure B using the trifluoroacetic acid salt of 2-((methylamino)methyl)benzoic acid with dioxane as solvent and contents were heated at 90° C. for 2 d. Purification of the crude reaction mixture by reverse phase HPLC (5-75% acetonitrile in water w/0.1% TFA, 20 min gradient) provided compound I-279 (15 mg, 37% yield) as a white solid.

$^1$H-NMR (400 MHz, DMSO-$d_6$) δ 13.17 (br s, 1H), 9.10 (m, 1H), 8.25 (d, 1H), 7.94 (d, 1H), 7.56-7.52 (m, 1H), 7.44 (s, 1H), 7.41-7.29 (m, 3H), 7.24-7.19 (m, 2H), 7.12-7.08 (m, 1H), 6.85-6.81 (m, 1H), 5.89 (s, 2H), 5.24 (s, 2H), 3.30 (s, 3H).

Compound I-280

This compound was synthesized according to the general procedure B using 4-(aminomethyl)benzoic acid with ethyl acetate as the extraction solvent. Purification of the crude reaction mixture by reverse phase HPLC (5-75% acetonitrile in water w/0.1% TFA, 20 min gradient) provided Compound I-280 (3.4 mg, 9% yield) as a white solid.

$^1$H-NMR (400 MHz, CD$_3$OD) δ 8.81 (s, 1H), 8.26 (d, 1H), 8.02 (d, 2H), 7.58 (d, 2H), 7.53 (s, 1H), 7.33-7.27 (m, 1H), 7.13-7.04 (m, 2H), 6.95-6.91 (m, 2H), 6.01 (s, 2H), 5.01 (s, 2H).

Compound I-281

This compound was synthesized according to the general procedure B using 6-methylpiperidine-2-carboxylic acid. Purification of the crude reaction mixture by silica gel chromatography (0-10% methanol in dichloromethane) provided Compound I-281 (3.4 mg, 9% yield) as a white solid.

$^1$H-NMR (400 MHz, CD$_3$OD) δ 8.75 (d, 1H), 8.15 (d, 1H), 7.40 (s, 1H), 7.29-7.23 (m, 1H), 7.11-7.06 (m, 1H), 7.02 (td, 1H), 6.88 (d, 1H), 6.82-6.78 (m, 1H), 5.95 (s, 2H), 5.46 (br s, 1H), 2.46-2.43 (m, 1H), 1.91-1.72 (m, 4H), 1.63-1.60 (m, 2H), 1.35 (d, 3H).

Compound I-282 and I-283

These were synthesized according to the general procedure B using a mixture of (1R,4S)-4-methylpiperidine-2-carboxylic acid and (1S,4S)-4-methylpiperidine-2-carboxylic acid. Purification of the crude reaction mixture by silica gel chromatography (0-10% methanol in dichloromethane) provided Compound I-282 (15 mg, 39% yield) as a white solid. Repurification of the mixed fractions by reverse phase HPLC (5-75% acetonitrile in water w/0.1% TFA) provided Compound I-283 (4 mg, 10% yield).

Compound I-282: $^1$H-NMR (400 MHz, CD$_3$OD) δ 8.74 (m, 1H), 8.22 (d, 1H), 7.41 (s, 1H), 7.26-7.21 (m, 1H), 7.08-7.04 (m, 1H), 7.01-6.98 (m, 1H), 6.84 (m, 1H), 6.81-6.78 (m, 1H), 5.93 (s, 2H), 4.44 (dd, 1H), 4.04-3.98 (m, 1H), 3.65-3.60 (m, 1H), 2.19 (dt, 1H), 1.93-1.70 (m, 3H), 1.46-1.38 (m, 1H), 1.04 (d, 3H).

Compound I-283: $^1$H-NMR (400 MHz, CD$_3$OD) δ 8.77 (d, 1H), 8.28 (d, 1H), 7.52 (s, 1H), 7.29-7.23 (m, 1H), 7.10-7.00 (m, 2H), 6.92 (d, 1H), 6.88-6.85 (m, 1H), 5.97 (s, 2H), 5.68 (br s, 1H), 4.74 (br s, 1H), 3.41 (br s, 1H), 2.44-2.39 (m, 1H), 1.87-1.82 (m, 1H), 1.74-1.65 (m, 1H), 1.58-1.50 (m, 1H), 1.38-1.28 (dq, 1H), 1.00 (d, 3H).

Compound I-237

This compound was synthesized according to the general procedure B using (R)—N,2-dimethyl-1-(1H-tetrazol-5-yl)propan-1-amine (2 equivalents). Purification of the crude reaction mixture by reverse phase HPLC (5-75% acetonitrile in water w/0.1% TFA) provided Compound I-237 (4 mg, 23% yield) as a clear oil.

$^1$H-NMR (400 MHz, CD$_3$OD) δ 8.80 (m, 1H), 8.31 (d, 1H), 7.53 (s, 1H), 7.28-7.25 (m, 1H), 7.09-7.01 (m, 3H), 6.96 (m, 1H), 6.05 (d, 1H), 5.98 (d, 1H), 5.76 (br s, 1H), 3.35 (d, 3H), 2.86-2.80 (m, 1H), 1.07 (d, 3H), 0.90 (d, 3H).

Compound I-284

This compound was synthesized according to the general procedure B using (R)-2-methyl-1-(1H-tetrazol-5-yl)propan-1-amine. Purification of the crude reaction mixture by silica gel chromatography (0-10% methanol in dichloromethane) provided Compound I-284 (16 mg, 37% yield) as a white solid.

$^1$H-NMR (400 MHz, CD$_3$OD) δ 8.75 (m, 1H), 8.12 (d, 1H), 7.27-7.21 (m, 2H), 7.06-7.03 (m, 1H), 7.01-6.98 (m, 1H), 6.88 (d, 1H), 6.82-6.78 (m, 1H), 5.96 (d, 1H), 5.91 (d, 1H), 5.50 (d, 1H), 2.61-2.52 (m, 1H), 1.14 (d, 3H), 0.93 (d, 3H).

Compound I-285

To a solution of compound I-147 (previously described, 1 equivalent) and pyridine (50 equivalents) in dichloromethane at 0° C. was added cyclopropanecarbonyl chloride (1.2 equivalents) over 30 seconds. The solution was immediately warmed to room temperature and stirred for an additional 2.5 hours. After diluting with saturated aqueous ammonium chloride and dichloromethane, the layers were separated and the aqueous layer was extracted with dichloromethane. The organics were dried over magnesium sulfate, filtered, and the solvent was removed under vacuum. Purification by silica gel chromatography (0-5% methanol in dichloromethane) gave Compound I-285 (11 mg, 34% yield) as a white solid.

¹H-NMR (400 MHz, CD₃OD) δ 8.73 (m, 1H), 8.18 (d, 1H), 7.43 (s, 1H), 7.27-7.22 (m, 1H), 7.09-7.04 (m, 1H), 7.00 (t, 1H), 6.90 (m, 1H), 6.77 (t, 1H), 5.95 (s, 2H), 3.98-3.95 (m, 4H), 3.46-3.44 (m, 4H), 1.65-1.59 (m, 1H), 0.92-0.84 (m, 4H).

Compound I-229

The title compound was prepared following general procedure B, except 2-(piperidin-3-yl)acetic acid was the amine reactant, 6 equivalents of Hunig's base was used instead of triethylamine, and contents were heated to 120° C. for 18 h as a solution in THF/water (10:1). Solvent was removed under a stream of nitrogen, and the resulting crude material was purified via reverse phase HPLC to deliver the desired compound, Compound I-229 (8.1 mg, 32% yield) as a solid.

¹H NMR (500 MHz, CD₃OD) δ ppm 8.84 (m, 1H), 8.28 (m, 1H), 7.73 (m, 1H), 7.32 (m, 1H), 7.12 (m, 2H), 6.98 (m, 2H), 6.04 (s, 2H), 4.96 (m, 1H), 4.67 (m, 1H), 3.54 (m, 1H), 3.27 (m, 1H), 2.42 (m, 2H), 2.25 (m, 1H), 2.00 (m, 2H), 1.79 (m, 1H), 1.54 (m, 1H).

Compound I-230 and Compound I-231

The title compound was prepared following general procedure B, except a mixture of 2-(piperidin-4-yl)acetic acid and methyl 2-(piperidin-4-yl)acetate was the amine reactant, 6 equivalents of Hunig's base was used instead of triethylamine, and contents were heated to 120° C. for 18 h as a solution in THF/water (10:1). Solvent was removed under a stream of nitrogen, and the resulting crude material was purified via reverse phase HPLC to deliver the desired compounds, Compound I-230 (6.5 mg, 25% yield) as a solid, and Compound I-231 (16.2 mg, 61% yield) as a solid.

¹H NMR for Compound I-230 (500 MHz, METHANOL-d₄) δ ppm 8.83 (m, 1H), 8.26 (m, 1H), 7.63 (m, 1H), 7.30 (m, 1H), 7.10 (m, 2H), 6.97 (m, 2H), 6.03 (s, 2H), 4.98 (m, 2H), 3.40 (m, 1H), 2.35 (m, 2H), 2.25 (m, 1H), 2.04 (m, 2H), 1.50 (m, 2H).

¹H NMR for Compound I-231 (500 MHz, METHANOL-d₄) δ ppm 8.84 (m, 1H), 8.30 (m, 1H), 7.66 (m, 1H), 7.28-7.37 (m, 1H), 7.05-7.17 (m, 2H), 7.00 (d, 2H), 6.04 (s, 2H), 4.93-5.02 (m, 2H), 3.70 (s, 3H), 3.35-3.45 (m, 2H), 2.358 (d, 2H), 2.22-2.34 (m, 1H), 1.99-2.08 (m, 2H), 1.50 (br.s., 2H).

Compound I-232

The title compound was prepared following general procedure B, except 2-amino-4-methoxybutanoic acid was the amine reactant, 6 equivalents of Hunig's base was used instead of triethylamine, and contents were heated to 120° C. for 18 h as a solution in THF/water (10:1). Solvent was removed under a stream of nitrogen, and the resulting crude material was purified via reverse phase HPLC to deliver the desired compound, Compound I-232 (10 mg, 40% yield) as a solid.

¹H NMR (500 MHz, CD₃OD) δ ppm 8.80 (m, 1H), 8.32 (m, 1H), 7.55 (s, 1H), 7.29 (m, 1H), 7.08 (m, 2H), 6.96 (m, 2H), 6.01 (s, 2H), 5.11 (m, 1H), 3.61 (m, 2H), 3.35 (s, 3H), 2.43 (m, 1H), 2.21 (m, 1H).

Compound I-234

The title compound was prepared following general procedure B, except 3-(piperidin-4-yl)propanoic acid was the amine reactant. Solvent was removed under a stream of nitrogen, and the resulting crude material was purified via reverse phase HPLC to deliver the desired compound, Compound I-234 (13 mg, 49% yield) as a solid.

¹H NMR (500 MHz, CD₃OD) δ ppm 8.81-8.86 (m, 1H), 8.25-8.31 (m, 1H), 7.61-7.67 (m, 1H), 7.29-7.36 (m, 1H), 7.05-7.16 (m, 2H), 6.95-7.02 (m, 2H), 6.04 (s, 2H), 4.93-5.02 (m, 2H), 3.37 (s, 2H), 2.36-2.45 (m, 2H), 1.96-2.06 (m, 2H), 1.76-1.88 (m, 1H), 1.61-1.70 (m, 2H), 1.35-1.48 (m, 2H).

Compound I-286

The title compound was prepared following general procedure B, except 4-(aminomethyl)phenol was the amine reactant (1.1 equiv.), 4 equivalents of triethylamine was used, and contents were heated to 90° C. for 12 h as a solution in dioxane/water (10:1). The crude material was purified via silica gel chromatography utilizing a 1-5% methanol/dichloromethane gradient over 40 min to deliver the desired compound, Compound I-286 (17.7 mg, 48% yield) as a white solid.

¹H NMR (500 MHz, CDCl₃) δ (ppm): 8.45 (d, 1H), 8.16 (d, 1H), 7.34 (s, 1H), 7.16-7.24 (m, 3H), 6.99-7.04 (m, 1H), 6.94-6.99 (m, 1H), 6.85-6.90 (m, 1H), 6.79-6.83 (m, 2H), 6.58 (d, 1H), 5.97 (s, 2H), 5.67 (br. s, 1H), 5.28-5.30 (m, 1H), 4.72 (d, 2H).

Compound I-287

The title compound was prepared following general procedure B, except (4-(methylsulfonyl)phenyl)methanamine was the amine reactant (1 equiv.), 4 equivalents of triethylamine was used, and contents were heated to 90° C. for 12 h as a solution in dioxane/water (10:1). The crude material was purified via silica gel chromatography utilizing a 1-5% methanol/dichloromethane gradient over 40 min to deliver the desired compound, Compound I-287 (23.3 mg, 56% yield) as a white solid.

¹H NMR (500 MHz, CDCl₃) δ (ppm): 8.47 (d, 1H), 8.22 (m, 1H), 7.90-7.96 (m, 2H), 7.64-7.68 (m, 2H), 7.20-7.25 (m, 2H), 6.98-7.08 (m, 2H), 6.88-6.93 (m, 1H), 6.57 (d, 1H), 5.98 (s, 2H), 5.52-5.63 (br. d, 1H), 4.93-4.97 (m, 2H), 3.06 (s, 3H).

Compound I-288

The title compound was prepared following general procedure B, except 2-(aminomethyl)phenol was the amine reactant (1.1 equiv.), 4 equivalents of triethylamine was used, and contents were heated to 90° C. for 12 h as a solution in dioxane/water (10:1). The crude material was purified via silica gel chromatography utilizing a 1-5% methanol/dichloromethane gradient over 40 min to deliver the desired compound, Compound I-288 (4.5 mg, 12% yield) as a white solid.

¹H NMR (500 MHz, CDCl₃) δ (ppm): 9.52 (s, 1H), 8.49 (d, 1H), 8.15 (d, 1H), 7.42 (s, 1H), 7.21-7.27 (m, 3H), 7.02-7.11 (m, 3H), 6.89-6.95 (m, 2H), 6.64 (d, 1H), 6.03 (s, 2H), 5.80-5.85 (m, 1H), 4.75 (d, 2H).

Compound I-289

The title compound was prepared following general procedure B, except 2-(4-methylpiperidin-4-yl)acetic acid (as the HCl salt, 1.15 equiv.) was the amine reactant, 4 equivalents of triethylamine was used, and contents were heated to 90° C. for 12 h as a solution in dioxane/water (3:1). A dichloromethane/isopropanol mix (5:1) was used as the extraction solvent. The crude material was purified via silica gel chromatography utilizing a 1-5% methanol/dichloromethane gradient over 40 min to deliver the desired compound, Compound I-289 (37.4 mg, 70% yield) as a foamy white solid.

¹H NMR (500 MHz, CDCl₃) δ (ppm): 8.45 (s, 1H), 8.12 (d, 1H), 7.30 (s, 1H), 7.16-7.22 (m, 1H), 7.00-7.06 (m, 1H), 6.94-6.98 (m, 1H), 6.82-6.88 (m, 1H), 6.59 (d, 1H), 5.97 (s, 2H), 3.83-3.96 (m, 2H), 3.59 (s, 2H), 2.42-2.49 (m, 2H), 1.76-1.86 (m, 4H), 1.15 (s, 3H).

Compound I-290

The title compound was prepared following general procedure B, except 4-cyclohexylpiperidine-4-carboxylic acid (as the TFA salt, 1.2 equiv.) was the amine reactant, 4 equivalents of triethylamine was used, and contents were heated to 90° C. for 12 h as a solution in dioxane/water (3:1). A dichloromethane/isopropanol mix (5:1) was used as the extraction solvent. The crude material was purified via silica gel chromatography utilizing a 1-5% methanol/dichloromethane gradient over 40 min to deliver the desired compound, Compound I-290 (44.6 mg, 76% yield) as a white solid.

$^1$H NMR (500 MHz, CDCl$_3$) δ (ppm): 8.47 (s, 1H), 8.17 (d, 1H), 7.31 (s, 1H), 7.16-7.24 (m, 1H), 7.01-7.08 (m, 1H), 6.95-7.00 (m, 1H), 6.83-6.88 (m, 1H), 6.60 (d, 1H), 5.99 (s, 2H), 4.58-4.65 (m, 2H), 3.07-3.18 (m, 2H), 2.24-2.32 (m, 2H), 1.77-1.86 (m, 4H), 1.45-1.70 (m, 3H), 1.13-1.26 (m, 3H), 1.03-1.13 (m, 3H).

Compound I-291

The title compound was prepared following general procedure B, except methyl 2-phenylpiperidine-2-carboxylate was the amine reactant, 4 equivalents of sodium biocarbonate instead of triethylamine was used, and contents were heated to 110° C. for 48 h. Ethyl acetate was used as the extraction solvent. First pass purification was achieved by silica gel chromatography using 1 to 5% methanol in dichloromethane gradient over 40 minutes to afford the product with 80% purity. Further purification was achieved using by reverse phase HPLC using a 5 to 95% acetonitrile in water gradient over 30 minutes to deliver the analytically pure desired compound, Compound I-291 (2 mg, 3% yield) as a white solid.

$^1$H NMR (500 MHz, CDCl$_3$) δ (ppm): 8.41 (s, 1H), 8.35 (br. s, 1H), 7.24-7.27 (m, 2H), 7.09-7.18 (m, 3H), 7.02-7.09 (m, 1H), 6.90-7.00 (m, 2H), 6.79-6.87 (m, 1H), 6.67-6.74 (m, 1H), 6.44-6.51 (m, 1H), 5.86 (d, 1H), 5.74 (d, 1H), 3.72-3.85 (m, 1H), 3.36-3.51 (m, 1H), 2.47-2.56 (m, 1H), 1.70-1.99 (m, 5H).

Compound I-292

The title compound was prepared following general procedure B, except 4-amino-2-phenylbutanoic acid (as the HCl salt) was the amine reactant, 4 equivalents of triethylamine was used, and contents were heated to 95° C. for 12 h. Ethyl acetate was used as the extraction solvent. The crude material was purified via silica gel chromatography using a 1 to 5% methanol in dichloromethane gradient over 40 minutes to deliver the desired compound, Compound I-292 (37.9 mg, 50% yield) as a white solid.

$^1$H NMR (500 MHz, CDCl$_3$) δ (ppm): 8.47 (d, 1H), 8.13 (d, 1H), 7.29-7.36 (m, 6H), 7.15-7.23 (m, 1H), 6.99-7.04 (m, 1H), 6.92-6.97 (m, 1H), 6.86-6.91 (m, 1H), 6.60 (d, 1H), 6.01 (d, 1H), 5.94 (d, 1H), 5.21-5.28 (m, 1H), 3.85-3.94 (m, 1H), 3.62-3.80 (m, 2H), 2.51-2.61 (m, 1H), 2.11-2.19 (m, 1H).

Compound I-293

The title compound was prepared following general procedure B, except 4-methoxypiperidine-4-carboxylic acid (as the TFA salt) was the amine reactant (2 equiv.), 4 equivalents of triethylamine was used, and contents were heated to 105° C. as a solution in dioxane/water (3:1) for 12 h. Ethyl acetate was used as the extraction solvent. The crude material was purified via silica gel chromatography using a 1 to 5% methanol in dichloromethane gradient over 40 minutes to deliver the desired compound, Compound I-293 (52.7 mg, 56% yield) as a white solid.

$^1$H NMR (500 MHz, CDCl$_3$) δ (ppm): 8.47 (s, 1H), 8.22 (d, 1H), 7.31 (s, 1H), 7.16-7.25 (m, 1H), 7.01-7.09 (m, 1H), 6.95-7.01 (m, 1H), 6.84-6.89 (m, 1H), 6.60 (d, 1H), 5.98 (s, 2H), 4.33-4.41 (m, 2H), 3.53-3.62 (m, 2H), 3.41 (s, 3H), 2.05-2.20 (m, 4H).

Compound I-294

The title compound was prepared following general procedure B, except 2-(piperidin-4-yl)propanoic acid was the amine reactant (2 equiv.), 4 equivalents of triethylamine was used, and contents were heated to 90° C. for 12 h as a solution in dioxane/water (3:1). A dichloromethane/isopropanol mix (5:1) was used as the extraction solvent. The crude material was purified via silica gel chromatography using a 1 to 5% methanol in dichloromethane gradient over 40 minutes to deliver the desired compound, Compound I-294 (42.8 mg, 68% yield) as an off-white solid.

$^1$H NMR (500 MHz, CDCl$_3$) δ (ppm): 8.47 (s, 1H), 8.20 (d, 1H), 7.31 (s, 1H), 7.17-7.23 (m, 1H), 7.00-7.07 (m, 1H), 6.94-7.02 (m, 1H), 6.81-6.89 (m, 1H), 6.60 (d, 1H), 5.98 (s, 2H), 4.70-4.84 (m, 2H), 3.01-3.06 (t, 2H), 2.39-2.44 (m, 1H), 1.93-2.01 (m, 1H), 1.82-1.93 (m, 2H), 1.37-1.54 (m, 2H), 1.24 (d, 3H).

Compound I-295

The title compound was prepared following general procedure B, except 4-phenylpiperidine-2-carboxylic acid (as the TFA salt) was the amine reactant (2 equiv.), 4 equivalents of triethylamine was used, and contents were heated to 110° C. for 64 h. Ethyl acetate was used as the extraction solvent. The crude material was purified via silica gel chromatography using a 1 to 5% methanol in dichloromethane gradient over 40 minutes to deliver the desired compound, Compound I-295 (12.0 mg, 18% yield) as a racemic mixture with a relative cis configuration (an off-white solid).

$^1$H NMR (500 MHz, CD$_3$OD) δ (ppm): 8.76 (s, 1H), 8.21 (d, 1H), 7.45 (s, 1H), 7.25-7.36 (m, 5H), 7.19-7.25 (m, 1H), 7.08-7.14 (m, 1H), 7.02-7.07 (m, 1H), 6.91 (d, 1H), 6.80-6.86 (m, 1H), 5.97 (s, 2H), 5.62-5.77 (m, 1H), 2.77-2.89 (m, 1H), 2.55-2.62 (m, 1H), 2.03-2.12 (m, 1H), 1.96-2.02 (m, 1H), 1.83-1.96 (m, 1H), 1.25-1.35 (m, 1H), 0.84-0.98 (m, 1H).

Compound I-296

The title compound was prepared following general procedure B, except 4-(4-methoxyphenyl)piperidine-4-carboxylic acid (as the TFA salt) was the amine reactant (2 equiv.), 4 equivalents of triethylamine was used, and contents were heated to 110° C. for 17 h as a solution in dixoane/water (3:1). Ethyl acetate was used as the extraction solvent. The crude material was purified via silica gel chromatography using a 1 to 5% methanol in dichloromethane gradient over 40 minutes to deliver the desired compound, Compound I-296 (41.1 mg, 66% yield) as a white solid.

$^1$H NMR (400 MHz, CDCl$_3$) δ (ppm): 8.43 (s, 1H), 8.12 (d, 1H), 7.34 (d, 2H), 7.28 (s, 1H), 7.12-7.16 (m, 1H), 6.94-7.02 (m, 1H), 6.88-6.93 (m, 1H), 6.86 (d, 2H), 6.75-6.80 (m, 1H), 6.56 (d, 1H), 5.94 (s, 2H), 4.44-4.52 (m, 2H), 3.78 (s, 3H), 3.36-3.41 (m, 2H), 2.63-2.72 (m, 2H), 1.96-2.08 (m, 2H).

Compound I-298

The title compound was prepared following general procedure B, except 4-aminopiperidine-4-carboxylic acid (as the HCl salt) was the amine reactant (2 equiv.), and contents were heated to 100° C. for 18 h as a solution in THF/DMF/triethylamine (1:1:1). After complete consumption of the starting material, the reaction was cooled to 0° C. and an excess of 2M solution of trimethylsilyldiazomethane was added and stirred at 23° C. for 3 d until complete conversion to the amino ester. Contents were diluted with 1N NaOH solution, and extracted with dichloromethane. The organic layer was dried, filtered, and concentrated in vacuo. The crude material was purified via silica gel chromatography using a 20 to 100% ethyl acetate in hexanes gradient to deliver the desired compound, Compound I-298 (22 mg, 63% yield) as a solid.

$^1$H NMR (500 MHz, DMSO-d$_6$) δ ppm 9.08 (d, 1H), 8.28 (d, 1H), 7.54 (s, 1H), 7.29-7.39 (m, 1H), 7.18-7.27 (m, 2H), 7.10 (t, 1H), 6.83 (t, 1H), 5.90 (s, 2H), 4.02-4.09 (m, 2H), 3.66-3.74 (m, 2H), 3.63-3.65 (m, 3H), 1.99-2.04 (m, 2H), 1.91-1.98 (m, 2H), 1.62 (d, 2H).

Compound I-299

The title compound was prepared following general procedure B, except 4-aminopiperidine-4-carboxylic acid (as the HCl salt) was the amine reactant (5 equiv.), 8 equivalents of triethylamine was used, and contents were heated to 90° C. for 18 h as a solution in THF/water (5:1). After complete consumption of the starting material, the reaction was cooled and filtered. The resulting solids were collected and purified via reverse phase HPLC to deliver the desired compound, Compound I-299 (2 mg, 7% yield) as a solid.

$^1$H NMR (500 MHz, METHANOL-d$_4$) δ ppm 8.80 (d, 1H), 8.31 (d, 1H), 7.54 (s, 1H), 7.23-7.35 (m, 1H), 7.08-7.15 (m, 1H), 7.05 (t, 1H), 6.92 (d, 1H), 6.81-6.90 (m, 1H), 5.99 (s, 2H), 4.45 (dt, 2H), 3.96-4.13 (m, 2H), 2.44 (dt, 2H), 2.02 (ddd, 2H).

Compound I-300

The title compound was prepared following general procedure B, except 4-hydroxypiperidine-4-carboxylic acid (as the HCl salt) was the amine reactant (5 equiv.), 8 equivalents of triethylamine was used, and contents were heated to 90° C. as a solution in THF/water (5:1) for 18 h. After complete consumption of the starting material, the reaction was cooled and filtered. The filtrated was collected and concentrated in vacuo. The crude material was purified via reverse phase HPLC to deliver the desired compound, Compound I-300 (22 mg, 81% yield) as a solid.

$^1$H NMR (500 MHz, METHANOL-d$_4$) δ ppm 8.83 (d, 1H), 8.22-8.35 (m, 1H), 7.58-7.70 (m, 1H), 7.25-7.37 (m, 1H), 7.04-7.18 (m, 2H), 6.90-7.02 (m, 2H), 6.03 (s, 2H), 4.76 (d, 2H), 3.69-3.82 (m, 2H), 2.16-2.33 (m, 2H), 1.94 (d, 2H).

Compound I-301

The title compound was prepared following general procedure B, except (S)-4,4-difluoropyrrolidine-2-carboxylic acid was the amine reactant (5 equiv.), 8 equivalents of triethylamine was used, and contents were heated to 90° C. for 18 h as a solution in THF/water (5:1). After complete consumption of the starting material, the reaction was concentrated in vacuo. The crude material was purified via reverse phase HPLC to deliver the desired compound, Compound I-301 (20 mg, 67% yield) as a solid.

$^1$H NMR (500 MHz, CD$_3$OD) δ ppm 8.80 (d, 1H), 8.34 (d, 1H), 7.35-7.42 (m, 1H), 7.24-7.34 (m, 1H), 7.10 (dd, 1H), 7.01-7.07 (m, 1H), 6.91 (td, 2H), 5.98 (s, 2H), 5.44-5.69 (m, 2H) 4.76-4.87 (m, 3H).

Compound I-302

The title compound was prepared following general procedure B, except (S)-2-amino-3-ethoxypropanoic acid was the amine reactant (4 equiv.), 6 equivalents of triethylamine was used, and contents were heated to 100° C. for 18 h as a solution in dioxane/water (3:1). After workup, the crude material was suspended in ethyl acetate and diluted with hexanes until precipitation occurred. The precipitate was filtered and collected to deliver the desired compound, Compound I-302 (9 mg, 24% yield) as a solid.

$^1$H NMR (500 MHz, DMSO-d$_6$) δ ppm 9.08 (s, 1H), 8.20 (d, 1H), 7.47 (s, 1H), 7.27-7.40 (m, 2H), 7.17-7.26 (m, 2H), 7.10 (t, 1H), 6.84 (t, 1H), 5.81-5.98 (m, 2H), 4.59 (br. s., 1H), 3.83-3.90 (m, 1H), 3.75-3.83 (m, 1H), 3.45-3.54 (m, 1H), 3.37-3.44 (m, 1H), 0.92-1.08 (m, 3H).

Compound I-303

The title compound was prepared following general procedure B, except 2-amino-3-methoxypropanoic acid was the amine reactant (4 equiv.), 6 equivalents of triethylamine was used, and contents were heated to 100° C. for 18 h as a solution in dioxane/water (3:1). After workup, the crude material was suspended in ethyl acetate and diluted with hexanes until precipitation occurred. The precipitate was filtered and collected to deliver the desired compound, Compound I-303 (8 mg, 22% yield) as a solid.

$^1$H NMR (500 MHz, DMSO-d$_6$) δ ppm 9.09 (d, 1H) 8.22 (d, 1H), 7.47 (s, 1H), 7.28-7.39 (m, 1H), 7.17-7.27 (m, 2H), 7.10 (t, 1H), 6.85 (t, 1H), 6.63 (br. s., 1H), 5.81-5.94 (m, 2H), 4.54-4.88 (m, 1H), 3.72-3.87 (m, 2H), 3.57 (s, 2H), 3.25 (s, 3H).

Compound I-304

The title compound was prepared following step 3 of the procedure described for Compound I-235, except 1-((methylamino)methyl)cyclopropanecarboxylic acid (as the TFA salt) was the amine reactant, and contents were heated to 100° C. for 6 h. The crude material was purified via silica gel chromatography (1-4% methanol in dichloromethane gradient) to deliver the desired compound, Compound I-304 (67 mg, 72% yield) as a white solid.

$^1$H-NMR (400 MHz, CDCl$_3$) δ 8.77 (d, 1H), 8.10 (d, 1H), 7.39 (s, 1H), 7.16 (app. q, 1H), 7.03 (app. q, 1H), 6.92 (d, 1H), 6.68 (app. t, 1H), 5.98 (s, 2H), 4.15 (s, 2H), 3.37 (d, 3H), 1.28 (m, 2H), 1.07 (m, 2H).

Compound I-305

The title compound was prepared following step 3 of the procedure described for Compound I-235, except (2R,3S)-3-methylpiperidine-2-carboxylic acid (as the acetic acid salt) was the amine reactant, and contents were heated to 100° C. for 21 h. The crude material was purified via silica gel chromatography (2-4% methanol in dichloromethane gradient) to deliver the desired compound, Compound I-305 (24 mg, 46% yield) as a white solid.

$^1$H-NMR (400 MHz, CDCl$_3$) δ 8.77 (d, 1H), 8.21 (d, 1H), 7.47 (s, 1H), 7.15 (app. q, 1H), 7.02 (app. q, 1H), 6.89 (d, 1H), 6.66 (app. t, 1H), 5.98 (s, 2H), 5.04 (d, 1H), 4.37 (br. d, 1H), 3.70 (app. t, 1H), 2.10 (m, 1H), 1.90 (br. d, 1H), 1.80-1.69 (m, 2H), 1.52 (app. q, 1H), 1.21 (d, 3H).

Compound I-306

The title compound was prepared following general procedure B, except 4-isopropylpiperidine-4-carboxylic acid was the amine reactant, and the contents were heated to 90° C. for 3 h as a solution in THF/water (10:1). The contents were cooled to 23° C., and organic solvents were removed in vacuo. Solids were treated with 1N HCl solution, and the resulting precipitate was filtered and dried in vacuo to deliver the desired compound, Compound I-306 (42 mg, 86% yield) as a white solid.

$^1$H-NMR (500 MHz, CDCl$_3$) δ 8.49 (d, 1H), 8.35 (d, 1H), 7.64 (s, 1H), 7.25-7.20 (m, 1H), 7.05-7.01 (m, 3H), 6.67 (d, 1H), 5.98 (s, 2H), 4.80 (d, 2H), 3.79-3.72 (m, 1H), 3.23 (t, 1H), 2.35 (d, 2H), 1.92-1.80 (m, 1H), 1.62 (td, 1H), 1.41 (t, 1H), 0.97 (d, 6H).

Compound I-307

The title compound was prepared following general procedure B, except 3-(methylamino)bicyclo[1.1.1]pentane-1-carboxylic acid was the amine reactant, and the contents were heated to 90° C. for 18 h as a solution in THF/water (10:1). The crude material was purified via silica gel chromatography utilizing a 0-10% methanol/dichloromethane gradient to deliver the desired compound, Compound I-307 (74 mg, 53% yield) as an off-white solid.

¹H-NMR (500 MHz, CDCl₃) δ 8.53 (d, 1H), 8.45 (d, 1H), 7.49 (s, 1H), 7.26-7.21 (m, 2H), 7.09-7.01 (m, 2H), 6.67 (d, 1H), 5.93 (s, 2H), 3.36 (d, 3H), 2.68 (s, 6H).

Compound I-308

The title compound was prepared following general procedure B, except 2-azabicyclo[4.1.0]heptane-1-carboxylic acid (as the HCl salt) was the amine reactant, and the contents were heated to 90° C. for 3 h as a solution in THF/water (10:1). The crude material was purified via silica gel chromatography utilizing a 0-10% methanol/dichloromethane gradient to deliver the desired compound, Compound I-308 (32 mg, 17% yield) as an off-white solid.

¹H-NMR (500 MHz, CDCl₃) δ 8.46 (d, 1H), 8.21 (d, 1H), 7.27 (s, 1H), 7.23-7.18 (m, 1H), 7.04 (t, 1H), 6.98 (t, 1H), 6.87 (t, 1H), 6.59 (d, 1H), 5.98 (s, 2H), 4.62 (br. s., 1H), 3.01 (br. s., 1H), 2.20-2.11 (m, 1H), 2.08-1.98 (m, 2H), 1.83-1.72 (m, 2H), 1.57-1.49 (m, 1H), 1.04 (br. s., 1H).

Compound I-309

The title compound was prepared following general procedure B, except (1R,3S)-3-(Boc-amino)cyclopentane-1-carboxylic acid (as the TFA salt) was the amine reactant, and the contents were heated to 90° C. for 3 h as a solution in THF/water (10:1). The crude material was purified via silica gel chromatography utilizing a 0-10% methanol/dichloromethane gradient to deliver an intermediate. This intermediate was immediately dissolved in THF, and cooled to 0° C. Contents treated with sodium hydride (60% in mineral oil, 2 equiv.) followed by methyl iodide (10 equiv.). Reaction was allowed to warm to 23° C. over 3 d. Contents poured over water, and extracted with ethyl acetate (3×). The organic portions were combined and washed with brine. The mixture was dried over MgSO₄, filtered, and concentrated in vacuo. The crude material was purified via silica gel chromatography utilizing a 0-15% methanol/dichloromethane gradient to deliver the desired compound, Compound I-309 (0.9 mg, 1% yield) as an off-white solid.

¹H-NMR (500 MHz, CDCl₃) δ 8.45 (s, 1H), 8.13 (d, 1H), 7.32 (s, 1H), 7.23-7.15 (m, 1H), 7.03 (t, 1H), 6.97 (t, 1H), 6.86 (t, 1H), 6.60 (s, 1H), 5.97 (s, 2H), 4.75 (d, 1H), 3.74 (s, 3H), 3.08-2.94 (m, 1H), 2.42-2.30 (m, 1H), 2.17-1.84 (m, 5H).

Compound I-310

The title compound was prepared following general procedure B, except (2S, 3S)-2-Methyl-piperidine-3-carboxylic acid was the amine reactant, and the contents were heated to 90° C. as a solution in THF/water (10:1) for 3 d. The crude material was purified via silica gel chromatography utilizing a 0-50% (acetonitrile:methanol=9:1 with 0.1% TFA)/dichloromethane gradient to deliver the desired compound, Compound I-310 (4.9 mg, 2% yield) as an off-white solid.

¹H-NMR (500 MHz, CDCl₃) δ 8.46 (d, 1H), 8.22 (d, 1H), 7.31 (s, 1H), 7.24-7.18 (m, 1H), 7.13-7.01 (m, 1H), 6.98 (t, 1H), 6.87 (t, 1H), 6.59 (d, 1H), 5.97 (s, 2H), 5.38 (br. s., 1H), 4.42 (d, 1H), 3.22 (t, 1H), 2.99-2.87 (m, 1H), 2.05-1.96 (m, 2H), 1.93-1.84 (m, 2H), 1.32 (d, 3H).

Compound I-311

The title compound was prepared following general procedure B, except (2R, 3R)-2-Methyl-piperidine-3-carboxylic acid was the amine reactant, and the contents were heated to 90° C. for 18 h as a solution in THF/water (10:1). The crude material was purified via silica gel chromatography utilizing a 0-10% methanol/dichloromethane gradient to deliver the desired compound, Compound I-311 (17.2 mg, 12% yield) as an off-white solid.

¹H-NMR (500 MHz, DMSO-d₆) δ 12.51 (br. s., 1H), 9.09 (d, 1H), 8.31 (d, 1H), 7.50 (s, 1H), 7.36-7.29 (m, 1H), 7.25-7.18 (m, 2H), 7.10 (t, 1H), 6.84 (t, 1H), 5.89 (s, 2H), 5.09 (br. s., 1H), 4.37 (br. s., 1H), 3.10 (t, 1H), 2.74 (br. s., 1H), 1.84-1.72 (m, 3H), 1.50 (br. s., 1H), 1.19 (d, 3H).

Compound I-312

The title compound was prepared following general procedure B, except 3-azabicyclo[3.1.0]hexane-1-carboxylic acid (as the HCl salt) was the amine reactant, the contents were heated to 100° C. for 18 h, and the aqueous layer during workup was treated with sodium chloride. The crude material was purified via silica gel chromatography utilizing a 0-10% methanol/dichloromethane gradient to deliver the desired compound, Compound I-312 (44 mg, 70% yield) as an off-white solid.

¹H-NMR (500 MHz, DMSO-d₆) δ 12.65 (br. s., 1H), 9.08 (d, 1H), 8.26 (d, 1H), 7.53 (s, 1H), 7.35-7.30 (m, 1H), 7.26 (d, 1H), 7.25-7.20 (m, 1H), 7.10 (td, 1H), 6.83-6.79 (m, 1H), 5.91 (s, 2H), 4.09-3.98 (m, 3H), 3.81 (br. s., 1H), 2.22-2.17 (m, 1H), 1.51 (dd, 1H), 0.97 (t, 1H).

Compound I-313

The title compound was prepared following general procedure B, except (S)-3-aminopropane-1,2-diol was the amine reactant, the contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-313 (39 mg, 85% yield) as an off-white solid.

¹H-NMR (500 MHz, CD₃OD) δ 8.74 (d, 1H), 8.07 (d, 1H), 7.42 (s, 1H), 7.29-7.22 (m, 1H), 7.11-7.05 (m, 1H), 7.02 (td, 1H), 6.88 (d, 1H), 6.81 (td, 1H), 5.95 (s, 2H), 3.88 (quin, 1H), 3.81-3.74 (m, 1H), 3.69-3.62 (m, 1H), 3.59 (s, 1H), 3.58 (s, 1H).

Compound I-314

The title compound was prepared following general procedure B, except cis-4-methylpyrrolidine-3-carboxylic acid was the amine reactant, the contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-314 (50 mg, 72% yield) as an off-white solid.

¹H-NMR (500 MHz, CD₃OD) δ 8.74 (d, 1H), 8.09 (d, 1H), 7.41 (s, 1H), 7.29-7.23 (m, 1H), 7.11-7.06 (m, 1H), 7.02 (t, 1H), 6.91 (d, 1H), 6.81 (t, 1H), 5.95 (s, 2H), 4.22-4.13 (m, 2H), 3.98-3.92 (m, 1H), 3.41 (t, 1H), 2.84-2.77 (m, 1H), 2.58 (d, 1H), 1.24 (d, 3H).

Compound I-315

The title compound was prepared following general procedure B, except serinol was the amine reactant, the contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-315 (49 mg, 84% yield) as an off-white solid.

¹H-NMR (500 MHz, CD₃OD) δ 8.75 (t, 1H), 8.08 (dd, 1H), 7.46 (d, 1H), 7.30-7.23 (m, 1H), 7.09 (dd, 1H), 7.03 (t, 1H), 6.91-6.88 (m, 1H), 6.80 (t, 1H), 5.96 (s, 2H), 4.54 (quin, 1H), 3.75-3.82 (m, 4H).

Compound I-316

The title compound was prepared following general procedure B, except (R)-3-aminopropane-1,2-diol (2 equiv.) was the amine reactant, the contents were heated to 100° C. for 20 h, and the aqueous layer during workup was treated with sodium chloride. The crude material was purified via silica gel chromatography utilizing a 0-10% methanol/dichloromethane gradient to deliver the desired compound, Compound I-316 (36 mg, 78% yield) as an off-white solid.

$^1$H-NMR (500 MHz, CD$_3$OD) δ 8.73 (d, 1H), 8.06 (d, 1H), 7.41 (s, 1H), 7.27-7.22 (m, 1H), 7.10-7.04 (m, 1H), 7.01 (t, 1H), 6.86 (d, 1H), 6.83-6.78 (m, 1H), 5.94 (s, 2H), 3.88 (quin, 1H), 3.80-3.74 (m, 1H), 3.68-3.62 (m, 1H), 3.58 (d, 2H).

Compound I-317

The title compound was prepared following general procedure B, except 4-(aminomethyl)-2,6-difluorophenol was the amine reactant, the contents were heated to 100° C. for 20 h, and the aqueous layer during workup was treated with sodium chloride. The crude material was purified via silica gel chromatography utilizing a 0-30% (acetonitrile:methanol=7:1)/dichloromethane gradient to deliver the desired compound, Compound I-317 (38 mg, 30% yield) as an off-white solid.

$^1$H-NMR (500 MHz, CD$_3$OD) δ 8.77-8.74 (m, 1H), 8.08 (d, 1H), 7.37 (s, 1H), 7.26 (dd, 1H), 7.11-7.06 (m, 1H), 7.06-7.01 (m, 3H), 6.88 (d, 1H), 6.84 (t, 1H), 5.96 (s, 2H), 4.69 (s, 2H).

Compound I-318

The title compound was prepared following general procedure B, except cis-piperidine-2,4-diyldimethanol was the amine reactant and the contents were heated to 100° C. for 20 h. The reaction was poured into a 1:1 mix of dichloromethane and water for workup, and the aqueous layer was treated with sodium chloride before extraction with dichloromethane. The crude material was purified via silica gel chromatography utilizing a 0-70% (acetonitrile:methanol=7:1)/dichloromethane gradient to deliver the desired compound, Compound I-318 (39 mg, 25% yield) as an off-white solid.

$^1$H-NMR (500 MHz, CD$_3$OD) δ 8.75 (d, 1H), 8.12 (d, 1H), 7.40 (s, 1H), 7.29-7.23 (m, 1H), 7.11-7.05 (m, 1H), 7.04-6.99 (m, 1H), 6.90 (d, 1H), 6.82 (td, 1H), 5.99-5.91 (m, 2H), 4.52-4.45 (m, 1H), 4.35-4.26 (m, 1H), 3.86-3.76 (m, 2H), 3.58-3.42 (m, 3H), 2.09-1.99 (m, 2H), 1.85-1.75 (m, 1H), 1.65-1.55 (m, 1H), 1.45-1.36 (m, 1H).

Compound I-319

The title compound was prepared following general procedure B, except 3-phenylpiperidine-2-carboxylic acid (as the AcOH salt) was the amine reactant, the contents were heated to 100° C. for 20 h, and the aqueous layer during workup was treated with sodium chloride. A portion of the crude material was purified via reverse phase HPLC utilizing a 5-75% acetonitrile/water gradient to deliver the desired compound, Compound I-319 (30 mg, 9% yield) as an off-white solid.

$^1$H-NMR (500 MHz, CDCl$_3$) δ 8.37 (d, 1H), 8.27 (d, 1H), 7.34-7.28 (m, 4H), 7.26-7.22 (m, 1H), 7.20 (s, 1H), 7.15 (ddd, 1H), 6.99-6.88 (m, 3H), 6.45 (d, 1H), 5.91-5.82 (m, 2H), 5.18 (d, 1H), 4.31 (d, 1H), 3.59 (td, 1H), 3.26-3.17 (m, 1H), 2.49 (qd, 1H), 2.06-1.99 (m, 1H), 1.98-1.81 (m, 2H).

Compound I-320

The title compound was prepared following general procedure B, except (S)-3-(methylamino)propane-1,2-diol was the amine reactant and the contents were heated to 100° C. for 20 h. The reaction was poured into a 1:1 mix of dichloromethane and water for workup, and the aqueous layer was treated with sodium chloride before extraction with dichloromethane. The crude material was purified via silica gel chromatography utilizing a 0-10% methanol/dichloromethane gradient to deliver the desired compound, Compound I-320 (81 mg, 84% yield) as a white solid.

$^1$H-NMR (500 MHz, CD$_3$OD) δ 8.75 (d, 1H), 8.10 (d, 1H), 7.42 (s, 1H), 7.29-7.23 (m, 1H), 7.11-7.06 (m, 1H), 7.02 (t, 1H), 6.88 (d, 1H), 6.85-6.80 (m, 1H), 5.95 (s, 2H), 4.03-3.94 (m, 2H), 3.73-3.66 (m, 1H), 3.58 (d, 2H), 3.42 (d, 3H).

Compound I-321

The title compound was prepared following general procedure B, except (R)-3-(methylamino)propane-1,2-diol was the amine reactant and the contents were heated to 100° C. for 2 d. The reaction was poured into a 1:1 mix of dichloromethane and water for workup, and the aqueous layer was treated with sodium chloride before extraction with dichloromethane. The crude material was purified via silica gel chromatography utilizing a 0-10% methanol/dichloromethane gradient to deliver the desired compound, Compound I-321 (88 mg, 77% yield) as a white solid.

$^1$H-NMR (500 MHz, CD$_3$OD) δ 8.74 (d, 1H), 8.09 (d, 1H), 7.41 (s, 1H), 7.28-7.22 (m, 1H), 7.10-7.05 (m, 1H), 7.04-6.99 (m, 1H), 6.87 (d, 1H), 6.82 (td, 1H), 5.94 (s, 2H), 4.02-3.93 (m, 2H), 3.72-3.66 (m, 1H), 3.58 (d, 2H), 3.41 (d, 3H).

Compound I-322

The title compound was prepared following general procedure B, except (S)-3-((cyclopropylmethyl)amino)propane-1,2-diol was the amine reactant and the contents were heated to 100° C. for 20 h. The reaction was poured into a 1:1 mix of dichloromethane and water for workup, and the aqueous layer was treated with sodium chloride before extraction with dichloromethane. The crude material was purified via silica gel chromatography utilizing a 0-10% methanol/dichloromethane gradient to deliver the desired compound, Compound I-322 (39 mg, 62% yield) as a white foam.

$^1$H-NMR (500 MHz, CDCl$_3$) δ 8.45 (d, 1H), 8.12 (d, 1H), 7.29 (s, 1H), 7.24-7.19 (m, 1H), 7.05-6.97 (m, 3H), 6.57 (d, 1H), 5.99-5.94 (m, 1H), 5.91-5.86 (m, 1H), 4.14 (dd, 1H), 4.02 (br. s., 1H), 3.93 (br. s., 1H), 3.86 (br. s., 1H), 3.68-3.57 (m, 4H), 3.43 (ddd, 1H), 1.15-1.06 (m, 1H), 0.65-0.53 (m, 2H), 0.38-0.32 (m, 1H), 0.32-0.26 (m, 1H).

Compound I-323

The title compound was prepared following general procedure B, except (S)-3-(isopropylamino)propane-1,2-diol was the amine reactant and the contents were heated to 100° C. for 20 h. The reaction was poured into a 1:1 mix of dichloromethane and water for workup, and the aqueous layer was treated with sodium chloride before extraction with dichloromethane. The crude material was purified via silica gel chromatography utilizing a 0-50% (acetonitrile:methanol=7:1)/dichloromethane gradient to deliver the desired compound, Compound I-323 (12 mg, 20% yield) as a white solid.

$^1$H-NMR (500 MHz, CDCl$_3$) δ 8.45 (d, 1H), 8.13 (d, 1H), 7.30 (s, 1H), 7.25-7.19 (m, 1H), 7.06-6.98 (m, 3H), 6.58 (d, 1H), 6.00-5.94 (d, 1H), 5.91-5.85 (d, 1H), 4.95 (br. s., 1H), 4.67-4.58 (m, 1H), 3.82-3.74 (m, 2H), 3.70-3.60 (m, 2H), 3.59-3.49 (m, 2H), 1.32 (d, 3H), 1.29 (d, 3H).

Compound I-324

The title compound was prepared following general procedure B, except 2-(aminomethyl)-1,1,1,3,3,3-hexafluoropropan-2-ol was the amine reactant, the contents were heated to 100° C. for 20 h, and the aqueous layer was treated with sodium chloride before extraction with dichloromethane during work up. The crude material was purified via silica gel chromatography utilizing a 0-10% ethyl acetate/hexane gradient to deliver the desired compound, Compound I-324 (5 mg, 9% yield) as a white solid.

¹H-NMR (500 MHz, CDCl₃) δ 8.48 (d, 1H), 8.36 (s, 1H), 8.26 (d, 1H), 7.25-7.20 (m, 2H), 7.14 (t, 1H), 7.05-6.99 (m, 2H), 6.59 (d, 1H), 5.94 (s, 2H), 5.59 (br. s., 1H), 4.12 (d, 2H).

Compound I-325

The title compound was prepared following general procedure B, except 1-amino-2-methylpropan-2-ol was the amine reactant, and the contents were heated to 100° C. for 20 h. The reaction was poured into a 1:1 mix of dichloromethane and water for workup, and the aqueous layer was treated with sodium chloride before extraction with dichloromethane. The crude material was purified via silica gel chromatography utilizing a 0-10% methanol/dichloromethane gradient to deliver the desired compound, Compound I-325 (43 mg, 93% yield) as a white solid.

¹H-NMR (500 MHz, CDCl₃) δ 8.43 (d, 1H), 8.14 (d, 1H), 7.27 (s, 1H), 7.21-7.15 (m, 1H), 7.04-6.98 (m, 1H), 6.95 (t, 1H), 6.84 (t, 1H), 6.59 (d, 1H), 5.95 (s, 2H), 5.62 (br. s., 1H), 3.70 (s, 1H), 3.63 (d, 2H), 1.31 (s, 6H).

Compound I-326

A mixture of (S)-trifluorolactic acid (1.5 equiv.) and 1,1'-carbodiimidazole (1.5 equiv.) in THF was heated to 70° C. for 2 h. 2-(1-(2-fluorobenzyl)-5-(isoxazol-3-yl)-1H-pyrazol-3-yl)-pyrimidin-4-amine (intermediate described in WO2012/3405 A1) (1 equiv.) was added to the reaction mixture, and contents stirred at 70° C. for 3 d. The contents were cooled to 23° C., diluted with ethyl acetate, and washed with 1N HCl solution. The organic layer was washed with brine, dried over MgSO₄, filtered, and concentrated in vacuo. The crude material was purified via silica gel chromatography utilizing a 0-100% ethyl acetate/hexanes gradient to deliver the desired compound, Compound I-326 (3 mg, 4% yield) as a white solid.

¹H-NMR (500 MHz, CDCl₃) δ 9.61 (br. s., 1H), 8.76 (d, 1H), 8.49 (d, 1H), 8.16 (d, 1H), 7.47 (s, 1H), 7.25-7.21 (m, 1H), 7.11-7.03 (m, 1H), 7.00 (t, 1H), 6.83 (t, 1H), 6.63 (d, 1H), 6.36 (br. s., 1H), 6.06-5.95 (m, 2H), 4.69 (d, 1H).

Compound I-329 and Compound I-330

Compound I-161 was resolved by chiral separation with chiracel-ODH 20 mm×250 mm semi-prep column, using a 10-90% isopropanol/hexanes gradient. Collection of the peak that eluted first and concentration in vacuo yielded Compound I-329 as a white solid. Collection of the peak that eluted second and concentration in vacuo yielded Compound-330 as a white solid.

¹H-NMR for Compound I-329 (500 MHz, CDCl₃) δ 8.38 (d, 1H), 8.16 (d, 1H), 7.21 (s, 1H), 7.20-7.15 (m, 1H), 7.04-6.99 (m, 1H), 6.97-6.93 (m, 1H), 6.89-6.84 (m, 1H), 6.48 (d, 1H), 6.06-6.00 (m, 1H), 5.93-5.88 (m, 1H), 4.76 (d, 1H), 4.15 (d, 1H), 3.54-3.43 (m, 1H), 2.09-1.98 (m, 1H), 1.91-1.82 (m, 1H), 1.81-1.64 (m, 3H), 1.17 (d, 3H).

¹H-NMR for Compound I-330 (500 MHz, CD₃OD) δ 8.78-8.74 (d, 1H), 8.21 (d, 1H), 7.45 (s, 1H), 7.30-7.23 (m, 1H), 7.11-7.06 (m, 1H), 7.03 (t, 1H), 6.86 (d, 1H), 6.83 (t, 1H), 5.95 (s, 2H), 5.04 (d, 1H), 4.37 (d, 1H), 3.69 (td, 1H), 2.16-2.07 (m, 1H), 1.93-1.86 (m, 1H), 1.82-1.70 (m, 2H), 1.52 (qd, 1H), 1.21 (d, 3H).

Compound I-331 and Compound I-332

A mixture of Compound I-329 and 1,1'-carbodiimidazole (1 equiv.) in DCM was heated to 45° C. until all starting material was consumed as observed on the LC/MS. Cyclopropanesulfonamide (4 equiv.) and DBU (2 equiv.) was added to the reaction mixture, and contents stirred at 45° C. for an additional 30 min. The contents were cooled to 23° C., quenched with 1N HCl solution, and the layers were separated. The aqueous layer was extracted with dichloromethane (×2), and the organic portions were combined and washed with brine. The mixture was dried over Na₂SO₄, filtered, and concentrated in vacuo. The crude material was purified via silica gel chromatography utilizing a 0-20% (acetonitrile:methanol=7:1)/dichloromethane gradient to deliver Compound I-331 (40 mg, 13% yield) as a white solid, and Compound I-332 (3 mg, 1% yield) as a white solid.

1H-NMR for Compound I-331 (400 MHz, DMSO-d₆) δ 12.09 (s, 1H), 9.14 (d, 1H), 8.38 (d, 1H), 7.25-7.18 (m, 1H), 7.37-7.29 (m, 1H), 7.55 (s, 1H), 7.12-7.06 (m, 2H), 6.87-6.80 (m, 1H), 5.94-5.84 (m, 2H), 4.73 (d, 1H), 4.23 (br. s., 1H), 3.66-3.54 (m, 1H), 2.94-2.85 (m, 1H), 2.38 (d, 1H), 1.89-1.81 (m, 1H), 1.68-1.51 (m, 3H), 1.15 (d, 3H), 0.97-0.92 (m, 2H), 0.89-0.84 (m, 2H).

¹H-NMR for Compound I-332 (400 MHz, DMSO-d₆) δ 11.97 (s, 1H), 9.14 (d, 1H), 8.41 (d, 1H), 7.65 (s, 1H), 7.37-7.28 (m, 1H), 7.26-7.17 (m, 1H), 7.14-7.05 (m, 2H), 6.88-6.79 (m, 1H), 5.97-5.86 (m, 2H), 4.70 (d, 1H), 4.13 (d, 1H), 3.83-3.72 (m, 1H), 2.97-2.87 (m, 1H), 2.10 (d, 1H), 1.85 (d, 1H), 1.74-1.60 (m, 2H), 1.53-1.39 (m, 1H), 1.16 (d, 3H), 1.05-0.93 (m, 3H), 0.87-0.78 (m, 1H).

Compound I-333

A mixture of 3-(3-(4-chloropyrimidin-2-yl)-1-(2-fluorobenzyl)-1H-pyrazol-5-yl)isoxazole (synthesis of which is described in the procedure towards Compound I-24) (1 equiv.), (2R,3S)-3-methylpiperidine-2-carboxylic acid (as the (1S)-(+)-camphorsulfonic acid salt, 1 equiv.), and triethylamine (1 equiv.) was heated to 110° C. for 48 h as a solution in dioxane/water (2:1). The contents were cooled to 23° C., and partitioned between a 1:1 mixture of dichloromethane and 1N HCl solution. The layers were separated, and the aqueous layer was extracted with dichloromethane (×2), and the organic portions were combined and washed with brine. The mixture was dried over Na₂SO₄, filtered, and concentrated in vacuo. The crude material was purified via silica gel chromatography utilizing a 0-20% (acetonitrile:methanol=7:1)/dichloromethane gradient to deliver the desired compound, Compound I-333 (10 mg, 4% yield) as a white solid.

¹H-NMR (400 MHz, DMSO-d₆) δ 12.64 (br. s., 1H), 9.10 (d, 1H), 8.30 (d, 1H), 7.55 (br. s., 1H), 7.38-7.29 (m, 1H), 7.27-7.16 (m, 2H), 7.15-7.06 (m, 1H), 6.83 (d, 2H), 5.90 (s, 2H), 3.21 (s, 1H), 1.94 (br. s., 1H), 1.89-1.80 (m, 1H), 1.69-1.35 (m, 5H), 1.13 (d, 3H).

Compound I-334

The title compound was prepared following general procedure B, except 2-amino-2-(hydroxymethyl)propane-1,3-diol was the amine reactant and the contents were heated to 110° C. for 20 h. The crude material was purified via silica gel chromatography utilizing a 0-20% (acetonitrile:methanol=7:1)/dichloromethane gradient to deliver the desired compound, Compound I-334 (185 mg, 72% yield) as an off-white solid.

¹H-NMR (400 MHz, DMSO-d₆) δ 9.10 (d, 1H), 8.24 (d, 1H), 7.46 (s, 1H), 7.36-7.29 (m, 1H), 7.25-7.18 (m, 2H), 7.10 (td, 1H), 6.91-6.84 (m, 1H), 6.36 (s, 1H), 5.86 (s, 2H), 4.95 (br. s., 3H), 3.76-3.72 (m, 6H).

Compound I-335

The title compound was prepared following general procedure B, except (S)-2-amino-3-hydroxypropanamide was the amine reactant and the contents were heated to 110° C. for 20 h. The crude material was purified via silica gel chromatography utilizing a 0-20% (acetonitrile:methanol=7:1)/dichloromethane gradient to deliver the desired compound, Compound I-335 (170 mg, 37% yield) as a white solid.

¹H-NMR (400 MHz, DMSO-d₆) δ 9.14 (d, 1H), 8.56 (br. s., 1H), 8.41 (d, 1H), 7.70 (s, 2H), 7.37-7.31 (m, 1H), 7.29-7.19 (m, 3H), 7.14-7.08 (m, 1H), 6.86 (t, 1H), 5.94 (s, 2H), 4.87-4.80 (m, 1H), 3.89-3.78 (m, 2H), 3.06 (qd, 1H).

Compound I-336

A solution of Compound I-112 (1 equiv.) in DMF was treated successively with Hunig's base (3 equiv.) and HATU (1 equiv.). After stirring for 5 minutes, serinol (1.5 equiv.) was added, and the reaction was stirred at 23° C. for 20 h. The mixture was partitioned between a 1:1 mixture of dichloromethane and 1N HCl solution. The layers were separated, and the aqueous layer was extracted with dichloromethane (×2). The combined organic portions were washed with brine. The mixture was dried over Na₂SO₄, filtered, and concentrated in vacuo. The crude material was purified via silica gel chromatography utilizing a 0-20% (acetonitrile:methanol=7:1)/dichloromethane gradient to deliver the desired compound, Compound I-336 (22 mg, 26% yield) as a white solid.

¹H-NMR (400 MHz, DMSO-d₆) δ 9.14 (d, 1H), 8.96 (br. s., 1H), 8.45 (d, 1H), 8.17 (d, 1H), 7.85 (s, 1H), 7.38-7.29 (m, 1H), 7.28-7.18 (m, 2H), 7.14-7.07 (m, 1H), 6.86 (t, 1H), 5.96 (s, 2H), 4.94-4.86 (m, 1H), 3.86-3.78 (m, 2H), 3.74-3.65 (m, 1H), 3.64-3.53 (m, 1H), 3.53-3.46 (m, 1H), 3.45-3.40 (m, 2H), 3.40-3.34 (m, 2H), 3.16-3.04 (m, 1H).

Compound I-337

The title compound was prepared following general procedure B, except 3-amino-1,1,1-trifluoropropan-2-ol (5 equiv.) was the amine reactant and the contents were heated to 110° C. for 20 h. The crude material was purified via silica gel chromatography utilizing a 0-20% (acetonitrile:methanol=7:1)/dichloromethane gradient to deliver the desired compound, Compound I-337 (70 mg, 53% yield) as a white solid.

¹H-NMR (400 MHz, CDCl₃) δ 8.76 (d, 1H), 8.10 (d, 1H), 7.38 (s, 1H), 7.30-7.23 (m, 1H), 7.08 (dd, 1H), 7.05-7.00 (m, 1H), 6.88-6.82 (m, 2H), 5.95 (s, 2H), 4.40-4.30 (m, 1H), 3.99 (dd, 1H), 3.70 (dd, 1H).

Compound I-339

The title compound was prepared in 2 steps:

Step 1: Synthesis of methyl 2-(5-fluoro-2-(1-(2-fluorobenzyl)-5-(isoxazol-3-yl)-1H-pyrazol-3-yl)pyrimidin-4-yl)-1,2,3,4-tetrahydroisoquinoline-8-carboxylate This intermediate was prepared following general procedure B, except methyl 1,2,3,4-tetrahydroisoquinoline-8-carboxylate (as the HCl salt) was the amine reactant. Work up delivered the desired methyl ester, methyl 2-(5-fluoro-2-(1-(2-fluorobenzyl)-5-(isoxazol-3-yl)-1H-pyrazol-3-yl)pyrimidin-4-yl)-1,2,3,4-tetrahydroisoquinoline-8-carboxylate (Compound I-338, 55 mg, 97% yield) as an orange oil, which was carried on without further purification.

Step 2: Synthesis of Compound I-339

A solution of methyl 2-(5-fluoro-2-(1-(2-fluorobenzyl)-5-(isoxazol-3-yl)-1H-pyrazol-3-yl)pyrimidin-4-yl)-1,2,3,4-tetrahydroisoquinoline-8-carboxylate and lithium hydroxide hydrate (1.5 equiv.) in tetrahydrofuran, water, and methanol (3:1:1 ratio) was stirred at 23° C. for 21 h. Additional base (1.5 equiv.) was added, and the solution was stirred for 24 h. The solution was poured into water, 1 N sodium hydroxide, and dichloromethane (10:1:10 ratio). The layers were separated and the aqueous layer was acidified to pH 1. The aqueous layer was extracted with dichloromethane, dried over magnesium sulfate, filtered, and the solvent was removed in vacuo to deliver the desired compound, Compound I-339 (9 mg, 17% yield over 2 steps) as a white solid.

¹H-NMR (400 MHz, DMSO-d₆) δ 13.14 (s, 1H), 9.12 (d, 1H), 8.32 (d, 1H), 7.79-7.77 (m, 1H), 7.48 (s, 1H), 7.43-7.41 (d, 1H), 7.34-7.30 (m, 2H), 7.24-7.20 (m, 2H), 7.11 (dt, 1H), 6.85 (dt, 1H), 5.89 (s, 2H), 5.34 (d, 2H), 4.07 (t, 2H), 3.04 (t, 2H).

Compound I-341

The title compound was prepared in 3 steps:

Step 1: Synthesis of cis-1-(5-fluoro-2-(1-(2-fluorobenzyl)-5-(isoxazol-3-yl)-1H-pyrazol-3-yl)pyrimidin-4-yl)-3-methylpiperidine-2-carboxamide (Compound I-340)

To a solution of Compound I-161 and triethylamine (1 equiv.) at 0° C. in tetrahydrofuran was added ethyl chloroformate (1.05 equiv.) dropwise over 5 minutes. The reaction mixture was maintained at 0° C. for 45 min, and then ammonium hydroxide (7 equiv.) was added. The solution was immediately warmed to 23° C. and stirred for an additional 15 hours. The reaction mixture was diluted with ethyl acetate and saturated aqueous ammonium chloride. The layers were separated and the aqueous layer was extracted with ethyl acetate. The organics were dried over magnesium sulfate, filtered, and the solvent was removed in vacuo. Purification via silica gel chromatography (20-100% hexanes in ethyl acetate gradient) provided cis-1-(5-fluoro-2-(1-(2-fluorobenzyl)-5-(isoxazol-3-yl)-1H-pyrazol-3-yl)pyrimidin-4-yl)-3-methylpiperidine-2-carboxamide (Compound I-340, 270 mg, 54% yield) as a yellow foam.

¹H NMR (400 MHz, CDCl₃) δ ppm 8.46 (d, 1H), 8.17 (d, 1H), 7.23 (s, 1H), 7.22-7.17 (m, 1H), 7.12-6.91 (m, 3H), 6.59 (d, 1H), 6.06-5.76 (m, 2H), 5.34 (br. s., 1H), 4.76 (d, 1H), 4.18 (d, 1H), 3.32 (ddd, 1H), 2.64-2.50 (m, 1H), 2.08-1.79 (m, 2H), 1.65-1.50 (m, 1H), 1.49-1.37 (m, 1H), 1.15 (d, 1H), 1.05 (d, 3H).

Step 2: Synthesis of cis-1-(5-fluoro-2-(1-(2-fluorobenzyl)-5-(isoxazol-3-yl)-1H-pyrazol-3-yl)pyrimidin-4-yl)-3-methylpiperidine-2-carbonitrile To a 0° C. solution of cis-1-(5-fluoro-2-(1-(2-fluorobenzyl)-5-(isoxazol-3-yl)-1H-pyrazol-3-yl)pyrimidin-4-yl)-3-methylpiperidine-2-carboxamide in pyridine was added trifluoroacetic anhydride (2 equiv.) dropwise over 5 minutes. After stirring for 45 min at 0° C., the solution was warmed to room temperature and then immediately poured into dichloromethane and saturated aqueous ammonium chloride. The layers were separated and the aqueous layer was extracted with dichloromethane. The organics were dried over magnesium sulfate, filtered, and the solvent was removed in vacuo. Purification via silica gel chromatography (10-75% hexanes in ethyl acetate gradient) gave cis-1-(5-fluoro-2-(1-(2-fluorobenzyl)-5-(isoxazol-3-yl)-1H-pyrazol-3-yl)pyrimidin-4-yl)-3-methylpiperidine-2-carbonitrile (215 mg, 83% yield) as a white foam.

¹H NMR (400 MHz, CDCl₃) δ ppm 8.44 (d, 1H), 8.31 (d, 1H), 7.30 (s, 1H), 7.22-7.11 (m, 1H), 7.06-6.91 (m, 2H), 6.82 (t, 1H), 6.59 (d, 1H), 5.95 (s, 2H), 5.40 (s, 1H), 4.35 (d, 1H), 3.32 (td, 1H), 2.48-2.35 (m, 1H), 2.20-1.84 (m, 2H), 1.61-1.76 (m, 2H), 1.17 (d, 3H).

Step 3: Synthesis of Compound I-341

A suspension of cis-1-(5-fluoro-2-(1-(2-fluorobenzyl)-5-(isoxazol-3-yl)-1H-pyrazol-3-yl)pyrimidin-4-yl)-3-methylpiperidine-2-carbonitrile, ammonia hydrochloride (5 equiv.), and sodium azide (5 equiv.) in N,N-dimethylformamide was heated to 90° C. for 60 hours. The solution was diluted with ethyl acetate and aqueous 1 N hydrochloric acid solution. The layers were separated and the aqueous layer was extracted with ethyl acetate. The organics were washed with water and brine, dried over magnesium sulfate, filtered, and the solvent was removed in vacuo. The crude solid was suspended in dichloromethane and filtered to give product contaminated with side product. The filtrate was concentrated in vacuo and the resulting solid was suspended in diethyl ether and filtered to deliver the desired compound, Compound I-341 (135 mg, 57% yield) as a white solid.

$^1$H-NMR (400 MHz, CDCl$_3$) δ 8.51 (d, 1H), 8.15 (d, 1H), 7.29 (s, 1H), 7.25-7.20 (m, 2H), 7.04-6.99 (m, 2H), 6.63 (d, 1H), 6.09 (d, 1H), 6.00 (d, 1H), 5.18 (d, 1H), 3.98 (dd, 1H), 3.31 (dt, 1H), 2.81-2.75 (m, 1H), 2.54-2.46 (m, 1H), 2.13-2.02 (m, 1H), 1.80-1.75 (m, 1H), 1.60-1.51 (m, 1H), 1.11 (d, 3H).

Compound I-342

The title compound was prepared following general procedure B, except 1-((methylamino)methyl)cyclobutanecarboxylic acid (as the TFA salt) was the amine reactant. Work up delivered the desired compound, Compound I-342 (64 mg, quantitative yield) as a yellow solid.

$^1$H-NMR (400 MHz, CD$_3$OD) δ 8.81 (d, 1H), 8.29 (d, 1H), 7.56 (m, 1H), 7.32-7.26 (m, 1H), 7.11-7.02 (m, 2H), 6.96-6.92 (m, 2H), 5.98 (s, 2H), 4.37 (s, 2H), 3.48 (d, 3H), 2.51-2.44 (m, 2H), 2.25-2.16 (m, 2H), 2.09-1.93 (m, 2H).

Compound I-343

A suspension of 5-fluoro-2-(1-(2-fluorobenzyl)-5-(thiazol-2-yl)-1H-pyrazol-3-yl) pyrimidin-4-ol (intermediate previously described in WO2013/101830 A1) in phosphoryl chloride (20 equiv.) was heated to 60° C. for 2 h. The phosphoryl chloride was removed under a stream of nitrogen and the resulting residue dissolved in dioxane and water (2:1 ratio). Following the addition of 1-((methylamino)methyl) cyclopropanecarboxylic acid hydrochloride (3 equiv.), and triethylamine (10 equiv.), the solution was heated to 90° C. for 4 h. The solution was diluted with dichloromethane and 1 N hydrochloric acid solution. The layers were separated and the aqueous layer extracted with dichloromethane. The organics were dried over magnesium sulfate, filtered, and the solvent was removed in vacuo. Purification via silica gel chromatography (0-5% methanol in dichloromethane gradient) delivered the desired compound, Compound I-343 (17 mg, 52% yield) as a white solid.

$^1$H-NMR (400 MHz, DMSO-d$_6$) δ 12.34 (s, 1H), 8.23 (d, 1H), 7.98 (d, 1H), 7.92 (d, 1H), 7.35 (s, 1H), 7.34-7.29 (m, 1H), 7.23-7.18 (m, 1H), 7.10 (dt, 1H), 6.93 (dt, 1H), 6.02 (s, 2H), 4.00 (s, 2H), 3.24 (d, 3H), 1.15-1.12 (m, 2H), 1.03-1.01 (m, 2H).

Compound I-344

To a solution of Compound I-248 in dichloromethane was added carbonyldiimidazole (1.2 equiv.). The resulting mixture was stirred at 40° C. for 45 min. The solution was cooled to 23° C. and 1,8-diazabicyclo[5.4.0]undec-7-ene (2 equiv.) was added, followed by cyclopropanesulfonamide (3 equiv.). After stirring for 16 h, the solution was poured into dichloromethane and 1N hydrochloric acid solution. The layers were separated and the aqueous layer was extracted with dichloromethane. The organics were dried over magnesium sulfate, filtered, and the solvent was removed in vacuo. Initial purification via silica gel chromatography (methanol in dichloromethane) gave impure product. The impure residue was brought up in diethyl ether, and hexanes were added until the solution became cloudy. After stirring for 20 min, the solid was filtered off to deliver the desired compound, Compound I-344 (29 mg, 48% yield) as a white solid.

$^1$H-NMR (400 MHz, CDCl$_3$) δ 8.44 (d, 1H), 8.09 (d, 1H), 7.23-7.17 (m, 2H), 7.03-6.97 (m, 3H), 6.51 (d, 1H), 5.95 (s, 2H), 3.96 (dd, 1H), 3.69-3.63 (m, 1H), 3.32 (d, 3H), 2.90-2.81 (m, 2H), 2.03-1.96 (m, 1H), 1.18-1.14 (m, 2H), 1.03 (dd, 6H), 0.92-0.90 (m, 2H).

Compound I-345

A suspension of 5-fluoro-2-(1-(2-fluorobenzyl)-5-(thiazol-4-yl)-1H-pyrazol-3-yl)pyrimidin-4-ol (intermediate previously described in WO2013/101830 A1) in phosphoryl chloride (50 equiv.) was heated to 60° C. for 2 h. The phosphoryl chloride was removed under a stream of nitrogen, and the resulting residue was dissolved in dioxane and water (2:1) and treated with 1-((methylamino)methyl)cyclopropanecarboxylic acid hydrochloride (3 equiv.), followed by triethylamine (10 equiv.). The resulting solution was heated to 90° C. for 7.5 days. The reaction mixture was poured into dichloromethane and 1N hydrochloric acid solution. The layers were separated and the aqueous layer was extracted with dichloromethane. The organics were dried over magnesium sulfate, filtered, and the solvent was removed in vacuo. Purification by silica gel chromatography (0-10% methanol in dichloromethane gradient) provided Compound I-345 (2.8 mg, 11% yield) as a white film.

$^1$H-NMR (400 MHz, CD$_3$OD) δ 9.03 (d, 1H), 8.07 (d, 1H), 7.89 (d, 1H), 7.24-7.19 (m, 2H), 7.04-6.96 (m, 2H), 6.81 (t, 1H), 5.94 (s, 2H), 4.13 (s, 2H), 3.34 (d, 3H), 1.28-1.25 (m, 2H), 1.08-1.05 (m, 2H).

Compound I-346

The title compound was prepared following general procedure B, except 3-(trifluoromethyl)-4,5,6,7-tetrahydro-1H-pyrazolo[4,3-c]pyridine (as the HCl salt) was the amine reactant. Following workup, the crude solid was suspended in diethyl ether and filtered to deliver the desired compound, Compound I-346 (57 mg, 84% yield) as a tan solid.

$^1$H-NMR (400 MHz, CD$_3$OD) δ 8.84 (d, 1H), 8.41 (d, 1H), 7.63 (s, 1H), 7.33-7.28 (m, 1H), 7.13-7.04 (m, 2H), 6.98-6.95 (m, 2H), 6.03 (s, 2H), 5.19 (s, 2H), 4.42 (t, 2H), 3.09 (t, 2H).

Compound I-347

The title compound was prepared following general procedure B, except racemic syn-piperidine-3,4,5-triol was the amine reactant. Upon completion of the reaction by LC/MS, the solvent was removed in vacuo. Methanol was added and the resulting suspension was filtered to deliver the desired compound, Compound I-347 (20 mg, 11% yield) as a solid.

1H-NMR (400 MHz, DMSO-d$_6$) δ 9.09 (d, 1H), 8.28 (d, 1H), 7.52 (s, 1H), 7.35-7.29 (m, 1H), 7.24-7.21 (m, 2H), 7.09 (t, 1H), 6.80 (t, 1H), 5.90 (s, 2H), 4.92 (d, 2H), 4.80 (d, 1H), 4.15-4.11 (m, 2H), 3.83-3.80 (m, 1H), 3.58-3.53 (m, 2H), 3.27-3.21 (m, 2H).

Compound I-348

The title compound was prepared following general procedure B, except 1,3-diaminopropan-2-ol was the amine reactant, and contents were heated to 40° C. for 45 min. Upon completion of the reaction by LC/MS, dioxane was removed in vacuo and enough methanol was added to solubilize the crude mixture. Purification via reverse-phase HPLC (5-75% acetonitrile in water w/0.1% trifluoroacetic acid, 20 min gradient) delivered the desired compound, Compound I-348 (58 mg, 80% yield) as a pink foam.

$^1$H-NMR (400 MHz, CD$_3$OD) δ 8.82 (d, 1H), 8.27 (d, 1H), 7.62 (s, 1H), 7.32-7.27 (m, 1H), 7.12-7.03 (m, 2H), 6.95-6.91 (m, 2H), 6.02 (d, 1H), 5.97 (d, 1H), 4.21-4.15 (m, 1H), 3.85-3.77 (m, 2H), 3.22-3.18 (dd, 1H), 2.96 (dd, 1H).

Compound I-349

To a solution of Compound I-340 and triethylamine (5 equiv.) in dichloromethane at 0° C. was added methanesulfonyl chloride (1 equiv.) dropwise. After stirring for 45 min, saturated aqueous sodium bicarbonate was added and the reaction mixture was warmed to 23° C. Dichloromethane was added and the layers were separated. The aqueous layer was extracted with dichloromethane and the organics were dried over magnesium sulfate, filtered, and the solvent was removed in vacuo. Purification via reverse phase HPLC (5-50% acetonitrile in water w/0.1% TFA) delivered the desired compound, Compound I-349 (6 mg, 25% yield) as a white solid.

$^1$H-NMR (400 MHz, CD$_3$OD) δ 8.78 (d, 1H), 8.24 (d, 1H), 7.70 (s, 1H), 7.31-7.25 (m, 1H), 7.11-7.02 (m, 3H), 6.92-6.88 (m, 1H), 6.04 (s, 2H), 4.10-4.01 (m, 2H), 3.61-3.56 (m, 1H), 3.18-3.17 (m, 2H), 2.95 (s, 3H).

Compound I-350

The title compound was prepared following general procedure B, except racemic cis-piperidine-3,4-diol (as the HCl salt) was the amine reactant. The crude material was purified via reverse phase HPLC (5-50% acetonitrile in water w/0.1% TFA, 20 min gradient) delivered the desired compound, Compound I-350 (1.7 mg, 3% yield) as a clear film.

$^1$H-NMR (400 MHz, CD$_3$OD) δ 8.81 (m, 1H), 8.28 (d, 1H), 7.64 (s, 1H), 7.32-7.26 (m, 1H), 7.12-7.03 (m, 2H), 6.97-6.93 (m, 2H), 6.01 (s, 2H), 4.52 (br s, 2H), 4.38 (dd, 1H), 3.97-3.90 (m, 2H), 3.77-3.72 (m, 1H), 2.02-1.97 (m, 1H), 1.90-1.86 (m, 1H).

Compound I-351

The title compound was prepared following general procedure B, except tert-butyl 3-(aminomethyl)-3-hydroxyazetidine-1-carboxylate was the amine reactant, and the reaction was run as a solution in dioxane. Ethyl acetate was used as solvent during work up. The crude material was purified via silica gel chromatography (0-5% methanol in dichloromethane gradient) to deliver the desired compound, Compound I-351 (144 mg, quantitative yield) as a white solid.

$^1$H-NMR (400 MHz, CD$_3$OD) δ 8.76 (d, 1H), 8.11 (d, 1H), 7.44 (s, 1H), 7.30-7.25 (m, 1H), 7.12-7.01 (m, 2H), 6.92 (d, 1H), 6.81 (t, 1H), 5.97 (s, 2H), 4.09 (d, 2H), 3.93 (br s, 2H), 3.78 (d, 2H), 1.40 (s, 9H).

Compound I-352

The title compound was prepared following general procedure B, except 3-(aminomethyl)oxetan-3-ol was the amine reactant, and the reaction was run as a solution in dioxane. After stirring for 1.5 h at 90° C., 2 additional equivalents of oxetane were added and the reaction mixture was stirred at 90° C. for 3 h. The reaction solution was then poured into ethyl acetate and aqueous 1N hydrochloric acid solution. The layers were separated, and the aqueous layer was extracted with 5:1 dichloromethane/isopropyl alcohol. The organics were dried over magnesium sulfate, filtered, and the solvent was removed in vacuo. Purification by reverse-phase HPLC (5-75% acetonitrile in water, 0.1% TFA, 15 min gradient) delivered Compound I-352 (25 mg, 53% yield) as a white solid.

$^1$H-NMR (400 MHz, CD$_3$OD) δ 8.83 (d, 1H), 8.29 (d, 1H), 7.65 (s, 1H), 7.32-7.28 (m, 1H), 7.13-7.05 (m, 2H), 6.99-6.94 (m, 2H), 6.02 (s, 2H), 4.05 (d, 1H), 3.98 (d, 1H), 3.78-3.63 (m, 4H).

Compound I-353

To a solution of Compound I-351 at 23° C. in dichloromethane was added trifluoroacetic acid (30 equiv.) in a single portion. After stirring for 30 min, the solution was concentrated in vacuo and the resulting residue was brought up in diethyl ether. The solid was filtered to deliver the desired compound, Compound I-353 (160 mg, quantitative yield) as a tan solid.

$^1$H-NMR (400 MHz, CD$_3$OD) δ 8.83 (m, 1H), 8.29-8.25 (m, 1H), 7.60-7.57 (m, 1H), 7.33-7.28 (m, 1H), 7.14-7.04 (m, 2H), 6.93-6.89 (m, 2H), 6.00 (s, 2H), 4.31 (d, 2H), 4.05 (m, 2H), 3.97 (d, 2H).

Compound I-354

The title compound was prepared following general procedure B, except N-(1-(aminomethyl)cyclopropyl)-1,1,1-trifluoromethanesulfonamide (as the HCl salt) was the amine reactant. The crude material was purified via silica gel chromatography (0-50% ethyl acetate in hexanes gradient) to deliver the desired compound, Compound I-354 (15 mg, 25% yield) as a white solid.

$^1$H-NMR (400 MHz, CD$_3$OD) δ 8.75 (d, 1H), 8.08 (d, 1H), 7.50 (s, 1H), 7.28-7.24 (m, 1H), 7.10-7.07 (m, 1H), 7.04-7.01 (m, 1H), 6.83-6.80 (m, 2H), 5.96 (s, 2H), 3.85 (s, 2H), 1.06-1.04 (m, 2H), 0.99-0.96 (m, 2H).

Compound I-355

The title compound was prepared following general procedure B, except 2-(aminomethyl)-3,3,3-trifluoropropane-1,2-diol was the amine reactant, and the reaction was run as a solution in dioxane. After workup with ethyl acetate and 1N hydrochloric acid solution, purification via silica gel chromatography (0-10% methanol in dichloromethane gradient) delivered the desired compound, Compound I-355 (17 mg, 36% yield) as a white solid.

$^1$H-NMR (400 MHz, CD$_3$OD) δ 8.75 (d, 1H), 8.15 (d, 1H), 7.39 (s, 1H), 7.28-7.23 (m, 1H), 7.09-7.01 (m, 2H), 6.88-6.85 (m, 2H), 5.96 (d, 1H), 5.93 (d, 1H), 4.02 (d, 1H), 3.90 (d, 1H), 3.75 (d, 1H), 3.62 (d, 1H).

Compound I-356

The title compound was prepared following general procedure B, except (S)-3-aminopyrrolidin-2-one (as the HCl salt) was the amine reactant. The crude residue was in suspended in 3:1 diethyl ether and dichloromethane. The resulting solid was filtered to deliver the desired compound, Compound I-356 (10 mg, 22% yield) as a tan solid.

$^1$H-NMR (400 MHz, CD$_3$OD) δ 8.83 (s, 1H), 8.34 (m, 1H), 7.63-7.62 (m, 1H), 7.33-7.29 (m, 1H), 7.13-7.05 (m, 2H), 6.98-6.96 (m, 2H), 6.03 (s, 2H), 5.36-5.32 (m, 1H), 3.56-3.49 (m, 2H), 2.66-2.61 (m, 1H), 2.38-2.30 (m, 1H).

Compound I-357

The title compound was prepared in 5 steps:

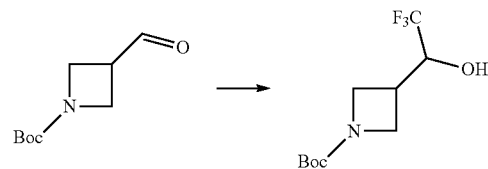 [SMILES: CC(C)(C)OC(=O)N1CC(C=O)C1 ; CC(C)(C)OC(=O)N1CC(C(O)C(F)(F)F)C1]

Step 1: Synthesis of Tert-Butyl 3-(2,2,2-trifluoro-1-hydroxyethyl)azetidine-1-carboxylate To a 0° C. solution of tert-butyl 3-formylazetidine-1-carboxylate (1 equiv.) and trimethyl(trifluoromethyl)silane (1.4 equiv.) in tetrahydrofuran was added tetrabutylammonium fluoride (1 M solution in tetrahydrofuran, 1.1 equiv.) over the course of 10 min. The solution was warmed immediately to 23° C. and stirred for 19 h. The reaction mixture was poured into 1N hydrochloric acid solution and diethyl ether. The layers were separated and the aqueous layer was extracted with diethyl ether. The organics were washed with saturated aqueous sodium chloride, dried over magnesium sulfate, filtered, and the solvent was removed in vacuo to give tert-butyl 3-(2,2,2-trifluoro-1-hydroxyethyl)azetidine-1-carboxylate (558 mg, 79% yield) as a pale yellow solid.

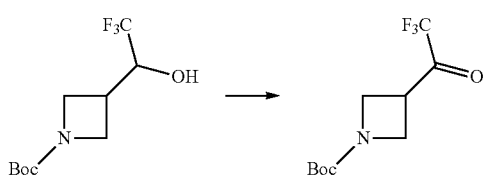 [SMILES: CC(C)(C)OC(=O)N1CC(C(O)C(F)(F)F)C1 ; CC(C)(C)OC(=O)N1CC(C(=O)C(F)(F)F)C1]

Step 2: Synthesis of Tert-Butyl 3-(2,2,2-trifluoroacetyl)azetidine-1-carboxylate To tert-butyl 3-(2,2,2-trifluoro-1-hydroxyethyl)azetidine-1-carboxylate (1 equiv.) in dichloromethane at 0° C. was added Dess-Martin periodinane (2 equiv.) in a single portion. After 5 minutes at 0° C., the solution was warmed to 23° C. After two hours, LC/MS showed complete conversion. The reaction mixture was poured into 5:1 saturated aqueous sodium dithionite and saturated aqueous sodium bicarbonate (75 mL). After stirring for 10 minutes, dichloromethane was added and the layers were separated. The aqueous layer was extracted with dichloromethane, the organics were dried over magnesium sulfate, filtered, and the solvent was removed in vacuo to give tert-butyl 3-(2,2,2-trifluoroacetyl)azetidine-1-carboxylate (263 mg, 92% yield) as a white greasy solid that was a mixture of ketone and hydrate by $^1$H-NMR.

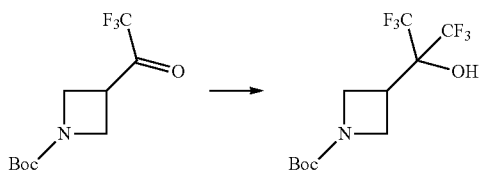 [SMILES: CC(C)(C)OC(=O)N1CC(C(=O)C(F)(F)F)C1 ; CC(C)(C)OC(=O)N1CC(C(O)(C(F)(F)F)C(F)(F)F)C1]

Step 3: Synthesis of Tert-Butyl 3-(1,1,1,3,3,3-hexafluoro-2-hydroxypropan-2-yl)azetidine-1-carboxylate To a 0° C. solution of tert-butyl 3-(2,2,2-trifluoroacetyl)azetidine-1-carboxylate (1 equiv.) and trimethyl(trifluoromethyl)silane (1.4 equiv.) in tetrahydrofuran was added tetrabutylammonium fluoride (1.1 equiv.) as a 1M solution in tetrahydrofuran dropwise over 5 min. The solution was warmed immediately to 23° C. and stirred for 2.5 d. The solution was then poured into ethyl acetate and aqueous 1N hydrochloric acid solution. The layers were separated and the aqueous layer was extracted with ethyl acetate (2×). The organics were washed with saturated aqueous sodium chloride, dried over magnesium sulfate, filtered, and the solvent was removed in vacuo. Purification via silica gel chromatography (0-60% ethyl acetate in hexanes gradient) provided tert-butyl 3-(1,1,1,3,3,3-hexafluoro-2-hydroxypropan-2-yl)azetidine-1-carboxylate (24 mg, 7% yield) as an oily solid.

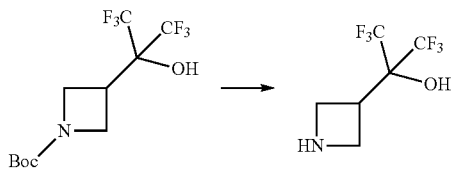 [SMILES: CC(C)(C)OC(=O)N1CC(C(O)(C(F)(F)F)C(F)(F)F)C1 ; OC(C1CNC1)(C(F)(F)F)C(F)(F)F]

Step 4: Synthesis of 2-(azetidin-3-yl)-1,1,1,3,3,3-hexafluoropropan-2-ol tert-butyl 3-(1,1,1,3,3,3-hexafluoro-2-hydroxypropan-2-yl)azetidine-1-carboxylate was stirred in trifluoroacetic acid and dichloromethane (1:2 ratio) for 1.5 h. The solution was then concentrated in vacuo to provide 2-(azetidin-3-yl)-1,1,1,3,3,3-hexafluoropropan-2-ol as the TFA salt.

Step 5: Synthesis of Compound I-357

The title compound was prepared following general procedure B, except 2-(azetidin-3-yl)-1,1,1,3,3,3-hexafluoropropan-2-ol (as the TFA salt, 1.5 equiv.) was the amine reactant. The crude residue was brought up in 1:1 dichloromethane and diethyl ether and the solid was filtered off and washed with additional diethyl ether to deliver the desired compound, Compound I-357 (17 mg, 64% yield) as a white solid.

$^1$H-NMR (400 MHz, CD$_3$OD) δ 8.83 (d, 1H), 8.27 (d, 1H), 7.62 (s, 1H), 7.35-7.30 (m, 1H), 7.15-7.07 (m, 2H), 7.00-6.96 (m, 2H), 6.05 (s, 2H), 4.82-4.70 (m, 4H), 3.79 (quint, 1H).

Compound I-359

This compound was prepared in two steps

Step 1: Synthesis of Ester I-358

The title compound was prepared following general procedure B, except 1-aminomethylcyclopropanol (2 equiv.) was the amine reactant, no triethylamine was used, and contents were heated to 100° C. for 96 h as a solution in dioxane/water (3:1). Ethyl acetate was the solvent used for work up. The crude material was first purified via silica gel chromatography utilizing a 0-100% ethyl acetate/hexanes gradient, then by reverse phase HPLC (water/acetonitrile with 0.1% trifluoroacetic acid). The water/acetonitrile fractions containing product were treated with excess 10% NaHCO$_3$(aq), concentrated to 5 mL, then extracted with ethyl acetate to recover the neutral material to deliver the desired compound, Compound I-358 (32 mg 28% yield) as a white solid.

$^1$H-NMR (400 MHz, CDCl$_3$) δ 8.42 (d, 1H), 8.11 (m, 1H), 7.24 (s, 1H), 7.15 (m, 1H), 6.99 (m, 1H), 6.94 (m, 1H), 6.85 (m, 1H), 6.56 (d, 1H), 5.93 (s, 2H), 5.63 (m, 1H), 4.77 (m, 1H), 3.74 (d, 2H), 0.86 (m, 2H), 0.65 (m, 2H).

Step 2: Synthesis of Compound I-359

Compound I-358 was dissolved in tetrahydrofuran at room temperature, and triethylamine (3 equiv.) and ethyl chloroformate (2 equiv.) were added in succession. Contents were allowed to stir for 1 h at room temperature. The mixture was diluted with ethyl acetate, washed with water (3×) then dried over sodium sulfate, filtered and concentrated in vacuo. The resulting residue was redissolved in tetrahydrofuran, treated with sodium borohydride (6 equiv.), and stirred for 1 h. This mixture was diluted with ethyl acetate, washed with water (3×), then dried over sodium sulfate, filtered and concentrated in vacuo. The crude material was purified via silica gel chromatography utilizing a 10-80% ethyl acetate/hexanes gradient to deliver the desired compound, Compound I-359 (11 mg, 76% yield) as a white solid.

$^1$H-NMR (400 MHz, CDCl$_3$) δ 8.41 (d, 1H), 8.11 (d, 1H), 7.28 (s, 1H), 7.16 (m, 1H), 7.00 (m, 1H), 6.95 (m, 1H), 6.87 (m, 1H), 6.54 (d, 1H), 5.93 (s, 2H), 5.53 (m, 1H), 4.61 (m, 1H), 3.60 (d, 2H), 3.35 (d, 2H), 0.53 (m, 4H).

Compound I-360

The title compound was prepared following general procedure B, except 1-(4-aminophenyl)cyclopropanecarboxylic acid (1 equiv.) was the amine reactant, 20 equivalents of triethylamine was used, and contents were heated to 100° C. for 18 has a solution in dioxane/water (3:1). Ethyl acetate was the solvent used for work up. The crude material was purified via silica gel chromatography utilizing a 5-95% ethyl acetate/hexanes gradient to deliver the desired compound, Compound I-360 (11 mg, 9% yield) as a white solid.

¹H-NMR (400 MHz, acetone-d₆) δ 8.89 (d, 1H), 8.81 (br d, 1H), 8.30 (d, 1H), 8.03 (d, 2H), 7.48 (s, 1H), 7.39 (d, 2H), 7.30 (m, 1H), 7.15 (m, 1H), 7.10 (m, 1H), 7.07 (d, 1H), 7.05 (m, 1H), 5.98 (s, 2H), 1.53 (m, 2H), 1.18 (m, 2H).

Compound I-361

The title compound was synthesized in 3 steps:

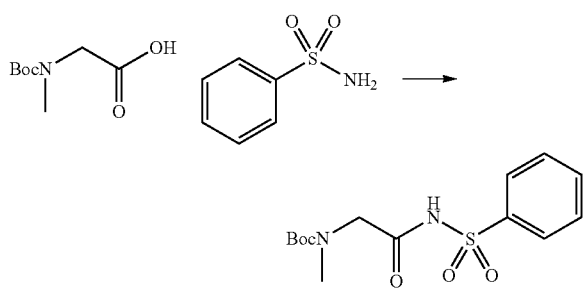

Step 1: Synthesis of Tert-Butyl Methyl (2-oxo-2-(phenyl-sulfonamido)ethyl)carbamate To a solution of 1,1'-carbonyldiimidazole (1.2 equiv.) in dichloromethane was added 2-((tert-butoxycarbonyl)(methyl)amino)acetic acid (1 equiv.). The mixture was stirred at 23° C. until gas evolution ceased. To this mixture were added benzenesulfonamide (3 equiv.) and DBU (1 equiv.). The mixture was stirred at 23° C. for 1 h. The mixture was diluted with dichloromethane and washed with water. The organic layer was dried, filtered and evaporated to give a white solid. Purification via silica gel chromatography (0 to 80% ethyl acetate in hexanes gradient) delivered tert-butyl methyl (2-oxo-2-(phenylsulfonamido)ethyl)carbamate (1.3 g) as a white solid.

¹H NMR (500 MHz, CD₃OD) δ ppm 7.91-7.95 (m, 2H), 7.59-7.65 (m, 3H), 3.86 (s, 2H), 2.82-2.88 (m, 3H), 1.20 (s, 9H).

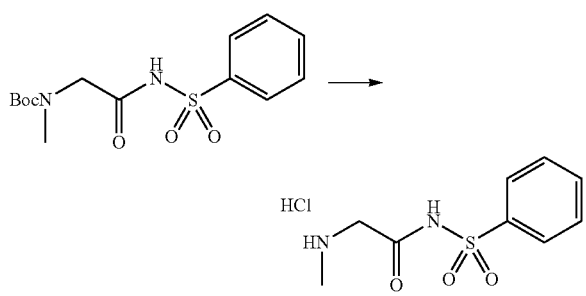

Step 2: Synthesis of 2-(methylamino)-N-(phenylsulfonyl)acetamide Hydrochloride

A mixture of tert-butyl methyl(2-oxo-2-(phenylsulfonamido)ethyl)carbamate (1 equiv.) and HCl [4.0 M in 1,4-dioxane] was stirred at 23° C. for 24 h. The mixture was concentrated to give 2-(methylamino)-N-(phenylsulfonyl)acetamide hydrochloride (3.2 g) as a cream colored solid.

¹H NMR (500 MHz, CD₃OD) δ ppm 8.04-8.07 (m, 2H), 7.57-7.64 (m, 3H), 3.88 (s, 2H), 2.67 (s, 3H).

Step 3: Synthesis of Compound I-31

The title compound was prepared following general procedure B, except 2-(methylamino)-N-(phenylsulfonyl)acetamide hydrochloride was the amine reactant, 6 equivalents of triethylamine was used, and contents were heated to 85° C. as a solution in dioxane/water (4:1) for 24 h. The mixture was cooled to 23° C. and diluted with ethyl acetate. The organic layer was washed with saturated solution of ammonium chloride, dried, filtered and evaporated to give a solid. The solid was purified by silica gel chromatography (0 to 100% ethyl acetate in hexanes gradient) to deliver the desired compound, Compound I-361 (6.5 mg, 14% yield for step 3) as a light yellow solid.

¹H NMR (500 MHz, CD₃OD) δ ppm 8.79 (d, 1H), 8.12 (d, 1H), 7.91-7.96 (m, 2H), 7.43-7.49 (m, 1H), 7.25-7.37 (m, 4H), 7.03-7.14 (m, 2H), 6.95 (d, 1H), 6.85-6.91 (m, 1H), 5.97 (s, 2H), 4.30 (s, 2H), 3.39 (d, 3H).

Compound I-363

The title compound was prepared following general procedure B, except piperidine-4-sulfonic acid (2 equiv.) was the amine reactant, 2 equivalents of triethylamine was used, and contents were heated to 70° C. as a solution in dioxane/water (1:1) for 2 h. Ethyl acetate was used as the extraction solvent during work up. The organic layer was dried, filtered, and concentrated in vacuo to deliver the desired compound, Compound I-363 (102 mg, 69% yield) as a white solid.

¹H NMR (500 MHz, DMSO-d₆) δ ppm 9.12 (d, 1H), 8.41 (d, 1H), 7.72 (s, 1H), 7.28-7.39 (m, 2H), 7.18-7.27 (m, 1H), 7.11 (t, 1H), 6.85 (t, 1H), 5.95 (s, 2H), 4.65 (d, 2H), 3.21 (t, 2H), 2.61-2.72 (m, 1H), 2.02-2.12 (m, 2H), 1.52-1.70 (m, 2H).

Compound I-364

The title compound was prepared following general procedure B, except 4,5,6,7-tetrahydroisoxazolo[5,4-c]pyridin-3-ol (as the HCl salt, 2 equiv.) was the amine reactant, 4 equivalents of triethylamine was used, and contents were heated to 70° C. as a solution in dioxane/water (3:1) for 2 h. Ethyl acetate was used as the extraction solvent during work up. The organic layer was dried, filtered, and concentrated in vacuo to yield a solid, which was further rinsed with diethyl ether and dichloromethane to deliver the desired compound, Compound I-364 (46 mg, 72% yield) as a white solid.

¹H NMR (500 MHz, DMSO-d₆) δ ppm 11.47 (s, 1H), 9.10 (d, 1H), 8.40 (d, 1H), 7.62 (s, 1H), 7.30-7.37 (m, 1H), 7.27 (d, 1H), 7.20-7.25 (m, 1H), 7.11 (t, 1H), 6.84 (t, 1H), 5.91 (s, 2H), 4.90 (s, 2H), 3.98 (t, 2H), 2.51-2.55 (m, 2H).

Compound I-365

The title compound was prepared following general procedure B, except (1R,3S,4S)-2-azabicyclo[2.2.1]heptane-3-carboxylic acid (as the HCl salt, 2 equiv.) was the amine reactant, 2.5 equivalents of triethylamine was used, and contents were heated to 60° C. for 24 h, followed by 80° C. for 3 h. Ethyl acetate was used as the extraction solvent during work up. The crude material was purified via silica gel chromatography utilizing a 0-100% ethyl acetate/hexanes gradient to yield a solid, which was further rinsed with diethyl ether and dichloromethane to deliver the desired compound, Compound I-365 (21 mg, 16% yield) as a white solid.

¹H NMR (500 MHz, CD₃OD) δ ppm 8.78 (d, 1H), 8.07-8.20 (m, 1H), 7.23-7.35 (m, 2H), 7.08-7.15 (m, 1H), 7.04 (t, 1H), 6.94 (br. s., 1H), 6.79-6.87 (m, 1H), 5.92-6.01 (m, 2H), 4.28-4.38 (m, 1H), 2.85-2.97 (m, 1H), 2.23 (d, 1H), 1.72-1.98 (m, 4H), 1.48-1.71 (m, 2H).

Compound I-366

The title compound was prepared following general procedure B, except piperidine-4-sulfonamide (2 equiv.) was the amine reactant, 2 equivalents of triethylamine was used, and contents were heated to 75° C. as a solution in dioxane/water (3:1) for 2 h. The mixture was diluted with ethyl acetate and washed with 1N HCl solution. The insoluble solids were collected via filtration and dried in vacuo to deliver the desired compound, Compound I-366 (64 mg, 48% yield) as a white solid.

¹H NMR (500 MHz, DMSO-d₆) δ ppm 9.10 (d, 1H), 8.35 (d, 1H), 7.60 (s, 1H), 7.31-7.37 (m, 1H), 7.21-7.28 (m, 2H), 7.11 (t, 1H), 6.79-6.85 (m, 3H), 5.91 (s, 2H), 4.66 (d, 2H), 3.24 (ddt, 1H), 3.16 (t, 2H), 2.13 (d, 2H), 1.67 (qd, 2H).

Compound I-367

The title compound was synthesized in 3 steps:

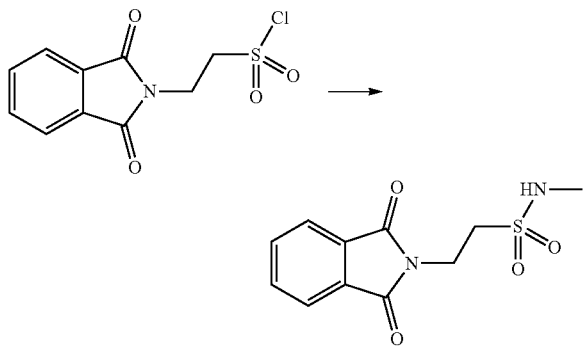

Step 1: Synthesis of 2-(1,3-dioxoisoindolin-2-yl)-N-methylethanesulfonamide

To a solution of 2-(1,3-dioxoisoindolin-2-yl)ethanesulfonyl chloride (1 equiv.) in THF was added methylamine [2.0 M solution in THF] (2 equiv.). The mixture was stirred at 23° C. for 1 h. The mixture was concentrated to yield 2-(1,3-dioxoisoindolin-2-yl)-N-methylethanesulfonamide (0.98 g) as a white solid.

¹H NMR (500 MHz, CD₃OD) δ ppm 7.79-7.92 (m, 4H), 4.06-4.13 (m, 2H), 3.42 (t, 2H), 2.74 (s, 3H).

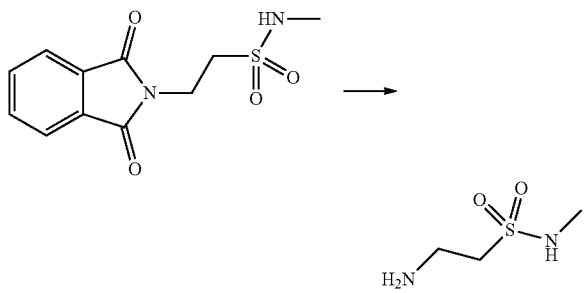

Step 2: Synthesis of 2-amino-N-methylethanesulfonamide

To a suspension of 2-(1,3-dioxoisoindolin-2-yl)-N-methylethanesulfonamide (1 equiv.) in ethanol was added hydrazine monohydrate (1.5 equiv.). The mixture was heated to 75° C. for 2 h. The white precipitate formed was removed by filtration. The filtrate was concentrated in vacuo to give 2-amino-N-methylethanesulfonamide as a white solid.

¹H NMR (500 MHz, CD₃OD) δ ppm 3.20-3.24 (m, 2H), 3.08-3.14 (m, 2H), 2.71 (s, 3H).

Step 3: Synthesis of Compound I-367

The title compound was prepared following general procedure B, except 2-amino-N-methylethanesulfonamide (2 equiv.) was the amine reactant, 2 equivalents of triethylamine was used, and contents were heated to 65° C. for 2 d. The mixture was diluted with ethyl acetate and washed with saturated sodium bicarbonate solution. The organic layer was dried, filtered and evaporated to give a solid. The solid was purified via silica gel chromatography (0 to 100% ethyl acetate in hexanes gradient) to deliver the desired compound, Compound I-367 (8.6 mg, 14% yield) as a cream colored solid.

¹H NMR (500 MHz, CD₃OD) δ ppm 8.76 (d, 1H), 8.10 (d, 1H), 7.49 (s, 1H), 7.24-7.30 (m, 1H), 7.07-7.13 (m, 1H), 7.03 (t, 1H), 6.87-6.90 (m, 1H), 6.81 (t, 1H), 5.96 (s, 2H), 4.01 (t, 2H), 3.42 (t, 2H), 2.68-2.70 (m, 3H).

Compound I-368

The title compound was prepared following general procedure B, except N-methyltaurine (as the sodium salt, 2 equiv.) was the amine reactant, 2 equivalents of triethylamine was used, and contents were heated to 65° C. as a solution in dioxane/water (3:1) for 24 h. Ethyl acetate was used as solvent for work up. The organic layer was dried, filtered and evaporated to give a solid. The solid was collected by filtration and dried under vacuum to deliver the desired compound, Compound I-368 (31 mg, 33% yield) as a white solid.

¹H NMR (500 MHz, DMSO-d₆) δ ppm 9.13 (d, 1H), 8.40 (d, 1H), 7.93 (br. s., 1H), 7.31-7.38 (m, 1H), 7.21-7.27 (m, 1H), 7.17 (s, 1H), 7.12 (t, 1H), 6.88 (t, 1H), 5.96 (s, 2H), 3.94-4.02 (m, 2H), 3.38 (d, 3H), 2.84-2.92 (m, 2H).

Compound I-369

The title compound was prepared following general procedure B, except cis-1-amino-1,2,3,4-tetrahydronaphthalene-2-carboxylic acid (2 equiv.) was the amine reactant, 2 equivalents of triethylamine was used, and contents were heated to 65° C. as a solution in dioxane/water (3:1) for 24 h. Ethyl acetate was used as solvent for work up. The crude material was purified via silica gel chromatography utilizing a 0-50% ethyl acetate/hexanes gradient to deliver the desired compound, Compound I-369 (7.0 mg, 10% yield) as a white solid.

¹H NMR (500 MHz, DMSO-d₆) δ ppm 9.07-9.10 (m, 1H), 8.22 (d, 1H), 7.70 (d, 1H), 7.57 (s, 1H), 7.30-7.41 (m, 2H), 7.08-7.24 (m, 6H), 6.89 (t, 1H), 5.91 (s, 2H), 2.99 (dt, 1H), 2.74-2.91 (m, 2H), 2.28-2.37 (m, 1H), 1.94-2.01 (m, 1H).

Compound I-370

The title compound was prepared following general procedure B, except 4,5,6,7-tetrahydro-1H-pyrazolo[3,4-c]pyridin-3(2H)-one (as the HCl salt, 3.2 equiv.) was the amine reactant, 6 equivalents of triethylamine was used, and contents were heated to 65° C. as a solution in dioxane/water (1:1) for 24 h. The mixture was diluted with ethyl acetate and extracted with 1H HCl solution. The aqueous layer was basified with saturated sodium bicarbonate solution and and extracted with ethyl acetate. The combined organic layers were dried, filtered, and evaporated to deliver the desired compound, Compound I-370 (83 mg, 65% yield) as a light brown solid.

¹H NMR (500 MHz, CDCl₃) δ ppm 8.38 (d, 1H), 8.08-8.21 (m, 1H), 7.22 (s, 1H), 7.07-7.13 (m, 1H), 6.91 (t, 1H), 6.85 (t, 1H), 6.73-6.78 (m, 1H), 6.52 (d, 1H), 5.85 (s, 2H), 4.69 (s, 2H), 3.83-3.91 (m, 2H), 2.52 (t, 2H).

Compound I-371

The title compound was prepared following general procedure B, except cis-1-amino-2,3-dihydro-1H-indene-2-carboxylic acid (2 equiv.) was the amine reactant, 2 equivalents of triethylamine was used, and contents were heated to 80° C. as a solution in dioxane/water (3:1) for 24 h. The mixture was diluted with ethyl acetate and washed with 1H HCl solution. The organic layer was dried, filtered, and concentrated in vacuo. The resulting solid was rinsed with minimal amounts of methanol to deliver the desired compound, Compound I-371 (11 mg, 16% yield) as a white solid.

¹H NMR (500 MHz, DMSO-d₆) δ ppm 9.10 (d, 1H) 8.25 (d, 1H) 7.63 (s, 1H) 7.29-7.39 (m, 3H) 7.20-7.28 (m, 3H) 7.09-7.19 (m, 2H) 6.88 (t, 1H) 6.22-6.29 (m, 1H) 5.87-5.97 (m, 2H) 3.67 (q, 1H) 3.52 (dd, 1H) 3.06 (dd, 1H).

Compound I-372

The title compound was synthesized in 3 steps:

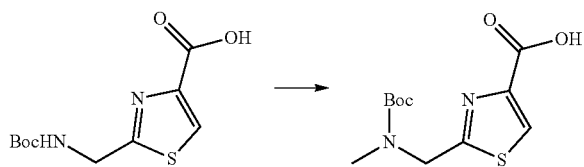 [SMILES: CC(C)(C)OC(=O)NCc1nc(C(=O)O)co1 ; CN(Cc1nc(C(=O)O)co1)C(=O)OC(C)(C)C]

Step 1: Synthesis of Tert-Butyl methyl(2-oxo-2-(phenylsulfonamido)ethyl)carbamate To a suspension of 2-(((tert-butoxycarbonyl)amino)methyl)thiazole-4-carboxylic acid (1 equiv.) and methyl iodide (10 equiv.) in THF at 0° C. was added sodium hydride [60 wt % dispersion on mineral oil] (10 equiv.). The mixture was stirred at 23° C. for 24 h. The mixture was diluted in ethyl acetate and washed with 1N HCl solution. The organic layer was dried, filtered and evaporated to give an oil, which was further purified via silica gel chromatography (0 to 50% ethyl acetate/hexanes gradient) to give 2-(((tert-butoxycarbonyl)(methyl)amino)methyl)thiazole-4-carboxylic acid (217 mg, 82% yield) as a red solid.

¹H NMR (500 MHz, CDCl₃) δ ppm 8.26-8.34 (m, 1H), 4.76 (d, 2H), 3.00 (d, 3H), 1.51 (br. s, 9H).

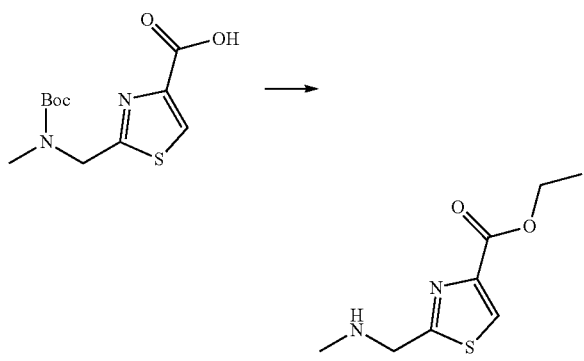

Step 2: Synthesis of Ethyl 2-((methylamino)methyl)thiazole-4-carboxylate Hydrochloride A mixture of 2-(((tert-butoxycarbonyl)(methyl)amino)methyl)thiazole-4-carboxylic acid (1 equiv.) and a solution of HCl [1.3 M in ethanol] (10 equiv.) was stirred at 23° C. for 24 h. The mixture was concentrated to deliver ethyl 2-((methylamino)methyl)thiazole-4-carboxylate (as the HCl salt, 222 mg) as a yellow solid.

¹H NMR (500 MHz, CD₃OD) δ ppm 8.46 (s, 1H), 4.63 (s, 2H), 4.27-4.37 (m, 2H), 2.80 (s, 3H), 1.28-1.35 (m, 3H).

Step 3: Synthesis of Compound I-372

The title compound was prepared following general procedure B, except ethyl 2-((methylamino)methyl)thiazole-4-carboxylate (as the HCl salt, 2 equiv.) was the amine reactant, 6 equivalents of triethylamine was used, and contents were heated to 80° C. as a solution in dioxane/water (4:1) for 24 h. The mixture was diluted in ethyl acetate and washed with saturated solution of sodium bicarbonate. The organic layer was dried, filtered and evaporated to give a solid, which was purified via silica gel chromatography (0 to 100% ethyl acetate in hexanes gradient) to deliver the desired compound, Compound I-372 (78 mg, 77% yield) as a light yellow gum.

¹H NMR (500 MHz, CDCl₃) δ ppm 8.45 (d, 1H), 8.26 (d, 1H), 8.12 (s, 1H), 7.28 (s, 1H), 7.17-7.23 (m, 1H), 6.94-7.06 (m, 2H), 6.86-6.92 (m, 1H), 6.58 (d, 1H), 5.97 (s, 2H), 5.22 (s, 2H), 4.44 (q, 2H), 3.42 (d, 3H), 1.42 (t, 3H).

Compound I-373

A mixture of Compound I-372 (1 equiv.) and lithium hydroxide (10 equiv.) in a THF/water/methanol (1:1:1) mix was stirred at 23° C. for 24 h. The mixture was concentrated in vacuo. The resulting solution was acidified to pH 1. The precipitate formed was collected by filtration and dried in vacuo to deliver the desired compound, Compound I-373 (38 mg, 67% yield) as a white solid.

¹H NMR (400 MHz, DMSO-d₆) δ ppm 13.05 (s, 1H), 9.09 (d, 1H), 8.36 (t, 2H), 7.57 (s, 1H), 7.30-7.37 (m, 1H), 7.18-7.26 (m, 2H), 7.11 (t, 1H), 6.89 (t, 1H), 5.89 (s, 2H), 5.17 (s, 2H), 3.32-3.39 (m, 3H).

Compound I-374

A suspension of Compound I-368 (1 equiv.) in thionyl chloride (50 equiv.) was heated to reflux for 24 h. The mixture was cooled and concentrated in vacuo to give the intermediate sulfonyl chloride 2-((5-fluoro-2-(1-(2-fluorobenzyl)-5-(is oxazol-3-yl)-1H-pyrazol-3-yl)pyrimidin-4-yl)(methyl) amino)-ethanesulfonyl chloride (169 mg) as a yellow solid. This material was then treated with ammonia [0.05 M solution in 1,4-dioxane] (5 equiv.) and the mixture was allowed to stir at 23° C. for 24 h. The reaction was diluted in ethyl acetate and washed with saturated solution of sodium bicarbonate. The organic layer was dried, filtered and evaporated to give an oil. The oil was purified via silica gel chromatography (0 to 30% methanol in dichloromethane gradient) and recrystallized from a methanol:dichloromethane mixture to deliver the desired compound, Compound I-374 (13 mg, 8% yield) as a light yellow solid.

¹H NMR (400 MHz, DMSO-d₆) δ ppm 9.10 (d, 1H) 8.28 (d, 1H) 7.58 (s, 1H) 7.33 (d, 1H) 7.19-7.25 (m, 1H) 7.14 (d, 1H) 7.08-7.13 (m, 2H) 5.89 (s, 2H) 4.00-4.06 (m, 2H) 3.36-3.41 (m, 2H) 3.28 (d, 3H).

Compound I-375

The title compound was prepared in 3 steps:

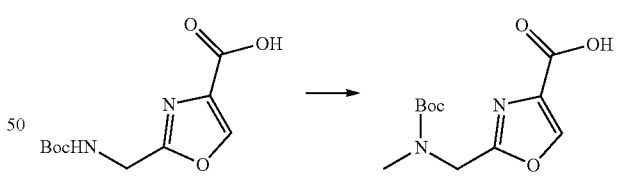

Step 1: Synthesis of 2-(((tert-butoxycarbonyl)(methyl)amino)methyl)oxazole-4-carboxylic Acid To a cold suspension of 2-(((tert-butoxycarbonyl)amino)methyl)oxazole-4-carboxylic acid (1 equiv.) and iodomethane (10 equiv.) in THF at 0° C., was added sodium hydride [60 wt % dispersion on mineral oil] (10 equiv.). The mixture was allowed to warm to 23° C. and stirred for 24 h. The mixture was diluted in ethyl acetate and washed with 1N HCl solution. The organic layer was dried, filtered and evaporated to give an oil. The oil was purified by column chromatography (0 to 100% ethyl acetate in hexanes gradient) to yield 2-(((tert-butoxycarbonyl)(methyl)amino)methyl)oxazole-4-carboxylic acid (215 mg, 81% yield) as a yellow oil.

¹H NMR (400 MHz, CDCl₃) δ ppm 8.27 (s, 1H), 4.52-4.69 (m, 2H), 2.93 (d, 3H), 1.37-1.53 (m, 9H).

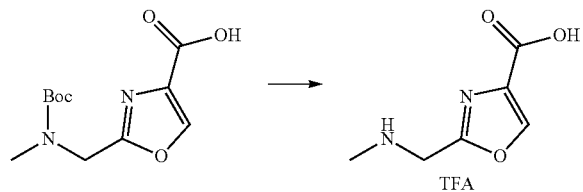 [SMILES: CN(Cc1nc(C(=O)O)co1)C(=O)OC(C)(C)C ; CNCc1nc(C(=O)O)co1]

Step 2: Synthesis of 2-((methylamino)methyl)oxazole-4-carboxylic Acid, TFA Salt

A mixture of 2-(((tert-butoxycarbonyl)(methyl)amino)methyl)oxazole-4-carboxylic acid (1 equiv) and TFA (10 equiv.) in DCM was stirred at 23° C. for 1 h. The mixture was concentrated to yield 2-((methylamino)methyl)oxazole-4-carboxylic acid, TFA salt (237 mg) as a clear oil.

¹H NMR (500 MHz, CD₃OD) δ ppm 8.62-8.64 (m, 1H), 4.49 (s, 2H), 2.86 (s, 3H).

Step 3: Synthesis of Compound I-375

The title compound was prepared following general procedure B, except 2-((methylamino)methyl)oxazole-4-carboxylic acid (as the TFA salt, 4 equiv.) was the amine reactant, 8 equivalents of triethylamine was used, and contents were heated to 80° C. as a solution in dioxane/water (4:1) for 24 h. Ethyl acetate was used as solvent during work up. The crude oil obtained after work up was treated with diethyl ether and the resulting precipitated solid was collected by filtration and dried in vacuo to deliver the desired compound, Compound I-375 (68% yield) as a white solid.

¹H NMR (500 MHz, DMSO-d₆) δ ppm 9.10 (d, 1H), 8.73 (s, 1H), 8.36 (d, 1H), 7.50 (s, 1H), 7.28-7.36 (m, 1H), 7.16-7.26 (m, 2H), 7.10 (t, 1H), 6.85 (t, 1H), 5.88 (s, 2H), 5.07 (s, 2H), 3.35-3.40 (m, 3H).

Compound I-376

The title compound was synthesized in 2 steps:

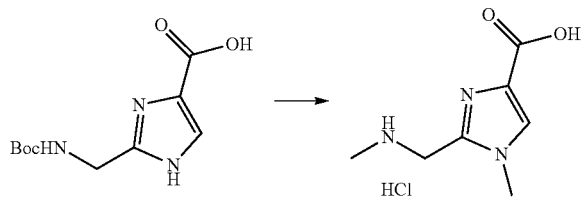 [SMILES: CC(C)(C)OC(=O)NCc1nc(C(=O)O)c[nH]1 ; CNCc1nc(C(=O)O)cn1C ; Cl]

Step 1: Synthesis of 1-methyl-2-((methylamino)methyl)-1H-imidazole-4-carboxylic Acid Hydrochloride To a suspension of 2-(((tert-butoxycarbonyl)amino)methyl)-1H-imidazole-4-carboxylic acid (1 equiv.) and methyl iodide (10 equiv.) in THF at 0° C., was added sodium hydride [60 wt % dispersion on mineral oil] (10 equiv.). The mixture was stirred at 23° C. for 24 h. The mixture was treated with a solution of HCl [4.0 M solution in 1,4-dioxane]. The mixture was concentrated in vacuo and the resulting solid was suspended in diethyl ether. The precipitate was collected by filtration and dried in vacuo to give 1-methyl-2-((methylamino)methyl)-1H-imidazole-4-carboxylic acid hydrochloride (80 mg, 38% yield) as a yellow solid.

¹H NMR (500 MHz, DMSO-d₆) δ ppm 9.34 (br. s., 2H), 7.91 (s, 1H), 4.29 (t, 2H), 3.71 (s, 3H), 2.64 (t, 3H).

Step 2: Synthesis of Compound I-376

The title compound was prepared following general procedure B, except 1-methyl-2-((methylamino)methyl)-1H-imidazole-4-carboxylic acid (as the HCl salt, 3 equiv.) was the amine reactant, 4 equivalents of triethylamine was used, and contents were heated to 80° C. as a solution in dioxane/water (4:1) for 24 h. The mixture was cooled to 23° C., diluted in ethyl acetate, and was washed with 1N HCl solution. The precipitate formed was collected by filtration and dried in vacuo to deliver the desired compound, Compound I-376 (26 mg, 37% yield) as a white solid.

¹H NMR (500 MHz, DMSO-d₆) δ ppm 9.10 (d, 1H), 8.39 (d, 1H), 8.11 (br. s., 1H), 7.56 (s, 1H), 7.28-7.39 (m, 1H), 7.18-7.26 (m, 2H), 7.07-7.14 (m, 1H), 6.82 (t, 1H), 5.91 (s, 2H), 5.08 (s, 2H), 3.85 (s, 3H), 3.41 (d, 3H).

Compound I-377

The title compound was prepared following general procedure B, except 3-(2-aminoethyl)benzoic acid was the amine reactant, 4 equivalents of triethylamine was used, and contents were heated to 90° C. as a solution in dioxane/water (3:1) for 24 h. Ethyl acetate was used as solvent during work up. The crude material was purified via silica gel chromatography, utilizing a 0-80% ethyl acetate/hexanes gradient to deliver the desired compound, Compound I-377 (25 mg, 31% yield) as a white solid.

¹H NMR (500 MHz, CDCl₃) δ ppm 8.44 (d, 1H), 8.17 (d, 1H), 8.04 (s, 1H), 7.98 (d, 1H), 7.50 (d, 1H), 7.40-7.45 (m, 1H), 7.37 (s, 1H), 7.14-7.21 (m, 1H), 7.00 (t, 1H), 6.92-6.97 (m, 1H), 6.85-6.92 (m, 1H), 6.64 (d, 1H), 5.99 (s, 2H), 5.24-5.31 (m, 1H), 3.90-3.97 (m, 2H), 3.08 (t, 2H).

Compound I-378

The title compound was prepared following general procedure B, except 5-hydroxy-1,2,3,6-tetrahydropyridine-4-carboxylate (as the TFA salt, 1 equiv.) was the amine reactant, 3 equivalents of triethylamine was used, and contents were heated to 70° C. as a solution in dioxane/water (3:1) for 24 h. Ethyl acetate was used as solvent during work up. The crude material was purified via silica gel chromatography, utilizing a 0-30% ethyl acetate/hexanes gradient to deliver the desired compound, Compound I-378 (68 mg, 15% yield) as a white solid.

¹H NMR (500 MHz, CDCl₃) δ ppm 12.17 (s, 1H), 8.46 (d, 1H), 8.23 (d, 1H), 7.31 (s, 1H), 7.16-7.22 (m, 1H), 7.02 (t, 1H), 6.96 (t, 1H), 6.84 (t, 1H), 6.62 (d, 1H), 5.98 (s, 2H), 4.47-4.50 (m, 2H), 4.26 (q, 2H), 3.94 (t, 2H), 2.51 (t, 2H), 1.33 (t, 3H).

Compound I-379

The title compound was prepared following general procedure B, except (1SR,2SR,3RS,4RS)-3-aminobicyclo[2.2.1]heptane-2-carboxylic acid (as the HCl salt, racemic, 3 equiv.) was the amine reactant, 6 equivalents of triethylamine was used, and contents were heated to 70° C. as a solution in dioxane/water (3:1) for 24 h. The reaction mixture was cooled, diluted with ethyl acetate, and washed with water. The organic layer was dried, filtered, and concentrated in vacuo. The crude material was purified via silica gel chromatography, utilizing a 0-80% ethyl acetate/hexanes gradient to deliver the desired compound, Compound I-379 (47 mg, 36% yield) as a white solid.

¹H NMR (500 MHz, CD₃OD) δ ppm 8.76-8.79 (m, 1H), 8.07 (d, 1H), 7.42 (s, 1H), 7.25-7.32 (m, 1H), 7.11 (ddd, 1H), 7.05 (td, 1H), 6.92 (d, 1H), 6.83 (td, 1H), 5.97 (s, 2H), 4.58-4.66 (m, 1H), 3.13 (ddd, 1H), 2.83 (br. s., 1H), 2.67 (br. s., 1H), 1.74 (d, 1H), 1.65-1.71 (m, 1H), 1.58-1.64 (m, 1H), 1.49-1.57 (m, 2H), 1.41-1.49 (m, 1H).

Compound I-380

The title compound was prepared following general procedure B, except (1S,3R)-3-aminocyclohexanecarboxylic acid (98% ee, 4 equiv.) was the amine reactant, 4 equivalents of triethylamine was used, and contents were heated to 80° C. as a solution in dioxane/water (3:1) for 24 h. Ethyl acetate was used as solvent during work up. The crude material was purified via silica gel chromatography, utilizing a 0-10% methanol/dichloromethane gradient to deliver the desired compound, Compound I-380 (70 mg, 55% yield) as a yellow solid.

$^1$H NMR (500 MHz, CD$_3$OD) δ ppm 8.81 (d, 1H), 8.18 (d, 1H), 7.59 (s, 1H), 7.29 (q, 1H), 7.07-7.14 (m, 1H), 7.05 (t, 1H), 6.98 (d, 1H), 6.92 (t, 1H), 6.00 (s, 2H), 4.46 (t, 1H), 2.59 (t, 1H), 2.31 (d, 1H), 2.04 (d, 2H), 1.95 (d, 1H), 1.51-1.65 (m, 2H), 1.35-1.51 (m, 2H).

Compound I-381

The title compound was synthesized in 3 steps:

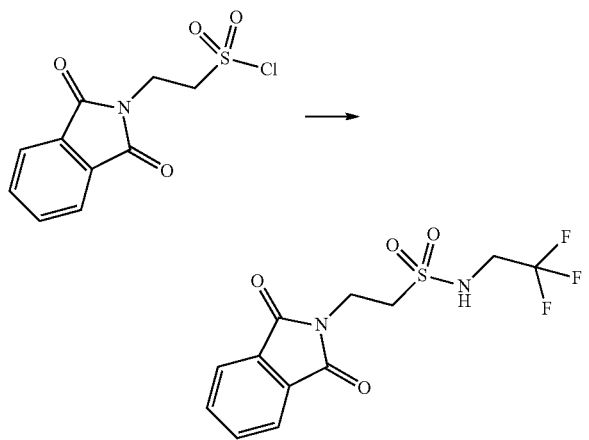

Step 1: Synthesis of 2-(1,3-dioxoisoindolin-2-yl)-N-(2,2,2-trifluoroethyl) Ethanesulfonamide A mixture of 2-[2-(Chlorosulfonyl)ethyl]benzo[c]azoline-1,3-dione (1 equiv.), 2,2,2-trifluoroethylamine hydrochloride (3 equiv.) and triethylamine (6 equiv.) in dichloromethane was stirred at 23° C. for 24 h. The mixture was diluted in dichloromethane and washed with 1N HCl solution. The organic layer was dried, filtered and evaporated to give a white solid The solid was purified via silica gel chromatography (0 to 100% ethyl acetate in hexanes) to give 2-(1,3-dioxoisoindolin-2-yl)-N-(2,2,2-trifluoroethyl)ethanesulfonamide (370 mg, 30% yield) as a white solid.

$^1$H NMR (500 MHz, DMSO-d$_6$) δ ppm 7.84-7.92 (m, 4H), 4.05-4.09 (m, 2H), 3.97-4.01 (m, 2H), 3.32 (s, 2H).

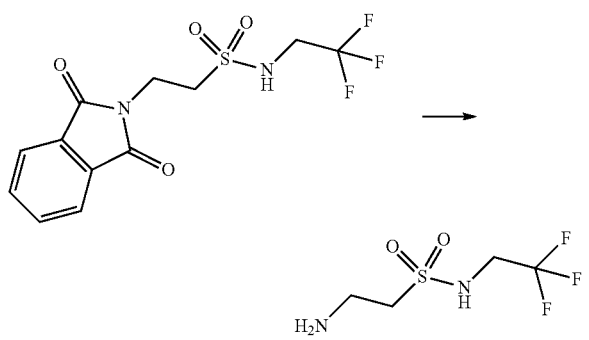

Step 2: Synthesis of 2-amino-N-(2,2,2-trifluoroethyl)ethanesulfonamide

A mixture of 2-(1,3-dioxoisoindolin-2-yl)-N-(2,2,2-trifluoroethyl)ethanesulfonamide (1 equiv.) and hydrazine monohydrate (1 equiv.) in ethanol was stirred at 80° C. for 24 h. The mixture was cooled to 23° C. and concentrated in vacuo. The resulting residue was treated with a minimal amount of methanol. The precipitate was collected by filtration and dried in vacuo to give a white solid containing 2-amino-N-(2,2,2-trifluoroethyl)ethanesulfonamide (136 mg). The material was used in the next reaction without further purification.

Step 3: Synthesis of Compound I-381

The title compound was prepared following general procedure B, except 2-amino-N-(2,2,2-trifluoroethyl)ethanesulfonamide (1 equiv.) was the amine reactant, 3 equivalents of triethylamine was used, and contents were heated to 80° C. as a solution in dioxane/water (3:1) for 24 h. The mixture was cooled, diluted in ethyl acetate, and washed with water. The organic layer was dried, filtered and evaporated to give an oil. The oil was purified via silica gel chromatography (0 to 70% ethyl acetate in hexanes gradient) to deliver the desired compound, Compound I-xxx (28 mg, 14% yield over step 2 and 3) as a white solid.

$^1$H NMR (500 MHz, DMSO-d$_6$) δ ppm 9.10 (d, 1H), 8.25 (d, 2H), 7.55 (s, 1H), 7.30-7.37 (m, 1H), 7.19-7.26 (m, 1H), 7.15 (d, 1H), 7.10 (t, 1H), 6.82 (t, 1H), 5.89 (s, 2H), 3.87-3.82 (m, 4H), 3.45 (t, 2H).

Compound I-382

The title compound was synthesized in 2 steps:

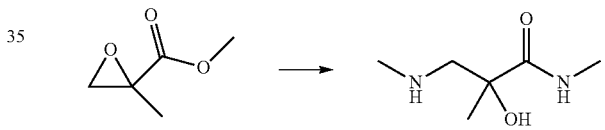

Step 1: Synthesis of 2-hydroxy-N-2-dimethyl-3-(methylamino)propanamide

In a sealed vial, a mixture of methyl 2-methylglycidate (1 equiv.) and methylamine [33 wt % in THF] (10 equiv.) was heated to 80° C. for 24 h. The mixture was concentrated under vacuum to give 2-hydroxy-N-2-dimethyl-3-(methylamino)propanamide (1.7 g, 100% yield) as a clear oil.

$^1$H NMR (500 MHz, CDCl$_3$) δ ppm 3.67-3.76 (m, 1H), 3.22-3.29 (m, 1H), 2.79-2.82 (m, 3H), 2.40-2.43 (m, 3H), 1.31-1.33 (m, 3H).

Step 2: Synthesis of Compound I-382

The title compound was prepared following general procedure B, except 2-hydroxy-N-2-dimethyl-3-(methylamino)propanamide (4 equiv.) was the amine reactant, 4 equivalents of triethylamine was used, and contents were heated to 80° C. as a solution in dioxane/water (3:1) for 4 h. Ethyl acetate was used as solvent during work up. The resulting solid was treated with a minimal amount of methanol and diethyl ether, collected by filtration, and dried in vacuo to deliver the desired compound, Compound I-382 (67 mg, 52% yield) as a white solid.

$^1$H NMR (500 MHz, DMSO-d$_6$) δ ppm 9.09-9.12 (m, 1H), 8.23 (d, 1H), 7.87 (q, 1H), 7.54 (s, 1H), 7.30-7.37 (m, 1H), 7.18-7.26 (m, 1H), 7.11 (td, 1H), 6.88 (t, 1H), 5.86-5.92 (m, 2H), 4.12 (d, 1H), 3.68 (d, 1H), 3.22 (s, 3H), 2.55 (d, 3H), 1.27 (s, 3H).

Compound I-383

The title compound was synthesized in 5 steps:

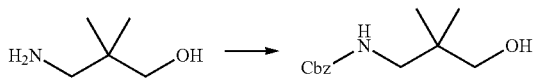

Step 1: Synthesis of Benzyl (3-hydroxy-2,2-dimethylpropyl) carbamate

To a cold mixture of 3-amino-2,2-dimethyl-1-propanol (1 equiv.) and triethylamine (1 equiv.) in dichloromethane was added benzyl chloroformate (1 equiv.). The mixture was stirred at 23° C. for 30 min, then diluted in dichloromethane and washed with 1N HCl solution. The organic layer was dried, filtered, and evaporated to give benzyl (3-hydroxy-2,2-dimethylpropyl)carbamate (1.9 g, 86% yield) as a white solid.

$^1$H NMR (500 MHz, CDCl$_3$) δ ppm 7.34-7.45 (m, 5H), 5.14 (s, 2H), 3.25 (d, 2H), 3.08 (d, 2H), 0.89 (s, 6H).

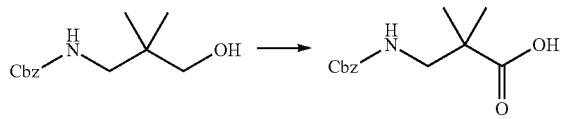 [SMILES: CC(C)(CO)CNC(=O)OCc1ccccc1 ; CC(C)(CNC(=O)OCc1ccccc1)C(=O)O]

Step 2: Synthesis of 3-(((benzyloxy)carbonyl)amino)-2,2-dimethylpropanoic acid

To a suspension of benzyl (3-hydroxy-2,2-dimethylpropyl)carbamate (1 equiv.) in CCl$_4$, water, and acetonitrile (1:1:1 mixture) were added sodium periodate (3 equiv.) and ruthenium (III) chloride (0.05 equiv.). The mixture was stirred at 23° C. for 24 h. To this mixture, additional amounts of sodium periodate (3 equiv.) and ruthenium(III) chloride (0.05 equiv.) were added, and contents stirred at 23° C. for 3 days. The mixture was diluted with water and extracted with ethyl acetate. The organic layer was extracted with saturated solution of sodium carbonate, then the aqueous layer was acidified to pH 1 and extracted with ethyl acetate. The organic layer was dried, filtered and evaporated to give an oil. The oil was purified via silica gel chromatography (0 to 100% ethyl acetate in hexanes gradient) to give 3-(((benzyloxy)carbonyl)amino)-2,2-dimethylpropanoic acid (943 mg, 45% yield) as a red colored oil.

$^1$H NMR (500 MHz, CDCl$_3$) δ ppm 7.35-7.42 (m, 5H), 5.12 (s, 2H), 3.35 (d, 2H), 1.23-1.28 (m, 6H).

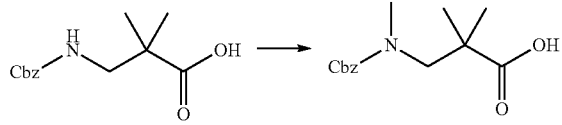 [SMILES: CC(C)(CNC(=O)OCc1ccccc1)C(=O)O ; CN(CC(C)(C)C(=O)O)C(=O)OCc1ccccc1]

Step 3: Synthesis of 3-(((benzyloxy)carbonyl)(methyl)amino)-2,2-dimethylpropanoic Acid To a cold solution of 3-(((benzyloxy)carbonyl)amino)-2,2-dimethylpropanoic acid (1 equiv.) in THF was added sodium hydride [60 wt % dispersion in mineral oil] (10 equiv.). The mixture was stirred at 0° C. for 30 min. To this mixture, was added methyl iodide (10 equiv.). The mixture was allowed to warm to 23° C. and stirred for 24 h. The mixture was poured over ice and acidified to pH 1. The mixture was extracted with diethyl ether, and the organic layer was dried, filtered, and evaporated to give an oil. The oil was purified via silica gel chromatography (0 to 80% ethyl acetate in hexanes gradient) to give 3-(((benzyloxy)carbonyl)(methyl)amino)-2,2-dimethylpropanoic acid (686 mg, 69% yield) as a clear oil.

$^1$H NMR (500 MHz, CDCl$_3$) δ ppm 7.36-7.39 (m, 4H), 7.32-7.35 (m, 1H), 5.13 (s, 2H), 3.53-3.60 (m, 2H), 2.96 (br. s., 3H), 1.18-1.26 (m, 6H).

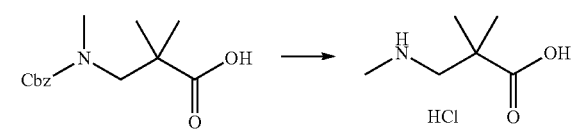

Step 4: Synthesis of 2,2-dimethyl-3-(methylamino)propanoic Acid Hydrochloride

A solution containing 3-(((benzyloxy)carbonyl)(methyl)amino)-2,2-dimethylpropanoic acid (1 equiv.) in methanol was hydrogenated using the H-cube (0.7 ml/min, catalyst: 10% Pd/C, 70° C.). The resulting mixture was treated with a solution of HCl [1.25 M in ethanol] and concentrated under vacuum to give 2,2-dimethyl-3-(methylamino)propanoic acid hydrochloride (569 mg, 100% yield) as a clear oil.

$^1$H NMR (500 MHz, CD$_3$OD) δ ppm 3.09 (s, 2H), 2.69-2.74 (m, 3H), 1.25-1.31 (m, 6H).

Step 5: Synthesis of Compound I-383

The title compound was prepared following general procedure B, except 2,2-dimethyl-3-(methylamino)propanoic acid (as the HCl salt, 4 equiv.) was the amine reactant, 8 equivalents of triethylamine was used, and contents were heated to 80° C. as a solution in dioxane/water (3:1) for 24 h. Ethyl acetate was used as solvent during work up. The crude material was purified via silica gel chromatography (0 to 60% ethyl acetate in hexanes gradient) to deliver the desired compound, Compound I-383 (38 mg, 30% yield) as a white solid.

$^1$H NMR (500 MHz, DMSO-d$_6$) δ ppm 12.51 (br. s., 1H), 9.10 (d, 1H), 8.25 (d, 1H), 7.49 (s, 1H), 7.30-7.37 (m, 1H), 7.18-7.25 (m, 2H), 7.11 (td, 1H), 6.92 (t, 1H), 5.88 (s, 2H), 3.96 (s, 2H), 3.33 (s, 3H), 1.13 (s, 6H).

Compound I-384

The title compound was prepared following general procedure B, except (1RS,2SR,3RS,4SR)-3-amino-7-oxabicyclo[2.2.1]heptane-2-carboxylic acid (i.e. racemic, 4 equiv.) was the amine reactant, 4 equivalents of triethylamine was used, and contents were heated to 80° C. as a solution in dioxane/water (3:1) for 24 h. Ethyl acetate was used as solvent during work up. The resulting solid was rinsed with methanol and diethyl ether, collected by filtration, and dried in vacuo to deliver the desired compound, Compound I-384 (43 mg, 33% yield) as a white solid.

$^1$H NMR (500 MHz, DMSO-d$_6$) δ ppm 12.40 (br. s., 1H), 9.10 (d, 1H), 8.23 (d, 1H), 7.54 (s, 1H), 7.30-7.36 (m, 1H), 7.20-7.25 (m, 2H), 7.09-7.13 (m, 1H), 6.94 (d, 1H), 6.83-6.87 (m, 1H), 5.89 (s, 2H), 4.86 (t, 1H), 4.72 (d, 1H), 4.47 (d, 1H), 3.10 (d, 1H), 1.53-1.68 (m, 4H).

Compound I-436

The title compound was prepared following general procedure B, except 2-aminoethanesulfonamide was the amine reactant, 3 equivalents of triethylamine was used, and contents were heated to 65° C. for 24 h as a solution in dioxane. The mixture was diluted in ethyl acetate and washed with saturated ammonium chloride solution. The organic layer was dried, filtered and evaporated to give a solid. The solid was purified via silica gel chromatography (0-100% ethyl acetate in hexanes gradient) to deliver the desired compound, Compound I-436 (26 mg, 42% yield) as a white solid.

$^1$H NMR (500 MHz, CD$_3$OD) δ ppm 8.77 (d, 1H), 8.12 (d, 1H), 7.50 (s, 1H), 7.25-7.32 (m, 1H), 7.03-7.14 (m, 2H), 6.90 (d, 1H), 6.82-6.88 (m, 1H), 5.98 (s, 2H), 4.07-4.15 (m, 5H), 3.47 (t, 2H).

Compound I-385

To a solution of acetic acid (10 equiv.) in DMF was added CDI (10 equiv.). The mixture was stirred at 45° C. for 30 min. To this mixture was added Compound I-436 and DBU (10 equiv.). The mixture was stirred at 23° C. for 3 d. The mixture was diluted in ethyl acetate and washed with 1N HCl solution. The organic layer was dried, filtered and evaporated to give an oil. The oil was purified by silica gel chromatography (0 to 10% methanol in dichloromethane gradient) to deliver the desired compound, Compound I-385 (8.2 mg, 25% yield) as a white solid.

$^1$H NMR (500 MHz, DMSO-d$_6$) δ ppm 9.10 (d, 1H), 8.24 (d, 1H), 7.55 (s, 1H), 7.30-7.37 (m, 1H), 7.17-7.26 (m, 2H), 7.11 (t, 1H), 6.86 (t, 1H), 5.90 (s, 2H), 3.75-3.87 (m, 4H), 1.99 (s, 3H).

Compound I-387

The title compound was synthesized in 3 steps:

Step 1: Synthesis of Tert-Butyl (1-(5-fluoro-2-(1-(2-fluorobenzyl)-5-(isoxazol-3-yl)-1H-pyrazol-3-yl)pyrimidin-4-yl)azetidin-3-yl)carbamate (Compound I-21)

The intermediate was prepared following general procedure B, except 3-(tert-butoxycarbonylamino)azetidine was the amine reactant, 3 equivalents of triethylamine was used, and contents were heated to 80° C. as a solution in dioxane/water (3:1) for 24 h. Ethyl acetate was used as solvent during work up. The organic layer was dried, filtered, and concentrated in vacuo to deliver the desired intermediate, tert-butyl (1-(5-fluoro-2-(1-(2-fluorobenzyl)-5-(isoxazol-3-yl)-1H-pyrazol-3-yl)pyrimidin-4-yl)azetidin-3-yl)carbamate (480 mg, 100% yield) as a white solid.

$^1$H NMR (500 MHz, DMSO-d$_6$) δ ppm 9.09 (d, 1H), 8.28 (d, 1H), 7.65 (d, 1H), 7.53 (s, 1H), 7.29-7.35 (m, 1H), 7.20-7.25 (m, 2H), 7.08-7.12 (m, 1H), 6.81 (t, 1H), 5.91 (s, 2H), 4.49 (br. s., 3H), 4.12 (br. s., 2H), 1.40 (s, 9H).

Step 2: Synthesis of 1-(5-fluoro-2-(1-(2-fluorobenzyl)-5-(isoxazol-3-yl)-1H-pyrazol-3-yl)pyrimidin-4-yl)azetidin-3-amine (Compound I-40)

A mixture of tert-butyl (1-(5-fluoro-2-(1-(2-fluorobenzyl)-5-(isoxazol-3-yl)-1H-pyrazol-3-yl)pyrimidin-4-yl)azetidin-3-yl)carbamate (1 equiv.) and TFA (10 equiv.) in dichloromethane was stirred at 23° C. for 24 h. The mixture was concentrated in vacuo. The resulting oil was treated with saturated solution of sodium bicarbonate and extracted with ethyl acetate. The precipitate formed was collected and dried in vacuo. The organic layer was also dried, filtered, and evaporated to give 1-(5-fluoro-2-(1-(2-fluorobenzyl)-5-(isoxazol-3-yl)-1H-pyrazol-3-yl)pyrimidin-4-yl)azetidin-3-amine (116 mg (combined), 36% yield) as a white solid.

$^1$H NMR (500 MHz, CD$_3$OD) δ ppm 8.81-8.83 (m, 1H) 8.32 (d, 1H) 7.52-7.55 (m, 1H) 7.27-7.34 (m, 1H) 7.02-7.14 (m, 2H) 6.89-6.95 (m, 2H) 6.00 (s, 2H) 4.84-4.88 (m, 2H) 4.55 (d, 2H) 4.35-4.42 (m, 1H).

Step 3: Synthesis of Compound I-387

To a white suspension containing 1-(5-fluoro-2-(1-(2-fluorobenzyl)-5-(isoxazol-3-yl)-1H-pyrazol-3-yl)pyrimidin-4-yl)azetidin-3-amine (1 equiv.) and pyridine (10 equiv.) in THF was added trifluoromethane sulfonic anhydride (2 equiv.). The mixture was stirred at 23° C. for 30 min. The mixture was diluted with ethyl acetate and washed with 1 N HCl solution. The organic layer was dried, filtered and evaporated to give an oil. The oil was purified via silica gel chromatography (0 to 80% ethyl acetate in hexanes gradient) to deliver the desired compound, Compound I-387 (61 mg, 48% yield) as a white solid.

$^1$H NMR (500 MHz, DMSO-d$_6$) δ ppm 10.10 (d, 1H), 9.08 (d, 1H), 8.30 (d, 1H), 7.52 (s, 1H), 7.30-7.36 (m, 1H), 7.16-7.27 (m, 2H), 7.10 (t, 1H), 6.81 (t, 1H), 5.90 (s, 2H), 4.71-4.83 (m, 1H), 4.52-4.63 (m, 2H), 4.27 (dd, 2H).

Compound I-388

To a cold suspension of 1-(5-fluoro-2-(1-(2-fluorobenzyl)-5-(isoxazol-3-yl)-1H-pyrazol-3-yl)pyrimidin-4-yl)azetidin-3-amine (generated in step 2 of procedure toward Compound I-387 1 equiv.) and pyridine (4 equiv.) in dichloromethane at −78° C. was added trifluoromethane sulfonic anhydride (2 equiv.). The mixture was stirred at −78° C. for 2 h. Then, it was removed from the dry ice-acetone bath and warmed to 23° C. The stirring was continued at 23° C. for an additional 1 h. The mixture was quenched with methanol, and concentrated in vacuo. The residue was dissolved in ethyl acetate and washed with 1N HCl solution. The organic layer was dried, filtered and evaporated to give an oil. The oil was purified via silica gel chromatography (0 to 100% ethyl acetate in hexanes gradient), and the isolated material was recrystallized from a diethyl ether and methanol mixture to deliver the desired compound, Compound I-388 (90 mg, 19% yield) as a light yellow solid.

$^1$H NMR (500 MHz, DMSO-d$_6$) δ ppm 9.10 (d, 1H), 8.35 (br. s., 1H), 7.57 (br. s., 1H), 7.31-7.37 (m, 1H), 7.19-7.28 (m, 2H), 7.11 (t, 1H), 6.82 (t, 1H), 5.92 (s, 2H), 4.67 (br. s., 2H), 4.61 (br. s., 1H), 4.22 (br. s., 2H).

Compound I-389

The title compound was synthesized in 2 steps:

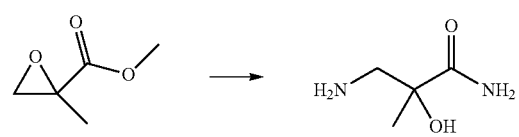

Step 1: Synthesis of 3-amino-2-hydroxy-2-methylpropanamide

A mixture of ammonia [7M in methanol] (20 equiv.) and methyl 2-methylglycidate (1 equiv.) was stirred in a sealed vial at 80° C. for 24 h. The mixture was concentrated in vacuo to give 3-amino-2-hydroxy-2-methylpropanamide (731 mg, 100% yield) as a clear oil which turned into a white solid upon standing at 23° C.

$^1$H NMR (500 MHz, CD$_3$OD) δ ppm 2.90-2.96 (m, 1H) 2.60-2.66 (m, 1H) 1.32-1.35 (m, 3H).

Step 2: Synthesis of Compound I-389

The title compound was prepared following general procedure B, except 3-amino-2-hydroxy-2-methylpropanamide (4 equiv.) was the amine reactant, 4 equivalents of triethylamine was used, and contents were heated to 80° C. as a solution in dioxane/water (3:1) for 24 h. The mixture was diluted in ethyl acetate and washed with water. The organic layer was dried, filtered and evaporated to give a solid. The solid was purified via silica gel chromatography (0 to 5% methanol in dichloromethane gradient) to deliver the desired compound, Compound I-389 (78 mg, 25% yield) as a white solid.

$^1$H NMR (500 MHz, DMSO-d$_6$) δ ppm 8.23 (d, 1H), 7.50 (s, 1H), 7.30-7.35 (m, 2H), 7.27 (t, 1H), 7.25-7.29 (m, 1H), 7.20-7.24 (m, 3H), 7.10 (td, 1H), 6.86 (t, 1H), 5.94 (s, 1H), 5.89 (s, 2H), 3.75 (dd, 1H), 3.59 (dd, 1H), 1.28 (s, 3H).

Compound I-390

The title compound was prepared following general procedure B, except tert-butyl N-(2-aminoethyl)carbamate (4 equiv.) was the amine reactant, 4 equivalents of triethylamine was used, and contents were heated to 85° C. as a solution in dioxane/water (3:1) for 3 h. Ethyl acetate was used as solvent during work up. The organic layers were dried, filtered, and concentrated in vacuo to deliver the desired compound, Compound I-390 (200 mg, 75% yield) as a white solid.

$^1$H NMR (500 MHz, DMSO-$d_6$) δ ppm 9.13 (s, 1H), 8.30 (d, 1H), 7.71 (s, 1H), 7.31-7.37 (m, 1H), 7.19-7.26 (m, 2H), 7.11 (t, 1H), 6.98 (t, 1H), 6.86 (t, 1H), 5.92 (s, 2H), 3.50-3.59 (m, 3H), 3.25 (q, 2H), 1.31-1.37 (m, 9H).

Compound I-391

A mixture of Compound I-390 (1 equiv.) and HCl [4.0 M in 1,4-dioxane] (50 equiv.) was stirred at 23° C. for 24 h. The mixture was concentrated in vacuo to deliver the desired compound, Compound I-391 (as the HCl salt, 157 mg, 100% yield) as a white solid.

$^1$H NMR (500 MHz, DMSO-$d_6$) δ ppm 9.11 (s, 1H), 8.31 (br. s., 1H), 7.73 (br. s., 1H), 7.26-7.38 (m, 2H), 7.21-7.26 (m, 1H), 7.11 (t, 1H), 6.83 (t, 1H), 5.91 (s, 2H), 3.74 (br. s., 2H), 3.07-3.15 (m, 2H).

Compound I-392

A mixture containing Compound I-391 (1 equiv.), DBU (2.0 equiv.), triethylamine (2 equiv.) and N-phenyl-bis(trifluoromethanesulfonimide) (1.2 equiv.) in acetonitrile was stirred at 23° C. for 24 h. The mixture was concentrated in vacuo. The resulting residue was diluted in ethyl acetate and washed with water. The organic layer was dried, filtered and evaporated to give an oil. The oil was purified by silica gel chromatography (0 to 100% ethyl acetate in hexanes gradient). Recrystallization of the purified material delivered the desired compound, Compound I-392 (123 mg, 19% yield) as a white solid.

$^1$H NMR (500 MHz, DMSO-$d_6$) δ ppm 9.56 (s, 1H), 9.11 (d, 1H), 8.22 (d, 1H), 7.87 (t, 1H), 7.51 (s, 1H), 7.30-7.35 (m, 1H), 7.20-7.24 (m, 1H), 7.08-7.13 (m, 2H), 6.83-6.87 (m, 1H), 5.89 (s, 2H), 3.60 (q, 2H), 3.46 (d, 2H).

Compound I-393

The title compound was synthesized in 3 steps:

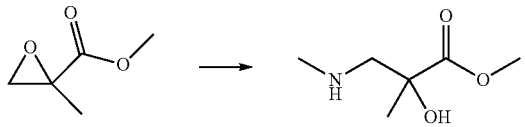

Step 1: Synthesis of Methyl 2-hydroxy-2-methyl-3-(methylamino)propanoate

A mixture of methanamine [2.0 M in THF] (1.3 equiv) and methyl 2-methylglycidate (1 equiv.) in ethanol was heated to 80° C. for 24 h. The mixture was concentrated to give methyl 2-hydroxy-2-methyl-3-(methylamino)propanoate (2.26 g) as a clear oil. The mixture was taken onto the next step without further purification.

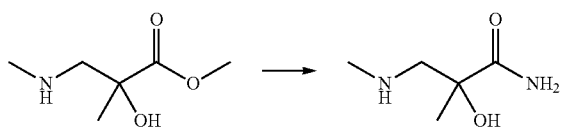

Step 2: Synthesis of 2-hydroxy-2-methyl-3-(methylamino)propanamide

A mixture of methyl 2-hydroxy-2-methyl-3-(methylamino)propanoate (1 equiv.) and ammonia [7.0 M in methanol] (5 equiv.) was heated to 85° C. in a sealed vial for 24 h. The mixture was concentrated to give 2-hydroxy-2-methyl-3-(methylamino)propanamide as a thick oil. The material was used in the next reaction without further purification.

Step 3: Synthesis of Compound I-393

The title compound was prepared following general procedure B, except 2-hydroxy-2-methyl-3-(methylamino)propanamide (4 equiv.) was the amine reactant, 4 equivalents of triethylamine was used, and contents were heated to 85° C. as a solution in dioxane/water (3:1) for 24 h. The mixture was cooled to 23° C. and the white precipitate formed was collected by filtration, rinsed with diethyl ether and dried in vacuo to deliver the desired compound, Compound I-393 (45 mg, 11% yield over step 3) as a white solid.

$^1$H NMR (500 MHz, DMSO-$d_6$) δ ppm 9.09 (d, 1H), 8.21 (d, 1H), 7.52 (s, 1H), 7.27-7.36 (m, 2H), 7.19-7.26 (m, 1H), 7.10 (t, 1H), 6.88 (t, 1H), 5.88 (s, 2H), 4.11 (d, 1H), 3.72 (d, 1H), 3.26 (d, 3H), 1.25 (s, 3H).

Compound I-394

The title compound was synthesized in 3 steps:

Step 1: Synthesis of Tert-Butyl 3-((5-fluoro-2-(1-(2-fluorobenzyl)-5-(isoxazol-3-yl)-1H-pyrazol-3-yl)pyrimidin-4-yl)amino)azetidine-1-carboxylate The intermediate was prepared following general procedure B, except tert-butyl 3-aminoazetidine-1-carboxylate (4 equiv.) was the amine reactant, 4 equivalents of triethylamine was used, and contents were heated to 80° C. as a solution in dioxane/water (3:1) for 24 h. Ethyl acetate was used as solvent during work up. The organic layer was dried, filtered and evaporated to give tert-butyl 3-((5-fluoro-2-(1-(2-fluorobenzyl)-5-(isoxazol-3-yl)-1H-pyrazol-3-yl)pyrimidin-4-yl)amino)azetidine-1-carboxylate (505 mg, 100% yield) as a white solid.

$^1$H NMR (500 MHz, DMSO-$d_6$) δ ppm 9.10 (d, 1H), 8.45 (br. s., 1H), 8.36 (d, 1H), 8.27 (d, 1H), 7.53-7.57 (m, 1H), 7.30-7.37 (m, 1H), 7.19-7.28 (m, 1H), 7.11 (t, 1H), 6.83-6.91 (m, 1H), 5.90 (s, 2H), 4.81-4.90 (m, 1H), 4.21 (br. s., 2H), 3.92 (dd, 2H), 1.36-1.41 (m, 9H).

Step 2: Synthesis of N-(azetidin-3-yl)-5-fluoro-2-(1-(2-fluorobenzyl)-5-(isoxazol-3-yl)-1H-pyrazol-3-yl)pyrimidin-4-amine Hydrochloride A mixture of tert-butyl 3-((5-fluoro-2-(1-(2-fluorobenzyl)-5-(isoxazol-3-yl)-1H-pyrazol-3-yl) pyrimidin-4-yl)amino)azetidine-1-carboxylate (1 equiv.) and hydrogen chloride [4.0 M in 1,4-dioxane] (10 equiv.) was stirred at 23° C. for 4 h. The mixture was concentrated in vacuo to give N-(azetidin-3-yl)-5-fluoro-2-(1-(2-fluorobenzyl) 5-(isoxazol-3-yl)-1H-pyrazol-3-yl)pyrimidin-4-amine (as the HCl salt, 450 mg, 100% yield) as a white solid.

$^1$H NMR (500 MHz, DMSO-$d_6$) δ ppm 9.13-9.16 (m, 1H), 8.40-8.49 (m, 1H), 7.62-7.70 (m, 1H), 7.32-7.39 (m, 1H), 7.28 (dd, 1H), 7.21-7.25 (m, 1H), 7.12 (td, 1H), 6.89 (t, 1H), 5.93 (s, 2H), 4.95-5.02 (m, 1H), 4.26-4.35 (m, 3H), 4.17-4.25 (m, 2H).

Step 3: Synthesis of Compound I-394

To a cold mixture of N-(azetidin-3-yl)-5-fluoro-2-(1-(2-fluorobenzyl)-5-(isoxazol-3-yl)-1H-pyrazol-3-yl)pyrimidin-4-amine hydrochloride (1 equiv.), triethylamine (3 equiv.) and pyridine (245 μl, 3 equiv.) in dichloromethane at -78° C. was added trifluoromethanesulfonic anhydride (4 equiv.). The mixture was stirred at -78° C. for 2 h before it was warmed up to 23° C. Then, the mixture was treated with 1N HCl solution and extracted with ethyl acetate. The organic layer was dried, filtered, and evaporated to give an oil. The oil was purified via silica gel chromatography (0 to 30% ethyl acetate in hexanes gradient) to deliver the desired compound, Compound I-394 (90 mg, 16% yield) as a white solid.

$^1$H NMR (500 MHz, CD$_3$OD) δ ppm 8.83 (d, 1H), 8.32 (d, 1H), 7.62 (s, 1H), 7.29-7.34 (m, 1H), 7.05-7.13 (m, 2H), 6.96-7.00 (m, 2H), 6.03 (s, 2H), 4.98 (br. s., 2H), 4.74-4.83 (m, 1H), 4.53 (br. s., 2H).

Compound I-395

The title compound was prepared following general procedure B, except (1R,2S)-(+)-cis-1-amino-2-indanol (4 equiv.) was the amine reactant, 4 equivalents of triethylamine was used, and contents were heated to 80° C. as a solution in dioxane/water (3:1) for 3 h. Ethyl acetate was used as solvent during work up. The crude material was purified via silica gel chromatography utilizing a 0-50% ethyl acetate/hexanes gradient to deliver the desired compound, Compound I-395 (4 mg, 27% yield) as a cream colored solid.

$^1$H NMR (500 MHz, DMSO-d$_6$) δ ppm 9.07 (d, 1H), 8.28 (d, 1H), 7.55 (s, 1H), 7.30-7.37 (m, 2H), 7.26-7.29 (m, 1H), 7.13-7.25 (m, 5H), 7.10 (td, 1H), 6.80-6.87 (m, 1H), 5.89 (s, 2H), 5.75 (dd, 1H), 5.27 (d, 1H), 4.60 (d, 1H), 3.15 (dd, 1H), 2.93 (dd, 1H).

Compound I-396

The title compound was prepared following general procedure B, except 3-(trifluoromethyl)azetidin-3-ol (3 equiv.) was the amine reactant, 3 equivalents of triethylamine was used, and contents were heated to 80° C. as a solution in dioxane/water (3:1) for 3 h. Ethyl acetate was used as solvent during work up. The organic layer was dried, filtered, and concentrated in vacuo to yield a solid, which was rinsed with minimal amounts of methanol and diethyl ether and dried in vacuo to deliver the desired compound, Compound I-396 (57 mg, 45% yield) as a white solid.

$^1$H NMR (500 MHz, DMSO-d$_6$) δ ppm 9.09 (d, 1H), 8.37 (d, 1H), 7.57 (s, 2H), 7.30-7.36 (m, 1H), 7.19-7.26 (m, 2H), 7.10 (td, 1H), 6.82 (t, 1H), 5.91 (s, 2H), 4.52 (d, 2H), 4.30 (d, 2H).

Compound I-397

The title compound was prepared following general procedure B, except 4-(aminomethyl)tetrahydro-2H-pyran-4-ol (3 equiv.) was the amine reactant, 3 equivalents of triethylamine was used, and contents were heated to 80° C. as a solution in dioxane/water (3:1) for 24 h. Ethyl acetate was used as solvent during work up. The organic layer was dried, filtered, and concentrated in vacuo to deliver the desired compound, Compound I-397 (30 mg, 24% yield) as a white solid.

$^1$H NMR (500 MHz, CD$_3$OD) δ ppm 8.80 (d, 1H), 8.20 (d, 1H), 7.57 (s, 1H), 7.24-7.32 (m, 1H), 7.02-7.13 (m, 2H), 6.87-6.97 (m, 2H), 5.99 (s, 2H), 3.74-3.80 (m, 6H), 1.76-1.85 (m, 2H), 1.59 (d, 2H).

Compound I-398

The title compound was prepared following general procedure B, except 2-amino-4,4-difluorobutanoic acid (3 equiv.) was the amine reactant, 3 equivalents of triethylamine was used, and contents were heated to 80° C. as a solution in dioxane/water (4:1) for 24 h. Ethyl acetate was used as solvent during work up. The organic layer was dried, filtered, and concentrated in vacuo to yield a solid, which was rinsed with minimal amounts of methanol and diethyl ether and dried in vacuo to deliver the desired compound, Compound I-398 (123 mg, 52% yield) as a white solid.

$^1$H NMR (500 MHz, DMSO-d$_6$) δ ppm 9.10 (d, 1H), 8.29 (d, 1H), 8.12 (d, 1H), 7.42 (s, 1H), 7.32 (d, 1H), 7.18-7.24 (m, 1H), 7.16 (d, 1H), 7.10 (t, 1H), 6.85 (t, 1H), 6.09-6.37 (m, 2H), 5.87 (s, 2H), 4.85 (d, 1H), 4.04 (s, 1H).

Compound I-399

To a suspension of Compound I-398 (1 equiv.) in THF was added lithium aluminum hydride [1.0 M solution in THF] (3 equiv.). The mixture was stirred at 23° C. for an additional 24 h. The mixture was quenched with water, followed by 15% NaOH solution followed by water. The mixture was diluted with ethyl acetate and washed with 1N HCl solution. The organic layer was dried, filtered, and evaporated to give an oil. The oil was purified via silica gel chromatography (0 to 100% ethyl acetate in hexanes gradient) to deliver the desired compound, Compound I-399 (23 mg, 12% yield) as a white solid.

$^1$H NMR (500 MHz, CD$_3$OD) δ ppm 8.75 (d, 1H), 8.08 (d, 1H), 7.43 (s, 1H), 7.23-7.30 (m, 1H), 7.06-7.12 (m, 1H), 7.03 (t, 1H), 6.87-6.89 (m, 1H), 6.81 (t, 1H), 6.05-6.21 (m, 1H), 5.93-5.98 (m, 2H), 4.71 (dq, 1H), 3.63-3.75 (m, 2H), 2.18-2.35 (m, 2H).

Compound I-400

A mixture of 2,2-bis(trifluoromethyl)-2-hydroxyacetic acid (1.5 equiv.) and CDI (1.5 equiv.) in THF was heated to reflux for 2 h. To this mixture was added 2-(1-(2-fluorobenzyl)-5-(is oxazol-3-yl)-1H-pyrazol-3-yl)pyrimidin-4-amine (Intermediate previous described in patent application publication WO2012/3405 A1) (1 equiv.) in one portion. The mixture was heated to reflux for 3 h. Then, it was cooled to 23° C., diluted in ethyl acetate and washed with 1N HCl solution. The organic layer was dried, filtered and evaporated to give an oil. The oil was purified by silica gel chromatography (0 to 80% ethyl acetate in hexanes gradient) to deliver the desired compound, Compound I-400 (111 mg, 35% yield) as a white solid.

$^1$H NMR (500 MHz, CD$_3$OD) δ ppm 8.79-8.82 (m, 1H), 8.75-8.77 (m, 1H), 8.07-8.10 (m, 1H), 7.54-7.56 (m, 1H), 7.22-7.31 (m, 1H), 6.99-7.12 (m, 2H), 6.86-6.93 (m, 2H), 5.95-6.00 (m, 2H).

Compound I-401

The title compound was synthesized in 2 steps:

Step 1: Synthesis of (S)-4-((5-fluoro-2-(1-(2-fluorobenzyl)-5-(isoxazol-3-yl)-1H-pyrazol-3-yl)pyrimidin-4-yl)amino)-5-methoxy-5-oxopentanoic Acid The intermediate was prepared following general procedure B, except L-glutamate methyl ester (4 equiv.) was the amine reactant, 4 equivalents of triethylamine was used, and contents were heated to 80° C. as a solution in dioxane/water (3:1) for 24 h. The mixture was concentrated under vacuum. The resulting solid was rinsed with diethyl ether and water, and collected by filtration and dried in vacuo to give (S)-4-((5-fluoro-2-(1-(2-fluorobenzyl)-5-(isoxazol-3-yl)-1H-pyrazol-3-yl) pyrimidin-4-yl)amino)-5-methoxy-5-oxopentanoic acid (274 mg, 69% yield) as a yellow solid.

$^1$H NMR (500 MHz, CD$_3$OD) δ ppm 8.76-8.78 (m, 1H) 8.15 (d, 1H) 7.37 (s, 1H) 7.23-7.31 (m, 2H) 6.99-7.13 (m, 2H) 6.84 (t, 1H) 5.94-5.99 (m, 2H) 3.73 (s, 1H) 3.34 (s, 3H) 2.29-2.43 (m, 2H) 2.12-2.24 (m, 2H).

Step 2: Synthesis of Compound I-401

To a solution of (S)-4-((5-fluoro-2-(1-(2-fluorobenzyl)-5-(isoxazol-3-yl)-1H-pyrazol-3-yl)pyrimidin-4-yl)amino)-5-methoxy-5-oxopentanoic acid (1 equiv.) in THF were added oxalyl chloride (1.5 equiv.) and a drop of DMF. The mixture was stirred at 23° C. for 30 min. Then, it was heated to reflux for 30 min. The mixture was cooled to 23° C., diluted with ethyl acetate, and washed with 1N HCl solution. The organic layer was dried, filtered, and evaporated to give an oil. The oil was purified by silica gel chromatography (0 to 50% ethyl acetate in hexanes gradient) to deliver the desired compound, Compound I-401 (81 mg, 33% yield) as a light yellow solid.

$^1$H NMR (500 MHz, CD$_3$OD) δ ppm 8.76-8.78 (m, 1H), 8.71-8.74 (m, 1H), 7.32-7.35 (m, 1H), 7.23-7.30 (m, 1H), 7.06-7.12 (m, 1H), 7.00-7.05 (m, 1H), 6.81-6.90 (m, 2H), 5.94 (s, 2H), 5.10 (dd, 1H), 3.75 (s, 3H), 2.59-2.80 (m, 3H), 2.23-2.33 (m, 1H).

Compound I-403

The title compound was prepared following general procedure B, except 2-amino-3,3,3-trifluoropropanoic acid (3 equiv.) was the amine reactant, 3 equivalents of triethylamine was used, and contents were heated to 70° C. for 24 h as a solution in dioxane/water (3:1). Ethyl acetate was used as solvent during work up. The organic layer was dried, filtered, and concentrated in vacuo to yield a solid, which was rinsed with minimal amounts of methanol and diethyl ether and dried in vacuo to deliver the desired compound, Compound I-403 (71 mg, 17% yield) as a yellow solid.

$^1$H NMR (500 MHz, CD$_3$OD) δ ppm 8.76 (d, 1H), 8.27 (d, 1H), 7.48-7.51 (m, 1H), 7.24-7.31 (m, 1H), 7.07-7.13 (m, 1H), 7.00-7.06 (m, 1H), 6.92 (d, 1H), 6.80 (t, 1H), 6.10-6.16 (m, 1H), 5.98 (s, 2H).

Compound I-404

To a suspension of Compound I-403 (1 equiv.) in THF was added lithium aluminum hydride [1.0 M solution in THF] (2 equiv.). The mixture was stirred at 23° C. for 1 h. The mixture was quenched with water, followed by 15% NaOH solution followed by water. The mixture was diluted with ethyl acetate and washed with 1N HCl solution. The organic layer was dried, filtered, and evaporated to give a solid. The solid was purified via silica gel chromatography (0 to 50% ethyl acetate in hexanes gradient) to deliver the desired compound, Compound I-404 (19 mg, 12% yield) as a white solid.

$^1$H NMR (500 MHz, CD$_3$OD) δ ppm 8.75-8.77 (m, 1H), 8.21 (d, 1H), 7.46-7.48 (m, 1H), 7.24-7.31 (m, 1H), 7.06-7.14 (m, 1H), 7.03 (t, 1H), 6.89-6.94 (m, 1H), 6.79 (t, 1H), 5.97 (d, 2H), 5.47-5.54 (m, 1H), 3.87-4.01 (m, 2H).

Compound I-405

The title compound was synthesized in 3 steps:

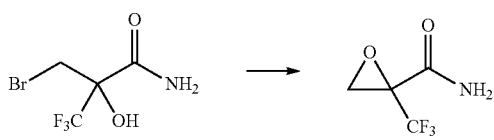

Step 1: Synthesis of 2-(trifluoromethyl)oxirane-2-carboxamide

To a solution of 2-(bromomethyl)-3,3,3-trifluoro-2-hydroxypropanamide (1 equiv.) in acetone was added potassium carbonate (2 equiv.). The mixture was heated to reflux for 2 h. The mixture was concentrated under in vacuo. The resulting residue was diluted with water and extracted with ethyl acetate. The organic layer was dried, filtered and evaporated to give 2-(trifluoromethyl)oxirane-2-carboxamide (1.44 g 76% yield) as a yellow gum.

$^1$H NMR (500 MHz, CD$_3$OD) δ ppm 3.17 (dd, 2H).

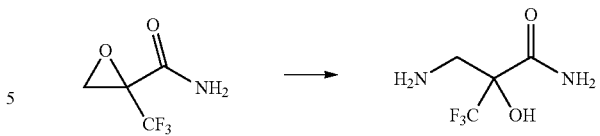

Step 2: Synthesis of 2-(aminomethyl)-3,3,3-trifluoro-2-hydroxypropanamide

A mixture of ammonia [7M in methanol] (10 equiv.) and 2-(trifluoromethyl)oxirane-2-carboxamide (1 equiv.) was stirred in a sealed vial at 80° C. for 24 h. The mixture was concentrated in vacuo to give 2-(aminomethyl)-3,3,3-trifluoro-2-hydroxypropanamide (1.3 g, 84% yield) as a brown gum.

$^1$H NMR (500 MHz, DMSO-d$_6$) δ 3.01-3.11 (m, 1H), 2.84 (d, 1H).

Step 3: Synthesis of Compound I-405

The title compound was prepared following general procedure B, except 2-(aminomethyl)-3,3,3-trifluoro-2-hydroxypropanamide (4 equiv.) was the amine reactant, 4 equivalents of triethylamine was used, and contents were heated to 90° C. for 24 h as a solution in dioxane/water (3:1). The mixture was diluted in ethyl acetate and washed with water. The organic layer was dried, filtered and evaporated to give a solid. The solid was purified via silica gel chromatography (0 to 80% ethyl acetate in hexanes gradient) to deliver the desired compound, Compound I-405 (262 mg, 40% yield) as a white solid.

$^1$H NMR (500 MHz, DMSO-d$_6$) δ ppm 9.08-9.13 (m, 1H), 8.33 (d, 1H), 7.49-7.55 (m, 1H), 7.28-7.37 (m, 1H), 7.17-7.25 (m, 2H), 7.10 (t, 1H), 6.98 (t, 1H), 5.86-5.92 (m, 2H), 3.92-4.04 (m, 2H).

Compound I-406

The title compound was prepared following general procedure B, except 3-methylpiperidine-3-carboxylic acid (as the HCl salt, 1.7 equiv.) was the amine reactant, and the contents were heated to 100° C. for 19 h. The reaction mixture was acidified to pH 3 with 1N HCl solution, and the resulting solids were collected by vacuum filtration to deliver the desired compound, Compound I-406 (95 mg, 94% yield) as a white solid.

$^1$H-NMR (500 MHz, CD$_3$OD) δ 8.75 (d, 1H), 8.10 (d, 1H), 7.40 (s, 1H), 7.26 (app. q, 1H), 7.09 (dd, 1H), 7.03 (app. t, 1H), 6.91 (d, 1H), 6.81 (app. t, 1H), 5.95 (s, 2H), 4.58 (d, 1H), 4.39 (br d, 1H), 3.43 (m, 1H), 3.41 (d, 1H), 2.24 (m, 1H), 1.77 (m, 2H), 1.61 (m, 1H), 1.23 (s, 3H).

Compound I-407

The title compound was prepared following general procedure B, except 2-aminoethanol (10 equiv.) was the amine reactant, no triethylamine was used, and the contents were heated to 100° C. for 40 min. The reaction mixture was acidified to pH 3 with 1N HCl solution, and the resulting solids were collected by vacuum filtration to deliver the desired compound, Compound I-407 (57 mg, 58% yield) as a white solid.

$^1$H-NMR (500 MHz, DMSO-d$_6$) δ 9.08 (d, 1H), 8.17 (d, 1H), 7.61 (app. t, 1H), 7.50 (s, 1H), 7.33 (app. q, 1H), 7.24 (d, 1H), 7.22 (app. t, 1H), 7.10 (app. t, 1H), 6.82 (app. t, 1H), 5.89 (s, 2H), 4.78 (t, 1H), 3.58 (m, 4H).

Compound I-408

The title compound was prepared following general procedure B, except 3-aminopropan-1-ol (10 equiv.) was the amine reactant, no triethylamine was used, and the contents were heated to 100° C. for 2 h. The reaction mixture was acidified to pH 3 with 1N HCl solution, and the resulting solids were collected by vacuum filtration to deliver the desired compound, Compound I-408 (26 mg, 37% yield) as an off-white solid.

$^1$H-NMR (500 MHz, DMSO-$d_6$) δ 9.08 (d, 1H), 8.16 (d, 1H), 7.66 (app. t, 1H), 7.49 (s, 1H), 7.32 (app. q, 1H), 7.23 (d, 1H), 7.21 (m, 1H), 7.10 (app. t, 1H), 6.83 (app. t, 1H), 5.89 (s, 2H), 4.54 (t, 1H), 3.51 (m, 4H), 1.75 (app. quintet, 2H).

Compound I-409

The title compound was synthesized in 2 steps:

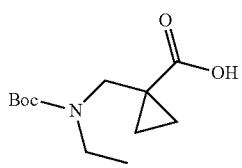 [SMILES: CCN(CC1(C(=O)O)CC1)C(=O)OC(C)(C)C]

Step 1. Synthesis of 1-(((tert-butoxycarbonyl)(ethyl)amino) methyl) Cyclopropanecarboxylic Acid A solution of 1-(((tert-butoxycarbonyl)amino)methyl)cyclopropanecarboxylic acid in THF at 0° C. was treated with iodoethane (10 equiv.) followed by sodium hydride (60% w/w mineral oil, 10 equivalents, added in 6 portions). After 2 days, the reaction mixture was carefully quenched with water and washed with ethyl acetate. The aqueous layer was acidified to pH 3 with 3N HCl and extracted with ethyl acetate. The organic phases were dried over sodium sulfate, filtered and the solvent was removed in vacuo to afford 1-(((tert-butoxycarbonyl)(ethyl)amino)methyl)cyclopropanecarboxylic acid (92% yield) as a pale yellow oil which was used without further purification.

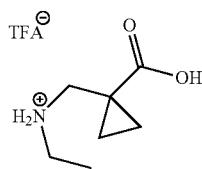

Step 2. Synthesis of N-((1-carboxycyclopropyl)methyl) ethanaminium Trifluoroacetate A solution of 1-(((tert-butoxycarbonyl)(ethyl)amino) methyl)cyclopropanecarboxylic acid in dichloromethane was treated with trifluoroacetic acid (30 equiv.). After 2 h, the reaction mixture was concentrated in vacuo to afford N-((1-carboxycyclopropyl)methyl)ethanaminium trifluoroacetate (>99% yield) as a dark yellow oil which was used without further manipulation.

Step 3: Synthesis of Compound I-409

The title compound was prepared following general procedure B, except N-((1-carboxycyclopropyl)methyl)ethanaminium trifluoroacetate (1.5 equiv.) was the amine reactant, and the contents were heated to 100° C. for 3 d. The crude material was purified via reverse phase HPLC (20-70% acetonitrile/water gradient with 0.1% TFA) to deliver the desired product, Compound I-409 (86 mg, 51% yield) as a white solid.

$^1$H-NMR (500 MHz, CD$_3$OD) δ 8.82 (d, 1H), 8.28 (d, 1H), 7.52 (s, 1H), 7.30 (app. q, 1H), 7.10 (m, 1H), 7.06 (app. t, 1H), 6.97 (d, 1H), 6.96 (m, 1H), 6.00 (s, 2H), 4.30 (s, 2H), 4.00 (q, 2H), 1.41 (q, 2H), 1.37 (t, 3H), 1.16 (q, 2H).

Compound I-410

The title compound was synthesized in 5 steps:

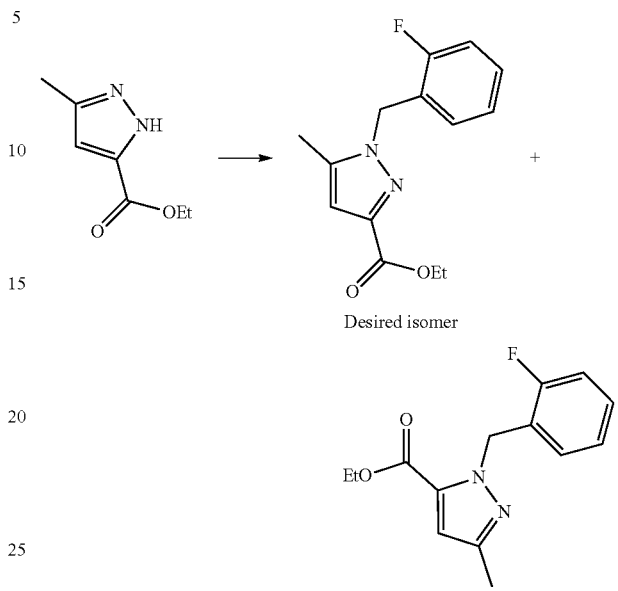

Desired isomer

Step 1: Synthesis of Ethyl 1-(2-fluorobenzyl)-5-methyl-1H-pyrazole-3-carboxylate To ethyl 3-methyl-1H-pyrazole-5-carboxylate in DMF was added sodium hydride (60 wt % in mineral oil, 1.2 equiv.). After 10 min, 2-fluorobenzyl bromide (1.2 equiv.) was added and the reaction was stirred for 20 h. Water was added and the resulting mixture was extracted with ethyl acetate. The combined organic phases were washed with water and brine, dried over sodium sulfate, filtered, and the solvent was removed in vacuo. Purification via silica gel chromatography (10-40% ethyl acetate/hexanes gradient) yielded ethyl 1-(2-fluorobenzyl)-5-methyl-1H-pyrazole-3-carboxylate (79% yield) and ethyl 1-(2-fluorobenzyl)-3-methyl-1H-pyrazole-5-carboxylate (9% yield).

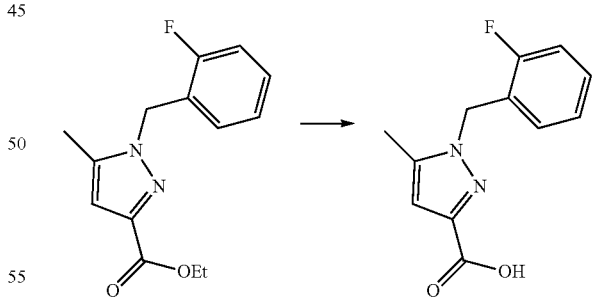

Step 2: Synthesis of 1-(2-fluorobenzyl)-5-methyl-1H-pyrazole-3-carboxylic Acid

To a solution of ethyl 1-(2-fluorobenzyl)-5-methyl-1H-pyrazole-3-carboxylate in THF/MeOH/Water (3:1:1 ratio) was added lithium hydroxide hydrate (1.5 equiv.). After 23 h, the volatile organics were removed in vacuo and the resultant mixture was acidified to pH 3 with 1N HCl. 1-(2-fluorobenzyl)-5-methyl-1H-pyrazole-3-carboxylic acid was collected by vacuum filtration (92% yield).

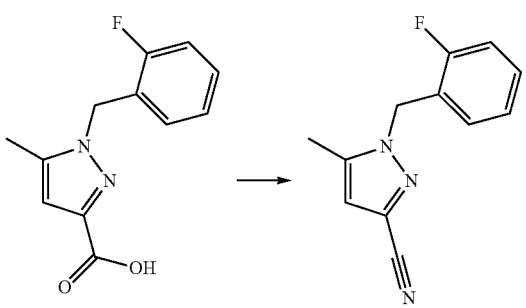 [SMILES: Cc1cc(C(=O)O)nn1Cc1ccccc1F ; Cc1cc(C#N)nn1Cc1ccccc1F]

Step 3: Synthesis of 1-(2-fluorobenzyl)-5-methyl-1H-pyrazole-3-carbonitrile

To a suspension of 1-(2-fluorobenzyl)-5-methyl-1H-pyrazole-3-carboxylic acid, 2-methylpropan-2-amine (3 equiv.), and triethylamine (2 equiv.) in ethyl acetate was added n-propylphosphonic anhydride (T3P, 50 wt % solution in ethyl acetate, 3 equiv.). The resultant yellow solution was heated at 65° C. for 2.5 h. The solvent was removed in vacuo. Phosphoryl trichloride (12 equiv.) was added and the resulting mixture was stirred at 70° C. for 1 hour 40 min. The reaction was quenched by carefully pouring into a mixture of water and ice, neutralized to pH 7 by addition of saturated sodium bicarbonate solution and extracted with dichloromethane. The combined organic phases were dried over sodium sulfate, filtered, and the solvent was removed in vacuo. Purification by silica gel chromatography (10% ethyl acetate/hexanes gradient) yielded 1-(2-fluorobenzyl)-5-methyl-1H-pyrazole-3-carbonitrile (49% yield).

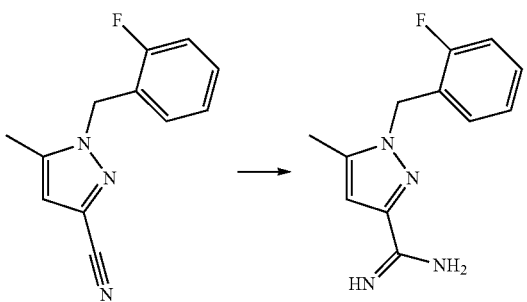 [SMILES: Cc1cc(C#N)nn1Cc1ccccc1F ; Cc1cc(C(=N)N)nn1Cc1ccccc1F]

Step 4: Synthesis of 1-(2-fluorobenzyl)-5-methyl-1H-pyrazole-3-carboximidamide

A solution of 1-(2-fluorobenzyl)-5-methyl-1H-pyrazole-3-carbonitrile in methanol was treated sodium methoxide (25 wt % solution in MeOH, 5 equiv.) and stirred for 24 h. Ammonium chloride (10 equivalents) was added. After 26 hours, the reaction mixture was concentrated in vacuo and partitioned between half-saturated sodium bicarbonate and ethyl acetate. The organic phases were dried over sodium sulfate, filtered, and the solvent was removed in vacuo. The crude product was contaminated with starting material due to incomplete reaction. This material was re-subjected to similar conditions to afford 1-(2-fluorobenzyl)-5-methyl-1H-pyrazole-3-carboximidamide (92% yield).

Step 5: Synthesis of Compound I-410

A suspension of 1-(2-fluorobenzyl)-5-methyl-1H-pyrazole-3-carboximidamide was treated with sodium (Z)-3-ethoxy-2-fluoro-3-oxoprop-1-en-1-olate (see also general procedure A, Step 4, 3.0 equiv.) and heated at 90° C. for 1 hour. After cooling to ambient temperature, the reaction mixture was neutralized by addition of HCl (1.25 M solution in EtOH). The resultant tan suspension was concentrated in vacuo. The residue was partitioned between dichloromethane and water and the aqueous layer was back-extracted with dichloromethane. The combined organic phases were dried over sodium sulfate, filtered, and the solvent was removed in vacuo. Trituration with dichloromethane yielded the titled compound (206 mg, 62% yield) as a white solid.

$^1$H-NMR (500 MHz, DMSO-$d_6$) δ 12.9 (br s, 1H), 8.07 (br s, 1H), 7.38 (app. q, 1H), 7.25 (m, 1H), 7.18 (app. t, 1H), 7.11 (m, 1H), 6.72 (s, 1H), 5.44 (s, 2H), 2.30 (s, 3H).

Compound I-411

The title compound was synthesized in 2 steps:

Step 1: Synthesis of 4-chloro-5-fluoro-2-(1-(2-fluorobenzyl)-5-methyl-1H-pyrazol-3-yl) Pyrimidine The intermediate was generated using the procedure described for the synthesis of Intermediate 1, with the exception of using Compound I-410 as the starting pyrimidone. An off-white solid (210 mg, 96% yield) was obtained, and contents used without further purification.

Step 2: Synthesis of Compound I-411

The title compound was prepared following general procedure B, except 1-((methylamino)methyl)cyclopropanecarboxylic acid (as the HCl salt) was the amine reactant. The reaction mixture was acidified to pH 3 and the resulting precipitate was collected by vacuum filtration to deliver the desired compound, Compound I-411 (48 mg, 93% yield) as a white solid.

$^1$H-NMR (500 MHz, DMSO-$d_6$) δ 12.3 (s, 1H), 8.16 (d, 1H), 7.36 (app. q, 1H), 7.25 (m, 1H), 7.17 (app. t, 1H), 6.99 (app. t, 1H), 6.61 (s, 1H), 5.38 (s, 2H), 3.97 (s, 2H), 3.22 (d, 3H), 2.29 (s, 3H), 1.13 (m, 2H), 1.01 (m, 2H).

Compound I-412

The title compound was prepared following general procedure B, except (2R,3S)-3-methylpiperidine-2-carboxylic acid was the amine reactant, and contents were heated to 100° C. for 20 h. The crude material was purified via reverse phase HPLC (25-80% acetonitrile/water gradient with 0.1% TFA) to deliver the desired compound, Compound I-412 (12 mg, 23% yield) as a white solid.

$^1$H-NMR (500 MHz, CD$_3$OD) δ 8.33 (d, 1H), 7.36 (app. q, 1H), 7.15 (m, 2H), 7.06 (app. t, 1H), 6.89 (s, 1H), 5.52 (s, 2H), 5.36 (d, 1H), 4.58 (br s, 1H), 3.83 (app. t, 1H), 2.36 (s, 3H), 1.99 (m, 1H), 1.96 (m, 1H), 1.79 (m, 2H), 1.58 (m, 1H), 1.24 (d, 3H).

Compound I-413

The title compound was prepared following general procedure B, except serinol (10 equiv.) was the amine reactant, and no triethylamine was used, and contents were heated to 90° C. for 40 min followed by 100° C. for 20 min. The reaction mixture was acidified to pH 3 and the resulting precipitate was collected by vacuum filtration to deliver the desired compound, Compound I-413 (46 mg, 88% yield) as a white solid.

$^1$H-NMR (500 MHz, DMSO-$d_6$) δ 8.11 (d, 1H), 7.35 (app. q, 1H), 7.24 (m, 1H), 7.16 (app. t, 1H), 7.03 (d, 1H), 6.92 (app. t, 1H), 6.64 (s, 1H), 5.40 (s, 2H), 4.71 (t, 2H), 4.24 (m, 1H), 3.56 (m, 4H), 3.12 (s, 3H).

Compound I-414

The title compound was prepared following general procedure B, except 2-(aminomethyl)-1,1,1,3,3,3-hexafluoropropan-2-ol (2.2 equiv.) was the amine reactant, 5 equivalents of triethylamine was used, and contents were heated to 90° C. for 18 h followed by 100° C. for 4 d. The crude material was purified via reverse phase HPLC (35-80% acetonitrile/water gradient with 0.1% TFA) to deliver the desired compound, Compound I-414 (35 mg, 58% yield) as a white solid.

$^1$H-NMR (500 MHz, MeOH-d$_4$) δ 8.29 (d, 1H), 7.35 (app. q, 1H), 7.13 (m, 3H), 6.79 (s, 1H), 5.50 (s, 2H), 4.29 (s, 2H), 2.36 (s, 3H).

Compound I-416

The title compound was synthesized in 3 steps:

Step 1: Synthesis of 3-(1-(2-fluorobenzyl)-5-(isoxazol-3-yl)-1H-pyrazol-3-yl)-1,2,4-triazin-5(4H)-one A solution of 1-(2-fluorobenzyl)-5-(isoxazol-3-yl)-1H-pyrazole-3-carboximidamide hydrochloride in absolute ethanol was treated with hydrazine hydrate (1.5 equiv.) at ambient temperature. After 45 min, ethyl 2-oxoacetate (50 wt % solution in toluene, 3.0 equiv.) was added and the resultant solution was heated at 50-60° C. for 65 h. The reaction mixture was then concentrated in vacuo, taken up in dichloromethane, filtered and concentrated in vacuo to afford an orange oil. Purification via silica gel chromatography (10-20% acetonitrile-methanol (7:1) in dichloromethane) yielded the desired compound 3-(1-(2-fluorobenzyl)-5-(isoxazol-3-yl)-1H-pyrazol-3-yl)-1,2,4-triazin-5(4H)-one (320 mg, 73% yield) as a light tan solid.

$^1$H-NMR (500 MHz, CDCl$_3$) δ 8.54 (d, 1H), 7.84 (br s, 1H), 7.44 (s, 1H), 7.31 (m, 1H), 7.12-7.04 (m, 3H), 6.63 (d, 1H), 5.95 (s, 2H).

Step 2: Synthesis of 3-(3-(5-chloro-1,2,4-triazin-3-yl)-1-(2-fluorobenzyl)-1H-pyrazol-5-yl)isoxazole 3-(1-(2-fluorobenzyl)-5-(isoxazol-3-yl)-1H-pyrazol-3-yl)-1,2,4-triazin-5(4H)-one was treated with phosphoryl trichloride (42 equivalents, excess). The resultant mixture was heated at 65° C. for 4 h. The resultant tan suspension was blown dry under a stream of nitrogen and dried azeotropically with toluene. The chloro-triazine was used in the next step without further manipulation.

Step 3: Synthesis of Compound I-416

The title compound was prepared following general procedure B, except serinol (10 equiv.) was the amine reactant, 3-(3-(5-chloro-1,2,4-triazin-3-yl)-1-(2-fluorobenzyl)-1H-pyrazol-5-yl)isoxazole was used in place of Intermediate 1, no triethylamine was used, and contents were heated at 100° C. for 24 h as a solution in dioxane/DMSO (7.5:1). The reaction mixture was diluted with water, neutralized to pH 4 with 1N HCl solution and extracted with dichloromethane/isopropanol (4:1). The combined organic phases were dried over sodium sulfate, filtered, and the solvent was removed in vacuo. The crude material was purified via reverse phase HPLC (10-70% acetonitrile/water gradient with 0.1% TFA) to deliver the desired compound, Compound I-416 (5.2 mg, 9.8% yield) as a white solid.

$^1$H-NMR (500 MHz, CD$_3$OD) δ 8.84 (d, 1H), 8.35 (s, 1H), 7.74 (s, 1H), 7.32 (app. q, 1H), 7.11 (m, 1H), 7.08 (app. t, 1H), 6.99 (app. t, 1H), 6.96 (d, 1H), 6.06 (s, 2H), 4.62 (app. quintet, 1H), 3.84 (m, 4H).

Compound I-417

The title compound was prepared following general procedure B, except glycinamide (as the HCl salt, 3.0 equiv.) was the amine reactant, and the contents were heated to 100° C. for 22 h. The reaction mixture was acidified to pH 4 with 1N HCl solution, and the resulting solids were collected by vacuum filtration to deliver the desired compound, Compound I-417 (110 mg, 94% yield) as a white solid.

$^1$H-NMR (500 MHz, DMSO-d$_6$) δ 9.09 (d, 1H), 8.22 (d, 1H), 7.83 (app. t, 1H), 7.51 (br s, 1H), 7.48 (s, 1H), 7.31 (app. q, 1H), 7.21 (m, 1H), 7.18 (d, 1H), 7.12-7.08 (m, 2H), 6.81 (app. t, 1H), 5.89 (s, 2H), 4.01 (d, 2H).

Compound I-418

The title compound was prepared following general procedure B, except 3-amino-4,4,4-trifluorobutanoic acid (3 equiv.) was the amine reactant, and contents were heated to 100° C. for 3.5 h then to 120° C. for 18 h as a solution in dioxane/DMSO (2:1). Additional 2 equivalents of Intermediate 1 were added to the reaction, and contents stirred at 120° C. for an additional 4 d. A dichloromethane:isopropanol (4:1) mixture was used as solvent during work up. The crude material was purified via silica gel chromatography (5% methanol/dichloromethane isocratic) to deliver the desired compound, Compound I-418 (38 mg, 10% yield) as an off-white solid.

1H NMR (500 MHz, DMSO-d6) δ ppm 12.65 (br. s., 1H), 9.09 (d, 1H), 8.35 (d, 1H), 8.29 (d, 1H), 7.51 (s, 1H), 7.32 (q, 1H), 7.26 (d, 1H), 7.24-7.19 (m, 1H), 7.10 (t, 1H), 6.83 (t, 1H), 5.91 (s, 2H), 5.53 (br. s., 1H), 2.96-2.85 (m, 2H).

Compound I-419

A solution of Compound I-418 in dichloromethane was treated with N,N-diisopropylethylamine (2.0 equiv.) followed by O-(7-azabenzotriazol-1-yl)-N,N,N',N'-tetramethyluronium hexafluorophosphate (HATU, 1.2 equiv.). After 15 min, ammonia (0.5 N solution in dioxane, 2.0 equiv.) was added and the resultant light brown suspension was stirred for 1.5 h. The reaction mixture was diluted with water and extracted with dichloromethane/2-propanol (4:1). The organic phases were dried over magnesium sulfate, filtered and the solvent was removed in vacuo. Purification via silica gel chromatography (0-3% methanol/dichloromethane gradient) yielded the desired compound, Compound I-419 (20 mg, 57% yield) as an off-white solid.

$^1$H-NMR (500 MHz, DMSO-d$_6$) δ 9.10 (d, 1H), 8.34 (d, 1H), 8.24 (d, 1H), 7.51 (m, 2H), 7.32 (app. q, 1H), 7.25 (d, 1H), 7.22 (app. t, 1H), 7.10 (app. t, 1H), 7.06 (br s, 1H), 6.82 (app. t, 1H), 5.91 (s, 2H), 5.55 (br s, 1H), 2.77 (dd, 1H), 2.67 (dd, 1H).

Compound I-420

The title compound was prepared in 2 steps:

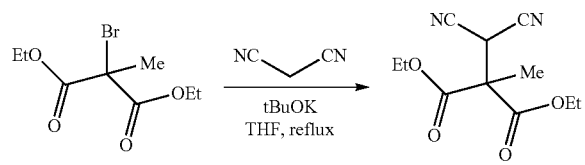 [SMILES: CCOC(=O)C(C)(Br)C(=O)OCC ; N#CCC#N ; CCOC(=O)C(C)(C(=O)OCC)C(C#N)C#N]

Step 1: Synthesis of diethyl 2-(dicyanomethyl)-2-methylmalonate

A mixture of diethyl 2-bromo-2-methylmalonate (1 equiv.), malononitrile (1 equiv.) and potassium t-butoxide (1 equiv.) in THF was heated to reflux for 15 h. The mixture was diluted with ethyl acetate and saturated aqueous ammonium chloride solution and the phases were separated. The aqueous phase was extracted twice with ethyl acetate. The combined organic phase was washed with brine, dried over anhydrous sodium sulfate, filtered and concentrated to give an oil. The oil was purified by silica gel chromatography (10-15% ethyl acetate in hexane gradient) to give diethyl 2-(dicyanomethyl)-2-methylmalonate (5.76 g, 32% yield) as a colorless oil.

$^1$H NMR (500 MHz, CDCl$_3$) δ ppm 4.53 (s, 1H), 4.27-4.39 (m, 4H), 1.81 (s, 3H), 1.33 (t, 6H).

Step 2: Synthesis of Compound I-420

A mixture of 1-(2-fluorobenzyl)-5-(isoxazol-3-yl)-1H-pyrazole-3-carboximidamide hydrochloride (generated in step 3 of general procedure A, by using 1-(isoxazol-3-yl)

ethanone in step 1 and 2-fluorobenzylhydrazine in step 2) (1 equiv.), diethyl 2-(dicyanomethyl)-2-methylmalonate (1.15 equiv.) and potassium bicarbonate (2 equiv.) in t-BuOH was heated to reflux for 5 h. After cooling, the reaction mixture was added with water and stirred for 30 min. The precipitate was filtered, washed with a minimum amount of water and diethyl ether and dried overnight under high vacuum to give Compound I-420 (385 mg, 52% yield) as a white solid.

$^1$H NMR (500 MHz, DMSO-$d_6$) δ ppm 11.30 (s, 1H), 9.10 (d, 1H), 7.38 (s, 1H), 7.29-7.36 (m, 1H), 7.18-7.26 (m, 2H), 7.08-7.14 (m, 1H), 6.81-6.90 (m, 1H), 6.65 (br. s., 2H), 5.88 (s, 2H), 4.04-4.16 (m, 2H), 1.59 (s, 3H), 1.11 (t, 3H).

Compound I-421

Ammonia (7.0 M in MeOH) (200 equiv.) was added to Compound I-420 (1 equiv.). The reaction mixture was heated at 50° C. for 16 h. The resultant solution was then concentrated in vacuo, and the residue was purified via reverse phase HPLC (5-60% acetonitrile in water with 1% TFA) to deliver the desired compound, Compound I-421 (24 mg, 63% yield) as a white solid.

$^1$H NMR (400 MHz, DMSO-$d_6$) δ ppm 11.35 (br. s., 1H), 9.08-9.13 (m, 1H), 7.47 (s, 1H), 7.43 (s, 1H), 7.28-7.38 (m, 1H), 7.23-7.27 (m, 1H), 7.17-7.23 (m, 2H), 7.06-7.14 (m, 1H), 6.77-7.00 (m, 3H), 5.91 (s, 2H), 1.56 (s, 3H).

Compound I-422

Cyclopropyl amine (150 equiv.) was added to Compound I-420 (1 equiv.), and the reaction mixture was heated at 50° C. for 30 h. The resultant solution was then concentrated in vacuo, and the residue was purified by reverse phase HPLC (25-50% acetonitrile in water with 1% TFA) to deliver the desired compound, Compound I-422 (29 mg, 57% yield) as a white solid.

$^1$H NMR (400 MHz, DMSO-$d_6$) δ ppm 11.29 (br. s., 1H), 9.11 (d, 1H), 7.59-7.66 (m, 1H), 7.42 (s, 1H), 7.29-7.37 (m, 1H), 7.16-7.28 (m, 2H), 7.06-7.15 (m, 1H), 6.65-6.89 (m, 3H), 5.90 (s, 2H), 2.59-2.69 (m, 1H), 1.54 (s, 3H), 0.53-0.65 (m, 2H), 0.39-0.52 (m, 2H).

Compound I-423

The title compound was prepared following general procedure B, except 4-(piperidin-4-ylsulfonyl)morpholine (as the TFA salt, 1.7 equiv.) was the amine reactant, 4 equivalents of triethylamine was used, and the contents were heated to 105° C. for 12 h. Ethyl acetate was the solvent used for work up. The crude material was purified via silica gel chromatography using a 1 to 5% methanol in dichloromethane gradient over 40 minutes to deliver the desired compound, Compound I-423 (32.7 mg, 35% yield) as a white solid.

$^1$H NMR (500 MHz, CDCl$_3$) δ (ppm): 8.48 (d, 1H), 8.25 (d, 1H), 7.30 (s, 1H), 7.20-7.25 (m, 1H), 7.03-7.08 (m, 1H), 6.96-7.01 (m, 1H), 6.83-6.88 (m, 1H), 6.60 (d, 1H), 5.98 (s, 2H), 4.83 (d, 2H), 3.76 (m, 4H), 3.41 (m, 4H), 3.23-3.29 (m, 1H), 3.06-3.11 (m, 2H), 2.20-2.26 (m, 2H), 1.91-2.03 (m, 2H).

Compound I-424

The title compound was prepared following general procedure B, except trans-4-(trifluoromethyl)pyrrolidine-3-carboxylic acid (as the TFA salt, 1.5 equiv.) was the amine reactant, 4 equivalents of triethylamine was used, and the contents were heated to 105° C. for 3 h. A dichloromethane:isopropanol mix (5:1) was used as solvent for work up. Concentration of the dried and filtered organic layer in vacuo delivered the desired compound, Compound I-424 (108.3 mg, 89% yield) as an off-white solid.

$^1$H NMR (500 MHz, CDCl$_3$) δ (ppm): 8.50 (d, 1H), 8.18 (d, 1H), 7.40 (s, 1H), 7.19-7.25 (m, 1H), 6.98-7.07 (m, 3H), 6.65 (d, 1H), 5.94 (s, 2H), 4.26 (m, 1H), 4.11-4.18 (m, 2H), 4.03-4.09 (m, 1H), 3.48-3.55 (m, 1H), 3.39-3.54 (m, 1H).

Compound I-425

To a suspension of Compound I-366 (1 equiv.) in dichloromethane was added cyclopropanecarboxylic acid chloride (1.08 equiv.) and triethylamine (1.1 equiv.). After stirring at room temperature for 24 h, the reaction was still heterogeneous and incomplete by LC/MS analysis. An additional 4 equivalents of the acid chloride and 1,8-Diazabicycloundec-7-ene were added, and the reaction was then heated to 60° C. for 1 h, after which the reaction was tan in color and completely homogeneous. The reaction was diluted in water, acidified by the addition of 1N hydrochloric acid solution, extracted with dichloromethane (3×), dried (sodium sulfate), filtered and concentrated to afford a white solid. Purification was achieved by silica gel using 1 to 8% methanol in dichloromethane over 38 minutes to deliver the desired compound, Compound I-425 (40.4 mg, 71% yield) as a white solid.

$^1$H NMR (500 MHz, CDCl$_3$) δ (ppm): 8.47 (d, 1H), 8.23 (d, 1H), 7.82 (br. s, 1H), 7.29 (s, 1H), 7.17-7.23 (m, 1H), 7.01-7.06 (m, 1H), 6.95-6.99 (m, 1H), 6.81-6.87 (m, 1H), 6.60 (d, 1H), 5.96 (s, 2H), 4.79-4.84 (m, 2H), 3.83-3.94 (m, 1H), 3.08-3.15 (m, 2H), 2.23-2.29 (m, 2H), 2.01-2.06 (m, 1H), 1.27 (m, 2H), 1.19 (m, 2H), 0.99-1.04 (m, 2H).

Compound I-426

To a suspension of Compound I-366 (1 equiv.) in dichloromethane was added acetic anhydride (1.25 equiv.) and 1,8-Diazabicycloundec-7-ene (1.25 equiv.). After stirring at room temperature for 24 h, the reaction was still heterogeneous and incomplete by LC/MS. An additional 4 equivalents of acetic anhydride and 1,8-Diazabicycloundec-7-ene were added, and the reaction was then heated to 60° C. for 1 h, after which the reaction was tan in color and completely homogeneous. The reaction was diluted in water, acidified by the addition of 1N hydrochloric acid solution, extracted with dichloromethane (3×), dried (sodium sulfate), filtered and concentrated to afford a white solid. Purification was achieved by silica gel chromatography using a 1 to 8% methanol in dichloromethane gradient over 38 minutes to deliver the desired compound, Compound I-426 (24.7 mg, 44% yield) as a white solid.

$^1$H NMR (500 MHz, CDCl$_3$) δ (ppm): 8.47 (d, 1H), 8.23 (d, 1H), 7.85 (br. s, 1H), 7.29 (s, 1H), 7.18-7.25 (m, 1H), 7.02-7.08 (m, 1H), 6.96-7.02 (m, 1H), 6.84-6.89 (m, 1H), 6.61 (d, 1H), 6.00 (s, 2H), 4.80-4.90 (m, 2H), 3.85-3.95 (m, 1H), 3.08-3.17 (m, 2H), 2.23-2.31 (m, 2H), 2.17 (s, 3H), 1.97-2.08 (m, 2H).

Compound I-427

The title compound was prepared following general procedure B, except pyrrolidine-3-sulfonamide (1.35 equiv.) was the amine reactant, 4 equivalents of triethylamine was used, and the contents were heated to 105° C. for 2 h. After cooling, the reaction was poured into a 1:1 mix of water and ethyl acetate, and the resulting precipitate was filtered and dried in vacuo delivered the desired compound, Compound I-427 (46.7 mg, 39% yield) as an off-white solid.

$^1$H NMR (500 MHz, DMSO-$d_6$) δ (ppm): 9.05-9.13 (m, 1H), 8.24-8.31 (m, 1H), 7.51-7.57 (m, 1H), 7.28-7.37 (m, 1H), 7.18-7.27 (m, 2H), 7.06-7.17 (m, 3H), 6.76-6.87 (m, 1H), 5.87-5.93 (m, 2H), 4.00-4.09 (m, 2H), 3.84-3.97 (m, 2H), 3.75-3.84 (m, 1H), 2.29-2.42 (m, 2H).

Compound I-428

The title compound was prepared following general procedure B, except diethanolamine (1.3 equiv.) was the amine reactant, 2 equivalents of triethylamine was used, and the contents were heated to 100° C. for 12 h. A dichloromethane:

isopropanol mix (5:1) was used as solvent for work up. The crude material was purified via silica gel chromatography using a 1 to 8% methanol in dichloromethane gradient over 40 minutes to deliver the desired compound, Compound I-428 (24.7 mg, 26% yield) as a white solid.

$^1$H NMR (500 MHz, CD$_3$OD) δ (ppm): 8.48 (d, 1H), 8.17 (d, 1H), 7.24 (s, 1H), 7.18-7.23 (m, 1H), 7.01-7.06 (m, 1H), 6.96-7.01 (m, 1H), 6.87-6.92 (m, 1H), 6.58 (d, 1H), 5.95 (s, 2H), 3.99 (m, 4H), 3.89 (m, 4H), 3.30 (br. s, 2H).

Compound I-429

To a solution of Compound I-427 (1 equiv.), in dichloromethane was added cyclopropanecarboxylic acid chloride (6 equiv.) followed by 1,8-diazabicycloundec-7-ene (8 equiv.). The reaction was heated for 1 h at 100° C. after which it was cooled, diluted in water and 1M hydrochloric acid solution, extracted with dichloromethane (2×), concentrated and purified directly via silica gel chromatography using a 1 to 8% methanol in dichloromethane gradient over 40 minutes to deliver the desired compound, Compound I-429 (26.5 mg, 70% yield) as a white solid.

$^1$H NMR (500 MHz, CDCl$_3$) δ (ppm): 8.47 (d, 1H), 8.18 (d, 1H), 7.31 (s, 1H), 7.18-7.23 (m, 1H), 7.01-7.06 (m, 1H), 6.96-7.01 (m, 1H), 6.83-6.88 (m, 1H), 6.60 (d, 1H), 5.97 (s, 2H), 4.40-4.47 (m, 2H), 4.04-4.15 (m, 2H), 3.90-3.97 (m, 1H), 2.65-2.73 (m, 1H), 2.45-2.53 (m, 1H), 1.30 (m, 1H), 1.17 (m, 2H), 0.99 (m, 2H).

Compound I-430

The title compound was prepared following general procedure B, except (2R,3R)-2-(hydroxymethyl)pyrrolidin-3-ol (as the TFA salt, 1.7 equiv.) was the amine reactant, 4 equivalents of triethylamine was used, and the contents were heated to 100° C. for 2 h. After cooling, the reaction was diluted with water and methanol, and the resulting precipitate was filtered, washed with water, and dried in vacuo to deliver the desired compound, Compound I-430 (79.3 mg, 64% yield) as a white solid.

$^1$H NMR (500 MHz, DMSO-d$_6$) δ (ppm): 9.09 (d, 1H), 8.24 (d, 1H), 7.51 (s, 1H), 7.30-7.36 (m, 1H), 7.19-7.25 (m, 2H), 7.08-7.13 (m, 1H), 6.82-6.87 (m, 1H), 5.90 (d, 1H), 5.85 (d, 1H), 5.23 (d, 1H), 4.71 (br. s, 1H), 4.35-4.42 (m, 1H), 4.15-4.20 (m, 1H), 3.77-3.87 (m, 2H), 3.64-3.74 (m, 2H), 2.04-2.09 (m, 2H).

Compound I-431

The title compound was prepared following general procedure B, except diisopropanolamine (1 equiv.) was the amine reactant, 4 equivalents of triethylamine was used, and the contents were heated to 100° C. for 24 h. Ethyl acetate was used as solvent for work up. The crude material was purified via silica gel chromatography using a 1 to 8% methanol in dichloromethane gradient over 40 minutes to deliver the desired compound, Compound I-431 (47.1 mg, 42% yield) as a white solid.

$^1$H NMR (500 MHz, CD$_3$OD) δ (ppm): 8.72 (d, 1H), 8.11 (d, 1H), 7.35 (s, 1H), 7.23-7.28 (m, 1H), 7.05-7.11 (m, 1H), 7.01-7.05 (m, 1H), 6.83-6.88 (m, 2H, 2 shifts isochronous), 5.96 (d, 1H), 5.92 (d, 1H), 4.10-4.21 (m, 2H), 3.90-3.97 (m, 2H), 3.61-3.67 (m, 2H), 1.21 (s, 6H).

Compound I-432

The title compound was prepared in 3 steps:

Step 1: Synthesis of 2-((5-fluoro-2-(1-(2-fluorobenzyl)-5-(isoxazol-3-yl)-1H-pyrazol-3-yl)pyrimidin-4-yl)amino)ethanesulfonic acid The intermediate was prepared following general procedure B, except taurine (1.3 equiv.) was the amine reactant, 2 equivalents of triethylamine was used, and the contents were heated to 100° C. for 8 h. After cooling, the reaction was diluted with 1N HCl solution, filtered, washed with water, and dried in vacuo to deliver the desired intermediate, 2-((5-fluoro-2-(1-(2-fluorobenzyl)-5-(isoxazol-3-yl)-1H-pyrazol-3-yl)pyrimidin-4-yl)amino)ethanesulfonic acid (60.2 mg, 64% yield) as a white solid. The intermediate was used without further purification.

Step 2: Synthesis of 2-((5-fluoro-2-(1-(2-fluorobenzyl)-5-(isoxazol-3-yl)-1H-pyrazol-3-yl)pyrimidin-4-yl)amino)ethanesulfonyl Chloride A suspension of 2-((5-fluoro-2-(1-(2-fluorobenzyl)-5-(isoxazol-3-yl)-1H-pyrazol-3-yl)pyrimidin-4-yl)amino)ethanesulfonic acid (1 equiv.) and thionyl chloride (5 equiv.) in dichloromethane was stirred at room temperature, after which 2 drops of DMF were added. The suspension was heated to 60° C. for 12 h, after which LC/MS indicated that the sulfonyl chloride had formed. The reaction mixture was concentrated to dryness to afford 90 mg of an off-white solid.

Step 3: Synthesis of Compound I-432

To a suspension of the crude 2-((5-fluoro-2-(1-(2-fluorobenzyl)-5-(isoxazol-3-yl)-1H-pyrazol-3-yl)pyrimidin-4-yl)amino)ethanesulfonyl chloride in tetrahydrofuran was added a 50% aqueous solution of hydroxylamine (10 equiv.). The reaction became homogeneous instantly, and was shown by LC/MS to be complete. The reaction was concentrated to one third of its volume and purified directly on silica gel using 3 to 10% methanol in dichloromethane over 45 minutes to deliver the desired compound, Compound I-432 (8.2 mg, 25% yield) as a white solid.

$^1$H NMR (500 MHz, CD$_3$OD) δ (ppm): 8.76 (d, 1H), 8.13 (d, 1H), 7.60 (s, 1H), 7.25-7.31 (m, 1H), 7.07-7.13 (m, 1H), 7.03-7.07 (m, 1H), 6.89 (d, 1H), 6.83-6.88 (m, 1H), 6.00 (s, 2H), 4.07 (t, 2H), 3.62 (t, 2H).

Compound I-433

The title compound was prepared following general procedure B, except piperidine-3,5-dione (as the HCl salt, 1.4 equiv.) was the amine reactant, 4 equivalents of triethylamine was used, and the contents were heated to 100° C. for 1 h. Ethyl acetate was used as solvent for work up. The crude material was purified via silica gel chromatography using a 3 to 20% methanol in dichloromethane gradient over 40 minutes to deliver the desired compound, Compound I-433 (45.6 mg, 44% yield) as a white solid.

$^1$H NMR (500 MHz, CD$_3$OD) δ (ppm): 8.77 (s, 1H), 8.30 (d, 1H), 7.50 (s, 1H), 7.26-7.32 (m, 1H), 7.07-7.13 (m, 1H), 7.03-7.07 (m, 1H), 6.94 (d, 1H), 6.83-6.88 (m, 1H), 5.98 (s, 2H), 4.58 (s, 4H).

Compound I-434

The title compound was prepared following general procedure B, except 4-(hydroxymethyl)piperidin-4-ol (as the HCl salt, 1.4 equiv.) was the amine reactant, 4 equivalents of triethylamine was used, and the contents were heated to 100° C. for 1 h. After cooling, the reaction was diluted with water and 1N HCl solution, and the resulting precipitate was filtered, washed with water, and dried in vacuo to deliver the desired compound, Compound I-434 (88.5 mg, 82% yield) as a white solid.

$^1$H NMR (500 MHz, CD$_3$OD) δ (ppm): 8.77 (d, 1H), 8.15 (d, 1H), 7.43 (s, 1H), 7.23-7.30 (m, 1H), 7.06-7.12 (m, 1H), 7.00-7.05 (m, 1H), 6.91 (d, 1H), 6.79-6.84 (m, 1H), 5.96 (s, 2H), 4.49-4.57 (m, 2H), 3.49-3.57 (m, 2H), 3.40 (s, 2H), 1.65-1.71 (m, 2H), 1.77-1.84 (m, 2H).

Compound I-435

The title compound was prepared following general procedure B, except (3R,5S)-5-(hydroxymethyl)pyrrolidin-3-ol (2.7 equiv.) was the amine reactant, 4 equivalents of triethylamine was used, and the contents were heated to 100° C. for 30 min. After cooling, the reaction was diluted with water and methanol, and the resulting precipitate was filtered, washed with water, and dried in vacuo to deliver the desired compound, Compound I-435 (77.3 mg, 87% yield) as a white solid.

$^1$H NMR (500 MHz, CD$_3$OD) δ (ppm): 8.75 (d, 1H), 8.12 (d, 1H), 7.40 (s, 1H), 7.24-7.28 (m, 1H), 7.06-7.10 (m, 1H), 7.01-7.05 (m, 1H), 6.90 (d, 1H), 6.80-6.85 (m, 1H), 5.95 (s, 2H), 4.63-4.68 (m, 1H), 4.53-4.57 (m, 1H), 3.81-3.94 (m, 3H), 3.73-3.80 (m, 1H), 2.10-2.25 (m, 2H).

Compound I-437

This compound was made in two steps

Step 1: Ketal Intermediate

To a suspension of the crude 2-((5-fluoro-2-(1-(2-fluorobenzyl)-5-(isoxazol-3-yl)-1H-pyrazol-3-yl)pyrimidin-4-yl)amino)ethanesulfonyl chloride (synthesis described in Step 2 of procedure for making Compound I-432 (1 equiv.) in dioxane was added (S)-(2,2-dimethyl-1,3-dioxolan-4-yl)methanamine (2 equiv.). The reaction was stirred for 24 h, after which the reaction mixture was diluted in 5:1 dichloromethane/isopropanol and acidified by the addition of 1M hydrochloric acid, extracted with 5:1 dichloromethane/isopropanol (3×30 mL), dried (sodium sulfate), filtered and concentrated to afford a residue. Purification was achieved via silica gel chromatography using a 7 to 12% methanol in dichloromethane gradient over 45 minutes to deliver the desired compound, Compound I-43 (31.0 mg, 42% yield) as white solid.

$^1$H NMR (500 MHz, CD$_3$OD) δ (ppm): 8.78 (d, 1H), 8.13 (d, 1H), 7.52 (s, 1H), 7.26-7.32 (m, 1H), 7.10-7.15 (m, 1H), 7.04-7.08 (m, 1H), 6.91 (d, 1H), 6.80-6.85 (m, 1H), 6.00 (s, 2H), 4.16-4.20 (m, 1H), 4.03-4.12 (m, 2H), 3.98-4.02 (m, 1H), 3.70-3.74 (m, 1H), 3.45-3.52 (m, 2H), 3.22 (d, 2H), 1.34 (s, 3H), 1.27 (s, 3H).

Step 2: Compound I-437

To a solution of the intermediate prepared in step 1 (1 equiv.) in dichloromethane was added a 4M in dioxane solution of hydrogen chloride (20 equiv.). After 1 h, the reaction was concentrated to dryness, diluted in water, extracted with 5:1 dichloromethane/isopropanol (3×), dried (sodium sulfate), filtered, and concentrated to afford a residue. Purification was achieved via silica gel chromatography to deliver the desired compound, Compound I-437 (10.3 mg, 38.2% yield) as an off-white solid.

$^1$H NMR (500 MHz, CD$_3$OD) δ (ppm): 8.77 (d, 1H), 8.12 (d, 1H), 7.53 (s, 1H), 7.26-7.32 (m, 1H), 7.08-7.13 (m, 1H), 7.03-7.08 (m, 1H), 6.93 (d, 1H), 6.81-6.86 (m, 1H), 6.00 (s, 2H), 4.03-4.13 (m, 2H), 3.70-3.75 (m, 1H), 3.47-3.54 (m, 3H), 3.24-3.29 (m, 2H), 3.08-3.13 (m, 1H).

Compound I-438

The title compound was prepared following general procedure B, except 4-hydroxypiperidine-4-carboxamide (1.4 equiv.) was the amine reactant, 4 equivalents of triethylamine was used, and the contents were heated to 100° C. for 30 min. Ethyl acetate was used as solvent for work up, and purification was achieved by precipitation of the product by trituration of an acetonitrile solution of the crude product with water. The resulting precipitate was filtered and dried in vacuo to deliver the desired compound, Compound I-438 (26.3 mg, 26% yield) as a white solid.

$^1$H NMR (500 MHz, DMSO-d$_6$) δ (ppm): 9.08 (d, 1H), 8.29 (d, 1H), 7.55 (s, 1H), 7.30-7.35 (m, 2H, 2 shifts isochronous), 7.26 (d, 2H), 7.19-7.25 (m, 1H), 7.16 (br. s, 1H), 7.08-7.13 (m, 1H), 6.79-6.84 (m, 1H), 5.90 (s, 2H), 4.39 (m, 2H), 3.34-3.39 (m, 2H), 1.95-2.01 (m, 2H), 1.58 (m, 2H).

Compound I-439

To a suspension of the 2-((5-fluoro-2-(1-(2-fluorobenzyl)-5-(isoxazol-3-yl)-1H-pyrazol-3-yl)pyrimidin-4-yl)amino)ethanesulfonyl chloride (synthesis described in Step 2 of procedure for Compound I-432, 1 equiv.) in dioxane was added ethanolamine (2.2 equiv.). The reaction was stirred for 24 h at room temperature, after which the reaction mixture was diluted in 5:1 dichloromethane/isopropanol and acidified by the addition of 1M hydrochloric acid, extracted with 5:1 dichloromethane/isopropanol (3×), dried (sodium sulfate), filtered and concentrated to afford a residue. Purification was achieved via silica gel chromatography using a 3 to 8% methanol gradient in dichloromethane over 45 minutes to deliver the desired compound, Compound I-439 (31.3 mg, 65% yield) as white solid.

$^1$H NMR (500 MHz, DMSO-d$_6$) δ (ppm): 9.09 (d, 1H), 8.24 (d, 1H), 7.78-7.83 (m, 1H), 7.54 (s, 1H), 7.30-7.35 (m, 1H), 7.21-7.25 (m, 2H), 7.17 (d, 1H), 7.08-7.13 (m, 1H), 6.81-6.86 (m, 1H), 5.90 (s, 2H), 4.80 (t, 1H), 3.84 (q, 2H), 3.44 (q, 2H), 3.39 (t, 2H), 3.03 (q, 2H).

Compound I-440

The title compound was synthesized in 2 steps:

Step 1: Synthesis of 1-(benzyloxy)-N-(1-(5-fluoro-2-(1-(2-fluorobenzyl)-5-(isoxazol-3-yl)-1H-pyrazol-3-yl)pyrimidin-4-yl)azetidin-3-yl)cyclopropanecarboxamide The intermediate was prepared following general procedure B, except N-(azetidin-3-yl)-1-(benzyloxy)cyclopropanecarboxamide (as the TFA salt, 1.2 equiv.) was the amine reactant, 4 equivalents of triethylamine was used, and the contents were heated to 100° C. for 2 h. After cooling, the reaction mixture was diluted with water, and the resulting precipitate was filtered, washed with water, and dried in vacuo to deliver the desired intermediate, 1-(benzyloxy)-N-(1-(5-fluoro-2-(1-(2-fluorobenzyl)-5-(isoxazol-3-yl)-1H-pyrazol-3-yl)pyrimidin-4-yl)azetidin-3-yl)cyclopropanecarboxamide (104.3 mg, 86% yield) as a white solid.

Step 2: Synthesis of Compound I-440

To a suspension of 1-(benzyloxy)-N-(1-(5-fluoro-2-(1-(2-fluorobenzyl)-5-(isoxazol-3-yl)-1H-pyrazol-3-yl)pyrimidin-4-yl)azetidin-3-yl)cyclopropanecarboxamide in ethanol was added 10% Palladium on Carbon (0.1 equiv). The reaction mixture was evacuated to dryness and a hydrogen balloon was applied. For solubility purposes, ethyl acetate was also added. After 24 h, a mixture of starting material, product and other byproducts were observed. The reaction mixture was filtered through celite, then purified via silica gel chromatography using a 1 to 8% dichloromethane in methanol gradient over 60 minutes to deliver the desired compound, Compound I-440 (3.8 mg, 5% yield). Several later fractions containing the desired product were contaminated with a close-running byproduct and discarded.

$^1$H NMR (400 MHz, CDCl$_3$) δ (ppm): 8.44 (d, 1H), 8.09 (d, 1H), 7.92 (br. s, 1H), 7.20-7.25 (m, 1H), 6.93-7.03 (m, 2H, 2 shifts isochronous), 6.83-6.88 (m, 2H), 6.56 (d, 1H), 5.94 (s, 2H), 4.81-4.91 (m, 1H), 4.55-4.63 (m, 1H), 4.05-4.12 (m, 2H), 2.31-2.36 (m, 1H), 1.33-1.37 (m, 2H), 1.04-1.09 (m, 2H).

Compound I-441

The title compound was prepared following general procedure B, except 3-(aminomethyl)-1H-1,2,4-triazol-5(4H)-one (1.3 equiv.) was the amine reactant, 4 equivalents of triethylamine was used, and the contents were heated to 100° C. for 12 h. After cooling, the reaction was filtered and purified via silica gel chromatography using a 3 to 10% methanol in dichloromethane gradient over 40 minutes to deliver the desired compound, Compound I-441 (12.9 mg, 13% yield) as a white solid.

¹H NMR (500 MHz, CD₃OD) δ (ppm): 8.78 (d, 1H), 8.17 (m, 1H), 7.42 (s, 1H), 7.25-7.31 (m, 1H), 7.07-7.12 (m, 1H), 7.02-7.07 (m, 1H), 6.88-6.93 (m, 2H, 2 shifts isochronous), 6.02 (s, 2H), 4.61 (s, 2H).

Compound I-442

To a suspension of 1,2,4-Triazolin-3-one (0.5 equiv.), potassium carbonate (1.5 equiv.), and copper (I) iodide (0.05 equiv.) in N,N-Dimethylformamide was added Intermediate 1 (1 equiv.) followed by trans-1,2-bis(methylamino)cyclohexane (0.1 equiv.). The reaction was heated to 100° C. for 24 h, after which the reaction was diluted in water, extracted with ethyl acetate, dried (sodium sulfate), filtered and concentrated. Two purification attempts were made by silica gel chromatography (5-7% methanol in dichloromethane), leading to one peak that was a composite of three compounds. Further purification by reverse phase HPLC (5 to 75% acetonitrile in water spiked with 0.1% trifluoroacetic acid over 20 minutes) delivered the desired compound, Compound I-442 (0.9 mg, 0.8% yield) as a white solid.

¹H NMR (500 MHz, CD₃OD) δ (ppm): 8.96 (s, 1H), 8.81 (d, 1H), 8.12 (s, 1H), 7.66 (s, 1H), 7.25-7.31 (m, 1H), 7.09-7.15 (m, 1H), 7.02-7.07 (m, 1H), 6.89-6.94 (m, 1H), 5.98 (s, 2H).

Compound I-443

The title compound was prepared following general procedure B, except 3-amino-2-hydroxypropanamide (2 equiv.) was the amine reactant, 4 equivalents of triethylamine was used, and the contents were heated to 110° C. for 6 h. A dichloromethane:isopropanol mix (5:1) was used as solvent for work up. The crude material was purified via silica gel chromatography using a 3 to 10% methanol in dichloromethane gradient over 45 minutes to deliver the desired compound, Compound I-443 (17.3 mg, 14% yield) as a white solid.

¹H NMR (500 MHz, CD₃OD) δ (ppm): 8.78 (d, 1H), 8.11 (d, 1H), 7.52 (s, 1H), 7.27-7.31 (m, 1H), 7.09-7.13 (m, 1H), 7.03-7.08 (m, 1H), 6.95 (d, 1H), 6.83-6.88 (m, 1H), 5.99 (s, 2H), 4.37 (dd, 1H), 4.05 (dd, 1H), 3.81 (dd, 1H).

Compound I-444

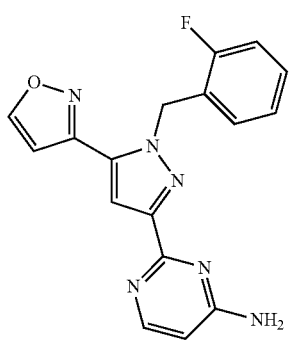

Intermediate-2

To a solution of Intermediate-2 (intermediate described in patent application publication WO2012/3405 A1) (1 equiv.) in dichloromethane was added 2,2,2-trifluoroethane sulfonyl chloride (1.08 equiv.) followed by 1,8-diazabicycloundec-7-ene (1.2 equiv.). The reaction was allowed to stir 16 h at 23° C., after which the reaction mixture was diluted in water and 1N hydrochloric acid solution, extracted with ethyl acetate (3×), washed with 1N hydrochloric acid solution (2×), dried (sodium sulfate), filtered and concentrated in vacuo. Purification of the crude material via silica gel chromatography using isocratic 5% methanol in dichloromethane gradient delivered the desired compound, Compound I-444 (28.9 mg, 27% yield) as an off-white solid.

¹H NMR (500 MHz, CD₃OD) δ (ppm): 8.82 (d, 1H), 8.24 (br. s, 1H), 7.57 (s, 1H), 7.26-7.32 (m, 1H), 7.08-7.13 (m, 1H), 7.03-7.08 (m, 1H), 6.93-6.99 (m, 2H, 2 overlapping shifts), 6.79-6.85 (br. s, 1H), 6.01 (s, 2H), 4.49-4.58 (m, 2H).

Compound I-445

To a suspension of sodium hydride (1.2 equiv.) in anhydrous tetrahydrofuran at 23° C. was added Intermediate-2 (1 equiv.). The reaction was allowed to stir 30 min at 23° C. 3,3,3-Trifluoropropane-1-sulfonyl chloride (1 equiv.) dissolved in tetrahydrofuran was added to the reaction mixture which was stirred for 18 h. The reaction mixture was diluted in water and 1N hydrochloric acid solution, extracted with ethyl acetate (3×), washed with 1N hydrochloric acid solution (2×), dried (sodium sulfate), filtered and concentrated in vacuo. Purification of the crude material via reverse phase HPLC delivered the desired compound, Compound I-445 (17.1 mg, 20% yield) as an off-white solid.

¹H NMR (500 MHz, CDCl₃) δ (ppm): 8.51 (d, 1H), 8.25 (br. s, 1H), 7.20-7.29 (m, 2H), 6.98-7.08 (m, 3H), 6.59 (d, 1H), 5.80-5.99 (m, 2H), 3.64 (br. s, 2H), 2.69-2.88 (m, 2H).

Compound I-446

To a suspension of sodium hydride (1.2 equiv.) in anhydrous tetrahydrofuran at 23° C. was added Intermediate-21 equiv.). The reaction was allowed to stir 30 min at 23° C. 2-Methoxyethanesulfonyl chloride (1 equiv.) dissolved in tetrahydrofuran was added to the reaction mixture which was stirred for 18 h. The reaction mixture was diluted in water and 1N hydrochloric acid solution, extracted with ethyl acetate (3×), washed with 1N hydrochloric acid solution (2×), dried (sodium sulfate), filtered and concentrated. Purification of the crude material via reverse phase HPLC delivered the desired compound, Compound I-446 (9.1 mg, 13.5% yield) as an off-white solid.

¹H NMR (500 MHz, CDCl₃) δ (ppm): 8.50 (d, 1H), 8.37 (br. s, 1H), 7.19-7.27 (m, 2H), 6.92-7.07 (m, 3H), 6.61 (d, 1H), 5.94 (s, 2H), 3.85-3.92 (m, 2H), 3.78 (br. s, 2H), 3.28 (s, 3H).

Compound I-447

Oxalyl chloride (4 equiv.) was added to a solution of triethylamine (4 equiv.) and Compound I-214 (1 equiv.) in DCM maintained at 0° C. The reaction was warmed and stirred at room temperature for 2 h. The reaction was then quenched by addition of water, extracted with dichloromethane, and organic extracts were concentrated in vacuo to deliver the desired compound, Compound I-447 (3.7 mg, 69% yield) as a solid.

¹H-NMR (500 MHz, DMSO-d₆) δ ppm 9.11 (d, 1H), 8.90 (d, 1H), 7.65 (s, 1H), 7.30-7.37 (m, 1H), 7.27 (d, 1H), 7.19-7.26 (m, 1H), 7.11 (t, 1H), 6.87 (t, 1H), 5.93 (s, 2H), 4.00-4.07 (m, 2H), 2.57 (t, 2H), 2.13-2.21 (m, 2H).

Compound I-448

The title compound was prepared following general procedure B, except 5-(aminomethyl)thiophene-2-carboxylic acid (4 equiv.) was the amine reactant, 9 equivalents of triethylamine was used, and the contents were heated to 110° C. as a solution in dioxane/water (4.5:1) for 2 d. Contents diluted with ethyl acetate and 1N HCl solution, and the resulting precipitate was filtered. The solids were collected and dried in vacuo to deliver the desired compound, Compound I-448 (12 mg, 27% yield) as a solid.

¹H NMR (500 MHz, DMSO-d₆) δ ppm 12.9 (br. s., 1H), 9.11 (d, 1H), 8.92-9.08 (m, 1H), 8.35 (t, 1H), 7.61-7.67 (m, 1H), 7.56 (d, 1H), 7.30-7.38 (m, 1H), 7.19-7.26 (m, 3H), 7.12 (t, 1H), 6.92 (t, 1H), 5.92 (s, 2H), 4.88-4.97 (m, 2H).

Compound I-449

The title compound was prepared following general procedure B, except 5-aminopentanoic acid (4 equiv.) was the amine reactant, 9 equivalents of triethylamine was used, and the contents were heated to 110° C. as a solution in dioxane/water (4.5:1) for 2 d. Contents diluted with ethyl acetate and 1N HCl solution, and the resulting precipitate was filtered. The solids were collected and dried in vacuo to deliver the desired compound, Compound I-449 (34 mg, 84% yield) as a solid.

$^1$H NMR (500 MHz, DMSO-$d_6$) δ ppm 12.01 (s, 1H), 9.12 (s, 1H), 8.32-8.62 (m, 1H), 8.27 (br. s., 1H), 7.61 (br. s., 1H), 7.29-7.40 (m, 1H), 7.18-7.27 (m, 2H), 7.11 (t, 1H), 6.88 (t, 1H), 5.93 (br. s., 2H), 2.29 (t, 3H), 1.49-1.72 (m, 5H).

Compound I-450

A suspension of 5-fluoro-2-(1-(2-fluorobenzyl)-5-(isoxazol-3-yl)-1H-pyrazol-3-yl)-pyrimidin-4-ol (generated via general procedure A, using 1-(isoxazol-3-yl)ethanone in step 1 and 2-fluorobenzylhydrazine in step 2) (1 equiv.) and sodium methoxide in methanol (0.5 M solution, 4 equiv.) was heated in a microwave vessel at 130° C. for 4 h. The reaction was quenched with 1N HCl solution to pH 2, and the resulting residue was filtered. The solids were washed with methanol and dried in vacuo to deliver the desired compound, Compound I-450 (1.45 g, 68%) as a white solid.

$^1$H NMR (500 MHz, CD$_3$OD) δ ppm 8.04 (d, 1H), 7.71 (s, 1H), 7.23-7.36 (m, 1H), 7.00-7.18 (m, 2H), 6.90 (t, 1H), 5.94 (s, 2H), 2.56 (s, 3H)

Compound I-451

The title compound was prepared in 2 steps:

Step 1: Synthesis of 1-(3-(4-chloro-5-fluoropyrimidin-2-yl)-1-(2-fluorobenzyl)-1H-pyrazol-5-yl)ethanone Compound I-450 was charged with phosphoryl trichloride (60 equiv.) and the resulting mixture was stirred at 45° C. until the reaction was judged complete by LC/MS. The reaction was then carefully poured over ice, extracted with 4:1 dichloromethane/isopropanol and the layers were separated. The organic portions were combined, dried with sodium sulfate, filtered, and concentrated in vacuo. The material was carried forward into the next step without further purification.

Step 2: Synthesis of Compound I-451

The title compound was prepared following general procedure B, except 1-((methylamino)methyl)cyclopropanecarboxylic acid was the amine reactant, 1-(3-(4-chloro-5-fluoropyrimidin-2-yl)-1-(2-fluorobenzyl)-1H-pyrazol-5-yl)ethanone was used in place of Intermediate 1, and contents were heated to 100° C. for 36 h as a solution in dioxane. The crude material was purified via reverse phase HPLC to deliver the desired compound, Compound I-451 (50 mg, 69% yield) as a tan solid.

$^1$H NMR (500 MHz, DMSO-$d_6$) δ ppm 12.53 (br. s, 1H), 8.19 (d, 1H), 7.65 (s, 1H), 7.33 (d, 1H), 7.17-7.26 (m, 1H), 7.11 (t, 1H), 6.86 (t, 1H), 5.81 (s, 2H), 4.00 (s, 2H), 3.24 (d, 3H), 2.57 (s, 3H), 1.03 (d, 2H), 0.74-0.91 (m, 2H).

Compound I-452 and Compound I-453

The title compound was prepared following general procedure B, except 4-(trifluoromethyl)piperidine-2-carboxylic acid was the amine reactant, Hunig's base (8 equiv.) was used in place of triethylamine, and the contents were heated to 120° C. for 18 h as a solution in THF/water (1:1). Solvent removed in vacuo, and the resulting residue was purified via reverse phase HPLC, then with silica gel chromatography utilizing a 0-10% methanol/dichloromethane gradient to deliver the desired compounds, Compound I-452 (14 mg, 15% yield) as a solid and Compound I-453 (18.4 mg, 21% yield) as a solid. Assignment of trans vs. cis was made in an arbitrary manner at time of synthesis; each diastereomer is a mix of racemates.

$^1$H NMR of Compound I-452 (500 MHz, CD$_3$OD) δ 8.72-8.79 (m, 1H), 8.20-8.25 (m, 1H), 7.41-7.47 (m, 1H), 7.22-7.32 (m, 1H), 6.99-7.14 (m, 2H), 6.87-6.92 (m, 1H), 6.76-6.84 (m, 1H), 5.93-5.99 (m, 2H), 5.59-5.76 (m, 1H), 4.64-4.80 (m, 1H), 3.38-3.46 (m, 1H), 2.55-2.63 (m, 1H), 2.40-2.54 (m, 1H), 2.00-2.08 (m, 1H), 1.84-1.96 (m, 1H), 1.64-1.75 (m, 1H).

$^1$H NMR of Compound I-453 (500 MHz, CD$_3$OD) δ 8.73-8.79 (m, 1H), 8.23-8.33 (m, 1H), 7.43 (s, 1H), 7.24-7.31 (m, 1H), 7.07-7.13 (m, 1H), 7.00-7.06 (m, 1H), 6.82-6.88 (m, 2H), 5.96 (s, 2H), 4.52-4.60 (m, 1H), 4.05-4.14 (m, 1H), 3.75-3.85 (m, 1H), 2.64-2.78 (m, 1H), 2.41-2.49 (m, 1H), 2.12 (dd, 2H), 1.77-1.87 (m, 1H).

Compound I-454

The title compound was prepared following general procedure B, except 3-(trifluoromethyl)piperidine-2-carboxylic acid (5 equiv.) was the amine reactant, and the contents were heated to 90° C. for 18 h as a solution in THF/water (3:1). Solvent removed in vacuo, and the resulting residue was purified via reverse phase HPLC, then with silica gel chromatography utilizing a 0-15% methanol/dichloromethane gradient to deliver the desired compound, Compound I-454 (1.6 mg, 4% yield) as a solid $^1$H NMR (500 MHz, CD$_3$OD) δ ppm 8.76-8.80 (m, 1H), 8.28-8.33 (m, 1H), 7.49 (s, 1H), 7.25-7.32 (m, 1H), 7.02-7.13 (m, 2H), 6.84-6.90 (m, 2H), 5.94-6.00 (m, 2H), 5.37-5.41 (m, 1H), 4.35-4.43 (m, 1H), 3.80-3.89 (m, 1H), 2.89-3.00 (m, 1H), 1.93-2.08 (m, 3H), 1.77-1.90 (m, 1H).

Compound I-455

The title compound was prepared following general procedure B, except 3-ethylpiperidine-2-carboxylic acid (1 equiv.) was the amine reactant, and the contents were heated to 90° C. for 18 h as a solution in THF/water (5:1). Solvent removed in vacuo, and the resulting residue was purified via reverse phase HPLC to deliver the desired compound, Compound I-455 (5 mg, 15% yield) as a solid.

$^1$H NMR (500 MHz, CD$_3$OD) δ ppm 8.81-8.86 (m, 1H), 8.33-8.40 (m, 1H), 7.53-7.59 (m, 1H), 7.27-7.35 (m, 1H), 7.03-7.16 (m, 2H), 6.91-7.00 (m, 2H), 5.99-6.05 (m, 2H), 5.39-5.47 (m, 1H), 4.55-4.68 (m, 1H), 3.78-3.89 (m, 1H), 1.75-2.06 (m, 5H), 1.46-1.60 (m, 2H), 1.07-1.13 (m, 3H).

Compound I-362

The title compound was prepared following general procedure B, except 1-(3-(4-chloro-5-fluoropyrimidin-2-yl)-1-(2-fluorobenzyl)-1H-pyrazol-5-yl)ethanone (described in step 1 towards the synthesis of Compound I-451 was used in place of Intermediate 1, 2-(aminomethyl)-1,1,1,3,3,3-hexafluoropropan-2-ol was the amine reactant, and contents were heated to 100° C. for 36 h as a solution in dioxane. The resulting crude material was purified via silica gel chromatography utilizing a 0-10% methanol/dichloromethane gradient followed by further purification by reverse phase HPLC to deliver the desired compound, Compound I-362 (7 mg, 14% yield) as an off-white solid.

$^1$H-NMR (500 MHz, DMSO-$d_6$) δ ppm 8.54 (s, 1H), 8.36 (d, 1H), 8.07 (br. s., 1H), 7.58-7.69 (m, 1H), 7.33 (q, 1H), 7.16-7.26 (m, 1H), 7.10 (t, 1H), 6.92-7.02 (m, 1H), 5.81 (s, 2H), 4.12 (d, 2H), 2.56 (s, 3H).

Compound I-462

The title compound was prepared following general procedure B, except 1-(3-(4-chloro-5-fluoropyrimidin-2-yl)-1-(2-fluorobenzyl)-1H-pyrazol-5-yl)ethanone (described in step 1 towards the synthesis of Compound I-451 was used in place of Intermediate 1, 2-aminopropane-1,3-diol was the amine reactant, and contents were heated to 100° C. for 36 h as a solution in dioxane. The resulting crude material was purified via silica gel chromatography utilizing a 0-10% methanol/dichloromethane gradient followed by further purification by reverse phase HPLC to deliver the desired compound, Compound I-462 (10 mg, 26% yield) as an off-white solid.

$^1$H-NMR (500 MHz, DMSO-d$_6$) δ ppm 8.18 (d, 1H), 7.65 (d, 1H), 7.33 (q, 1H), 7.21 (dd, 2H), 7.10 (t, 1H), 6.79 (t, 1H), 5.82 (s, 2H), 4.72 (t, 2H), 4.33 (d, 1H), 3.52-3.64 (m, 4H), 2.57 (s, 3H).

Compound I-463

The title compound was prepared following general procedure B, except 1-(3-(4-chloro-5-fluoropyrimidin-2-yl)-1-(2-fluorobenzyl)-1H-pyrazol-5-yl)ethanone (described in step 1 towards the synthesis of Compound I-451 was used in place of Intermediate 1, (2R,3S)-3-methylpiperidine-2-carboxylic acid was the amine reactant, and contents were heated to 100° C. for 36 h as a solution in dioxane. The crude material was purified via silica gel chromatography utilizing a 0-10% methanol/dichloromethane gradient followed by further purification by reverse phase HPLC to deliver the desired compound, Compound I-463 (6.5 mg, 15% yield) as an off-white solid.

$^1$H-NMR (500 MHz, DMSO-d$_6$) δ ppm 8.38 (d, 1H), 7.69 (s, 1H), 7.33 (q, 1H), 7.17-7.27 (m, 1H), 7.11 (t, 1H), 6.77-6.89 (m, 1H), 5.82 (s, 2H), 4.85 (d, 1H), 4.26-4.28 (m, 1H), 3.48-3.57 (m, 1H), 2.56 (s, 3H), 1.98-2.12 (m, 1H), 1.83 (d, 1H), 1.58-1.71 (m, 2H), 1.34-1.47 (m, 1H), 1.11 (d, 3H), COOH protons exchanged.

Compound I-519

2-((Tert-butoxycarbonyl)amino)acetic acid (1 equiv.), HATU (1.1 equiv.), and Hunig's Base (1.3 equiv.) was stirred as a solution in DMF at 23° C. for 2 h. Intermediate 2 (1 equiv.) was then added in a single portion, and contents were heated in the microwave at 100° C. for 30 min. The reaction was quenched by addition of water, extracted with ethyl acetate, and the organic extracts were washed with water and brine. The mixture was dried, filtered, concentrated in vacuo, and purified via silica gel chromatography to deliver the desired compound, Compound I-519 (60 mg, 53% yield) as a yellow solid.

$^1$H-NMR (500 MHz, DMSO-d$_6$) δ ppm 11.03-11.19 (m, 1H), 9.11 (d, 1H), 8.73 (d, 1H), 7.93-8.04 (m, 1H), 7.65 (s, 1H), 7.33 (q, 1H), 7.20-7.29 (m, 2H), 7.06-7.16 (m, 2H), 6.89 (t, 1H), 5.92 (s, 2H), 3.83 (d, 2H), 1.36-1.42 (m, 9H).

Compound I-520

To a solution of Compound I-519 in dichloromethane at 0° C. was added trifluoroacetic acid of equal volume, and contents were allowed to warm to 23° C. over a period of 12 h. Contents were dried in vacuo, and the resulting residue was taken up in saturated NaHCO$_3$ solution and extracted with a mixture of isopropanol/dichloromethane. Contents were dried, filtered, and concentrated in vacuo to deliver the desired compound, Compound I-520 (37 mg, 79% yield) as a brown solid.

$^1$H-NMR (400 MHz, DMSO-d$_6$) δ ppm 9.10 (d, 1H), 8.74 (d, 1H), 8.04 (d, 1H), 7.68 (s, 1H), 7.34 (q, 1H), 7.29 (d, 1H), 7.18-7.26 (m, 1H), 7.11 (t, 1H), 6.88 (t, 1H), 5.93 (s, 2H), 3.36 (s, 2H), NH protons were exchanged.

Compound I-535

To a solution of Compound I-520 (1 equiv.) and triethylamine (2 equiv.) in dichloromethane maintained at 0° C. was added acetyl chloride (1.2 equiv.), and the resulting mixture was allowed to warm to 23° C., over a period of 18 h. The solvents were removed in vacuo, and the resulting residue was triturated with a mixture of ethyl acetate/hexanes. Contents were filtered, and the resulting solid was dried in vacuo to deliver the desired compound, Compound I-535 (6 mg, 53% yield) as a white solid.

$^1$H-NMR (500 MHz, DMSO-d$_6$) δ ppm 11.18 (s, 1H), 9.11 (d, 1H), 8.73 (d, 1H), 8.22 (t, 1H), 7.98 (d, 1H), 7.66 (s, 1H), 7.30-7.39 (m, 1H), 7.27 (d, 1H), 7.20-7.26 (m, 1H), 7.12 (td, 1H), 6.89 (t, 1H), 5.93 (s, 2H), 3.97 (d, 2H), 1.83-1.93 (m, 3H).

Compound I-543

To a solution of Compound I-520 (1 equiv.) and triethylamine (6 equiv.) in dichloromethane maintained at 0° C. was added methanesulfonyl chloride (3.3 equiv.), and the resulting mixture was allowed to warm to 23° C. over a period of 3 h. The reaction was quenched by addition of water, and the mixture was extracted with dichloromethane. Contents were dried, concentrated in vacuo, and purified via silica gel chromatography to deliver the desired compound, Compound I-543 (6.2 mg, 47% yield) as a white solid.

$^1$H-NMR (500 MHz, DMSO-d$_6$) δ ppm 11.17 (s, 1H), 9.11 (d, 1H), 8.76 (d, 1H), 8.00 (d, 1H), 7.66 (s, 1H), 7.54 (t, 1H), 7.30-7.39 (m, 1H), 7.27 (d, 1H), 7.21-7.26 (m, 1H), 7.12 (t, 1H), 6.89 (t, 1H), 5.93 (s, 2H), 3.99 (d, 2H), 2.98 (s, 3H).

Compound I-584

To a solution of Compound I-520 (1 equiv.) in dichloromethane was added isocyanatotrimethylsilane (1.1 equiv.), and the resulting suspension was heated to 40° C. for 18 h. After the reaction was complete, the solvent was removed in vacuo, and the resulting residue was purified via reverse phase HPLC to deliver the desired compound, Compound I-584 (16 mg, 55% yield) as a white solid.

$^1$H-NMR (500 MHz, DMSO-d$_6$) δ ppm 11.02 (s, 1H), 9.10 (d, 1H), 8.73 (d, 1H), 7.99 (d, 1H), 7.59-7.68 (m, 1H), 7.30-7.37 (m, 1H), 7.19-7.27 (m, 2H), 7.12 (t, 1H), 6.89 (t, 1H), 6.25 (t, 1H), 5.93 (s, 2H), 5.72 (s, 2H), 3.90 (d, 2H).

Compound I-585

To a solution of Compound I-520 (1 equiv.) in dichloromethane was added isopropyl isocyanate (1.1 equiv.), and the resulting mixture was heated to 40° C. for 18 h. After the reaction was complete, the solvents were removed in vacuo and the resulting residue was purified via reverse phase HPLC to deliver the desired compound, Compound I-585 (19 mg, 59% yield) as a white solid.

$^1$H-NMR (500 MHz, DMSO-d$_6$) δ ppm 11.04 (s, 1H), 9.10 (d, 1H), 8.72 (d, 1H), 7.98 (d, 1H), 7.64 (s, 1H), 7.30-7.38 (m, 1H), 7.19-7.28 (m, 2H), 7.12 (td, 1H), 6.85-6.95 (m, 1H), 6.09 (d, 1H), 6.01 (t, 1H), 5.92 (s, 2H), 3.92 (d, 2H), 3.58-3.71 (m, 1H), 1.03 (d, 6H).

Compound I-586

To a solution of Compound I-520 (1 equiv.) and triethylamine (2 equiv.) in dichloromethane was added dimethylsulfamoyl chloride (1.5 equiv.), and the mixture was heated at 40° C. for 18 h. After the reaction was complete, the solvents were removed in vacuo, and the resulting residue was purified via reverse phase HPLC to deliver the desired compound, Compound I-586 (9 mg, 28% yield) as a white solid.

$^1$H-NMR (500 MHz, DMSO-d$_6$) δ ppm 11.12 (s, 1H), 9.10 (d, 1H), 8.75 (d, 1H), 8.00 (d, 1H), 7.64 (s, 1H), 7.58 (t, 1H), 7.30-7.38 (m, 1H), 7.19-7.27 (m, 2H), 7.12 (td, 1H), 6.90 (t, 1H), 5.92 (s, 2H), 3.92 (d, 2H), 2.67 (s, 6H).

Compound I-633

The title compound was prepared following general procedure B, except (3-(trifluoromethyl)-5,6,7,8-tetrahydro-[1,2,4]triazolo[4,3-a]pyrazin-6-yl)methanol was the amine reactant, and the contents were heated to 100° C. for 48 h as a solution in THF/dioxane/water (1:10:1). The crude material was purified via silica gel chromatography utilizing a 0-10% methanol/dichloromethane gradient followed by reverse phase HPLC to deliver the desired compound, Compound I-633 (6 mg, 36% yield) as an off-white solid.

$^1$H-NMR (500 MHz, DMSO-d$_6$) δ ppm 9.11 (d, 1H), 8.46 (d, 1H), 7.67 (s, 1H), 7.30-7.38 (m, 1H), 7.28 (d, 1H), 7.19-7.25 (m, 1H), 7.11 (t, 1H), 6.85 (t, 1H), 5.88-5.98 (m, 2H), 5.61 (d, 1H), 5.20 (t, 1H), 5.13 (br. s., 1H), 4.82 (d, 1H), 4.38-4.51 (m, 2H), 3.64 (dt, 1H), 3.50-3.59 (m, 1H).

Compound I-466

The title compound was prepared following general procedure B, except 2,2,2-trifluoroethanamine (as the HCl salt) was the amine reactant, and the contents were heated to 90-100° C. for 42 h. The crude material was purified via preparative HPLC utilizing a 25-80% acetonitrile/water gradient (with 0.1% TFA) to deliver the desired compound, Compound I-466 (35 mg, 60% yield) as a white solid.

$^1$H-NMR (500 MHz, CD$_3$OD) δ ppm 8.76 (d, 1H), 8.20 (d, 1H), 7.46 (s, 1H), 7.28 (app. q, 1H), 7.10 (m, 1H), 7.03 (app. t, 1H), 6.92 (d, 1H), 6.80 (app. t, 1H), 5.97 (s, 2H), 4.44 (q, 2H).

Compound I-487

The title compound was prepared following general procedure B, except 2-(methylsulfonyl)ethanamine (as the HCl salt) was the amine reactant, and the contents were heated to 100° C. for 17 h. The contents were cooled to ambient temperature, diluted with water and acidified to pH 3 with 1N HCl solution. The resulting precipitate was filtered and dried in vacuo to deliver the desired compound, Compound I-487 (56 mg, 91% yield) as a white solid.

$^1$H-NMR (500 MHz, DMSO-d$_6$) δ ppm 9.10 (d, 1H), 8.24 (d, 1H), 7.93 (br. t, 1H), 7.54 (s, 1H), 7.33 (app. q, 1H), 7.22 (m, 1H), 7.18 (d, 1H), 7.11 (app. t, 1H), 6.88 (app. t, 1H), 5.89 (s, 2H), 3.87 (dt, 2H), 3.46 (t, 2H), 3.06 (s, 3H).

Compound I-502

The title compound was prepared following general procedure B, except (1-aminocyclopropyl)methanol (as the HCl salt) was the amine reactant, and the contents were heated to 100° C. for 6.5 h. The crude material was purified via silica gel chromatography utilizing a 15% acetonitrile-methanol (7:1) in dichloromethane gradient to deliver the desired compound, Compound I-502 (54 mg, 90% yield) as a white solid.

$^1$H-NMR (500 MHz, DMSO-d$_6$) δ ppm 9.10 (d, 1H), 8.18 (d, 1H), 8.00 (s, 1H), 7.41 (s, 1H), 7.33 (app. q, 1H), 7.24-7.20 (m, 1H), 7.22 (d, 1H), 7.11 (app. t, 1H), 6.89 (app. t, 1H), 5.86 (s, 2H), 4.89 (t, 1H), 3.63 (d, 2H), 0.85 (m, 2H), 0.77 (m, 2H).

Compound I-581

The title compound was prepared following general procedure B, except 3-aminopropanamide (as the HCl salt) was the amine reactant, and the contents were heated to 100° C. for 21 h. The contents were cooled to ambient temperature, diluted with water and acidified to pH 4 with 1N HCl solution. The resulting precipitate was filtered and dried in vacuo to deliver the desired compound, Compound I-581 (66 mg, 89% yield) as a white solid.

$^1$H-NMR (500 MHz, DMSO-d$_6$) δ ppm 9.08 (d, 1H), 8.17 (d, 1H), 7.65 (t, 1H), 7.50 (s, 1H), 7.34 (br. s, 1H), 7.32 (app. q, 1H), 7.24-7.18 (m, 1H), 7.21 (d, 1H), 7.10 (app. t, 1H), 6.86 (br. s, 1H), 6.84 (m, 1H), 5.90 (s, 2H), 3.67 (dt, 2H), 2.45 (t, 2H).

Compound I-515

A solution of Compound I-358 in dichloromethane was treated with N,N-diisopropylethylamine (2 equiv.) followed by O-(7-azabenzotriazol-1-yl)-N,N,N',N'-tetramethyluronium hexafluorophosphate (HATU, 1.5 equiv.). After 1 h, ammonia (0.5N solution in dioxane, 3 equiv.) was added and the light brownish orange solution was stirred for 21 h. The resultant light tan suspension was diluted with water and extracted with dichloromethane. The organic phases were dried over sodium sulfate, filtered and the solvent was removed in vacuo. The crude material was purified via silica gel chromatography utilizing a 10-15% acetonitrile-methanol (7:1) in dichloromethane gradient to deliver the desired compound, Compound I-515 (36 mg, 73% yield) as a white solid.

$^1$H-NMR (500 MHz, CD$_3$OD) δ ppm 8.76 (s, 1H), 8.10 (d, 1H), 7.42 (s, 1H), 7.28 (app. q, 1H), 7.10 (m, 1H), 7.05 (app. t, 1H), 6.90 (s, 1H), 6.89 (m, 1H), 5.96 (s, 2H), 3.88 (s, 2H), 1.20 (m, 2H), 1.02 (m, 2H).

Compound I-536

A solution of Compound I-86 in dichloromethane was treated with N,N-diisopropylethylamine (2 equiv.) followed by HATU (1.5 equiv.). After 1 h, ammonia (0.5 N solution in dioxane, 3 equiv.) was added and the reaction was stirred for 24 h. The resultant mixture was diluted with water and extracted with dichloromethane. The organic phases were dried over sodium sulfate, filtered and the solvent was removed in vacuo. The crude material was purified via silica gel chromatography utilizing a 10-25% acetonitrile-methanol (7:1) in dichloromethane gradient to deliver the desired compound, Compound I-536 (33 mg, 81% yield) as an off-white solid.

$^1$H-NMR (500 MHz, CDCl$_3$) δ ppm 8.47 (d, 1H), 8.15 (d, 1H), 7.28 (s, 1H), 7.22 (app. q, 1H), 7.03 (app. t, 1H), 6.99 (app. t, 1H), 6.94 (app. t, 1H), 6.61 (d, 1H), 6.56 (br. s, 1H), 5.99 (d, 1H), 5.89 (d, 1H), 5.60 (d, 1H), 5.50 (br. s, 1H), 4.57 (app. t, 1H), 2.32 (m, 1H), 1.09 (d, 3H), 1.07 (d, 3H).

Compound I-537

A solution of Compound I-69 in dichloromethane was treated with N,N-diisopropylethylamine (2 equiv.) followed by HATU (1.5 equiv.). After 1 h, ammonia (0.5 N solution in dioxane, 3 equiv.) was added and the reaction was stirred for 24 h. The resultant mixture was diluted with water and extracted with dichloromethane. The organic phases were dried over sodium sulfate, filtered and the solvent was removed in vacuo. The crude material was purified via silica gel chromatography utilizing a 10-25% acetonitrile-methanol (7:1) in dichloromethane gradient to deliver the desired compound, Compound I-537 (27 mg, 65% yield) as a white solid.

$^1$H-NMR (500 MHz, DMSO-d$_6$) δ ppm 9.11 (d, 1H), 8.23 (d, 1H), 7.57 (br. s, 1H), 7.53 (s, 1H), 7.38-7.30 (m, 2H), 7.24-7.16 (m, 2H), 7.16 (d, 1H), 7.10 (app. t, 1H), 6.85 (app. t, 1H), 5.87 (s, 2H), 4.42 (app. t, 1H), 2.20 (m, 1H), 0.97 (app. t, 6H).

Compound I-538

A solution of Compound I-85 in dichloromethane was treated with N,N-diisopropylethylamine (2 equiv.) followed by HATU (1.5 equiv.). After 1 h, ammonia (0.5 N solution in dioxane, 3 equiv.) was added and the reaction was stirred for 24 h. The resultant mixture was diluted with water and extracted with dichloromethane. The organic phases were dried over sodium sulfate, filtered and the solvent was removed in vacuo. The crude material was purified via silica gel chromatography utilizing a 10-25% acetonitrile-methanol (7:1) in dichloromethane gradient to deliver the desired compound, Compound I-538 (36 mg, 86% yield) as a white solid.

$^1$H-NMR (500 MHz, DMSO-d$_6$) δ ppm 9.10 (d, 1H), 8.22 (m, 2H), 7.40 (br. s, 1H), 7.36-7.28 (m, 2H), 7.23 (m, 1H), 7.15 (s, 1H), 7.11 (app. t, 1H), 6.98 (br. s, 1H), 6.86 (app. t, 1H), 5.86 (s, 2H), 1.42 (m, 2H), 1.02 (m, 2H).

Compound I-546

A suspension of Compound I-67 in dichloromethane was treated with di(1H-imidazol-1-yl)methanone (CDI, 3 equiv.) and the resultant mixture was heated at 45° C. for 1 h 40 min. After cooling to ambient temperature, methanesulfonamide (5 equiv.) and 1,8-diazabicyclo[5.4.0]undec-7-ene (DBU, 1 equiv.) were added and the reaction was heated at 45° C. for 1 h. The resultant mixture was cooled to ambient temperature, quenched with 1N HCl solution and extracted with dichloromethane/isopropanol (4:1). The crude solid was dissolved in water with the aid of 1N NaOH solution and acidified to pH 3-4 by dropwise addition of 1N HCl. The resulting precipitate was filtered and dried in vacuo to deliver the desired compound, Compound I-546 (39 mg, 80% yield) as a tan solid.

$^1$H-NMR (500 MHz, DMSO-$d_6$) δ ppm 12.1 (s, 1H), 9.11 (d, 1H), 8.27 (d, 1H), 8.17 (br. s, 1H), 7.52 (s, 1H), 7.32 (app. q, 1H), 7.22 (m, 1H), 7.12 (d, 1H), 7.10 (m, 1H), 6.79 (app. t, 1H), 5.88 (s, 2H), 4.12 (d, 2H), 3.17 (s, 3H).

Compound I-566

The title compound was synthesized in 4 steps:

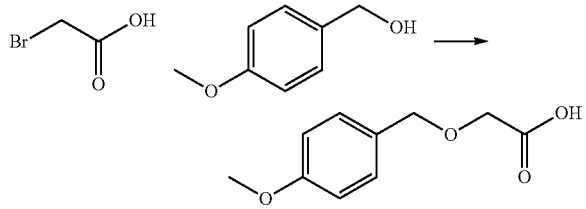

Step 1: Synthesis of 2-((4-methoxybenzyl)oxy)acetic Acid

To a solution of (4-methoxyphenyl)methanol (1 equiv.) and 2-bromoacetic acid (1.2 equiv.) in anhydrous THF at 0° C. was added sodium hydride (60% w/w in mineral oil, 3 equiv.) in 3 portions. The mixture was stirred at 70° C. for 4 h. After cooling to ambient temperature, water was added the resultant mixture was washed with hexanes. The aqueous phase was acidified to pH 2 with 1N HCl and extracted with ethyl acetate. The organic layer was dried, filtered and the solvent was removed in vacuo. Purification via silica gel chromatography with 50% ethyl acetate in hexanes delivered 2-((4-methoxybenzyl)oxy)acetic acid (0.51 g, 71% yield) as a clear solid.

$^1$H NMR (500 MHz, CDCl$_3$) δ ppm 7.29 (m, 2H), 6.90 (m, 2H), 4.59 (s, 2H), 4.10 (s, 2H), 3.81 (s, 3H).

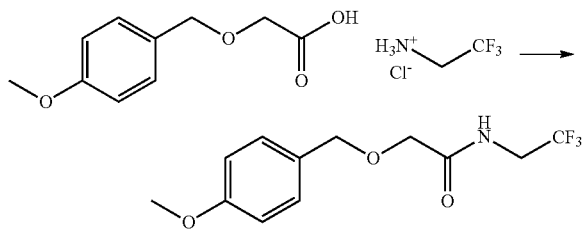

Step 2: Synthesis of 2-((4-methoxybenzyl)oxy)-N-(2,2,2-trifluoroethyl)acetamide

A solution of 2-((4-methoxybenzyl)oxy)acetic acid (1 equiv.) in dichloromethane was treated with N,N-diisopropylethylamine (1.5 equiv.) followed by HATU (1.2 equiv.). After 30 min, N,N-diisopropylethylamine (2 equiv.) and 2,2,2-trifluoroethanamine hydrochloride (2 equiv.) were added and the reaction was stirred for 17 h. The resultant mixture was diluted with water and extracted with dichloromethane. The organic phases were dried over sodium sulfate, filtered and the solvent was removed in vacuo. The crude material was purified via silica gel chromatography utilizing a 10-20% ethyl acetate/hexanes gradient to deliver 2-((4-methoxybenzyl)oxy)-N-(2,2,2-trifluoroethyl)acetamide (0.28 g, 78% yield) as a white solid.

$^1$H NMR (500 MHz, CDCl$_3$) δ ppm 7.26 (d, 2H), 6.91 (d, 2H), 6.89 (br. s, 1H), 4.52 (s, 2H), 4.02 (s, 2H), 3.93 (dq, 2H), 3.82 (s, 3H).

Step 3: Synthesis of N-(5-fluoro-2-(1-(2-fluorobenzyl)-5-(isoxazol-3-yl)-1H-pyrazol-3-yl)pyrimidin-4-yl)-2-((4-methoxybenzyl)oxy)-N-(2,2,2-trifluoroethyl)acetamide A suspension of 3-(3-(4-chloro-5-fluoropyrimidin-2-yl)-1-(2-fluorobenzyl)-1H-pyrazol-5-yl)isoxazole (1 equiv.), 2-((4-methoxybenzyl)oxy)-N-(2,2,2-trifluoroethyl)acetamide (1 equiv.) and cesium carbonate (0.8 equiv.) in anhydrous dioxane was heated at 100° C. for 4 d. The resultant mixture was poured into half-saturated sodium bicarbonate solution and extracted with ethyl acetate. The organic phase was dried over sodium sulfate, filtered and the solvent was removed in vacuo. The crude material was purified via silica gel chromatography utilizing a 10-20% ethyl acetate/hexanes gradient to deliver N-(5-fluoro-2-(1-(2-fluorobenzyl)-5-(isoxazol-3-yl)-1H-pyrazol-3-yl)pyrimidin-4-yl)-2-((4-methoxybenzyl)oxy)-N-(2,2,2-trifluoroethyl)acetamide (16 mg, 12% yield) as a clear oil.

$^1$H NMR (500 MHz, CDCl$_3$) δ ppm 8.65 (d, 1H), 8.49 (d, 1H), 7.32 (s, 1H), 7.22 (app. q, 1H), 7.07-6.96 (m, 4H), 6.89 (app. t, 1H), 6.73 (d, 2H), 6.60 (d, 1H), 6.01 (s, 2H), 4.68 (q, 2H), 4.33 (s, 2H), 4.31 (s, 2H), 3.71 (s, 3H).

Step 4: Synthesis of Compound I-566

A biphasic solution of N-(5-fluoro-2-(1-(2-fluorobenzyl)-5-(isoxazol-3-yl)-1H-pyrazol-3-yl)-pyrimidin-4-yl)-2-((4-methoxybenzyl)oxy)-N-(2,2,2-trifluoroethyl)acetamide (1 equiv.) in dichloromethane/water (10:1) was treated with 2,3-dichloro-5,6-dicyano-p-benzoquinone (DDQ, 1.2 equiv.) and stirred for 20 h. Additional amounts of DDQ (2.4 equiv.) were added and the reaction was stirred for 5 d. The reaction mixture was diluted with dichloromethane and filtered. The crude solution was dried over sodium sulfate, filtered, and the solvent was removed in vacuo. The crude material was purified via silica gel chromatography utilizing a 15-50% ethyl acetate/hexanes gradient to deliver the desired compound, Compound I-566 (2.6 mg, 45% yield) as a white solid.

$^1$H-NMR (500 MHz, CD$_3$OD) δ ppm 8.78 (d, 1H), 8.55 (d, 1H), 7.44 (s, 1H), 7.26 (app. q, 1H), 7.09 (m, 1H), 7.03 (app. t, 1H), 6.87 (d, 1H), 6.80 (app. t, 1H), 5.97 (s, 2H), 5.16 (s, 2H), 3.94 (q, 2H).

Compound I-457

The title compound was synthesized in 2 steps:

Step 1: Synthesis of 3-(4-chloro-5-fluoropyrimidin-2-yl)-1-(2-fluorobenzyl)-1H-pyrazole-5-carbonitrile A suspension of 3-(5-fluoro-6-oxo-1,6-dihydropyrimidin-2-yl)-1-(2-fluorobenzyl)-1H-pyrazole-5-carbonitrile (this compound was described in previous patent application publication WO2013/101830) in phosphoryl trichloride (50 equiv.) as solvent was heated to 65° C. for 2 h 15 min. The reaction mixture was blown dried under a stream of nitrogen and then concentrated twice from toluene. The resultant reddish brown oil/solid was dried in vacuo and used in the next step without further manipulation.

Step 2: Synthesis of Compound I-457

The title compound was prepared following general procedure B, except 3-(4-chloro-5-fluoropyrimidin-2-yl)-1-(2- fluorobenzyl)-1H-pyrazole-5-carbonitrile was the chloropyrimidine reactant and (2R,3S)-3-methylpiperidine-2-carboxylic acid was the amine reactant, and the contents were heated to 100° C. for 18 h. The contents were cooled to ambient temperature, diluted with water, acidified to pH 3 with 1N HCl solution and extracted with dichloromethane. The organic phases were dried over sodium sulfate, filtered and the solvent was removed in vacuo. The crude material was purified via reverse phase HPLC utilizing a 25-80% acetonitrile/water gradient (with 0.1% TFA) to deliver the desired compound, Compound I-457 (18 mg, 38% yield over 2 steps) as a white solid.

$^1$H-NMR (500 MHz, CD$_3$OD) δ ppm 8.32 (d, 1H), 7.65 (s, 1H), 7.41 (app. q, 1H), 7.36 (app. t, 1H), 7.23-7.13 (m, 2H), 5.71 (s, 2H), 5.17 (d, 1H), 4.48 (br. d, 1H), 3.78 (app. t, 1H), 2.13 (m, 1H), 1.94 (m, 1H), 1.78 (m, 2H), 1.54 (m, 1H), 1.22 (d, 3H).

Compound I-474

The title compound was prepared following general procedure B, except 3-(4-chloro-5-fluoropyrimidin-2-yl)-1-(2-fluorobenzyl)-1H-pyrazole-5-carbonitrile (generated in step 1 towards the synthesis of Compound I-457 was used in place of Intermediate 1, 2-(aminomethyl)-1,1,1,3,3,3-hexafluoropropan-2-ol was the amine reactant, and the contents were heated to 100° C. for 16 h. The contents were cooled to ambient temperature, diluted with water, acidified to pH 3 with 1N HCl solution and extracted with dichloromethane. The organic phases were dried over sodium sulfate, filtered and the solvent was removed in vacuo. The crude material was purified via reverse phase HPLC utilizing a 25-80% acetonitrile/water gradient (with 0.1% TFA) to deliver the desired compound, Compound I-474 (31 mg, 49% yield over 2 steps from 3-(5-fluoro-6-oxo-1,6-dihydropyrimidin-2-yl)-1-(2-fluorobenzyl)-1H-pyrazole-5-carbonitrile) as a white solid.

$^1$H-NMR (500 MHz, CDCl$_3$) δ ppm 8.30 (s, 1H), 7.49 (app. t, 1H), 7.38 (s, 1H), 7.35 (app. q, 1H), 7.17 (app. t, 1H), 7.12 (app. t, 1H), 5.65 (br. s, 1H), 5.60 (s, 2H), 4.12 (d, 2H). One of the exchangeable protons was not observed.

Compound I-480

The title compound was prepared following general procedure B, except 3-(4-chloro-5-fluoropyrimidin-2-yl)-1-(2-fluorobenzyl)-1H-pyrazole-5-carbonitrile (generated in step 1 towards the synthesis of Compound I-457 was used in place of Intermediate 1, and 1-(1-carboxycyclopropyl)-N-methylmethanamine (as the HCl salt) was the amine reactant, and the contents were heated to 100° C. for 17 h. The contents were cooled to ambient temperature, diluted with water, acidified to pH 3 with 1N HCl solution and extracted with dichloromethane. The organic phases were dried over sodium sulfate, filtered and the solvent was removed in vacuo. The crude material was purified via preparative HPLC utilizing a 15-70% acetonitrile/water gradient (with 0.1% TFA) to deliver the desired compound, Compound I-480 (90 mg, 66% yield over 2 steps from 3-(5-fluoro-6-oxo-1,6-dihydropyrimidin-2-yl)-1-(2-fluorobenzyl)-1H-pyrazole-5-carbonitrile) as an off-white solid.

$^1$H-NMR (500 MHz, DMSO-d$_6$) δ ppm 12.3 (br. s, 1H), 8.24 (d, 1H), 7.66 (s, 1H), 7.44 (app. q, 1H), 7.36 (app. t, 1H), 7.30-7.22 (m, 2H), 5.65 (s, 2H), 3.99 (s, 2H), 3.24 (d, 3H), 1.13 (m, 2H), 1.01 (m, 2H).

Compound I-476

A solution of Compound I-474 in 1 N NaOH solution (excess) was heated at 65° C. for 70 min. The reaction mixture was cooled to ambient temperature and acidified to pH 3 with 1N HCl solution. The resulting precipitate was filtered and dried in vacuo to deliver the desired compound, Compound I-476 (13 mg, 77% yield) as a white solid.

$^1$H-NMR (500 MHz, DMSO-d$_6$) δ ppm 8.50 (s, 1H), 8.34 (d, 1H), 8.03 (br. t, 1H), 7.35 (app. q, 1H), 7.32 (s, 1H), 7.22 (m, 1H), 7.13 (app. t, 1H), 7.02 (app. t, 1H), 5.87 (s, 2H), 4.13 (d, 2H). The exchangeable carboxylic acid proton was not observed.

Compound I-481

A suspension of Compound I-480 in water was treated with 1 N NaOH solution (2 equiv.) and stirred at ambient temperature for 18 h. The reaction mixture was acidified to pH 3 with 1N HCl solution. The resulting precipitate was filtered and dried in vacuo to deliver the desired compound, Compound I-481 (7.4 mg, 64% yield) as a white solid.

$^1$H-NMR (500 MHz, DMSO-d$_6$) δ ppm 12.3 (br. s, 1H), 8.22 (d, 1H), 8.14 (br. s, 1H), 7.60 (br. s, 1H), 7.53 (s, 1H), 7.33 (app. q, 1H), 7.21 (m, 1H), 7.12 (app. t, 1H), 6.90 (app. t, 1H), 5.90 (s, 2H), 3.99 (s, 2H), 3.24 (d, 3H), 1.14 (m, 2H), 1.02 (m, 2H).

Compound I-327

To a mixture containing 1,2-diethoxycyclobutenedione (1.3 equiv.) and sodium hydride [60% dispersion in mineral oil] (1 equiv.) in THF was added Intermediate 2 (1 equiv.). The mixture was stirred at 0° C. for 1 h, then removed from the ice bath and allowed to stir at 23° C. for 24 h. The mixture was diluted with ethyl acetate and washed with 1N HCl solution. The organic layer was dried over MgSO$_4$, filtered and evaporated to give a solid. The crude material was purified via silica gel chromatography utilizing a 0-100% ethyl acetate/hexanes gradient to deliver the desired compound, Compound I-327 (90 mg, 43% yield) as a light yellow solid.

$^1$H NMR (400 MHz, DMSO-d$_6$) δ ppm 9.12 (d, 1H), 8.69 (d, 1H), 7.67 (s, 1H), 7.30-7.38 (m, 1H), 7.29 (d, 1H), 7.24 (d, 1H), 7.20 (d, 1H), 7.09-7.15 (m, 1H), 6.86-6.92 (m, 1H), 5.92 (s, 2H), 4.81 (q, 2H), 1.36 (t, 3H).

Compound I-402

A mixture of Compound I-327 (1 equiv.) and HCl [1.0 M aqueous solution] (1 equiv.) in MeOH was heated to 65° C. for 2 h. Upon cooling the mixture to 23° C. a yellow precipitate formed, which was collected via filtration and rinsed with a minimal amount of methanol. The precipitate collected was dried under vacuum to deliver the desired compound, Compound I-402 (50 mg, 76% yield) as a yellow solid.

$^1$H NMR (500 MHz, DMSO-d$_6$) δ ppm 9.08-9.17 (m, 1H), 8.64 (d, 1H), 7.73 (s, 1H), 7.30-7.42 (m, 1H), 7.28 (s, 1H), 7.17-7.26 (m, 2H), 7.12 (t, 1H), 6.90-7.04 (m, 1H), 5.85-6.03 (m, 2H).

Compound I-456

To a cold solution of triethylamine (1.5 equiv.) in dichloromethane at 0° C. was added chlorosulfonyl isocyanate (1.5 equiv.). The mixture was stirred at 0° C. for 30 min. To this mixture was added Intermediate 2 (1 equiv.) and tert-butanol (1.5 equiv.), and contents were stirred at 23° C. for 24 h. The mixture was diluted with ethyl acetate and washed with water. The precipitate was removed by filtration. The organic layer was dried over MgSO$_4$, filtered, and concentrated in vacuo to yield a crude oil, which was purified via silica gel chromatography utilizing a 0-100% ethyl acetate/hexanes gradient to deliver tert-butyl N-(2-(1-(2-fluorobenzyl)-5-(isoxazol-3-yl)-1H-pyrazol-3-yl)pyrimidin-4-yl)sulfamoylcarbamate, the desired Boc-protected sulfamide intermediate. This intermediate was dissolved in methanol and treated with HCl [a 4.0 M solution in 1,4-dioxane] (5 equiv.) and stirred at 23° C. for 24 h. The mixture was concentrated in vacuo to deliver the desired compound, Compound I-456 (26 mg, 6% yield, HCl salt) as a white solid.

¹H NMR (500 MHz, CD₃OD) δ ppm 8.85 (d, 1H), 8.54 (d, 1H), 7.88 (s, 1H), 7.26-7.34 (m, 2H), 7.00-7.14 (m, 4H), 6.05-6.08 (m, 2H).

Compound I-467

The title compound was synthesized in 3 steps:

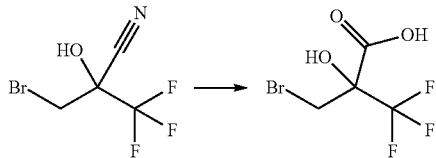 [SMILES: N#CC(O)(CBr)C(F)(F)F ; O=C(O)C(O)(CBr)C(F)(F)F]

Step 1: Synthesis of 2-(bromomethyl)-3,3,3-trifluoro-2-hydroxypropanoic Acid

A mixture of 2-(bromomethyl)-3,3,3-trifluoro-2-hydroxypropanenitrile (1 equiv.), water (1 equiv.) and concentrated sulfuric acid (4 equiv.) was heated to 110° C. in a sealed vial for 1 h. The mixture was poured over ice and extracted with diethyl ether. The organic layer was dried over MgSO₄, filtered, and concentrated in vacuo to deliver 2-(bromomethyl)-3,3,3-trifluoro-2-hydroxypropanoic acid (1.3 g, 33% yield) as a clear oil.

¹H NMR (500 MHz, CDCl₃) δ ppm 3.89 (d, 1H), 3.63-3.69 (m, 1H).

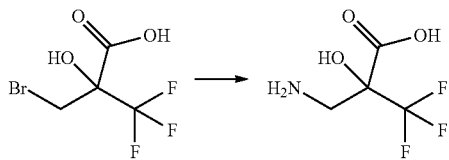 [SMILES: O=C(O)C(O)(CBr)C(F)(F)F ; NCC(O)(C(=O)O)C(F)(F)F]

Step 2: Synthesis of 2-(aminomethyl)-3,3,3-trifluoro-2-hydroxypropanoic acid

A mixture of ammonium hydroxide [28% solution in water] (10 equiv.) and 2-(bromomethyl)-3,3,3-trifluoro-2-hydroxypropanoic acid (1 equiv.) was stirred at 23° C. for 24 h. The mixture was concentrated in vacuo. The resulting solid was treated with a minimal amount of ethanol. The precipitate was collected by filtration and dried under vacuum to deliver 2-(aminomethyl)-3,3,3-trifluoro-2-hydroxypropanoic acid (412 mg, 43% yield) as a white solid.

¹H NMR (500 MHz, DMSO-d₆) δ ppm 2.86-3.27 (m, 2H).

Step 3: Synthesis of Compound I-467

The title compound was prepared following general procedure B, except 2-(aminomethyl)-3,3,3-trifluoro-2-hydroxypropanoic acid (4 equiv.) was the amine reactant, 6 equivalents of triethylamine was used, and contents were heated to 85° C. as a solution in 1,4-dioxane/water (4:1) for 24 h. The mixture was cooled to 23° C. and diluted with ethyl acetate. The organic layer was washed with saturated solution of ammonium chloride, dried over MgSO₄, filtered, and concentrated in vacuo to yield a crude solid. The crude material was purified via silica gel chromatography utilizing a 0-100% ethyl acetate/hexanes gradient to deliver the desired compound, Compound I-467 (50 mg, 7% yield for step 3) as a white solid.

¹H NMR (500 MHz, DMSO-d₆) δ ppm 8.28 (d, 1H), 7.59 (t, 1H), 7.46 (s, 1H), 7.30-7.36 (m, 1H), 7.16-7.24 (m, 2H), 7.10 (t, 1H), 6.91 (d, 1H), 5.88 (s, 2H), 4.24 (dd, 1H), 3.84 (dd, 1H).

Compound I-468

A mixture of CDI (6 equiv.) and 3,3,3-trifluoro-2-hydroxy-2-(trifluoromethyl)propanoic acid (6 equiv.) in THF was heated to 90° C. for 1 h. To this mixture, was added 2-(1-(2-fluorobenzyl)-5-(isoxazol-3-yl)-1H-pyrazol-3-yl)-5-morpholinopyrimidin-4-amine (this intermediate was described in previously published patent application WO2012/3405A1; 1 equiv.). The mixture was stirred at 90° C. for 24 h. The mixture was diluted in ethyl acetate and washed with 1N HCl solution. The organic layer was dried over MgSO₄, filtered and evaporated to give a crude oil. The oil was purified via silica gel chromatography utilizing a 0-100% ethyl acetate/hexanes gradient to deliver the desired compound, Compound I-468 (18 mg, 62%) as a light yellow solid.

¹H NMR (500 MHz, CD₃OD) δ ppm 8.76 (d, 1H), 8.64 (s, 1H), 7.60-7.63 (m, 1H), 7.20-7.26 (m, 1H), 7.00-7.06 (m, 1H), 6.98 (t, 1H), 6.92 (d, 1H), 6.74-6.83 (m, 1H), 5.93 (s, 2H), 3.88-3.92 (m, 4H), 3.04-3.09 (m, 4H).

Compound I-473

To a mixture of 5-fluoro-2-(1-(2-fluorobenzyl)-5-(isoxazol-3-yl)-1H-pyrazol-3-yl)-pyrimidin-4-amine (this intermediate was described in previously published patent application WO2012/3405 A1, 1 equiv.) and 3,3,3-trifluoro-2-(trifluoromethyl)-2-((trimethylsilyl)oxy)propanoyl chloride (3 equiv.) [prepared according to the procedure described in Aicher, T. D. et al. J. Med. Chem. 2000, 43, 245, Method J.] in THF at 23° C., was added, very slowly, LiHMDS (2.0 M in THF, 3 equiv.). The exothermic reaction turned dark brown immediately. The mixture was stirred at 23° C. for 1 h, then diluted in ethyl acetate and washed with 1N HCl solution. The precipitate was removed by filtration. The organic layer was dried over MgSO₄, filtered, and concentrated in vacuo to give a crude oil. The oil was purified via silica gel chromatography utilizing a 0-30% ethyl acetate/hexanes gradient to deliver the desired compound, Compound I-473 (11 mg, 3% yield) as a yellow solid.

¹H NMR (500 MHz, CD₃OD) δ ppm 8.83 (d, 1H), 8.80 (s, 1H), 7.60 (s, 1H), 7.27-7.33 (m, 1H), 7.09-7.15 (m, 1H), 7.06 (t, 1H), 6.94 (d, 1H), 6.90 (t, 1H), 6.00 (s, 2H).

Compound I-477

To a mixture of 5-fluoro-2-(1-(2-fluorobenzyl)-5-(isoxazol-3-yl)-1H-pyrazol-3-yl)-pyrimidin-4-amine (described in WO2012/3405 A1, 1 equiv.) and morpholine-4-carbonyl chloride (1.2 equiv.) in THF at 23° C., was added, very slowly, LiHMDS (2.0 M in THF, 1.2 equiv.). The mixture was stirred at 23° C. for 24 h. The mixture was diluted in ethyl acetate and washed with 1N HCl solution. The organic layer was dried over MgSO₄, filtered and evaporated to give a crude oil. The oil was purified via silica gel chromatography utilizing a 0-5% methanol/DCM gradient to deliver the desired product, Compound I-477 (24 mg, 18% yield) as a light yellow solid.

¹H NMR (500 MHz, CD₃OD) δ ppm 8.49-8.54 (m, 1H), 7.47 (s, 1H), 7.33-7.42 (m, 1H), 7.23-7.30 (m, 1H), 7.12-7.22 (m, 1H), 6.99-7.11 (m, 2H), 6.87 (d, 1H), 5.95 (s, 2H), 3.72 (q, 4H), 3.56-3.62 (m, 4H).

Compound I-482

To a cold mixture of triphosgene (0.75 equiv.) and 3-bromo-1,1,1-trifluoro-propan-2-ol (1.5 equiv.) in dichloromethane was added pyridine (1.5 equiv.). The mixture was stirred at 0° C. for 30 min. In a separate flask, a suspension of Intermediate 2 (1 equiv.) in pyridine was cooled to 0° C. To this suspension was transferred the mixture of triphosgene and bromopropanol via syringe. The resulting mixture was heated to 60° C. for 24 h. The contents were diluted in ethyl acetate and washed with 1N HCl solution. The organic layer was dried over MgSO₄, filtered and evaporated to give a crude oil. The oil was purified via silica gel chromatography utilizing a 0-100% ethyl acetate/hexanes gradient to deliver the desired compound, Compound I-482 (46 mg, 9% yield) as a white solid.

¹H NMR (500 MHz, CDCl₃) δ ppm 8.79 (d, 1H), 8.50 (d, 1H), 8.11-8.14 (m, 1H), 7.43 (s, 1H), 7.19-7.27 (m, 1H), 6.96-7.10 (m, 2H), 6.87-6.93 (m, 1H), 6.62 (d, 1H), 5.99-6.03 (m, 2H), 4.99-5.07 (m, 1H), 4.57-4.65 (m, 1H), 4.49-4.56 (m, 1H).

Compound I-492

A solution of 2,2-bis(trifluoromethyl)-2-hydroxyacetic acid (3 equiv.) and CDI (3 equiv.) in THF was heated to 80° C. for 1 h. To this mixture was added a solution of 5-fluoro-2-(1-(2-fluorobenzyl)-5-(isoxazol-3-yl)-1H-pyrazol-3-yl)pyrimidin-4-amine (intermediate described in previous WO2012/3405 A1; 1 equiv.) in NMP. The resulting mixture was heated in a microwave to 200° C. for 1 h. Contents were diluted in ethyl acetate and washed with water. The organic layer was dried over MgSO₄, filtered, and dried in vacuo to give a crude oil. The oil was purified via silica gel chromatography utilizing a 0-100% ethyl acetate/hexanes gradient to deliver the desired product, Compound I-492 (25 mg, 8% yield) as a yellow solid.

¹H NMR (500 MHz, CDCl₃) δ ppm 8.48 (d, 1H), 7.37 (s, 1H), 7.18-7.25 (m, 2H), 7.00-7.06 (m, 1H), 6.98 (t, 1H), 6.85 (t, 1H), 6.59 (d, 1H), 5.99 (s, 2H).

Compound I-493

A mixture of Compound I-403 (1 equiv.), HOBT (3 equiv.), triethylamine (3 equiv.), HATU (3 equiv.) and cyclopropylamine (3 equiv.) in DMF was stirred at 23° C. for 24 h. The mixture was diluted with ethyl acetate and washed in sequence with 1N HCl solution, saturated sodium bicarbonate solution, and brine. The organic layer was dried over MgSO₄, filtered, and concentrated in vacuo to yield a crude oil. The oil was purified via silica gel chromatography utilizing a 0-100% ethyl acetate/hexanes gradient to deliver the desired product, Compound I-493 (20.4 mg, 27% yield) as a white solid.

¹H NMR (500 MHz, CD₃OD) δ ppm 8.76-8.80 (m, 1H), 8.25-8.29 (m, 1H), 7.47-7.49 (m, 1H), 7.24-7.31 (m, 1H), 7.07-7.14 (m, 1H), 7.03 (t, 1H), 6.87-6.90 (m, 1H), 6.77 (t, 1H), 5.95-5.99 (m, 2H), 5.87-5.94 (m, 1H), 2.70-2.77 (m, 1H), 0.70-0.78 (m, 2H), 0.47-0.54 (m, 2H).

Compound I-504

The title compound was synthesized in 2 steps:

Step 1: Synthesis of 2-bromo-3,3,3-trifluoropropyl (2-(1-(2-fluorobenzyl)-5-(isoxazol-3-yl)-1H-pyrazol-3-yl)pyrimidin-4-yl)carbamate To a cold mixture of triphosgene (0.9 equiv.) and 2-bromo-3,3,3-trifluoropropan-1-ol (2 equiv.) in THF was added pyridine (2 equiv.). The mixture was stirred at 0° C. for 30 min. In a separate flask, a suspension of Intermediate 2 (1 equiv.) in pyridine (2 equiv.) was cooled to 0° C. To this suspension was added the mixture of triphosgene and bromopropanol via syringe, and the resulting mixture was heated to 60° C. for 24 h. Contents were concentrated in vacuo, and the residue was diluted with ethyl acetate and washed with 1N HCl solution. The organic layer was dried over MgSO₄, filtered, and concentrated in vacuo to give a crude oil. The oil was purified via silica gel chromatography utilizing a 0-100% ethyl acetate/hexanes gradient to deliver the desired carbamate intermediate, 2-bromo-3,3,3-trifluoropropyl (2-(1-(2-fluorobenzyl)-5-(isoxazol-3-yl)-1H-pyrazol-3-yl)pyrimidin-4-yl) carbamate (77 mg, 4% yield) as a light brown oil.

¹H NMR (500 MHz, CDCl₃) δ ppm 8.46-8.48 (m, 1H), 8.07 (br. s., 1H), 7.86 (d, 1H), 7.44-7.47 (m, 1H), 7.17-7.24 (m, 1H), 7.00-7.07 (m, 1H), 6.93-7.00 (m, 1H), 6.78-6.85 (m, 1H), 6.57-6.62 (m, 1H), 6.02 (s, 2H), 4.28 (quind, 1H), 3.93-4.15 (m, 2H).

Step 2: Synthesis of Compound I-504

To a solution of 2-bromo-3,3,3-trifluoropropyl (2-(1-(2-fluorobenzyl)-5-(isoxazol-3-yl)-1H-pyrazol-3-yl)pyrimidin-4-yl)carbamate (1 equiv.) in THF was added LiHMDS (2.0 M in THF, 1 equiv.). The mixture was sealed and heated to 60° C. for 2 d. The mixture was diluted with ethyl acetate and washed with water. The organic layer was dried MgSO₄, filtered, and evaporated to give a crude oil. The oil was purified via silica gel chromatography utilizing a 0-100% ethyl acetate/hexanes gradient and recrystallized from a diethyl ether-hexanes mixture to deliver the desired product, Compound I-504 (7 mg, 11% yield) as a white solid.

¹H NMR (500 MHz, DMSO-d₆) δ ppm 9.13 (s, 1H), 8.84 (s, 1H), 7.99 (d, 1H), 7.70 (s, 1H), 7.31-7.38 (m, 1H), 7.19-7.26 (m, 2H), 7.12 (t, 1H), 6.91 (t, 1H), 6.03-6.09 (m, 1H), 5.86-5.98 (m, 2H), 4.73-4.80 (m, 2H).

Compound I-544

A mixture of Compound I-419 (1 equiv.) and lithium aluminum hydride (2 equiv.) in THF was heated to 60° C. for 24 h. The mixture was cooled to 23° C., then sequentially treated with water (× mL/× g of lithium aluminum hydride), 15% NaOH (aq) (× mL/× g of lithium aluminum hydride), and water (3× mL/× g of lithium aluminum hydride). The precipitate was removed by filtration, and the filtrate was concentrated in vacuo to yield the intermediate amine as a yellow solid. The intermediate was suspended in THF, and a solution of methanesulfonyl chloride (1 M in THF, 2 equiv.) and pyridine (3 equiv.) in THF was added to the suspension dropwise via syringe. The mixture was stirred at 23° C. for 3 h, then diluted in ethyl acetate and washed with 1N HCl solution. The organic layer was dried, filtered, and evaporated to yield a crude oil. The oil was purified via silica gel chromatography utilizing a 0-100% ethyl acetate/hexanes gradient to deliver the desired product, Compound I-544 (4 mg, 19% yield) as a yellow solid.

¹H NMR (400 MHz, CD₃OD) δ ppm 8.71-8.78 (m, 1H), 8.22 (d, 1H), 7.51 (s, 1H), 7.22-7.32 (m, 1H), 6.97-7.15 (m, 2H), 6.89-6.96 (m, 1H), 6.69-6.83 (m, 1H), 5.99-6.05 (m, 2H), 5.56 (s, 1H), 3.03-3.23 (m, 2H), 2.68-2.83 (s, 3H), 1.95-2.08 (m, 2H).

Compound I-575

The title compound was synthesized in 3 steps:

Step 1: Synthesis of (R)-1-((tert-butyldimethylsilyl)oxy)-3-((5-fluoro-2-(1-(2-fluorobenzyl)-5-(isoxazol-3-yl)-1H-pyrazol-3-yl)pyrimidin-4-yl)amino)propan-2-ol A mixture of Compound I-316 (1 equiv.), imidazole (2 equiv.) and TBDMS-Cl (1 equiv.) in DMF was stirred at rt for 24 h. The mixture was diluted in ethyl acetate and washed with 1N HCl solution. The organic layer was dried, filtered and evaporated to give a crude oil. The oil was purified via silica gel chromatography utilizing a 0-100% ethyl acetate/hexanes gradient to deliver the desired intermediate, (R)-1-((tert-butyldimethylsilyl)oxy)-3-((5-fluoro-2-(1-(2-fluorobenzyl)-5-(isoxazol-3-yl)-1H-pyrazol-3-yl)pyrimidin-4-yl)amino)propan-2-ol (258 mg, 63% yield).

¹H NMR (500 MHz, CDCl₃) δ ppm 8.04-8.07 (m, 1H), 7.23 (br. s., 1H), 7.06-7.13 (m, 1H), 6.82-6.97 (m, 3H), 6.76 (t, 1H), 5.84-5.90 (m, 2H), 3.80-3.89 (m, 1H), 3.47-3.66 (m, 4H), 0.79-0.84 (m, 9H), 0.03 (m, 6H).

Step 2: Synthesis of (R)-5-(((tert-butyldimethylsilyl)oxy)methyl)-3-(5-fluoro-2-(1-(2-fluorobenzyl)-5-(isoxazol-3-yl)-1H-pyrazol-3-yl)pyrimidin-4-yl)oxazolidin-2-one A mixture of (R)-1-((tert-butyldimethylsilyl)oxy)-3-((5-fluoro-2-(1-(2-fluorobenzyl)-5-(isoxazol-3-yl)-1H-pyrazol-3-yl)pyrimidin-4-yl)amino)propan-2-ol (1 equiv.), 2,6-dimethylpyridine (2 equiv.) and triphosgene (0.7 equiv.) in THF was stirred at 23° C. for 30 min. Then, the mixture was heated to 60° C. for 24 h. Contents were diluted in ethyl acetate and washed with water. The organic layer was dried, filtered and evaporated to give a crude oil. The oil was purified via silica gel chromatography utilizing a 0-100% ethyl acetate/hexanes gradient to deliver the desired TBS-protected carbamate intermediate, (R)-5-(((tert-butyldimethylsilyl)oxy)methyl)-3-(5-fluoro-2-(1-(2-fluorobenzyl)-5-(isoxazol-3-yl)-1H-pyrazol-3-yl)pyrimidin-4-yl)oxazolidin-2-one (221 mg, 82% yield).

$^{1}$H NMR (500 MHz, CDCl$_{3}$) δ ppm 8.54 (d, 1H), 8.36 (d, 1H), 7.24 (s, 1H), 7.05-7.13 (m, 1H), 6.84-6.97 (m, 2H), 6.72-6.81 (m, 1H), 6.47 (d, 1H), 5.87 (s, 2H), 4.65-4.74 (m, 1H), 4.24-4.32 (m, 1H), 4.16 (dd, 1H), 3.83 (m, 2H), 0.74-0.82 (m, 9H), 0.00 (d, 6H).

Step 3: Synthesis of Compound I-575

To a cold solution of (R)-5-(((tert-butyldimethylsilyl)oxy)methyl)-3-(5-fluoro-2-(1-(2-fluorobenzyl)-5-(isoxazol-3-yl)-1H-pyrazol-3-yl)pyrimidin-4-yl)oxazolidin-2-one (1 equiv.) in THF at 25° C., was added a solution of TBAF (1M in THF, 1 equiv.). After stirring the mixture at 23° C. for 30 min, the mixture was quenched with water and diluted with ethyl acetate. The organic layer was dried, filtered and evaporated to give a crude oil. The oil was purified via silica gel chromatography utilizing a 0-100% ethyl acetate/hexanes gradient. Further purification by recrystallization from a dichloromethane-diethyl ether mixture gave the desired compound, Compound I-575 (10 mg, 4% yield over 3 steps) as a white solid.

$^{1}$H NMR (500 MHz, DMSO-d$_{6}$) δ ppm 8.25 (d, 1H), 8.02 (t, 1H), 7.53 (s, 1H), 7.30-7.39 (m, 1H), 7.17-7.25 (m, 2H), 7.11 (td, 1H), 6.85-6.91 (m, 1H), 5.88 (s, 2H), 5.06 (dq, 1H), 4.61 (t, 1H), 4.45 (dd, 1H), 3.83 (m, 2H).

Compound I-490

A mixture of 4,4,4-trifluoro-3-hydroxy-3-(trifluoromethyl)butanoic acid (1.5 equiv.) and CDI (1.5 equiv.) in THF was heated to reflux for 2 h. To this mixture was added Intermediate 2 (1 equiv.) in one portion. The mixture was diluted in ethyl acetate and washed with 1N HCl solution. The organic layer was dried, filtered, and evaporated to yield an oil. The oil was purified by silica gel chromatography utilizing a 80% isocratic gradient of ethyl acetate in hexanes to deliver the desired product, Compound I-490 (2 mg, 1.2% yield) as a white solid.

$^{1}$H-NMR (500 MHz, CDCl$_{3}$) δ ppm 8.80 (d, 1H), 8.51 (s, 1H), 8.05 (d, 1H), 7.44-7.50 (m, 1H), 7.19-7.32 (m, 2H), 6.95-7.08 (m, 2H), 6.87 (d, 1H), 6.58-6.65 (m, 1H), 5.97 (s, 2H), 2.93-2.99 (m, 2H).

Compound I-496

The title compound was prepared following general procedure B, except (5-methyl-1,3,4-oxadiazol-2-yl)methanamine (as the HCl salt) was the amine reactant, and the contents were heated to 110° C. for 24 h as a solution in THF/water (10:1). The contents were cooled to 23° C., and organic solvents were removed in vacuo. The resulting residue was purified by reverse phase HPLC to deliver the desired product, Compound I-496 (81 mg, 64% yield) as a white solid.

$^{1}$H NMR (500 MHz, DMSO-d$_{6}$) δ ppm 9.09-9.12 (m, 1H), 8.57 (br. s., 1H), 8.32 (d, 1H), 7.48 (s, 1H), 7.30-7.36 (m, 1H), 7.19-7.25 (m, 1H), 7.16 (d, 1H), 7.11 (t, 1H), 6.84 (t, 1H), 5.88 (s, 2H), 4.92 (d, 2H), 2.45 (s, 3H).

Compound I-508

The title compound was prepared in 3 steps:

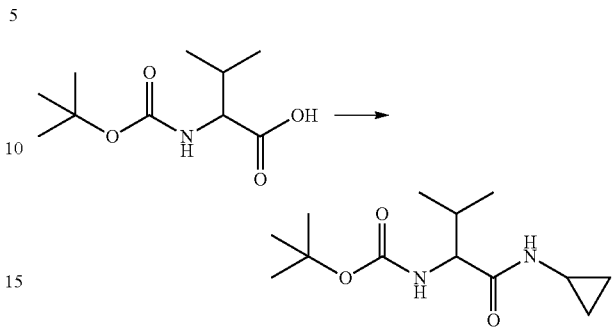

Step 1: Synthesis of Tert-Butyl (1-(cyclopropylamino)-3-methyl-1-oxobutan-2-yl)carbamate To a solution of 2-((tert-butoxycarbonyl)amino)-3-methylbutanoic acid (1 eq) and cyclopropanamine (1 eq) in THF (10 ml) were added PyAOP (1.0 eq) followed by DIPEA (3 eq). Reaction mixture was stirred at room temperature for 4 hours. With complete conversion of starting material to the desired product, the solvent was removed by vacuum and purified by flash chromatography eluent with ethyl acetate/hexane 1:1 The fractions containing desired product were collected and concentrated to provide the amide intermediate as an oil.

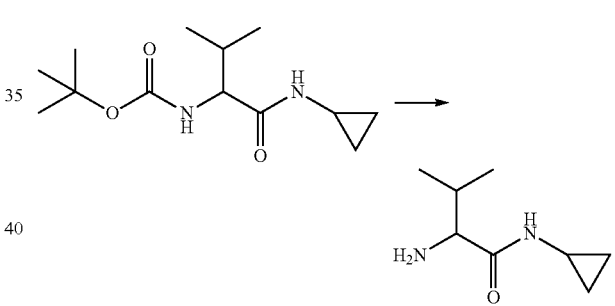

Step 2: Synthesis of 2-amino-N-cyclopropyl-3-methylbutanamide

The amide intermediate tert-butyl (1-(cyclopropylamino)-3-methyl-1-oxobutan-2-yl)carbamate (1 equiv.) was dissolved in dichloromethane and TFA (3:1 ratio) and stirred for 4 h at 23° C. The solvent was removed in vacuo to yield the free amine intermediate 2-amino-N-cyclopropyl-3-methylbutanamide (0.25 g 42% yield) as a semi-solid.

Step 3: Synthesis of Compound I-508

The title compound was prepared following general procedure B, except 2-amino-N-cyclopropyl-3-methylbutanamide was the amine intermediate, and the contents were heated to 110° C. for 24 h as a solution in THF/water (10:1). The contents were cooled to 23° C., and organic solvents were removed in vacuo. The resulting residue was purified via reverse phase HPLC to deliver the desired product, Compound I-508 (15 mg, 22% yield) as a white solid.

$^{1}$H NMR (500 MHz, CDCl$_{3}$) δ ppm 8.51-8.55 (m, 1H), 8.15 (d, 1H), 7.40-7.45 (m, 1H), 7.23-7.28 (m, 1H), 6.99-7.12 (m, 2H), 6.70-6.75 (m, 1H), 6.62-6.69 (m, 1H), 6.65 (br. s., 1H), 5.93-5.98 (m, 2H), 4.58 (t, 1H), 2.75 (tq, 1H), 2.31 (dq, 1H), 0.99-1.08 (m, 6H), 0.67-0.79 (m, 2H), 0.44-0.55 (m, 2H).

Compound I-509

The title compound was prepared following general procedure B, except 2-((trifluoromethyl)thio)ethanamine was the amine reactant, and the contents were heated to 110° C. for 24 h as a solution in THF/water (10:1). The contents were cooled to 23° C., and organic solvents were removed in vacuo. The resulting residue was purified utilizing a 5-50% ethyl acetate in hexane gradient to deliver the desired product, Compound I-509 (81 mg, 60% yield) as an off-white solid.

$^1$H NMR (500 MHz, CDCl$_3$) δ ppm 8.45-8.48 (m, 1H), 8.20 (d, 1H), 7.30 (s, 2H), 7.16-7.23 (m, 1H), 7.00-7.06 (m, 1H), 6.97 (t, 1H), 6.86 (t, 1H), 6.57-6.60 (m, 1H), 5.95-6.01 (m, 2H), 3.96 (q, 2H), 3.27 (t, 2H).

Compound I-514

To a stirred solution of Compound I-509 (1 equiv.) in dichloromethane was added mCPBA (2 equiv.), and the mixture was stirred for 12 h. Solvent was removed in vacuo, and the resulting residue was purified via reverse phase HPLC to deliver the desired product, Compound I-514 (5 mg, 6% yield) as a white solid.

$^1$H NMR (500 MHz, CDCl$_3$) δ ppm 8.41 (d, 1H), 8.17 (d, 1H), 7.28-7.32 (m, 1H), 7.10-7.17 (m, 1H), 6.89-6.99 (m, 2H), 6.80-6.86 (m, 1H), 6.53 (d, 1H), 5.99 (d, 1H), 5.90 (s, 2H), 4.20 (q, 2H), 3.70 (t, 2H).

Compound I-529

The title compound was prepared following general procedure B, except 1,1,1,3,3,3-hexafluoro-2-((methylamino)methyl)propan-2-ol was the amine reactant, and the contents were heated to 110° C. for 24 h as a solution in THF/water (10:1). The contents were cooled to 23° C., and organic solvents were removed in vacuo. The resulting residue was purified via reverse phase HPLC to deliver the desired product, Compound I-529 (2.5 mg, 2% yield) as an off-white solid.

$^1$H NMR (500 MHz, CDCl$_3$) δ ppm 8.53 (d, 1H), 8.36 (d, 1H), 7.42 (br. s., 1H), 7.23-7.28 (m, 2H), 7.03-7.25 (m. 2H), 6.64 (s, 1H), 5.95 (s, 2H), 4.22 (br. s., 1H), 3.49-3.53 (m, 3H), 3.02-3.08 br. 2H).

Compound I-545

The title compound was prepared following general procedure B, except (1-(methylsulfonyl)cyclopropyl)methanamine (as the HCl salt) was the amine reactant, and the contents were heated to 110° C. for 24 h as a solution in dioxane/water (10:1). The contents were cooled to 23° C., and organic solvents were removed in vacuo. The resulting residue was purified via reverse phase HPLC to deliver the desired product, Compound I-545 (81 mg, 59% yield) as a white solid.

$^1$H NMR (500 MHz, DMSO-d$_6$) δ ppm 9.12 (d, 1H), 8.30 (d, 1H), 8.19 (br. s., 1H), 7.55-7.61 (m, 1H), 7.31-7.38 (m, 1H), 7.19-7.26 (m, 2H), 7.13 (t, 1H), 6.96 (t, 1H), 5.89 (s, 2H), 4.04 (d, 2H), 3.09 (s, 3H), 1.22 (s, 4H).

Compound I-567

The title compound was prepared in 5 steps:

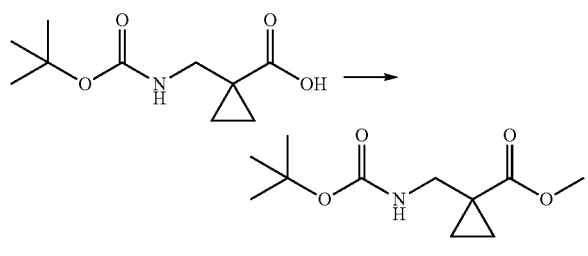

Step 1: Synthesis of Methyl 1-(((tert-butoxycarbonyl)amino)methyl)cyclopropanecarboxylate To a stirred solution of 1-(((tert-butoxycarbonyl)amino)methyl)cyclopropanecarboxylic acid (1 equiv.) in diethyl ether and methanol (5:1 ratio) was slowly added (diazomethyl)trimethylsilane (1 equiv.) at 25° C. The mixture was stirred overnight, and solvents were removed in vacuo to yield the desired methyl ester intermediate, methyl 1-(((tert-butoxycarbonyl) amino)methyl)cyclopropanecarboxylate (0.400 g, 75% yield).

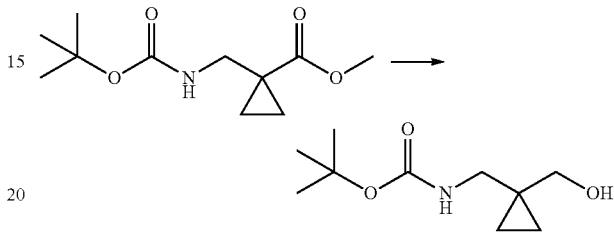

Step 2: Synthesis of Tert-Butyl ((1-(hydroxymethyl)cyclopropyl)methyl)carbamate

Methyl 1-(((tert-butoxycarbonyl)amino)methyl)cyclopropanecarboxylate (1 equiv.) was dissolved in THF and cooled to 0° C. Lithium aluminum hydride (3 equiv.) was added slowly to the vessel, and contents were stirred while allowing warming up to 23° C. over a period of 4 h. The reaction solution was then re-cooled to 0° C., then water (× mL of water/× g of LiAlH$_4$ used), 15% sodium hydroxide solution (× mL of water/× g of LiAlH$_4$ used), and water (3× mL of water/× g of LiAlH$_4$ used) were slowly added to the reaction in a sequential manner. The reaction was filtered through celite, and the filtrate was concentrated in vacuo. The residue was purified via silica gel chromatography to deliver the desired alcohol intermediate, tert-butyl ((1-(hydroxymethyl)cyclopropyl)methyl)carbamate (0.41 g, 88% yield).

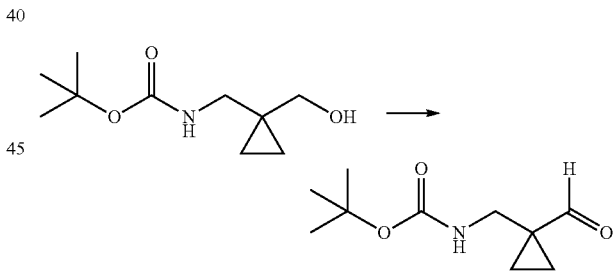

Step 3: Synthesis of Tert-Butyl ((1-formylcyclopropyl)methyl)carbamate

To a solution of tert-butyl ((1-(hydroxymethyl)cyclopropyl)methyl)carbamate (1 equiv.) in dichloromethane at 25° C. was added PCC (1.15 equiv.) in a single portion. Reaction was stirred for 2 h. Diethyl ether was added to the vessel, and the heterogeneous mixture was filtered through silica gel to yield the desired aldehyde intermediate, which was used without further purification.

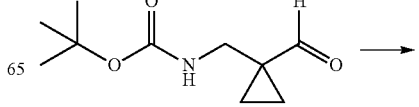

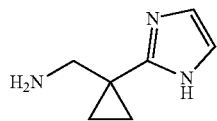

Step 4: Synthesis of (1-(1H-imidazol-2-yl)cyclopropyl)methanamine

A stirred solution of tert-butyl ((1-formylcyclopropyl)methyl)carbamate (1 equiv.) in methanol was treated with ammonium hydroxide (10 equiv.) followed by oxalaldehyde (1.1 equiv.). The contents were allowed to stir at 23° C. for 3 h before methanol was removed in vacuo. The residue was then treated with TFA in dichloromethane (1:1 ratio) and stirred at 23° C. for 5 h. The mixture was diluted with brine and extracted with dichloromethane. The organics were dried over sodium sulfate and concentrated in vacuo to deliver the desired imidazole intermediate, (1-(1H-imidazol-2-yl)cyclopropyl)methanamine (0.124 g, 100% yield), which was carried onto the next reaction without further purification.

Step 4: Synthesis of Compound I-567

The title compound was prepared following general procedure B, except (1-(1H-imidazol-2-yl)cyclopropyl)methanamine was the amine reactant, and the contents were heated to 110° C. for 24 h as a solution in dioxane/water (10:1). The contents were cooled to 23° C., and organic solvents were removed in vacuo. The residue was purified via reverse phase HPLC to deliver the desired product, Compound I-567 (36 mg, 27% yield) as a white solid.

$^1$H NMR (400 MHz, CDCl$_3$) δ ppm 9.16 (br. s., 1H), 8.53 (d, 1H), 7.98-8.05 (m, 1H), 7.51 (s, 1H), 7.22-7.31 (m, 2H), 6.97-7.09 (m, 2H), 6.90 (s, 2H), 6.81 (d, 2H), 5.92 (s, 2H), 4.05 (d, 2H), 1.40-1.47 (m, 2H), 1.32-1.39 (m, 2H).

Compound I-589

A solution of 5-fluoro-2-(1-(2-fluorobenzyl)-5-(isoxazol-3-yl)-1H-pyrazol-3-yl)pyrimidin-4-amine (intermediate described in previous patent: WO2012/3405 A1) (1 equiv.), 2-(methylsulfonyl)propanoic acid (3 equiv.), triethylamine (10 equiv.), and 2,4,6-tripropyl-1,3,5,2,4,6-trioxatriphosphinane 2,4,6-trioxide (4 equiv.) in DMF was heated to 90° C. for 4 h. The reaction was cooled to 23° C., then poured into a 1:1 mixture of ethyl acetate and water. The layers were separated and the aqueous layer was extracted with ethyl acetate (2×). The organics were washed with water (3×), dried over magnesium sulfate, filtered, and concentrated in vacuo. The resulting residue was purified via reverse phase HPLC to deliver the desired product, Compound I-589 (10 mg, 28% yield) as a white solid.

$^1$H NMR (500 MHz, DMSO-d$_6$) δ ppm 11.49 (s, 1H), 9.11 (d, 1H), 8.92 (d, 1H), 7.61 (s, 1H), 7.31-7.37 (m, 1H), 7.27 (d, 1H), 7.19-7.25 (m, 1H), 7.12 (td, 1H), 6.92-6.97 (m, 1H), 5.92 (s, 2H), 4.40 (d, 1H), 3.07 (s, 3H), 1.58 (d, 3H).

Compound I-608

The title compound was prepared in 4 steps:

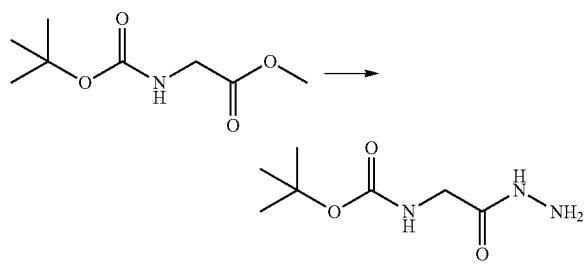

Step 1: Synthesis of Tert-Butyl (2-hydrazinyl-2-oxoethyl)carbamate

To a solution of methyl 2-((tert-butoxycarbonyl)amino)acetate (1 equiv.) in ethanol was added hydrazine hydrate (15 equiv.), and the reaction was allowed to stir overnight. The solvent was removed in vacuo, and the residue was triturated with hexane, filtered, and dried under high vacuum to yield the desired acyl hydrazine intermediate tert-butyl (2-hydrazinyl-2-oxoethyl)carbamate, intermediate B (0.89 g, 92% yield) as a white solid.

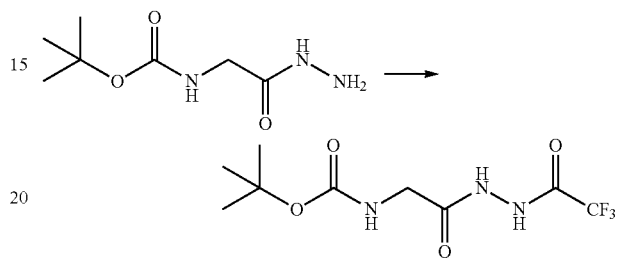

Step 2: Synthesis of Tert-Butyl (2-oxo-2-(2-(2,2,2-trifluoroacetyl)hydrazinyl)ethyl)carbamate To a solution of tert-butyl (2-hydrazinyl-2-oxoethyl)carbamate (1 equiv.) in acetonitrile was added DIEA (1.1 equiv.). Contents were cooled to −45° C., and 2,2,2-trifluoroacetic anhydride (1.1 equiv.) was added to the reaction. The resulting mixture was stirred while slowly warming to 23° C. The solvent was removed in vacuo and the residue was partitioned between water and ethyl acetate. The layers were separated, and the aqueous layer was extracted with ethyl acetate. The combined organic phases were washed with water and brine, dried with Na$_2$SO$_4$, filtered, and concentrated in vacuo. The residue was purified via silica gel chromatography, utilizing a 5-45% ethyl acetate in hexanes gradient to deliver the desired intermediate, tert-butyl (2-oxo-2-(2-(2,2,2-trifluoroacetyl)hydrazinyl)ethyl)carbamate (0.73 g, 54% yield).

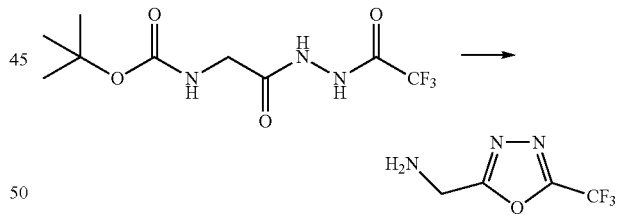

Step 3: Synthesis of (5-(trifluoromethyl)-1,3,4-oxadiazol-2-yl)methanamine

To a suspension of tert-butyl (2-oxo-2-(2-(2,2,2-trifluoroacetyl)hydrazinyl)ethyl)carbamate (1 equiv.) in acetonitrile was added DIEA (5.8 equiv.) and triphenylphosphine (4.1 equiv.), which was stirred for 5 min. Perchloroethane (2.3 equiv.) was then added to the reaction, and the mixture was stirred for 20 h at 23° C. The solvent was removed in vacuo, and the residue was partitioned between water and ethyl acetate. The layers were separated, and the aqueous layer was extracted with ethyl acetate. The combined organic phases were washed with water and brine, dried with Na$_2$SO$_4$, filtered, and concentrated in vacuo. The residue was purified via silica gel chromatography, utilizing a 5-45% ethyl acetate in hexanes gradient to deliver the N-Boc protected oxadiazole intermediate, tert-butyl ((5-(trifluoromethyl)-1,3,4-oxadiazol-2-yl)methyl)carbamate (0.24 g, 35% yield). To a stirred solution of this N-Boc protected oxadiazole intermediate (1 equiv.) in dichloromethane was added TFA (8 equiv.), and the mixture was stirred at 23° C. for 4 h. The solvent was removed in vacuo to deliver the desired free amine oxadiazole intermediate, (5-(trifluoromethyl)-1,3,4-oxadiazol-2-yl)methanamine (as the HCl salt, 0.15 g, 100% yield), which was used in the next step without further purification.

Step 4: Synthesis of Compound I-608

To a stirred solution of (5-(trifluoromethyl)-1,3,4-oxadiazol-2-yl)methanamine (as the HCl salt, 2 equiv.) in dioxane cooled to 0° C. was added cesium carbonate (3 equiv.), and the mixture was stirred for 1 h. Intermediate 1 (1 equiv.) was added to the reaction, and the resulting mixture was stirred at 90° C. for 24 h. The reaction was cooled to 23° C. and diluted with ethyl acetate. The organics were washed with water and brine, concentrated in vacuo, and the resulting residue was purified via reverse phase HPLC to deliver the desired product, Compound I-608 (2.5 mg, 5% yield) as a white solid.

¹H NMR (500 MHz, CD₃OD) δ ppm 8.67 (d, 1H), 8.15 (d, 1H), 7.31 (s, 1H), 7.17 (ddd, 1H), 6.96-7.01 (m, 1H), 6.90-6.95 (m, 1H), 6.76 (d, 1H), 6.70-6.74 (m, 1H), 5.85 (s, 2H), 5.09 (s, 2H).

Compound I-622

The title compound was prepared in 4 steps:

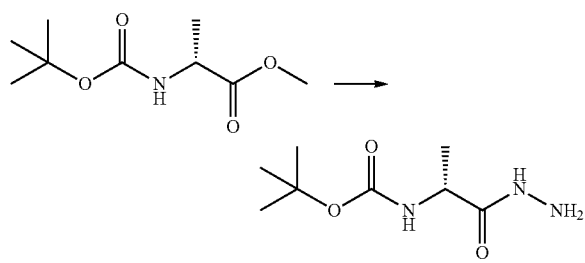

Step 1: Synthesis of (R)-Tert-Butyl (1-hydrazinyl-1-oxopropan-2-yl)carbamate

The title compound was prepared according to the procedure described in Step 1 towards the synthesis of Compound I-608, except using (R)-methyl 2-((tert-butoxycarbonyl)amino)propanoate as the starting material (97% yield).

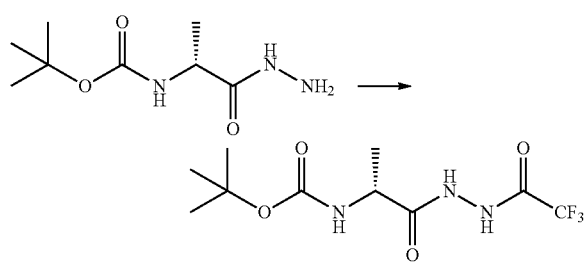

Step 2: Synthesis of (R)-Tert-Butyl (1-oxo-1-(2-(2,2,2-trifluoroacetyl)hydrazinyl) propan-2-yl)carbamate This was prepared according to the procedure described in Step 2 towards the synthesis of Compound I-608, except using (R)-tert-butyl (1-hydrazinyl-1-oxopropan-2-yl)carbamate as the starting material (82% yield).

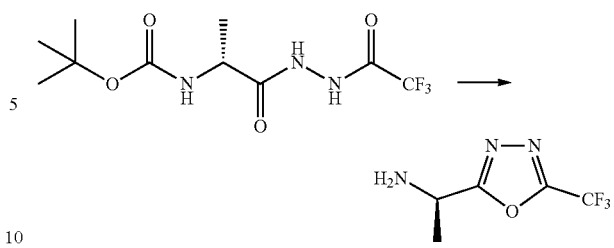

Step 3: Synthesis of (R)-1-(5-(trifluoromethyl)-1,3,4-oxadiazol-2-yl)ethanamine

This was prepared according to the procedure described in Step 3 towards the synthesis of Compound I-608, except using (R)-tert-butyl(1-oxo-1-(2-(2,2,2-trifluoroacetyl)hydrazinyl)propan-2-yl)-carbamate as the starting material (37% yield).

Step 4: Synthesis of Compound I-622

To a stirred solution of (R)-1-(5-(trifluoromethyl)-1,3,4-oxadiazol-2-yl)ethanamine, (R)-1-(5-(trifluoromethyl)-1,3,4-oxadiazol-2-yl)ethanamine (2 equiv.) and Intermediate 1 (1 equiv.) in DMF was added cesium carbonate (3 equiv.). The mixture was heated to 90° C. and stirred for 24 h. Contents cooled to 23° C. and diluted with ethyl acetate. The mixture was washed with water and brine, concentrated in vacuo, and the resulting residue was purified via reverse phase HPLC to deliver the desired product, Compound I-622 (5 mg, 9% yield) as a white solid.

¹H NMR (500 MHz, CD₃OD) δ ppm 8.66-8.69 (m, 1H), 8.14 (d, 1H), 7.27 (s, 1H), 7.15-7.21 (m, 1H), 6.99 (dd, 1H), 6.93 (t, 1H), 6.76 (d, 1H), 6.72 (t, 1H), 5.87-5.91 (m, 1H), 5.85 (s, 2H), 1.74 (d, 3H).

Compound I-616

To a stirred solution of 2-(methylsulfonyl)acetamide (1 equiv.) in DMF was added cesium carbonate (3 equiv.) at 0° C., and the mixture was stirred for 1 h. Intermediate 1 (1 equiv.) was added to the vessel, and the reaction was heated to 90° C. and stirred for 24 h. Contents were cooled to 23° C., and diluted with ethyl acetate. The mixture was washed with water and brine, concentrated in vacuo, and the resulting residue was purified via reverse phase HPLC to deliver the desired product, Compound I-616 (11 mg, 22% yield) as a white solid.

¹H NMR (500 MHz, CD₃OD) δ ppm 8.67 (d, 1H), 8.59 (d, 1H), 7.45 (s, 1H), 7.17 (ddd, 1H), 6.91-7.02 (m, 2H), 6.77-6.82 (m, 2H), 5.87 (s, 2H), 4.58 (br. s., 2H), 3.11 (s, 3H).

Compound I-386

The title compound was prepared following general procedure C, except 1H-pyrazole-3-carboxylic acid was the acid reactant, and the crude material was purified via silica gel chromatography utilizing a 3-8% methanol in dichloromethane gradient to deliver the desired compound, Compound I-386 (20.2 mg, 40% yield) as a light-tan solid.

¹H-NMR (500 MHz, CDCl₃) δ ppm 9.93 (s, 1H), 8.77 (d, 1H), 8.50 (s, 1H), 8.33 (d, 1H), 7.51 (s, 1H), 7.44 (d, 1H), 7.19-7.25 (m, 1H), 7.02-7.08 (m, 1H), 6.96-7.02 (m, 1H), 6.94 (d, 1H), 6.83-6.87 (m, 1H), 6.65 (s, 1H), 6.02 (s, 2H); 1 N—H proton not observed.

Compound I-164

To a solution of Intermediate 2 (1 equiv.) in dichloromethane was added trifluoroacetic anhydride (3 equiv.) followed by triethylamine (3 equiv.). The reaction was heated to 60° C. for 20 min, after which the reaction was concentrated in vacuo. The crude material was purified via silica gel chromatography utilizing a 1-3% methanol in dichloromethane gradient to deliver the desired compound, Compound I-635 (16.4 mg, 32% yield) as a white solid.

$^1$H-NMR (500 MHz, CDCl$_3$) δ 8.95 (br. s, 1H), 8.86 (d, 1H), 8.49 (d, 1H), 8.10 (d, 1H), 7.49 (s, 1H), 7.20-7.26 (m, 1H), 7.03-7.07 (m, 1H), 6.98-7.02 (m, 1H), 6.82-6.87 (m, 1H), 6.62 (d, 1H), 6.04 (s, 2H).

Compound I-458

The title compound was prepared following general procedure C, except 3-hydroxy-5-oxocyclohex-3-enecarboxylic acid (1.3 equiv.) was the acid reactant, and 2.5 equivalents of T3P was used. The crude material was purified via silica gel chromatography utilizing a 3-10% methanol in dichloromethane gradient to deliver the desired compound, Compound I-458 (26.4 mg, 30% yield) as a white solid.

$^1$H-NMR (500 MHz, CD$_3$OD) δ 8.79 (m, 1H), 8.68 (d, 1H), 8.13 (d, 1H), 7.53 (s, 1H), 7.24-7.33 (m, 1H), 7.08-7.13 (m, 1H), 7.01-7.08 (m, 1H), 6.86-6.92 (m, 2H, 2 shifts isochronous), 5.97 (s, 2H), 2.66-2.75 (m, 2H), 2.56-2.64 (m, 2H); 1 C—H proton not observed (isochronous with solvent peak).

Compound I-459

The title compound was prepared following general procedure C, except 5-oxopyrrolidine-2-carboxylic acid (1.2 equiv.) was the acid reactant, and 2.5 equivalents of T3P was used. The crude material was purified via silica gel chromatography utilizing a 3-10% methanol in dichloromethane gradient, followed by a second purification via silica gel chromatography utilizing a 7-12% (7:1 methanol/acetonitrile) in dichloromethane gradient to deliver the desired compound, Compound I-459 (12.6 mg, 15% yield) as a white solid.

$^1$H-NMR (500 MHz, CD$_3$OD) δ 8.79 (s, 1H), 8.70 (d, 1H), 8.13 (d, 1H), 7.52 (s, 1H), 7.26-7.32 (m, 1H), 7.08-7.13 (m, 1H), 7.02-7.08 (m, 1H), 6.87-6.93 (m, 2H, 2 shifts isochronous), 5.95 (s, 2H), 4.41-4.49 (m, 1H), 2.52-2.60 (m, 1H), 2.40-2.50 (m, 1H), 2.32-2.40 (m, 1H), 2.20-2.30 (m, 1H).

Compound I-464

The title compound was prepared following general procedure C, except 5-oxopyrrolidine-3-carboxylic acid (1.2 equiv.) was the acid reactant, and 2.5 equivalents of T3P was used. The crude material was purified via silica gel chromatography utilizing a 3-10% methanol in dichloromethane gradient to deliver the desired compound, Compound I-464 (31.3 mg, 31% yield) as a white solid.

$^1$H-NMR (500 MHz, CD$_3$OD) δ 8.79 (s, 1H), 8.69 (d, 1H), 8.13 (d, 1H), 7.51 (s, 1H), 7.26-7.31 (m, 1H), 7.07-7.13 (m, 1H), 7.02-7.07 (m, 1H), 6.86-6.93 (m, 2H, 2 shifts isochronous), 5.97 (s, 2H), 3.67-3.76 (m, 1H), 3.57-3.65 (m, 2H), 2.60-2.72 (m, 2H).

Compound I-461

The title compound was prepared following general procedure C, except 1-(benzyloxy)cyclopropanecarboxylic acid (1 equiv.) was the acid reactant, and 2.5 equivalents of T3P was used. The crude material was purified via silica gel chromatography utilizing a 30-50% ethyl acetate in hexanes gradient to deliver the desired compound, Compound I-461 (14.2 mg, 19% yield) as a tan solid.

$^1$H-NMR (500 MHz, CDCl$_3$) δ 9.33 (s, 1H), 8.73 (d, 1H), 8.48 (d, 1H), 8.08 (d, 1H), 7.42 (s, 1H), 7.34-7.41 (m, 4H), 7.29-7.32 (m, 1H), 7.18-7.23 (m, 1H), 7.02-7.06 (m, 1H), 6.97-7.01 (m, 1H), 6.84-6.88 (m, 1H), 6.61 (d, 1H), 6.03 (s, 2H), 4.68 (s, 2H), 1.45-1.51 (m, 2H), 1.32-1.37 (m, 2H).

Compound I-469

The title compound was prepared following general procedure C, except 2-(thiazol-2-yl)acetic acid was the acid reactant. The crude material was purified via silica gel chromatography utilizing a 3-8% methanol in dichloromethane gradient, followed by a second purification via reverse phase HPLC utilizing a 10-95% acetonitrile in water gradient to deliver the desired compound, Compound I-469 (4.3 mg, 6% yield) as a tan solid.

$^1$H-NMR (500 MHz, CD$_3$OD) δ 8.81 (s, 1H), 8.69 (d, 1H), 8.20 (d, 1H), 7.81 (d, 1H), 7.61 (d, 1H), 7.57 (s, 1H), 7.25-7.33 (m, 1H), 7.08-7.13 (m, 1H), 7.02-7.07 (m, 1H), 6.87-6.96 (m, 2H, 2 shifts isochronous), 5.99 (s, 2H), 3.30 (s, 2H).

Compound I-465

To a solution of 5-fluoro-2-(1-(2-fluorobenzyl)-5-(isoxazol-3-yl)-1H-pyrazol-3-yl)-pyrimidin-4-amine (intermediate described in WO2012/3405 A1; 1 equiv.) in dichloromethane was added trifluoroacetic anhydride (3 equiv.) followed by triethylamine (3 equiv.). The reaction was heated to 60° C. for 20 min, after which the reaction was concentrated in vacuo. The crude material was purified via silica gel chromatography utilizing a 1-3% methanol in dichloromethane gradient to deliver the desired compound, Compound I-465 (26.8 mg, 28% yield) as a white solid.

$^1$H-NMR (500 MHz, CDCl$_3$) δ 8.77 (s, 1H), 8.56 (br. s, 1H), 8.40 (s, 1H), 7.44 (s, 1H), 7.19-7.25 (m, 1H), 7.02-7.08 (m, 1H), 6.96-7.02 (m, 1H), 6.81-6.88 (m, 1H), 6.62 (d, 1H), 6.02 (s, 2H).

Compound I-470

To a mixture of Compound I-38 (1 equiv.), 1-hydroxycyclopropanecarboxylic acid (1.1 equiv.), and 4-dimethylamino pyridine (0.1 equiv.) in dichloromethane was added triethylamine (3 equiv.) followed by 1-ethyl-3-(3-dimethylaminopropyl)carbodiimide (1.1 equiv.). The reaction was stirred at room temperature for 12 h, after which the reaction was diluted with water and 1N hydrochloric acid solution and extracted with dichloromethane. The combined organic layers were dried over sodium sulfate, filtered, and concentrated in vacuo. The crude material was purified via reverse phase HPLC utilizing a 10-95% acetonitrile in water gradient to deliver the desired compound, Compound I-470 (1.3 mg, 4% yield) as a white solid.

$^1$H-NMR (500 MHz, CDCl$_3$) δ 8.50 (d, 1H), 8.26 (s, 1H), 7.33 (s, 1H), 7.19-7.26 (m, 1H), 6.97-7.07 (m, 3H), 6.67 (m, 1H), 5.93 (s, 2H), 5.31 (m, 1H), 4.91-5.04 (m, 2H), 4.42-4.75 (m, 2H), 4.16-4.32 (m, 1H), 1.28-1.43 (m, 2H), 0.79-0.92 (m, 2H); 1 exchangeable proton not observed.

Compound I-471

The title compound was prepared following general procedure C, except 3,3,3-trifluoropropanoic acid was the acid reactant, 2.5 equivalents of T3P was used, and the reaction was stirred at 23° C. for 24 h. The crude material was purified via silica gel chromatography utilizing a 3-10% methanol in dichloromethane gradient to deliver the desired compound, Compound I-471 (79.3 mg, 85% yield) as a tan solid.

$^1$H-NMR (500 MHz, CDCl$_3$) δ 8.78 (d, 1H), 8.48 (d, 1H), 8.47 (br. s, 1H), 8.09 (d, 1H), 8.03 (s, 1H), 7.47 (s, 1H), 7.19-7.24 (m, 1H), 7.02-7.09 (m, 1H), 6.96-7.01 (m, 1H), 6.81-6.86 (m, 1H), 6.61 (d, 1H), 6.03 (s, 1H), 3.29 (q, 2H).

Compound I-472

To a solution of Intermediate 2 (1 equiv.) in dichloromethane was added methylsulfonylmethylsulfonyl chloride (1.08 equiv.) followed by 1,8-diazabicyclo[5.4.0]undec-7-ene (1 equiv.). The reaction was heated to 60° C. for 1 h, after which the reaction was diluted with water and 1N hydrochloric acid solution and extracted with dichloromethane. The combined organic layers were dried over sodium sulfate, filtered, and concentrated in vacuo. The crude material was purified via silica gel chromatography utilizing a 3-8% methanol in dichloromethane gradient to deliver the desired compound, Compound I-472 (39.6 mg, 37% yield) as a white solid.

$^1$H-NMR (500 MHz, CDCl$_3$) δ 8.55 (d, 1H), 8.26 (br. s, 1H), 7.36 (s, 1H), 7.26-7.30 (m, 1H), 7.07-7.16 (m, 3H), 6.84-6.91 (m, 1H), 6.62-6.67 (m, 1H), 5.95 (s, 2H), 4.60 (s, 2H), 3.17 (s, 3H); 1 N—H proton not observed.

Compound I-486

The title compound was prepared following general procedure C, except 4-sulfamoylbutanoic acid was the acid reactant, and 2.5 equivalents of T3P was used. The crude material was purified via silica gel chromatography utilizing a 3-10% methanol in dichloromethane gradient to deliver the desired compound, Compound I-486 (14.7 mg, 15% yield) as a white solid.

$^1$H-NMR (500 MHz, CD$_3$OD) δ 8.78 (s, 1H), 8.66 (d, 1H), 8.12 (d, 1H), 7.52 (s, 1H), 7.25-7.32 (m, 1H), 7.07-7.13 (m, 1H), 7.02-7.07 (m, 1H), 6.86-6.91 (m, 2H, 2 shifts isochronous), 5.97 (s, 2H), 3.19 (t, 2H), 2.71 (t, 2H), 2.21 (m, 2H).

Compound I-496

To 0° C. suspension of Intermediate 2 (1 equiv.) in dichloromethane was added trimethylaluminum (2M solution in toluene, 0.45 equiv.). The reaction was warmed to 23° C. after which α,α-dimethyl-γ-butyrolactone (1.1 equiv.) was added. The reaction was heated to 80° C. for 16 h, cooled to 23° C., then diluted with saturated ammonium chloride solution, extracted with ethyl acetate, and washed with 1N hydrochloric acid solution. The combined organic layers were dried over sodium sulfate, filtered, and concentrated in vacuo. The crude material was purified via reverse phase HPLC utilizing 5-75% of an acetonitrile in water gradient to deliver the desired compound, Compound I-496 (7.7 mg, 25% yield) as a white solid.

$^1$H-NMR (500 MHz, CDCl$_3$) δ 8.71 (d, 1H), 8.47 (d, 1H), 8.34 (d, 1H), 7.41 (s, 1H), 7.17-7.24 (m, 1H), 7.01-7.07 (m, 1H), 6.95-6.99 (m, 1H), 6.85-6.90 (m, 1H), 6.60 (d, 1H), 6.00 (s, 2H), 4.15 (t, 2H), 2.04 (t, 2H), 1.29 (s, 6H).

Compound I-501

To a mixture of Intermediate 1 (1 equiv.) and 5-(trifluoromethyl)pyrrolidin-2-one (1.2 equiv.) in 1,4-dioxane was added cesium carbonate (1.5 equiv.). The reaction was heated to 100° C. for 16 h, after which the reaction was diluted with water, extracted with dichloromethane, and washed with saturated sodium bicarbonate solution. The combined organic layers were dried over sodium sulfate, filtered, and concentrated in vacuo. The crude material was purified via reverse phase HPLC utilizing a 10-95% acetonitrile in water gradient to deliver the desired compound, Compound I-501 (13.4 mg, 13% yield) as an off-white solid.

$^1$H-NMR (500 MHz, CDCl$_3$) δ 8.76 (d, 1H), 8.49 (d, 1H), 7.38 (s, 1H), 7.21-7.26 (m, 1H), 7.03-7.07 (m, 1H), 6.98-7.02 (m, 1H), 6.86-6.92 (m, 1H), 6.61 (d, 1H), 6.01 (s, 2H), 5.34-5.39 (m, 1H), 2.88-2.99 (m, 1H), 2.58-2.70 (m, 2H), 2.40-2.46 (m, 1H).

Compound I-503

To a mixture of Intermediate 1 (1 equiv.) and isothiazolidine 1,1-dioxide (1.2 equiv.) in 1,4-dioxane was added cesium carbonate (1.5 equiv.). The reaction was heated to 100° C. for 16 h, after which the reaction was diluted with water, and extracted with ethyl acetate. The combined organic layers were dried over sodium sulfate, filtered, and concentrated in vacuo. The crude material was purified via silica gel chromatography utilizing a 3-10% methanol in dichloromethane gradient to deliver the desired compound, Compound I-503 (71.3 mg, 73% yield) as an off-white solid.

$^1$H-NMR (500 MHz, CDCl$_3$) δ 8.57 (d, 1H), 8.47 (d, 1H), 7.36 (s, 1H), 7.20-7.25 (m, 1H), 7.03-7.07 (m, 1H), 6.96-7.01 (m, 1H), 6.84-6.88 (m, 1H), 6.61 (m, 1H), 5.99 (s, 2H), 4.27 (t, 2H), 3.44 (t, 2H), 2.66 (t, 2H).

Compound I-506

To a mixture of Intermediate 1 (1 equiv.) and piperidin-2-one (1.2 equiv.) in 1,4-dioxane was added cesium carbonate (1.5 equiv.). The reaction was heated to 100° C. for 16 h, after which the reaction was diluted with water, extracted with dichloromethane, and washed with 1N sodium hydroxide solution. The combined organic layers were dried over sodium sulfate, filtered, and concentrated in vacuo. The crude material was purified via reverse phase HPLC utilizing 5-95% of an acetonitrile in water gradient to deliver the desired compound, Compound I-506 (4.9 mg, 5% yield) as a white solid.

$^1$H-NMR (500 MHz, CDCl$_3$) δ 8.64 (d, 1H), 8.48 (d, 1H), 7.38 (s, 1H), 7.19-7.23 (m, 1H), 7.03-7.07 (m, 1H), 6.97-7.01 (m, 1H), 6.85-6.88 (m, 1H), 6.60 (d, 1H), 6.00 (s, 2H), 4.00 (t, 2H), 2.65 (t, 2H), 1.98-2.07 (m, 4H).

Compound I-512

To a mixture of Intermediate 1 (1 equiv.) and 5,5-dimethylpyrrolidin-2-one (1.2 equiv.) in 1,4-dioxane was added cesium carbonate (1.5 equiv.). The reaction was heated to 100° C. for 16 h, after which the reaction was diluted with water, extracted with dichloromethane, and washed with saturated sodium bicarbonate solution. The combined organic layers were dried over sodium sulfate, filtered, and concentrated in vacuo. The crude material was purified via reverse phase HPLC utilizing a 10-95% acetonitrile in water gradient to deliver the desired compound, Compound I-512 (0.6 mg, 1% yield) as an off-white solid.

$^1$H-NMR (500 MHz, CDCl$_3$) δ 8.69 (d, 1H), 8.49 (d, 1H), 7.28 (s, 1H), 7.20-7.25 (m, 1H), 7.01-7.06 (m, 1H), 6.98-7.01 (m, 1H), 6.89-6.95 (m, 1H), 6.60 (d, 1H), 5.97 (s, 2H), 2.67 (t, 2H), 2.14 (t, 2H), 1.63 (s, 6H).

Compounds I-526 and Compound I-527

To a mixture of Intermediate 1 (1 equiv.) and an inseparable mixture of 3-methyl-3-(methylsulfonyl)pyrrolidin-2-one and 4-hydroxy-2-methyl-2-(methylsulfonyl)-butanamide (combined, 1 equiv.) in 1,4-dioxane was added carbonate (1.5 equiv.). The reaction was heated to 100° C. for 16 h, after which the reaction was diluted with water, and extracted with ethyl acetate. The combined organic layers were dried over sodium sulfate, filtered, and concentrated in vacuo. The crude material was purified via reverse phase HPLC utilizing a 5-95% acetonitrile in water gradient to deliver the desired compounds, Compound I-526 (0.5 mg, 2% yield), and Compound I-527 (1.3 mg, 5% yield) as white solids.

$^1$H-NMR for Compound I-526 (500 MHz, CDCl$_3$) δ 8.73 (d, 1H), 8.49 (d, 1H), 7.37 (s, 1H), 7.20-7.25 (m, 1H), 7.02-7.06 (m, 1H), 6.96-7.01 (m, 1H), 6.84-6.89 (m, 1H), 6.61 (d, 1H), 6.01 (s, 2H), 4.28-4.33 (m, 1H), 4.18-4.23 (m, 1H), 3.20-3.25 (m, 1H), 3.12 (s, 3H), 2.29-2.35 (m, 1H), 2.87 (s, 3H).

$^1$H-NMR for Compound I-527 (500 MHz, CDCl$_3$) δ 8.50 (d, 1H), 8.44 (d, 1H), 7.38 (s, 1H), 7.20-7.26 (m, 1H), 7.06-7.11 (m, 1H), 7.02-7.06 (m, 1H), 6.95-7.03 (m, 1H), 6.65 (d, 1H), 6.00 (d, 1H), 5.98 (d, 1H), 5.91 (br. s, 1H), 4.82-4.86 (m, 1H), 4.74-4.78 (m, 1H), 3.03 (s, 3H), 2.86-2.90 (m, 1H), 2.48-2.52 (m, 1H), 1.76 (s, 3H).

Compound I-533

To a mixture of Intermediate 1 (1 equiv.) and pyrrolidine-2,5-dione (1.3 equiv.) in 1,4-dioxane was added cesium carbonate (1.5 equiv.). The reaction was heated to 100° C. for 16 h, after which the reaction was diluted with water, extracted with ethyl acetate, and washed with 1N sodium hydroxide solution. The combined organic layers were dried over sodium sulfate, filtered, and concentrated in vacuo. The crude material was purified via reverse phase HPLC utilizing a 5-95% acetonitrile in water gradient to deliver the desired compound, Compound I-533 (3.8 mg, 5% yield) as a white solid.

$^1$H-NMR (500 MHz, CDCl$_3$) δ 8.86 (d, 1H), 8.47 (d, 1H), 7.42 (s, 1H), 7.20-7.24 (m, 1H), 7.01-7.06 (m, 1H), 6.96-7.00 (m, 1H), 6.81-6.85 (m, 1H), 6.59 (d, 1H), 6.02 (s, 2H), 3.02 (s, 4H).

Compound I-534

To a mixture of Intermediate 1 (1 equiv.) and 5-oxopyrrolidine-2-carboxamide (1.2 equiv.) in 1,4-dioxane was added cesium carbonate (1.5 equiv.). The reaction was heated to 100° C. for 24 h, after which the reaction was diluted with water and extracted with ethyl acetate. The combined organic layers were dried over sodium sulfate, filtered, and concentrated in vacuo. The crude material was purified via reverse phase HPLC utilizing a 5-75% acetonitrile in water gradient to deliver the desired compound, Compound I-534 (0.6 mg, 1% yield) as a white solid.

$^1$H-NMR (500 MHz, CDCl$_3$) δ 8.62 (d, 1H), 8.50 (d, 1H), 7.31 (s, 1H), 6.99-7.07 (m, 3H), 6.61 (d, 1H), 6.01 (d, 1H), 5.85 (d, 2H), 5.29 (s, 2H), 4.92-4.96 (m, 1H), 2.87-2.93 (m, 1H), 2.58-2.63 (m, 1H), 2.43-2.55 (m, 2H).

Compound I-590

To a mixture of Intermediate 1 (1 equiv.) and 5-oxopyrrolidine-3-carboxamide (1.3 equiv.) in 1,4-dioxane was added cesium carbonate (1.5 equiv.). The reaction was heated to 100° C. for 16 h, after which the reaction was diluted with water, extracted with ethyl acetate, and washed with 1N hydrochloric acid solution. The combined organic layers were dried over sodium sulfate, filtered, and concentrated in vacuo. The crude material was purified via silica gel chromatography utilizing a 5-12% methanol in dichloromethane gradient to deliver the desired compound, Compound I-590 (3.2 mg, 3% yield) as a tan solid.

$^1$H-NMR (500 MHz, CD$_3$OD) δ 8.76 (d, 1H), 8.74 (d, 1H), 7.53 (s, 1H), 7.25-7.29 (m, 1H), 7.07-7.11 (m, 1H), 7.02-7.07 (m, 1H), 6.91 (d, 1H), 6.83-6.87 (m, 1H), 5.97 (s, 2H), 4.26-4.37 (m, 2H), 3.45-3.49 (m, 1H), 2.84-2.94 (m, 2H).

Compound I-691

To a mixture of Intermediate 1 (1 equiv.) and ethyl 3-methyl-2-oxopyrrolidine-3-carboxylate (1.2 equiv.) in 1,4-dioxane was added cesium carbonate (1.5 equiv.). The reaction was heated to 75° C. for 16 h, after which the reaction was diluted with saturated ammonium chloride solution, and extracted with dichloromethane. The combined organic layers were dried over sodium sulfate, filtered, and concentrated in vacuo. The crude material was purified via silica gel chromatography utilizing a 3-7% methanol in dichloromethane gradient to deliver the desired compound, Compound I-691 (377 mg, 92% yield) as a white solid.

$^1$H-NMR (500 MHz, CDCl$_3$) δ 8.68 (d, 1H), 8.48 (d, 1H), 7.37 (s, 1H), 7.19-7.25 (m, 1H), 7.01-7.06 (m, 1H), 6.96-7.01 (m, 1H), 6.86-6.90 (m, 1H), 6.60 (d, 1H), 6.00 (s, 2H), 4.26 (q, 2H), 4.15-4.21 (m, 2H), 2.75-2.80 (m, 1H), 2.17-2.23 (m, 1H), 1.59 (s, 3H), 1.30 (t, 3H).

Compound I-604

To a suspension of Compound I-591 (1 equiv.) in 1:1 tetrahydrofuran/water was added a 1M aqueous solution of sodium hydroxide (2 equiv.). The reaction was stirred at room temperature for 2 h, after which the reaction was concentrated to ~50% of its volume, acidified by the addition of 1M aqueous hydrochloric acid solution, and extracted with ethyl acetate. The combined organic layers were dried over sodium sulfate, filtered, and concentrated in vacuo to deliver the desired compound, Compound I-604 (154.6 mg, 95% yield) as a white solid.

$^1$H-NMR (500 MHz, CDCl$_3$) δ 8.77-8.80 (m, 2H, 2 overlapping shifts), 7.57 (s, 1H), 7.28-7.32 (m, 1H), 7.09-7.13 (m, 1H), 7.04-7.09 (m, 1H), 6.94 (d, 1H), 6.86-6.90 (m, 1H), 6.00 (s, 2H), 4.26-4.31 (m, 1H), 4.16-4.20 (m, 1H), 2.75-2.79 (m, 1H), 2.27-2.31 (m, 1H), 1.54 (s, 3H).

Compound I-605

To a −78° C. solution of Compound I-604 (1 equiv.) in dichloromethane was added oxalyl chloride (2M solution in dichloromethane, 2.5 equiv.). The reaction was stirred at −78° C. for 30 min, then warmed up to 0° C., and stirred at that temperature for 1 h. The reaction was then concentrated in vacuo, reconstituted in dichloromethane, and cooled to −78° C. To this solution was added cyclopropylamine (5 equiv.), after which the reaction was allowed to warm up to room temperature. After 20 min, the reaction was concentrated in vacuo. The crude material was purified via silica gel chromatography utilizing a 1-8% methanol in dichloromethane gradient to deliver the desired compound, Compound I-604 (14.5 mg, 23% yield) as a white solid.

$^1$H-NMR (500 MHz, CDCl$_3$) δ 8.70 (d, 1H), 8.49 (d, 1H), 7.36 (s, 1H), 7.20-7.25 (m, 1H), 7.01-7.08 (m, 1H), 6.97-7.01 (m, 1H), 6.86-6.90 (m, 1H), 6.60 (d, 1H), 6.00 (s, 2H), 4.06-4.09 (m, 2H), 3.00-3.06 (m, 1H), 2.75-2.80 (m, 1H), 2.14-2.29 (m, 1H), 1.58 (s, 3H), 0.78-0.82 (m, 2H), 0.51-0.54 (m, 2H); 1 N—H proton not observed.

Compound I-606

To a −78° C. solution of Compound I-604 (1 equiv.) in dichloromethane was added a 2M in dichloromethane solution of oxalyl chloride (2.5 equiv.). The reaction was stirred at −78° C. for 30 minutes, then warmed up to 0° C., and stirred at that temperature for 1 h. The reaction was then concentrated in vacuo, reconstituted in dichloromethane, and cooled to −78° C. To this solution was added ammonium hydroxide solution (50 equiv.), after which the reaction was allowed to warm up to room temperature. After 20 minutes, the reaction was diluted in water and extracted with ethyl acetate. The combined organic layers were dried over sodium sulfate, filtered, and concentrated in vacuo to deliver the desired compound, Compound I-619 (43.3 mg, 75% yield) as an off-white solid.

$^1$H-NMR (500 MHz, CDCl$_3$) δ 8.71 (d, 1H), 8.49 (d, 1H), 7.37 (s, 1H), 7.20-7.25 (m, 1H), 7.03-7.07 (m, 1H), 6.97-7.01 (m, 1H), 6.86-6.91 (m, 1H), 6.60 (d, 1H), 6.00 (s, 2H), 4.07-4.13 (m, 2H), 2.97-3.03 (m, 1H), 2.17-2.22 (m, 1H), 1.65 (s, 3H); 2 N—H protons not observed.

Compound I-612

A suspension of Intermediate 1 (1 equiv) and potassium ((2-carboxylatoethyl)sulfonyl)amide (1.15 equiv.) in DMSO was stirred at room temperature for 72 h. The reaction was diluted in water, washed with dichloromethane, acidified by the addition of 1M hydrochloric acid solution, and extracted with ethyl acetate. The combined organic layers were dried over sodium sulfate, filtered, and concentrated in vacuo to deliver the acid intermediate. To a suspension of this acid intermediate in dichloromethane was added triethylamine (3 equiv.), followed by oxalyl chloride (2M solution in dichloromethane, 2 equiv). After 15 min, the reaction was concentrated in vacuo. The crude material was purified via reverse phase HPLC utilizing a 5-75% acetonitrile in water gradient to deliver the desired compound, Compound I-612 (5.8 mg, 12% yield) as a white solid.

¹H-NMR (500 MHz, CDCl₃) δ 8.86 (d, 1H), 8.47 (d, 1H), 7.43 (s, 1H), 7.19-7.24 (m, 1H), 7.01-7.06 (m, 1H), 6.96-7.01 (m, 1H), 6.83-6.88 (m, 1H), 6.63 (d, 1H), 6.02 (s, 2H), 3.89 (t, 2H), 3.35 (t, 2H).

Compound I-615

To a mixture of Intermediate 1 (1 equiv.) and 3-hydroxypyrrolidin-2-one (1.2 equiv.) in 1,4-dioxane was added cesium carbonate (1.5 equiv.). The reaction was heated to 70° C. for 12 h, after which the reaction was diluted with water and extracted with ethyl acetate. The combined organic layers were dried over sodium sulfate, filtered, and concentrated in vacuo to deliver the desired compound, Compound I-615 (59.7 mg, 48% yield) as a white solid.

¹H-NMR (500 MHz, CDCl₃) δ 8.48 (d, 1H), 8.46 (d, 1H), 7.32 (s, 1H), 7.19-7.24 (m, 1H), 7.02-7.07 (m, 1H), 6.98-7.02 (m, 1H), 6.89-6.94 (m, 1H), 6.60 (d, 1H), 5.97 (s, 2H), 5.92-5.96 (m, 1H), 3.60-3.65 (m, 1H), 3.47-3.52 (m, 1H), 2.82-2.86 (m, 1H), 2.33-2.41 (m, 1H); 1 O—H proton not observed.

Compound I-628

A solution of 1-(2-fluorobenzyl)-5-(isoxazol-3-yl)-1H-pyrazole-3-carboximidamide hydrochloride (generated in step 3 of general procedure A, by using 1-(isoxazol-3-yl)ethanone in step 1 and 2-fluorobenzylhydrazine in step 2, 1 equiv.), methyl 4-oxotetrahydrothiophene-3-carboxylate (3 equiv.), and 1,8-diazabicyclo[5.4.0]undec-7-ene (1 equiv.) in pyridine was heated to 80° C. for 12 h. The reaction was concentrated in vacuo, slurried in methanol, concentrated in vacuo, and slurried again in methanol. The precipitate was filtered and dried to provide the desired cyclic sulfide intermediate (190 mg, 45% yield) as a light-tan solid. To a solution of this sulfide intermediate (1 equiv.) in dichloromethane was added peracetic acid (2.3 equiv.). After 30 min, the reaction was concentrated in vacuo, slurried in water, and filtered to deliver the desired compound, Compound I-628 (148.8 mg, 73% yield) as an off-white solid.

¹H-NMR (500 MHz, CDCl₃) δ 10.2 (br. s, 1H), 8.56 (s, 1H), 7.31-7.34 (m, 1H), 7.30 (s, 1H), 7.07-7.12 (m, 3H), 6.64 (m, 1H), 5.93 (s, 2H), 4.36 (s, 2H), 4.35 (s, 2H).

Compound I-632

A suspension of Compound I-628 (1 equiv.) in phosphorus oxychloride (62 equiv.) was heated to 90° C. for 2 h, after which the reaction mixture was concentrated in vacuo to afford the desired chloropyrimidine intermediate (155 mg, 100% yield) as a tan solid. To a suspension of this intermediate (1 equiv.) in dioxane was added an ammonium hydroxide solution (440 equiv.). The reaction was stirred at 23° C. for 15 h, then heated to 60° C. for 1 h, after which the mixture was diluted in water and extracted with ethyl acetate. The combined organic layers were dried over sodium sulfate, filtered, and concentrated in vacuo to deliver the desired compound, Compound I-632 (44.5 mg, 60% yield) as a tan solid.

¹H-NMR (500 MHz, DMSO-d₆) δ 9.09 (d, 1H), 7.51 (s, 1H), 7.31-7.35 (m, 1H), 7.27 (d, 1H), 7.21-7.24 (m, 1H), 7.09-7.13 (m, 1H), 6.83-6.87 (m, 1H), 5.90 (s, 2H), 4.49 (s, 2H), 4.31 (s, 2H).

Compound I-497 and I-524

A solution of Intermediate 2 (1 equiv.), triethylamine (3.5 equiv.), DMAP (0.1 equiv.), and 2-chloro-2-oxoethylacetate (2.2 equiv.) in dichloromethane was heated to 60° C. for 26 h. Solvent removed in vacuo, and crude material was purified via reverse phase HPLC to deliver the desired compound, Compound I-497 (30 mg, 23% yield) as a white solid, and a side product, Compound I-524 (4.5 mg, 4% yield) as a white solid.

¹H-NMR for Compound I-497 (500 MHz, DMSO-d₆) δ ppm 11.37 (m, 1H), 9.11 (d, 1H), 8.75 (d, 1H), 7.94 (m, 1H), 7.66 (s, 1H), 7.35 (m, 1H), 7.27 (d, 2H), 7.11 (m, 1H), 6.89 (m, 1H), 5.93 (s, 2H), 4.77 (s, 2H), 2.12 (s, 3H).

¹H-NMR for Compound I-524 (500 MHz, DMSO-d₆) δ ppm 11.13 (m, 1H), 9.09 (m, 1H), 8.72 (m, 1H), 8.00 (m, 1H), 7.65 (s, 1H), 7.35 (m, 1H), 7.26 (s, 2H), 7.12 (m, 1H), 6.88 (m, 1H), 5.93 (s, 2H), 2.15 (s, 3H).

Compound I-499

Into a slurry of Compound I-497 (1 equiv.) in methanol was added a solution of potassium carbonate (0.5 equiv.) in water. After stirring for 1 h at 23 C, an additional 0.5 equivalents of potassium carbonate in water was added to the vessel, along with THF (equal volume to starting volume of methanol). Reaction was allowed to stir for an additional 1 h at 23° C. Solvent was removed in vacuo, and the resulting crude material was purified via silica gel chromatography utilizing a 0-5% methanol in dichloromethane gradient to deliver the desired compound, Compound I-499 (10.5 mg, 17% yield) as a white solid.

¹H-NMR (500 MHz, DMSO-d₆) δ ppm 10.43 (m, 1H), 9.11 (m, 1H), 8.75 (m, 1H), 8.01 (m, 1H), 7.68 (s, 1H), 7.34 (m, 1H), 7.24 (m, 2H), 7.12 (m, 1H), 6.89 (m, 1H), 5.93 (s, 2H), 5.61 (m, 1H), 4.11 (m, 2H).

Compound I-525

The title compound was prepared following general procedure C in library format, except 4-(benzyloxy)tetrahydro-2H-pyran-4-carboxylic acid was the acid reactant, and the crude material was purified via reverse phase HPLC to deliver the desired compound, Compound I-525 (9 mg, 27% yield) as a white solid.

¹H-NMR (500 MHz, DMSO-d₆) δ ppm 9.39 (m, 1H), 8.91 (m, 1H), 8.56 (s, 1H), 8.36 (m, 1H), 7.53 (m, 1H), 7.38 (m, 5H), 7.26 (m, 1H), 7.07 (s, 3H), 6.65 (s, 1H), 6.02 (s, 2H), 4.51 (s, 2H), 3.96 (m, 2H), 3.87 (m, 2H), 2.28 (m, 2H), 1.99 (m, 2H).

Compound I-528

The title compound was prepared following general procedure C in library format, except 2-methoxyacetic acid was the acid reactant, and the crude material was purified via reverse phase HPLC to deliver the desired compound, Compound I-528 (7 mg, 58% yield) as a white solid.

¹H-NMR (500 MHz, DMSO-d₆) δ ppm 9.18 (m, 1H), 8.75 (m, 1H), 8.47 (m, 1H), 8.18 (m, 1H), 7.50 (m, 1H), 7.21 (m, 1H), 7.05 (m, 1H), 6.97 (m, 1H), 6.83 (m, 1H), 6.61 (m, 1H), 6.05 (m, 2H), 4.08 (m, 2H), 3.52 (s, 3H).

Compound I-532

The title compound was prepared following general procedure C in library format, except oxazole-4-carboxylic acid was the acid reactant, and the crude material was purified via reverse phase HPLC to deliver the desired compound, Compound I-532 (3.8 mg, 15% yield) as a white solid.

¹H-NMR (500 MHz, DMSO-d₆) δ ppm 10.39 (m, 1H), 9.09 (m, 2H), 8.82 (m, 1H), 8.65 (m, 1H), 8.11 (m, 1H), 7.73 (m, 1H), 7.29 (m, 3H), 7.13 (m, 1H), 6.88 (m, 1H), 5.94 (m, 2H).

Compound I-547

The title compound was prepared following general procedure C in library format, except 3-methoxypropanoic acid was the acid reactant, and the crude material was purified via reverse phase HPLC to deliver the desired compound, Compound I-547 (4.9 mg, 20% yield) as a white solid.

¹H-NMR (500 MHz, DMSO-d₆) δ ppm 11.09 (m, 1H), 9.09 (m, 1H), 8.72 (m, 1H), 8.02 (m, 1H), 7.64 (s, 1H), 7.34 (m, 1H), 7.23 (m, 2H), 7.12 (m, 1H), 6.89 (m, 1H), 5.92 (s, 2H), 3.61 (t, 2H), 3.23 (s, 3H), 2.70 (t, 2H).

Compound I-548

The title compound was prepared following general procedure C in library format, except tosylalanine was the acid reactant, and the crude material was purified via reverse phase HPLC to deliver the desired compound, Compound I-548 (3.1 mg, 9% yield) as a white solid.

Compound I-549

The title compound was prepared following general procedure C in library format, except thiazole-4-carboxylic acid was the acid reactant, and the crude material was purified via reverse phase HPLC to deliver the desired compound, Compound I-549 (3.7 mg, 14% yield) as a white solid.

$^1$H-NMR (500 MHz, DMSO-$d_6$) δ ppm 10.20 (m, 1H), 9.31 (m, 1H), 9.09 (m, 1H), 8.84 (m, 1H), 8.72 (m, 1H), 8.14 (m, 1H), 7.73 (m, 1H), 7.29 (m, 3H), 7.13 (m, 1H), 6.89 (m, 1H), 5.94 (m, 2H).

Compound I-550

The title compound was prepared following general procedure C in library format, except 1H-pyrrole-2-carboxylic acid was the acid reactant, and the crude material was purified via reverse phase HPLC to deliver the desired compound, Compound I-550 (3.4 mg, 13% yield) as a white solid.

$^1$H-NMR (500 MHz, DMSO-$d_6$) δ ppm 11.84 (m, 1H), 10.84 (m, 1H), 9.09 (m, 1H), 8.73 (m, 1H), 8.16 (m, 1H), 7.68 (s, 1H), 7.36 (m, 2H), 7.24 (m, 2H), 7.13 (m, 1H), 7.06 (m, 1H), 6.88 (m, 1H), 6.19 (m, 1H), 5.94 (s, 2H).

Compound I-551

The title compound was prepared following general procedure C in library format, except 1-cyanocyclopropane-1-carboxylic acid was the acid reactant, and the crude material was purified via reverse phase HPLC to deliver the desired compound, Compound I-551 (3.3 mg, 13% yield) as a white solid.

$^1$H-NMR (500 MHz, DMSO-$d_6$) δ ppm 11.02 (m, 1H), 9.09 (m, 1H), 8.74 (m, 1H), 7.88 (m, 1H), 7.67 (s, 1H), 7.33 (m, 1H), 7.27 (m, 1H), 7.23 (m, 1H), 7.12 (m, 1H), 6.89 (m, 1H), 5.94 (s, 2H), 1.74 (m, 4H).

Compound I-552

The title compound was prepared following general procedure C in library format, except thiazole-5-carboxylic acid was the acid reactant, and the crude material was purified via reverse phase HPLC to deliver the desired compound, Compound I-552 (2.3 mg, 9% yield) as a white solid.

$^1$H-NMR (500 MHz, DMSO-$d_6$) δ ppm 11.71 (m, 1H), 9.35 (m, 1H), 9.12 (m, 1H), 8.96 (m, 1H), 8.79 (m, 1H), 8.08 (m, 1H), 7.70 (m, 1H), 7.34 (m, 1H), 7.24 (m, 2H), 7.12 (m, 1H), 6.89 (m, 1H), 5.95 (m, 2H).

Compound I-553

The title compound was prepared following general procedure C in library format, except 6-oxo-1,6-dihydropyridine-2-carboxylic acid was the acid reactant, and the crude material was purified via reverse phase HPLC to deliver the desired compound, Compound I-553 (1.9 mg, 7% yield) as a white solid.

Compound I-554

The title compound was prepared following general procedure C in library format, except 3-methoxyisoxazole-5-carboxylic acid was the acid reactant, and the crude material was purified via reverse phase HPLC to deliver the desired compound, Compound I-554 (4.6 mg, 17% yield) as a white solid.

Compound I-555

The title compound was prepared following general procedure C in library format, except pyrimidine-4-carboxylic acid was the acid reactant, and the crude material was purified via reverse phase HPLC to deliver the desired compound, Compound I-555 (1.6 mg, 6% yield) as a white solid.

Compound I-556

The title compound was prepared following general procedure C in library format, except oxazole-5-carboxylic acid was the acid reactant, and the crude material was purified via reverse phase HPLC to deliver the desired compound, Compound I-556 (4.4 mg, 17% yield) as a white solid.

Compound I-557

The title compound was prepared following general procedure C in library format, except oxazole-4-carboxylic acid was the acid reactant, and the crude material was purified by reverse phase HPLC to deliver the desired compound, Compound I-557 (4.4 mg, 17% yield) as a white solid.

Compound I-558

The title compound was prepared following general procedure C in library format, except cyclopropanecarboxylic acid was the acid reactant, and the crude material was purified via reverse phase HPLC to deliver the desired compound, Compound I-558 (5.1 mg, 21% yield) as a white solid.

$^1$H-NMR (500 MHz, DMSO-$d_6$) δ ppm 11.42 (m, 1H), 9.11 (m, 1H), 8.69 (m, 1H), 8.01 (m, 1H), 7.66 (m, 1H), 7.34 (m, 1H), 7.24 (m, 2H), 7.12 (m, 1H), 6.89 (m, 1H), 5.93 (m, 2H), 2.12 (m, 1H), 0.87 (d, 4H).

Compound I-559

The title compound was prepared following general procedure C in library format, except (S)-2-methoxy-2-phenylacetic acid was the acid reactant, and the crude material was purified via reverse phase HPLC to deliver the desired compound, Compound I-559 (6.8 mg, 24% yield) as a white solid.

$^1$H-NMR (500 MHz, DMSO-$d_6$) δ 11.03 (m, 1H), 9.09 (m, 1H), 8.72 (m, 1H), 7.96 (m, 1H), 7.67 (m, 1H), 7.51 (m, 2H), 7.36 (m, 4H), 7.23 (m, 2H), 7.12 (m, 1H), 6.87 (m, 1H), 5.93 (m, 2H), 5.12 (m, 1H), 3.34 (s, 3H).

Compound I-560

The title compound was prepared following general procedure C in library format, except furan-2-carboxylic acid was the acid reactant, and the crude material was purified via reverse phase HPLC to deliver the desired compound, Compound I-560 (5.2 mg, 20% yield) as a white solid.

$^1$H-NMR (500 MHz, DMSO-$d_6$) δ ppm 11.10 (m, 1H), 9.09 (m, 1H), 8.75 (m, 1H), 8.10 (m, 1H), 8.00 (m, 1H), 7.78 (m, 1H), 7.69 (m, 1H), 7.34 (m, 1H), 7.24 (m, 2H), 7.12 (m, 1H), 6.89 (m, 1H), 6.73 (m, 1H), 5.94 (s, 2H).

Compound I-561

The title compound was prepared following general procedure C in library format, except thiophene-2-carboxylic acid was the acid reactant, and the crude material was purified via reverse phase HPLC to deliver the desired compound, Compound I-561 (3.9 mg, 15% yield) as a white solid.

$^1$H-NMR (500 MHz, DMSO-$d_6$) δ ppm 11.39 (m, 1H), 9.10 (m, 1H), 8.78 (m, 1H), 8.36 (m, 1H), 8.10 (m, 1H), 7.95 (m, 1H), 7.70 (s, 1H), 7.34 (m, 1H), 7.25 (m, 3H), 7.12 (m, 1H), 6.88 (m, 1H), 5.95 (m, 2H).

Compound I-562

The title compound was prepared following general procedure C in library format, except 2-ethoxyacetic acid was the acid reactant, and the crude material was purified via reverse phase HPLC to deliver the desired compound, Compound I-562 (5.7 mg, 23% yield) as a white solid.

$^1$H-NMR (500 MHz, DMSO-$d_6$) δ ppm 10.70 (m, 1H), 9.10 (m, 1H), 8.73 (m, 1H), 8.00 (m, 1H), 7.66 (m, 1H), 7.33

(m, 1H), 7.23 (m, 2H), 7.11 (m, 1H), 6.89 (m, 1H), 5.93 (s, 2H), 4.17 (s, 2H), 3.55 (m, 2H), 1.17 (m, 3H).

Compound I-563

The title compound was prepared following general procedure C in library format, except 2-(methylsulfonyl)acetic acid was the acid reactant, and the crude material was purified via reverse phase HPLC to deliver the desired compound, Compound I-563 (3 mg, 11% yield) as a white solid.

$^1$H-NMR (500 MHz, DMSO-$d_6$) δ ppm 11.53 (m, 1H), 9.08 (m, 1H), 8.78 (m, 1H), 7.99 (m, 1H), 7.66 (m, 1H), 7.34 (m, 1H), 7.23 (m, 2H), 7.12 (m, 1H), 6.91 (m, 1H), 5.93 (m, 2H), 4.46 (m, 2H), 3.17 (s, 3H).

Compound I-564

The title compound was prepared following general procedure C in library format, except 3-cyclopropyl-1H-pyrazole-5-carboxylic acid was the acid reactant, and the crude material was purified via reverse phase HPLC to deliver the desired compound, Compound I-564 (1.2 mg, 4% yield) as a white solid.

$^1$H-NMR (500 MHz, DMSO-$d_6$) δ ppm 9.84 (br s, 1H), 9.10 (m, 1H), 8.77 (m, 1H), 8.07 (m, 1H), 7.72 (m, 1H), 7.34 (m, 1H), 7.28 (m, 1H), 7.23 (m, 1H), 7.12 (m, 1H), 6.89 (m, 1H), 6.61 (m, 1H), 5.95 (m, 2H), 1.96 (m, 1H), 0.98 (m, 2H), 0.76 (m, 2H).

Compound I-565

The title compound was prepared following general procedure C in library format, except 2-acetoxy-2-phenylacetic acid was the acid reactant, and the crude material was purified via reverse phase HPLC to deliver the desired compound, Compound I-565 (4.1 mg, 14% yield) as a white solid.

$^1$H-NMR (500 MHz, DMSO-$d_6$) δ ppm 11.60 (m, 1H), 9.08 (m, 1H), 8.72 (m, 1H), 7.92 (m, 1H), 7.65 (m, 1H), 7.59 (m, 2H), 7.41 (m, 3H), 7.33 (m, 1H), 7.23 (m, 2H), 7.11 (m, 1H), 6.88 (m, 1H), 6.17 (s, 1H), 5.92 (s, 2H), 2.15 (s, 3H).

Compound I-569

The title compound was prepared following general procedure C in library format, except 1-methylcyclopropane-1-carboxylic acid was the acid reactant, and the crude material was purified via reverse phase HPLC to deliver the desired compound, Compound I-569 as a white solid.

$^1$H-NMR (500 MHz, CD$_3$OD) δ ppm 8.81 (m, 1H), 8.69 (m, 1H), 8.18 (m, 1H), 7.59 (m, 1H), 7.31 (m, 1H), 7.10 (m, 2H), 6.93 (m, 2H), 6.01 (m, 2H), 1.52 (s, 3H), 1.32 (m, 2H), 0.84 (m, 2H).

Compound I-570

The title compound was prepared following general procedure C in library format, except tetrahydrofuran-2-carboxylic acid was the acid reactant, and the crude material was purified via reverse phase HPLC to deliver the desired compound, Compound I-570 as a white solid.

$^1$H-NMR (500 MHz, CD$_3$OD) δ ppm 8.79 (m, 1H), 8.72 (m, 1H), 8.17 (m, 1H), 7.55 (m, 1H), 7.29 (m, 1H), 7.09 (m, 2H), 6.92 (m, 2H), 5.99 (m, 2H), 4.53 (m, 1H), 4.13 (m, 1H), 3.98 (m, 1H), 2.39 (m, 1H), 2.14 (m, 1H), 2.01 (m, 2H).

Compound I-571

The title compound was prepared following general procedure C in library format, except 2-(5-methyl-2,4-dioxo-3,4-dihydropyrimidin-1(2H)-yl)acetic acid was the acid reactant, and the crude material was purified via reverse phase HPLC to deliver the desired compound, Compound I-571 as a white solid.

$^1$H-NMR (500 MHz, CD$_3$OD) δ ppm 8.79 (d, 1H), 8.69 (d, 1H), 8.09 (d, 1H), 7.54 (s, 1H), 7.43 (d, 1H), 7.32-7.25 (m, 1H), 7.14-7.01 (m, 2H), 6.96-6.89 (m, 1H), 6.88 (d, 1H), 5.98 (s, 2H), 4.70 (s, 2H), 1.91 (d, 3H).

Compound I-572

The title compound was prepared following general procedure C in library format, except 3,3,3-trifluoro-2-methoxy-2-phenylpropanoic acid was the acid reactant, and the crude material was purified via reverse phase HPLC to deliver the desired compound, Compound I-572 as a white solid.

$^1$H-NMR (500 MHz, CD$_3$OD) δ 8.79 (m, 2H), 8.19 (m, 1H), 7.64 (m, 2H), 7.57 (m, 1H), 7.48 (m, 3H), 7.30 (m, 1H), 7.08 (m, 2H), 6.92 (m, 2H), 5.99 (m, 2H), 3.63 (d, 3H).

Compound I-574

The title compound was prepared following general procedure C in library format, except tetrahydro-2H-pyran-4-carboxylic acid was the acid reactant, and the crude material was purified via reverse phase HPLC to deliver the desired compound, Compound I-574 as a white solid.

$^1$H-NMR (500 MHz, CD$_3$OD) δ ppm 8.81 (d, 1H), 8.66 (s, 1H), 8.20 (d, 1H), 7.54 (s, 1H), 7.30 (m, 1H), 7.09 (m, 2H), 6.93 (m, 1H), 6.88 (d, 1H), 5.98 (s, 2H), 4.02 (m, 2H), 3.52 (m, 2H), 2.80 (m, 1H), 1.85 (d, 4H).

Compound I-577

The acetyl-protected intermediate was prepared following general procedure C in library format, except 2-acetoxybenzoic acid was the acid reactant. The crude material was purified via reverse phase HPLC to deliver the desired intermediate. The intermediate was then dissolved in a methanol:water mixture (8:1) and treated with lithium hydroxide (4.5 equiv.) and a small amount of THF (300 μL). After reaction was complete, volatiles were removed in vacuo, and the residue was treated with 1N HCl solution until pH was ~4. The mixture was extracted with ethyl acetate, and the organic layers were washed with water and brine. Contents were dried over sodium sulfate, filtered, and concentrated to deliver the desired compound, Compound I-577 (10 mg, 33% yield over 2 steps) as a white solid.

$^1$H-NMR (500 MHz, DMSO-$d_6$) δ ppm 11.81 (m, 1H), 11.12 (m, 1H), 9.10 (d, 1H), 8.79 (m, 1H), 8.20 (m, 1H), 8.00 (m, 1H), 7.66 (s, 1H), 7.51 (m, 1H), 7.34 (m, 1H), 7.28 (d, 1H), 7.23 (m, 1H), 7.08 (m, 3H), 6.90 (m, 1H), 5.96 (s, 2H).

Compound I-579

A solution of 2-cyanoacetic acid (4 equiv.) in DMF was cooled to 0° C., and treated with oxalyl chloride (4.1 equiv.) as a solution in DMF. Gas evolution was observed, and contents were stirred at 0° C. for 30 min. Intermediate 2 (1 equiv.) was added to the reaction, and contents stirred for 18 h as it was allowed to warmed to 23° C. Solvents were removed in vacuo, and the crude material was purified via reverse phase HPLC to deliver the desired compound, Compound I-579 (2.3 mg, 10% yield) as a white solid.

$^1$H-NMR (500 MHz, DMSO-$d_6$) δ ppm 11.47 (m, 1H), 9.10 (d, 1H), 8.78 (m, 1H), 7.94 (m, 1H), 7.65 (s, 1H), 7.34 (d, 1H), 7.24 (m, 2H), 7.12 (m, 1H), 6.91 (t, 1H), 5.92 (s, 2H), 4.05 (s, 2H).

Compound I-594

The title compound was prepared following general procedure C in library format, except 2-methyl-2,3-dihydrobenzo[b]thiophene-2-carboxylic acid 1,1-dioxide was the acid reactant, and the crude material was purified via reverse phase HPLC to deliver the desired compound, Compound I-594 (7.4 mg, 23% yield) as a yellow solid.

$^1$H-NMR (500 MHz, DMSO-$d_6$) δ ppm 10.96 (m, 1H), 9.09 (m, 1H), 8.77 (m, 1H), 7.93 (m, 1H), 7.79 (m, 1H), 7.68 (s, 2H), 7.57 (m, 2H), 7.34 (m, 1H), 7.24 (m, 2H), 7.12 (m, 1H), 6.89 (m, 1H), 5.94 (s, 2H), 4.11 (m, 1H), 3.30 (m, 1H), 1.89 (s, 3H).

Compound I-596

The title compound was prepared following general procedure C in library format, except 2-(1,3-dioxoisoindolin-2-yl)acetic acid was the acid reactant, and the crude material was purified via reverse phase HPLC to deliver the desired compound, Compound I-596 (17.4 mg, 56% yield) as a white solid.

$^1$H-NMR (500 MHz, DMSO-d$_6$) δ ppm 11.60 (m, 1H), 9.09 (m, 1H), 8.74 (m, 1H), 7.91 (m, 5H), 7.65 (m, 1H), 7.35 (m, 1H), 7.24 (m, 2H), 7.12 (m, 1H), 6.92 (m, 1H), 5.93 (m, 2H), 4.58 (s, 2H).

Compound I-597

The title compound was prepared following general procedure C in library format, except (2-phenylacetyl)glycine was the acid reactant, and the crude material was purified via reverse phase HPLC to deliver the desired compound, Compound I-597 (4.4 mg, 15% yield) as a white solid.

$^1$H-NMR (500 MHz, CD$_3$OD) δ ppm 8.83 (m, 1H), 8.68 (m, 1H), 8.24 (m, 1H), 7.58 (s, 1H), 7.34 (m, 5H), 7.26 (m, 1H), 7.10 (m, 2H), 6.97 (m, 1H), 6.90 (m, 1H), 6.01 (s, 2H), 4.17 (s, 2H), 3.66 (s, 2H).

Compound I-598

The title compound was prepared following general procedure C in library format, except ((benzyloxy)carbonyl) glycine was the acid reactant, and the crude material was purified via reverse phase HPLC to deliver the desired compound, Compound 1598 (4 mg, 13% yield) as a white solid.

$^1$H-NMR (500 MHz, DMSO-d$_6$) δ ppm 11.15 (m, 1H), 9.10 (d, 1H), 8.73 (m, 1H), 7.98 (m, 1H), 7.65 (s, 1H), 7.57 (m, 1H), 7.37 (m, 6H), 7.23 (m, 2H), 7.12 (m, 1H), 6.90 (m, 1H), 5.92 (m, 2H), 5.05 (s, 2H), 3.93 (m, 2H).

Compound I-599

The title compound was prepared following general procedure C in library format, except 2-(1-oxoisoindolin-2-yl) acetic acid was the acid reactant, and the crude material was purified via reverse phase HPLC to deliver the desired compound, Compound I-599 (11.7 mg, 39% yield) as a white solid.

$^1$H-NMR (500 MHz, DMSO-d$_6$) δ ppm 11.42 (m, 1H), 9.10 (m, 1H), 8.74 (m, 1H), 7.95 (m, 1H), 7.72 (m, 1H), 7.66 (m, 1H), 7.63 (m, 2H), 7.52 (m, 1H), 7.34 (m, 1H), 7.24 (m, 2H), 7.13 (m, 1H), 6.92 (m, 1H), 5.93 (m, 2H), 4.55 (m, 4H).

Compound I-610

The title compound was prepared following general procedure C in library format, except 2-(2-oxooxazolidin-3-yl) acetic acid was the acid reactant, and the crude material was purified via reverse phase HPLC to deliver the desired compound, Compound I-610 (11.4 mg, 42% yield) as a white solid.

$^1$H-NMR (500 MHz, DMSO-d$_6$) δ ppm 11.33 (m, 1H), 9.10 (m, 1H), 8.75 (m, 1H), 7.96 (m, 1H), 7.64 (m, 1H), 7.35 (m, 1H), 7.24 (m, 2H), 7.12 (m, 1H), 6.91 (m, 1H), 5.93 (m, 2H), 4.33 (m, 2H), 4.15 (s, 2H), 3.64 (m, 2H).

Compound I-601

The title compound was prepared following general procedure C in library format, except 2-(4-oxoquinazolin-3 (4H)-yl)acetic acid was the acid reactant, and the crude material was purified via reverse phase HPLC to deliver the desired compound, Compound I-601 (3.3 mg, 11% yield) as a white solid.

$^1$H-NMR (500 MHz, DMSO-d$_6$) δ ppm 11.69 (m, 1H), 9.10 (m, 1H), 8.75 (m, 1H), 8.37 (s, 1H), 8.15 (m, 1H), 7.90 (m, 2H), 7.73 (m, 1H), 7.67 (s, 1H), 7.56 (m, 1H), 7.34 (m, 1H), 7.24 (m, 2H), 7.13 (m, 1H), 6.93 (m, 1H), 5.94 (s, 2H), 4.99 (s, 2H).

Compound I-602

The title compound was prepared following general procedure C in library format, except (2-(1,3-dioxoisoindolin-2-yl)acetyl)glycine was the acid reactant, and the crude material was purified via reverse phase HPLC to deliver the desired compound, Compound I-602 (1.2 mg, 4% yield) as a white solid.

$^1$H-NMR (500 MHz, DMSO-d$_6$) δ ppm 11.20 (m, 1H), 9.09 (m, 1H), 8.74 (m, 1H), 8.62 (m, 1H), 7.98 (m, 1H), 7.91 (s, 2H), 7.88 (s, 2H), 7.64 (s, 1H), 7.33 (m, 1H), 7.24 (d, 1H), 7.20 (m, 1H), 7.11 (m, 1H), 6.89 (m, 1H), 5.92 (m, 2H), 4.29 (s, 2H), 4.05 (m, 2H).

Compound I-603

The title compound was prepared following general procedure C in library format, except (methoxycarbonyl)glycine was the acid reactant, and the crude material was purified via reverse phase HPLC to deliver the desired compound, Compound I-603 (2.2 mg, 8% yield) as a white solid.

$^1$H-NMR (500 MHz, DMSO-d$_6$) δ ppm 11.13 (m, 1H), 9.09 (m, 1H), 8.73 (m, 1H), 7.97 (m, 1H), 7.66 (m, 1H), 7.42 (m, 1H), 7.34 (m, 1H), 7.23 (m, 2H), 7.12 (m, 1H), 6.90 (m, 1H), 5.92 (m, 2H), 3.90 (m, 2H), 3.56 (s, 3H).

Compound I-592

The title compound was prepared following general procedure C, except 2-(phenylsulfonyl)acetic acid was the acid reactant, and the crude material was purified via reverse phase HPLC to deliver the desired compound, Compound I-592 (1.7 mg, 5% yield) as a white solid.

$^1$H-NMR (500 MHz, DMSO-d$_6$) δ ppm 11.44 (m, 1H), 9.10 (m, 1H), 8.75 (m, 1H), 7.92 (m, 1H), 7.91 (m, 1H), 7.89 (m, 1H), 7.88 (m, 1H), 7.76 (m, 1H), 7.65 (m, 2H), 7.34 (m, 1H), 7.26 (m, 1H), 7.22 (m, 1H), 7.12 (m, 1H), 6.91 (m, 1H), 5.92 (m, 2H), 4.67 (m, 2H).

Compound I-594

The title compound was prepared following general procedure C, except 2-((4-chlorophenyl)sulfonyl)acetic acid was the acid reactant, and the crude material was purified by reverse phase HPLC to deliver the desired compound, Compound I-594 (5.8 mg, 15% yield) as a white solid.

$^1$H-NMR (500 MHz, DMSO-d$_6$) δ ppm 11.48 (s, 1H), 9.10 (d, 1H), 8.76 (d, 1H), 7.92 (m, 2H), 7.87 (m, 1H), 7.76 (m, 2H), 7.65 (s, 1H), 7.34 (m, 1H), 7.24 (m, 2H), 7.12 (m, 1H), 6.91 (m, 1H), 5.93 (s, 2H), 4.73 (m, 2H).

Compound I-498

To a mixture of 5-fluoro-2-(1-(2-fluorobenzyl)-5-(isoxazol-3-yl)-1H-pyrazol-3-yl)-pyrimidin-4-amine (intermediate described in WO2012/3405 A1; 1 equiv.), triethylamine (6 equiv.), and N,N-dimethylpyridin-4-amine (0.01 equiv.) in dichloromethane was added 2-chloro-2-oxoethyl acetate (3 equiv.) at 23° C. Contents were heated to 60° C. and stirred for 18 h. Solvent removed in vacuo, and purification of the crude material via reverse phase HPLC delivered the desired compound, Compound I-498 (1.0 mg, 2% yield) as a solid.

$^1$H-NMR (500 MHz, DMSO-d$_6$) δ ppm 11.21 (m, 1H), 9.09 (m, 1H), 8.84 (m, 1H), 7.61 (m, 1H), 7.34 (m, 1H), 7.27 (m, 1H), 7.22 (m, 1H), 7.12 (m, 1H), 6.94 (m, 1H), 5.92 (m, 2H), 4.91 (s, 2H), 2.13 (s, 3H).

Compound I-578

The title compound was prepared following general procedure B, except tetrahydrofuran-3-amine was the amine reactant, 6 equivalents of triethylamine was used, and contents were heated to 100° C. as a solution in dioxane/water (4:1) for 24 h. The mixture was cooled to 23° C. and solvent removed in vacuo. The solid was purified via reverse phase HPLC to deliver the desired compound, Compound I-578 (12 mg, 53% yield) as a solid.

¹H-NMR (500 MHz, DMSO-d₆) δ ppm 9.11 (m, 1H), 8.58 (m, 1H), 8.31 (m, 1H), 7.61 (m, 1H), 7.34 (m, 1H), 7.24 (m, 2H), 7.11 (m, 1H), 6.89 (m, 1H), 5.93 (s, 2H), 4.76 (m, 1H), 4.04 (m, 1H), 3.89 (m, 1H), 3.77 (m, 1H), 3.64 (m, 1H), 2.27 (m, 1H), 2.04 (s, 1H).

Compound I-613

A solution of Intermediate 1 (1 equiv.) in DMSO was treated with potassium benzenesulfonamide (2 equiv.). The resulting reaction mixture was stirred at 100° C. for 8 h. Contents were filtered, and the filtrate was directly purified via reverse phase HPLC to deliver the desired compound, Compound I-613 (7 mg, 26% yield) as a solid.

¹H-NMR (500 MHz, CD₃OD) δ ppm 8.82 (m, 1H), 8.37 (m, 1H), 8.26 (m, 2H), 7.58 (m, 1H), 7.47 (m, 2H), 7.31 (m, 2H), 7.11 (m, 2H), 6.94 (m, 2H), 5.98 (m, 2H).

Compound I-614

A solution of Intermediate 1 (1 equiv.) in DMSO was treated with potassium 3,4-dimethoxybenzenesulfonamide (2 equiv.). The resulting reaction mixture was stirred at 100° C. for 8 h. Contents were filtered, and the filtrate was directly purified via reverse phase HPLC to deliver the desired compound, Compound I-614 (1.3 mg, 5% yield) as a solid.

¹H-NMR (500 MHz, DMSO-d₆) δ ppm 9.12 (m, 1H), 8.56 (m, 1H), 7.90 (m, 1H), 7.60 (m, 1H), 7.38 (m, 2H), 7.27 (d, 2H), 7.12 (m, 1H), 6.92 (m, 2H), 5.94 (s, 2H), 3.71 (d, 6H).

Compound I-607

A solution of Intermediate 1 (1 equiv.) in DMSO was treated with potassium (4-fluorophenyl)methanesulfonamide (2 equiv.). The resulting reaction mixture was stirred at 60° C. for 0.5 h, after which the reaction was diluted with water and 1N hydrochloric acid solution, and extracted with ethyl acetate. The combined organic layers were dried over sodium sulfate, filtered, and concentrated in vacuo. The crude material was purified via silica gel chromatography utilizing a 0-5% methanol in dichloromethane gradient to deliver the desired compound, Compound I-607 (2.8 mg, 6% yield) as a solid.

¹H-NMR (500 MHz, CD₃OD) δ ppm 8.79 (m, 1H), 8.45 (m, 1H), 7.52 (m, 1H), 7.40 (m, 2H), 7.26 (m, 1H), 6.94 (d, 6H), 5.98 (s, 2H), 5.04 (m, 2H).

Compound I-624

To a solution of 4-fluorobenzenesulfonamide (4 equiv.) in DMF was added potassium bis(trimethylsilyl)amide (4 equiv.) at 23° C. After 15 minutes of stirring, Intermediate 1 (1 equiv.) was added and reaction stirred for 3 days at 75° C. Without workup, product was purified by reverse phase HPLC to deliver the desired compound, Compound I-624 (1.9 mg, 7% yield) as a solid.

¹H-NMR (500 MHz, DMSO-d₆) δ ppm 9.13 (m, 1H), 8.51 (m, 1H), 8.30 (m, 2H), 7.40 (m, 2H), 7.27 (m, 2H), 7.15 (m, 3H), 6.95 (m, 1H), 5.99 (s, 2H).

Compound I-625

A solution of Intermediate 1 (1 equiv.) in DMSO was treated with potassium pyridine-3-sulfonamide (1 equiv.) and potassium carbonate (0.5 equiv.). The resulting reaction mixture was heated at 150° C. for 10 min. in a microwave. Contents were filtered, and the filtrate was directly purified via reverse phase HPLC to deliver the desired compound, Compound I-625 (4.4 mg, 33% yield) as a solid.

¹H-NMR (500 MHz, DMSO-d₆) δ ppm 9.24 (m, 1H), 9.14 (m, 1H), 8.69 (m, 1H), 8.59 (m, 1H), 8.40 (m, 1H), 7.42 (m, 1H), 7.34 (m, 2H), 7.24 (m, 2H), 7.13 (m, 1H), 6.96 (m, 1H), 5.95 (m, 2H).

Compound I-583

A solution of Intermediate 2 (1 equiv.) in DMF was treated with isocyanatobenzene (2 equiv.) and triethylamine (2 equiv.). The resulting reaction mixture was heated at 100° C. for 18 h. Contents were filtered, and the filtrate was directly purified via reverse phase HPLC to deliver the desired compound, Compound I-583 (1.0 mg, 4% yield) as a solid.

¹H-NMR (500 MHz, DMSO-d₆) δ ppm 10.20 (m, 1H), 9.10 (m, 1H), 8.62 (m, 1H), 7.71 (m, 1H), 7.63 (m, 2H), 7.27 (m, 7H), 7.09 (m, 1H), 7.01 (m, 1H), 6.88 (m, 1H), 5.99 (m, 2H).

Compound I-491

To a solution of Intermediate 2 (1 equiv.) in dichloromethane was added (4-fluorophenyl)methanesulfonyl chloride (1 equiv.), followed by DBU (1 equiv.). The reaction was stirred at 90° C. for 18 h. The reaction mixture was diluted with water, extracted with dichloromethane (3×), washed with 1N hydrochloric acid solution (2×), dried (sodium sulfate), filtered, and concentrated in vacuo. Purification of the crude material via reverse phase HPLC delivered the desired compound, Compound I-491 (17.8 mg, 17% yield) as a solid.

¹H NMR (500 MHz, CDCl₃) δ ppm 8.52 (d, 1H), 8.28 (br. s., 1H), 7.38 (br. s., 1H), 7.30 (dd, 2H), 7.25 (br. s., 1H), 7.14-6.97 (m, 4H), 6.92-6.73 (m, 3H), 6.63 (d, 1H), 5.91 (s, 2H), 4.54 (br. s., 2H).

Compound I-495

The title compound was prepared following general procedure B, except ethanol-1,1,2,2-d4-amine was the amine reactant, and the contents were heated to 90° C. for 20 h. The contents were cooled to 23° C., and partitioned between a 1:1 mixture of dichloromethane and 1N HCl solution. The layers were separated, and the aqueous layer was extracted with dichloromethane (×2), and the organic portions were combined and washed with brine. The mixture was dried over magnesium sulfate, filtered, and concentrated in vacuo. The crude material was purified via silica gel chromatography utilizing a 0-10% methanol in dichloromethane gradient to deliver the desired compound, Compound I-495 (120 mg, 74% yield) as a solid.

¹H NMR (500 MHz, DMSO-d₆) δ ppm 9.09 (d, 1H), 8.17 (d, 1H), 7.61 (s, 1H), 7.51 (s, 1H), 7.33 (d, 1H), 7.14-7.28 (m, 2H), 7.10 (t, 1H), 6.82 (s, 1H), 5.90 (s, 2H), 4.74 (br. s., 1H).

Compound I-505

5-fluoro-2-(1-(2-fluorobenzyl)-5-(isoxazol-3-yl)-1H-pyrazol-3-yl)pyrimidin-4-amine (intermediate described in WO2012/3405 A1; 1 equiv.) was added to a suspension of NaH (1.2 equiv.) in anhydrous THF at 23° C. After stirring for 30 min at 23° C., a solution of propane-2-sulfonyl chloride (1 equiv.) in THF was added to the reaction mixture. Contents were heated to 70° C. and stirred for an additional 18 h. The reaction mixture was diluted with water, extracted with dichloromethane (3×), dried (sodium sulfate), filtered, and concentrated in vacuo. Purification of the crude material via reverse phase HPLC delivered the desired compound, Compound I-505 (2.9 mg, 6% yield) as a solid.

¹H NMR (500 MHz, CDCl₃) δ ppm 11.59 (br. s., 1H), 9.13 (d, 1H), 8.66 (br. s., 1H), 7.45 (s, 1H), 7.38-7.31 (m, 1H), 7.26 (d, 1H), 7.24-7.17 (m, 1H), 7.13 (t, 1H), 7.08-7.02 (m, 1H), 5.89 (s, 2H), 4.24 (br. s., 1H), 1.35 (d, 6H).

Compound I-510

To a solution of Intermediate 2 (1 equiv.) in dichloromethane was added DBU (1 equiv.) followed by methyl 2-(chlorosulfonyl)acetate (1 equiv.). The reaction was stirred at 90° C. for 18 h. The reaction mixture was diluted with water, extracted with dichloromethane (3×), washed with 1N hydrochloric acid solution (2×), dried (sodium sulfate), filtered, and concentrated in vacuo. Purification of the crude material via reverse phase HPLC delivered the desired compound, Compound I-510 (8.3 mg, 12% yield) as a solid.

¹H NMR (500 MHz, CDCl₃) δ ppm 8.52 (d, 1H), 8.37 (d, 1H), 7.40 (s, 1H), 7.26-7.22 (m, 1H), 7.08-6.99 (m, 4H), 6.63 (d, 1H), 5.93 (s, 2H), 4.31 (s, 2H), 3.71 (s, 3H).

Compound I-521

The title compound was prepared following general procedure B, except 3-amino-2,2-difluoropropan-1-ol (1.5 equiv., as the HCl salt) was the amine reactant, 1 equivalent of triethylamine was used, and the contents were heated to 60° C. for 20 h. The contents were cooled to 23° C., and partitioned between a 1:1 mixture of dichloromethane and 1N HCl solution. The layers were separated, and the aqueous layer was extracted with dichloromethane (×2), and the organic portions were combined and washed with brine. The mixture was dried over Na₂SO₄, filtered, and concentrated in vacuo. The crude material was purified via silica gel chromatography utilizing a 0-10% methanol in dichloromethane gradient to deliver the desired compound, Compound I-521 (36 mg, 60% yield) as a solid.

¹H-NMR (500 MHz, CDCl₃) δ ppm 8.48 (d, 1H), 8.32 (d, 1H), 7.42 (s, 1H), 7.24-7.19 (m, 1H), 7.04-6.97 (m, 3H), 6.60 (d, 1H), 6.05 (br. s., 1H), 5.93 (s, 2H), 4.12 (td, 2H), 3.74 (t, 2H).

Compound I-539

To a solution of Compound I-510 (1 equiv.) in THF was added sodium borohydride (3 equiv.) at 23° C. The reaction mixture was heated to 75° C., methanol (4 equiv.) was added dropwise via syringe, and contents stirred for 1 h. After cooling to 23° C., reaction was concentrated in vacuo, and the resulting crude material was purified via reverse phase HPLC delivered the desired compound, Compound I-539 (1.5 mg, 27% yield) as a solid.

¹H NMR (500 MHz, CD₃OD) δ ppm 8.69 (d, 1H), 8.35 (d, 1H), 7.47 (s, 1H), 7.19 (d, 1H), 6.96 (s, 3H), 6.89 (d, 1H), 6.84-6.82 (m, 1H), 5.89 (s, 2H), 3.92 (t, 2H), 3.66 (t, 2H).

Compound I-610

A solution of Intermediate 1 (1 equiv.) in DMSO was treated with potassium (cyclopropylsulfonyl)amide (2 equiv.). The resulting reaction mixture was stirred at 23° C. for 16 h. Contents were filtered, and the filtrate was directly purified via reverse phase HPLC to deliver the desired compound, Compound I-610 (34 mg, 55% yield) as a solid.

¹H-NMR (500 MHz, CD₃OD) δ ppm 8.66 (d, 1H), 8.35 (d, 1H), 7.37 (s, 1H), 7.23-7.11 (m, 1H), 7.02-6.89 (m, 2H), 6.86-6.74 (m, 2H), 5.91-5.77 (m, 2H), 3.36-3.26 (m, 1H), 1.35-1.17 (m, 2H), 1.08-0.89 (m, 2H).

Compound I-611

A solution of Intermediate 1 (1 equiv.) in DMSO was treated with potassium (propylsulfonyl)amide (2 equiv.). The resulting reaction mixture was stirred at 23° C. for 16 h. Contents were filtered, and the filtrate was directly purified via reverse phase HPLC to deliver the desired compound, Compound I-611 (50 mg, 81% yield) as a solid.

¹H-NMR (500 MHz, CD₃OD) δ ppm 8.67 (d, 1H), 8.36 (d, 1H), 7.33 (s, 1H), 7.23-7.13 (m, 1H), 7.03-6.89 (m, 2H), 6.87-6.81 (m, 1H), 6.79 (d, 1H), 5.91-5.68 (m, 2H), 3.63 (t, 2H), 1.93-1.74 (m, 2H), 0.97 (t, 3H).

Compound I-629

A solution of Intermediate 1 (1 equiv.) in DMSO was treated with potassium methyl(methylsulfonyl)amide (1 equiv.). The resulting reaction mixture was stirred at 23° C. for 16 h. Contents were filtered, and the filtrate was directly purified via reverse phase HPLC to deliver the desired compound, Compound I-629 (8 mg, 33% yield) as a solid.

¹H-NMR (500 MHz, DMSO-d₆) δ ppm 9.11 (d, 1H), 8.93 (d, 1H), 7.62 (s, 1H), 7.34 (d, 1H), 7.28 (d, 1H), 7.24-7.19 (m, 1H), 7.12 (td, 1H), 6.94 (td, 1H), 5.92 (s, 2H), 3.49 (s, 3H), 3.37 (d, 3H).

Compound I-475

The title compound was prepared following general procedure C, except (S)-2-acetoxy-3,3,3-trifluoropropanoic acid was the acid reactant (3 equiv.), 7 equivalents of triethylamine was used, and 4 equivalents of T3P was used. The solution was heated to 50° C. for 10 minutes, at which point the solution was diluted with ethyl acetate and water. The layers were separated and the organic layer was washed with water and saturated aqueous sodium chloride. The organics were dried over magnesium sulfate, filtered, and the solvent was removed in vacuo. Purification via silica gel chromatography (0-5% methanol in dichloromethane gradient) delivered the desired compound, Compound I-475 (98 mg, quantitative yield) as a white solid.

¹H-NMR (500 MHz, CDCl₃) δ ppm 8.81 (d, 1H), 8.78 (s, 1H), 8.50 (d, 1H), 8.15 (d, 1H), 7.51 (s, 1H), 7.25-7.22 (m, 1H), 7.09-7.05 (m, 1H), 7.00 (t, 1H), 6.85-6.82 (m, 1H), 6.63 (d, 1H), 6.06 (s, 2H), 5.77 (q, 1H), 2.39 (s, 3H).

Compound I-485

The title compound was prepared following general procedure B, except 4-aminopyrrolidin-2-one was the amine reactant. After stirring at 90° C. for 16 h, additional water was added to solubilize the reactants. After 5 h, the reaction mixture was partitioned between dichloromethane and saturated aqueous sodium bicarbonate. The layers were separated and the aqueous layer was extracted with dichloromethane. The organics were dried over magnesium sulfate, filtered, and the solvent was removed in vacuo. Purification via silica gel chromatography (0-15% methanol in dichloromethane gradient) delivered the desired compound, Compound I-485 (11 mg, 19% yield) as a white solid.

¹H-NMR (500 MHz, CD₃OD) δ ppm 8.76 (s, 1H), 8.11 (d, 1H), 7.46 (s, 1H), 7.27 (q, 1H), 7.11-7.07 (m, 1H), 7.03 (t, 1H), 6.93 (s, 1H), 6.83-6.80 (m, 1H), 5.96 (s, 2H), 5.11-5.06 (m, 1H), 3.90 (dd, 1H), 3.40 (dd, 1H), 2.84 (dd, 1H), 2.51 (dd, 1H).

Compound I-500

A solution of 2-(1-(2-fluorobenzyl)-5-(isoxazol-3-yl)-1H-pyrazol-3-yl)pyrimidin-4-ol (Intermediate described in WO2012/003405 A1; 1 equiv.) and phosphoryl trichloride (20 equiv.) was heated to 60° C. for 1 h, after which time the phosphoryl trichloride was removed in vacuo. The resulting residue was dissolved in dioxane and water (2:1 ratio). 2-(Aminomethyl)-1,1,1,3,3,3-hexafluoropropan-2-ol (3 equiv.) and triethylamine (10 equiv.) were added and the resulting solution was heated to 110° C. for 7 d. The solution was partitioned between aqueous 1 N hydrochloric acid and dichloromethane. The aqueous layer was extracted with dichloromethane. The organics were dried over magnesium sulfate, filtered, and the solvent was removed in vacuo. Purification via silica gel chromatography (0-100% (7:1=acetonitrile:methanol) in dichloromethane gradient) delivered the desired compound, Compound I-500 (16 mg, 21% yield) as a yellow solid.

¹H-NMR (500 MHz, CD₃OD) δ ppm 8.77 (s, 1H), 8.20 (d, 1H), 7.37 (s, 1H), 7.29-7.24 (m, 1H), 7.09-7.00 (m, 3H), 6.85 (s, 1H), 6.61 (d, 1H), 5.95 (s, 2H), 4.08 (s, 2H).

Compound I-518

The title compound was prepared following general procedure B, except 3,3,3-trifluoropropane-1,2-diamine (9 equiv.) was the amine reactant, and 30 equivalents of triethylamine was used. After stirring for 16 h, the crude reaction mixture was partitioned between water and ethyl acetate. The aqueous layer was extracted with ethyl acetate. The organics were dried over magnesium sulfate, filtered, and the solvent was removed in vacuo. Purification via silica gel chromatography (0-5% methanol in dichloromethane gradient) delivered the desired compound, Compound I-518 (10 mg, 21% yield) as a white solid.

$^1$H-NMR (500 MHz, CD$_3$OD) δ ppm 8.39 (d, 1H), 8.11 (d, 1H), 7.19 (s, 1H), 7.14-7.10 (m, 1H), 6.97-6.93 (m, 1H), 6.89 (t, 1H), 6.81-6.78 (m, 1H), 6.52 (d, 1H), 5.90 (s, 2H), 5.57 (br s, 1H), 4.17 (ddd, 1H), 3.51-3.44 (m, 1H), 3.34 (ddd, 1H).

Compound I-540

A solution of Compound I-403 (1 equiv.) in dichloromethane was treated with diisopropylethylamine (2 equiv.), followed by HATU (1.5 equiv.). After stirring for 20 min, ammonia (3 equiv., 0.5 M solution in dioxane) was added. After 22 h, additional ammonia (3 equiv.) was added. After 4 hours, the solution was diluted with aqueous 1N hydrochloric acid solution and dichloromethane. The layers were separated and the aqueous layer was extracted with dichloromethane. The organics were dried over magnesium sulfate, filtered, and the solvent was removed in vacuo. Purification via silica gel chromatography (0-15% methanol in dichloromethane gradient) delivered the desired compound, Compound I-540 (3 mg, 13% yield) as a yellow film.

$^1$H-NMR (500 MHz, CDCl$_3$) δ ppm 8.47 (d, 1H), 8.27 (d, 1H), 7.30 (s, 1H), 7.24-7.20 (m, 1H), 7.07-6.98 (m, 2H), 6.91 (m, 1H), 6.80 (br s, 1H), 6.59 (d, 1H), 6.10 (d, 1H), 5.97 (d, 1H), 5.92 (d, 1H), 5.84 (quint, 1H), 5.74 (br s, 1H).

Compound I-568

A solution of Compound I-418 (1 equiv.), diphenyl phosphorazidate (1.5 equiv.), and triethylamine (1.5 equiv.) in toluene was heated to 50° C. for 15 h. The solution was cooled to 23° C. and treated with sodium methanolate (3 equiv., 0.5 N solution in methanol). After stirring at 23° C. for 1 h, saturated aqueous sodium bicarbonate solution was added and the resulting solution was stirred for an additional 1 h. The reaction was diluted with water and dichloromethane, and the aqueous layer was extracted with dichloromethane. The organics were dried over magnesium sulfate, filtered, and the solvent was removed in vacuo to give the crude product. Purification via silica gel chromatography (0-15% (7:1=acetonitrile:methanol) in dichloromethane gradient) delivered the desired compound, Compound I-568 (11 mg, 52% yield) as a white solid.

$^1$H-NMR (500 MHz, CD$_3$OD) δ ppm 8.76 (d, 1H), 8.21 (d, 1H), 7.49 (s, 1H), 7.29-7.24 (m, 1H), 7.12-7.06 (m, 1H), 7.03 (t, 1H), 6.94 (d, 1H), 6.80 (t, 1H), 5.97 (s, 2H), 5.67-5.58 (m, 1H), 3.73 (dd, 1H), 3.51 (s, 3H), 3.42 (dd, 1H).

Compound I-576

The title compound was synthesized in 2 steps:

Step 1: Synthesis of (S)-1-((2-(1-(2-fluorobenzyl)-5-(isoxazol-3-yl)-1H-pyrazol-3-yl)pyrimidin-4-yl)amino)-1-oxopropan-2-yl acetate The intermediate was prepared following general procedure C, except (S)-2-acetoxypropanoic acid was the acid reactant (3 equiv.), 10 equivalents of triethylamine was used, and 4 equivalents of T3P was used. The solution was heated to 50° C. for 16 h, at which point the solution was diluted with ethyl acetate and water. The layers were separated and the organic layer was washed with water and saturated aqueous sodium chloride. The organics were dried over magnesium sulfate, filtered, and the solvent was removed in vacuo. Purification via silica gel chromatography (0-5% methanol in dichloromethane gradient) delivered impure intermediate, which was taken onto the next step without further manipulation.

Step 2: Synthesis of Compound I-576

To a solution of (S)-1-((2-(1-(2-fluorobenzyl)-5-(isoxazol-3-yl)-1H-pyrazol-3-yl)-pyrimidin-4-yl)amino)-1-oxopropan-2-yl acetate (1 equiv.) in 4:1=methanol:water was added potassium carbonate (0.5 equiv.) in a single portion. After stirring for 10 min, the reaction solution was acidified with 3N hydrochloric acid solution and diluted with water and dichloromethane. The layers were separated and the aqueous layer was extracted with dichloromethane. The organics were dried over magnesium sulfate, filtered, and the solvent was removed in vacuo. Purification via silica gel chromatography (0-5% methanol in dichloromethane) delivered the desired compound, Compound I-576 (4.5 mg, 29% yield) as a white solid.

$^1$H-NMR (500 MHz, CD$_3$OD) δ ppm 8.77 (m, 1H), 8.71 (d, 1H), 8.14 (d, 1H), 7.54 (s, 1H), 7.30-7.26 (m, 1H), 7.11-7.03 (m, 2H), 6.91-6.88 (m, 2H), 5.98 (s, 2H), 4.32 (q, 1H), 1.45 (d, 3H).

Compound I-580

The title compound was prepared following general procedure C, except 2-methyl-2-(methylsulfonyl)propanoic acid was the acid reactant (3 equiv.), 10 equivalents of triethylamine was used, and 4 equivalents of T3P was used. The solution was heated to 70° C. for 3 h, at which point the solution was diluted with ethyl acetate and water. The layers were separated and the organic layer was washed with water and saturated aqueous sodium chloride. The organics were dried over magnesium sulfate, filtered, and the solvent was removed in vacuo. Purification via silica gel chromatography (0-100% ethyl acetate in hexanes gradient) delivered the desired compound, Compound I-580 (30 mg, 42% yield) as yellow foam.

$^1$H-NMR (500 MHz, CDCl$_3$) δ 9.13 (br s, 1H), 8.78 (d, 1H), 8.48 (d, 1H), 8.06 (d, 1H), 7.46 (s, 1H), 7.24-7.19 (m, 1H), 7.06-7.02 (m, 1H), 7.00-6.97 (m, 1H), 6.89-6.86 (m, 1H), 6.63 (d, 1H), 6.03 (s, 2H), 3.00 (s, 3H), 1.81 (s, 6H).

Compound I-582

The title compound was prepared following general procedure C, except 5-fluoro-2-(1-(2-fluorobenzyl)-5-(isoxazol-3-yl)-1H-pyrazol-3-yl)pyrimidin-4-amine (Intermediate described in a previous patent: WO2012/003405 A1; 1 equiv.) was used in place of Intermediate 2, 2-methyl-2-(methylsulfonyl)propanoic acid was the acid reactant (3 equiv.), 10 equivalents of triethylamine was used, and 4 equivalents of propylphosphonic anhydride (T3P, 50 wt % in ethyl acetate) was used. After heating the mixture at 90° C. for 4 hours, the solution was diluted with ethyl acetate and water. The layers were separated and the aqueous layer was extracted with ethyl acetate. The organics were washed with water, dried over magnesium sulfate, filtered, and the solvent was removed in vacuo. Purification via silica gel chromatography ((7:1 acetonitrile:methanol) in dichloromethane gradient) delivered the desired compound, Compound I-582 (29 mg, 41% yield) as a white solid.

$^1$H-NMR (500 MHz, CDCl$_3$) δ 9.10 (br s, 1H), 8.67 (d, 1H), 8.48 (d, 1H), 7.42 (s, 1H), 7.23-7.19 (m, 1H), 7.06-7.02 (m, 1H), 7.10-6.97 (t, 1H), 6.86 (t, 1H), 6.63 (d, 1H), 6.02 (s, 2H), 3.02 (s, 3H), 1.82 (s, 6H).

Compound I-587

The title compound was prepared following general procedure C, except 2-(methylsulfonyl)propanoic acid was the acid reactant (3 equiv.), 10 equivalents of triethylamine was used, and 4 equivalents of T3P was used. After stirring for 1 h at 70° C., the reaction mixture was diluted with ethyl acetate and water. The layers were separated and the aqueous layer extracted with ethyl acetate. The organics were washed with water, dried over magnesium sulfate, filtered, and the solvent was removed in vacuo. Purification via silica gel chromatography (0-5% methanol in dichloromethane gradient) delivered the desired compound, Compound I-587 (45 mg, 64% yield) as a brown solid.

$^1$H-NMR (500 MHz, CDCl$_3$) δ 9.45 (br s, 1H), 8.72 (d, 1H), 8.48 (d, 1H), 8.01 (d, 1H), 7.34 (s, 1H), 7.21-7.16 (m, 1H), 7.04-7.01 (m, 1H), 6.92 (t, 1H), 6.80-6.77 (m, 1H), 6.65 (d, 1H), 6.00 (s, 2H), 4.14 (q, 1H), 3.02 (s, 3H), 1.73 (d, 3H).

Compound I-609

To a solution of potassium ((2,2,2-trifluoroethyl)sulfonyl) amide (2 equiv.) in dimethylsulfoxide was added Intermediate 1 (1 equiv.). After stirring for 62 h, the solution was diluted with ethyl acetate and aqueous 1N hydrochloric acid solution. The layers were separated and the aqueous layer was extracted with ethyl acetate. The organics were washed with water and brine, dried over magnesium sulfate, filtered, and the solvent was removed in vacuo. The crude residue was brought up in methanol and the resulting solid was filtered and washed with additional methanol. The residue was brought up again in methanol and the resulting solids were filtered and rinsed with methanol to deliver the desired compound, Compound I-609 (24 mg, 28% yield) as a solid.

$^1$H-NMR (500 MHz, DMSO-d$_6$) δ 9.14 (d, 1H), 8.44 (br s, 1H), 7.51 (s, 1H), 7.37-7.31 (m, 1H), 7.24-7.20 (m, 2H), 7.12 (t, 1H), 7.02-6.99 (m, 1H), 5.92 (s, 2H), 4.74 (br s, 2H).

Compound I-627

A suspension of 2-(1-(2-fluorobenzyl)-5-(isoxazol-3-yl)-1H-pyrazol-3-yl)pyrimidin-4-ol (Intermediate described in WO2012/003405 A1; 1 equiv.) in phosphoryl trichloride (20 equiv.) was heated to 60° C. for 2 h. After evaporating to dryness in vacuo, the resulting residue and 2-(aminomethyl)-3,3,3-trifluoro-2-hydroxypropanamide (3 equiv.) were dissolved in 2:1 mix of dioxane:water and treated with triethylamine (10 equiv.). The solution was heated to 110° C. for 38 h. The solution was diluted with dichloromethane and 1N hydrochloric acid, layers were separated, and the aqueous layer was extracted with dichloromethane. The organics were dried over magnesium sulfate, filtered, and the solvent was removed in vacuo. Purification via silica gel chromatography (0-65% (7:1=acetonitrile:methanol) in dichloromethane gradient) provided contaminated product. The crude product was partitioned between water and dichloromethane. The layers were separated and the organic layer was washed with water. The organic layer was dried over magnesium sulfate, filtered, and the solvent was removed in vacuo to deliver the desired compound, Compound I-627 (1 mg, 1% yield) as a clear film.

$^1$H-NMR (500 MHz, CD$_3$OD) δ 8.78 (s, 1H), 8.17 (d, 1H), 7.42 (s, 1H), 7.30-7.26 (m, 1H), 7.11-7.04 (m, 2H), 7.01-6.98 (m, 1H), 6.89 (s, 1H), 6.59 (d, 1H), 5.97 (s, 2H), 4.10-4.02 (m, 2H).

Compound I-634

The title compound was prepared following general procedure B, except 3-amino-1,1,1-trifluoro-2-methylpropan-2-ol (as the HCl salt, 2 equiv.) was the amine reactant, and 4 equivalents of triethylamine was used. After stirring at 90° C. for 21 h, workup and purification via silica gel chromatography (0-70% ethyl acetate in hexanes gradient) delivered the desired compound, Compound I-634 (33 mg, 48% yield) as a white solid.

$^1$H-NMR (500 MHz, CDCl$_3$) δ ppm 8.48 (m, 1H), 8.22 (d, 1H), 7.27 (s, 1H), 7.24-7.19 (m, 1H), 7.05-6.95 (m, 3H), 6.61 (m, 1H), 6.04-5.93 (m, 3H), 5.74 (br s, 1H), 4.00 (dd, 1H), 3.81 (dd, 1H), 1.44 (s, 3H).

Compound I-631

The title compound was prepared following general procedure B, except 4,5,6,7-tetrahydro-1H-pyrazolo[4,3-c]pyridin-3(2H)-one dihydrochloride (2 equiv) was the amine reactant, and 4 equivalents of triethylamine was used. After stirring at 90° C. for 1.5 h, workup and purification via silica gel chromatography (0-15% methanol in dichloromethane gradient) delivered the desired compound, Compound I-631 (9 mg, 14% yield) as a white solid.

$^1$H-NMR (500 MHz, CD$_3$OD) δ ppm 8.79 (d, 1H), 8.22 (d, 1H), 7.50 (s, 1H), 7.31-7.27 (m, 1H), 7.13-7.09 (m, 1H), 7.05 (t, 1H), 6.94 (m, 1H), 6.85-6.82 (m, 1H), 5.98 (s, 2H), 4.76 (s, 2H), 4.17 (t, 2H), 2.85 (t, 2H).

Compound I-328

The title compound was prepared following general procedure C, except 1-(trifluoromethyl)cyclopropanecarboxylic acid (2 equiv.) was the acid reactant, 3 equivalents of triethylamine was used, and 3 equivalents of T3P was used. The solution was stirred at 23° C. for 18 h, at which point the solution was diluted with water and extracted with ethyl acetate. The organic phase was washed with water (2×) and saturated aqueous sodium chloride. The organics were dried over sodium sulfate, filtered, and concentrated in vacuo. Purification of the residue via silica gel chromatography (ethyl acetate in hexanes) delivered the desired compound, Compound I-328 (2 mg, 14% yield).

$^1$H-NMR (400 MHz, CDCl$_3$) δ ppm 8.73 (d, 1H), 8.57 (br s, 1H), 8.45 (d, 1H), 8.02 (d, 1H), 7.45 (s, 1H), 7.19 (m, 1H), 7.02 (m, 1H), 6.96 (m, 1H), 6.83 (m, 1H), 6.60 (d, 1H), 6.01 (s, 2H), 1.40 (m, 4H).

Compound I-415

The title compound was prepared following general procedure C, except 5-fluoro-2-(1-(2-fluorobenzyl)-5-(isoxazol-3-yl)-1H-pyrazol-3-yl)pyrimidin-4-amine (Intermediate described in a previous patent: WO2012/003405 A1; 1 equiv.) was used in place of Intermediate 2, 1-(trifluoromethyl)cyclopropanecarboxylic acid (3 equiv.) was the acid reactant, 7 equivalents of triethylamine was used, and 4 equivalents of T3P was used. After heating at 90° C. for 2 d, the vial was cooled to 23° C. and the contents were diluted with ethyl acetate. Contents were washed with water (3×), brine, then dried over sodium sulfate, filtered, and concentrated via rotary evaporation. Purification of the residue via silica gel chromatography (ethyl acetate in hexanes) delivered the desired compound, Compound I-415 (42 mg, 30% yield) as a white solid.

$^1$H-NMR (400 MHz, CDCl$_3$) δ ppm 8.67 (s, 1H), 8.49 (s, 1H), 8.31 (br s, 1H), 7.43 (s, 1H), 7.23 (m, 1H), 7.06 (m, 1H), 6.99 (m, 1H), 6.84 (m, 1H), 6.63 (s, 1H), 6.04 (s, 2H), 1.64 (m, 2H), 1.45 (m, 2H).

Compound I-460

The title compound was prepared following general procedure C, except 5-fluoro-2-(1-(2-fluorobenzyl)-5-(isoxazol-3-yl)-1H-pyrazol-3-yl)pyrimidin-4-amine (Intermediate described in a previous patent: WO2012/003405 A1; 1 equiv.) was used in place of Intermediate 2, 1-cyanocyclopropanecarboxylic acid (3 equiv.) was the acid reactant, 7 equivalents of triethylamine was used, and 4 equivalents of T3P was used. After heating at 50° C. for 18 h, the vial was cooled to 23° C. and the contents were diluted with ethyl acetate. Contents were washed with water (3×), brine, then dried over sodium sulfate, filtered, and concentrated via rotary evaporation. Purification of the residue via silica gel chromatography (ethyl acetate in hexanes) delivered the desired compound, Compound I-460 (29 mg, 23% yield) as a white solid.

¹H-NMR (400 MHz, CDCl₃) δ ppm 8.61 (s, 1H), 8.50 (br s, 1H), 8.41 (s, 1H), 7.34 (s, 1H), 7.14 (m, 1H), 6.97 (m, 1H), 6.91 (m, 1H), 6.77 (m, 1H), 6.54 (s, 1H), 5.95 (s, 2H), 1.80 (m, 2H), 1.67 (m, 2H).

Compound I-483

The title compound was synthesized in 2 steps:

Step 1: Synthesis of 3-(3-(4-chloro-5-nitropyrimidin-2-yl)-1-(2-fluorobenzyl)-1H-pyrazol-5-yl)isoxazole 2-(1-(2-fluorobenzyl)-5-(isoxazol-3-yl)-1H-pyrazol-3-yl)-5-nitropyrimidin-4-ol (Intermediate described in a previous patent: WO2012/003405 A1; 1 equiv.) was added to phosphorus oxychloride (22 equiv.) and the mixture was heated for 4 h at 90° C. Contents were concentrated in vacuo, and the residue was taken up in ethyl acetate and subsequently washed with 10% sodium bicarbonate solution (2×), water (2×), and brine. The organic layer was dried over sodium sulfate, filtered, and concentrated in vacuo to deliver the desired intermediate, 3-(3-(4-chloro-5-nitropyrimidin-2-yl)-1-(2-fluorobenzyl)-1H-pyrazol-5-yl)isoxazole as a tan solid (1.86 g, 96% yield).

¹H-NMR (400 MHz, CDCl₃) δ ppm 9.35 (s, 1H), 8.53 (d, 1H), 7.59 (s, 1H), 7.25 (m, 1H), 7.07 (m, 1H), 7.02 (m, 1H), 6.91 (m, 1H), 6.65 (d, 1H), 6.08 (s, 2H).

Step 2: Synthesis of Compound I-483

The title compound was prepared following general procedure B, except 3-(3-(4-chloro-5-nitropyrimidin-2-yl)-1-(2-fluorobenzyl)-1H-pyrazol-5-yl)isoxazole was used in place of Intermediate 1, 2-(aminomethyl)-1,1,1,3,3,3-hexafluoropropan-2-ol (1.5 equiv.) was the amine reactant, 3 equivalents of triethylamine was used, and contents were heated to 30° C. for 1 h as a solution in dioxane:water (3:1). The reaction was cooled and diluted with ethyl acetate. The organic layer was washed with water (2×) and brine, then dried over sodium sulfate, filtered, and concentrated in vacuo. The crude material was purified via silica gel chromatography utilizing a 0-100% ethyl acetate/hexanes gradient to deliver the desired compound, Compound I-483 (77 mg, 73% yield) as a white solid.

¹H-NMR (400 MHz, CDCl₃) δ ppm 9.36 (s, 1H), 8.59 (m, 1H), 8.55 (d, 1H), 7.64 (br s, 1H), 7.42 (s, 1H), 7.28 (m, 1H), 7.08 (m, 1H), 7.06 (m, 1H), 6.64 (d, 1H), 5.98 (s, 2H), 4.27, (d, 2H).

Compound I-484

A solution of Compound I-483 (1 equiv.) in methanol at 23° C. was treated with 10% palladium on carbon (0.2 equiv.), then placed under an atmosphere of H₂ delivered via a balloon filled with hydrogen attached to a needle. The mixture was stirred for 1 h under positive H₂ pressure, and filtered through celite. The filter cake was rinsed with methanol, and the combined washes were concentrated in vacuo. The resulting crude residue was purified via silica gel chromatography utilizing a ethyl acetate in hexanes gradient to deliver the desired compound, Compound I-484 (53 mg, 66% yield) as a white solid.

¹H-NMR (400 MHz, CDCl₃) δ ppm 9.39 (s, 1H), 7.92 (br s, 1H), 7.19 (m, 1H), 7.13 (m, 2H), 7.98 (m, 1H), 6.92 (m, 2H), 6.52 (s, 1H), 5.85 (s, 2H), 4.01, (s, 2H).

Compound I-541

A mixture of 3-(3-(4-chloro-5-nitropyrimidin-2-yl)-1-(2-fluorobenzyl)-1H-pyrazol-5-yl)isoxazole (as described in step 1 of synthesis of Compound I-483 (1 equiv.), methyl carbamate (5 equiv.) and cesium carbonate (5 equiv.) was heated at 90° C. for 18 h. After cooling to 23° C., the mixture was diluted with ethyl acetate and washed with water (3×) and brine. Contents were dried over sodium sulfate, filtered, and concentrated in vacuo. The resulting crude residue was purified via silica gel chromatography utilizing a ethyl acetate/hexanes gradient to deliver the desired compound, Compound I-541 (35 mg, 19% yield) as a light yellow solid.

¹H-NMR (400 MHz, CDCl₃) δ ppm 10.09 (br s, 1H), 9.51 (s, 1H), 8.50 (d, 1H), 7.60 (s, 1H), 7.24 (m, 1H), 7.06 (m, 1H), 7.02 (m, 1H), 6.87 (m, 1H), 6.67 (d, 1H), 6.07 (s, 2H), 3.95 (s, 3H).

Compound I-542

A solution of Compound I-541 (1 equiv.) in methanol at 23° C. was treated with 10% palladium on carbon (0.2 equiv.), then placed under an atmosphere of H₂ delivered via a balloon filled with hydrogen attached to a needle. The mixture was stirred for 1 h under positive H₂ pressure, and filtered through celite. The filter cake was rinsed with methanol, and the combined washes were concentrated in vacuo. The resulting crude residue was purified via silica gel chromatography utilizing a ethyl acetate in hexanes gradient to deliver the desired compound, Compound I-542 (26 mg, 87% yield) as a solid.

¹H-NMR (400 MHz, CDCl₃) δ ppm 8.43 (d, 1H), 8.27 (s, 1H), 7.52 (s, 1H), 7.32 (s, 1H), 7.18 (m, 1H), 7.02 (m, 1H), 6.99 (m, 1H), 6.77 (m, 1H), 6.57 (d, 1H), 5.99 (s, 2H), 4.61 (br s, 2H), 3.81 (s, 3H).

Compound I-488

The title compound was prepared following general procedure B, except 2-(aminomethyl)-1,1,1,3,3,3-hexafluoropropan-2-ol (2.3 equiv.) was the amine reactant, 3-(3-(4-chloro-5-fluoropyrimidin-2-yl)-1-(2,3-difluorobenzyl)-1H-pyrazol-5-yl)isoxazole (described in step 2 towards the synthesis of Compound I-235) was used in place of Intermediate 1, and contents were heated to 90° C. for 3 d. Contents were cooled to 23° C. and the mixture was diluted with ethyl acetate. The organic layer was washed with water (2×) and brine, then dried over sodium sulfate, filtered, and concentrated in vacuo. The crude material was purified via silica gel chromatography (ethyl acetate in hexanes gradient) to deliver the desired compound, Compound I-488 (62 mg, 44% yield) as a white solid.

¹H-NMR (400 MHz, CDCl₃) δ ppm 8.52 (s, 1H), 8.39 (s, 1H), 8.29 (s, 1H), 7.25 (s, 1H), 7.09 (m, 1H), 6.98 (m, 1H), 6.96 (m, 1H), 6.64 (s, 1H), 5.99 (s, 2H), 5.58 (br s, 1H), 4.14 (d, 2H).

Compound I-489

The title compound was prepared following general procedure B, except 2-(aminomethyl)-3,3,3-trifluoro-2-hydroxypropanoic acid (1.3 equiv.) was the amine reactant, 3-(3-(4-chloro-5-fluoropyrimidin-2-yl)-1-(2,3-difluorobenzyl)-1H-pyrazol-5-yl)isoxazole (described in step 2 towards the synthesis of Compound I-235) was used in place of Intermediate 1, and contents were heated to 90° C. for 3 d. Contents were cooled to 23° C. and the mixture was diluted with water, and the pH was adjusted to 5 with 3N HCl solution. The mixture was filtered, and the filter cake was washed with water (2×) and dried under vacuum. A portion of the residue dissolved in dichloromethane/methanol (4 mL, 1:1). Filtration left 62 mg of insoluble material. The soluble fraction was subjected to silica gel chromatography utilizing a dichloromethane/methanol gradient to yield Compound I-489 as a white solid (60 mg). Analysis of the insoluble material left from filtration also showed to be Compound I-489 (total: 0.122 g, 90% yield).

1H-NMR (400 MHz, CD₃OD) δ ppm 8.77 (d, 1H), 8.16 (d, 1H), 7.51 (s, 1H), 7.15 (m, 1H), 7.01 (m, 1H), 6.94 (d, 1H), 6.71 (m, 1H), 6.00 (s, 2H), 4.43 (d, 1H), 4.12 (d, 1H).

Compound I-522

A solution of Compound I-489 (1 equiv.) in dichloromethane was treated with Hunig's base (3 equiv.) and HATU (1.5 equiv.). The resulting solution was stirred for 2 h, then a solution of ammonia (0.5 M in dioxane, 8 equiv.) was added to the reaction. Contents were allowed to stir overnight at 23° C. The mixture was diluted with dichloromethane and washed with water (3×) and brine. The solution was then dried over sodium sulfate, filtered, and concentrated in vacuo. Purification of the crude residue via silica gel chromatography utilizing a dichloromethane/methanol gradient delivered the desired compound, Compound I-522 (5 mg, 8% yield) as a white solid.

$^1$H-NMR (400 MHz, CDCl$_3$) δ ppm 8.45 (s, 1H), 8.14 (s, 1H), 7.98 (s, 1H), 7.18 (s, 1H), 7.13 (s, 1H), 7.01 (m, 1H), 6.90 (m, 2H), 6.56 (s, 1H), 5.90 (s, 2H), 5.65 (br s, 1H), 5.53 (br s, 1H), 4.12 (d, 2H).

Compound I-507

The title compound was synthesized in 4 steps:

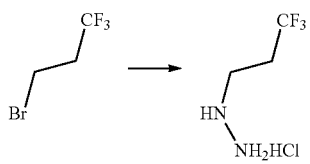

Step 1: Synthesis of (3,3,3-trifluoropropyl)hydrazine Hydrochloride

3-Bromo-1,1,1-trifluoropropane (1 equiv.) and hydrazine hydrate (10 equiv.) were dissolved in absolute ethanol and heated at 80° C. for 18 h. The solution was cooled to 23° C. and concentrated under vacuum at 15° C. The thick oil was diluted with water and dichloromethane, then solid potassium carbonate was added to saturate the aqueous layer. The phases were mixed and separated, then the aqueous phase was extracted with additional dichloromethane (2×). The combined organic phases were dried over sodium sulfate, filtered, and concentrated under vacuum to give a colorless oil. A small portion of the neutral hydrazine product was removed for characterization by NMR. The remainder was taken up in diethyl ether and treated with hydrochloric acid (2.5 M solution in ethanol), and the resulting mixture was concentrated in vacuo to deliver the desired intermediate (3,3,3-trifluoropropyl)hydrazine hydrochloride (2.02 g, 43% yield) as a white solid.

$^1$H-NMR (400 MHz, CDCl$_3$) δ ppm 3.18 (br s, 4H), 3.02 (m, 2H), 2.36 (m, 2H).

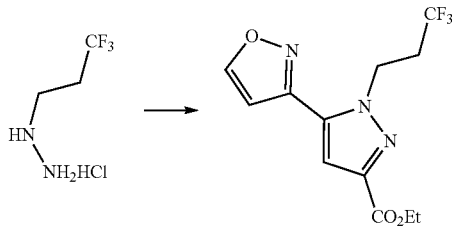

Step 2: Synthesis of ethyl 3-(isoxazol-3-yl)-1-(3,3,3-trifluoropropyl)-1H-pyrazole-5-carboxylate A solution of (3,3,3-Trifluoropropyl)hydrazine hydrochloride (1 equiv.) in a mixture of ethanol and water (9:1) at 23° C. was treated with potassium carbonate (0.6 equiv.) followed by ethyl 4-(isoxazol-3-yl)-2-(methoxy(methyl)amino)-4-oxobut-2-enoate (2 equiv., generated in step 1 of general procedure A, by using 1-(isoxazol-3-yl)ethanone in step 1). The solution was stirred 2 d at 23° C., then 6N hydrochloric acid (1.5 equiv.) was added drop wise to the reaction. Solvents were removed in vacuo, and the residue was taken up in ethyl acetate. The organics were washed with water (5×), brine, dried over sodium sulfate, filtered, and concentrated in vacuo. The crude residue was purified via silica gel chromatography utilizing a ethyl acetate in dichloromethane gradient to yield the desired pyrazole ester, ethyl 3-(isoxazol-3-yl)-1-(3,3,3-trifluoropropyl)-1H-pyrazole-5-carboxylate (1.34 g, 36% yield) as a light yellow solid.

$^1$H-NMR (400 MHz, CDCl$_3$) δ ppm 8.55 (d, 1H), 7.15 (s, 1H), 6.63 (d, 1H), 4.95 (m, 2H), 4.46 (q, 2H), 2.85 (m, 2H), 1.44 (t, 3H).

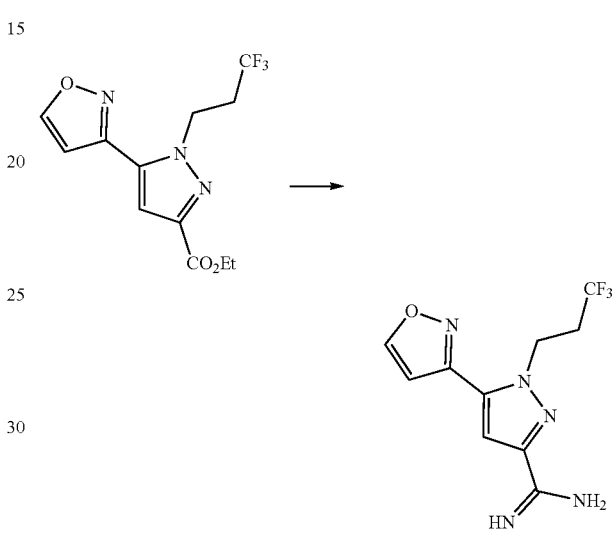

Step 3: Synthesis of 5-(isoxazol-3-yl)-1-(3,3,3-trifluoropropyl)-1H-pyrazole-3-carboximidamide The desired amidine intermediate was generated according to the procedure described in step 3 of general procedure A, with the exception of using ethyl 3-(isoxazol-3-yl)-1-(3,3,3-trifluoropropyl)-1H-pyrazole-5-carboxylate as the starting ester, and the mixture was heated 4 h at 110° C. The reaction mixture was cooled in ice, then methanol (14 equiv.) and aqueous hydrochloric acid (17 equiv.) were added in succession over 5 min. This mixture was heated 30 min at 80° C., then cooled in ice and filtered. The filter cake was washed with toluene (2×) and air dried to yield the crude amidine hydrochloride salt. This material was stirred in saturated aqueous sodium carbonate, and was extracted with ethyl acetate/isopropyl alcohol (5:1 mix). The organic phase was washed with water and brine, dried over sodium sulfate, filtered, and concentrated in vacuo to deliver the desired neutral amidine 5-(isoxazol-3-yl)-1-(3,3,3-trifluoropropyl)-1H-pyrazole-3-carboximidamide as a light yellow solid.

$^1$H-NMR (400 MHz, CDCl$_3$) δ ppm 8.45 (d, 1H), 6.99 (s, 1H), 6.55 (d, 1H), 5.61 (br. s., 3H), 4.83-4.74 (m, 2H), 2.81-2.65 (m, 2H).

Step 4: Synthesis of Compound I-507

The title product was prepared following step 4 of general procedure A, except 5-(isoxazol-3-yl)-1-(3,3,3-trifluoropropyl)-1H-pyrazole-3-carboximidamide was the starting amidine, 2.5 equivalents of sodium (Z)-3-ethoxy-2-fluoro-3-oxoprop-1-en-1-olate was used, and the mixture was heated for 2 h at 90° C. The reaction was cooled to 23° C. and the solvent was removed in vacuo. The residue was redissolved in dichloromethane and treated with hydrochloric acid (2.5M in ethanol, 3 equiv.). The resulting solids were filtered, washed with dichloromethane (2x), and air dried to deliver the desired compound, Compound I-507 (0.43 g, 110% yield) as a white solid.

¹H-NMR (400 MHz, CD₃OD) δ ppm 8.84 (d, 1H), 8.03 (d, 1H), 7.40 (s, 1H), 6.95 (d, 1H), 4.96 (t, 2H), 2.92 (m, 2H).

Compound I-511

The title compound was synthesized in 2 steps:

Step 1: Synthesis of 3-(3-(4-chloro-5-fluoropyrimidin-2-yl)-1-(3,3,3-trifluoropropyl)-1H-pyrazol-5-yl)isoxazole A mixture of Compound I-507 (1 equiv.) in phosphorus oxychloride (28 equiv.) was heated for 2 h at 90° C. The solvent was removed in vacuo and the residue rinsed with dichloromethane (2x) to deliver the desired intermediate 3-(3-(4-chloro-5-fluoropyrimidin-2-yl)-1-(3,3,3-trifluoropropyl)-1H-pyrazol-5-yl)isoxazole (0.28 g, 69% yield) as a tan solid.

¹H-NMR (400 MHz, CDCl₃) δ ppm 8.59 (s, 1H), 8.47 (d, 1H), 7.30 (s, 1H), 6.60 (d, 1H), 4.92 (t, 2H), 2.81 (m, 2H).

Step 2: Synthesis of Compound I-511

The title compound was prepared following general procedure B, except 2-aminoacetamide (as the HCl salt, 2 equiv.) was the amine reactant, 3-(3-(4-chloro-5-fluoropyrimidin-2-yl)-1-(3,3,3-trifluoropropyl)-1H-pyrazol-5-yl)isoxazole (described above) was used in place of Intermediate 1, 5 equivalents of triethylamine was used, and contents were heated to 90° C. for 2 h. The mixture was cooled to 23° C., diluted with water and the pH taken to ~5 with aqueous 3N hydrochloric acid. The crude product was collected by filtration, then purified via silica gel chromatography utilizing a methanol in dichloromethane gradient to deliver the desired compound, Compound I-511 (12 mg, 45% yield) as a white solid.

¹H-NMR (400 MHz, CD₃OD) δ ppm 8.81 (s, 1H), 8.13 (d, 1H), 7.34 (s, 1H), 6.93 (s, 1H), 4.91 (m, 2H), 4.21 (s, 2H), 2.89 (m, 2H).

Compound I-513

3-(3-(4-chloro-5-fluoropyrimidin-2-yl)-1-(3,3,3-trifluoropropyl)-1H-pyrazol-5-yl)isoxazole (described in step 1 of synthesis of Compound I-511 (1 equiv.) and concentrated aqueous ammonium hydroxide (2.8 equiv.) in dioxane were sealed in a screw-cap vial and heated for 2 h at 95° C. The mixture was cooled to 23° C., diluted with water, then filtered. The filter cake was washed with water (2x) and air dried to deliver the desired compound, Compound I-513 (0.14 g, 76% yield) as a light tan powder.

¹H-NMR (400 MHz, CDCl₃) δ ppm 8.51 (d, 1H), 8.21 (d, 1H), 7.26 (s, 1H), 6.63 (d, 1H), 5.26 (s, 2H), 4.95 (m, 2H), 2.85 (m, 2H).

Compound I-516 and Compound I-517

The title compound was prepared following general procedure B, except 2-(aminomethyl)-1,1,1,3,3,3-hexafluoropropan-2-ol (2 equiv.) was the amine reactant, 3-(3-(4-chloro-5-fluoropyrimidin-2-yl)-1-(3,3,3-trifluoropropyl)-1H-pyrazol-5-yl)isoxazole (described in step 1 of synthesis of Compound I-511 (1 equiv.) was used in place of Intermediate 1, 6 equivalents of triethylamine was used, and contents were heated to 95° C. for 3 d. The mixture was cooled to 23° C. and diluted with ethyl acetate, then washed with water (2x) and brine. Contents dried over sodium sulfate, filtered, and concentrated in vacuo to yield the crude product. Residue was purified via silica gel chromatography utilizing a hexane/ethyl acetate gradient to deliver two products, Compound I-516 (27 mg, 37% yield) as a white solid, and Compound I-517 (9 mg, 16% yield) as a white solid.

¹H-NMR for Compound I-516 (400 MHz, CDCl₃) δ ppm 8.56 (s, 1H), 8.40 (s, 1H), 8.31 (d, 1H), 7.21 (s, 1H), 6.67 (s, 1H), 5.60 (m, 1H), 4.95 (m, 2H), 4.16 (d, 2H), 2.93 (m, 2H).

¹H-NMR for Compound I-517 (400 MHz, CDCl₃) δ ppm 8.54 (s, 1H), 8.15 (d, 1H), 7.17 (s, 1H), 6.68 (s, 1H), 4.94 (m, 2H), 3.69 (q, 4H), 2.89 (m, 2H), 1.31 (t, 6H).

Compound I-523

The title compound was prepared following general procedure B, except 1-((methylamino)methyl)cyclopropanecarboxylic acid (as the HCl salt) was the amine reactant, 3-(3-(4-chloro-5-fluoropyrimidin-2-yl)-1-(3,3,3-trifluoropropyl)-1H-pyrazol-5-yl)isoxazole (described in step 1 of synthesis of Compound I-511 (1 equiv.) was used in place of Intermediate 1, 6.6 equivalents of triethylamine was used, and contents were heated to 90° C. for 18 h. The reaction mixture was diluted with water and carefully taken to pH 4 with aqueous 3N hydrochloric acid solution. The mixture was filtered, and the filter cake was washed with water (2x) and air dried to deliver the desired compound, Compound I-523 (9 mg, 60% yield) as a white solid.

1H-NMR (400 MHz, CDCl₃) δ ppm 8.51 (d, 1H), 8.16 (d, 1H), 7.16 (s, 1H), 6.64 (s, 1H), 4.92 (m, 2H), 4.10 (s, 2H), 3.35 (d, 3H), 2.87 (m, 2H), 1.44 (m, 2H), 1.13 (m, 2H).

Compound I-573

The title compound was synthesized in 2 steps:

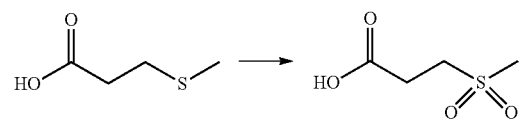

Step 1: Synthesis of Give 3-(methylsulfonyl)propanoic Acid

A solution of 3-(methylthio)propanoic acid (1 equiv.) in glacial acetic acid was cooled in ice as aqueous hydrogen peroxide (27%, 6 equiv.) was added at a rate to keep the internal temperature<50° C. The cooling bath was removed and stirring was continued for 18 h at 23° C. The solvents were removed in vacuo to leave a white paste. The paste was mixed in dichloromethane and filtered. The filter cake was washed with additional dichloromethane (3x) and air dried to deliver the desired carboxylic acid, 3-(methylsulfonyl)propanoic acid (3.0 g, 47% yield) as a white solid. ¹H-NMR (400 MHz, acetone-d₆) δ ppm 10.2 (br s, 1H), 3.38 (t, 2H), 3.00 (s, 3H), 2.85 (t, 2H).

The title compound was prepared following general procedure C, except 3-(methylsulfonyl)propanoic acid (2 equiv.) was the acid reactant, 6 equivalents of triethylamine was used, and 3 equivalents of propylphosphonic anhydride (T3P, 50 wt % in ethyl acetate) was used, and the solution was heated to 70° C. for 18 h. Contents cooled to 23° C., diluted with ethyl acetate, then washed with water (3x) and brine. Contents were dried over sodium sulfate, filtered, and concentrated in vacuo. Purification of the residue via silica gel chromatography utilizing an ethyl acetate in hexanes gradient delivered the desired compound, Compound I-573 (6 mg, 8% yield) as a white solid.

¹H-NMR (400 MHz, acetone-d₆) δ ppm 8.77 (d, 1H), 8.58 (d, 1H), 7.92 (d, 1H), 7.40 (s, 1H), 7.20 (m, 1H), 7.03 (m, 1H), 6.98 (m, 1H), 6.94 (d, 1H), 6.83 (m, 1H), 5.88 (s, 2H), 3.38 (t, 2H), 3.07 (t, 2H), 2.88 (s, 3H).

Compound I-588

The title compound was synthesized in 6 steps:

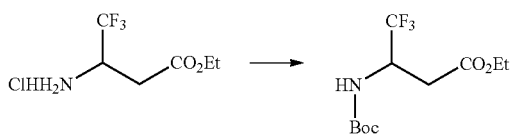

Step 1: Synthesis of Ethyl 3-((tert-butoxycarbonyl)amino)-4,4,4-trifluorobutanoate A solution of ethyl 3-amino-4,4,4-trifluorobutanoate hydrochloride (1 equiv.) in THF was cooled in ice as triethylamine (2.2 equiv.) was added over 5 min. Di-tert-butyl dicarbonate (2 equiv.) in THF was added to the vessel and the mixture was stirred for 2 d at 23° C. The solvent was removed in vacuo and the residue was taken up in ethyl acetate, then washed sequentially with water, 10% aqueous sodium bicarbonate solution, water (3×), then brine. Contents dried over sodium sulfate, filtered, and concentrated in vacuo. Purification of the residue via silica gel chromatography utilizing a ethyl acetate in hexanes gradient delivered the desired Boc protected amine, ethyl 3-((tert-butoxycarbonyl)amino)-4,4,4-trifluorobutanoate (1.9 g, 74% yield) as a white solid.

$^1$H-NMR (400 MHz, CDCl$_3$) δ ppm 5.25 (br d, 1H), 4.68 (m, 1H), 4.16 (q, 2H), 2.74 (dd, 1H), 2.57 (dd, 1H), 1.43 (s, 9H), 1.25 (t, 3H).

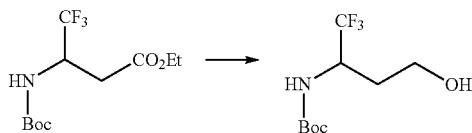 [SMILES: CCOC(=O)CC(NC(=O)OC(C)(C)C)C(F)(F)F ; CC(C)(C)OC(=O)NC(CCO)C(F)(F)F]

Step 2: Synthesis of Tert-Butyl (1,1,1-trifluoro-4-hydroxybutan-2-yl)carbamate

A solution of ethyl 3-((tert-butoxycarbonyl)amino)-4,4,4-trifluorobutanoate (1 equiv.) in THF was cooled in ice as lithium aluminum hydride (2M in THF, 2.5 equiv.) was added over 5 min. The solution was stirred for 3 h at 23° C., then re-cooled in ice and treated sequentially with water, 15% aqueous NaOH, and water. Stirring was continued for 15 min at 23° C., then the mixture was filtered through Celite and the filter cake was rinsed with ethyl acetate (4×). The combined organic filtrates were dried over sodium sulfate, filtered, and concentrated in vacuo to deliver the desired alcohol intermediate, tert-butyl (1,1,1-trifluoro-4-hydroxybutan-2-yl)carbamate (0.26 g, 98% yield) as a white solid.

$^1$H-NMR (400 MHz, CDCl$_3$) δ ppm 4.79 (br d, 1H), 4.44 (m, 1H), 3.76 (m, 1H), 3.68 (m, 1H), 2.63 (br s, 1H), 2.08 (m, 1H), 1.55 (m, 1H), 1.45 (s, 9H).

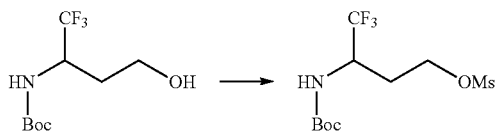 [SMILES: CC(C)(C)OC(=O)NC(CCO)C(F)(F)F ; CC(C)(C)OC(=O)NC(CCOS(C)(=O)=O)C(F)(F)F]

Step 3: Synthesis of 3-((tert-butoxycarbonyl)amino)-4,4,4-trifluorobutyl Methanesulfonate A solution of tert-butyl (1,1,1-trifluoro-4-hydroxybutan-2-yl)carbamate (1 equiv.) and triethylamine (2.5 equiv.) in dichloromethane was stirred at 23° C. as methansulfonyl chloride (1.7 equiv.) was added to the vessel. The resulting solution was stirred for 2 h at 23° C., then diluted with ethyl acetate and washed with water (4×) and brine. Contents were dried over sodium sulfate, filtered, and concentrated in vacuo to deliver the desired mesyl-protected alcohol intermediate 3-((tert-butoxycarbonyl)amino)-4,4,4-trifluorobutyl methanesulfonate (0.29 g, 89% yield) as a colorless solid.

$^1$H-NMR (400 MHz, CDCl$_3$) δ ppm 4.67 (br d, 1H), 4.45 (m, 1H), 4.31 (m, 2H), 3.05 (s, 3H), 2.28 (m, 1H), 1.84 (m, 1H), 1.45 (s, 9H).

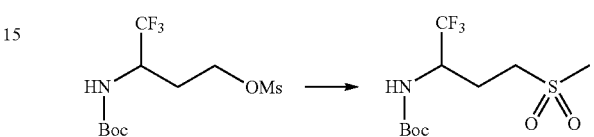

Step 4: Synthesis of Tert-Butyl (1,1,1-trifluoro-4-(methylsulfonyl)butan-2-yl)carbamate A solution of 3-((tert-butoxycarbonyl)amino)-4,4,4-trifluorobutyl methanesulfonate (1 equiv.) in THF at 23° C. was treated with sodium methanethiolate (10 equiv.), and the resulting solution was heated for 6 h at 60° C. The reaction mixture was then cooled in ice as m-chloroperoxybenzoic acid (70% wt/wt, 12.5 equiv.) was added in portions. The reaction was assayed by LC/MS to confirm complete conversion to sulfone. The mixture was diluted with ethyl acetate and washed sequentially with 7:1=10% aqueous bicarbonate/3N aqueous sodium hydroxide solution (2×), 10% aqueous sodium bicarbonate solution (2×), water (4×), then brine. The contents were dried over sodium sulfate, filtered, and concentrated in vacuo to yield a residue. The crude product was purified via silica gel chromatography, utilizing a ethyl acetate in hexanes gradient to deliver the desired sulfone intermediate, tert-butyl (1,1,1-trifluoro-4-(methylsulfonyl)butan-2-yl)carbamate (0.18 g, 72% yield) as a white solid.

$^1$H-NMR (400 MHz, CDCl$_3$) δ ppm 4.75 (br d, 1H), 4.36 (m, 1H), 3.16 (m, 2H), 2.99 (s, 3H), 2.37 (m, 1H), 2.07 (m, 1H), 1.49 (s, 9H).

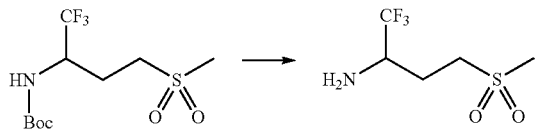 [SMILES: CC(C)(C)OC(=O)NC(CCS(C)(=O)=O)C(F)(F)F ; CS(=O)(=O)CCC(N)C(F)(F)F]

Step 5: Synthesis of 1,1,1-trifluoro-4-(methylsulfonyl)butan-2-amine

Tert-butyl (1,1,1-trifluoro-4-(methylsulfonyl)butan-2-yl)carbamate (1 equiv.) was dissolved in dichloromethane at 23° C., then treated with trifluoroacetic acid (25 equiv.) and stirred for 3 h at 23° C. The reaction was diluted with dichloromethane and 10% aqueous sodium bicarbonate solution, and the phases were well mixed and separated. The aqueous phase was extracted with dichloromethane (3×), and the combined organic phases were dried over sodium sulfate, filtered, and concentrated in vacuo to deliver the desired deprotected amine intermediate, 1,1,1-trifluoro-4-(methylsulfonyl)butan-2-amine (18 mg, 54% yield) as a colorless oil.

¹H-NMR (400 MHz, CDCl₃) δ ppm 3.25 (m, 2H), 3.15 (m, 1H), 2.89 (s, 3H), 2.23 (m, 1H), 1.80 (m, 1H), 1.36 (br s, 2H).

Step 6: Synthesis of Compound I-588

The title compound was prepared following general procedure B, except 1,1,1-trifluoro-4-(methylsulfonyl)butan-2-amine (6 equiv.) was the amine reactant, 6 equivalents of triethylamine was used, and contents were heated via microwave to 215° C. for 2 h as a solution in NMP. Direct purification of the resulting mixture via silica gel chromatography utilizing an ethyl acetate in hexanes gradient gave impure product. Further purification via reverse phase HPLC delivered the desired compound, Compound I-588 (17 mg, 16% yield).

¹H-NMR (400 MHz, CDCl₃) δ ppm 8.40 (d, 1H), 8.23 (d, 1H), 7.29 (s, 1H), 7.13 (m, 1H), 6.97 (m, 1H), 6.91 (m, 1H), 6.81 (m, 1H), 6.56 (d, 1H), 5.93 (d, 1H), 5.88 (d, 1H), 5.35 (m, 1H), 5.18, (br s, 1H), 3.19 (m, 1H), 3.11 (m, 1H), 2.86 (s, 3H), 2.53 (m, 1H), 2.21 (m, 1H).

Compound I-626

The title compound was prepared following general procedure B, except 1,1,1-trifluoro-4-(methylsulfonyl)butan-2-amine (1.3 equiv.) was the amine reactant, 3-(3-(4-chloro-5-fluoropyrimidin-2-yl)-1-(3,3,3-trifluoropropyl)-1H-pyrazol-5-yl)isoxazole (described in step 1 of synthesis of Compound I-511 (1 equiv.) was used in place of Intermediate 1, 1.3 equivalents of triethylamine was used, and contents were heated via microwave to 215° C. for 2.5 h as a solution in NMP. Direct purification of the resulting mixture via silica gel chromatography utilizing an ethyl acetate in hexanes gradient gave impure product. Further purification via reverse phase HPLC delivered the desired compound, Compound I-626 (1 mg, 1% yield).

¹H-NMR (400 MHz, CDCl₃) δ ppm 8.53 (d, 1H), 8.32 (d, 1H), 7.30 (s, 1H), 6.71 (d, 1H), 5.44 (m, 1H), 5.27 (br d, 1H), 4.94 (m, 2H), 3.21 (m, 2H), 2.95 (s, 3H), 2.87 (m, 2H), 2.61 (m, 1H), 2.28 (m, 1H).

Compound I-617

The title compound was prepared in 3 steps:

Step 1: Synthesis of Diethyl 2-(2-(1-(2-fluorobenzyl)-5-(isoxazol-3-yl)-1H-pyrazol-3-yl)-5-nitropyrimidin-4-yl)-2-methylmalonate A mixture of 3-(3-(4-chloro-5-nitropyrimidin-2-yl)-1-(2-fluorobenzyl)-1H-pyrazol-5-yl)isoxazole (described in step 1 towards the synthesis of Compound I-483, 1.2 equiv.), diethyl 2-methylmalonate (1 equiv.) and potassium t-butoxide (0.9 equiv.) in THF was stirred at room temperature for 15 min. The solution was diluted with saturated aqueous ammonium chloride solution and ethyl acetate. The phases were separated and the aqueous phase was extracted twice with ethyl acetate. The combined organic phase was washed with brine, dried over anhydrous sodium sulfate, filtered, and concentrated. The crude material was purified via silica gel chromatography (10-50% ethyl acetate in hexane gradient) to deliver the desired intermediate diethyl 2-(2-(1-(2-fluorobenzyl)-5-(isoxazol-3-yl)-1H-pyrazol-3-yl)-5-nitropyrimidin-4-yl)-2-methylmalonate (94.5 mg, 40% yield) as a yellow solid.

¹H NMR (500 MHz, DMSO-d₆) δ ppm 9.56 (s, 1H), 9.14 (d, 1H), 7.69 (s, 1H), 7.36 (s, 1H), 7.30 (d, 1H), 7.19-7.25 (m, 1H), 7.12 (t, 1H), 6.97-7.03 (m, 1H), 5.95-5.97 (m, 2H), 4.12-4.19 (m, 4H), 1.94 (s, 3H), 1.11 (t, 6H).

Step 2: Synthesis of Diethyl 2-(5-amino-2-(1-(2-fluorobenzyl)-5-(isoxazol-3-yl)-1H-pyrazol-3-yl)pyrimidin-4-yl)-2-methylmalonate A mixture of diethyl 2-(2-(1-(2-fluorobenzyl)-5-(isoxazol-3-yl)-1H-pyrazol-3-yl)-5-nitropyrimidin-4-yl)-2-methylmalonate (1 equiv.) and 20% Palladium on Carbon (0.5 equiv.) in ethanol and ethyl acetate (1:1) was stirred in a hydrogen atmosphere at 23° C. for 18 h. The reaction mixture was then filtered through celite, and the residue was washed with ethyl acetate. The filterate was concentrated in vacuo, and the residue was carried forward to the next step without any further purification or characterization.

Step 3: Synthesis of Compound I-617

A solution of diethyl 2-(5-amino-2-(1-(2-fluorobenzyl)-5-(isoxazol-3-yl)-1H-pyrazol-3-yl)-pyrimidin-4-yl)-2-methylmalonate in ethanol and THF (2:1) was heated at 85° C. for 16 h. The resultant solution was concentrated in vacuo, and the residue was purified via reverse phase HPLC (20-60% acetonitrile in water gradient, with 1% TFA) to deliver the desired compound, Compound I-617 (12 mg, 20% yield) as a pale yellow solid.

¹H NMR (500 MHz, DMSO-d₆) δ ppm 11.26 (s, 1H), 9.07 (d, 1H), 8.44 (s, 1H), 7.57 (s, 1H), 7.30 (d, 2H), 7.17-7.25 (m, 1H), 7.06-7.13 (m, 1H), 6.80-6.88 (m, 1H), 5.88-5.99 (m, 2H), 4.01-4.20 (m, 2H), 1.60 (s, 3H), 1.05 (s, 3H).

Compound I-618

The title compound was prepared in 2 steps:

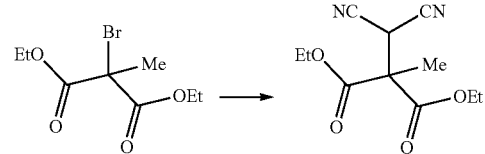 [SMILES: CCOC(=O)C(C)(Br)C(=O)OCC ; CCOC(=O)C(C)(C(=O)OCC)C(C#N)C#N]

Step 1: Synthesis of Diethyl 2-(dicyanomethyl)-2-methylmalonate

A mixture of diethyl 2-bromo-2-methylmalonate (1 equiv.), malononitrile (1 equiv.) and potassium t-butoxide (1 equiv.) in THF was heated to reflux for 15 h. The mixture was diluted with ethyl acetate and saturated aqueous ammonium chloride solution, and the phases were separated. The aqueous phase was extracted twice with ethyl acetate. The combined organic phase was washed with brine, dried over anhydrous sodium sulfate, filtered, and concentrated in vacuo to give an oil. The oil was purified via silica gel chromatography, utilizing a 10-15% ethyl acetate in hexane gradient to deliver the desired intermediate, diethyl 2-(dicyanomethyl)-2-methylmalonate (5.76 g, 32% yield) as a colorless oil.

¹H NMR (500 MHz, CDCl₃) δ ppm 4.53 (s, 1H), 4.27-4.39 (m, 4H), 1.81 (s, 3H), 1.33 (t, 6H).

Step 2: Synthesis of Compound I-618

A mixture of 5-(isoxazol-3-yl)-1-(3,3,3-trifluoropropyl)-1H-pyrazole-3-carboximidamide (generated in step 3 towards the synthesis of Compound I-507 (1 equiv.), diethyl 2-(dicyanomethyl)-2-methylmalonate (1.15 equiv.) and potassium bicarbonate (2 equiv.) in t-BuOH was heated to reflux for 5 h. The resultant solution was then concentrated in vacuo, and the residue was purified via silica gel chromatography utilizing a 0-5% methanol in dichloromethane gradient to deliver the desired compound, Compound I-618 (88.5 mg, 51% yield) as a white solid.

¹H NMR (500 MHz, DMSO-d₆) δ ppm 11.31 (s, 1H), 9.14 (d, 1H), 7.34 (s, 1H), 7.24 (d, 1H), 6.57-6.71 (m, 2H), 4.85 (t, 2H), 4.11 (t, 2H), 2.85-2.98 (m, 2H), 1.61 (s, 3H), 1.12 (t, 3H).

Compound I-619

Ammonia (7.0 M in MeOH, 200 equiv.) was added to Compound I-618 (1 equiv.). The reaction mixture was heated at 50° C. for 16 h. The resultant solution was then concentrated in vacuo, and the residue was purified via reverse phase HPLC (20-40% acetonitrile in water gradient, with 1% TFA) to deliver the desired compound, Compound I-619 (4.7 mg, 31% yield) as a white solid.

$^1$H NMR (500 MHz, DMSO-d$_6$) δ ppm 11.30 (s, 1H), 9.14 (d, 1H), 7.42-7.50 (m, 1H), 7.36 (s, 1H), 7.25 (d, 1H), 7.17-7.22 (m, 1H), 6.67-6.92 (m, 2H), 4.83-4.89 (m, 2H), 2.86-2.99 (m, 2H), 1.56 (s, 3H).

Compound I-620

The title compound was prepared in 3 steps:

Step 1: Synthesis of (E)-2-(1-(2-fluorobenzyl)-5-(isoxazol-3-yl)-1H-pyrazol-3-yl)-5-(phenyldiazenyl)pyrimidine-4,6-diamine A mixture of 1-(2-fluorobenzyl)-5-(isoxazol-3-yl)-1H-pyrazole-3-carboximidamide (generated in step 3 towards the synthesis of Compound I-507 (1 equiv.), (E)-2-(phenyldiazenyl)malononitrile (1.2 equiv.) and potassium bicarbonate (2 equiv.) in t-BuOH was heated to reflux for 18 h. After cooling, the reaction mixture was concentrated in vacuo, and carried forward to the next step without any further purification.

Step 2: Synthesis of 2-(1-(2-fluorobenzyl)-5-(isoxazol-3-yl)-1H-pyrazol-3-yl)-pyrimidine-4,5,6-triamine A mixture of (E)-2-(1-(2-fluorobenzyl)-5-(isoxazol-3-yl)-1H-pyrazol-3-yl)-5-(phenyldiazenyl) pyrimidine-4,6-diamine (1 equiv.) and 20% palladium on carbon (0.5 equiv.) in DMF was stirred under a hydrogen atmosphere at 23° C. for 18 h. The reaction mixture was then filtered through celite and the residue was washed with DMF followed by a small portion of methanol. The filtrate was concentrated in vacuo, and the residue was suspended in ethyl acetate and a drop of methanol and stirred vigorously. The precipitate was filtered, washed with ethyl acetate, and dried under vacuum to deliver the desired triaminopyrimidine intermediate, 2-(1-(2-fluorobenzyl)-5-(isoxazol-3-yl)-1H-pyrazol-3-yl)-pyrimidine-4,5,6-triamine (278 mg, 46% yield over 2 steps) as a dark yellow solid.

Step 3: Synthesis of Compound I-620

A solution of 2-(1-(2-fluorobenzyl)-5-(isoxazol-3-yl)-1H-pyrazol-3-yl) pyrimidine-4,5,6-triamine (1 equiv.) in pyridine at 0° C. was treated with methyl chloroformate (1 equiv.). The reaction mixture was slowly warmed to 23° C. and stirred for 18 h. Volatiles were removed in vacuo, and the residue was dissolved in ethyl acetate and washed with water. Contents were dried over anhydrous sodium sulfate, filtered, and concentrated to give a dark yellow solid. The crude material was purified via reverse phase HPLC (20-40% acetonitrile in water gradient, with 1% TFA) to deliver the desired compound, Compound I-620 (15 mg, 26% yield) as a pale yellow solid.

$^1$H NMR (500 MHz, CD$_3$OD) δ ppm 8.82 (d, 1H), 7.51 (s, 1H), 7.27-7.35 (m, 1H), 7.04-7.15 (m, 2H), 6.92-6.99 (m, 1H), 6.89 (d, 1H), 6.00 (s, 2H), 3.78 (br. s., 3H), 3.34-3.35 (m, 1H).

Compound I-621

A solution of Compound I-620 (1 equiv.) and LiHMDS (1M in toluene, 6 equiv.) in THF at 0° C. was stirred for 20 min. Iodomethane (12 equiv.) added to the reaction vessel, and mixture was warmed to 23° C. and stirred for 1 h. The mixture was diluted with dichloromethane and saturated aqueous ammonium chloride solution, and the phases were separated. The aqueous phase was extracted twice with dichloromethane. The combined organic phases were dried over anhydrous magnesium sulfate, filtered, and concentrated. The crude material was purified via reverse phase HPLC (20-40% acetonitrile in water gradient, with 1% TFA) to deliver the desired compound, Compound I-621 (1.6 mg, 17% yield) as a yellow solid.

$^1$H NMR (500 MHz, CD$_3$OD) δ ppm 8.83 (d, 1H), 7.53 (s, 1H), 7.27-7.35 (m, 1H), 7.05-7.15 (m, 2H), 6.96 (t, 1H), 6.90 (d, 1H), 6.00 (s, 2H), 3.66-3.86 (m, 3H), 3.13 (d, 3H).

Compound I-623

The title compound was prepared in 2 steps:

Step 1: Synthesis of 4-amino-2-(1-(2-fluorobenzyl)-5-(isoxazol-3-yl)-1H-pyrazol-3-yl)-5-methyl-6-oxo-6,7-dihydro-5H-pyrrolo[2,3-d]pyrimidine-5-carbohydrazide A mixture of Compound I-420 (1 equiv.), anhydrous hydrazine (325 equiv.), and water (11.2 equiv.) in methanol was heated at 50° C. for 2 h. The resultant solution was concentrated in vacuo. Excess hydrazine was azeotropically removed by treatment with methanol and dichloromethane to deliver the desired acyl hydrazine intermediate, 4-amino-2-(1-(2-fluorobenzyl)-5-(isoxazol-3-yl)-1H-pyrazol-3-yl)-5-methyl-6-oxo-6,7-dihydro-5H-pyrrolo[2,3-d]pyrimidine-5-carbohydrazide as a yellow solid. The material was used as-is in the next step without further purification.

Step 2: Synthesis of Compound I-623

A mixture of 4-amino-2-(1-(2-fluorobenzyl)-5-(isoxazol-3-yl)-1H-pyrazol-3-yl)-5-methyl-6-oxo-6,7-dihydro-5H-pyrrolo[2,3-d]pyrimidine-5-carbohydrazide (1 equiv.) and N-acetyl imidazole (4 equiv.) in THF was stirred at 23° C. for 16 h. The resultant solution was concentrated in vacuo, and the residue was purified via reverse phase HPLC (20-80% acetonitrile in water gradient, with 1% TFA) to deliver the desired compound, Compound I-623 (71 mg, 46% yield) as a white solid.

$^1$H NMR (500 MHz, CD$_3$OD) δ ppm 8.80 (d, 1H), 7.52 (s, 1H), 7.25-7.32 (m, 1H), 7.06-7.14 (m, 1H), 7.01-7.06 (m, 1H), 6.87-6.92 (m, 2H), 5.98 (s, 2H), 2.66 (s, 1H), 2.00 (s, 3H), 1.82 (s, 3H).

Compound I-478

To a stirred solution of Compound I-461 (1 equiv.) in DMF and ethanol (3:2) was added 10% palladium on carbon (10 equiv.), and the reaction vessel was placed under a hydrogen atmosphere via a balloon and needle. Contents stirred for 18 h at 23° C., and the mixture was filtered and concentrated in vacuo. The crude material was purified via reverse phase HPLC to deliver the desired compound, Compound I-461 (5 mg, 19% yield) as a solid.

$^1$H-NMR (500 MHz, DMSO-d$_6$) δ ppm 9.69 (s, 1H), 9.11 (d, 1H), 8.78 (d, 1H), 8.00 (d, 1H), 7.72 (s, 1H), 7.31-7.38 (m, 1H), 7.29 (d, 1H), 7.21-7.26 (m, 1H), 7.12 (t, 1H), 6.86-6.94 (m, 2H), 5.95 (s, 2H), 1.22-1.28 (m, 2H), 1.09-1.14 (m, 2H).

Compound I-479

To a stirred solution of Intermediate 2 (1 equiv.) and 2-methoxyethanesulfonyl chloride (1 equiv.) in dichloromethane was added DBU (1 equiv.). The reaction was heated to 60° C. for 24 h, then cooled to 23° C. Contents diluted in water and extracted with dichloromethane (3×). The combined organic layers were washed with 1N HCl solution, dried over sodium sulfate, filtered, and concentrated in vacuo. The crude material was purified via reverse phase HPLC to deliver the desired compound, Compound I-479 (8 mg, 6% yield) as a solid.

$^1$H-NMR (500 MHz, CD$_3$OD) δ ppm 8.82 (d, 1H), 8.50 (d, 1H), 7.60 (s, 1H), 7.27-7.35 (m, 1H), 7.05-7.15 (m, 3H), 6.94-6.98 (m, 2H), 6.02 (s, 2H), 3.86 (s, 4H), 3.27 (s, 3H).

Compound I-595

A solution of 2-(1-(2-fluorobenzyl)-5-(isoxazol-3-yl)-1H-pyrazol-3-yl)pyrimidin-5-amine (this compound was described in previous patent application WO2012003405 A1) in dichloromethane/pyridine (2:1) was treated with 3,3,3-trifluoropropane-1-sulfonyl chloride (1.8 equiv.). After 3 h, 1N NaOH solution was added and the reaction was stirred for 1.5 h. Water was then added and the resultant mixture was acidified to pH 3 with 1N HCl solution and extracted with dichloromethane. The organic phases were dried over sodium sulfate, filtered and the solvent was removed in vacuo. The crude material was purified via silica gel chromatography utilizing a 0-10% methanol/dichloromethane gradient to deliver the desired compound, Compound I-595 (6.8 mg, 15% yield) as a white solid.

$^1$H-NMR (500 MHz, $CD_3OD$) δ ppm 8.77 (d, 1H), 8.74 (s, 2H), 7.52 (s, 1H), 7.27 (app. q, 1H), 7.09 (m, 1H), 7.04 (app. t, 1H), 6.90 (d, 1H), 6.87 (m, 1H), 5.97 (s, 2H), 3.49 (m, 2H), 2.77 (m, 2H).

Compound I-530 and Compound I-531

Compound I-405 was resolved by SFC chiral separation with chiralcel AD-H 50 mm×250 mm semi-prep column, using a 15:85 ethanol+0.5% diethylamine:$CO_2$. Collection of the two peaks and concentration in vacuo yielded Compound I-530 (first peak eluting by analytical HPLC, Chiralcel AD-H 4.6 mm×250 mm, 15:85 ethanol+0.5% diethylamine:hexane) as a light orange solid. Collection of the peak that eluted second and concentration in vacuo yielded Compound I-531 (second peak eluting by analytical HPLC, Chiralcel AD-H 4.6 mm×250 mm, 15:85 ethanol+0.5% diethylamine:hexane) as a light orange solid.

$^1$H-NMR for Compound I-530 (500 MHz, DMSO-$d_6$) δ ppm 9.11 (d, 1H), 8.32 (d, 1H), 7.93 (t, 1H), 7.90 (s, 1H), 7.78 (br s, 1H), 7.69 (br s, 1H), 7.51 (s, 1H), 7.35-7.31 (m, 1H), 7.22-7.19 (m, 2H), 7.10 (t, 1H), 7.00-6.97 (m, 1H), 5.90 (s, 2H), 4.02-3.94 (m, 2H).

$^1$H-NMR for Compound I-531 (500 MHz, DMSO-$d_6$) δ ppm 9.11 (d, 1H), 8.33 (d, 1H), 7.93 (t, 1H), 7.90 (s, 1H), 7.78 (br s, 1H), 7.69 (br s, 1H), 7.52 (s, 1H), 7.35-7.31 (m, 1H), 7.22-7.19 (m, 2H), 7.10 (t, 1H), 7.00-6.97 (m, 1H), 5.90 (s, 2H), 4.02-3.94 (m, 2H).

Compound I-630

The title compound was synthesized in 2 steps:

Step 1: Synthesis of Methyl (2-(1-(2-fluorobenzyl)-5-(isoxazol-3-yl)-1H-pyrazol-3-yl)pyrimidin-5-yl)carbamate To a solution of 2-(1-(2-fluorobenzyl)-5-(isoxazol-3-yl)-1H-pyrazol-3-yl)pyrimidin-5-amine (this compound was described in patent application publication WO2012003405 A1) (1 equiv.) in anhydrous pyridine at 0° C. was added methyl chloroformate (1.2 equiv.). After stirring for 10 min, the reaction mixture was warmed to ambient temperature and monitored closely by LC/MS. Additional portions of methyl chloroformate (3.2 equiv.) were added at 0° C. After stirring at ambient temperature for 20 h, the crude mixture was diluted with water. The resultant tan solids were collected by filtration and used in the next step without further purification.

Step 2: Synthesis of Compound I-630

A suspension of methyl (2-(1-(2-fluorobenzyl)-5-(isoxazol-3-yl)-1H-pyrazol-3-yl)pyrimidin-5-yl)carbamate (1 equiv.) in DMF at 0° C. was treated with sodium hydride (60% w/w in mineral oil, 1.1 equiv.) and warmed to ambient temperature. After 30 min, the reaction mixture was cooled to 0° C. and iodomethane (1.1 equiv.) was added. After 25 min, the crude reaction mixture was poured into water and extracted with ethyl acetate. The combined organic phases were dried over sodium sulfate, filtered and the solvent was removed in vacuo. The crude material was purified via silica gel chromatography utilizing a 20% acetonitrile/methanol (7:1) in dichloromethane gradient to deliver the desired compound, Compound I-630 (12 mg, 21% yield over two steps) as a white solid.

$^1$H NMR (500 MHz, $CD_3OD$) δ ppm 8.88 (s, 2H), 8.77 (d, 1H), 7.55 (s, 1H), 7.28 (app. q, 1H), 7.09 (app. t, 1H), 7.04 (app. t, 1H), 6.91 (d, 1H), 6.88 (app. t, 1H), 5.99 (s, 2H), 3.79 (s, 3H), 3.40 (s, 3H).

Example 2A: Biological Activity Measurement by the sGC-HEK-cGMP Assay (Assay Run with SNP Incubation)

Human embryonic kidney cells (HEK293), endogenously expressing soluble guanylate cyclase (sGC), were used to evaluate the activity of test compounds. Compounds stimulating the sGC receptor should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 μL volume at a density of 1×10$^5$ cells/well in a poly-D-lysine coated 96 well flat bottom plate and grown overnight at 37° C. Medium was aspirated and cells were washed with 1× Hank's Buffered Saline Salt Solution (200 μL). Cells were then incubated for 15 minutes at 37° C. with 200 μL of a 0.5 mM 3-isobutyl-1-methylxanthine (IBMX) solution. Test article and sodium nitroprusside solutions (x μM concentration for test article solution and 10 μM concentration for SNP solution; wherein x is one of the following concentrations: 30 μM, 10 μM, 3 μM, 1 μM, 0.3 μM, 0.1 μM, 0.03 μM, 0.01 μM, 0.003 μM, 0.001 μM, 0.0003 μM or 0.0001 μM) were then added to the assay mixture (2 μL each) and the resulting mixture incubated at 37° C. for 10 minutes. After the 10 minute incubation, the assay mixture was aspirated and 0.1M HCl (200 μL) was added to the cells. The plate was incubated at 4° C. for 30 minutes in the 0.1M HCl to stop the reaction and lyse the cells. The plates were then centrifuged at 1,200 g for 5 minutes at room temperature. Supernatants were collected and transferred to a new flat bottom 96 well plate for analysis by HPLC-MS. Vehicle controls were carried out using DMSO (1%) solutions. A known sGC stimulator, BAY 41-2272, was used as the positive control. Samples were diluted with an equal volume of 1 M Ammonium Acetate (pH 7) to neutralize samples for better chromatography. A 2× cGMP standard solution was prepared in 0.1 M HCl and then diluted with an equal volume of 1 M Ammonium Acetate, with the following final concentrations in nM: 1024, 512, 256, 128, 64, 32, 16, 8, 4, 2, 1. cGMP concentrations in the test plates were determined from each sample using the LC/MS conditions shown in Table 2 below and the calculated cGMP standard curve. $EC_{50}$ values were calculated from concentration-response curves generated with GraphPad Prism Software. Data were normalized to a high control using the following equation: 100*(Sample−Low Control)/(High Control−Low Control), where the low control is the average of 6 samples treated with 1% DMSO, and the high control is the average of 8-12 samples treated with 10 uM BAY 41-2272. Data were fit using a non-linear regression, sigmoidal dose response, 3 parameter fits. Samples were typically run in n=1, but for samples that were run with n=2 (or more) the results given herein correspond to the arithmetic mean of the various results obtained for each given compound. If a curve did not plateau, then it was constrained to 100% Compounds failing to elicit a minimum response of 30% were reported as ND and EC50 values were not determined. The biological activities of some of the compounds of Formula I and Formula I' determined with the sGC-HEK assay with SNP incubation are summarized in Table 3.

TABLE 2

| (HPLC LC/MS experimental conditions) | |
|---|---|
| MS: | Thermo Quantum or Waters LCMS |
| Ion Mode: | ESI+ |
| Scan Type: | MRM |

| Compound: | Transition | Dwell Time (msec) | Collision Energy (V) | Tube Lens | Retention Time (min) |
|---|---|---|---|---|---|
| cGMP | 346 > 152 | 100 | 28 | 139 | 1.0 |

| | |
|---|---|
| HPLC: | Agilent Technologies 1200 Series with CTC Analytics HTS PAL |
| Column: | Thermo Hypersil Gold 2.1 × 50 mm 5 micron particle size |
| Flow Rate: | 400 uL/min |
| Column Temperature: | RT |
| Autosampler Temperature: | 6° C. |
| Injection Volume: | 20 uL |
| Mobile Phases: | A = 98:2 Water:Acetonitrile + 0.1% Formic Acid |
| | B = 2:98 Water:Acetonitrile + 0.1% Formic Acid |

| Gradient: | Time (min) | % A | % B |
|---|---|---|---|
| | 0 | 100 | 0 |
| | 0.3 | 30 | 70 |
| | 2.00 | 30 | 70 |
| | 2.01 | 100 | 0 |
| | 4 | 100 | 0 |

TABLE 3

Whole cell activity in the HEK assay with LC/MS detection.

| Compound No. | HEK assay Emax - unconstrained (%)+ | HEK assay EC50 - unconstrained (μM)# | HEK assay EC50 - constrained (μM)# |
|---|---|---|---|
| I-1 | E | C | |
| I-2 | E | B | |
| I-3 | E | B | |
| I-4 | E | C | |
| I-6 | D | C | |
| I-7 | D | D | |
| I-8 | E | B | |
| I-9 | F | B | |
| I-10 | F | B | |
| I-11 | | | C |
| I-12 | G | D | |
| I-13 | E | B | |
| I-14 | | | F |
| I-16 | G | A | |
| I-17 | E | B | |
| I-18 | E | B | |
| I-19 | | | D |
| I-20 | E | B | |
| I-21 | D | B | |
| I-22 | E | B | |
| I-24 | D | B | |
| I-25 | D | C | |
| I-26 | E | B | |
| I-27 | E | C | |
| I-28 | E | D | |
| I-30 | F | B | |
| I-31 | E | C | |
| I-32 | E | B | |
| I-33 | E | B | |
| I-34 | D | C | |
| I-35 | D | C | |
| I-36 | D | D | |
| I-37 | E | D | |
| I-38 | E | E | |
| I-39 | E | E | |
| I-40 | E | D | |
| I-41 | E | D | F |
| I-42 | F | B | |
| I-43 | E | A | |
| I-45 | D | D | |
| I-46 | E | D | |
| I-47 | D | B | |
| I-48 | E | D | |
| I-51 | | | D |
| I-52 | E | D | |
| I-53 | | | D |
| I-54 | | | B |
| I-55 | | | D |
| I-56 | F | B | |
| I-57 | F | B | |
| I-58 | E | B | |
| I-59 | | | F |
| I-60 | G | C | |
| I-61 | F | C | |
| I-62 | E | B | |
| I-63 | E | B | |
| I-64 | F | A | |
| I-65 | E | C | |
| I-66 | E | B | |
| I-67 | F | E | F |
| I-68 | E | E | |
| I-69 | F | C | B |
| I-70 | F | B | |
| I-71 | E | B | |
| I-72 | E | B | |
| I-73 | D | E | |
| I-74 | D | D | |
| I-75 | E | B | |
| I-76 | E | C | |
| I-77 | E | A | |
| I-78 | D | B | |
| I-79 | D | B | |
| I-80 | F | C | |
| I-81 | | | F |
| I-82 | E | B | |
| I-83 | | | F |
| I-84 | E | C | |
| I-85 | | | F |

TABLE 3-continued

Whole cell activity in the HEK assay with LC/MS detection.

| Compound No. | HEK assay Emax - unconstrained (%)[+] | HEK assay EC50 - unconstrained (μM)[#] | HEK assay EC50 - constrained (μM)[#] |
|---|---|---|---|
| I-86 | F | B | |
| I-87 | E | B | |
| I-88 | E | D | |
| I-89 | E | A | |
| I-90 | D | E | |
| I-91 | D | E | |
| I-92 | E | D | |
| I-94 | E | D | |
| I-95 | | | E |
| I-96 | | | F |
| I-97 | E | A | |
| I-98 | D | D | |
| I-99 | E | D | |
| I-101 | | | E |
| I-102 | E | D | |
| I-103 | F | A | |
| I-104 | C | D | |
| I-105 | D | B | |
| I-108 | | | E |
| I-109 | E | B | |
| I-110 | C | F | |
| I-111 | | | F |
| I-112 | C | D | |
| I-113 | E | C | |
| I-114 | D | D | |
| I-115 | D | A | |
| I-116 | E | B | |
| I-117 | D | D | |
| I-118 | F | D | |
| I-119 | D | B | |
| I-120 | E | B | |
| I-121 | E | B | |
| I-123 | E | B | |
| I-124 | E | A | |
| I-125 | D | A | |
| I-126 | | | C |
| I-127 | | | F |
| I-129 | | | B |
| I-133 | | | F |
| I-135 | | | F |
| I-137 | F | B | |
| I-138 | | | D |
| I-139 | F | B | |
| I-140 | F | D | |
| I-141 | E | B | |
| I-142 | F | A | |
| I-143 | F | B | |
| I-144 | F | C | |
| I-145 | F | D | |
| I-146 | F | B | |
| I-148 | F | B | |
| I-149 | | | F |
| I-150 | D | B | |
| I-151 | E | C | |
| I-152 | F | A | |
| I-153 | E | B | |
| I-154 | E | B | |
| I-155 | E | B | |
| I-156 | F | B | |
| I-157 | E | B | |
| I-158 | E | A | |
| I-159 | | | F |
| I-160 | F | B | |
| I-161 | F | A | |
| I-162 | F | A | |
| I-163 | | | F |
| I-452 | F | B | |
| I-165 | | | F |
| I-166 | D | B | |
| I-167 | F | A | |
| I-168 | E | B | |
| I-169 | E | B | |
| I-170 | E | B | |
| I-171 | E | A | |
| I-172 | | | F |
| I-173 | E | B | |
| I-174 | E | C | |
| I-175 | G | A | |
| I-176 | D | D | |
| I-177 | E | B | |
| I-178 | D | E | |
| I-179 | F | B | |
| I-180 | F | D | |
| I-181 | G | C | |
| I-182 | F | A | |
| I-183 | E | B | |
| I-184 | F | C | |
| I-185 | G | D | |
| I-186 | F | A | |
| I-188 | | | D |
| I-189 | E | B | |
| I-190 | E | D | |
| I-191 | | | F |
| I-192 | H | A | |
| I-193 | E | D | |
| I-194 | F | B | |
| I-195 | E | A | |
| I-196 | F | B | |
| I-197 | F | D | |
| I-198 | D | A | |
| I-199 | E | E | |
| I-200 | F | E | D |
| I-201 | G | B | |
| I-202 | F | B | |
| I-203 | D | B | |
| I-204 | | | F |
| I-205 | E | C | |
| I-206 | | | F |
| I-207 | G | C | |
| I-208 | F | A | |
| I-209 | F | C | |
| I-210 | G | A | |
| I-211 | H | D | |
| I-212 | H | C | |
| I-213 | H | C | |
| I-214 | H | B | |
| I-215 | D | D | |
| I-216 | D | B | |
| I-217 | E | B | |
| I-218 | D | D | |
| I-219 | C | F | |
| I-221 | A | F | |
| I-223 | D | D | |
| I-224 | E | D | |
| I-225 | F | A | |
| I-226 | E | A | |
| I-227 | C | B | |
| I-228 | A | F | |
| I-229 | C | F | |
| I-230 | D | F | |
| I-231 | D | F | |
| I-232 | F | D | |
| I-233 | E | B | |
| I-234 | F | B | |
| I-235 | G | A | |
| I-236 | G | B | |
| I-237 | E | B | |
| I-238 | E | B | |
| I-239 | E | A | |
| I-240 | E | C | |
| I-241 | F | B | |
| I-242 | G | B | |
| I-243 | F | A | |
| I-244 | F | C | |
| I-245 | | | B |
| I-246 | D | D | |

TABLE 3-continued

Whole cell activity in the HEK assay with LC/MS detection.

| Compound No. | HEK assay Emax - unconstrained (%)[+] | HEK assay EC50 - unconstrained (μM)[#] | HEK assay EC50 - constrained (μM)[#] |
|---|---|---|---|
| I-187 | F | A | |
| I-274 | G | A | |
| I-273 | E | C | |
| I-275 | F | A | |
| I-286 | F | A | |
| I-247 | F | A | |
| I-248 | F | A | |
| I-287 | F | B | |
| I-288 | F | B | |
| I-299 | D | D | |
| I-300 | E | C | |
| I-301 | E | D | |
| I-276 | D | B | |
| I-249 | E | D | |
| I-250 | F | A | |
| I-298 | E | B | |
| I-289 | E | B | |
| I-290 | E | B | |
| I-272 | E | B | |
| I-251 | E | B | |
| I-277 | E | B | |
| I-252 | E | A | |
| I-253 | E | A | |
| I-278 | F | B | |
| I-254 | F | A | |
| I-255 | F | A | |
| I-279 | F | B | |
| I-256 | F | B | |
| I-257 | | | F |
| I-280 | G | B | |
| I-292 | F | A | |
| I-285 | G | A | |
| I-258 | G | D | |
| I-259 | G | B | |
| I-305 | A | F | |
| I-306 | F | A | |
| I-307 | G | D | |
| I-361 | A | B | |
| I-364 | F | A | |
| I-365 | F | D | |
| I-366 | D | A | |
| I-367 | E | A | |
| I-368 | C | B | |
| I-369 | E | A | |
| I-371 | B | F | |
| I-372 | E | B | |
| I-374 | G | B | |
| I-375 | G | B | |
| I-376 | G | E | |
| I-453 | A | D | |
| I-454 | C | F | |
| I-455 | F | A | |

[+]Code definitions for the sGC enzyme activity values, expressed as % $E_{max}$ in the presence of 10 μM of SNP (wherein $E_{max}$ = 100% was the activity in the HEK assay obtained with the positive control BAY 41-2272 at 10 μM in the presence of 100 μM SNP) are:
A = 0 to <10%
B = 10 to <20%
C = 20 to <40%
D = 40 to <60
E = 60 or <80%
F = 80 to <100%
G = 100 to <120%
H = 120% or higher
— = not determined

[+]The same code definitions apply for Emax unconstrained, wherein this value is defined as the maximum activity value obtained from the full concentration-response curve for the compound, relative to the positive control value of 100% obtained as above. Here, the term "unconstrained" means that, during analysis of the sGC enzyme activity data, the top portion of the concentration-response curve was not fitted to 100%.

[#]$EC_{50}$ values were obtained from the full concentration response curve following two methods: EC50 constrained refers to the value obtained when the top of the curve was fitted to 100% (wherein $E_{max}$ = 100% was the activity in the HEK assay obtained with the positive control BAY 41-2272 at 10 μM in the presence of 100 μM SNP); $EC_{50}$ unconstrained here reported refer to the value obtained from a full concentration-response curve when the top of the curve is not fitted to 100%. The EC50 code definitions in micromolar (μM) are:
0.001 ≤ EC50 < 0.1 = A
0.1 ≤ EC50 < 0.5 = B
0.5 ≤ EC50 < 1.0 = C
1.0 ≤ EC50 < 5.0 = D
5.0 ≤ EC50 < 10.0 = E
EC50 ≥ 10.0 = F

Example 2B: Biological Activity Measurement by the sGC-HEK-cGMP Assay (Using HTRF Detection) (Assay Run with SNP Incubation)

Human embryonic kidney cells (HEK293), endogenously expressing soluble guanylate cyclase (sGC), were used to evaluate the activity of test compounds. Compounds stimulating the sGC enzyme should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 μL volume at a density of $1\times10^5$ cells/well in a poly-D-lysine coated 96 well flat bottom plate and grown overnight at 37° C. Medium was aspirated and cells were washed with 1× Hank's Buffered Saline Salt Solution (200 μL). Cells were then incubated for 15 minutes at 37° C. with 200 μL of a 0.5 mM 3-isobutyl-1-methylxanthine (IBMX) solution. Test article and sodium nitroprusside solutions were then added to the assay mixture (2 μL each) and the resulting mixture incubated at 37° C. for 10 minutes. After the 10 minute incubation, the assay mixture was aspirated and 0.1M HCl (200 μL) was added to the cells. The plate was incubated at 4° C. for 30 minutes in the 0.1M HCl to stop the reaction and lyse the cells. The plates were then centrifuged at 1,200 g for 5 minutes at room temperature. GMP levels were determined using a cGMP HTRF assay (Cisbio Product #62GM2PEC). For each sample, 5 uL of HEK assay supernatant was diluted 1:5 in HTRF kit assay diluent and transferred to a well of the assay plate, and the HTRF assay was performed according to the HTRF kit manufacturer's instructions. Sample calculations were performed using high and low controls, where high control was supernatant from HEK assay performed in the presence of 10 uM Bay 41-2272+100 uM SNP, and the low control was the supernatant from the HEK assay performed in the presence of vehicle. A cGMP standard solution was prepared in 0.1 M HCl and diluted in order to perform a cGMP standard curve using the HTRF assay. Using Mean Ratio data from the HTRF assay, sample date were normalized according to the equation: 100*(Sample–Low Control)/(High Control–Low Control). Data were fit to a 3-parameter log agonist dose response (Top (% EMax), Bottom, log EC50) using Graphpad (Prism Software). Data in Table 4 was obtained using this modified assay procedure. (x μM concentration for test article solution and 10 μM concentration for SNP solution; wherein x is one of the following concentrations: 30 μM, 10 μM, 3 μM, 1 μM, 0.3 μM, 0.1 μM, 0.03 μM, 0.01 μM, 0.003 μM, 0.001 μM, 0.0003 μM and 0.01 nM.

TABLE 4

Whole cell activity in the HEK assay with HTRF detection.

| Compound No. | HEK assay Emax - unconstrained (%)[+] | HEK assay EC50 - unconstrained (μM)[#] |
|---|---|---|
| I-3 | F | A |
| I-16 | G | A |
| I-29 | D | B |
| I-36 | F | B |
| I-51 | F | C |
| I-67 | E | D |
| I-161 | F | B |
| I-200 | G | D |
| I-221 | G | D |
| I-248 | F | A |
| I-249 | G | C |
| I-253 | F | A |
| I-271 | F | A |

[+]Code definitions for the sGC enzyme activity values, expressed as % $E_{max}$ in the presence of 10 μM of SNP (wherein $E_{max}$ = 100% was the activity in the HEK assay obtained with the positive control BAY 41-2272 at 10 μM in the presence of 100 μM SNP) are:
A = 0 to <10%
B = 10 to <20%
C = 20 to <40%
D = 40 to <60
E = 60 or <80%
F = 80 to <100%
G = 100 to <120%
H = 120% or higher
— = not determined

[+]The same code definitions apply for Emax unconstrained, wherein this value is defined as the maximum activity value obtained from the full concentration-response curve for the compound, relative to the positive control value of 100% obtained as above. Here, the term "unconstrained" means that, during analysis of the sGC enzyme activity data, the top portion of the concentration-response curve was not fitted to 100%.
[#]$EC_{50}$ values were obtained from the full concentration response
*these samples were undiluted.
$0.001 \leq EC_{50} < 0.1 = A$
$0.1 \leq EC_{50} < 0.5 = B$
$0.5 \leq EC_{50} < 1.0 = C$
$1.0 \leq EC_{50} < 5.0 = D$
$5.0 \leq EC_{50} < 10.0 = E$
$EC_{50} \geq 10.0 = F$ Compounds I-306 to I-455 were tested in this assay with the majority of them displaying $EC_{50}$ values of less than 5.0 μM, with $E_{max}$ values of at least 80%.

Example 2C: Biological Activity Measurement by the sGC-HEK-cGMP Assay, New Protocol with LC/MS Detection Human embryonic kidney cells (HEK293), endogenously expressing soluble guanylate cyclase (sGC), were used to evaluate the activity of test compounds. Compounds stimulating the sGC enzyme should cause an increase in the intracellular concentration of cGMP. HEK 293 cells were seeded in Dulbecco's Modification of Eagle's Medium supplemented with fetal bovine serum (10% final) and penicillin (100 U/mL)/streptomycin (100 μg/mL) in a 50 μL volume at a density of $1.5 \times 10^4$ cells/well in a poly-D-lysine coated 384 well flat bottom plate. Cells were incubated overnight at 37° C. in a humidified chamber with 5% $CO_2$. Medium was aspirated and cells were washed with 1× Hank's Buffered Saline Salt Solution (50 μL). Cells were then incubated for 15 minutes at 37° C. with 50 μL of a 0.5 mM 3-isobutyl-1-methylxanthine (IBMX) solution. Test article and Diethylenetriamine NONOate (DETA-NONOate) solutions (x μM concentration for test article solution and 10 μM concentration for DETA-NONOate solution; wherein x is one of the following concentrations):

30000 nM
7500 nM
1875 nM
468.75 nM
117.19 nM
29.29 nM
7.32 nM
1.83 nM
0.46 nM
0.114 nM
0.029 nM were then added to the assay mixture and the resulting mixture incubated at 37° C. for 20 minutes. After the 20 minute incubation, the assay mixture was aspirated and 10% acetic acid containing 150 ng/mL+3-cGMP (internal standard for LCMS) (50 μL) was added to the cells. The plate was incubated at 4° C. for 30 minutes in the acetic acid solution to stop the reaction and lyse the cells. The plates were then centrifuged at 1,000 g for 3 minutes at 4° C. and the supernatant transferred to a clean reaction plate for LCMS analysis.

cGMP concentrations were determined from each sample using the LCMS conditions below (Table 5) and calculated standard curve. The standard curve was prepared in 10% acetic acid with 150 ng/mL+3cGMP (isotopically labelled cGMP with a weight 3 units higher than wild type) with the following final concentrations of cGMP in ng/mL: 1, 5, 10, 50, 100, 250, 500, 1000, 2000.

TABLE 5

LC/MS conditions, Example 2C

| MS: | Thermo Vantage |
|---|---|
| Ion Mode: | ESI[+] |
| Scan Type: | MRM |

| Compound: | Transition | Dwell Time (msec) | Collision Energy (V) | S Lens | Retention Time (min) |
|---|---|---|---|---|---|
| cGMP | 346 > 152 | 100 | 32 | 75 | 0.6 |
| (+3) cGMP IS | 349 > 155 | 100 | 32 | 75 | 0.6 |

| HPLC: | Waters Acquity UPLC |
|---|---|
| Column: | Thermo Hypersil Gold 2.1 × 50 mm 1.9 micron particle size |
| Flow Rate: | 750 uL/min |
| Column Temperature: | RT |
| Autosampler Temperature: | 6° C. |
| Injection Volume: | 20 uL |
| Mobile Phases: | A = 100% Water + 0.1% Formic Acid |
| | B = 100% Acetonitrile + 0.1% Formic Acid |

| | Time (min) | % A | % B |
|---|---|---|---|
| Gradient: | 0 | 100 | 0 |
| | 0.2 | 100 | 0 |
| | 0.3 | 50 | 50 |
| | 0.7 | 50 | 50 |
| | 0.8 | 100 | 0 |

Data were normalized to a high control using the following equation: 100*(Sample−Low Control)/(High Control−Low Control), where the low control is the average of 16 samples treated with 1% DMSO, and the high control is the average of 16 samples treated with 30 μM of I-329 Data were fit using a 4-parameter fit (log(agonist) vs. response-variable slope) using GraphPad Prism Software v.5. n=2 for all compounds. The Absolute $EC_{50}$ was interpolated from the curve fit and is defined as the concentration at which a given compound elicits 50% of the high control response. Compounds failing to elicit a minimum response of 50% are reported as >30 μM. For compounds run in duplicate or n higher than 2, the result herein given is the geometric mean of the several results obtained. Table 6 summarizes results obtained for selected compounds of the invention in this assay.

TABLE 6

Whole cell activity in the HEK assay with LC/MS detection (updated assay conditions, Example 2C).

| Compound | Absolute EC50 (uM) - binned (~) | Compound | Absolute EC50 (uM) - binned (~) |
|---|---|---|---|
| I-3 | B | I-200 | C |
| I-4 | B | I-204 | B |
| I-11 | B | I-206 | A |
| I-14 | C | I-213 | A |
| I-16 | A | I-214 | A |
| I-19 | A | I-219 | A |
| I-24 | A | I-221 | A |
| I-35 | B | I-230 | A |
| I-39 | B | I-236 | A |
| I-41 | A | I-239 | A |
| I-53 | B | I-245 | B |
| I-54 | A | I-187 | A |
| I-55 | B | I-300 | B |
| I-59 | B | I-250 | A |
| I-67 | C | I-306 | A |
| I-69 | B | I-453 | B |
| I-81 | C | I-361 | A |
| I-85 | C | I-257 | C |
| I-88 | B | I-258 | B |
| I-89 | A | I-454 | A |
| I-90 | C | I-363 | C |
| I-95 | C | I-364 | A |
| I-96 | C | I-365 | B |
| I-101 | B | I-366 | A |
| I-104 | C | I-455 | A |
| I-108 | B | I-367 | A |
| I-111 | A | I-368 | C |
| I-114 | C | I-369 | A |
| I-126 | A | I-370 | A |
| I-127 | C | I-268 | A |
| I-129 | A | I-371 | A |
| I-133 | C | I-269 | C |
| I-135 | C | I-372 | B |
| I-138 | C | I-329 | A |
| I-140 | B | I-330 | A |
| I-149 | C | I-373 | B |
| I-159 | C | I-374 | A |
| I-162 | A | I-375 | C |
| I-163 | C | I-307 | B |
| I-452 | A | I-305 | A |
| I-186 | A | I-376 | C |
| I-188 | B | I-339 | A |
| I-191 | A | I-377 | A |
| I-192 | A | I-308 | B |
| I-198 | A | I-312 | B |
| I-341 | A | I-348 | C |
| I-313 | A | I-321 | A |
| I-378 | A | I-432 | A |
| I-379 | A | I-433 | C |
| I-380 | A | I-350 | A |
| I-342 | A | I-434 | A |
| I-448 | B | I-334 | B |
| I-449 | A | I-335 | B |
| I-343 | A | I-336 | C |
| I-409 | A | I-435 | A |
| I-309 | A | I-407 | A |
| I-310 | A | I-437 | B |
| I-406 | A | I-410 | C |
| I-381 | A | I-337 | A |
| I-382 | A | I-408 | A |
| I-331 | B | I-395 | A |
| I-332 | A | I-411 | B |

TABLE 6-continued

Whole cell activity in the HEK assay with LC/MS detection (updated assay conditions, Example 2C).

| Compound | Absolute EC50 (uM) - binned (~) | Compound | Absolute EC50 (uM) - binned (~) |
|---|---|---|---|
| I-344 | A | I-322 | A |
| I-311 | B | I-351 | A |
| I-345 | A | I-352 | A |
| I-346 | C | I-413 | C |
| I-383 | A | I-438 | A |
| I-384 | C | I-323 | B |
| I-423 | A | I-353 | C |
| I-314 | A | I-439 | A |
| I-424 | A | I-324 | B |
| I-385 | B | I-396 | A |
| I-387 | A | I-397 | A |
| I-425 | A | I-398 | C |
| I-426 | A | I-399 | A |
| I-388 | A | I-354 | A |
| I-389 | A | I-440 | B |
| I-315 | A | I-355 | A |
| I-333 | A | I-358 | A |
| I-427 | A | I-441 | B |
| I-390 | A | I-451 | B |
| I-391 | B | I-400 | B |
| I-316 | A | I-325 | A |
| I-428 | A | I-442 | C |
| I-429 | A | I-443 | B |
| I-317 | A | I-326 | B |
| I-347 | A | I-414 | C |
| I-392 | A | I-360 | A |
| I-393 | B | I-356 | B |
| I-450 | C | I-401 | C |
| I-318 | A | I-416 | C |
| I-319 | A | I-412 | C |
| I-320 | A | I-357 | C |
| I-394 | C | I-164 | B |
| I-430 | A | I-405 | B |
| I-431 | A | I-327 | C |
| I-349 | A | I-328 | C |
| I-415 | C | I-499 | C |
| I-362 | B | I-500 | B |
| I-386 | C | I-501 | C |
| I-402 | C | I-502 | B |
| I-456 | B | I-503 | B |
| I-457 | B | I-504 | C |
| I-458 | C | I-505 | B |
| I-459 | C | I-506 | C |
| I-460 | C | I-507 | C |
| I-461 | C | I-418 | B |
| I-462 | C | I-508 | A |
| I-463 | B | I-509 | A |
| I-464 | B | I-446 | C |
| I-465 | B | I-445 | B |
| I-466 | A | I-510 | B |
| I-467 | C | I-511 | C |
| I-468 | B | I-419 | C |
| I-469 | B | I-512 | C |
| I-470 | A | I-513 | C |
| I-471 | B | I-514 | A |
| I-472 | C | I-515 | A |
| I-474 | C | I-516 | C |
| I-475 | B | I-517 | C |
| I-476 | C | I-518 | A |
| I-477 | C | I-519 | B |
| I-478 | A | I-520 | B |
| I-479 | B | I-521 | A |
| I-480 | B | I-522 | A |
| I-481 | C | I-523 | C |
| I-482 | C | I-524 | C |
| I-483 | C | I-525 | C |
| I-484 | B | I-526 | C |
| I-403 | B | I-527 | B |
| I-404 | B | I-528 | C |
| I-485 | A | I-529 | C |
| I-486 | C | I-530 | B |
| I-487 | A | I-531 | A |
| I-488 | B | I-532 | C |

TABLE 6-continued

Whole cell activity in the HEK assay with LC/MS detection (updated assay conditions, Example 2C).

| Compound | Absolute EC50 (uM) - binned (~) | Compound | Absolute EC50 (uM) - binned (~) |
|---|---|---|---|
| I-489 | C | I-420 | A |
| I-490 | B | I-533 | B |
| I-491 | B | I-534 | C |
| I-492 | B | I-535 | B |
| I-493 | B | I-536 | A |
| I-494 | B | I-537 | A |
| I-495 | A | I-538 | A |
| I-417 | B | I-539 | C |
| I-444 | B | I-540 | B |
| I-496 | A | I-541 | C |
| I-497 | B | I-542 | B |
| I-498 | B | I-543 | B |
| I-444 | B | I-544 | A |
| I-545 | A | I-547 | B |
| I-546 | C | I-548 | C |
| I-549 | C | I-600 | B |
| I-550 | C | I-601 | C |
| I-551 | C | I-602 | C |
| I-552 | C | I-603 | B |
| I-553 | C | I-604 | B |
| I-554 | C | I-605 | B |
| I-555 | C | I-606 | B |
| I-556 | C | I-607 | B |
| I-557 | C | I-608 | A |
| I-558 | B | I-609 | C |
| I-559 | B | I-610 | B |
| I-560 | C | I-611 | B |
| I-561 | C | I-612 | A |
| I-562 | B | I-613 | B |
| I-563 | C | I-614 | B |
| I-564 | C | I-615 | C |
| I-565 | B | I-616 | B |
| I-566 | B | I-617 | C |
| I-567 | C | I-618 | C |
| I-568 | A | I-619 | C |
| I-422 | B | I-620 | C |
| I-421 | B | I-621 | C |
| I-569 | C | I-622 | A |
| I-570 | B | I-623 | C |
| I-571 | C | I-624 | B |
| I-572 | C | I-625 | C |
| I-573 | B | I-626 | C |
| I-574 | B | I-627 | B |
| I-575 | A | I-628 | C |
| I-576 | B | I-629 | C |
| I-577 | B | I-630 | C |
| I-578 | A | I-634 | A |
| I-579 | C | I-631 | A |
| I-580 | B | I-632 | C |
| I-581 | A | I-633 | A |
| I-582 | C | I-591 | B |
| I-583 | C | I-592 | C |
| I-584 | C | I-593 | C |
| I-585 | B | I-594 | C |
| I-586 | B | I-595 | B |
| I-587 | B | I-596 | C |
| I-588 | B | I-597 | C |
| I-589 | B | I-598 | C |
| I-590 | C | I-599 | C |

(~) Code definitions for the sGC enzyme activity values, expressed as Absolute $EC_{50}$ which is defined as the concentration at which a given compound elicits 50% of the high control response (I-329). Compounds failing to elicit a minimum response of 50% are reported as >30 µM. EC50Abs < 100 nM = A; 101 nM ≤ EC50Abs < 1000 nM = B; 1001 nM ≤ EC50Abs = C.

Example 3A: Biological Activity Measurement by the Thoracic Aortic Rings Assay

Thoracic aortic rings are dissected from anesthetized (isoflurane) male Sprague-Dawley rats weighing 275-299 g. Tissues are immediately transferred to ice-cold Krebs-Henseleit solution, which has been aerated with 95% $O_2$ and 5% $CO_2$ for 30 minutes. Following removal of connective tissue, aortic sections are cut into 4 rings (~2 mm each) and suspended on 2 L-shaped hooks, with one hook fixed at the bottom of the tissue bath (Schuler Organ Bath, Harvard Apparatus) and the other connected to a force transducer (F30 Force Transducer, Harvard Apparatus). Baths containing Krebs Henseleit solution (10 mL) are heated to 37° C. and aerated with 95% $O_2$ and 5% $CO_2$. Rings are brought to an initial tension of 0.3-0.5 g and gradually raised to a resting tension of 1.0 g over 60 minutes. Rings are rinsed with Krebs Henseleit solution (heated to 37° C. and aerated with 95% 02 and 5% $CO_2$) at 15 minute intervals until a stable baseline is obtained. Rings are considered to be stable after a resting tension of 1.0 g is maintained (for approximately 10 minutes) without need for adjustment. Rings are then contracted with 100 ng/mL phenylephrine by adding 100 uL of a 10 µg/mL phenylephrine stock solution. Tissues achieving a stable contraction are then treated in a cumulative, dose dependent manner with test compounds prepared in dimethylsulfoxide (DMSO). In some cases, tissues are rinsed three times over a 5 minute period with Krebs-Heinseleit's solution (heated to 37° C. and aerated with 95% $O_2$ and 5% $CO_2$), allowed to stabilize at baseline, and then used for characterization of other test articles or DMSO effects. All data are collected using the HSE-ACAD software provided by Harvard Apparatus. Percent relaxation effects are calculated in Microsoft Excel using the recorded tension value of 100 ng/mL phenylephrine treatment as 0% inhibition and treatment with 100 µM 3-isobutyl-1-methylxanthine as 100% inhibition. EC50 values are calculated from concentration-response curves generated with Graph-Pad Prism Software.

Example 3B: Biological Activity Measurement by the Thoracic Aortic Rings Assay, Alternative Method As an alternative thoracic aortic rings assay, the procedure of Example 3 is used except that percent relaxation effects are calculated in Microsoft Excel using the recorded tension value of 100 ng/mL phenylephrine treatment as 0% inhibition and, after washing the tissue with buffer, the original resting tension of the tissue is used as 100% inhibition.

Example 4: Blood Pressure Change in Sprague-Dawley Rats

Male rats (250-350 g body weight, supplied by Harlan Laboratories) were anesthetized with ketamine/xylazine and a heparinized saline fluid filled catheter implanted into the right femoral artery. The catheter was exteriorized between the scapula, capped, and the animal allowed to recover for at least 7 days post surgery prior to any compound testing. Prior to testing animals were maintained on normal diet, with free access to drinking water, under a 12 hour light-dark cycle.

On the day of experimentation, under inhaled isoflurane anesthesia, the catheter was uncapped and connected to a tether (Instech Labs) and pressure transducer (Harvard Apparatus). Blood pressure and heart rate were subsequently captured and analyzed with a dedicated data capture system (PowerLab, ADInstruments). Data sampling rates were set at 1 cycle per second. Once connected, each rat was allowed to recover from anesthesia and baseline blood pressure and heart rate levels were established in these conscious, freely-moving animals. Once baseline was established either vehicle (0.5% methylcellulose or 100% PEG400) or test article was administered orally (PO, 10 mg/kg) and the effects on blood pressure and heart rate monitored for up to 24 hours.

Data are reported as hourly averages and changes in blood pressure are calculated from subtracting individual baseline on an hourly basis.

| Compound Number | Rat Mean Arterial Pressure peak change from baseline at 10 mpk@ |
|---|---|
| I-89 | C |
| I-121 | A |
| I-124 | B |
| I-142 | A |
| I-143 | B |
| I-161 | B |
| I-185 | A |
| I-186 | B |
| I-248 | C |
| I-253 | B |
| I-306 | B |
| I-313 | C |
| I-315 | C |
| I-316 | C |
| I-324 | C |
| I-187 | A |
| I-329 | B |
| I-330 | C |
| I-337 | C |
| I-341 | A |
| I-342 | C |
| I-388 | B |
| I-389 | C |
| I-400 | B |
| I-405 | C |

@Code definitions for Rat Mean Arterial Pressure peak change from baseline at 10 mpk:
A = −10 < peak change from baseline at 10 mpk < 0
B = −20 ≤ peak change from baseline at 10 mpk ≤ −10
C = peak change from baseline at 10 mpk < −20

Example 5: Animal Models Descriptions

Lamb Model of Pulmonary Hemodynamics Using Inhaled sGC Stimulator ("Inhaled Agonists of Soluble Guanylate Cyclase Induce Selective Pulmonary Vasodilation", Oleg V. et al, American J of Resp and Critical Care Medicine, Vol 176, 2007, p 1138)

It is possible to test whether inhalation of novel dry-powder microparticle formulations containing sGC stimulators would produce selective pulmonary vasodilation in lambs with acute pulmonary hypertension by following a published procedure. It is also possible to evaluate the combined administration of the microparticles of sGC stimulator and inhaled nitric oxide (iNO) in this system. Finally, it is possible to examine whether inhaling microparticles of an sGC stimulator would produce pulmonary vasodilation when the response to iNO (inducible nitric oxide synthase) is impaired.

Protocol: In awake, spontaneously breathing lambs instrumented with vascular catheters and a tracheostomy tube, U-46619 is infused intravenously to increase mean pulmonary arterial pressure to 35 mm Hg. Inhalation of microparticles composed of either BAY 41-2272, BAY 41-8543, or BAY 58-2667 and excipients (dipalmitoylphosphatidylcholine, albumin, lactose) produced dose dependent pulmonary vasodilation and increased transpulmonary cGMP release without significant effect on mean arterial pressure. Inhalation of microparticles containing BAY 41-8543 or BAY 58-2667 increased systemic arterial oxygenation. The magnitude and duration of pulmonary vasodilation induced by iNO were augmented after inhaling BAY 41-8543 microparticles. Intravenous administration of 1H-[1,2,4]oxadiazolo[4,3-a]quinoxalin-1-one (ODQ), which oxidizes the prosthetic heme group of sGC, markedly reduced the pulmonary vasodilator effect of iNO. In contrast, pulmonary vasodilation and transpulmonary cGMP release induced by inhaling BAY 58-2667 microparticles were greatly enhanced after treatment with ODQ. Thus, inhalation of microparticles containing agonists of sGC may provide an effective novel treatment for patients with pulmonary hypertension, particularly when responsiveness to iNO is impaired by oxidation of sGC. Note: BAY 41-2272, BAY 41-8543 are sGC stimulators whereas BAY 58-2667 is an sGC activator.

Electrical Field Stimulated Guinea Pig Tracheal Smooth Muscle In Vitro (Ex Vivo) Model for the Assessment of Bronchodilation.

It is possible to assess the bronchodilating effects of sGC stimulators by using the system described below. This system allows us to determine potency, efficacy and duration of action of several sGC stimulators, as well as to assess potential side effects such as blood pressure, or heart rate changes.

Animals: Guinea pig, Dunkin Hartley, male, Full barrier-bred and certified free of specific micro-organisms on receipt 525-609 g on the experimental day, Harlan UK Ltd. Guinea pigs are housed in a group of 4 in solid-bottomed cages with Gold Flake bedding in a controlled environment (airflow, temperature and humidity). Food (FD1, Special Diet Services) and water are provided ad libitum.

Guinea Pig Tracheal Smooth Muscle Contraction in Response to EFS. Assessment of Compound Potency and Efficacy:

On each experimental day, a guinea pig is killed by exposure to a rising concentration of CO2 and the trachea removed. The trachea is cleaned of extraneous tissue and cut open longitudinally in a line opposite the muscle, opened out and cut into strips 2-3 cartilage rings wide. A cotton loop is attached to one end of each tracheal strip and a length of cotton to the other end. Tracheal strips are then suspended between two platinum electrodes, using tissue holders, in a Myobath system (World Precision Instruments Stevenage, UK). The loop is attached over the hook at the bottom of the tissue holder and the other end attached to the arm of a FORT10 force transducer (World Precision Instruments Stevenage, UK) ensuring that the tissue is positioned between the two platinum electrodes. The whole assembly is then lowered into a 10 ml tissue bath containing modified Kreb's-Henseleit buffer, at 37° C., bubbled with Carbogen. A 1 g tension is applied to each piece of tissue and the tissue washed, followed by a 1 hour stabilization period. Once the tissues has been allowed to stabilize, the apparatus for electrical field stimulation is set to deliver a stimulation of frequency 80 Hz pulse width 0.1 ms, with a gated, uni-polar pulse, every 2 minutes using a DS8000 8 channel digital stimulator (World Precision Instruments Stevenage, UK). A voltage response curve is carried out on each tracheal strip at 2, 4, 6, 7, 8, 10, 12 V and a sub-maximal voltage then selected to apply to each tissue during the remainder of the experiment. Guinea pig tracheal smooth muscle (GPTSM) contraction is induced using sub-maximal Electrical Field Stimulation (EFS) (It is also possible to induce contraction by using a spasmogen substance, such as methacholine or histamine as described in Coleman et al.*). Compounds are dissolved in 100% DMSO at 3×10-2M and aliquots stored at −200 C. A separate aliquot is used for each experiment. Tissues are washed with Kreb's buffer and stimulated using the previously determined sub-maximal voltage for 1 hour to establish a stable baseline contraction prior to assessment of compound activity.

A cumulative dose response curve (DRC) to each test substance is then performed and changes in smooth muscle contraction measured. The effect of each test substance in each experiment is expressed as a percentage inhibition of the baseline contraction, normalized to the relevant vehicle controls. The experiment is performed three times, using tissue from three different animals. The data from all three experiments are pooled, the DRC plotted, and the test substance potency and efficacy determined. The potency of Ipratropium bromide is assessed alongside the test compounds and the IC50 determined to be 0.86 nM (95% Cl, 0.78-0.94), in agreement with data previously produced in the system.

Novel and Versatile Superfusion System. Its use in the Evaluation of Some Spasmogenic and Spasmolytic Agents Using Guinea pig isolated Tracheal Smooth Muscle.", R. A. Coleman et al., J. Pharmacol. Methods, 21, 71-86, 1989.

Mouse Model for Diseases in which Altered CFTR-Function is Causally Involved

These diseases comprise cystic fibrosis, pancreatic disorders, gastrointestinal disorders, liver disorders, cystic fibrosis-related diabetes (CFRO), dry eye, dry mouth and Sjoegren's syndrome.

By using transgenic mice expressing or not expressing the delta F508CFTR channel it is possible to measure differences on nasal potential difference and salivation in the presence of a test sGC stimulator by using the literature protocol described below (see WO2011095534).

Salivary Secretion Assay in Delta(.6.)50S-CFTR Mice

15 Male and female homozygous, heterozygous .6.505-CFTR (backcrossed on the FVB genetic background for more than 12 generations, originally obtained from Erasmus University, Rotterdam; 10-14 weeks old and weighing 1S-36 g of both sexes were used in this assay. Solutions of Vardenafil in concentrations of 0.07, 0.14 and 0.42 mg/kg BW were 20 prepared in sterile saline, whereas the sGC stimulator BAY 41-2272 was dissolved to 0.01, 0.03, 0.1 and 0.3 mg/kg BW in a solvent containing 50% ddH20, 40% PEG 400 (polyethylene glycol 400) and 10% ethanol. The substances or the appropriate vehicles were administered to mice via intraperitoneal injection (5 ml/kg BW) 60 min prior to the salivary secretion assay. After 60 min, mice were anaesthetized with a combination of 25 ketamine and diazepam. The solution was prepared to contain 1 ml of 5 mg/ml diazepam. and 1 ml of 100 mg/ml ketamine in 8 ml sterile saline. Anaesthesia was induced by intraperitoneal injection of the solution (10 ml/kg BW). After anaesthesia, mice were pretreated with a subcutaneous injection of 1 mM atropine (50 1-11) into the left cheek in order to avoid a cross-stimulation of cholinergic receptors. Small strips of Whatman filter 5 paper were placed inside the previously injected cheek for 4 min to absorb any saliva secreted after the injection of atropine. This first piece of filter paper was removed and replaced with a second pre-weighed filter paper. Thereafter, 50 1-11 of a solution containing 100 I-IM isoprenaline and 1 mM atropine was injected into the left cheek at the same site to induce the salivary secretion by adrenergic mechanisms. The time of the 10 isoprenaline injection was taken as time zero, and filter paper stripes were replaced every 10 minutes for a total collection period of 30 minutes. Each piece of filter paper was immediately placed and sealed in a pre-weighed vial. After all samples had been collected, each vial was re-measured and the weights of all samples were recorded. The difference in total weight of vial plus paper measured before and after collecting saliva 15 was taken as the net weight of saliva secreted during the collection period. The total amounts of salivary secretion were calculated as the weight of saliva divided by the number of minutes required for each collection and then normalized to the mass of the mouse in grams. Results are expressed as the mean percentage increase of n mice compared to placebo treatment. Statistics was analyzed by one way ANOVA test 20 followed by post-hoc Bonferoni analysis; *//* means statistical significant with p values<0.05/<0.01/0.001 and n.s. means non significant.

These animal studies were carried out with a number of sGC stimulators, sGC activators and PDE5 inhibitors. The results suggests that compounds of the invention are useful for the treatment of cystic fibrosis, pancreatic disorders, gastrointestinal disorders, liver disorders, Cystic Fibrosis-related diabetes (CFRO), dry eye, dry mouth and Sjoegren's syndrome.

Neuromuscular Disorders

It has previously been shown that neuronal Nitric Oxide Synthase (nNOS) mislocalization from the sarcolemmal membrane to the sarcoplasm is observed in a broad range of nondystrophic neuromuscular conditions associated with impaired motility status and catabolic stress. One tool for the evaluation of muscle biopsies of patients with a variety of inherited and acquired forms of neuromuscular disorders is the assessment of sarcolemal localization of nNOS. It was found that the level of nNOS at the sarcolemma correlates with mobility and functional status.

An analogous assessment can be used to determine nNOS localization in animal models of nondystrophic myopathy following the literature protocols described below ("Loss of sarcolemmal nNOS is common in acquired and inherited neuromuscular disorders"; E. L. Finanger Hedderick et al., Neurology, 2011, 76(11), 960-967).

nNOS Mislocalization in Mouse Models of Acquired Muscle Atrophy

Two mouse models have been described that demonstrate muscle atrophy without compromised mobility: high-dose corticosteroids therapy and short-term starvation. Mice treated with steroids or starved for 48 hours showed significant decreases in overall body mass and in normalized wet skeletal muscle mass. Morphometric analysis of skeletal muscle specimens of both models demonstrated muscle atrophy, as defined by a significant decrease in mean minimal Feret fiber diameter as compared to age-matched controls (n=5 for each group). Immunofluorescence staining for dystrophin, $\alpha$-sarcoglycan, and $\alpha$-1-syntrophin showed normal dystrophin localization suggestive of an intact DGC complex However, both steroid-treated and starved mice showed absent or severely reduced sarcolemmal nNOS staining. Real-time PCR for NOS family proteins (nNOS, eNOS, iNOS) revealed no significant differences in expression levels of any of the 3 transcripts in steroid-treated mice (n=8 for each group). Moreover, Western blot analysis for nNOS, iNOS, and eNOS showed no differences in protein levels.

These murine animal models could be used to assess the effects of sGC stimulators (for example an sGC stimulator of the invention) in the symptoms of muscle atrophy and related disease states.

Starved mice exhibited a 1-fold decrease of nNOS and iNOS transcript expression as compared to wildtype mice (n=9 for controls, n=7 for starved). However, the protein level of nNOS, iNOS, and eNOS revealed no differences between control and starved mice (n=4 for each group). These data demonstrate that abnormal localization of nNOS occurs in mice with severe muscle atrophy even if overall mobility is preserved, supporting the notion that, in addition to impaired mobility, other triggers such as catabolic stress may be associated with sarcolemmal loss of nNOS.

Skeletal Muscle nNOS Localization is Maintained During Hibernation (Studies with Squirrels)

Skeletal muscle specimens from hibernating 13-lined ground squirrels have been used to evaluate the impact of immobility and catabolic stress on nNOS localization in the context of maintained muscle homeostasis and integrity. These animals are obligate hibernating mammals that are protected against skeletal muscle atrophy during hibernation. Despite hibernating for 5 months with almost complete immobility and no caloric intake, sarcolemmal expression of nNOS is preserved. These data together with patient and mouse data indicate that biochemical control of nNOS localization is complex and, importantly, that preserved sarcolemmal nNOS may be significant in maintaining muscle homeostasis.

These results also suggest that targeting aberrant NO signaling (for instance with sGC stimulators such as the ones here described) may prove beneficial for a broad group of patients with neuromuscular disorders.

Mouse Models of Muscular Dystrophy (BMD and DMD)

Becker muscular dystrophy (BMD), characterized by progressive skeletal muscle wasting, is caused by mutations of the muscle protein dystrophin. In a human study, Martin et al. (see "Tadalafil Alleviates Muscle Ischemia in Patients with Becker Muscular Dystrophy"; Elizabeth A. Martin et al., *Sci. Transl. Med.* 4, 162ra155 (2012); "Vascular-targetted therapies for Duchenne muscular dystrophy"; Ennen et al., *Skeletal Muscle,* 2013, 3:9) assessed exercise-induced attenuation of reflex sympathetic vasoconstriction in the muscles of 10 patients with BMD and 7-age matched healthy male controls. This is a protective mechanism that optimizes perfusion of skeletal muscle to meet the metabolic demands of exercise. Reflex vasoconstriction was induced by simulated orthostatic stress and was measured as the forearm muscles were rested or lightly exercised in the form of rhythmic handgrip. First, the investigators showed that exercise-induced attenuation of reflex vasoconstriction was defective in 9 out of 10 patients with BMD in whom the common dystrophin mutations disrupt targeting of neuronal NO synthase (nNOS) to the muscle sarcolemma. Then, in a double-blind randomized placebo-controlled crossover trial, the authors showed that normal blood flow regulation was restored in eight of nine patients by a single oral dose of 20 mg of tadalafil, a specific PDE5 inhibitor.

It is possible to assess the effects of drugs acting on the NO pathway by using a dystrophin-deficient mdx mouse model of related disease Duchene muscular dystrophy (DMD). This model has also shown that inhibitors of phosphodiesterase 5 (PDE5) alleviate some features of the dystrophic phenotype including vasospasm of skeletal muscle microvessels that can lead to muscle injury and fatigue.

With exercise of healthy skeletal muscle, sarcolemmal nNOS derived NO attenuates local α-adrenergic vasoconstriction, thereby optimizing perfusion to meet the metabolic demands of the active muscle. This protective mechanism (termed functional sympatholysis) is lost in mdx mice (a model of BMD and DMD), nNOS null mice, and boys with DMD causing functional muscle ischemia. Repeated bouts of functional ischemia could accelerate use-dependent injury of muscle fibers already weakened by dystrophin deficiency.

In the mdx mouse, many features of the dystrophic phenotype can be improved by multiple strategies that boost NO signaling, including transgenic expression of nNOS, transgenic expression of dystrophin minigenes that restore sarcolemmal nNOS (and thereby restore functional sympatholysis), administration of the NOS substrate L-arginine (24, 25), treatment with NO-donating drugs, and phosphodiesterase 5A (PDE5A) inhibition with the drug tadalafil or sildenafil. These PDE5A inhibitors, which prolong the hal-flife of guanosine 3',5'-monophosphate (cGMP)—the downstream target of NO in vascular smooth muscle—were shown in the mdx mouse to alleviate muscle ischemia, as well as injury and fatigue, after a brief bout of exercise. Also, these drugs were shown to improve cardiac dynamics in mdx mice and to rescue dystrophic skeletal muscle and prolong survival in dystrophin-deficient zebrafish.

These findings support an essential role for sarcolemmal nNOS in modulating sympathetic vasoconstriction in exercising human skeletal muscles and suggests that targeting the aberrant NO pathway (for instance by using an sGC stimulator of the invention) may be a useful therapeutic approach for treating BMD and DMD in humans.

Sickle Cell Disease

Sickle-cell disease (SCD), or sickle-cell anaemia (SCA) or drepanocytosis, is a hereditary blood disorder, characterized by red blood cells that assume an abnormal, rigid, sickle shape. Sickling decreases the cells' flexibility and results in a risk of various complications. The sickling occurs because of a mutation in the haemoglobin gene. Individuals with one copy of the defunct gene display both normal and abnormal haemoglobin. This is an example of codominance. In 1994, in the US, the average life expectancy of persons with this condition was estimated to be 42 years in males and 48 years in females, but today, thanks to better management of the disease, patients can live into their 70s or beyond.

Sickle-cell anaemia is a form of sickle-cell disease in which there is homozygosity for the mutation that causes HbS. Sickle-cell anaemia is also referred to as "HbSS", "SS disease", "haemoglobin S" or permutations of those names. In heterozygous people, that is, those who have only one sickle gene and one normal adult haemoglobin gene, the condition is referred to as "HbAS" or "sickle cell trait". Other, rarer forms of sickle-cell disease are compound heterozygous states in which the person has only one copy of the mutation that causes HbS and one copy of another abnormal haemoglobin allele. They include sickle-haemoglobin C disease (HbSC), sickle beta-plus-thalassaemia (HbS/$\beta^+$) and sickle beta-zero-thalassaemia(HbS/$\beta^0$).

Although red blood cell (RBC) sickling and rheologic abnormalities are central to the pathophysiology of sickle cell disease, vascular dysfunction resulting from complex interactions between sickled red blood cells (sRBC), endothelial cells, platelets and leukocytes play an equally important role. In sickle cell disease, endothelial activation is associated with sickle cell-mediated hypoxia-reperfusion events (see for example "Advances in understanding of the pathogenesis of cerebrovascular vasculopathy in sicke cell anemia", P. Connes et al., *Br. J. Haematol.* 2013, 161, 484-98). Red blood cell sickling and adhesion to endothelium initiate vaso-occlusion by impairing blood flow. The subsequent surge of inflammatory mediators and endothelial activation trigger a cascade of events leading to vascular damage. Pathophysiological responses to intermittent hypoxia-reperfusion from these vaso-occlusive events are demonstrated by an increased production of cytokines, leukocyte up-regulation and activation of pro-coagulant and adhesion molecules, with simultaneous inhibition of cytoprotective mediators.

Leukocytosis is correlated with nearly every manifestation of sickle cell disease, emphasizing the influential role of inflammation in the pathophysiology of sickle vasculopathy. Even at baseline, sickle cell disease patients exhibit elevations in pro-inflammatory cytokines, including C-reactive protein (CRP), tumor necrosis factor (TNF), interleukin-1 (IL-1) and interleukin-8 (IL-8). In vitro studies have shown that sRBC promote endothelial up-regulation of TNF-α and IL-1β (8-10). Microarray studies of activated monocytes have shown differential expression of genes involved in inflammation, heme metabolism, cell cycle regulation, antioxidant responses, and angiogenesis. More recently, it was shown that differential expression of nuclear factor κ-light-chain-enhancer of activated B cells (NFκB/p65), Kruppel-like factor 2 (KLF2), and other transcription factors that regulate pathways of inflammation in sickle cell disease children at increased risk for stroke.

In transgenic mouse models (see "Novel Therapies Targetting the Endothelium in sickle cell disaease", C. C Hoppe, *Hemoglobin,* 35(5-6):530-546 (2011) and references cited therein), sickling inducing oxidative stress has been shown to affect microvascular regulatory mechanisms leading to endothelial activation and exaggerated inflammatory and pro-adhesive responses. Oxidative stress occurs through formation of reactive oxygen species (ROS). Depletion of NO occurs through hemoglobin (Hb) mediated scavenging, consumption by ROS and arginase-mediated substrate depletion. In sickle cell disease, the scavenger systems that normally remove circulating free Hb are saturated. Free Hb depletes NO, leading to endothelial dysfunction. Consequently, the normal balance of vasoconstriction and vasodilation is skewed towards vasoconstriction, endothelial activation, oxidative stress and proliferative vasculopathy.

Therapies directed at restoring NO homeostasis have shown promise in preliminary studies in patients with sickle cell disease. Previous in vitro studies and studies in other patient populations showed NO-mediated down-regulation of endothelial adhesion molecule expression. Following these observations, the use of inhaled NO was studied in sickle cell disease children presenting with VOE and found associated trends toward lower pain scores, decreased analgesic requirements and a shorter hospital stay.

These findings were reproduced in a recent randomized placebo controlled trial evaluating inhaled NO for the treatment of acute VOE in adult patients with sickle cell disease, showing that inhaled NO significantly reduced pain scores and was associated with a trend towards decreased use of parenteral morphine compared with placebos. Results from a completed phase II trial of adult sickle cell disease patients treated with inhaled NO for acute VOE have not yet been made available (clinicaltrials.gov NCT00023296). Another phase II trial of inhaled NO for VOE treatment in children with sickle cell disease is expected to be completed (clinicaltrials.gov NCT00094887). The possible therapeutic role of inhaled NO for ACS in sickle cell disease is currently being assessed in both children and adults in two separate French phase II/III trials comparing the use of inhaled NO to placebo or standard care in children with ACS (clinicaltrials.gov NCT01089439 and NCT00748423).

Dietary supplementation of the NO synthase substrate, L-arginine, has been studied extensively in sickle cell disease as a means of increase NO bioavailability. In sickle mice, oral L-arginine at high doses has been shown to decrease Gardos channel activity, dense cell formation and hemolysis, as well as functional improvements in vascular reactivity.

Sildenafil, an agent aimed at amplifying the effect of endogenous NO by inhibiting PDE5, a downstream mediator of NO, is used widely in the general population to treat primary PHT. Preliminary studies in sickle cell disease patients with severe PHT reported improvements in PAP and exercise capacity after treatment with sildenafil. A multicenter trial (Treatment of Pulmonary Hypertension and Sickle Cell Disease with Sildenafil Therapy, Walk-PHaSST) testing the safety and efficacy of sildenafil in sickle cell disease patients with Doppler-defined PI-IT was stopped prematurely due to a higher frequency of serious side effects, including increased rates of VOE, headache, and visual disturbance in the treatment group.

Nitrite and niacin have also been investigated for their direct NO donor properties. In a pilot phase I/II clinical trial, sodium nitrite infusions in adult sickle cell disease patients enhanced forearm blood flow, consistent with a NO donor mechanism of action. A larger phase I/II trial is now investigating whether nitrite infusions administered as adjunctive therapy during acute VOE will improve microvascular blood flow and tissue oxygenation (clinicaltrials.gov NCT01033227). The effect of niacin on improvement in endothelial-dependent vasodilation is also being assessed in a phase II randomized, controlled trial (clinicaltrials.gov NCT 00508989).

The above results suggest that targeting the aberrant NO pathway in sicke cell disease (for instance by using an sGC stimulator of the invention) may be a useful therapy for the treatment of the disease. Murine models of sickle cell anemia that could be used to assess the effect of sGC stimulators (e.g., an sGC stimulator of the invention) in this disease state, are described in *Blood,* 2001, 98(5), 1577-84; *J. Clin. Invest.* 2004, 114(8), 1136-45; and *Br. J. Haematol.,* 2004, 124(3), 391-402.

Bladder Dysfunction

It has been shown that the sGC activator BAY 60-2770 ameliorates overactive bladder in obese mice (see "The Soluble Guanylyl Cyclase Activator BAY 60-2770 ameliorates overactive bladder in obese mice", Luiz O Leiria et al., *The Journal of Urology,* 2013, doi:10.1016/j.juro.2013.09.020). The animal model described in this publication can analogously be used to assess the effect of an sGC stimulator (for example, an sGC stimulator of the invention) on overactive bladder.

The same group of researchers have also described a rat model of bladder dysfunction (NO-deficient rats, F Z Monica et al., *Neurology and Urodynamics,* 30, 456-60, 2011) and have shown the protective effects of BAY-2272 (an sGC activator) in this model. The animal model described in this publication can analogously be used to assess the effect of an sGC stimulator (for example, an sGC stimulator of the invention) on bladder dysfunction related to detrusor smooth muscle overactivity.

A number of embodiments have been described. Nevertheless, it will be understood that various modifications may be made without departing from the spirit and scope of the invention.

The invention claimed is:
1. A method of treating diabetic nephropathy in a subject in need of treatment, comprising administering a therapeutically effective amount of compound 1-324

I-324

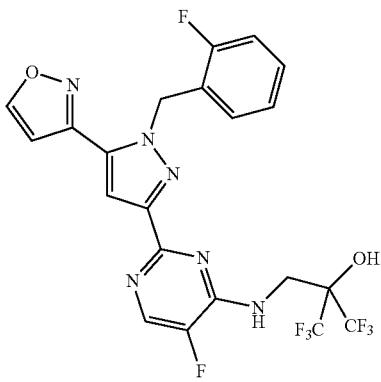

or a pharmaceutically acceptable salt thereof, to the subject in need of treatment.

2. The method of claim 1, further comprising administering an effective amount of one or more additional therapeutic agents to the subject.

3. The method of claim 2, wherein the one or more additional therapeutic agents are selected from anti-diabetic agents, neprilysin inhibitors, angiotensin receptor blockers (ARB), angiotensin converting enzyme (ACE) inhibitors, mineralocorticoid receptor (MR) antagonists, endothelin receptor antagonists (ERAs), calcium channel blockers, beta blockers, prostacyclin derivatives or analogues, diuretics, and antihyperlipidemics, wherein prostacyclin derivatives or analogues are selected from prostacyclin, epoprostenol, treprostinil, iloprost, and beraprost.

4. The method of claim 3, wherein the one or more additional therapeutic agents are anti-diabetic agents selected from insulin and insulin mimetics, sulfonylureas, biguanides, α-glucosidase inhibitors, thiazolidinone compounds, insulin sensitizers, insulin secretagogues, GLP-1 receptor agonists, SGLT-2 inhibitors, incretin mimetics, amylin analogues, glucose lowering agents, dipeptidyl peptidase IV (DPP4) inhibitors, and tolimidone.

5. The method of claim 4, wherein the insulin and insulin mimetics are selected from insulin degludec, insulin degludec combined with insulin aspart, insulin human (rDNA origin) inhalation powder, recombinant human insulin, hepatic-directed vesicle insulin, human isophane insulin, insulin tregopi (IN-105), insulin degludec combined with liraglutide, insulin peglispro (LY-2605541), insulin glargine (LY-2963016), and nodlin; wherein the sulfonylureas are selected from glyburide, glybenclamide, glipizide, gliclazide, gliquidone, glimepiride, atorvastatin calcium combined with glimerpiride, meglinatide, tolbutamide, chlorpropamide, acetohexamide, and tolazimide; the α-glucosidase inhibitors are selected from acarbose, epalrestat, voglibose, and miglitol; the thiazolidinone compounds are selected from rosiglitazone, troglitazone, ciglitazone, pioglitazone, englitazone, lobeglitazone sulfate, and balaglitazone; the insulin sensitizers are selected from pioglitazone and rosiglitazone; the insulin secretagogues are selected from repaglinide, nateglinide, and mitiglinide; the GLP-1 receptor agonists are selected from lixisenatide, lixisenatide combined with insulin glargine, albiglutide, dulaglutide, and pegapamodutide (TT-401); the SGLT-2 inhibitors are selected from dapagliflozin, tofoglifozin (CSG-452), canagliflozin, canagliflozin combined with metformin hydrochloride, dapagliflozin combined with metformin hydrochloride, empagliflozin, empaglifozin combined with linagliptin, luseoglifozin, and ipragliflozin L-proline; the incretin mimetics are selected from exanatide and liraglutide; the amylin analogue is pramlintide; and the dipeptidyl peptidase IV inhibitors are selected from sitagliptin, vildagliptin, saxagliptin, alogliptin, linagliptin, alogliptin benzoate combined with metformin hydrochloride, anagliptin, teneligliptin, atorvastatin calcium and glimepiride, empagliflozin combined with linagliptin, gemigliptin, sitagliptin phosphate monohydrate combined with pioglitazone hydrochloride, sitagliptin combined with atorvastatin calcium, and (2S,4S)-1-[2-(1,1-dimethyl-3-oxo-3-pyrrolidin-1-yl-propylamino)acetyl]-4-fluoro-pyrrolidine-2-carbonitrile (DBPR-108).

6. The method of claim 4, wherein the one or more additional therapeutic agents is the biguanide metformin.

7. The method of claim 4, wherein the one or more additional therapeutic agents is a GLP-1 receptor agonist.

8. The method of claim 3, wherein the one or more additional therapeutic agents are SGLT-2 inhibitors selected from dapagliflozin, tofoglifozin (CSG-452), canagliflozin, canagliflozin combined with metformin hydrochloride, dapagliflozin combined with metformin hydrochloride, empagliflozin, empagliflozin combined with linagliptin, luseoglifozin, and ipragliflozin L-proline.

9. The method of claim 3, wherein the one or more additional therapeutic agents are selected from neprilysin inhibitors.

10. The method of claim 3, wherein the one or more additional therapeutic agents are angiotensin converting enzyme (ACE) inhibitors.

11. The method of claim 10, wherein the angiotensin converting enzyme (ACE) inhibitors selected from sulfhydryl-containing agents, dicarboxylate-containing agents, phosphonate-containing agents, naturally occurring ACE inhibitors, alacepril, delapril, cilazapril, imidapril, trandolapril, temocapril, moexipril, and spirapril.

12. The method of claim 3, wherein the one or more additional therapeutic agents are mineralocorticoid receptor (MR) antagonists.

13. The method of claim 12, wherein the one or more additional therapeutic agents are mineralocorticoid receptor (MR) antagonists selected from spironolactone, amiloride hydrochloride combined with spironolactone, apararenone or MT-3995, and finerenone or BAY-94-8862.

14. The method of claim 3, wherein the one or more additional therapeutic agents are endothelin receptor antagonists.

15. The method of claim 3, wherein the one or more additional therapeutic agents are SGLT-2 inhibitors.

16. The method of claim 8, wherein the one or more additional therapeutic agents are SGLT-2 inhibitors selected from dapagliflozin, canagliflozin, canagliflozin combined with metformin hydrochloride, dapagliflozin combined with metformin hydrochloride, empagliflozin, and empaglifozin combined with linagliptin.

17. The method of claim 3, wherein the one or more additional therapeutic agents are angiotensin receptor blockers (ARB).

18. The method of claim 3, wherein the one or more additional therapeutic agents are calcium channel blockers.

19. The method of claim 3, wherein the one or more additional therapeutic agents are beta blockers.

20. The method of claim 3, wherein the one or more additional therapeutic agents are selected from selexipag, alprostadil, prostacyclin, epoprostenol, treprostinil, iloprost, and beraprost.

21. The method of claim 3, wherein the one or more additional therapeutic agents are antihyperlipidemics.

22. The method of claim 3, wherein the one or more additional therapeutic agents are diuretics.

23. The method of claim 11, wherein sulfhydryl-containing agents are selected from captopril and zofenopril; the dicarboxylate-containing agents are selected from enalapril, ramipril, quinapril, perindopril, lisinopril and benazepril; the phosphonate-containing agent is fosinopril; and the naturally occurring ACE inhibitors are selected from casokinins, lactokinins and lactotripeptides Val-Pro-Pro and Ile-Pro-Pro.

24. The method of claim 14, wherein the endothelin receptor antagonists are selected from bosentan, sitaxentan, ambrisentan, actelion-1 and macitentan.

25. The method of claim 17, wherein the angiotensin receptor blockers (ARB) are selected from losartan, balsartan, candesartan cilexetil, eprosaran, irbesartan, telmisartan, olmesartran medoxomil and azilsartan medoxomil.

26. The method of claim 18, wherein the calcium channel blockers are selected from:
   i. dihydropyridine calcium channel blockers selected from amlodipine, aranidipine, azelnidipine, barnidipine, benidipine, cilnidipine, clevidipin, diltiazem, efonidipine, felodipin, lacidipine, lercanidipine, manidipine, nicardipine, nifedipine, nilvadipine, nimodipine, nisoldipine, nitrendipine, pranidipine and isradipine;
   ii. phenylalkylamine calcium channel blockers selected from verapamil and gallopamil;
   iii. benzothiazepine calcium channel blocker diltiazem; and
   iv. nonselective calcium channel inhibitors selected from mibefradil, bepridil, fluspirilene and fendiline.

27. The method of claim 19, wherein the beta blockers are selected from alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol, timolol, acebutolol, atenolol, betaxolol, bisoprolol, celiprolol, dobutamine hydrochloride, irsogladine maleate, carvedilol, talinolol, esmolol, metoprolol and nebivolol.

28. The method of claim 21, wherein the antihyperlipidemics are selected from (i) bile acid sequestrants selected from cholestyramine, colestipol, colestilan and colesevelam; (ii) statins selected from atorvastatin, simvastatin, lovastatin, fluvastatin, pitavastatin, rosuvastatin and pravastatin; (iii) cholesterol absorption inhibitors selected from ezetimibe; (iv) other lipid lowering agents selected from icosapent ethyl ester, omega-3-acid ethyl esters, reducol; (v) fibric acid derivatives selected from clofibrate, bezafibrate, clinofibrate, gemfibrozil, ronifibrate, binifibrate, fenofirate, ciprofibrate, choline and fenofibrate; (vi) nicotinic acid derivatives selected from acipimox and niacin; (vii) combinations of statins, niacin, intestinal cholesterol absorption-inhibiting supplement ezetimibe, and fibrates; and (viii) antiplatelet therapy clopidogrel bisulfate.

29. The method of claim 22, wherein the diuretics are selected from (i) thiazide diuretics selected from chlorothiazide, chlorthalidone, hydrochlorothiazide, bendroflumethiazide, cyclopenthiazide, methyclothiazide, polythiazide, quinethazone, xipamide, metolazone, indapamide, cicletanine; (ii) loop diuretics selected from furosemide and toresamide; (iii) potassium-sparing diuretics selected from amiloride, spironolactone, canrenoate potassium, eplerenone and triamterene; (iv) other diuretics selected from acetazolamid and carperitide.

30. The method of claim 3, wherein the one or more additional therapeutic agents are selected from neprilysin inhibitors and angiotensin receptor blockers.

31. The method of claim 30, wherein the one or more additional therapeutic agents are a combination of sacubitril and valsartan.

* * * * *